(12) United States Patent
Zheng et al.

(10) Patent No.: US 12,312,318 B2
(45) Date of Patent: May 27, 2025

(54) ORGANIC COMPOUND, ELECTRONIC DEVICE AND ELECTRONIC APPARATUS USING SAME

(71) Applicant: Shaanxi Lighte Optoelectronics Material Co., Ltd., Xi'an (CN)

(72) Inventors: Yiyi Zheng, Xi'an (CN); Tiantian Ma, Xi'an (CN); Xinying Liu, Xi'an (CN)

(73) Assignee: SHAANXI LIGHTE OPTOELECTRONICS MATERIAL CO., LTD., Xi'An (CN)

( * ) Notice: Subject to any disclaimer, the term of this patent is extended or adjusted under 35 U.S.C. 154(b) by 772 days.

(21) Appl. No.: 17/621,654

(22) PCT Filed: Nov. 23, 2020

(86) PCT No.: PCT/CN2020/130914
§ 371 (c)(1),
(2) Date: Dec. 21, 2021

(87) PCT Pub. No.: WO2021/135725
PCT Pub. Date: Jul. 8, 2021

(65) Prior Publication Data
US 2022/0315542 A1 Oct. 6, 2022

(30) Foreign Application Priority Data

Dec. 31, 2019 (CN) .......................... 201911416944.6
Aug. 18, 2020 (CN) .......................... 202010833965.4

(51) Int. Cl.
*C07D 251/24* (2006.01)
*C07D 239/26* (2006.01)
(Continued)

(52) U.S. Cl.
CPC ......... *C07D 251/24* (2013.01); *C07D 239/26* (2013.01); *C07D 401/14* (2013.01);
(Continued)

(58) Field of Classification Search
CPC ... H10K 85/622; H10K 85/654; C07D 251/24
See application file for complete search history.

(56) References Cited

FOREIGN PATENT DOCUMENTS

| CN | 1950479 A | 4/2005 |
| CN | 106716665 A | 5/2017 |

(Continued)

OTHER PUBLICATIONS

Computer-generated English-language translation of CN-107778260-A.*

(Continued)

*Primary Examiner* — Vu A Nguyen
(74) *Attorney, Agent, or Firm* — Tucker Ellis LLP

(57) ABSTRACT

The present disclosure relates to an organic compound, an electronic device and an electronic apparatus using the same. The organic compound of the present disclosure has a chemical structure comprising a fluoranthene and a nitrogen-containing heteroaromatic cyclic group. The organic compound can be used as a material for a functional layer of the electronic device, so as to increase the electron mobility of the electron transport material, thereby increasing the luminous efficiency and reducing the driving voltage of the electronic device.

18 Claims, 1 Drawing Sheet

(51) Int. Cl.
- *C07D 401/14* (2006.01)
- *C07D 403/04* (2006.01)
- *C07D 403/10* (2006.01)
- *C07D 405/04* (2006.01)
- *C07D 405/10* (2006.01)
- *C07D 409/10* (2006.01)
- *C07D 409/14* (2006.01)
- *H10K 50/16* (2023.01)
- *H10K 85/60* (2023.01)

(52) U.S. Cl.
CPC ......... *C07D 403/04* (2013.01); *C07D 403/10* (2013.01); *C07D 405/04* (2013.01); *C07D 405/10* (2013.01); *C07D 409/10* (2013.01); *C07D 409/14* (2013.01); *H10K 85/615* (2023.02); *H10K 85/622* (2023.02); *H10K 85/631* (2023.02); *H10K 85/649* (2023.02); *H10K 85/654* (2023.02); *H10K 85/6572* (2023.02); *H10K 85/6574* (2023.02); *H10K 85/6576* (2023.02); *C07B 2200/05* (2013.01); *H10K 50/16* (2023.02)

(56) References Cited

FOREIGN PATENT DOCUMENTS

| | | | | |
|---|---|---|---|---|
| CN | 107778260 | A * | 3/2018 | ............ C07C 13/66 |
| CN | 110386905 | A | 10/2019 | |
| JP | 2014096572 | A | 5/2014 | |
| JP | 6187080 | B2 | 8/2017 | |
| TW | 201923033 | A | 6/2019 | |
| WO | 2019117440 | A1 | 6/2019 | |
| WO | 2019182402 | A1 | 9/2019 | |

OTHER PUBLICATIONS

International Search Report from corresponding International Application No. PCT/CN2020/130914, mailed on Jan. 13, 2021, 4 pages.

* cited by examiner

ORGANIC COMPOUND, ELECTRONIC DEVICE AND ELECTRONIC APPARATUS USING SAME

CROSS REFERENCE TO RELATED APPLICATIONS

The present application claims the priority of Chinese patent application CN201911416944.6, filed on Dec. 31, 2019, and Chinese patent application CN202010833965.4, filed on Aug. 18, 2020, which are incorporated herein by reference in their entireties.

TECHNICAL FIELD

The present application relates to the technical field of organic luminescent material, and specifically provides an organic compound, an electronic device and an electronic apparatus using the same.

BACKGROUND

Organic electroluminescent device (OLED) is a kind of a self-luminescent device. The principle is that holes on the side of anode and electrons on the cathode will move towards to an luminescent layer and bind with each other to form excitons when electric field is applied on the the cathode and anode; and the excitons are in an excited state to release energy, thus emitting light to the outside during the process of releasing energy from the excited state to a ground state. Therefore, it is crucial to improve a recombination between electrons and holes in the OLED device.

To improve the luminance, efficiency and lifetime of the organic electroluminescent device, multilayer structures are used in the device usually. These multilayer structures include: a hole injection layer, a hole transport layer, an luminescent layer, an electron transport layer and the like. These multilayer structures have the abilities of improving the injection efficiency of carriers (holes and electrons) in each layer of interface, and balancing the transmission of carriers in each layer, thus the luminance and efficiency of the device are improved.

An electron injection/transport layer is disposed in an organic electroluminescent device to turn up the luminous efficiency, which is common technical means in the prior art. By means of this way, the luminance of the device is improved, but there are still problems of short luminescence lifetime and low luminous efficiency in the electron transport layer material at present.

SUMMARY

The objective of the present disclosure is to provide an organic electroluminescent material with excellent performance, capable of being used as an electron transport layer of an organic electroluminescent device.

To achieve the above objective, the present disclosure provides an organic compound; and the organic compound has a structure as shown in the following Formula (1):

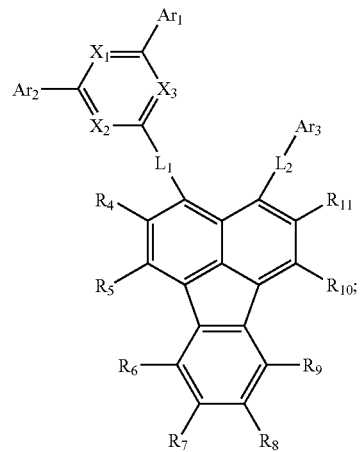

Formula (1)

wherein, $X_1$, $X_2$ and $X_3$ are the same or different; $X_1$ is $C(R^1)$ or N, $X_2$ is $C(R^2)$ or N, $X_3$ is $C(R^3)$ or N, and at least one of $X_1$, $X_2$ and $X_3$ is N;

$R^1$, $R^2$ and $R^3$ are the same as or different from each other, and are each independently selected from the group consisting of hydrogen, deuterium, fluorine, chlorine, alkyl with 1 to 12 carbon atoms, haloalkyl with 1 to 12 carbon atoms, alkoxy with 1 to 12 carbon atoms, cycloalkyl with 3 to 10 carbon atoms, aryl with 6 to 20 carbon atoms, and heteroaryl with 3 to 20 carbon atoms;

$L_1$ and $L_2$ are the same as or different from each other, and are each independently selected from the group consisting of single bond, substituted or unsubstituted arylene with 6 to 30 carbon atoms, and substituted or unsubstituted heteroarylene with 1 to 30 carbon atoms;

$Ar_1$ and $Ar_2$ are the same as or different from each other, and are each independently selected from the group consisting of substituted or unsubstituted alkyl with 1 to 12 carbon atoms, substituted or unsubstituted cycloalkyl with 3 to 10 carbon atoms, substituted or unsubstituted aralkyl with 7 to 30 carbon atoms, substituted or unsubstituted heteroaralkyl with 2 to 30 carbon atoms, substituted or unsubstituted aryl with 6 to 30 carbon atoms, and substituted or unsubstituted heteroaryl with 3 to 30 carbon atoms;

wherein, $Ar_3$ is selected from the group consisting of substituted aryl with 6 to 30 carbon atoms, and substituted heteroaryl with 3 to 30 carbon atoms;

$R_4$ to $R_{11}$ are the same or different, and are each independently selected from the group consisting of hydrogen, deuterium, halogen, cyano, substituted or unsubstituted alkyl with 1 to 10 carbon atoms, substituted or unsubstituted alkenyl with 2 to 10 carbon atoms, haloalkyl with 1 to 12 carbon atoms, alkoxy with 1 to 12 carbon atoms, alkylthio with 1 to 12 carbon atoms, alkylsilyl with 1 to 12 carbon atoms, substituted or unsubstituted cycloalkyl with 3 to 20 carbon atoms, substituted or unsubstituted heterocycloalkyl with 3 to 20 carbon atoms, alkylamino with 1 to 12 carbon atoms, aryl with 6 to 30 carbon atoms and heteroaryl with 1 to 30 carbon atoms;

substituents in $L_1$, $L_2$, $Ar_1$, $Ar_2$, $Ar_3$ and $R_4$ to $R_{11}$ are the same as or different from each other, and are each independently selected from the group consisting of deuterium; halogen; cyano; alkyl with 1 to 10 carbon atoms; haloalkyl with 1 to 10 carbon atoms; aryl with 6 to 20 carbon atoms, which can be optionally substituted by 0, 1, 2 or 3 substituents selected from deuterium, fluorine, chlorine, bromine, cyano, alkyl with 1 to 5 carbon atoms, aryl with 6 to 12 carbon atoms and heteroaryl with 5 to 12 carbon atoms; heteroaryl with 3 to 20 carbon atoms, which can be optionally substituted by 0, 1, 2 or 3 substituents selected from deuterium, fluorine, chlorine, bromine, cyano, alkyl with 1 to 5 carbon atoms, aryl with 6 to 12 carbon atoms and heteroaryl with 5 to 12 carbon atoms; aryloxy with 6 to 20 carbon atoms; arylthio with 6 to 20 carbon atoms; alkylsilyl with 3 to 12 carbon atoms; alkylamino with 1 to 10 carbon atoms and cycloalkyl with 3 to 10 carbon atoms; and at least one of substituents of the $Ar_3$ is cyano; optionally, any two adjacent substituents form a ring.

A second aspect of the present disclosure is to provide an electronic device, including an anode and a cathode disposed oppositely, and a functional layer disposed between the anode and the cathode; the functional layer includes an electron transport layer, and the electron transport layer includes the organic compound of the first aspect of the present disclosure.

A third aspect of the present disclosure is to provide an electronic apparatus containing the electronic device of the second aspect of the present disclosure.

According to the above technical solution, the chemical structure of the organic compound of the present disclosure includes fluoranthenyl, nitrogen-containing heteroaromatic cyclic group and a cyano-substituted aromatic group; and the organic compound can be used as a material for a functional layer of the electronic device. The advantages are as follows: (1) fluoranthene and such type of structures are a rigid large-planar structure and can improve the thermal stability of the material and thus beneficial to extending the lifetime of the device; (2) the aryl is linked with an strong-polarity electron-withdrawing cyano to deepen LUMO energy level, thereby further improving electronic mobility. Therefore, the cyano and electron-deficient nitrogen-containing heteroaryl are bound to greatly promote the electron attracting capacity, thereby obtaining an organic material with high electronic mobility capable of improving the electron transport efficiency; further, the organic compound can promote the luminous efficiency and lifetime of the device, and reduce the working voltage when the organic compound serves as an electron transport layer of an organic electroluminescent device.

Other features and advantages of the present disclosure will be partially described in the subsequent specific embodiments specifically.

BRIEF DESCRIPTION OF THE DRAWINGS

Drawings are used to provide a further understanding of the present disclosure, and constitute a portion of the description, and are intended for explaining the present disclosure together with the following specific embodiments, but are not construed as limiting the present disclosure. In the drawings.

Figure 1:
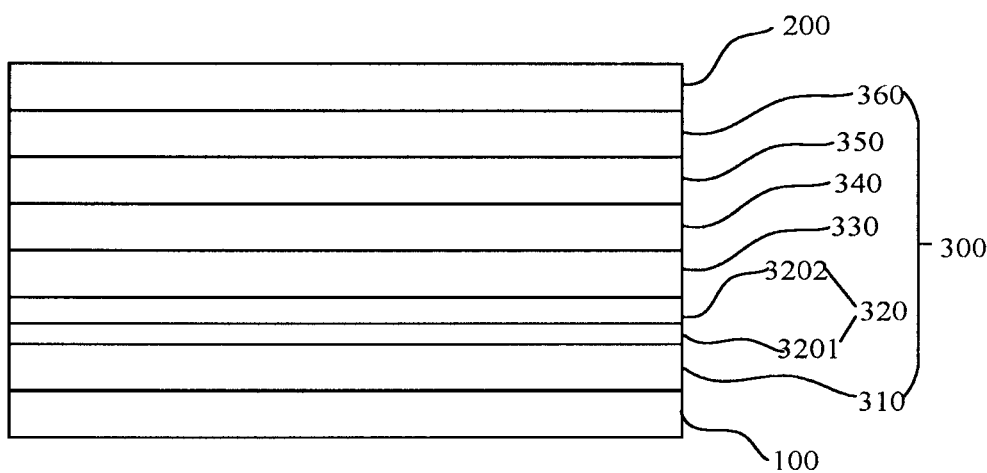
FIG. 1 is a structure diagram showing a specific embodiment (an organic electroluminescent device) of an electronic device of the present disclosure.

| Description of Reference Numerals in the Drawings |
|---|
| 100: anode |
| 200: cathode |
| 300: Functional layer |
| 310: Hole injection layer |
| 320: Hole transport layer |
| 3201: First hole transport layer |
| 3202: Second hole transport layer |
| 330: Electron blocking layer |
| 340: luminescent layer |
| 350: Electron transport layer |
| 360: Electron injection layer |
| 370: Photoelectric conversion layer |
| 400: Electronic apparatus |

DETAILED DESCRIPTION

Specific embodiments of the present disclosure will be described in detail with reference to the accompanying drawings below. It should be understood that the specific embodiments described herein are merely used to describe and explain the present disclosure, but are not construed as limiting the present disclosure.

Provided is an organic compound, and the organic compound has a structure as shown in the following Formula (1):

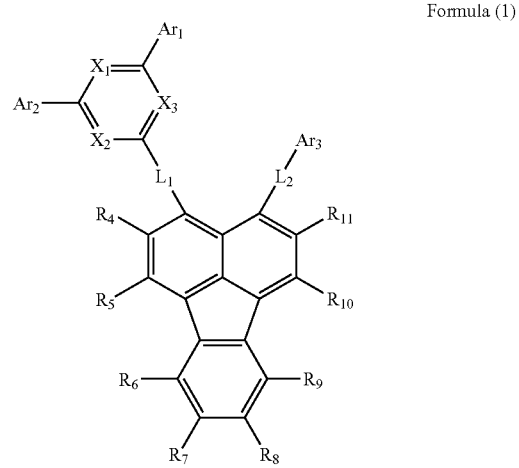

Formula (1)

wherein, $X_1$, $X_2$ and $X_3$ are the same or different; $X_1$ is $C(R^1)$ or N, $X_2$ is $C(R^2)$ or N, $X_3$ is $C(R^3)$ or N, and at least one of $X_1$, $X_2$ and $X_3$ is N;

$R^1$, $R^2$ and $R^3$ are the same as or different from each other, and are each independently selected from the group consisting of hydrogen, deuterium, fluorine, chlorine, alkyl with 1 to 12 carbon atoms, haloalkyl with 1 to 12 carbon atoms, alkoxy with 1 to 12 carbon atoms, cycloalkyl with 3 to 10 carbon atoms, aryl with 6 to 20 carbon atoms, and heteroaryl with 3 to 20 carbon atoms;

$L_1$ and $L_2$ are the same as or different from each other, and are each independently selected from the group consisting of single bond, substituted or unsubstituted arylene with 6 to 30 carbon atoms, and substituted or unsubstituted heteroarylene with 1 to 30 carbon atoms;

Ar$_1$ and Ar$_2$ are the same as or different from each other, and are each independently selected from the group consisting of substituted or unsubstituted alkyl with 1 to 12 carbon atoms, substituted or unsubstituted cycloalkyl with 3 to 10 carbon atoms, substituted or unsubstituted aralkyl with 7 to 30 carbon atoms, substituted or unsubstituted heteroaralkyl with 2 to 30 carbon atoms, substituted or unsubstituted aryl with 6 to 30 carbon atoms, and substituted or unsubstituted heteroaryl with 3 to 30 carbon atoms;

wherein, Ar$_3$ is selected from the group consisting of substituted aryl with 6 to 30 carbon atoms, and substituted heteroaryl with 3 to 30 carbon atoms;

R$_4$ to R$_{11}$ are the same or different, and are each independently selected from the group consisting of hydrogen, deuterium, halogen, cyano, substituted or unsubstituted alkyl with 1 to 10 carbon atoms, substituted or unsubstituted alkenyl with 2 to 10 carbon atoms, haloalkyl with 1 to 12 carbon atoms, alkoxy with 1 to 12 carbon atoms, alkylthio with 1 to 12 carbon atoms, alkylsilyl with 1 to 12 carbon atoms, substituted or unsubstituted cycloalkyl with 3 to 20 carbon atoms, substituted or unsubstituted heterocycloalkyl with 3 to 20 carbon atoms, alkylamino with 1 to 12 carbon atoms, aryl with 6 to 30 carbon atoms and heteroaryl with 1 to 30 carbon atoms;

substituents in L$_1$, L$_2$, Ar$_1$, Ar$_2$, Ar$_3$ and R$_4$ to Rn are the same as or different from each other, and are each independently selected from the group consisting of deuterium; halogen; cyano; alkyl with 1 to 10 carbon atoms; haloalkyl with 1 to 10 carbon atoms; aryl with 6 to 20 carbon atoms, which can be optionally substituted by 0, 1, 2 or 3 substituents selected from deuterium, fluorine, chlorine, bromine, cyano, alkyl with 1 to 5 carbon atoms, aryl with 6 to 12 carbon atoms and heteroaryl with 5 to 12 carbon atoms; heteroaryl with 3 to 20 carbon atoms, which can be optionally substituted by 0, 1, 2 or 3 substituents selected from deuterium, fluorine, chlorine, bromine, cyano, alkyl with 1 to 5 carbon atoms, aryl with 6 to 12 carbon atoms and heteroaryl with 5 to 12 carbon atoms; aryloxy with 6 to 20 carbon atoms; arylthio with 6 to 20 carbon atoms; alkylsilyl with 3 to 12 carbon atoms; alkylamino with 1 to 10 carbon atoms and cycloalkyl with 3 to 10 carbon atoms; and at least one of substituents of the Ar$_3$ is cyano; optionally, any two adjacent substituents form a ring.

The chemical structure of the organic compound in the present disclosure includes fluoranthenyl, nitrogen-containing heteroaromatic cyclic group and cyano-substituted aryl; and the organic compound can be used as a material for a functional layer of the electronic device. The advantages are as follows: (1) fluoranthenyl and such type of structures are large-planar rigid structures and can improve the thermal stability of the material and beneficial to extending the lifetime of the device; (2) the aryl is linked with strong-polarity electron-withdrawing cyano to deepen LUMO energy level, thereby further improving electronic mobility. Therefore, the cyano and electron-deficient nitrogen-containing heteroaryl are bound to greatly promote the electron attracting capacity, thereby obtaining an organic material with high electronic mobility capable of improving the electron transport efficiency; further, the organic compound can promote the luminous efficiency and lifetime of the device when the organic compound serves as an electron transport layer of an organic electroluminescent device.

In the present disclosure, the carbon number of L$_1$, L$_2$, Ar$_1$, Ar$_2$, Ar$_3$, R$^{s1}$, R$^{s2}$ and R$^{s3}$ refers to the number of all the carbon atoms. For example, if L$_1$ is selected from arylene with 10 carbon atoms, and the total carbon number on the arylene and substituents thereof is 10. For example, if Ar$_1$ is 9,9-dimethylfluorenyl, the Ar$_1$ is substituted fluorenyl with 15 carbon atoms, and the number of ring-forming carbon atoms on the Ar$_1$ is 13.

In this description, the two expressions of "substituted or unsubstituted aryl with 6 to 30 carbon atoms" and "aryl with 6 to 30 carbon atoms that is substituted or unsubstituted" have the same meaning, namely, the total carbon number on the aryl and substituents thereof is 6 to 30. Similarly, in the description, the two expressions of "substituted or unsubstituted heteroaryl with 3 to 30 carbon atoms" and "heteroaryl with 3 to 30 carbon atoms that is substituted or unsubstituted" have the same meaning, namely, the total carbon number on the heteroaryl and substituents thereof is 3 to 30.

The term "optional" or "optionally" means that the subsequently described incident or environment may, but need not occur, which includes the occasions where the incident or environment occurs or does not occur. For example, "a heterocyclic group substituted by alkyl optionally" means that the alkyl may be present, but not be present inevitably, which both includes the situation that the heterocyclic group is substituted by alkyl and the situation that the heterocyclic group is not substituted by alkyl. The expression "optionally, R$^{v2}$ and R$^{v3}$ linked on a same atom are linked with each other to form a saturated or unsaturated ring", means that R$^{v2}$ and R$^{v3}$ linked on a same atom may form a ring, but do not form a ring inevitably; the solution both includes the situation that R$^{v2}$ and R$^{v3}$ linked to form a ring, and the situation that the R$^{v2}$ and R$^{v3}$ are present independently.

In this present disclosure, the three expressions used herein, "each . . . is independently", " . . . is respectively and independently"and" . . . is independently selected from" can be exchanged with each other, and should be understood in broad sense, which may mean that in different groups, specific items expressed by a same symbol are not influenced with each other, and may further refer that in a same group, specific options expressed by a same symbol are not influenced with each other.

For example, in the description

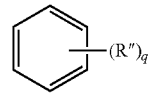

Formula Q-1

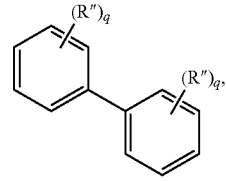

Formula Q-2 wherein, each q is independently 0, 1, 2, or 3, and each R" is independently selected from hydrogen, fluorine and chlorine", the meaning is as follows: Formula Q-1 indicates that the benzene ring has q substituents R", and each R" may be the same or different, and options in each R" are not influenced with each other; Formula Q-2 indicates that each benzene ring on biphenyl has q substituents R", and the number q of the R" substituents of two benzene rings may be the same or different, and each R" may be the same or different, and options in each R" are not influenced with each other.

In this present disclosure, when there is no specific definition provided additionally, "hetero" refers that one functional group includes at least one of B, N, O, S, Se, Si or P and other heteroatoms, and the rest are carbon and hydrogen.

In this present disclosure, such a term "substituted or unsubstituted" refers that the functional group described behind the term may have or have no a substituent. For example, "substituted or unsubstituted alkyl" refers to alkyl having a substituent or unsubstituted alkyl. The "substituted" refers to substitution by a substituent selected from the following groups: deuterium, halogen, heteroaryl, aryl, trialkylsilyl, alkyl, haloalkyl, alkenyl, cycloalkyl, heterocycloalkyl, cycloalkenyl, heterocycloalkenyl, alkoxy, alkylthio, aryloxy, arylthio, triarylsilyl, alkylboryl, alkylphosphinooxy, and the like.

In the present disclosure, "alkyl" may include linear alkyl or branched alkyl. Alkyl may have 1 to 12 carbon atoms; in the present disclosure, a range of value, such as, "1 to 12" refers to each integer in the given range; for example, "1 to 12 carbon atoms" refer to alkyl which may contain 1 carbon atom, 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, or 12 carbon atoms. Alkyl may further be medium-sized alkyl having 1 to 10 carbon atoms. Alkyl may further be lower alkyl having 1 to 6 carbon atoms. In some further embodiments, the alkyl contains 1 to 4 carbon atoms; and in some further embodiments, the alkyl contains 1 to 3 carbon atoms. The alkyl may be optionally substituted by one or more substituents described in the present disclosure. Examples of the alkyl contain, but not limited to, methyl (Me, —CH$_3$), ethyl (Et, —CH$_2$CH$_3$), n-propyl (n-Pr, —CH$_2$CH$_2$CH$_3$), isopropyl (i-Pr, —CH(CH$_3$)$_2$), n-butyl (n-Bu, —CH$_2$CH$_2$CH$_2$CH$_3$), isobutyl (i-Bu, —CH$_2$CH(CH$_3$)$_2$), sec-butyl (s-Bu, —CH(CH$_3$)CH$_2$CH$_3$), tert-butyl (t-Bu, —C(CH$_3$)$_3$), and the like. Moreover, alkyl may be substituted or unsubstituted.

In this present disclosure, "alkenyl" refers to alkyl including one or more double bonds in a linear or branched hydrocarbon chain. Alkenyl may be substituted or unsubstituted. For example, alkenyl may be ethenyl, butadiene, or 1,3,5-hexatriene.

In this present disclosure, cycloalkyl refers to a cyclic saturated hydrocarbon, containing monocyclic and polycyclic structures. Cycloalkyl may have 3 to 20 carbon atoms; such as, a range of value "3 to 20" refers to each integer in the given range; for example, "3 to 20 carbon atoms" refer to cycloalkyl which may contain 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms or 20 carbon atoms. Cycloalkyl may further be a small ring, common ring or large ring having 3 to 20 carbon atoms. Cycloalkyl may be further divided into a monocyclic ring-only one ring, dual rings-two rings or multiple rings-three or above rings. Cycloalkyl may be further a spiro that one carbon atom is shared by two rings, a fused ring that two carbon atoms are shared by two rings, and a bridge ring that more than two carbon atoms are shared by two rings. Furthermore, cycloalkyl may be substituted or unsubstituted. In some embodiments, cycloalkyl is 5- to 10-membered cycloalkyl; in some other embodiments, cycloalkyl is 5- to 8-membered cycloalkyl; for example, examples of cycloalkyl may be, but not limited to, five-membered cycloalkyl, namely, cyclopentyl, six-membered cycloalkyl, namely, cyclohexyl, ten-membered polycycloalkyl such as adamantyl and the like.

In this present disclosure, aryl refers to an optional functional group derived from an aromatic hydrocarbon ring or a substituent. Aryl may be monocyclic aryl or polycyclic aryl, in other words, aryl may be monocyclic aryl, fused cyclic aryl, two or more monocyclic aryls conjugated via carbon-carbon bond, monocyclic aryl and fused cyclic aryl conjugated via carbon-carbon bond, and two or more fused cyclic aryls conjugated via carbon-carbon bond. That is, two or more aryl conjugated via carbon-carbon bond may be regarded as aryl of the present disclosure. Aryl is free of B, N, O, S, Se, Si, or P, or other hetero atoms. For example, in this present disclosure, phenyl, biphenyl, terphenyl and the like are aryl. Examples of aryl may include, but not limited to, phenyl, naphthyl, fluorenyl, anthracyl, phenanthryl, biphenyl, terphenyl, quarterphenyl, quinquephenyl, sexiphenyl, benzo[9,10]phenanthryl, pyrenyl, perylene, benzofluoranthenyl, chrysenyl, 9,9-dimethylfluorenyl, 9,9-diphenylfluorenyl, spirobifluorenyl, indenyl, and the like. "Aryl" in the present disclosure may contain 6 to 30 carbon atoms; in some embodiments, the carbon number in aryl may be 6 to 25; in some other embodiments, the carbon number in aryl may be 6 to 18; and in some other embodiments, the carbon number in aryl may be 6 to 13. For example, the carbon number may be 6, 10, 12, 13, 15, 18, 20, 25 or 30, of course, the carbon number may be in other quantity, but will be not enumerated one by one herein.

In this present disclosure, the substituted aryl refers to that one or more hydrogen atoms in aryl are substituted by other groups. For example, at least one hydrogen atom is substituted by a deuterium atom, F, Cl, I, CN, hydroxy, amino, branched alkyl, linear alkyl, haloalkyl, cycloalkyl, alkoxy, alkylamino, alkylthio, aryl, heteroaryl, alkylsilyl, arylsilyl or other groups. For example, specific examples of heteroaryl-substituted aryl include, but not limited to, dibenzofuryl-substituted phenyl, dibenzothiophenyl-substituted phenyl, carbazolyl-substituted phenyl, or pyridinyl-substituted phenyl, and the like. It should be understood that the carbon number of the substituted aryl refers to the total carbon number of the aryl and substituents thereof. For example, the substituted aryl with 18 carbon atoms refers that the total carbon number of the aryl and substituents thereof is 18. For example, 9,9-dimethylfluorenyl is a substituted aryl with 15 carbon atoms.

In this present disclosure, fluorenyl as aryl may be substituted, and the two substituents may be combined with each other to form a spiro structure; specific examples include, but not limited to the following structure:

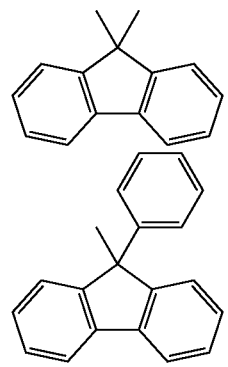

-continued

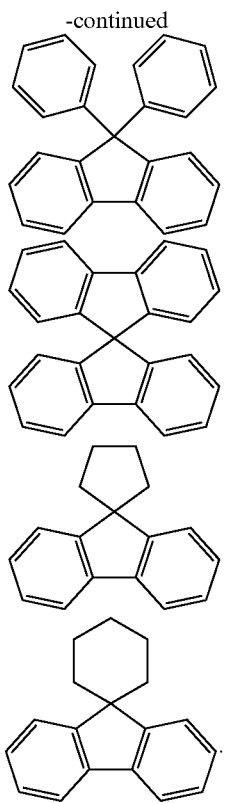

In this present disclosure, heteroaryl may be heteroaryl including at least one of B, O, N, P, Si, Se and S as a hetero atom. Heteroaryl may be monocyclic heteroaryl or polycyclic heteroaryl; in other words, heteroaryl may be a single aromatic ring system, or a multi-aromatic ring system conjugated via carbon-carbon bond; any aromatic ring system is an aromatic monocyclic ring or an aromatic fused ring, and any aromatic ring system contains the hetero atom. For example, heteroaryl may include, but not limited to, thienyl, furyl, pyrryl, imidazolyl, thiazolyl, oxazolyl, oxadiazol, triazolyl, pyridyl, dipyridyl, pyrimidyl, triazinyl, acridinyl, pyridazinyl, pyrazinyl, quinolyl, quinazolinyl, quinoxalinyl, phenoxazinyl, phthalazinyl, pyridopyrimidyl, pyridopyrazinyl, pyrazinopyrazinyl, isoquinolyl, indolyl, carbazolyl, N-arylcarbazolyl, N-heteroarylcarbazolyl, N-alkylcarbazolyl, benzoxazolyl, benzimidazolyl, benzothiazolyl, benzocarbazolyl, benzothiophenyl, dibenzothienyl, thienothiophenyl, benzofuryl, phenanthrolinyl, isoxazolyl, thiadiazolyl, benzothiazolyl, phenothiazinyl, dibenzosilyl, dibenzofuryl, phenyl-substituted dibenzofuryl, dibenzofuryl-substituted phenyl, and the like. Wherein, thienyl, furyl, phenanthrolinyl, and the like are heteroaryl of a single aromatic ring system; N-arylcarbazolyl, N-heteroarylcarbazolyl, phenyl-substituted dibenzofuryl and the like are heteroaryl of multiple aromatic ring systems conjugated via carbon-carbon bond. The "heteroaryl" in the present disclosure may contain 1 to 30 carbon atoms; in some embodiments, heteroaryl is heteroaryl with 3 to 12 carbon atoms; in some other embodiments, heteroaryl is heteroaryl with 3 to 15 carbon atoms; in some other embodiments, heteroaryl is heteroaryl with 5 to 12 carbon atoms. For example, the carbon atom may be 1, 3, 4, 5, 6, 7, 8, 9, 10, 11, 12, 13, 14, 15, 16, 17, 18, 20, 21, 22, 23, 24, 25, 26, 27, 28, 29 or 30; of course, the carbon atom may be further other values, but will be not enumerated one by one here.

In this present disclosure, substituted heteroaryl refers that one or more hydrogen atoms in the heteroaryl are substituted by other groups, for example, at least one hydrogen atom is substituted by a deuterium atom, F, Cl, I, CN, amino, alkyl, haloalkyl, cycloalkyl, aryl, heteroaryl, aryloxy, arylthio, alkylsilyl, alkylamino, arylamino, boronyl, phosphoryl or other groups. For example, specific examples of aryl-substituted heteroaryl include, but not limited to, phenyl-substituted dibenzofuryl, phenyl-substituted dibenzothienyl, phenyl-substituted carbazolyl, and phenyl-substituted pyridyl, and the like.

In this present disclosure, the explanation to aryl may be applied to arylene; the explanation to heteroaryl may be similarly applied to heteroarylene; the explanation to alkyl may be applied to alkylene, and the explanation to cycloalkyl may be applied to cycloalkylene.

In this present disclosure, "aryloxy" denotes that aryl is linked with the rest part of a molecule via oxygen atoms; and the aryl has the meaning of the present disclosure. In this present disclosure, "arylthio" denotes that aryl is linked with the rest part of a molecule via sulphur atoms; wherein the aryl has the meaning of the present disclosure.

In this present disclosure, the cyclic system formed by n atoms is, namely, an n-membered ring. For example, phenyl is a 6-membered aryl. 6- to 10-membered aromatic ring may refer to a benzene ring, an indene ring, a naphthalene and the like.

The "ring" in this present disclosure contains a saturated ring and unsaturated ring; the saturated ring is namely, cycloalkyl and heterocycloalkyl; the unsaturated ring is namely, cycloalkenyl, heterocycloalkenyl, aryl and heteroaryl.

In this present disclosure, alkylsilyl refers to

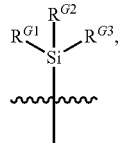

wherein, $R^{G1}$, $R^{G2}$ and $R^{G3}$ are independently alkyl; specific examples of alkylsilyl include, but not limited to, trimethylsilyl, triethylsilyl, tert-butyldimethylsilyl, and propyldimethylsilyl.

In this present disclosure, "alkoxy" denotes that alkyl is linked with the rest part of a molecule via oxygen atoms; wherein the alkyl has the meaning of the present disclosure. Unless specified otherwise, the alkoxy contains 1 to 12 carbon atoms. Examples of the alkoxy include, but not limited to, methoxy (MeO, —OCH₃), ethyoxyl (EtO, —OCH₂CH₃), 1-propoxy (n-PrO, n-propoxy, —OCH₂CH₂CH₃), 2-propoxy (i-PrO, i-propoxy, —OCH(CH₃)₂), 1-butoxy(n-BuO, n-butoxy, —OCH₂CH₂CH₂CH₃), 2-methyl-1-propoxy (i-BuO, i-butoxy, —OCH₂CH(CH₃)₂), 2-butoxy (s-BuO, s-butoxy, —OCH(CH₃)CH₂CH₃), —OCH(CH₃)CH₂CH₃), 2-methyl-2-propoxy(t-BuO, t-butoxy, —OC(CH₃)₃), and the like.

In this present disclosure, "alkylamino" or "alkyl amino" includes "N-alkylamino" and "N,N-dialkylamino", wherein, the amino is independently substituted by one or two alkyl, wherein the alkyl has the meaning of the present disclosure. Suitable alkylamino may be monoalkyl amino or dialkyl amino; and the examples include, but not limited to, N-methylamino, N-ethylamino, N,N-dimethylamino, N,N- diethylamino, and the like. The alkylamino is optionally substituted by one or more substituents described in the present disclosure.

The non-localized bond in the present disclosure refers to a single bond

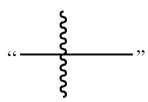

stretching out of the cyclic system, indicating that one end of the binding bond may be linked to any position in the cyclic system penetrated by the bond, and another end is linked with the rest part of a compound molecule.

For example, as shown in the Formula (f) below, the naphthyl denoted by the Formula (f) is linked with other positions of the molecule via two non-localized bonds penetrating dual rings, and the meaning includes any possible linking mode as shown in formulae (f-1) to (f-10).

Formula (f)

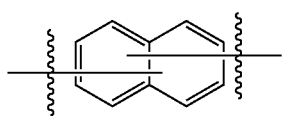

Formula (f-1)

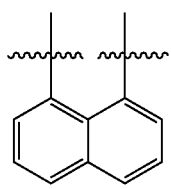

Formula (f-2)

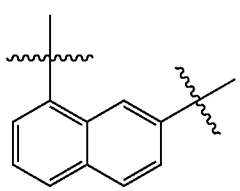

Formula (f-3)

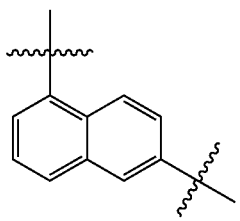

Formula (f-4)

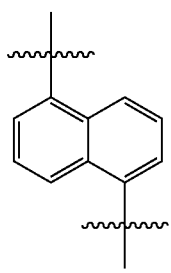

Formula (f-5)

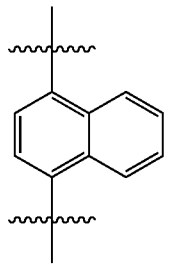

Formula (f-6)

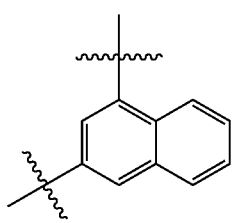

Formula (f-7)

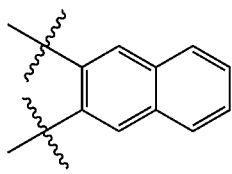

Formula (f-8)

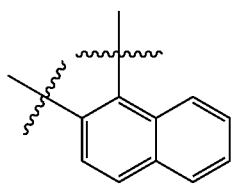

Formula (f-9)

Formula (f-10)

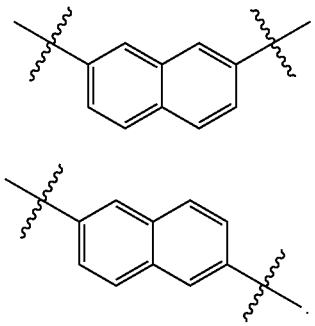

For another example, as shown in the Formula (X') below, the phenanthryl denoted by the Formula (X') is linked with other positions of the molecule via a non-localized bond stretching from the middle part of one side of a benzene ring, and the meaning includes any possible linking mode as shown in formulae (X'-1) to (X'-4).

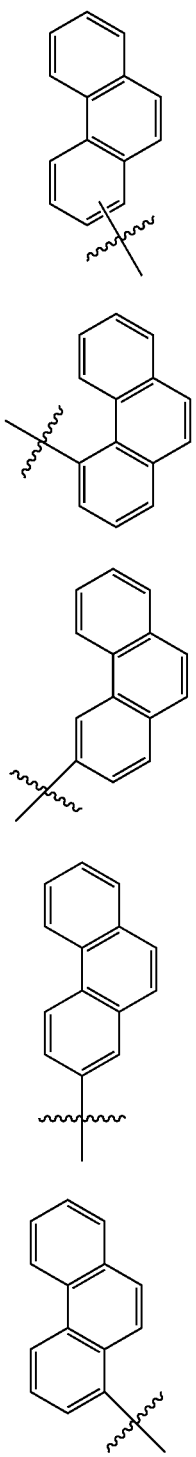

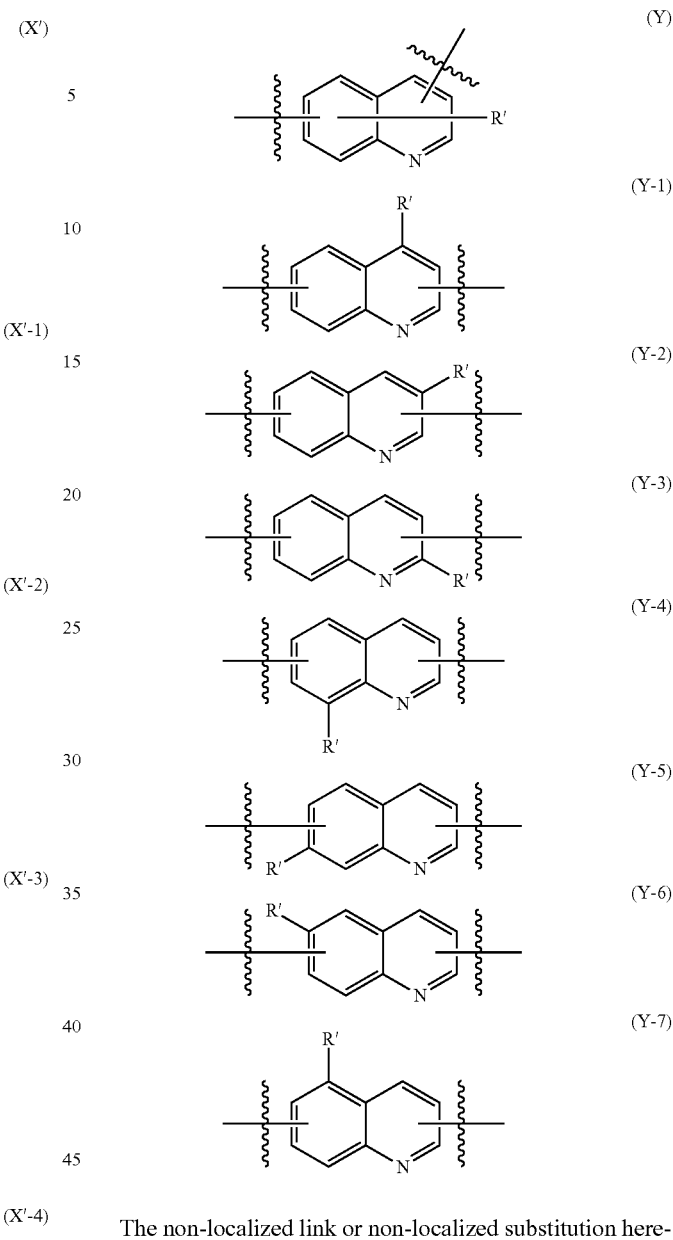

The non-localized substituent in the present disclosure refers to a substituent linked via a single bond stretching out of a cyclic system, indicating that the substituent may be linked to any possible position in the cyclic system. For example, as shown in the Formula (Y) below, the substituent R denoted by the Formula (Y) is linked with a quinoline ring via a non-localized bond, and the meaning includes any possible linking mode as shown in formulae (Y-1) to (Y-7).

The non-localized link or non-localized substitution hereafter has the same meaning, which thus will be not described any more.

In one embodiment of the present disclosure, at least one of $X_1$, $X_2$ and $X_3$ is N. Specifically, $X_1$ may be N, $X_2$ may be $C(R^2)$, $X_3$ may be $C(R^3)$; further, $X_2$ may be N, $X_1$ may be $C(R^1)$, $X_3$ may be $C(R^3)$, and further $X_3$ may be N, $X_1$ may be $C(R^1)$, and $X_2$ may be $C(R^2)$.

In one embodiment of the present disclosure, substituents in $L_1$, $L_2$, $Ar_1$, $Ar_2$, $Ar_3$ and $R_4$ to $R_{11}$ are the same as or different from each other, and are each independently selected from the group consisting of deuterium, halogen, cyano, alkyl with 1 to 10 carbon atoms, haloalkyl with 1 to 10 carbon atoms, aryl with 6 to 20 carbon atoms, heteroaryl with 3 to 20 carbon atoms, aryloxy with 6 to 20 carbon atoms, arylthio with 6 to 20 carbon atoms, alkylsilyl with 3 to 12 carbon atoms, alkylamino with 1 to 10 carbon atoms and cycloalkyl with 3 to 10 carbon atoms; and at least one of substituents in the $Ar_3$ is cyano.

In one embodiment of the present disclosure, $Ar_1$, $Ar_2$, and $Ar_3$ are the same as or different from each other, and are each independently selected from the group consisting of substituted or unsubstituted aryl with 6 to 25 carbon atoms, and substituted or unsubstituted heteroaryl with 3 to 18 carbon atoms; substituents in $Ar_1$, $Ar_2$ and $Ar_3$ are the same as or different from each other, and are each independently selected from the group consisting of deuterium, fluorine, chlorine, bromine, cyano, alkyl with 1 to 10 carbon atoms, haloalkyl with 1 to 10 carbon atoms, alkoxy with 1 to 10 carbon atoms, alkylthio with 1 to 10 carbon atoms, aryl with 6 to 20 carbon atoms, heteroaryl with 3 to 20 carbon atoms, aryloxy with 6 to 20 carbon atoms, arylthio with 6 to 20 carbon atoms, alkylsilyl with 3 to 12 carbon atoms, alkylamino with 1 to 10 carbon atoms and cycloalkyl with 3 to 10 carbon atoms; and the $Ar_3$ is substituted by at least one cyano. In further embodiments, $Ar_1$, $Ar_2$ and $Ar_3$ are the same as or different from each other, and are each independently selected from substituted or unsubstituted aryl with 6 to 20 carbon atoms, and substituted or unsubstituted heteroaryl with 3 to 15 carbon atoms.

In some more detailed examples, substituents in the $Ar_1$ to $Ar_3$ are the same or different, and are each independently selected from deuterium, fluorine, cyano, methyl, ethyl, isopropyl, n-propyl, tert-butyl, trifluoromethyl, trimethylsilyl, propoxy, ethyoxyl, isopropoxy, methylthio, cyclopentyl, cyclohexyl, phenyl, cyano-substituted phenyl, fluoro-substituted phenyl, biphenyl, terphenyl, naphthyl, fluorenyl, 9,9-dimethylfluorenyl, pyridyl, quinolyl, isoquinolyl, pyrimidyl, carbazolyl, dibenzofuryl, dibenzothienyl; and the $Ar_3$ is substituted by at least one cyano. Further, in some embodiments of the present disclosure, $Ar_1$, $Ar_2$ and $Ar_3$ are the same as or different from each other, and are each independently selected from the group consisting of the following group

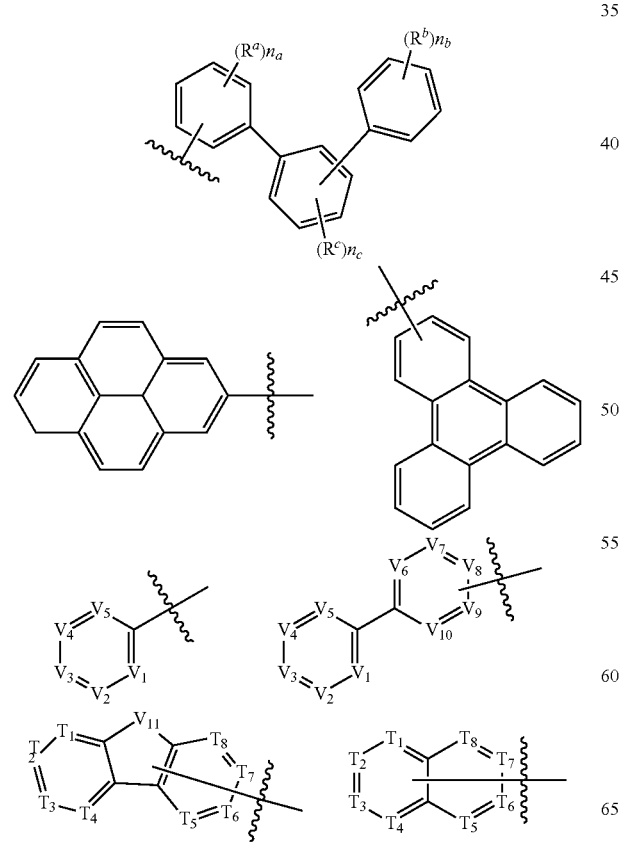

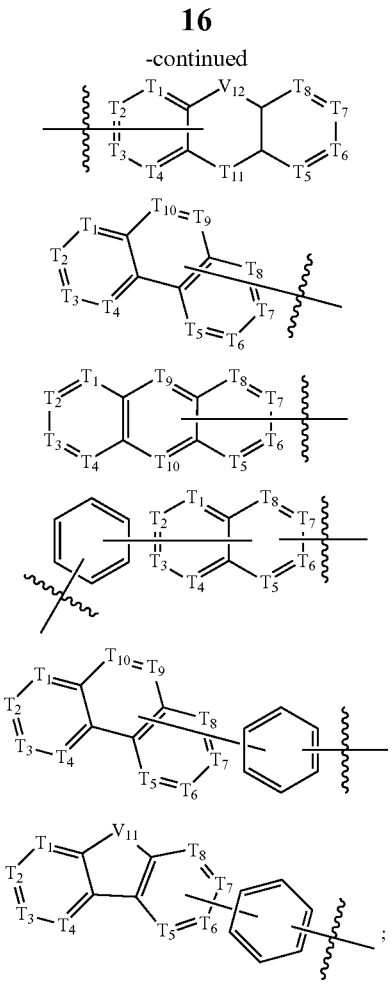

wherein, $n_a$ and $n_c$ are each independently selected from 1, 2, 3 or 4; when a group contains two or more $R^a$, each of $R^a$ is the same as or different from each other; when a group contains two or more $R^c$, each of $R^c$ is the same as or different from each other; $n_b$ is selected from 1, 2, 3, 4 or 5; when a group contains two or more $R^b$, each of $R^b$ is the same as or different from each other;

$V_1$ to $V_{10}$ are each independently selected from $C(R^v)$ and N, when a group contains two or more $R^v$, any two of $R^v$ are the same or different;

$V_{11}$, $V_{12}$ and $V_{13}$ are each independently selected from the group consisting of O, S, Se, $N(R^{v1})$, $C(R^{v2}R^{v3})$ and $Si(R^{v2}R^{v3})$;

$T_{11}$ is O, S or $N(R^{v1})$;

$T_1$ to $T_{10}$ are each independently selected from $C(R)$ and N, when a group contains two or more $R^t$, any two of $R^t$ are the same as or different from each other;

$R^a$, $R^b$, $R^c$, $R^t$, $R^v$, $R^{v2}$ and $R^{v3}$ are independently hydrogen, deuterium, fluorine, chlorine, bromine, cyano, alkyl with 1 to 6 carbon atoms, haloalkyl with 1 to 6 carbon atoms, alkoxy with 1 to 6 carbon atoms, alkylsilyl with 3 to 12 carbon atoms, aryl with 6 to 12 carbon atoms, heteroaryl with 3 to 12 carbon atoms, and cycloalkyl with 3 to 10 carbon atoms; alternatively, optionally, $R^{v2}$ and $R^{v3}$ linked on a same atom are linked with each other to form a saturated or unsaturated 5- to 13-membered ring; for example, in

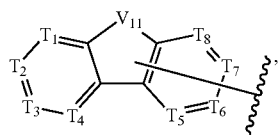

when $T_1$ to $T_8$ are CH, and V is $C(R^{v2}R^{v3})$, $R^{v2}$ and $R^{v3}$ are linked with each other to form a ring, which means that $R^{v2}$ and $R^{v3}$ may be linked with each other to form a ring, and may be further present independently;

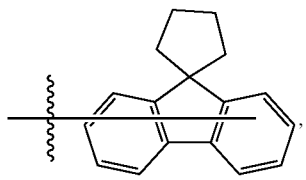

when $R^{v2}$ and $R^{v3}$ form a ring, the ring may be a 5-membered ring, for example,

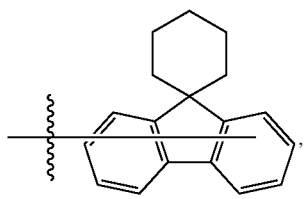

6-membered ring, for example,

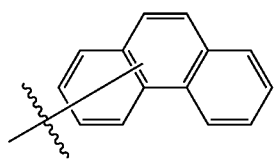

and further 13-membered ring, for example, Of course, the atom number on the ring formed by mutually linking $R^{v2}$ with $R^{v3}$ may be further other values, but will be not enumerated one by one here.

Each of $R^{v1}$ is selected from the group consisting of hydrogen, deuterium, alkyl with 1 to 6 carbon atoms, haloalkyl with 1 to 6 carbon atoms, aryl with 6 to 12 carbon atoms, heteroaryl with 3 to 12 carbon atoms and cycloalkyl with 3 to 10 carbon atoms, and when the same group has two $R^{v1}$, each of $R^{v1}$ is the same or different.

Further, in some embodiments of the present disclosure, $Ar_1$ and $Ar_2$ are the same or different, and are each independently selected from a substituted or unsubstituted group $Y_1$; and the group $Y_1$ is selected from the following groups:

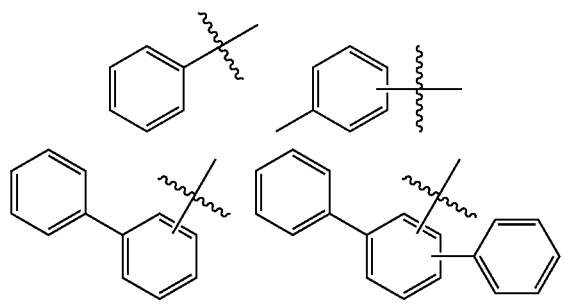

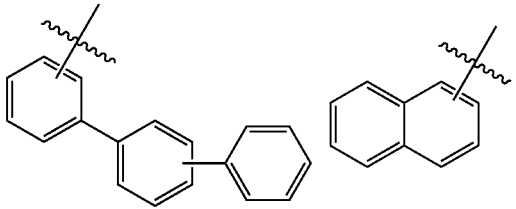

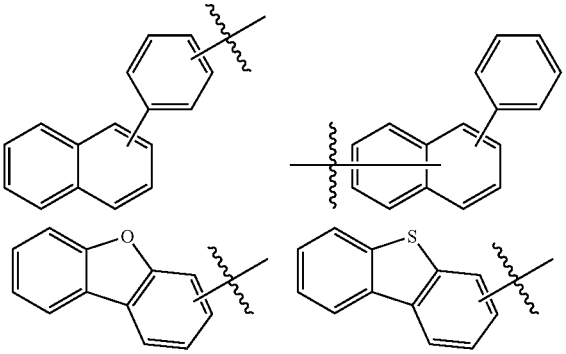

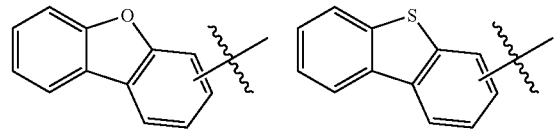

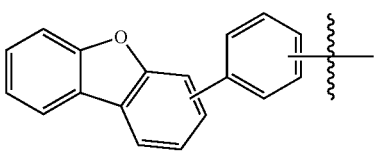

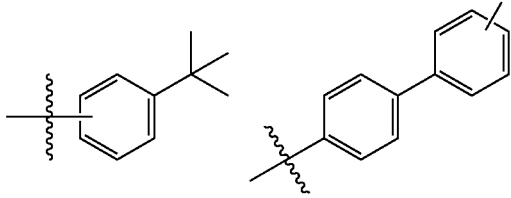

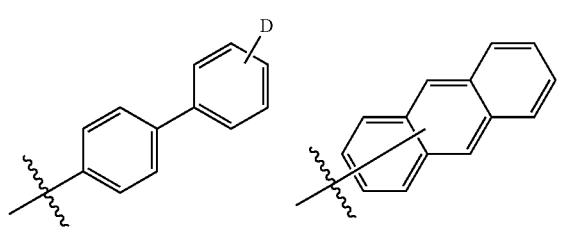

-continued
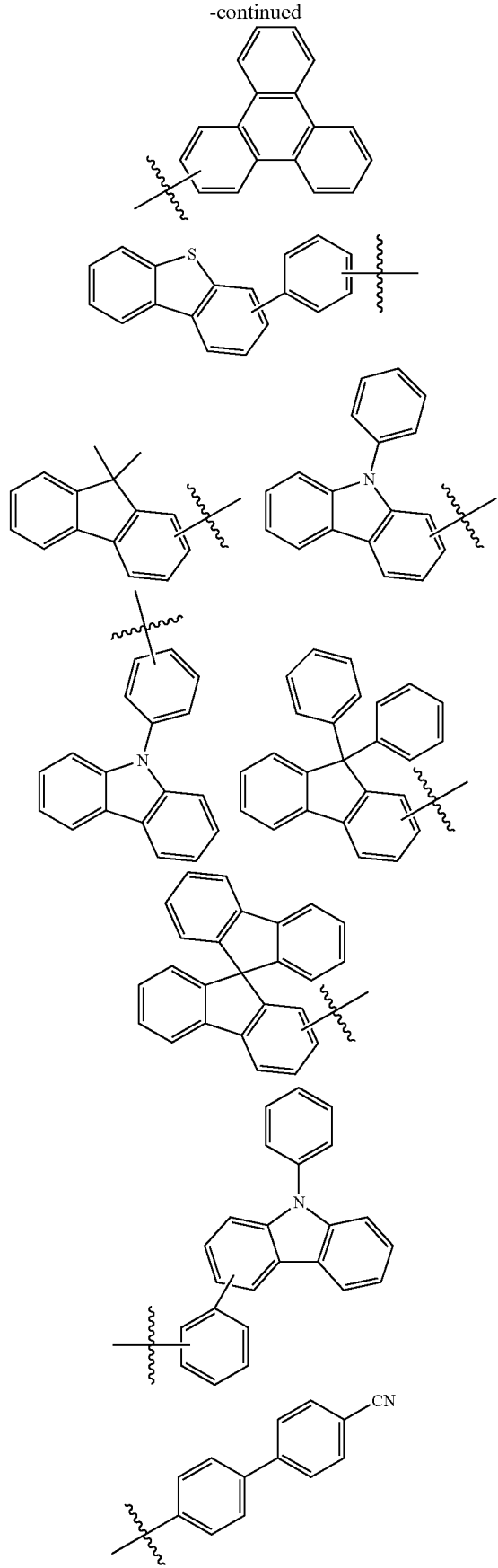
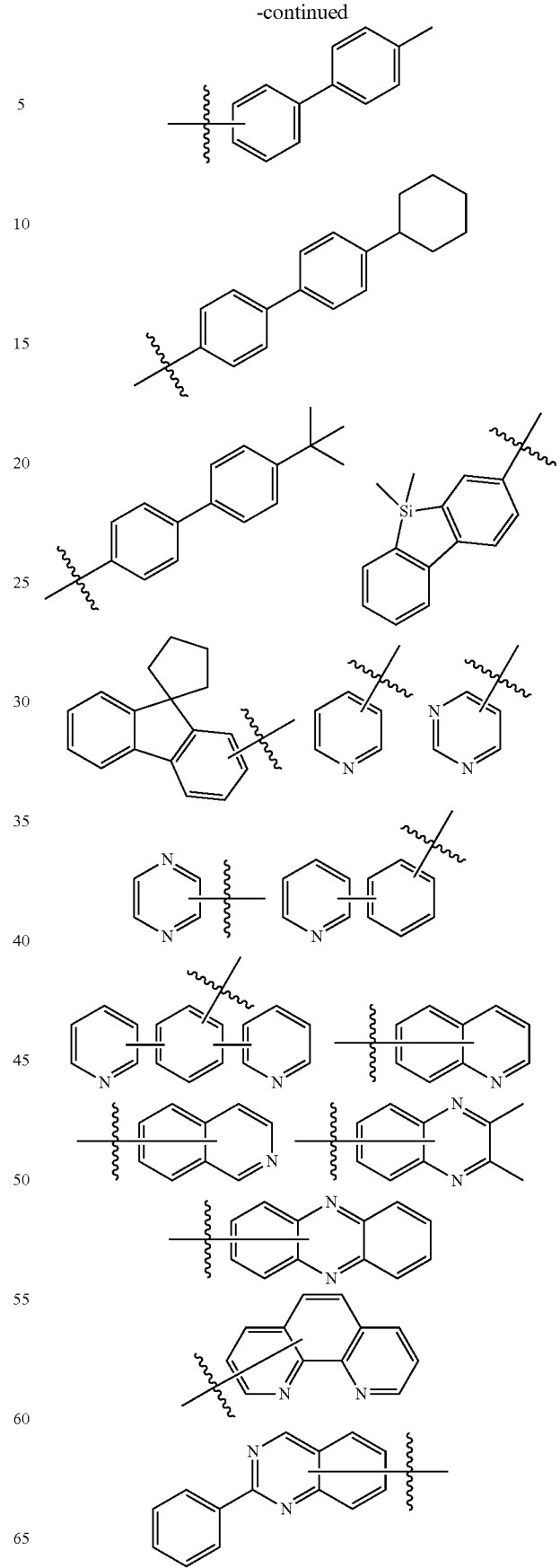

-continued

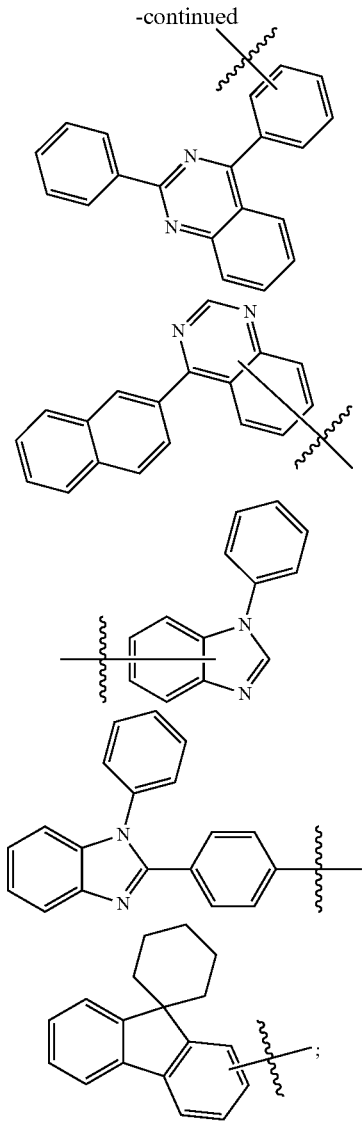

when the group $Y_1$ is substituted, substituents of the $Y_1$ are selected from deuterium, fluorine, chlorine, bromine, cyano, alkyl with 1 to 4 carbon atoms, alkoxy with 1 to 4 carbon atoms, haloalkyl with 1 to 4 carbon atoms, alkylsilyl with 3 to 9 carbon atoms, cycloalkyl with 3 to 10 carbon atoms, aryl with 6 to 12 carbon atoms, and heteroaryl with 3 to 12 carbon atoms; when the $Y_1$ has a plurality of substituents, the plurality of the substituents are the same or different.

Further, $Ar_1$ and $Ar_2$ may be each independently selected from substituted or unsubstituted phenyl, substituted or unsubstituted naphthyl, substituted or unsubstituted biphenyl, substituted or unsubstituted terphenyl, substituted or unsubstituted phenanthryl, substituted or unsubstituted quinolyl, substituted or unsubstituted isoquinolyl, substituted or unsubstituted pyridyl, substituted or unsubstituted carbazolyl, substituted or unsubstituted dibenzofuryl, substituted or unsubstituted dibenzothienyl, substituted or unsubstituted dibenzofuryl-phenyl, substituted or unsubstituted dibenzothienyl-phenyl, substituted or unsubstituted fluorenyl, or selected from the groups that formed by linking two or three of the above groups via single bonds.

Further, in some more specific embodiments of the present disclosure, $Ar_1$, and $Ar_2$ are the same or different, and are each independently selected from the group consisting of the following groups:

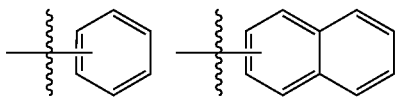
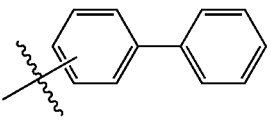
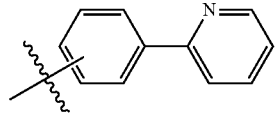
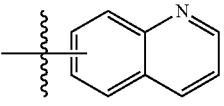
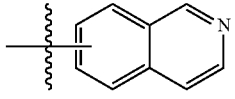
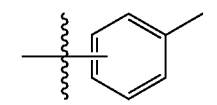
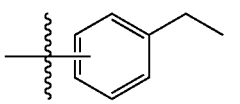
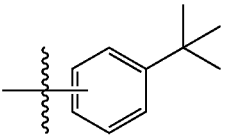
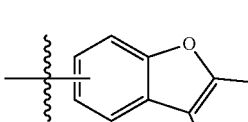
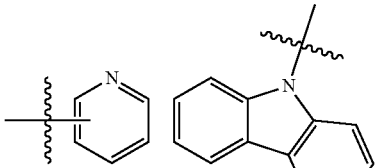
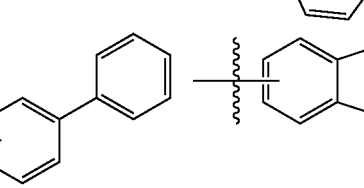
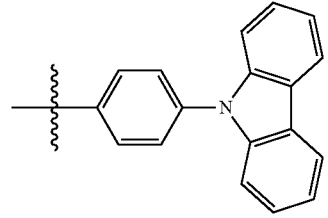
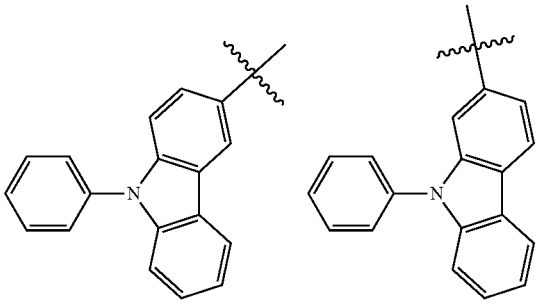

23
-continued

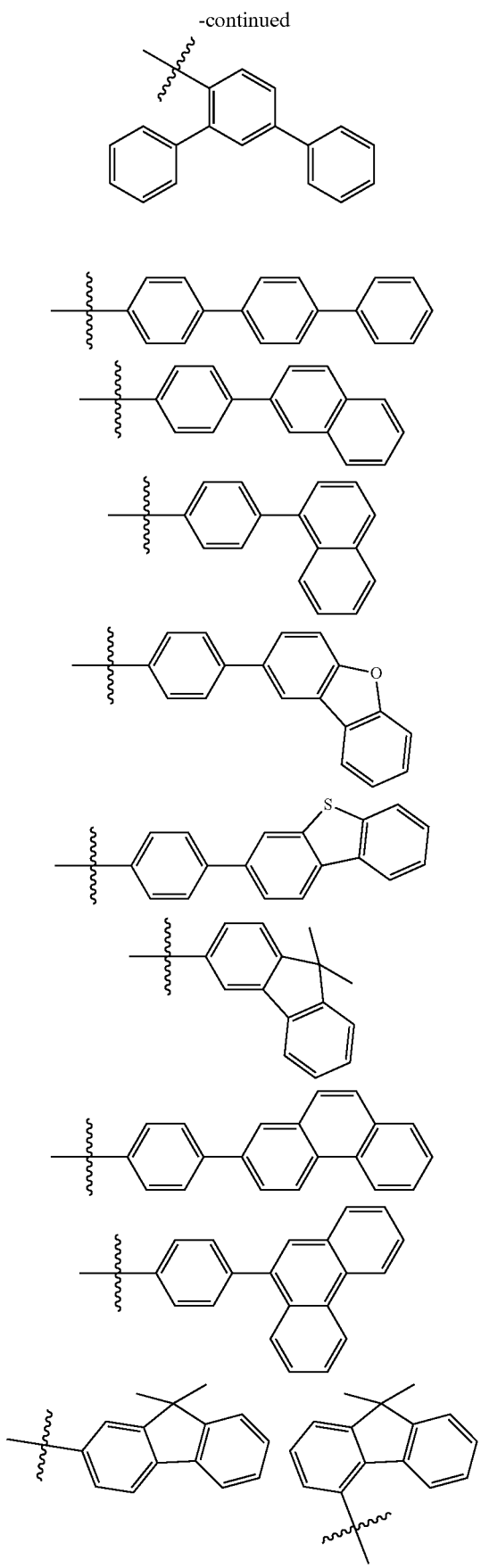

24
-continued

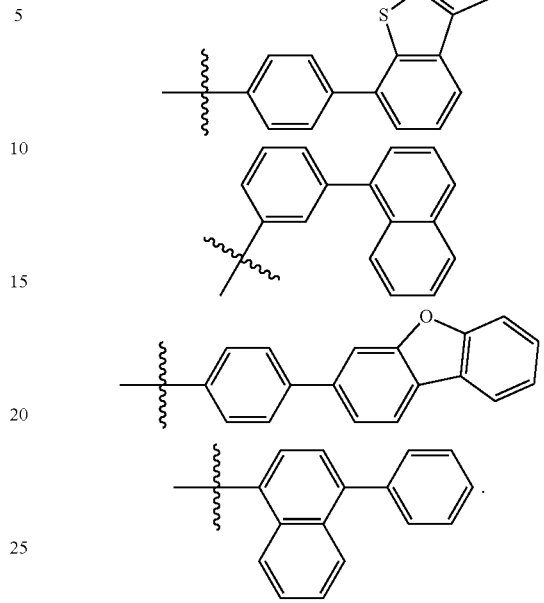

Ar₁ and Ar₂ in the compound of the present disclosure are not limited to the above groups.

Further, in some more specific embodiments of the present disclosure, $Ar_1$ and $Ar_2$ may be the same or different, and are each independently selected from the group consisting of substituted or unsubstituted phenyl, substituted or unsubstituted naphthyl, substituted or unsubstituted fluorenyl, substituted or unsubstituted biphenyl, substituted or unsubstituted pyridyl, substituted or unsubstituted carbazolyl, substituted or unsubstituted dibenzofuryl, substituted or unsubstituted dibenzothienyl, substituted or unsubstituted fluorenyl or selected from the groups that formed by linking two or three of the above groups via single bonds. In such an embodiment, substituents of $Ar_1$ and $Ar_2$ may be alkyl with 1 to 5 carbon atoms, fluorine, chlorine, cyano, aryl with 6 to 12 carbon atoms, heteroaryl with 3 to 12 carbon atoms, and hetero atoms in the heteroaryl may be selected from O, S and N. In such an embodiment, substituents in the $Ar_1$ to $Ar_2$ are the same or different, and are each independently selected from fluorine, cyano, methyl, ethyl, isopropyl, n-propyl, tert-butyl, phenyl, cyano-substituted phenyl, fluoro-substituted phenyl, biphenyl, terphenyl, naphthyl, fluorenyl, 9,9-dimethylfluorenyl, pyridyl, quinolyl, isoquinolyl, carbazolyl, dibenzofuryl, and dibenzothienyl.

In some embodiments of the present disclosure, $Ar_3$ is selected from a substituted or unsubstituted group $Z_1$; and the group $Z_1$ is selected from the following groups:

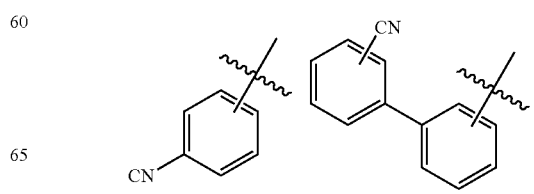

-continued
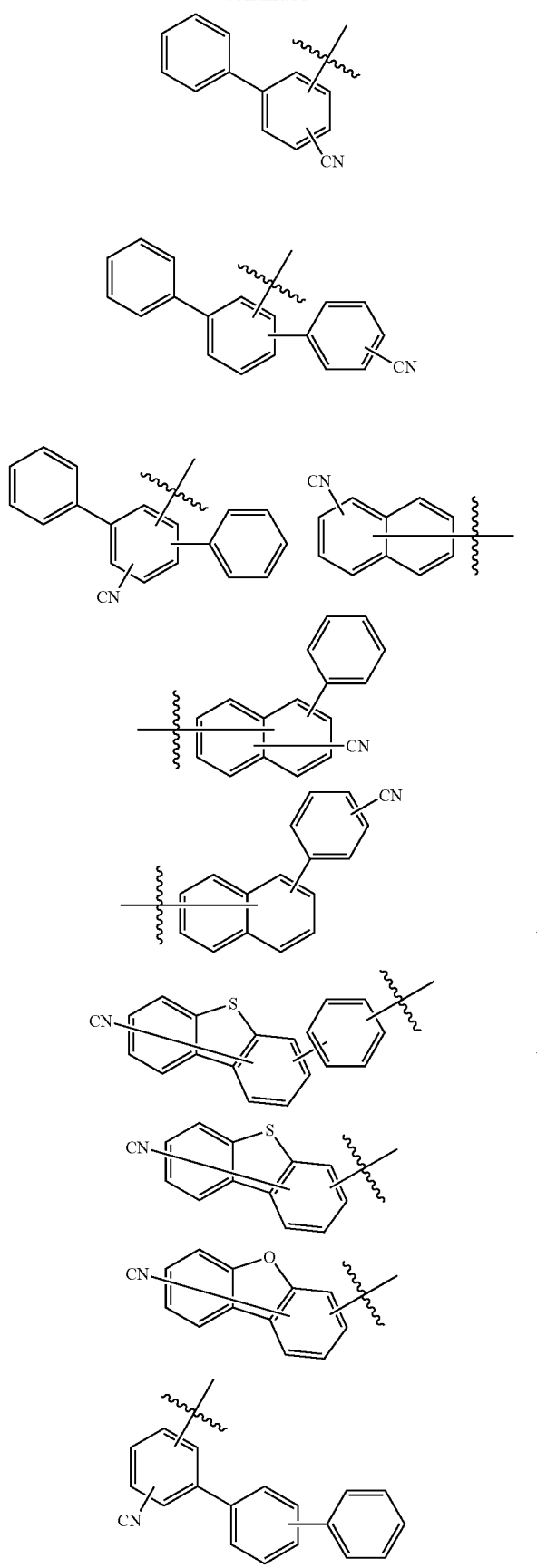
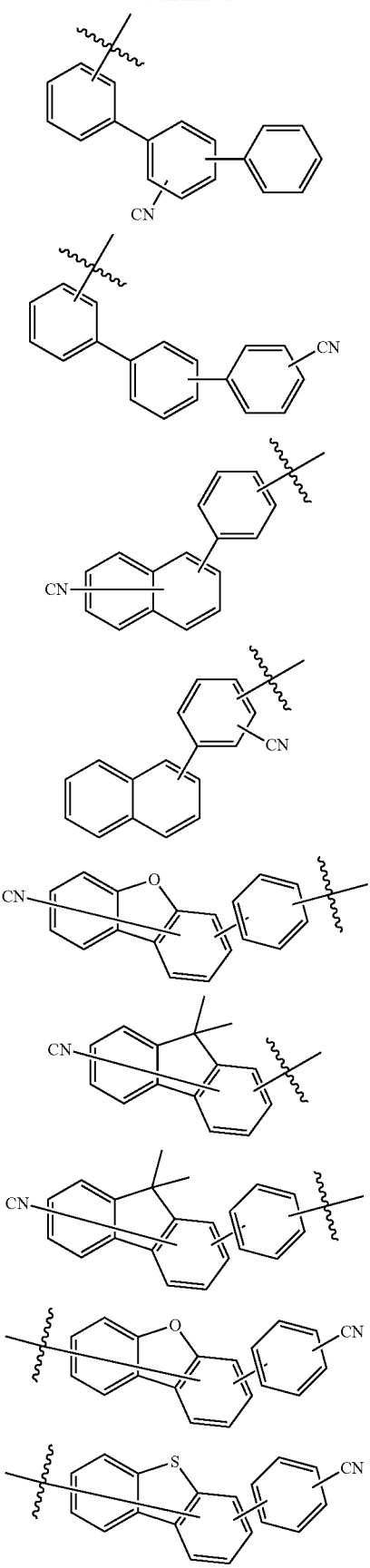

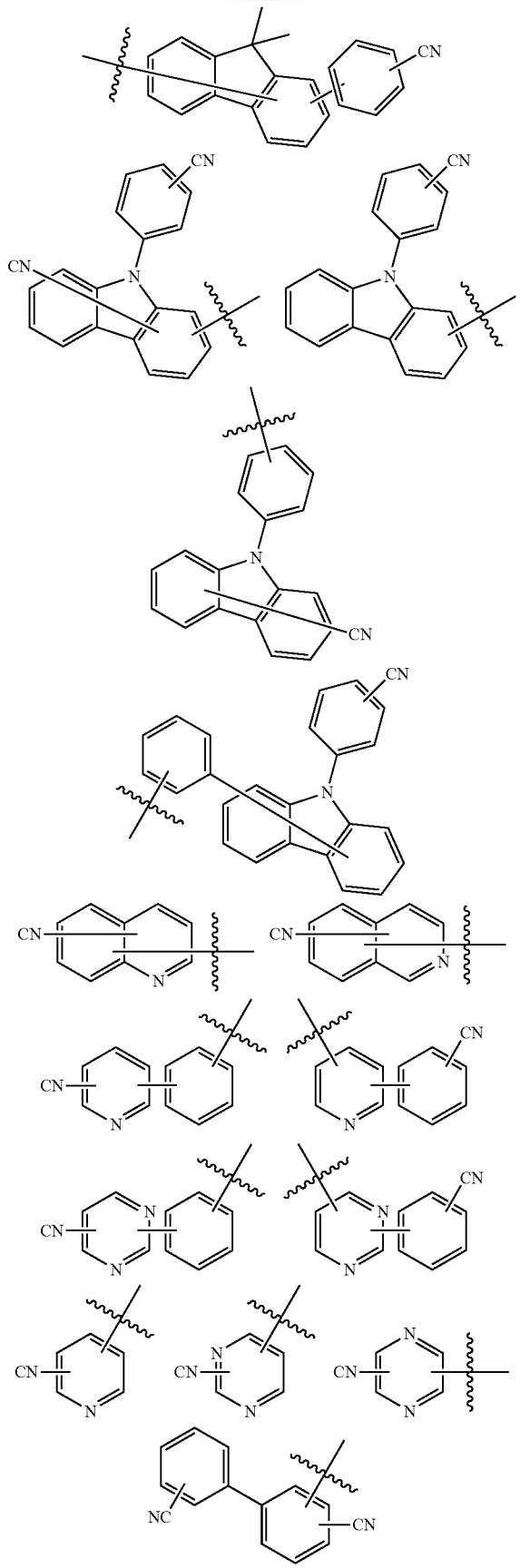
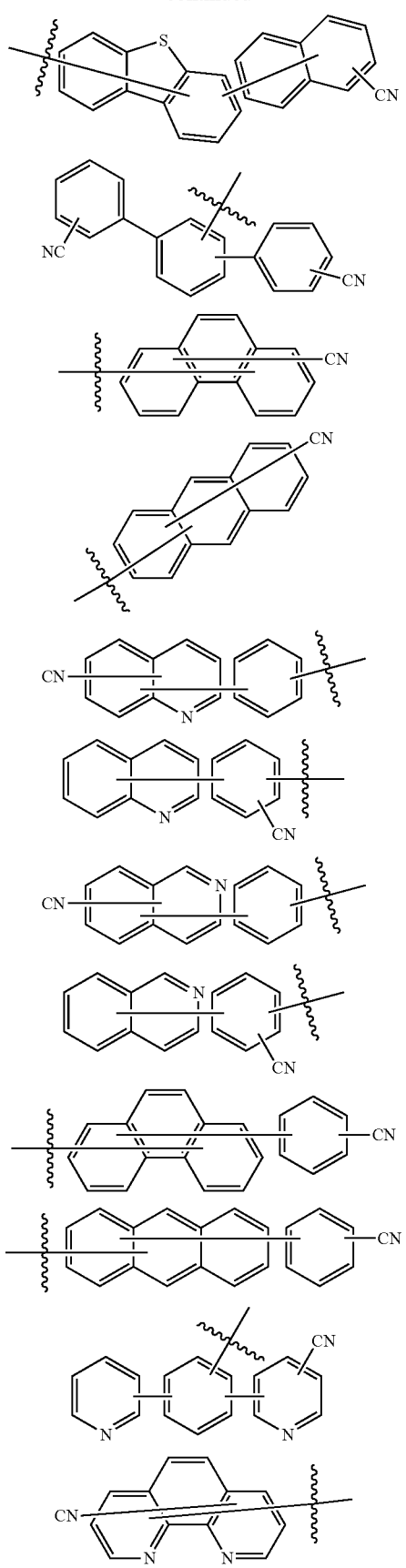

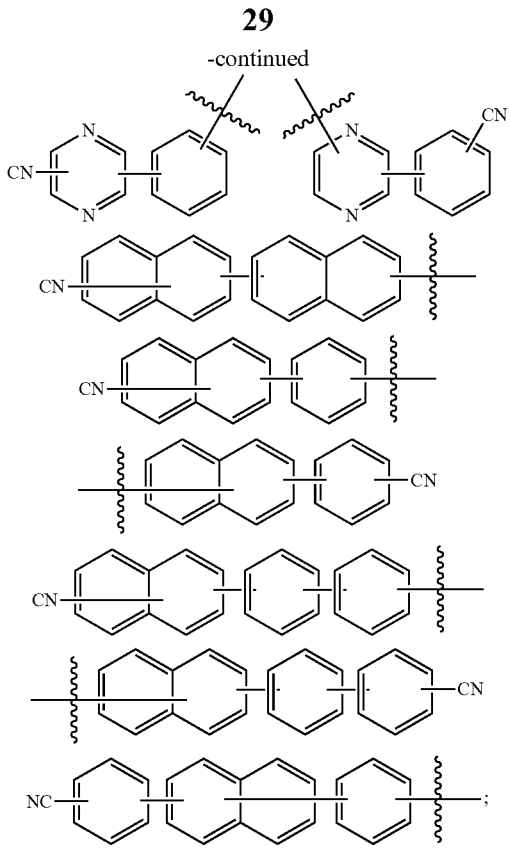

when Ar₃ is substituted $Z_1$, substituents of the $Z_1$ are selected fro, deuterium, fluorine, chlorine, cyano, alkyl with 1 to 4 carbon atoms, alkoxy with 1 to 4 carbon atoms, haloalkyl with 1 to 4 carbon atoms, alkylsilyl with 3 to 9 carbon atoms, cycloalkyl with 3 to 10 carbon atoms, aryl with 6 to 12 carbon atoms, and heteroaryl with 3 to 12 carbon atoms; when the $Z_1$ has a plurality of substituents, the plurality of the substituents are the same or different.

Further, in some other embodiments of the present disclosure, the Ar₃ is selected from a substituted or unsubstituted group $Z_2$; and the group $Z_2$ is selected from the following group:

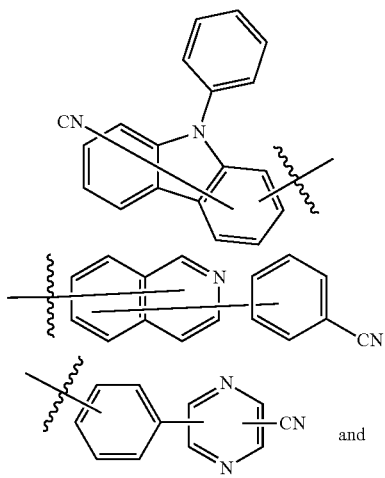

and

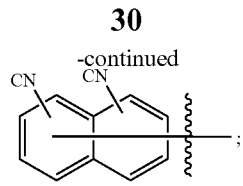

when the group $Z_2$ is substituted, substituents of the $Z_2$ are selected from deuterium, fluorine, chlorine, bromine, cyano, alkyl with 1 to 4 carbon atoms, alkoxy with 1 to 4 carbon atoms, haloalkyl with 1 to 4 carbon atoms, alkylsilyl with 3 to 9 carbon atoms, cycloalkyl with 3 to 10 carbon atoms, aryl with 6 to 12 carbon atoms, and heteroaryl with 3 to 12 carbon atoms; when the $Z_2$ has a plurality of substituents, the plurality of the substituents are the same or different.

Further, in the above embodiments, when Ar₃ is a substituted group $Z_1$ or substituted group $Z_2$, substituents in the $Z_1$ or $Z_2$ are selected from deuterium, fluorine, chlorine, cyano, methyl, ethyl, isopropyl, n-propyl, tert-butyl, trifluoromethyl, trimethylsilyl, methoxy, ethyoxy, isopropoxy, methylthio, cyclopentyl, cyclohexyl, phenyl, biphenyl, terphenyl, naphthyl, fluorenyl, 9,9-dimethylfluorenyl, pyridyl, quinolyl, isoquinolyl, pyrimidyl, carbazolyl, dibenzofuryl, and dibenzothienyl. Further, in some more specific embodiments of the present disclosure, Ar₃ is selected from the group consisting of cyano-substituted phenyl, cyano-substituted naphthyl, cyano-substituted 9,9-dimethylfluorenyl, cyano-substituted biphenyl, cyano-substituted pyridyl, cyano-substituted carbazolyl, cyano-substituted N-phenylcarbazolyl, cyano-substituted phenyl-naphthyl-phenyl, cyano-substituted phenyl-naphthyl, cyano-substituted naphthyl-phenyl, cyano-substituted dibenzofuryl, cyano-substituted dibenzothienyl, cyano-substituted dibenzothienyl-phenyl, cyano-substituted dibenzofuryl, cyano-substituted dibenzofuryl-phenyl and cyano-substituted fluorenyl.

Further, in some more specific embodiments of the present disclosure, further, Ar₃ in the Formula (1) is selected from the group consisting of the following groups:

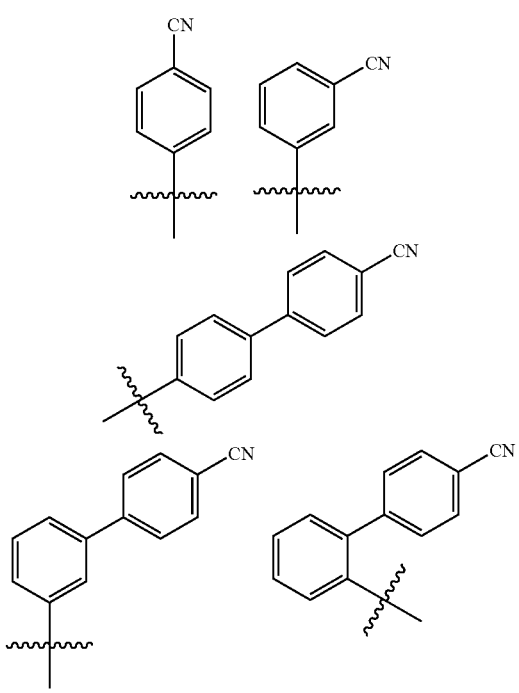

31
-continued
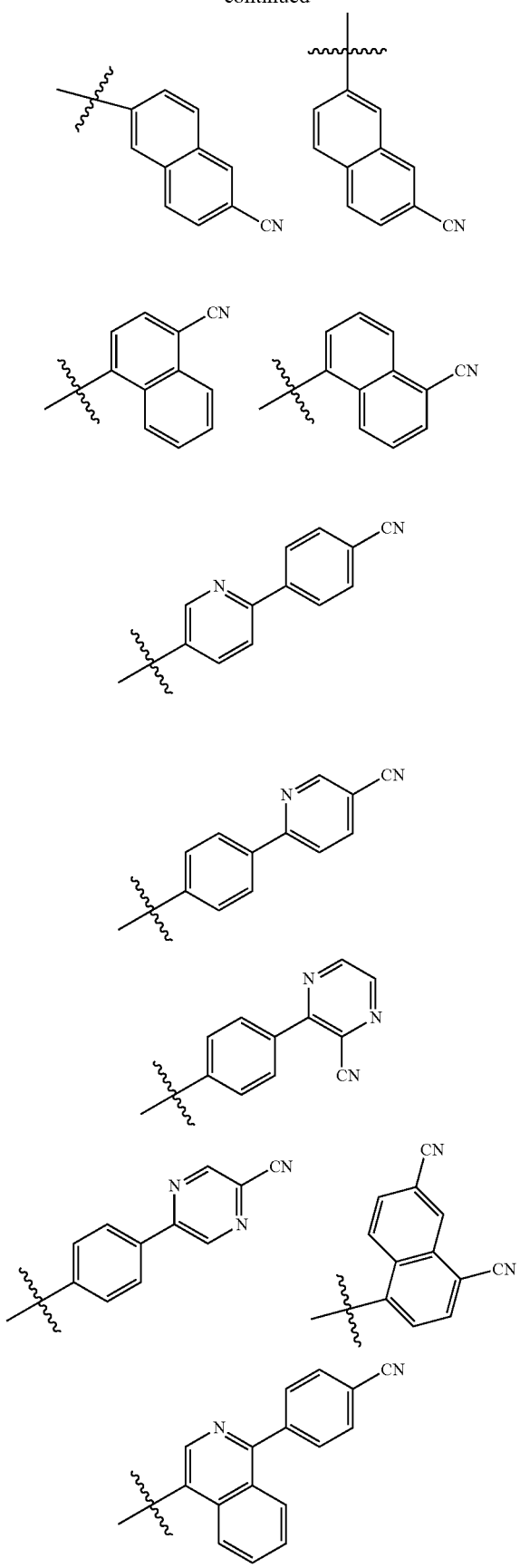
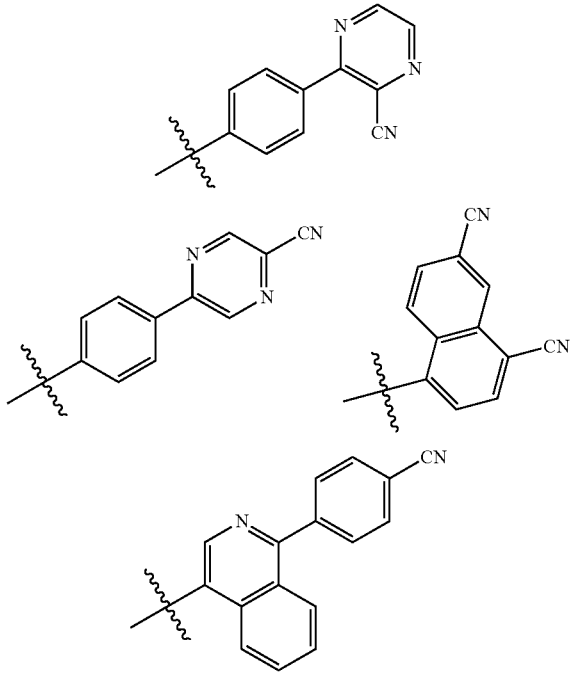
32
-continued
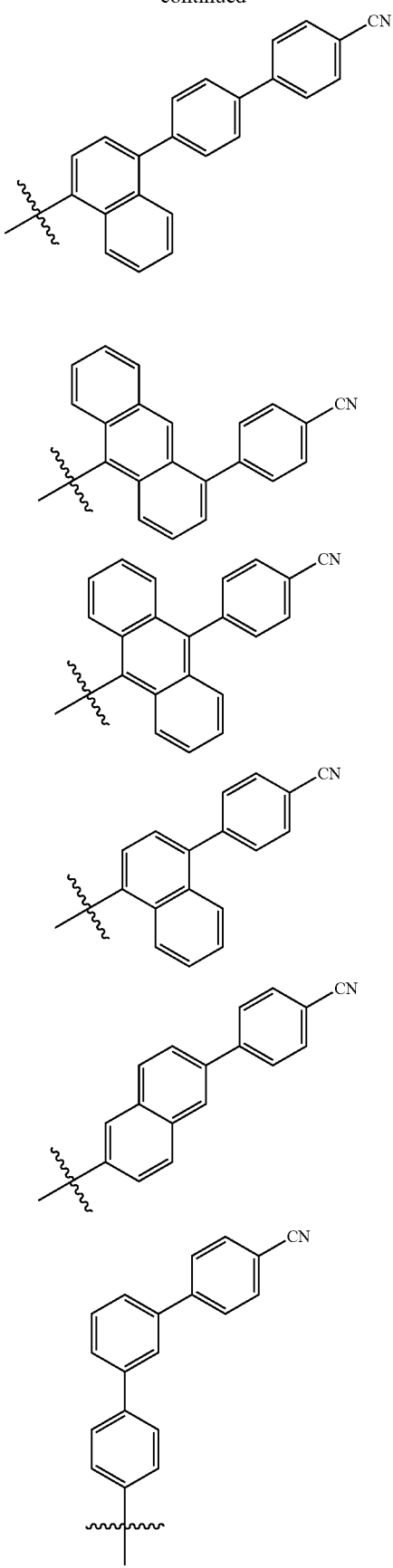

-continued
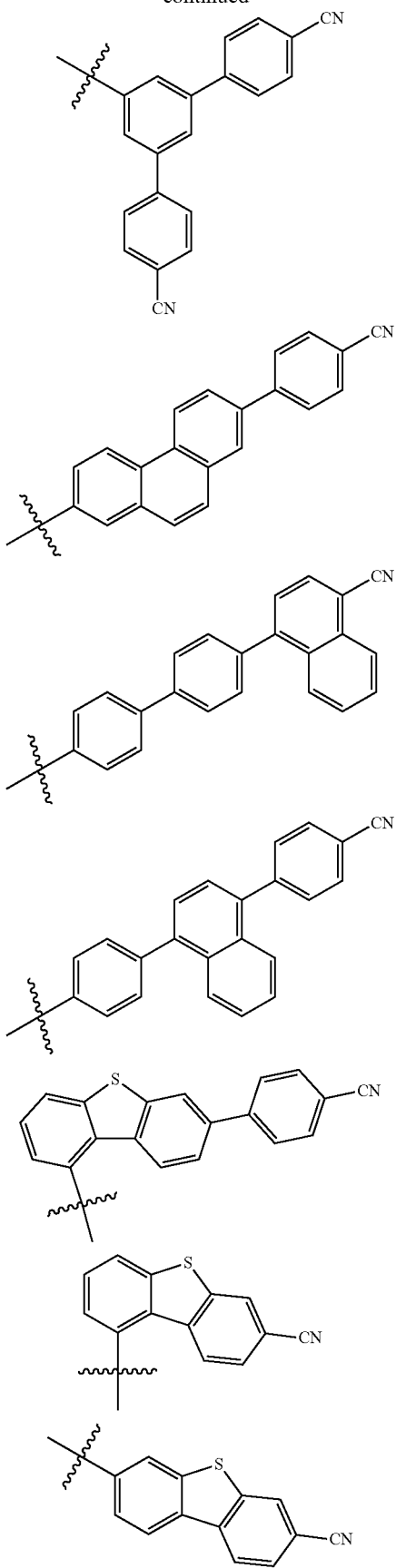
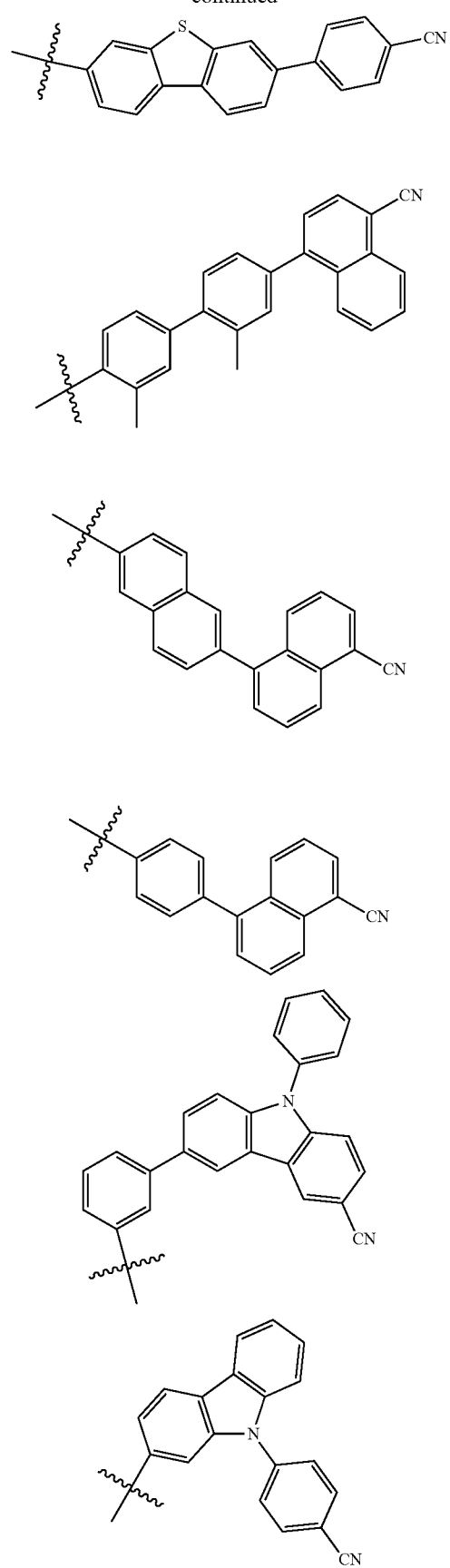

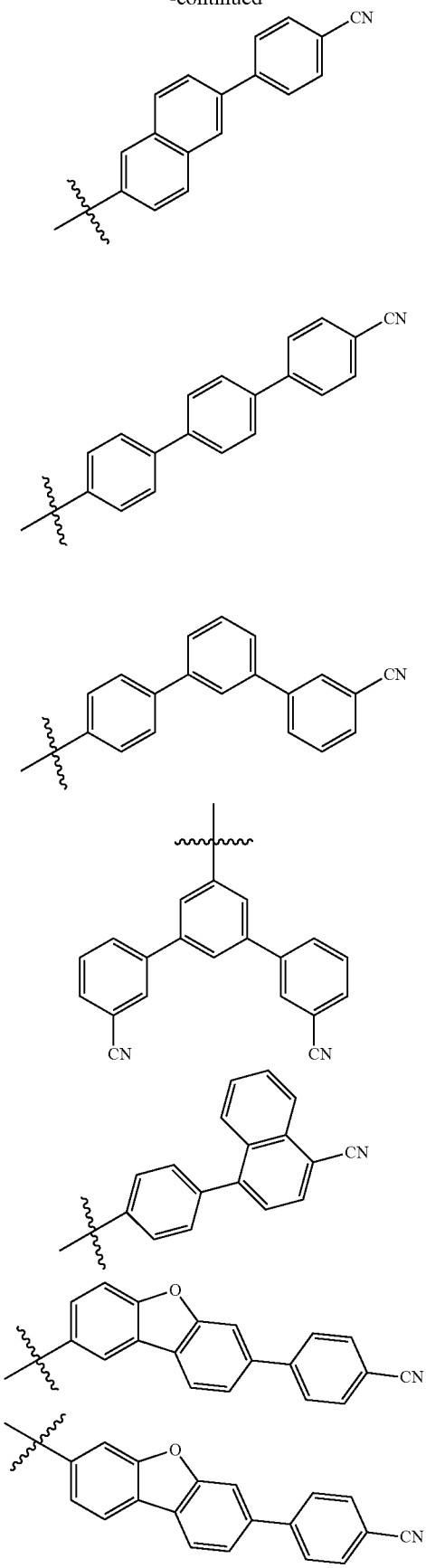
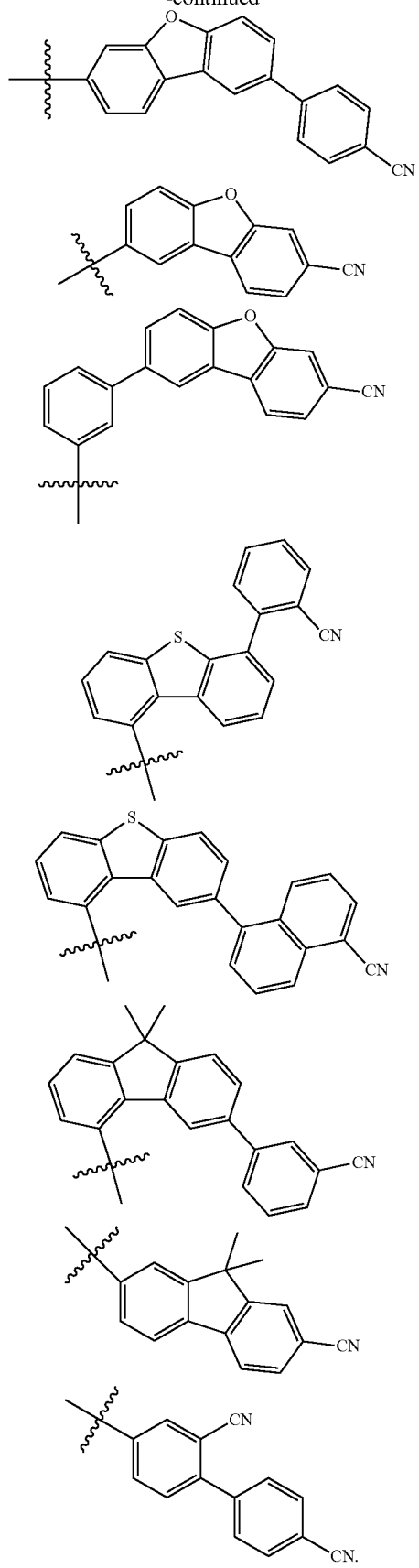

Further, in some more specific embodiments of the present disclosure, further, Ar₃ in the Formula (1) is selected from the group consisting of the following groups:

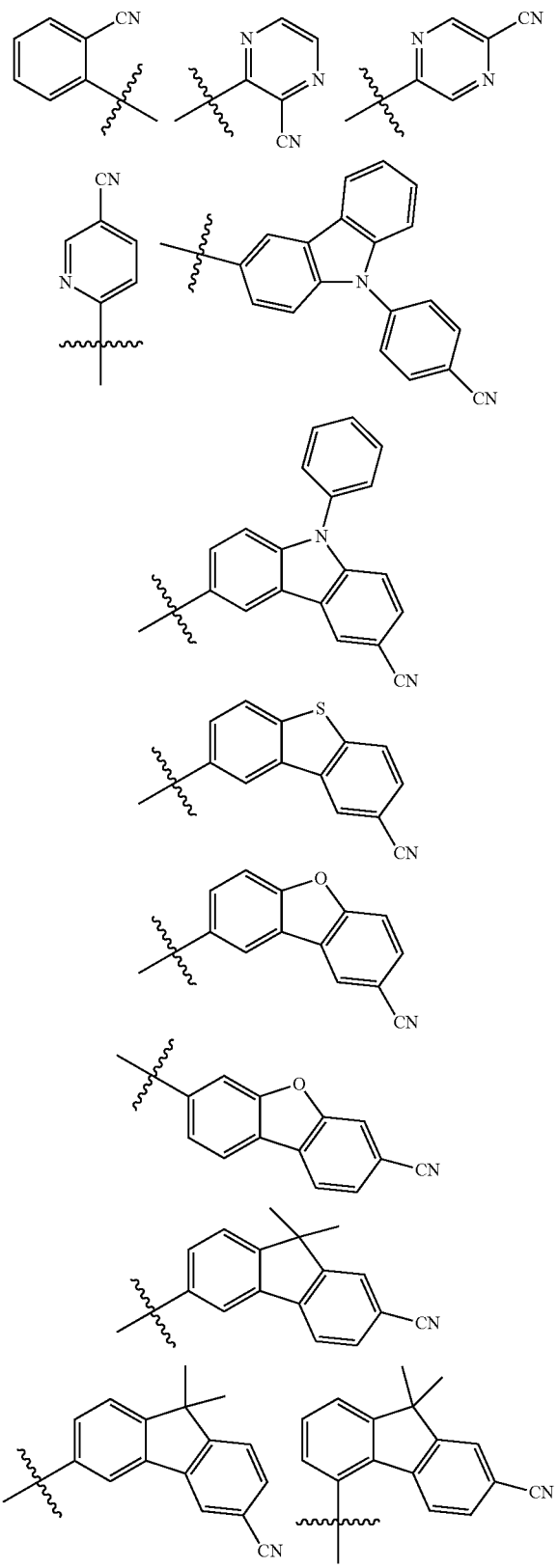

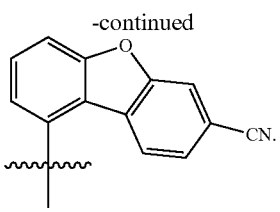

Further, in some specific embodiments of the present disclosure, Ar₃ may be cyano-substituted phenyl, cyano-substituted naphthyl, cyano-substituted biphenyl, cyano-substituted terphenyl, cyano-substituted dimethylfluorenyl, cyano-substituted phenanthryl, cyano-substituted carbazolyl, cyano-substituted dibenzothienyl, cyano-substituted N-phenylcarbazolyl, cyano-substituted dibenzofuryl, cyano-substituted pyridyl, cyano-substituted quinolyl, cyano-substituted isoquinolyl, or a group that formed by linking any one of the above groups with one or more of phenyl, biphenyl, methyl-substituted biphenyl, naphthyl, phenanthryl, carbazolyl, dibenzofuryl, dibenzothienyl, pyridyl, quinolyl, isoquinolyl, and dimethylfluorenyl via a single bond. In such an embodiment, the Ar₃ may further optionally have other substituents, the other substituents are the same or different, and are each independently selected from fluorine, cyano, methyl, ethyl, isopropyl, n-propyl, tert-butyl, phenyl, and cyano-substituted phenyl.

In a further specific embodiment, Ar₃ may be selected from the group consisting of the following groups:

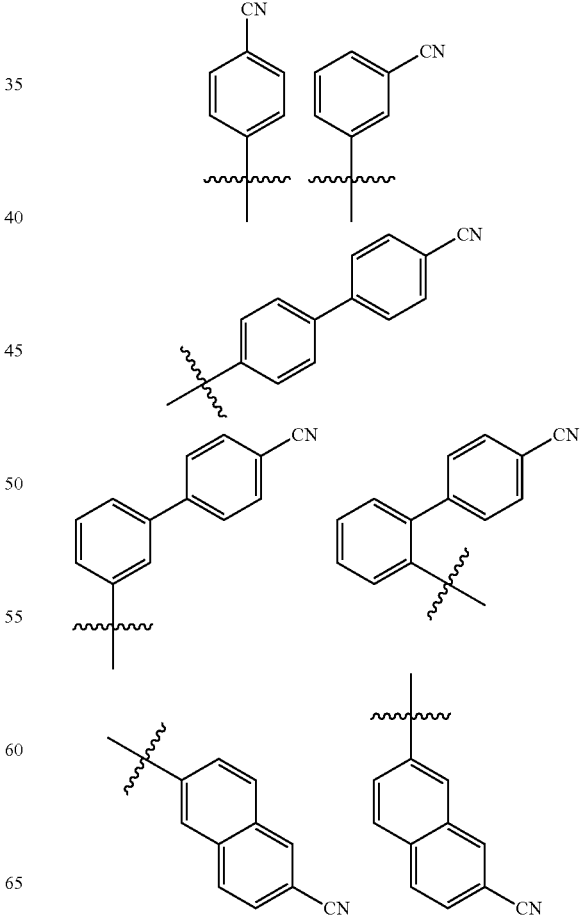

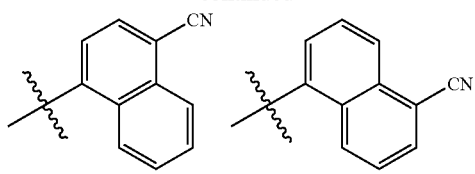

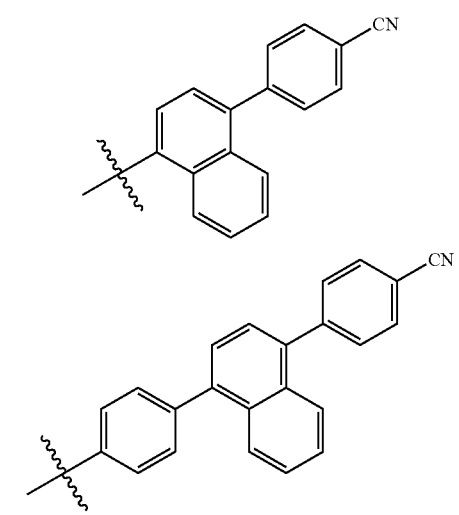

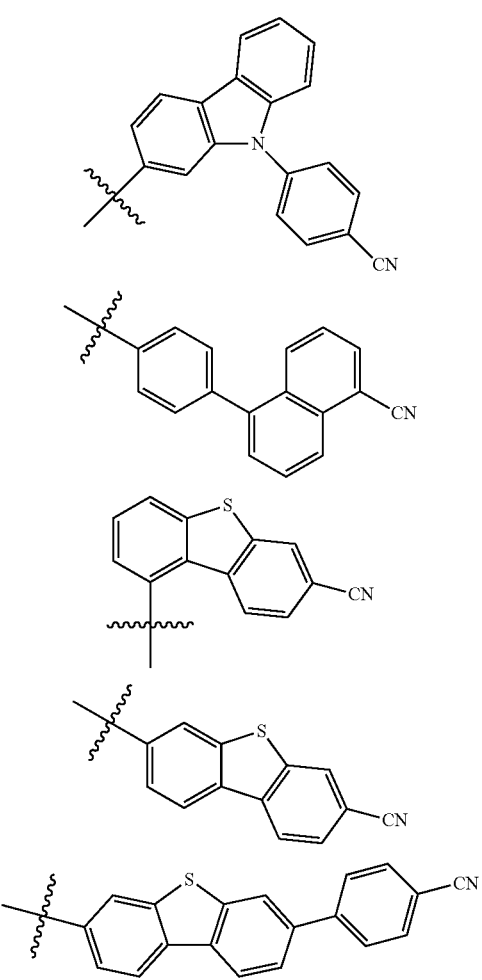

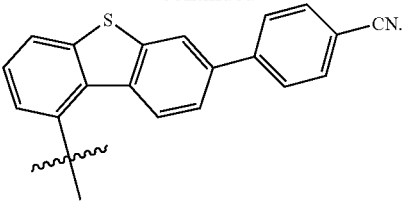

Ar₃ in the compound of the present disclosure is not limited to the above groups.

In some specific embodiments of the present disclosure, the $L_1$ and $L_2$ are the same as or different from each other, and are each independently selected from the group consisting of single bond, substituted or unsubstituted arylene with 6 to 25 carbon atoms, substituted or unsubstituted heteroarylene with 1 to 18 carbon atoms; substituents in the $L_1$ and $L_2$ are the same as or different from each other, and are each independently selected from the group consisting of deuterium, fluorine, chlorine, bromine, cyano, alkyl with 1 to 10 carbon atoms, haloalkyl with 1 to 10 carbon atoms, aryl with 6 to 18 carbon atoms, heteroaryl with 3 to 18 carbon atoms, aryloxy with 6 to 18 carbon atoms, arylthio with 6 to 18 carbon atoms, alkylsilyl with 3 to 12 carbon atoms, alkylamino with 1 to 10 carbon atoms and cycloalkyl with 3 to 10 carbon atoms; and the Ar₃ is substituted by at least one cyano.

In some specific embodiments of the present disclosure, $L_1$ and $L_2$ are selected from a single bond or the group consisting of the groups as shown in chemical formulae j-1 to chemical formulae j-20:

j-1

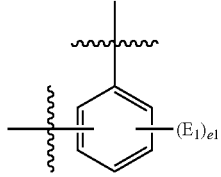

j-2

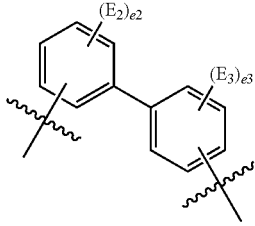

j-3

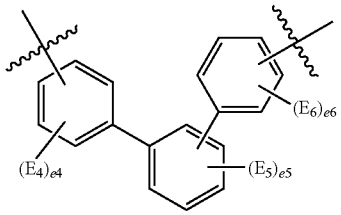

j-4

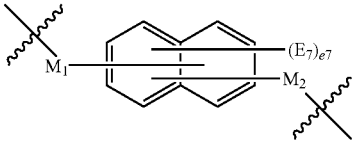

-continued
j-5
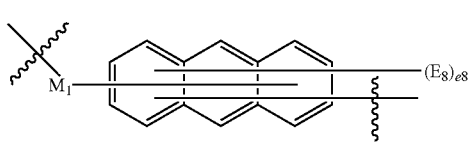
j-6
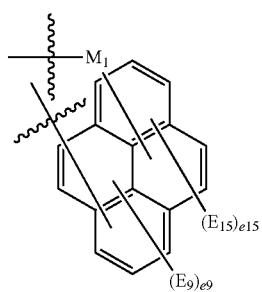
j-7
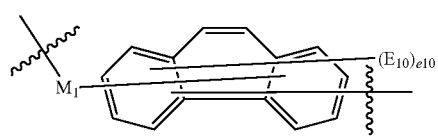
j-8
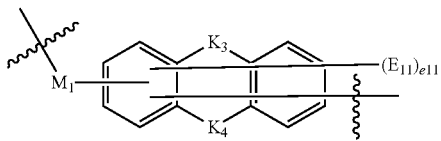
j-9
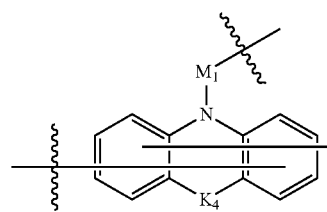
j-10
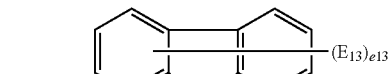
j-11
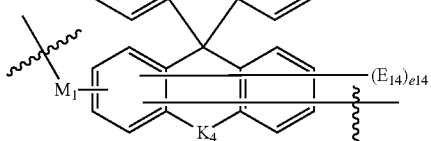
j-12
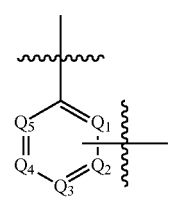
j-13
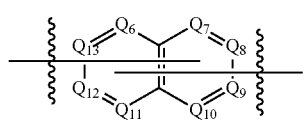
j-13
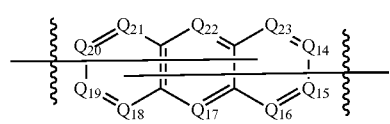
-continued
j-14
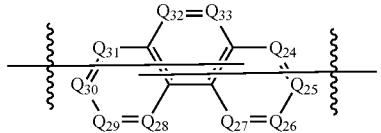
j-15
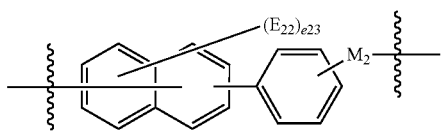
j-16
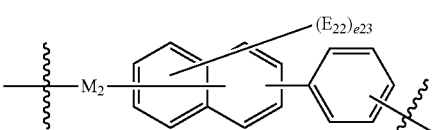
j-17
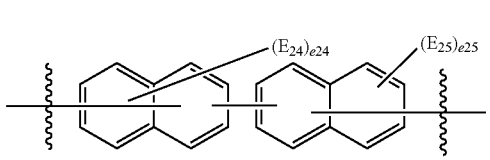
j-14
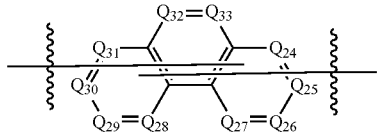
j-15
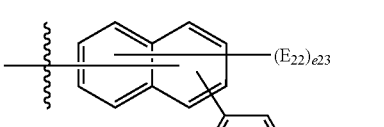
j-16
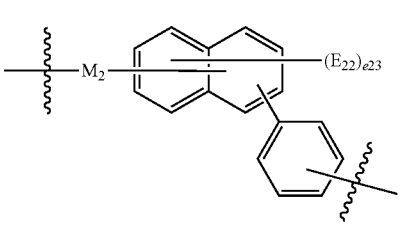
j-17
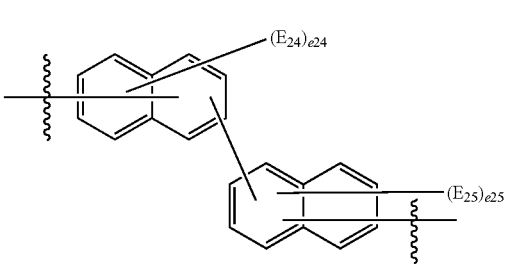

-continued j-18

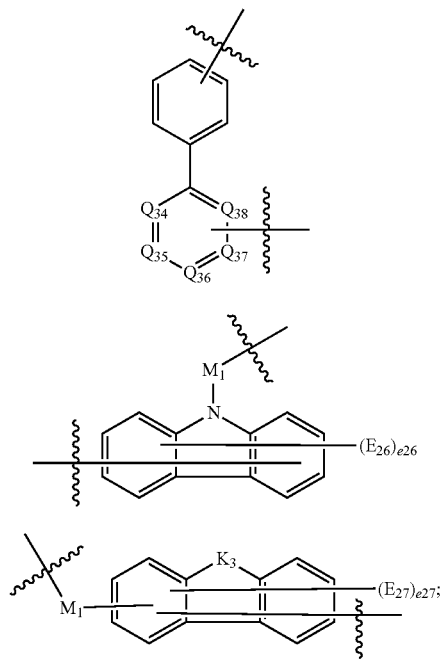

j-19 j-20 wherein, $M_1$ is selected from a single bond or

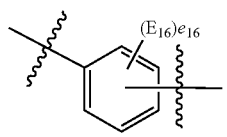

$Q_1$ to $Q_5$ are each independently selected from N or $C(J_1)$, and at least one of $Q_1$ to $Q_5$ is selected from N; when two or more of $Q_1$ to $Q_5$ are selected from $C(J_1)$, any two of $J_1$ are the same or different;

$Q_6$ to $Q_{13}$ are each independently selected from N or $C(J_2)$, and at least one of $Q_6$ to $Q_{13}$ is selected from N; when two or more of $Q_6$ to $Q_{13}$ are selected from $C(J_2)$, any two of $J_2$ are the same or different;

$Q_{14}$ to $Q_{23}$ are each independently selected from N or $C(J_3)$, and at least one of $Q_{14}$ to $Q_{23}$ is selected from N; when two or more of $Q_{14}$ to $Q_{23}$ are selected from $C(J_3)$, any two of $J_3$ are the same or different;

$Q_{24}$ to $Q_{33}$ are each independently selected from N or $C(J_4)$, and at least one of $Q_{24}$ to $Q_{33}$ is selected from N; when two or more of $Q_{24}$ to $Q_{33}$ are selected from $C(J_4)$, any two of $J_4$ are the same or different;

$Q_{34}$ to $Q_{38}$ are each independently selected from N or $C(J_5)$, and at least one of $Q_{34}$ to $Q_{38}$ is selected from N; when two or more of $Q_{34}$ to $Q_{38}$ are selected from $C(J_5)$, any two of $J_5$ are the same or different;

$E_1$ to $E_{16}$, $E_{23}$ to $E_{27}$, and $J_1$ to $J_5$ are each independently selected from the group consisting of: hydrogen, deuterium, fluorine, chlorine, bromine, cyano, heteroaryl with 3 to 18 carbon atoms, aryl with 6 to 18 carbon atoms, trialkylsilyl with 3 to 12 carbon atoms, arylsilyl with 8 to 12 carbon atoms, alkyl with 1 to 10 carbon atoms, haloalkyl with 1 to 10 carbon atoms, alkenyl with 2 to 6 carbon atoms, cycloalkyl with 3 to 10 carbon atoms, heterocycloalkyl with 2 to 10 carbon atoms, alkoxy with 1 to 10 carbon atoms, alkylamino with 1 to 10 carbon atoms, alkylthio with 1 to 10 carbon atoms, aryloxy with 6 to 18 carbon atoms, and arylthio with 6 to 18 carbon atoms;

$e_r$ is the quantity of $E_r$, r is any integer of 1 to 27; for example, $e_1$ to $e_{16}$ respectively correspond to the number of groups $E_1$ to $E_{16}$; similarly, $e_{23}$ to $e_{27}$ respectively correspond to the number of groups $E_{23}$ to $E_{27}$; when $e_1$ to $e_{15}$ and $e_{23}$ to $e_{27}$ are each independently greater than 0, the corresponding groups may be the same or different; for example, $e_{15}$ denotes the number of group $E_{15}$, $e_5$ may be 1, 2, 3 or 4; when $e_5$ may be 2, $E_{15}$ of the two groups may be the same or different.

$e_1$, $e_2$, $e_3$, $e_4$, $e_5$, $e_6$, $e_9$, $e_{15}$ and $e_{16}$ are each independently selected from 1, 2, 3 or 4; $e_7$, $e_{11}$, $e_{14}$, $e_{23}$, $e_{24}$, $e_{25}$ and $e_{27}$ are each independently selected from 1, 2, 3, 4, 5, or 6; $e_{12}$ and $e_{26}$ are each independently selected from 1, 2, 3, 4, 5, 6 or 7; $e_8$, $e_{10}$ and $e_{13}$ are each independently selected from 1, 2, 3, 4, 5, 6, 7 or 8;

$K_3$ is selected from the group consisting of O, S, Se, $N(E_{17})$, $C(E_{18}E_{19})$ and $Si(E_{18}E_{19})$; wherein, $E_{17}$, $E_{18}$ and $E_{19}$ are each independently selected from the group consisting of: aryl with 6 to 18 carbon atoms, heteroaryl with 3 to 18 carbon atoms, alkyl with 1 to 10 carbon atoms, alkenyl with 2 to 6 carbon atoms, cycloalkyl with 3 to 10 carbon atoms and heterocycloalkyl with 2 to 10 carbon atoms; or $E_{18}$ and $E_{19}$ are linked with each other to form a saturated or unsaturated 5- to 13-membered ring together with the atoms to which they are both linked. For example, in chemical formulae j-20, when $M_2$ is a single bond and $K_3$ is $C(E_{18}E_{19})$, $E_{18}$ and $E_{19}$ may be linked with each other to form a saturated or unsaturated ring together with the atoms to which they are both linked, and also may be present independently. In case that $E_{18}$ and $E_{19}$ form a ring, the ring formed by $E_{18}$ and $E_{19}$ and other parts of the molecule are the spiro link. It should be indicated that when $E_{18}$ and $E_{19}$ are linked with each other to form a saturated or unsaturated ring together with the atoms to which they are both linked, the ring may be a 5-membered ring, namely,

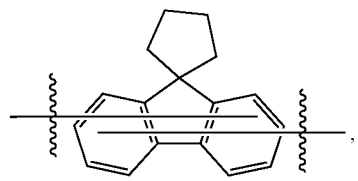

further may be a 6-membered ring, namely,

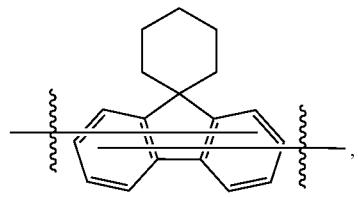

and further may be a 13-membered ring, namely,

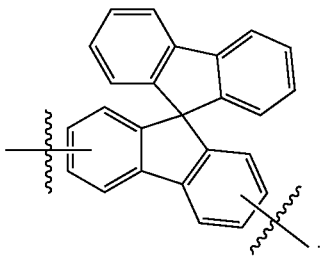

Of course, the atom number on the ring formed by $E_{18}$ and $E_{19}$ may be further other values, but will be not enumerated one by one here.

$K_4$ is selected from the group consisting of O, S, Se, $N(E_{20})$, $C(E_{21}E_{22})$ and $Si(E_{21}E_{22})$; wherein, $E_{20}$, $E_{21}$ and $E_{22}$ are each independently selected from the group consisting of: aryl with 6 to 18 carbon atoms, heteroaryl with 3 to 18 carbon atoms, alkyl with 1 to 10 carbon atoms, alkenyl with 2 to 6 carbon atoms, cycloalkyl with 3 to 10 carbon atoms and heterocycloalkyl with 2 to 10 carbon atoms; or $E_{21}$ and $E_{22}$ are linked with each other to form a saturated or unsaturated 5- to 13-membered ring together with the atoms to which they are both linked. Understanding to the "$E_{21}$ and $E_{22}$ form a ring optionally" is the same way as that in other solutions (when $E_{18}$ and $E_{19}$ are linked with each other to form a ring).

In one specific embodiment of the present disclosure, $L_1$ and $L_2$ is the same or different, and is each independently selected from single bond, and substituted or unsubstituted group $W_1$; and the group $W_1$ is selected from the following group:

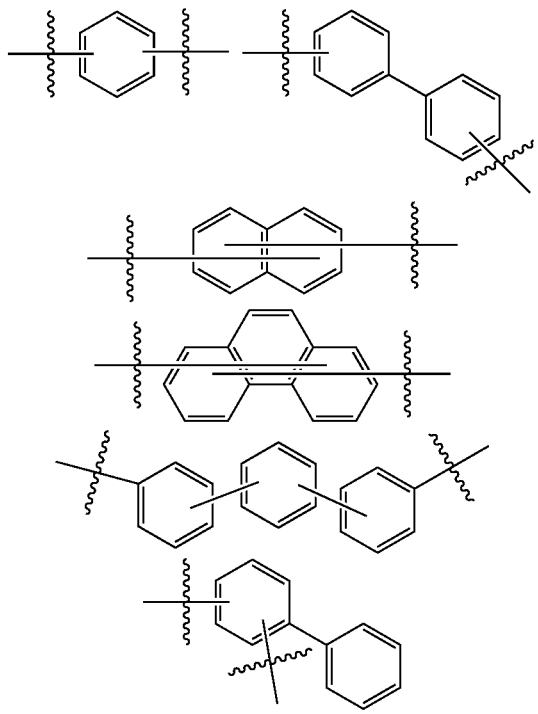

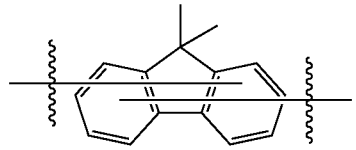
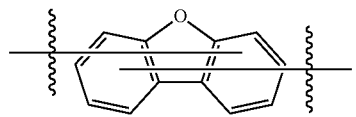
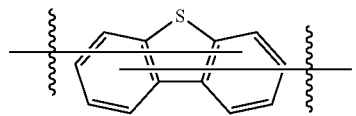
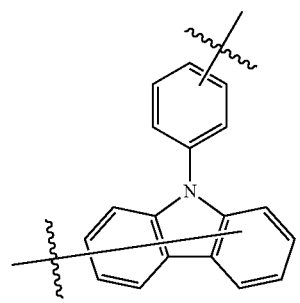
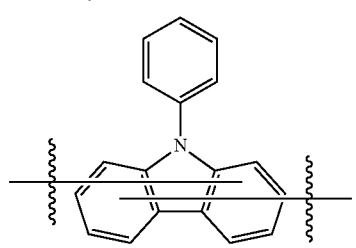
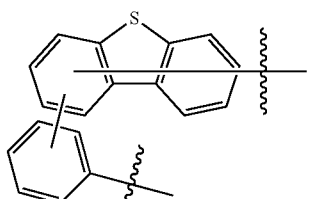
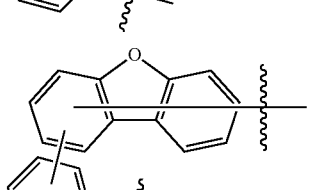
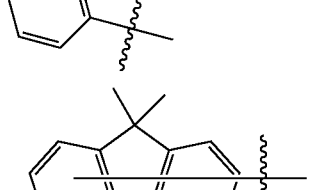
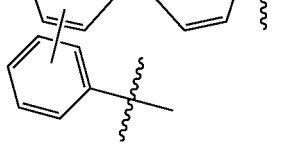

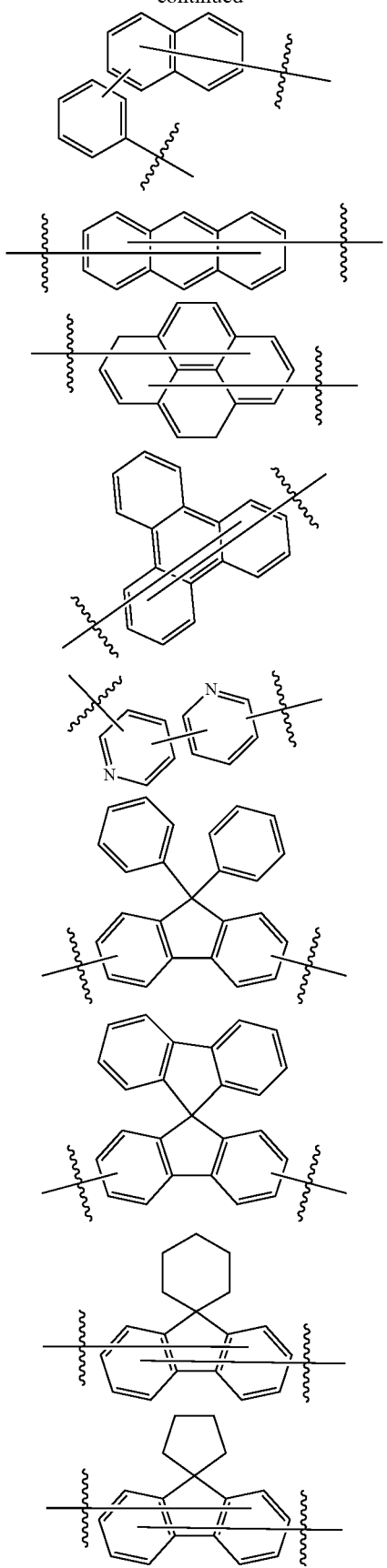
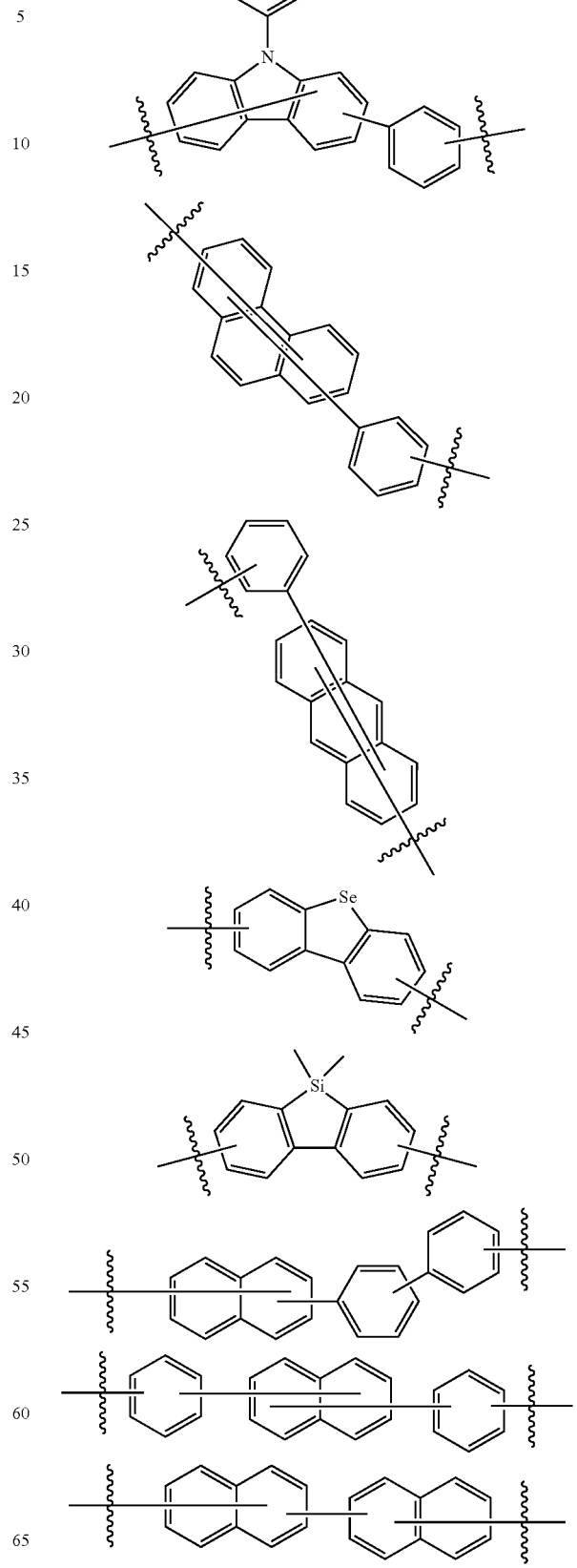

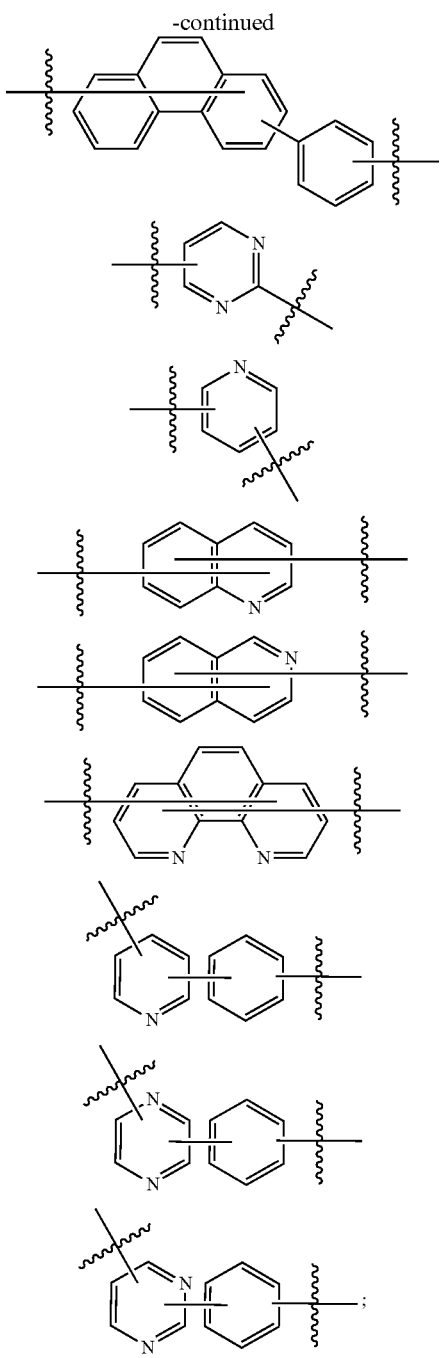

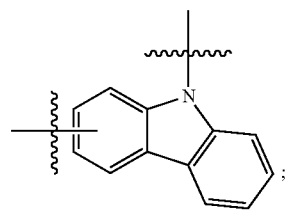

when the group $W_1$ is substituted, substituent of the $W_1$ is selected from the group consisting of deuterium, fluorine, chlorine, cyano, alkyl with 1 to 6 carbon atoms, alkoxy with 1 to 4 carbon atoms, haloalkyl with 1 to 4 carbon atoms, alkylsilyl with 3 to 9 carbon atoms, cycloalkyl with 3 to 10 carbon atoms, aryl with 6 to 13 carbon atoms, and heteroaryl with 3 to 12 carbon atoms; when the $W_1$ has a plurality of substituents, the plurality of the substituents are the same or different.

In a further embodiment, $L_1$ and $L_2$ may be further each independently selected from a substituted or unsubstituted group $W_2$; the unsubstituted group $W_2$ has a structure as shown in and the substituted group $W_2$ is optionally substituted by 1, 2, or 3 groups selected from deuterium, fluorine, chlorine, cyano, and alkyl with 1 to 4 carbon atoms.

In a specific embodiment of the present disclosure, $L_1$ and $L_2$ may be each independently selected from one of a single bond, substituted or unsubstituted phenylene, substituted or unsubstituted naphthylene, substituted or unsubstituted anthrylene, substituted or unsubstituted phenanthrylene, substituted or unsubstituted diphenylene, substituted or unsubstituted terphenylene, substituted or unsubstituted fluorenylene, substituted or unsubstituted dibenzofurylene, substituted or unsubstituted dibenzothenylene, substituted or unsubstituted pyridylene, substituted or unsubstituted quinolylene, substituted or unsubstituted carbazolylene, and substituted or unsubstituted N-phenylcarbazolylene, or a subunit group formed by linking two or three of the above groups via single bonds.

Further, $L_1$ and $L_2$ may be each independently selected from at least one of a single bond, substituted or unsubstituted 1,4-phenylene, substituted or unsubstituted 1,3-phenylene, substituted or unsubstituted 1,2-phenylene, substituted or unsubstituted 1,4-naphthylene, substituted or unsubstituted 1,5-naphthylene, substituted or unsubstituted 2,6-naphthylene, substituted or unsubstituted 2,7-naphthylene, substituted or unsubstituted 1,4-anthrylene, substituted or unsubstituted 1,5-anthrylene, substituted or unsubstituted 2,6-anthrylene, substituted or unsubstituted 9,10-anthrylene, substituted or unsubstituted 2,7-phenanthrylene, substituted or unsubstituted 2,7-fluorenylene, substituted or unsubstituted 3,6-fluorenylene, substituted or unsubstituted 2,7-biphenylene, substituted or unsubstituted 3,6-biphenylene, substituted or unsubstituted 2,7-dibenzofurylene, substituted or unsubstituted 2,6-dibenzofurylene, substituted or unsubstituted 3,6-dibenzofurylene, substituted or unsubstituted 2,7-dibenzothenylene, substituted or unsubstituted 1,6-dibenzothenylene and substituted or unsubstituted 3,6-dibenzothenylene.

In the above embodiment, substituents in the $L_1$ and $L_2$ are the same or different, and are each independently selected from the group consisting of deuterium, fluorine, chlorine, cyano, methyl, ethyl, isopropyl, n-propyl, tert-butyl, methoxy, ethyoxyl, trifluoromethyl, trimethylsilyl, phenyl, biphenyl, naphthyl, pyridyl, carbazolyl, dibenzofuryl, and dibenzothienyl.

In a further embodiment, $L_1$ and $L_2$ may be each independently selected from a single bond or the group consisting of the following groups:

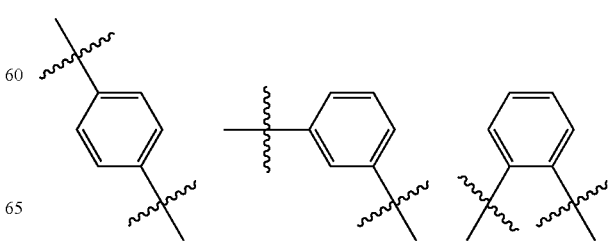

-continued
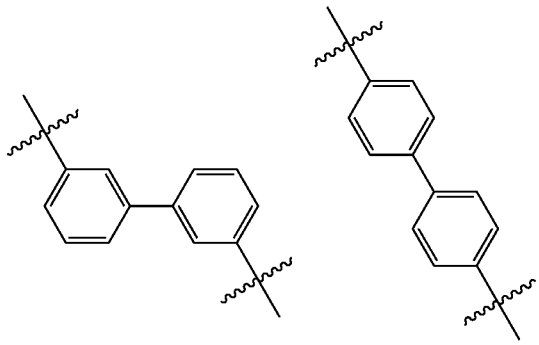
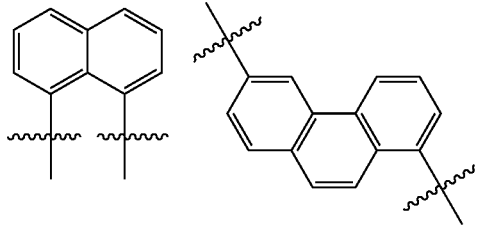
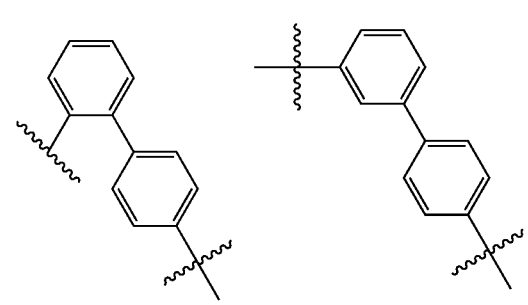
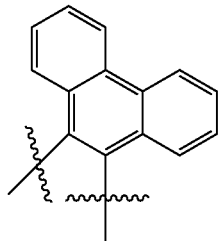
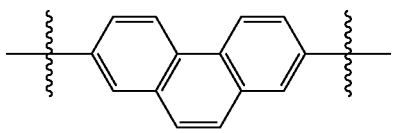
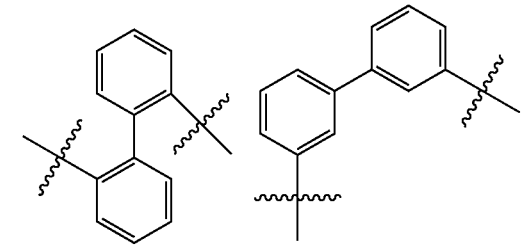
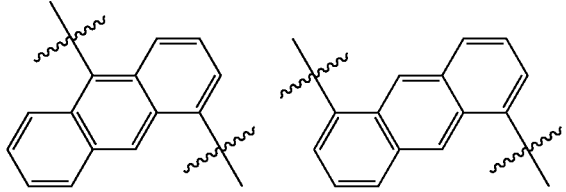
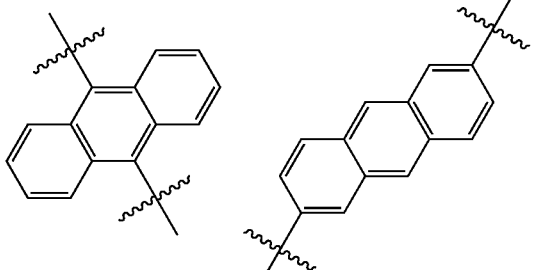
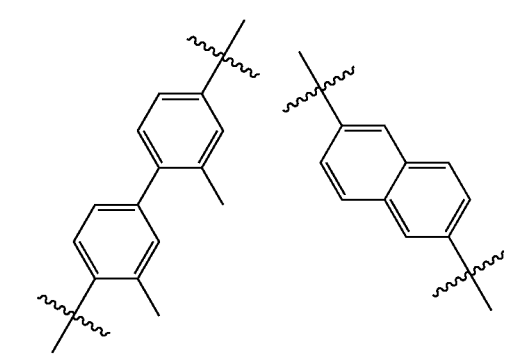
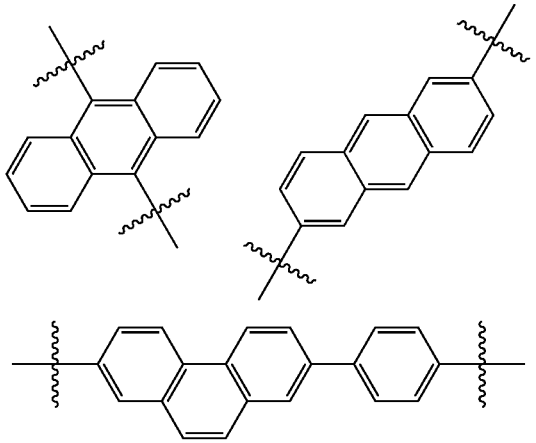
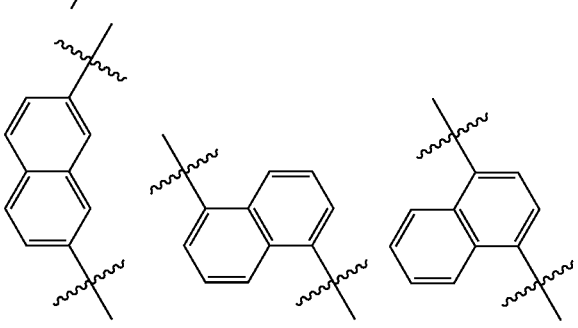
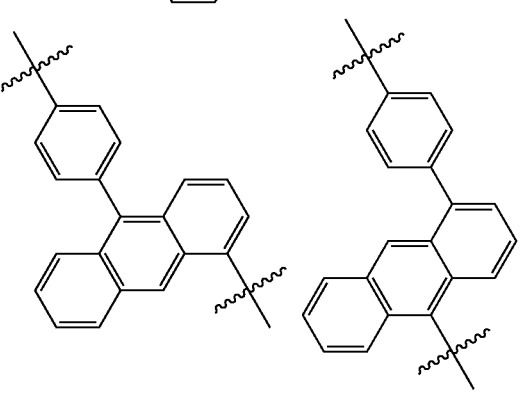

53
-continued
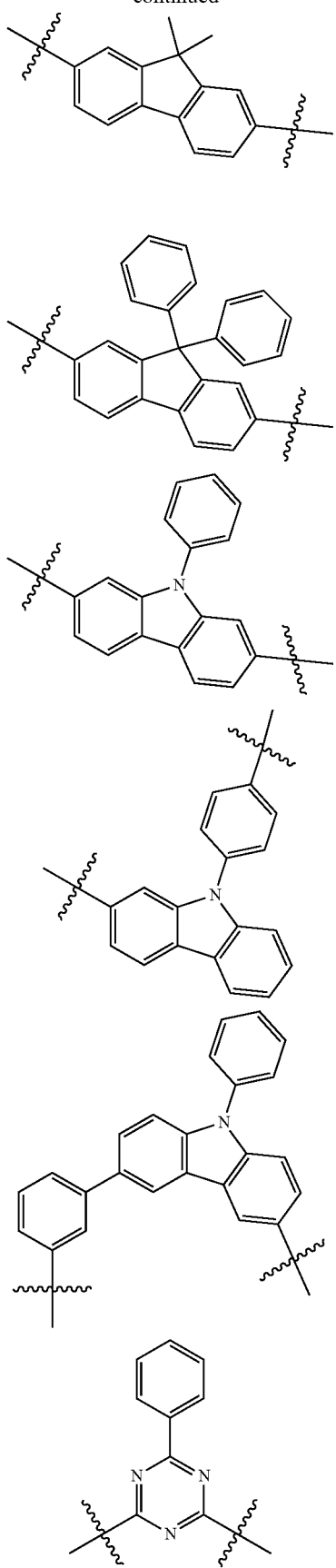
54
-continued
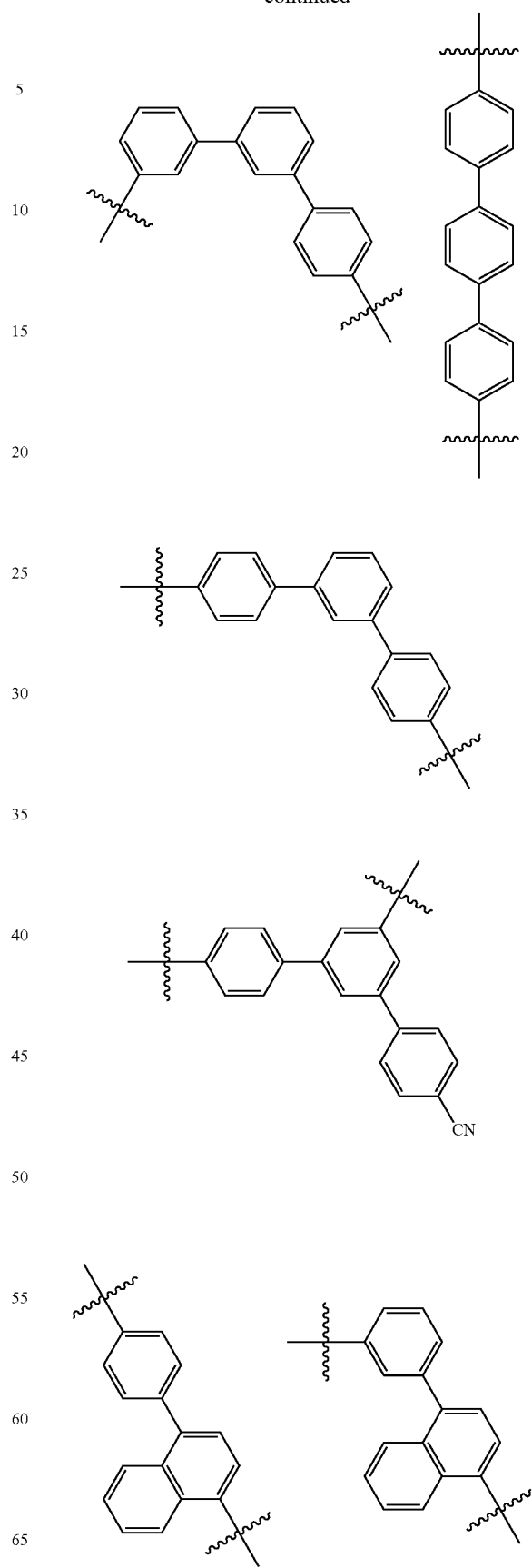

-continued
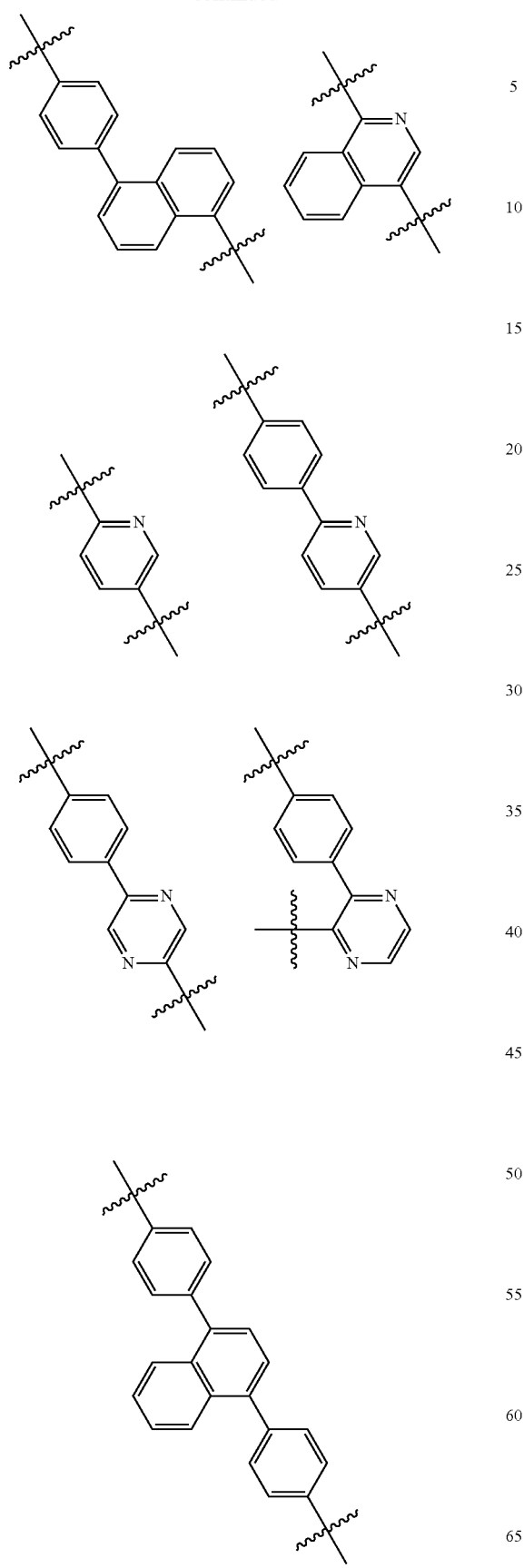
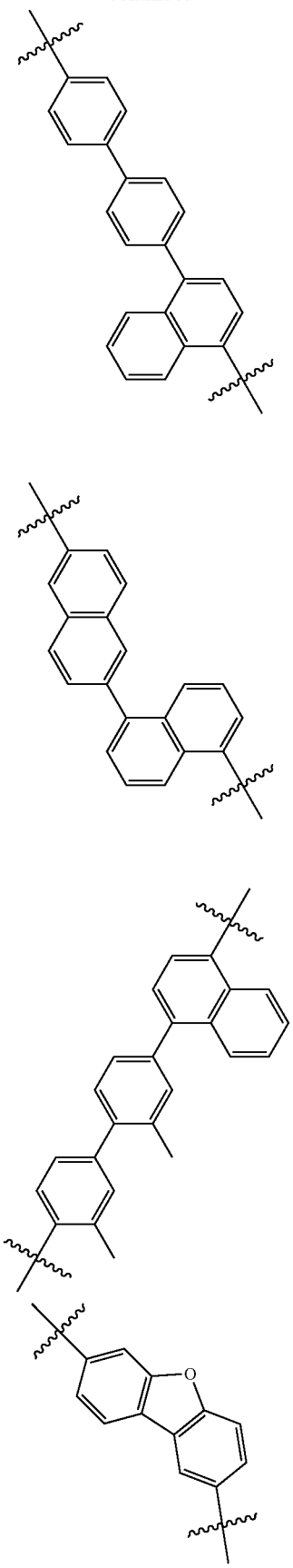

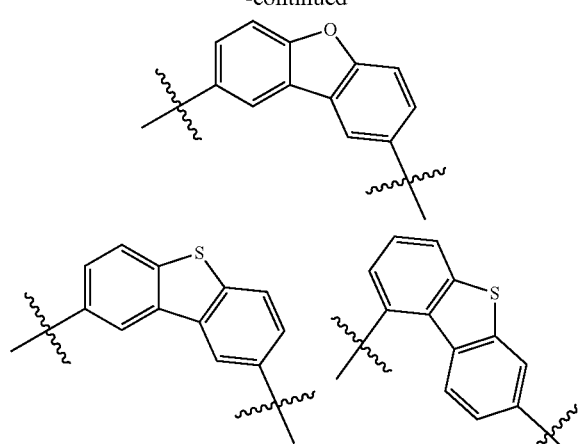

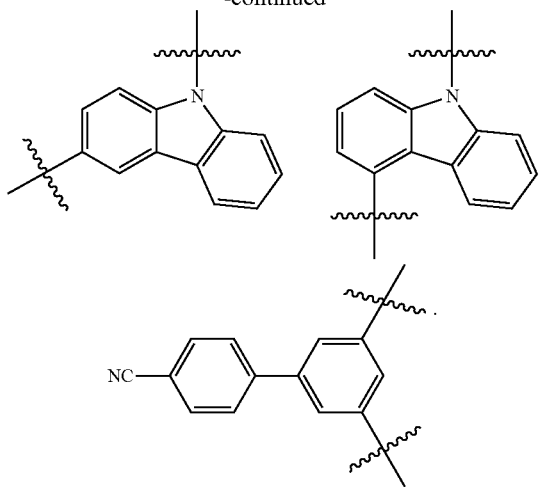

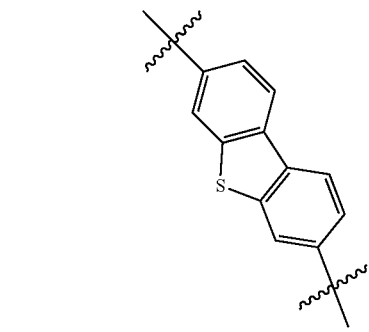

$L_1$ and $L_2$ in the compound of the present disclosure are not limited to the above groups.

Further, in another more specific embodiment of the present disclosure, $L_1$ and $L_2$ may be the same or different, and are each independently selected from the group consisting of the following groups:

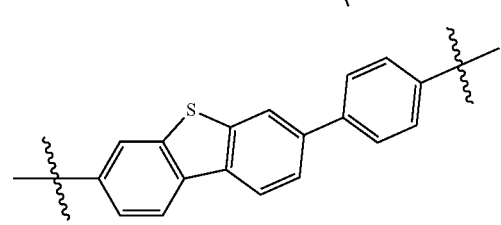

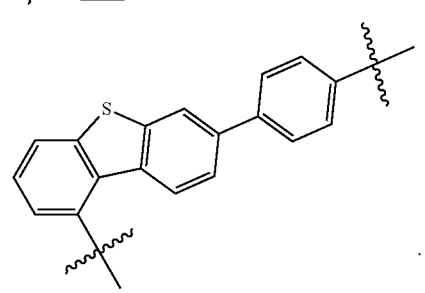

Further, in another more specific embodiments of the present disclosure, $L_1$ and $L_2$ may be the same or different, and are each independently selected from the group consisting of the following groups:

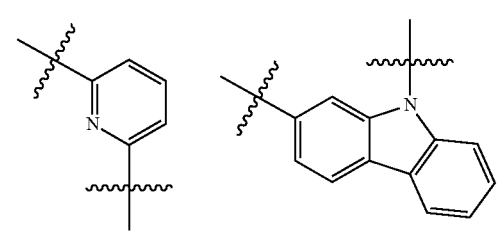

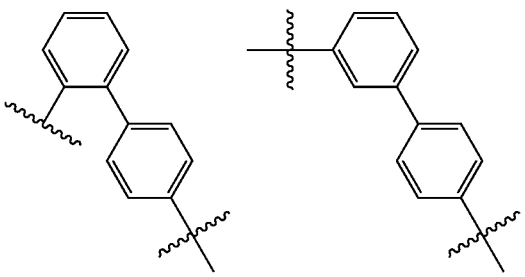

-continued
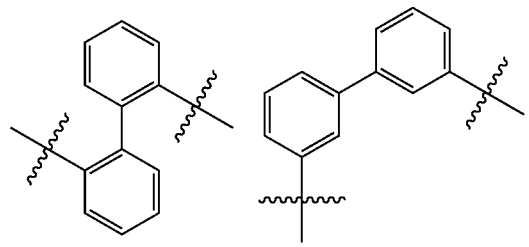
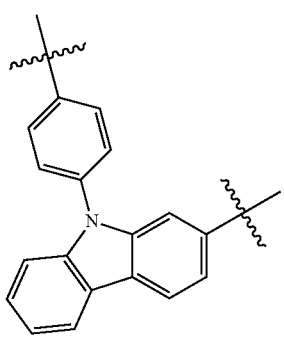
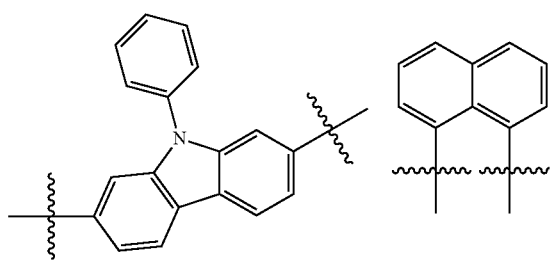
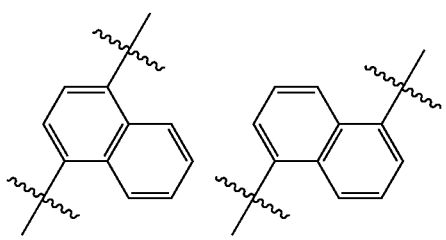
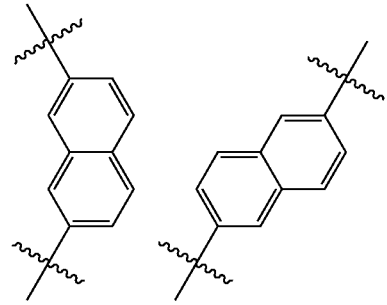
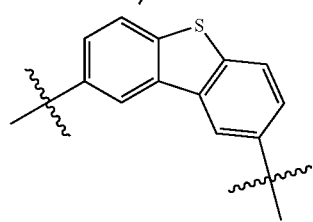
-continued
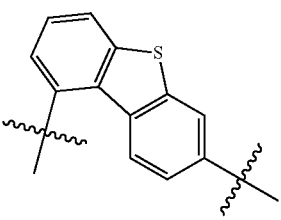
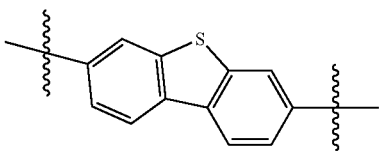
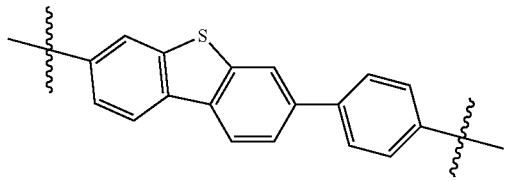
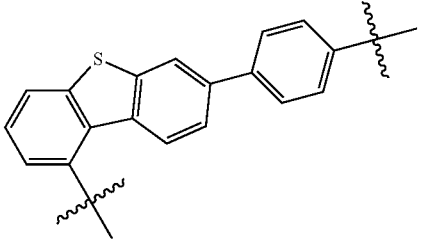
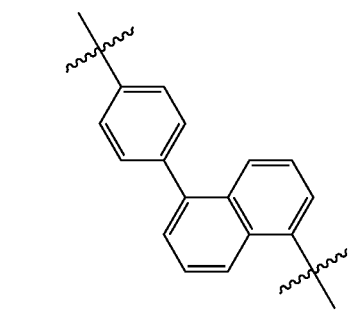
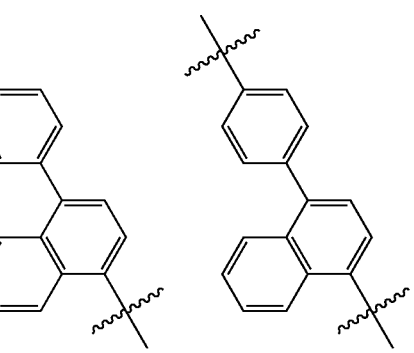
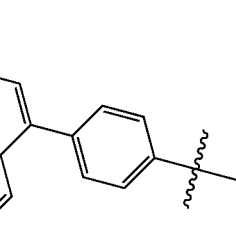

-continued

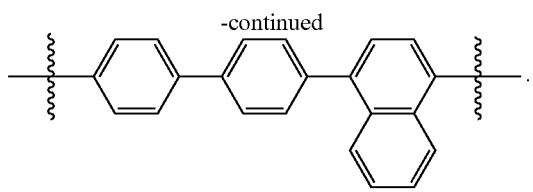

In one embodiment of the present disclosure, the substituents in the $Ar_1$, $Ar_2$, $Ar_3$, $L_1$, $L_2$ and $R_4$ to $R_{11}$ are selected from the group consisting of deuterium, fluorine, chlorine, cyano, alkyl with 1 to 4 carbon atoms, alkoxy with 1 to 4 carbon atoms, haloalkyl with 1 to 4 carbon atoms, alkylsilyl with 3 to 9 carbon atoms, cycloalkyl with 3 to 10 carbon atoms, aryl with 6 to 12 carbon atoms, and heteroaryl with 3 to 12 carbon atoms; when there are a plurality of substituents, the plurality of the substituents are the same or different.

In one embodiment of the present disclosure, at least two of $X_1$, $X_2$ and $X_3$ are N. Specifically, $X_1$ may be N, $X_3$ may be N, $X_2$ may be $C(R^2)$; further, $X_2$ may be N, $X_3$ may be N, $X_1$ may be $C(R^1)$, or $X_1$ is N, $X_2$ is N and $X_3$ is $C(R^3)$.

In one embodiment of the present disclosure, $X_1$, $X_2$ and $X_3$ are respectively N; that is, the organic compound of the present disclosure has the structure as shown in the following Formula (1'):

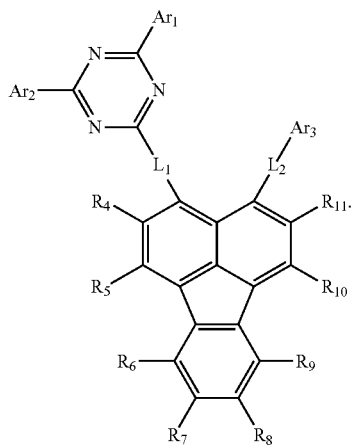

Formula (1')

In one embodiment of the present disclosure, $R_5$, $R_6$, $R_7$, $R_8$, $R_9$ and $R_{10}$ are the same or different, and are each independently selected from the group consisting of hydrogen, deuterium, halogen, cyano, alkyl with 1 to 6 carbon atoms, haloalkyl with 1 to 6 carbon atoms, alkoxy with 1 to 6 carbon atoms, alkylsilyl with 1 to 12 carbon atoms, cycloalkyl with 3 to 20 carbon atoms, alkylamino with 1 to 6 carbon atoms, aryl with 6 to 20 carbon atoms, and heteroaryl with 2 to 20 carbon atoms; $R_4$ and $R_{11}$ are respectively hydrogen.

In a more specific embodiment of the present disclosure, $R_4$ to $R_{11}$ are the same as or different from each other, and are each independently selected from the group consisting of deuterium, fluorine, chlorine, cyano, methyl, ethyl, isopropyl, tert-butyl, methoxy, ethyoxyl, isopropoxy, trimethylsilyl, trifluoromethyl, dimethylamino, phenyl, naphthyl, and quinolyl.

In one embodiment of the present disclosure, $R_4$, $R_5$, $R_6$, $R_7$, $R_8$, $R_9$, $R_{10}$ and $R_{11}$ are respectively N; that is, the organic compound of the present disclosure has the structure as shown in the following Formula (1'):

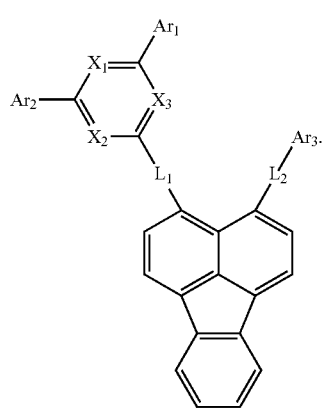

Formula (1")

In a more specific embodiment of the present disclosure, the organic compound may be selected from one or more of the following compounds 1 to 400:

1

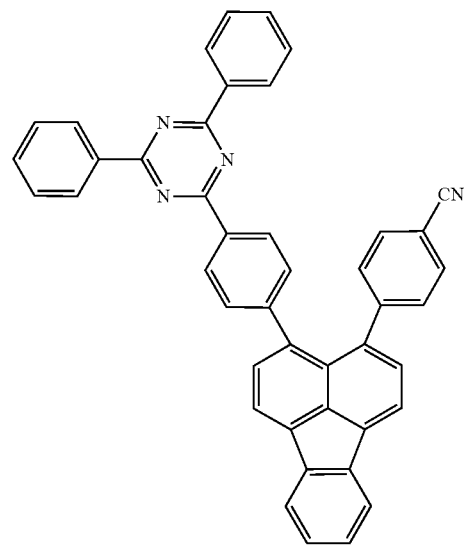

2

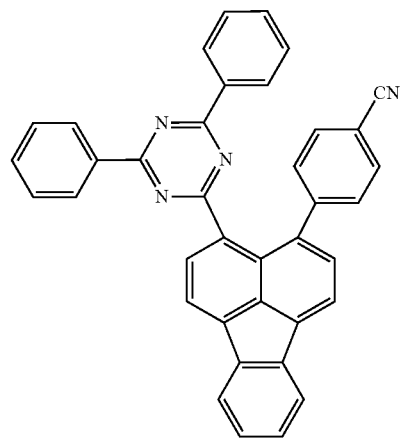

-continued
3
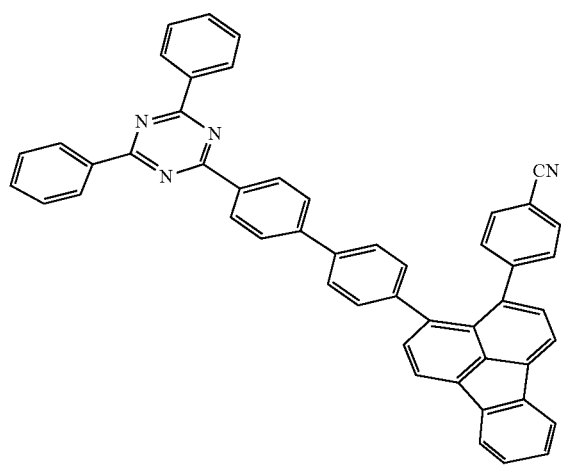
4
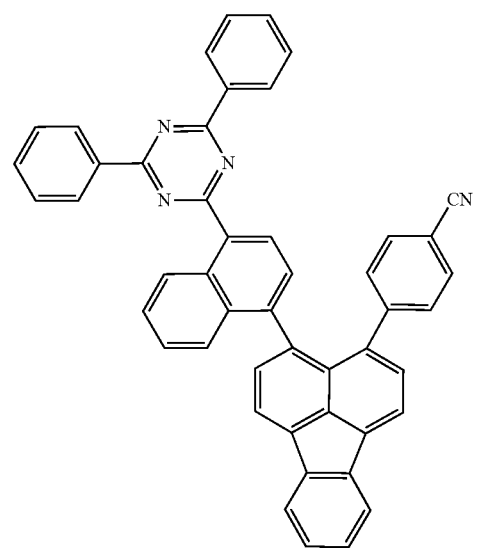
5
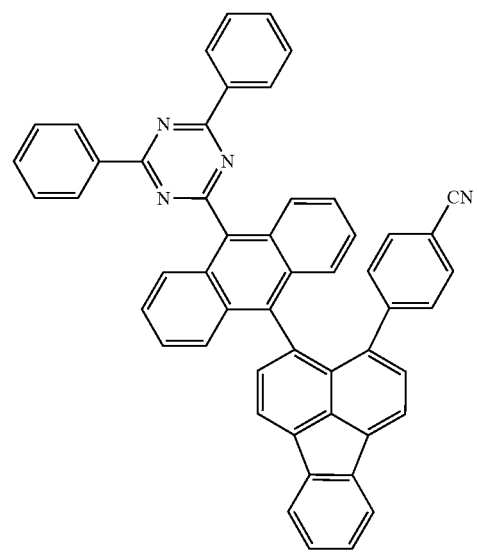
-continued
6
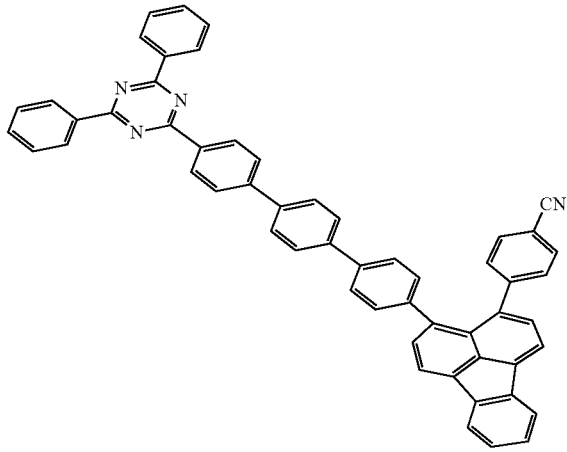
7
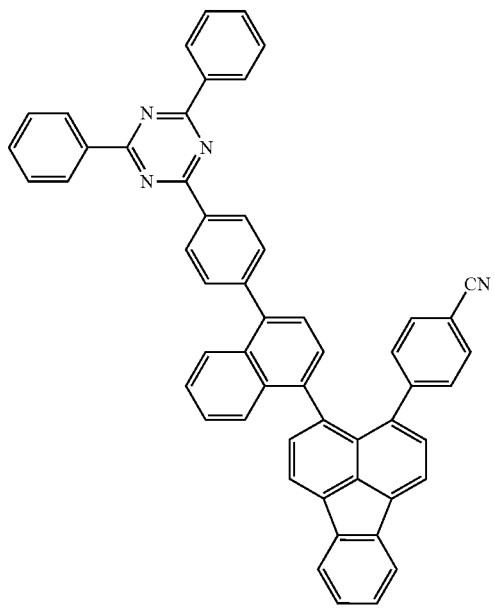
8
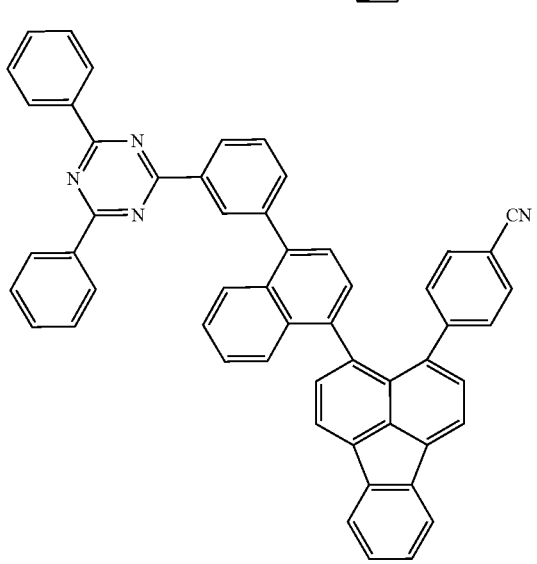

9
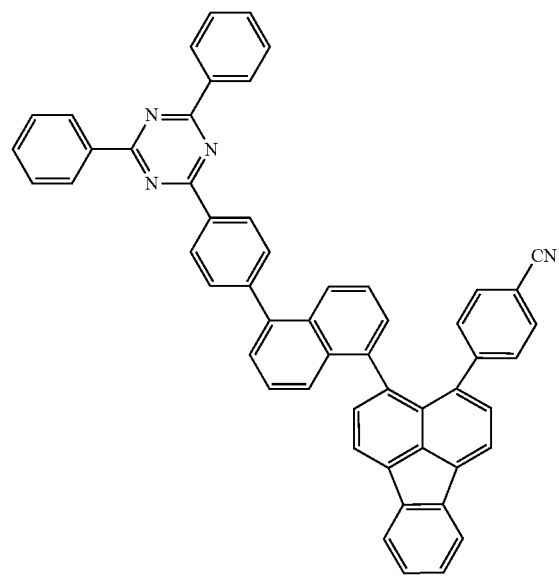
10
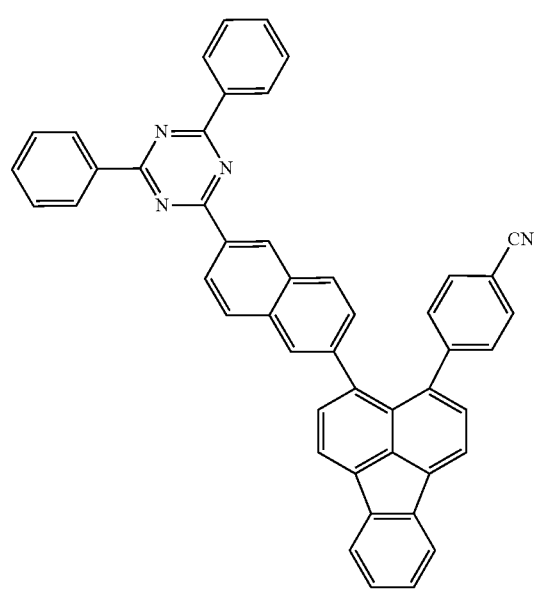
11
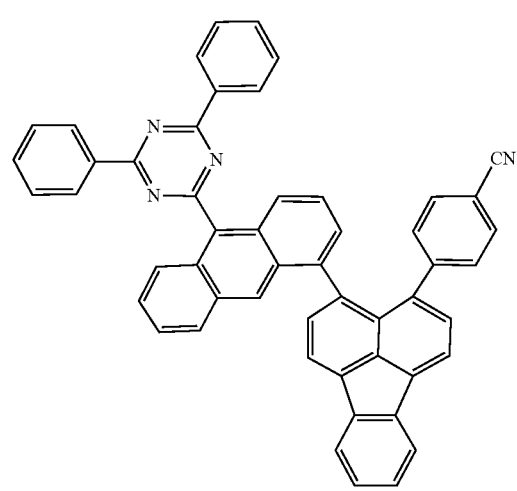
12
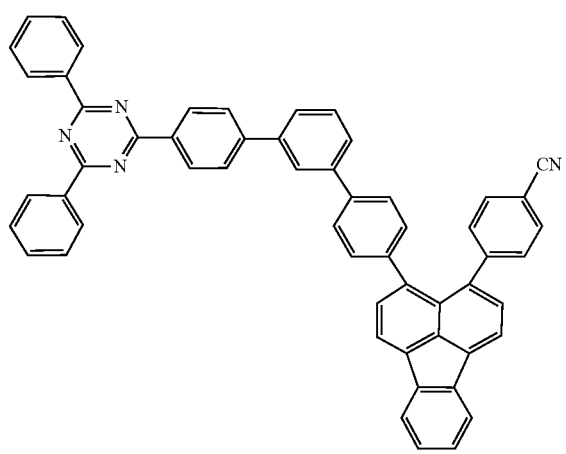
13
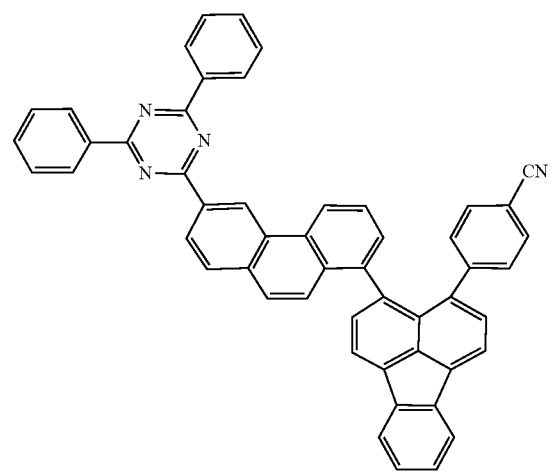
14
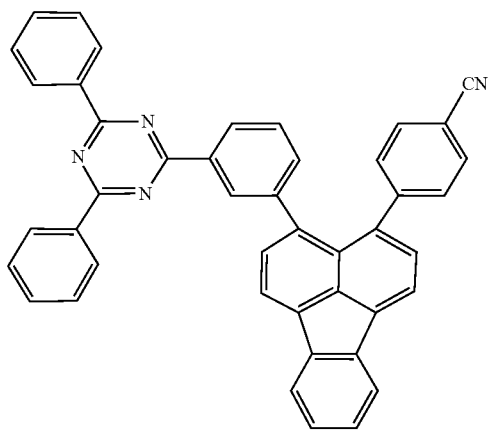

15
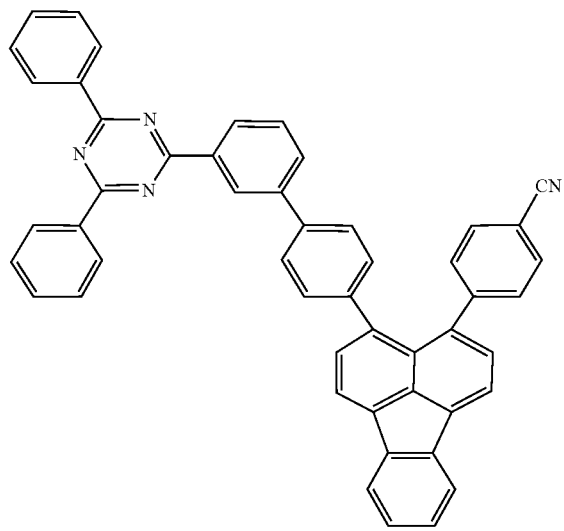
16
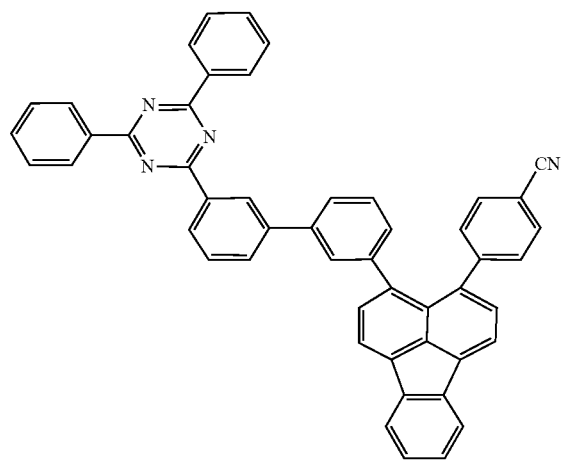
17
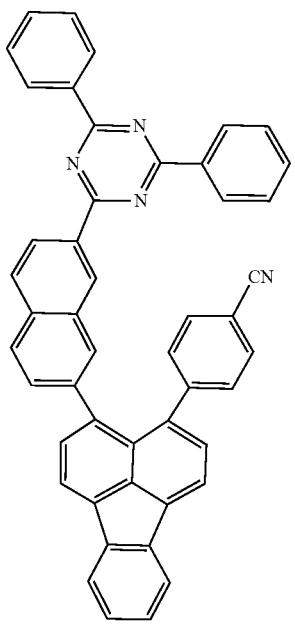
18
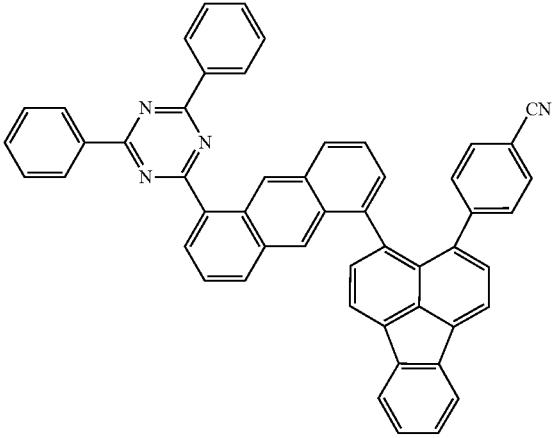
19
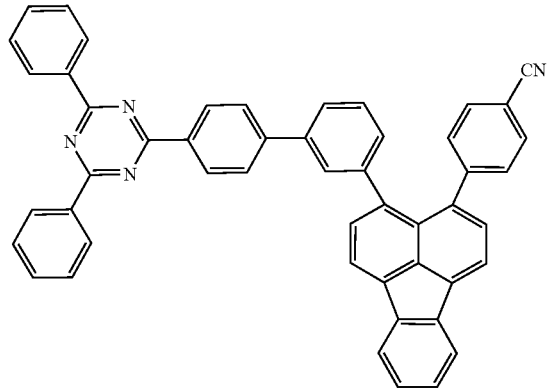
20
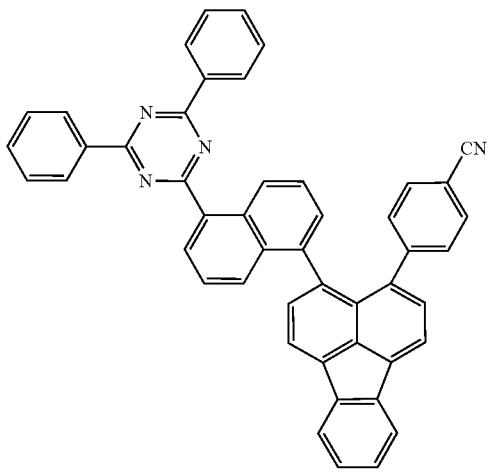

21
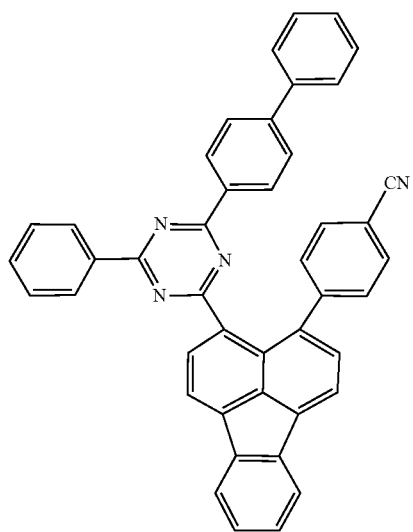
22
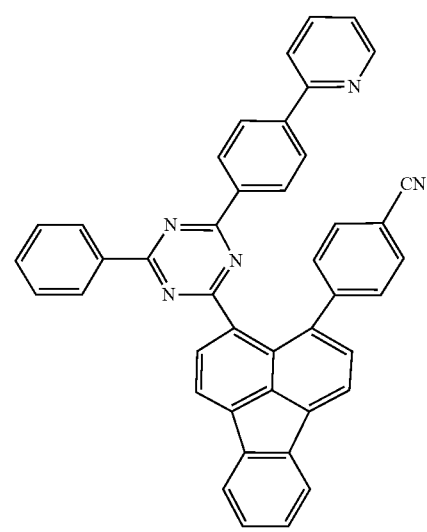
23
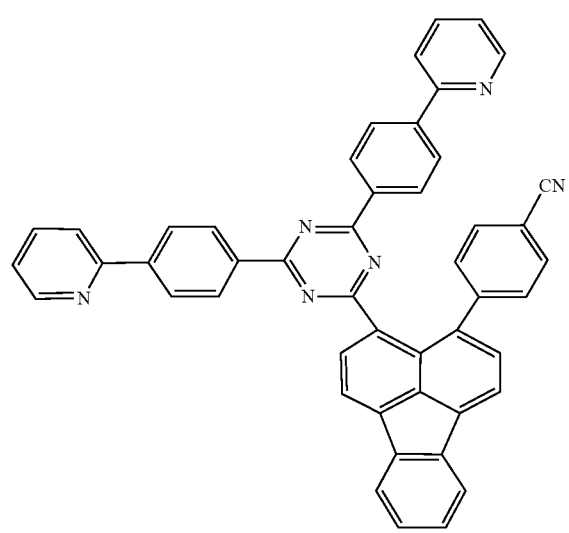
24
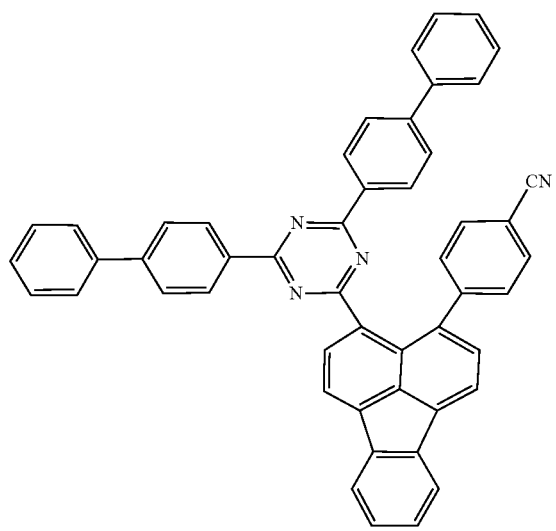
25
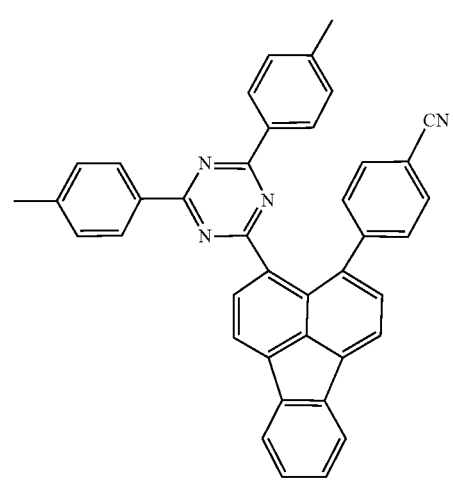
26
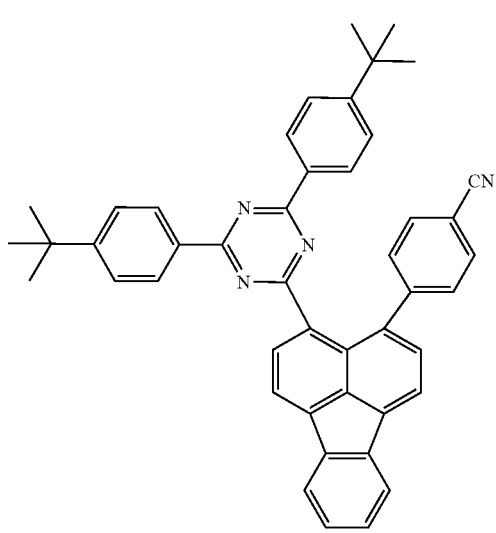

27
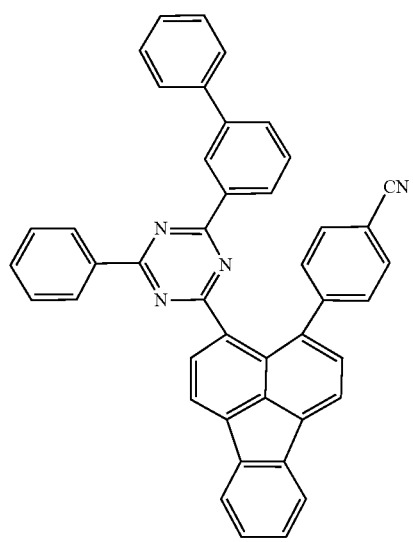
28
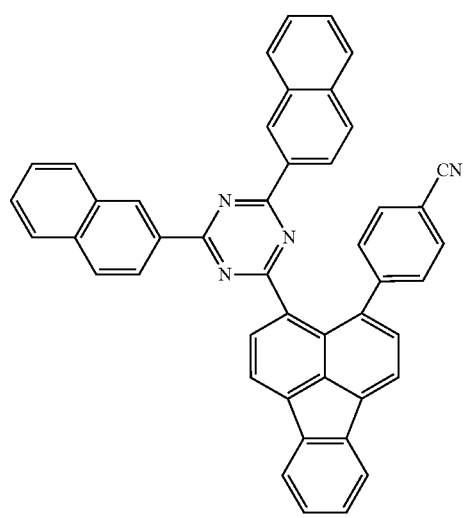
29
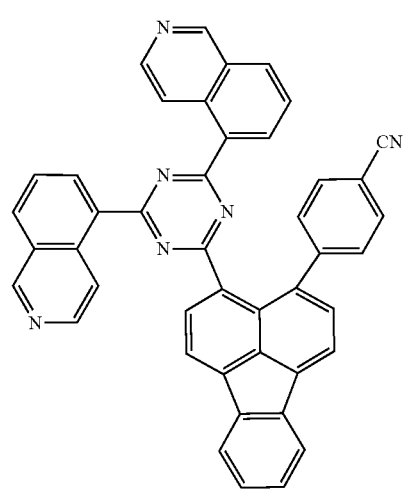
30
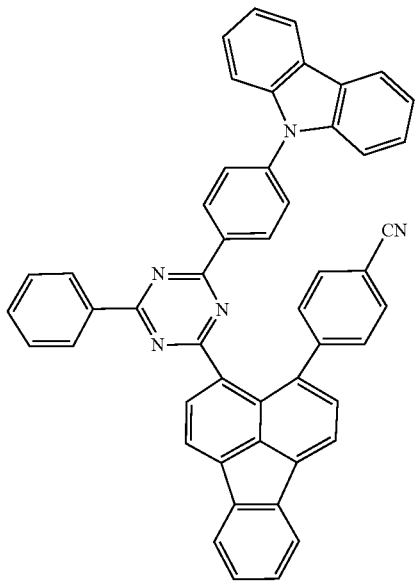
31
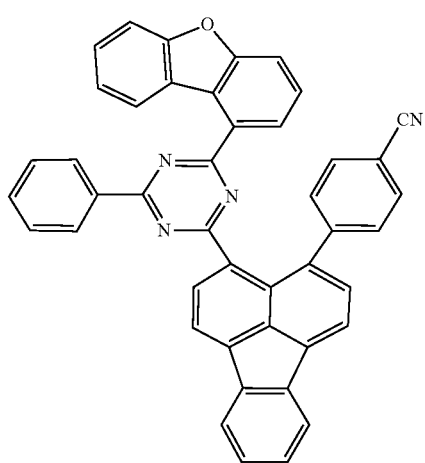
32
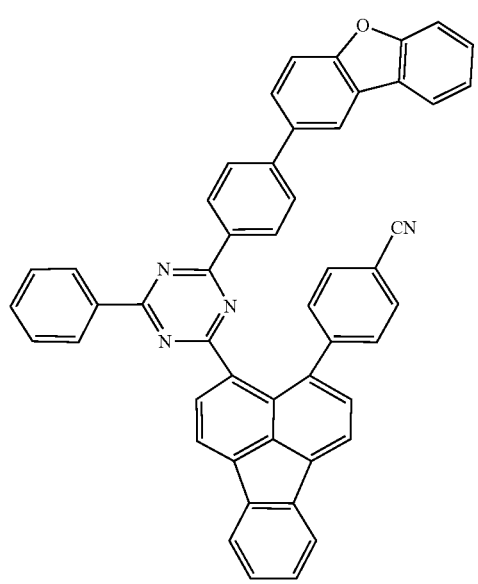

-continued
33
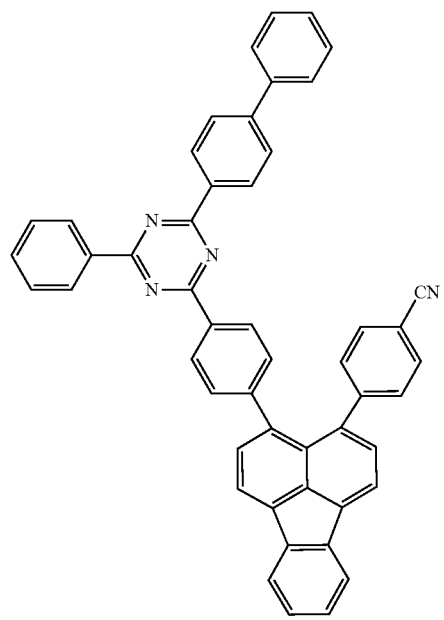
35
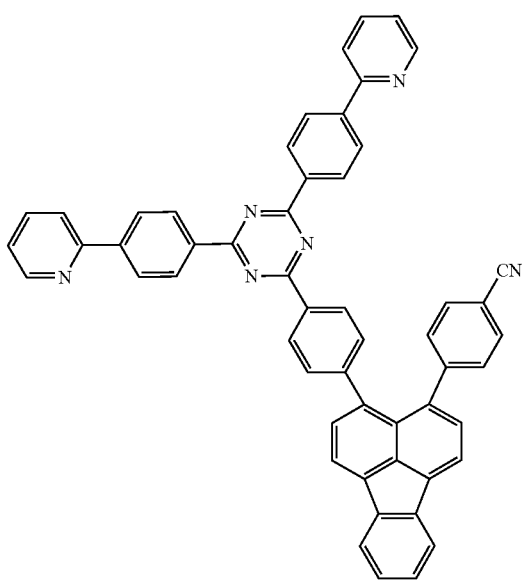
34
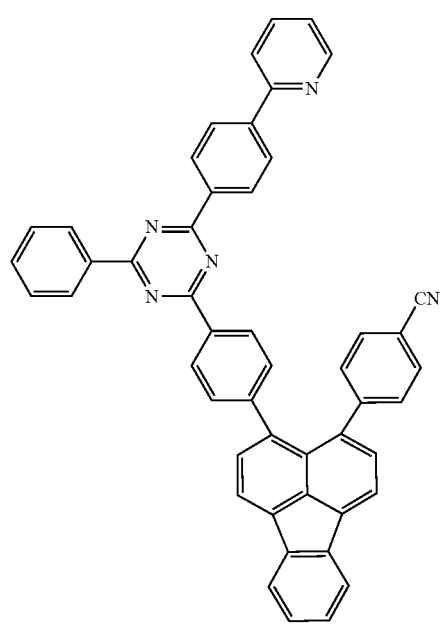
36
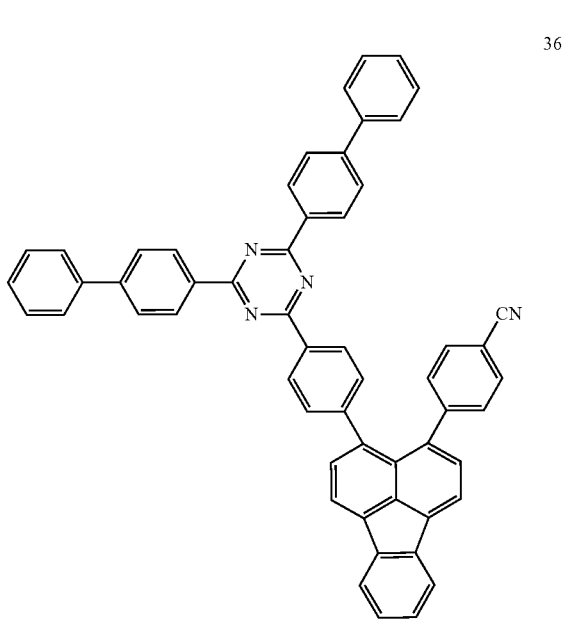

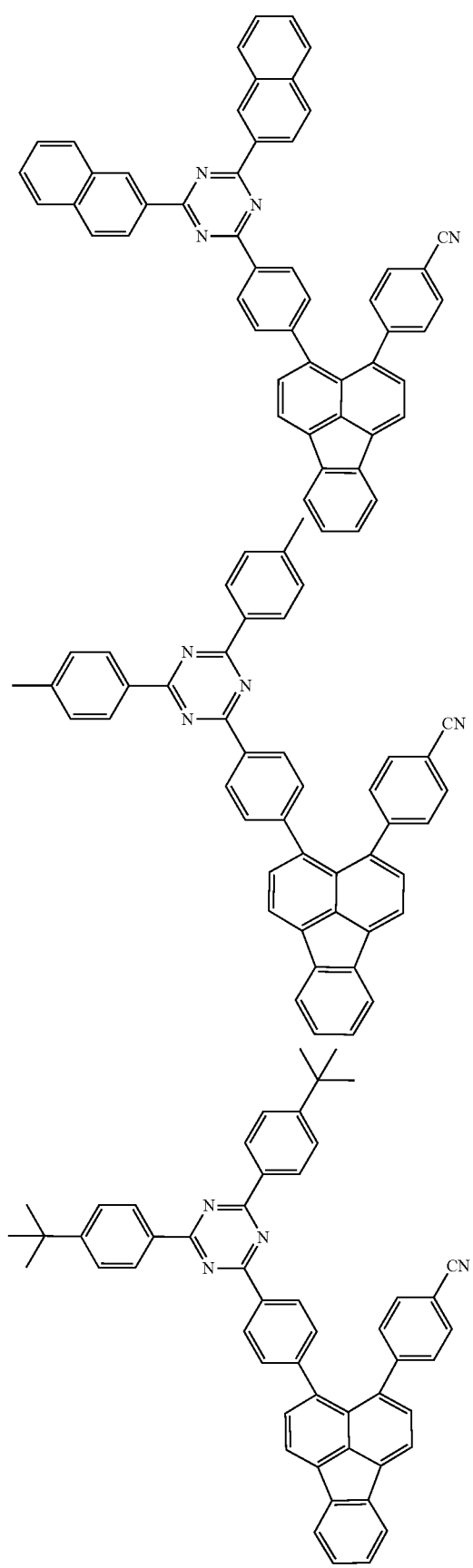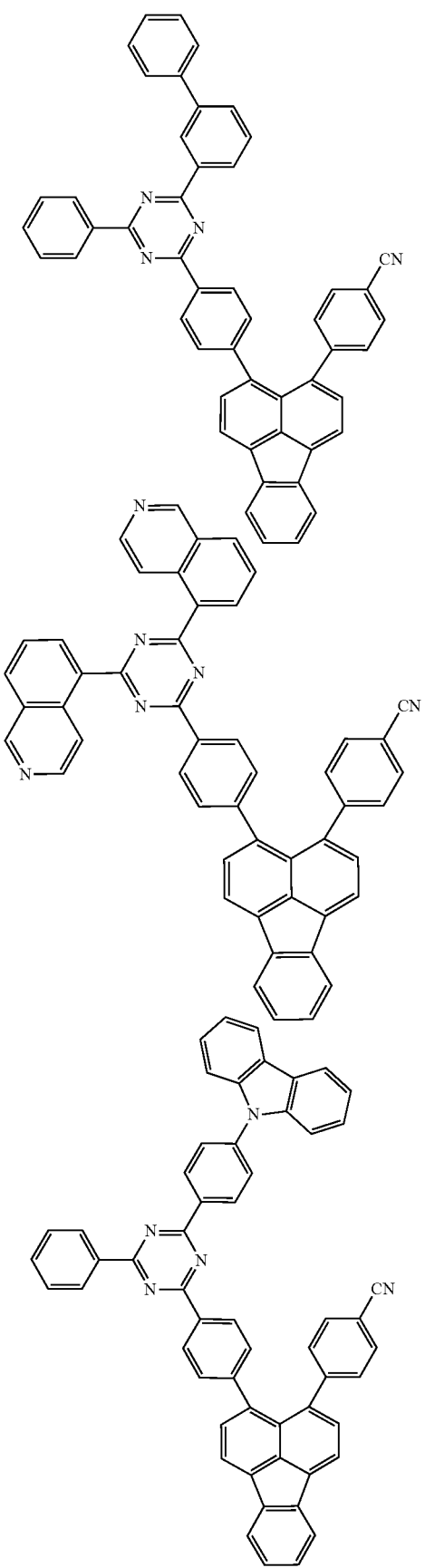

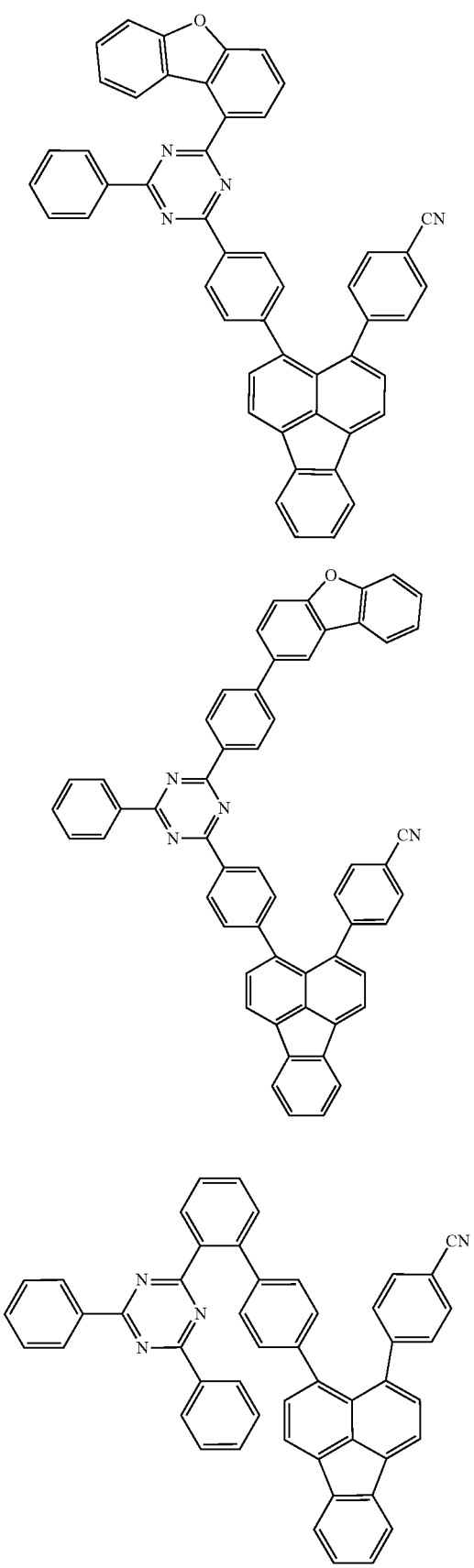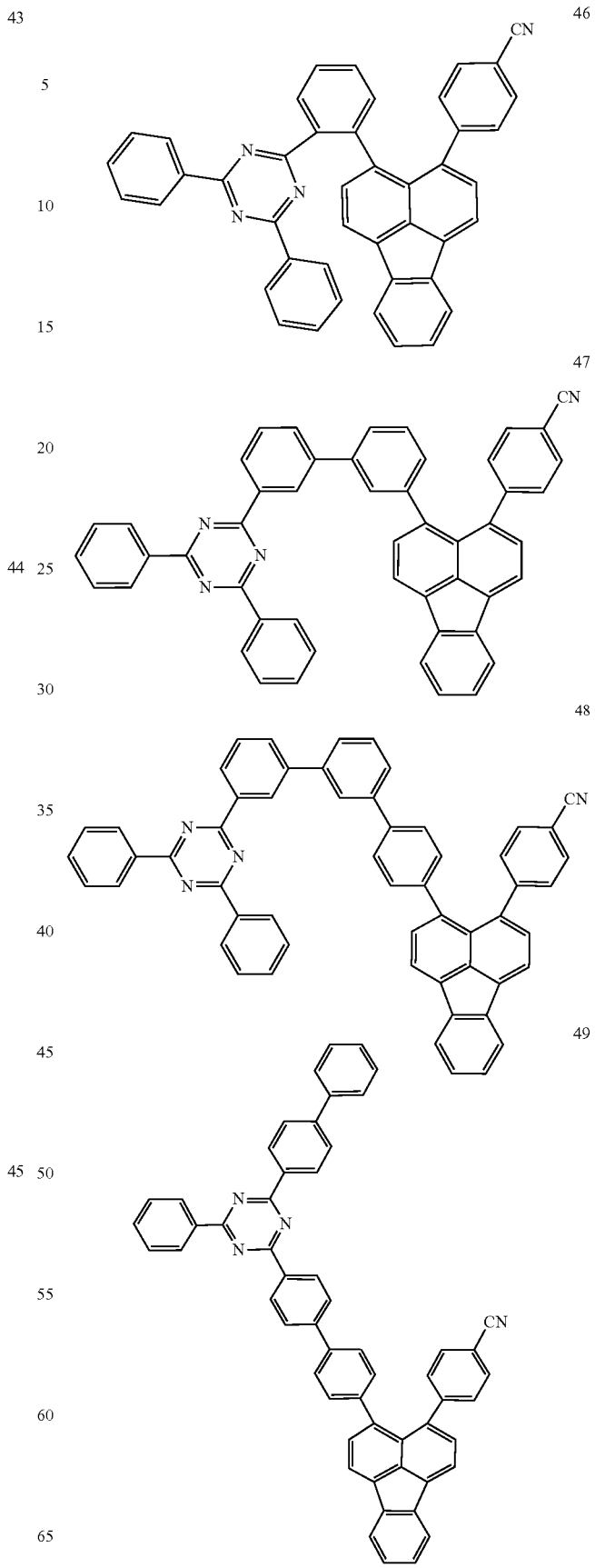

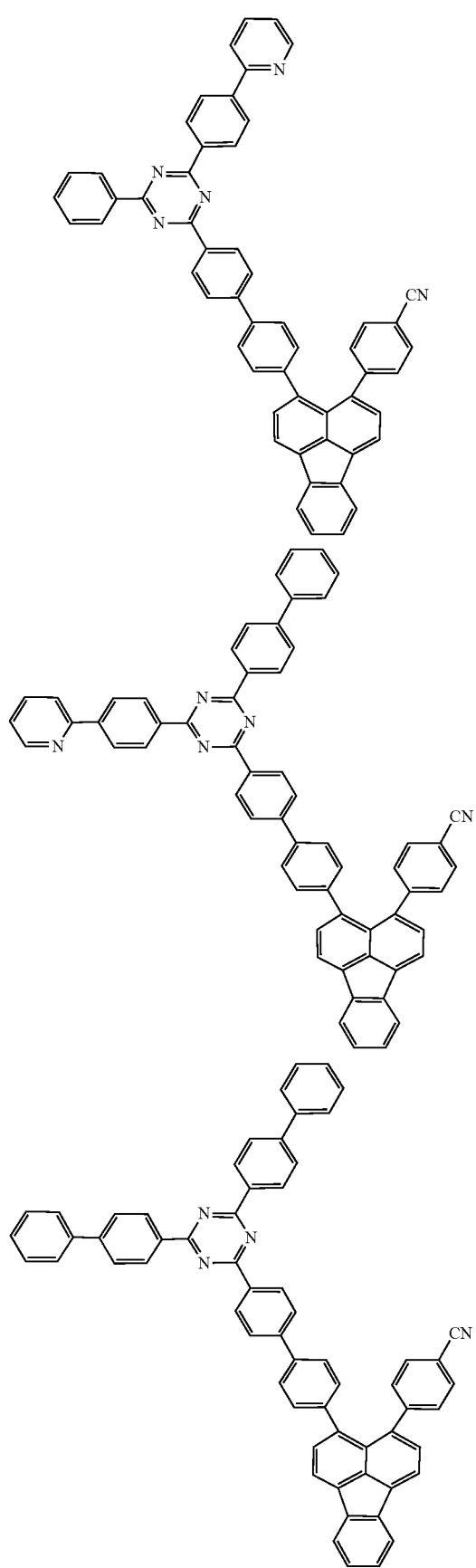
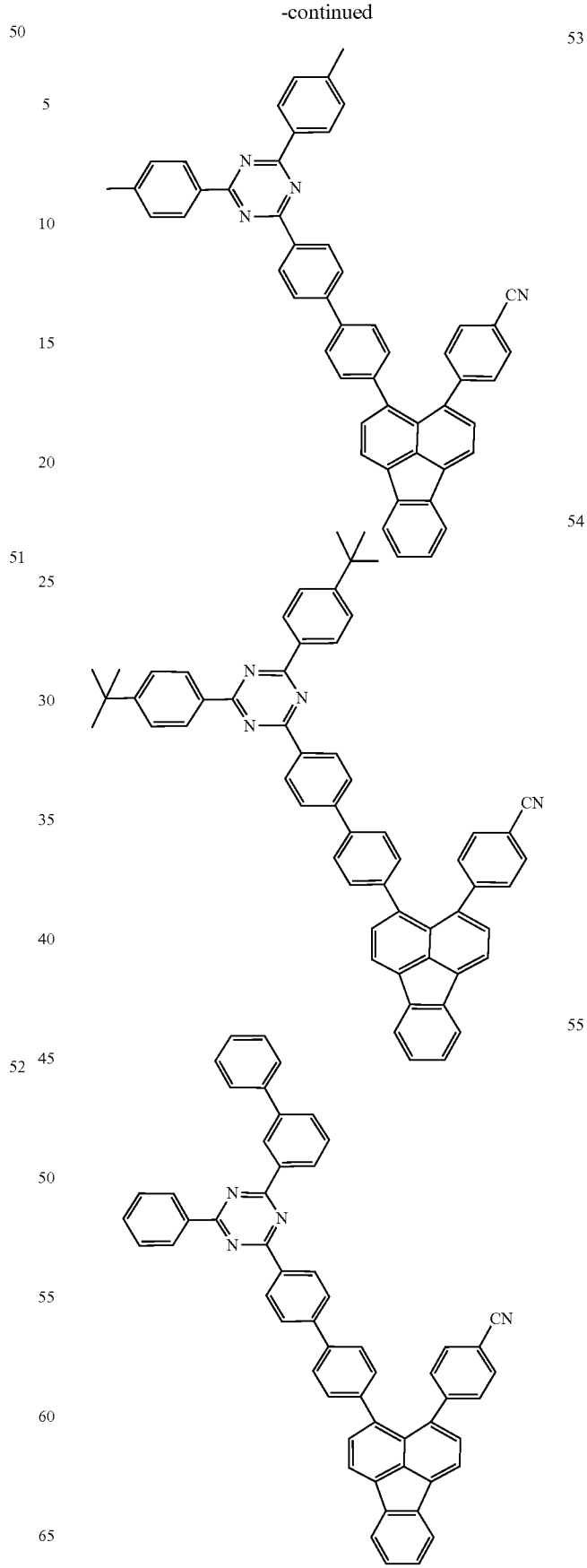

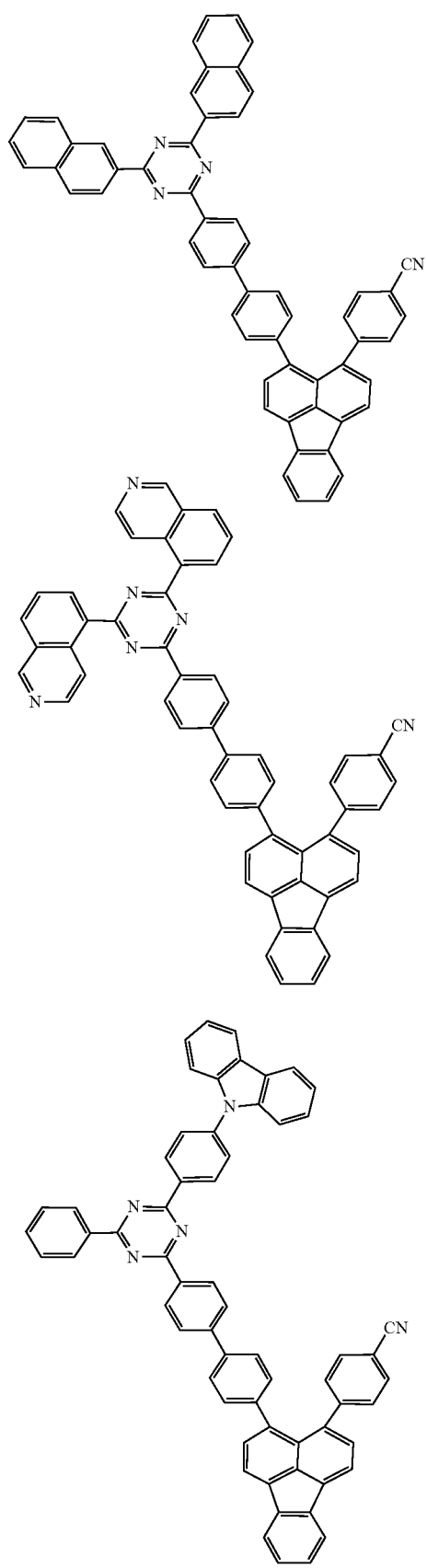
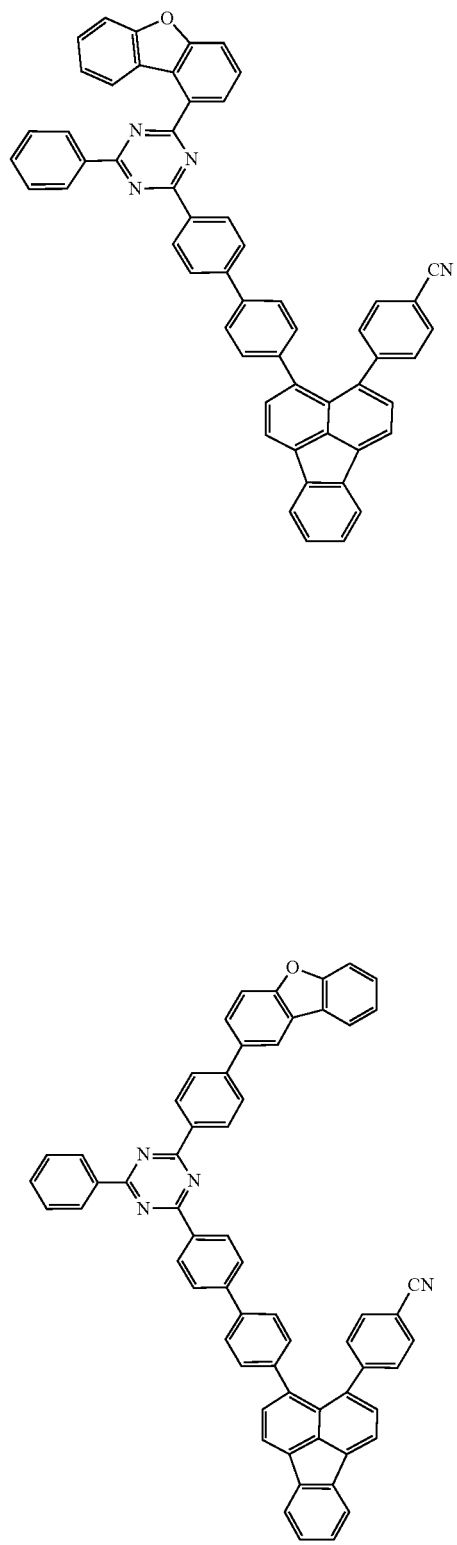

61
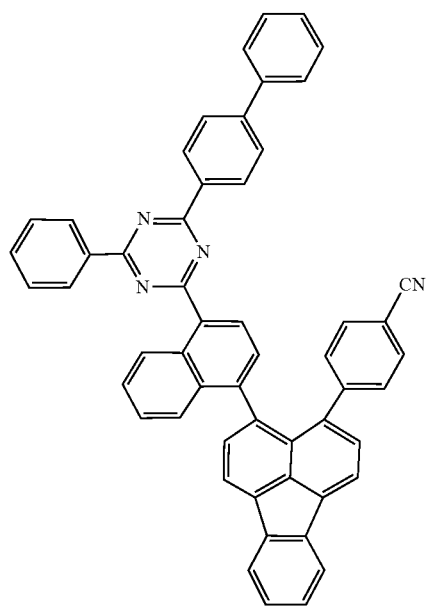
62
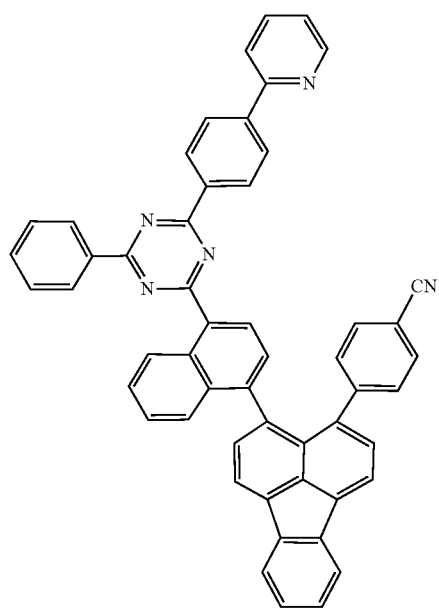
63
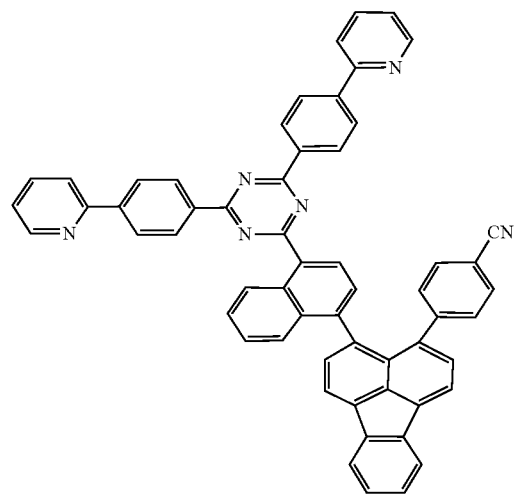
64
65
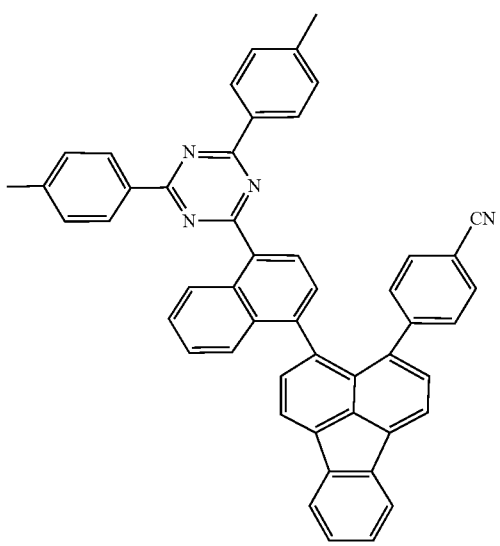

66
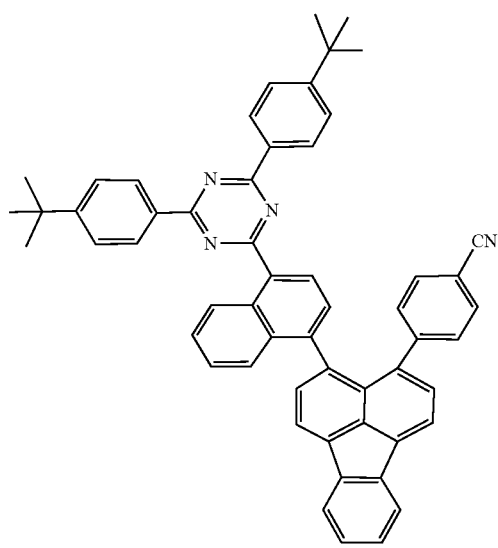
67
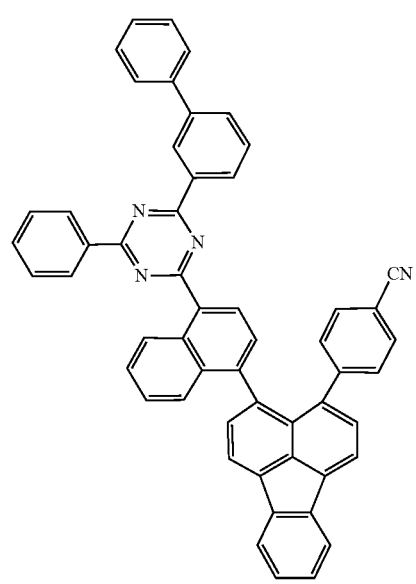
68
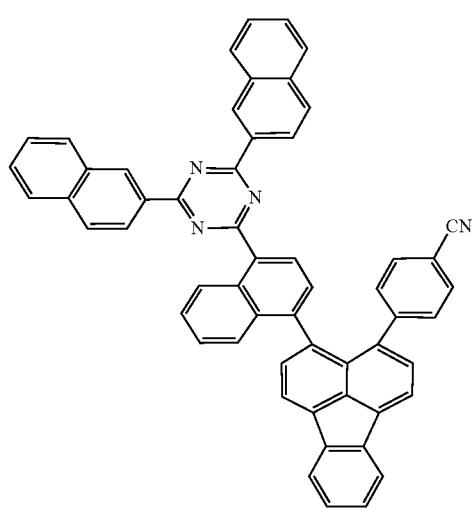
69
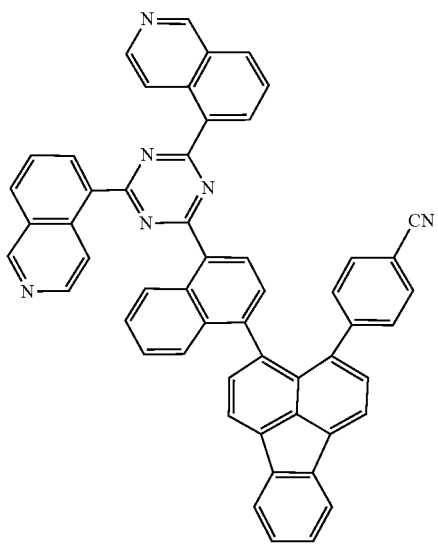
70
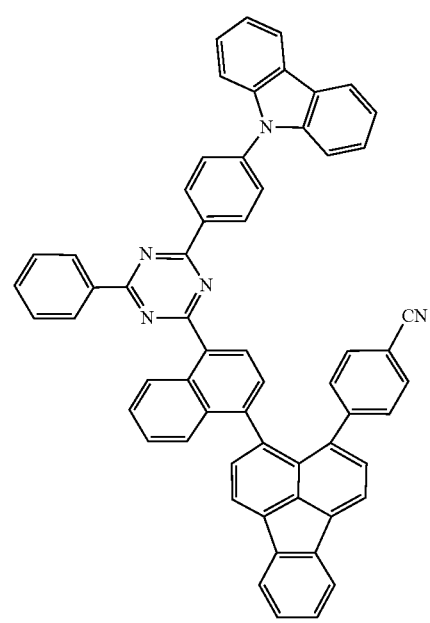
71
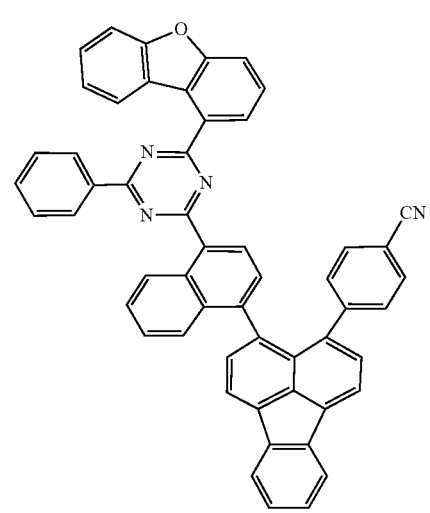

72
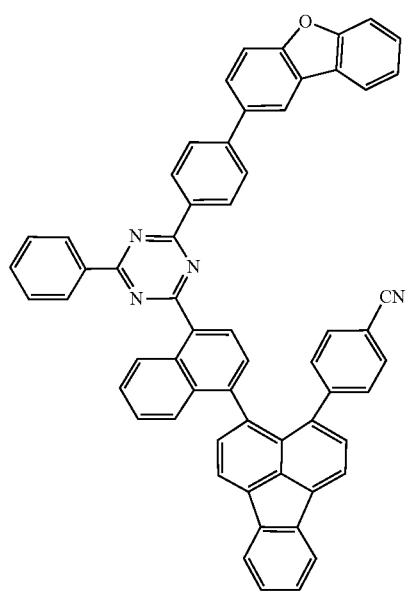
73
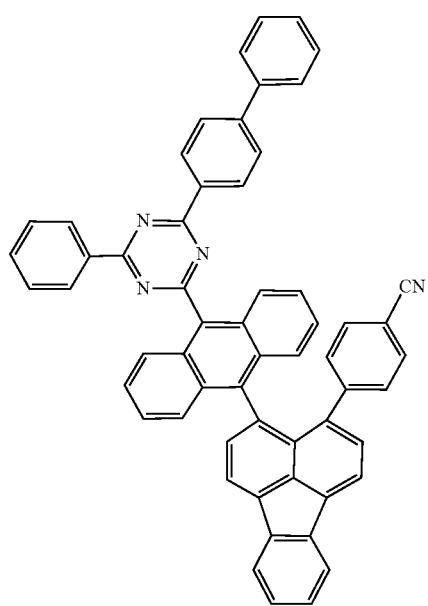
74
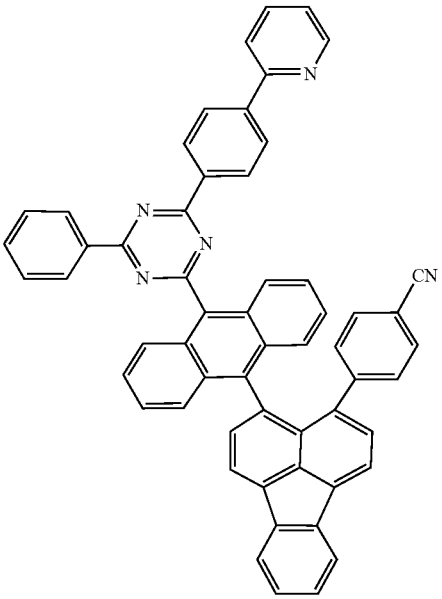
75
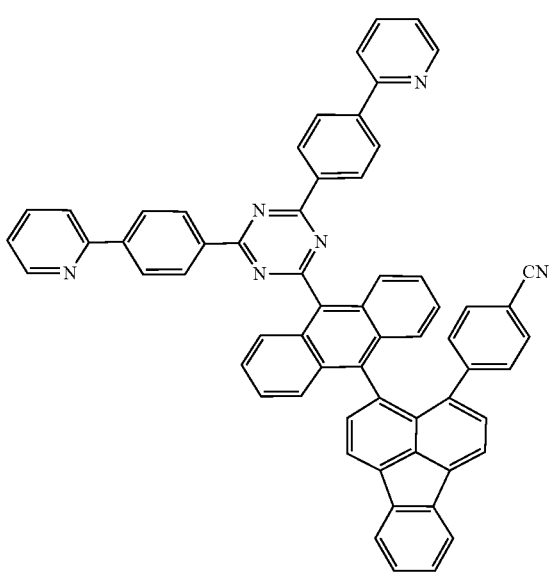

76
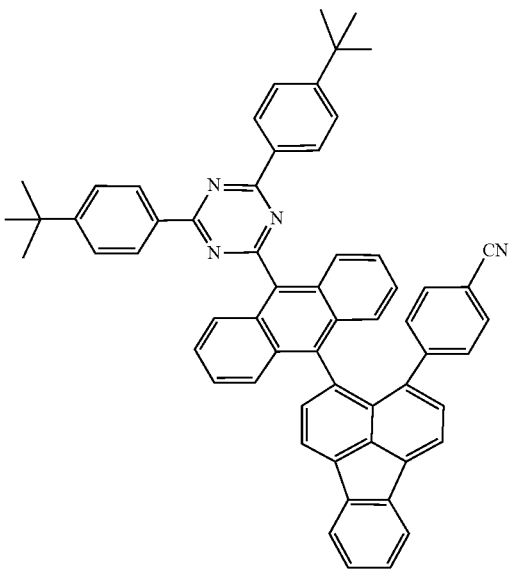
78
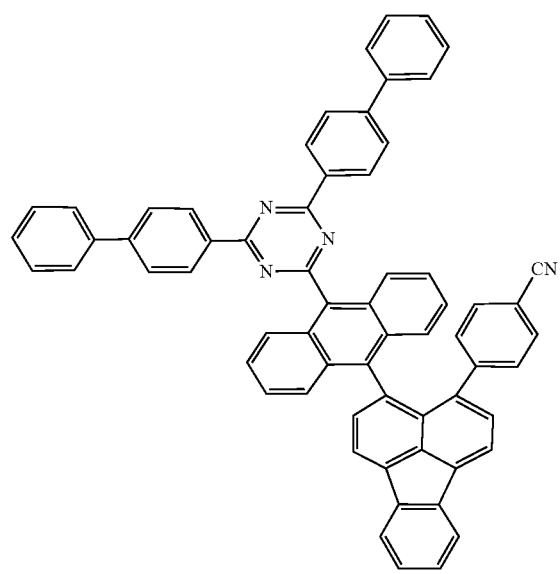
77
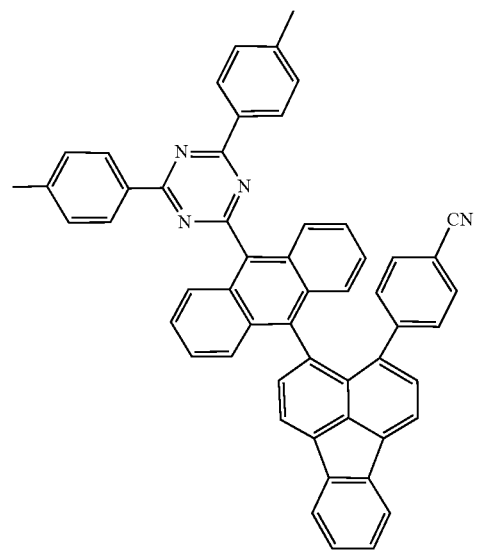
79
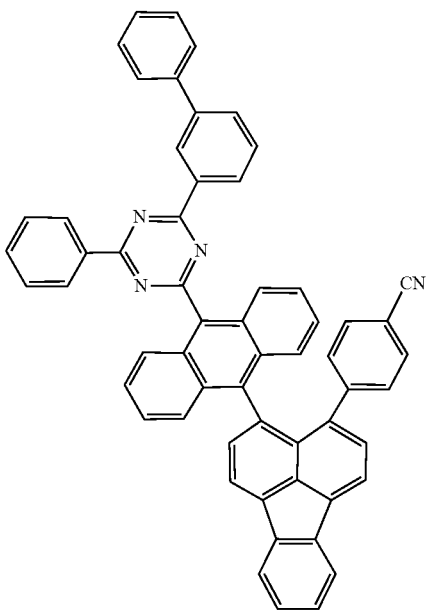

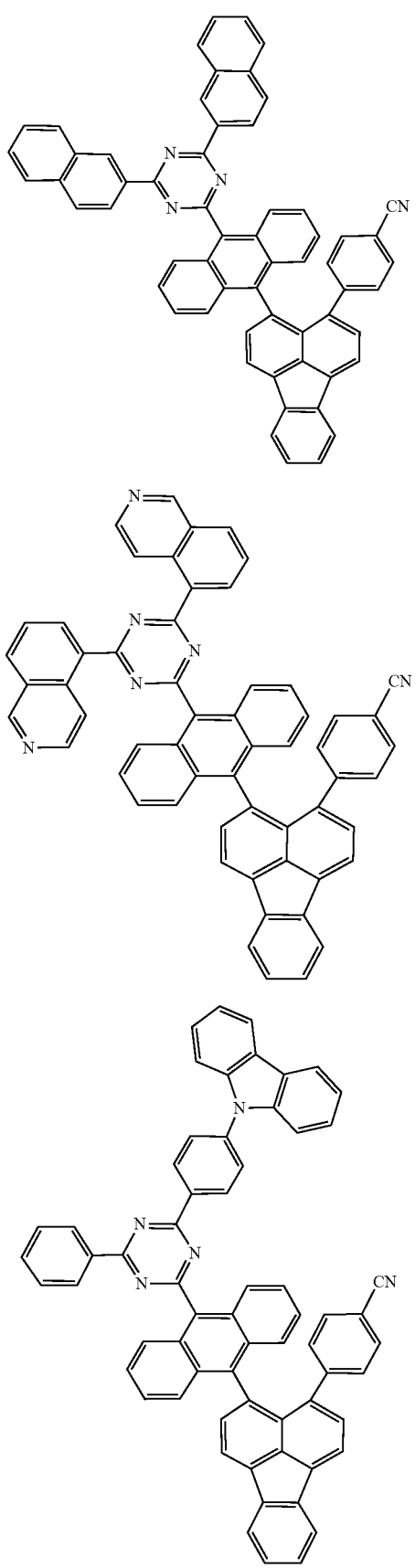
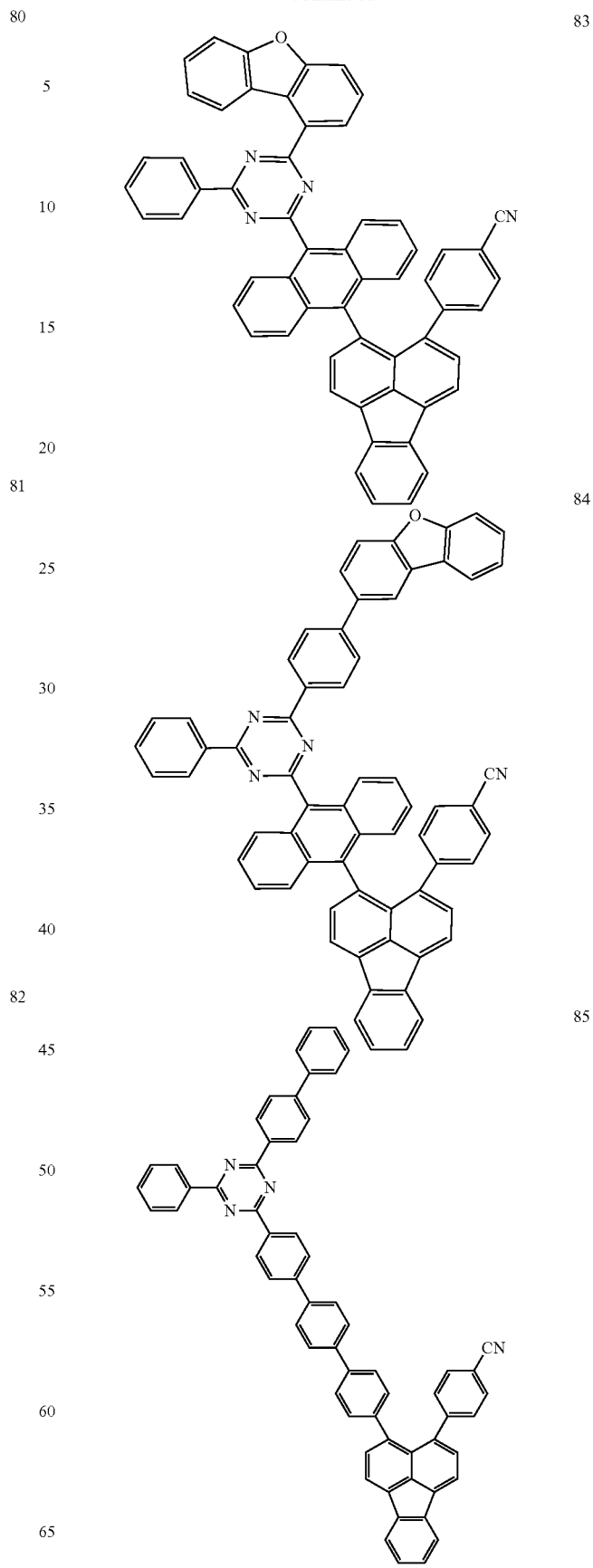

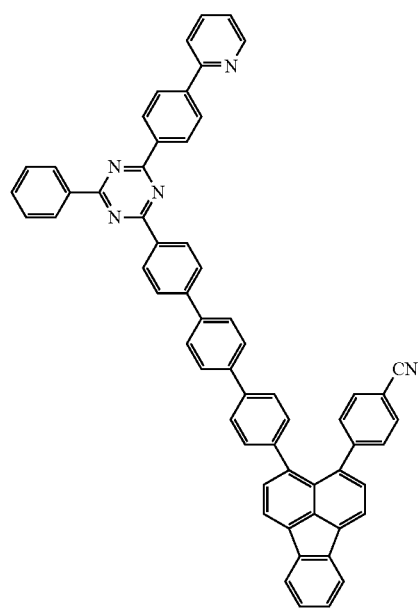
86
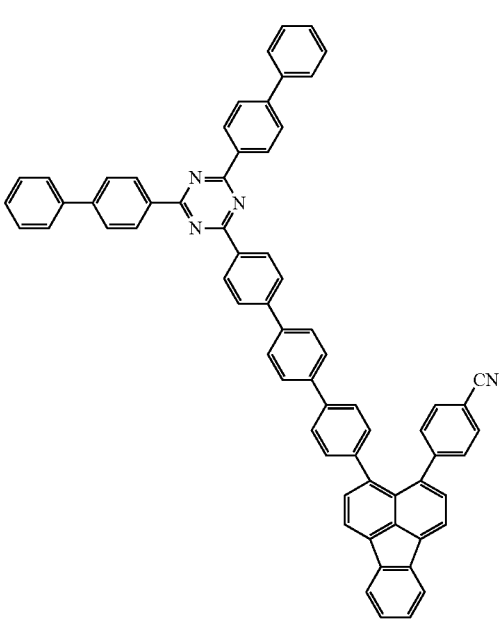
88
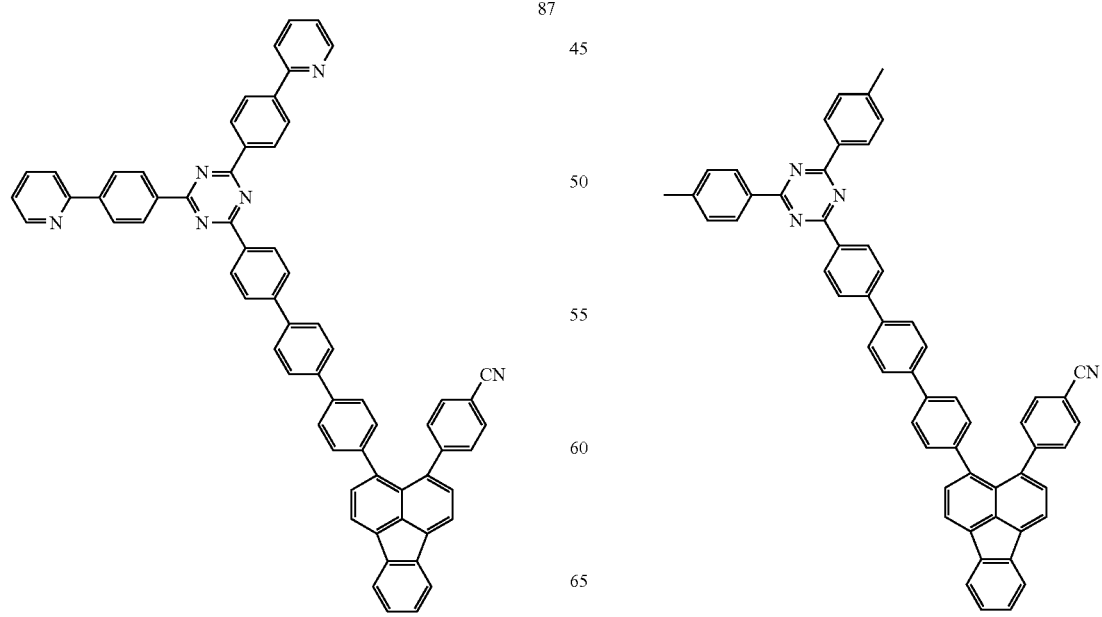
87
89

90
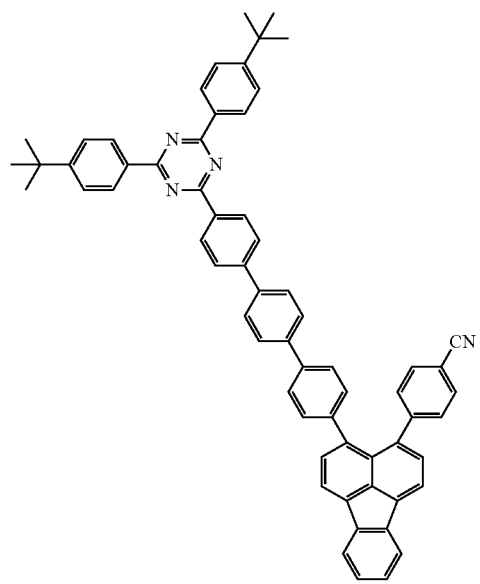
91
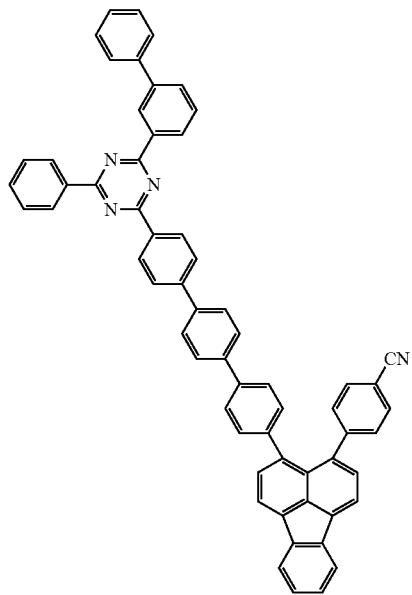
92
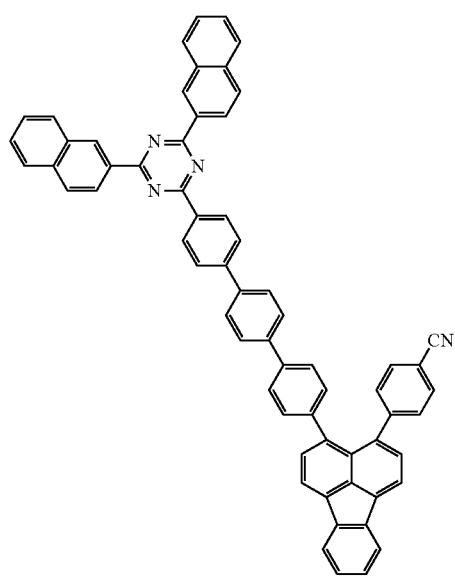
93
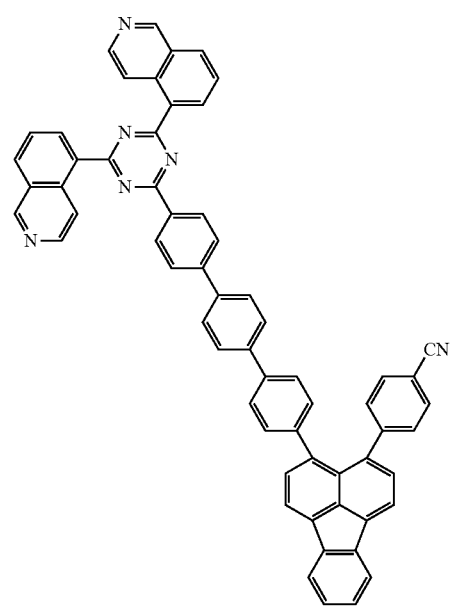

94
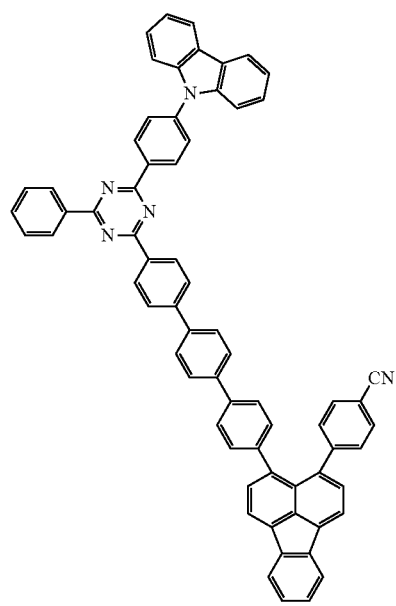
95
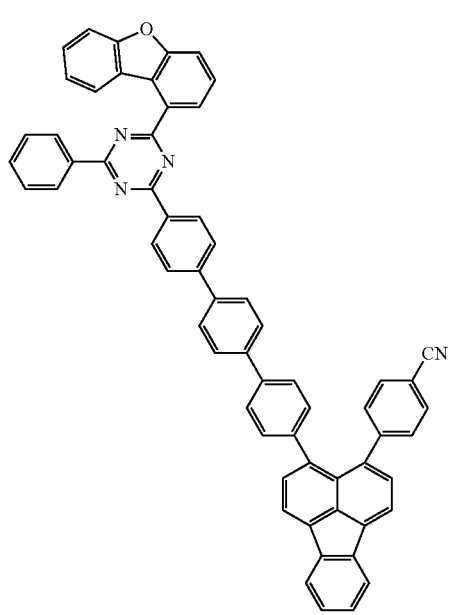
96
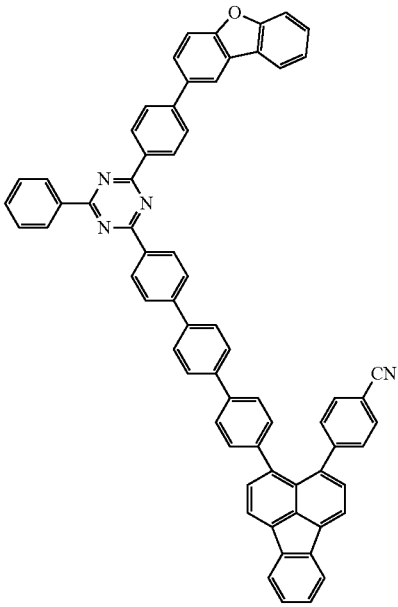
97
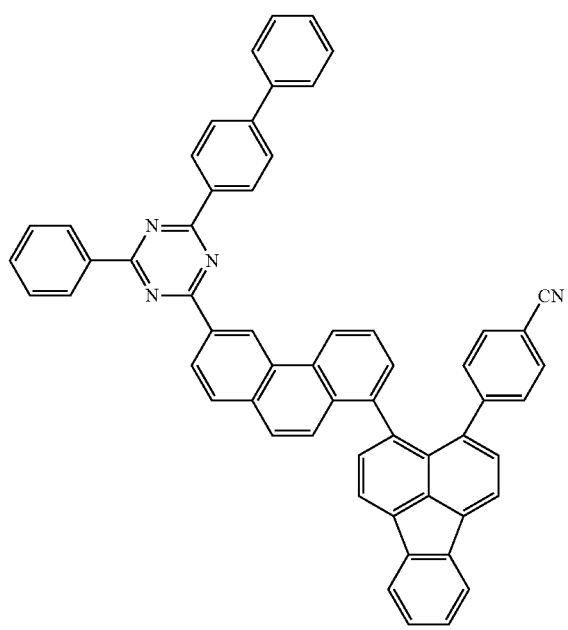

98
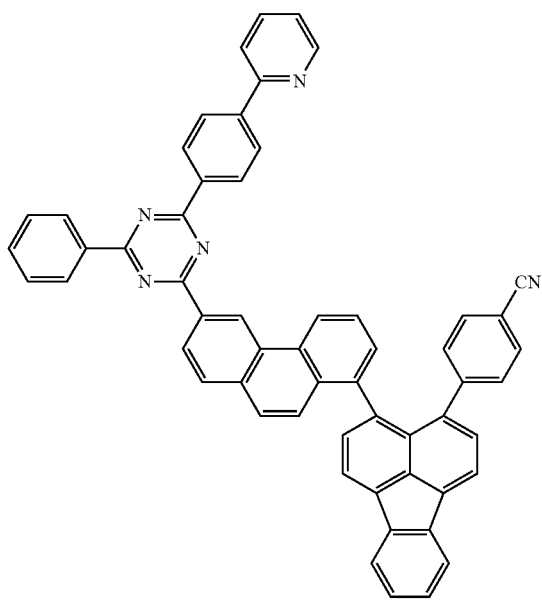
99
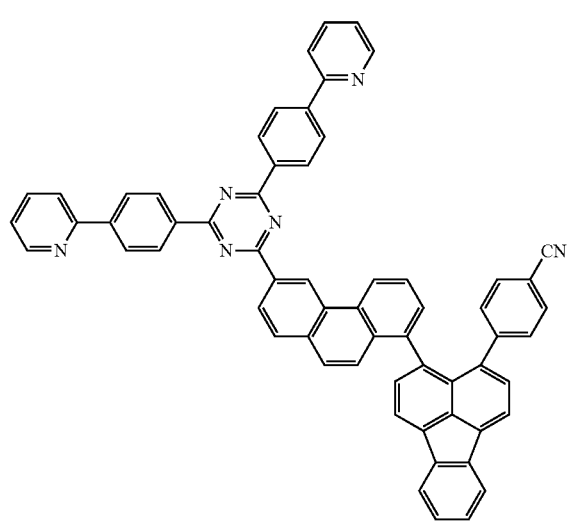
100
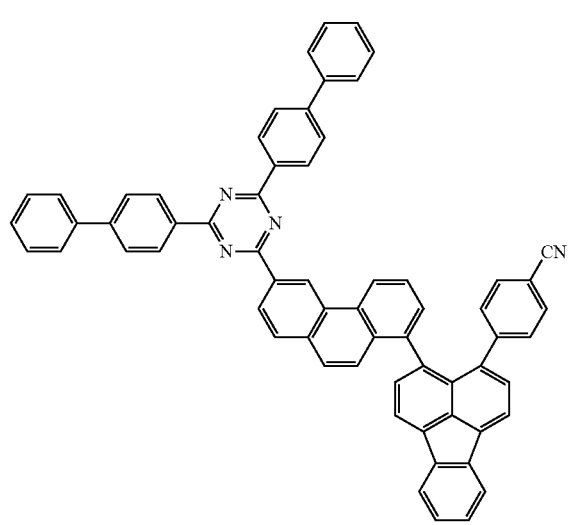
101
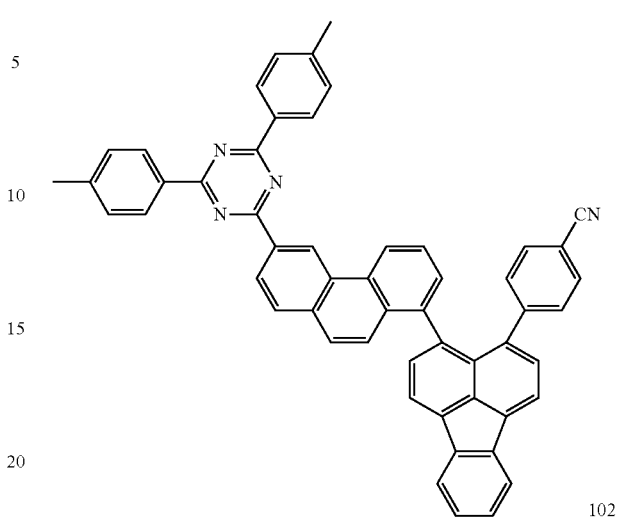
102
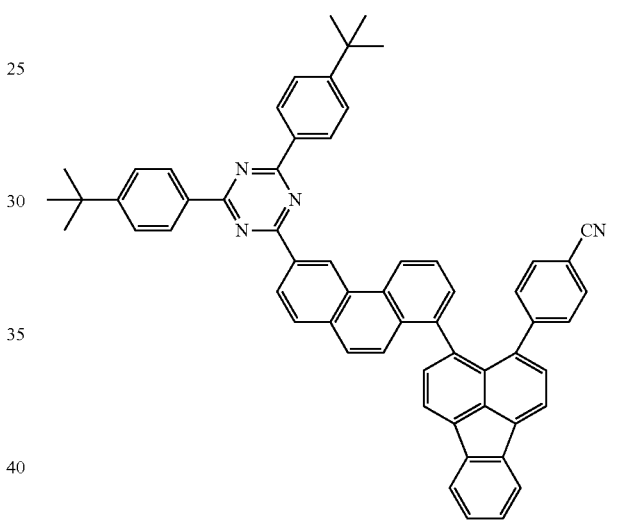
103
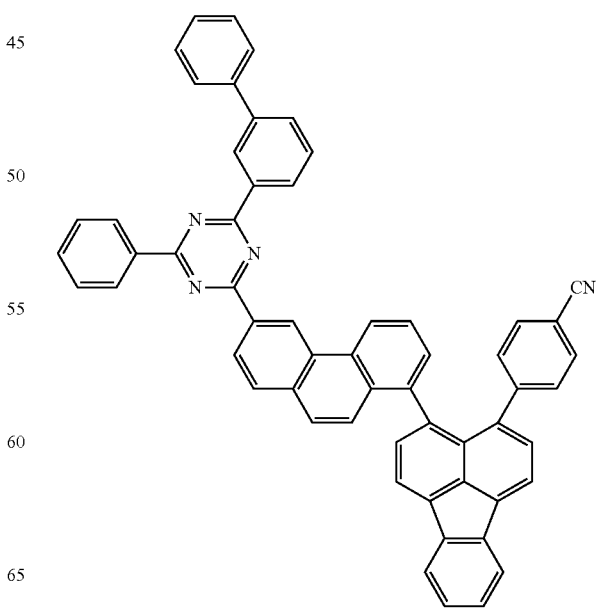

104
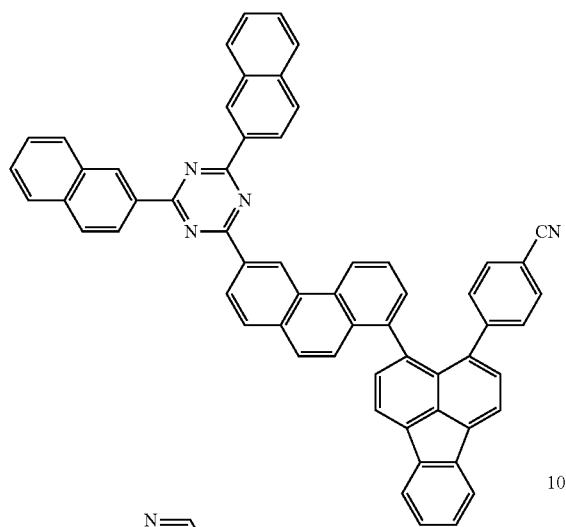
105
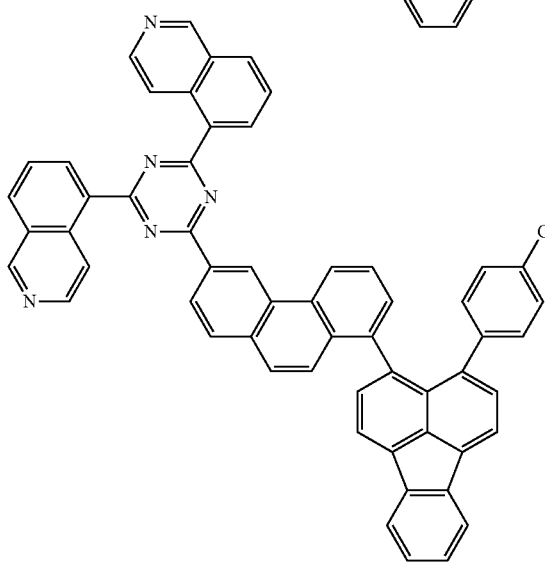
106
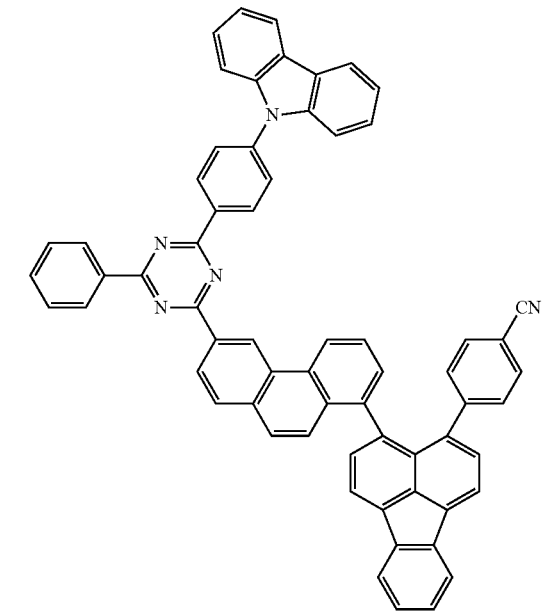
107
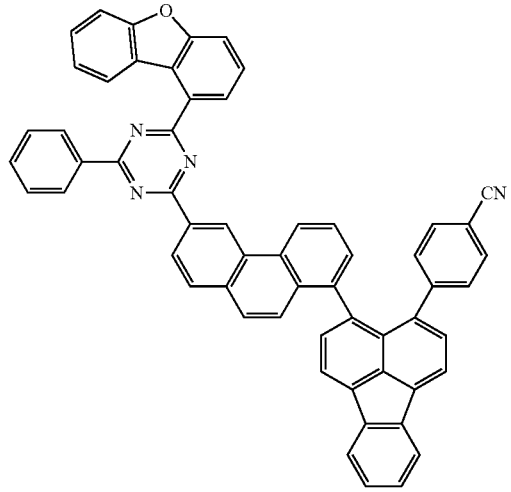
108
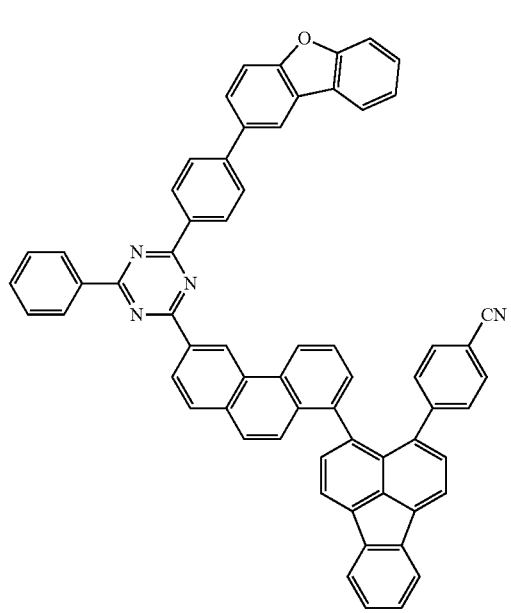
109
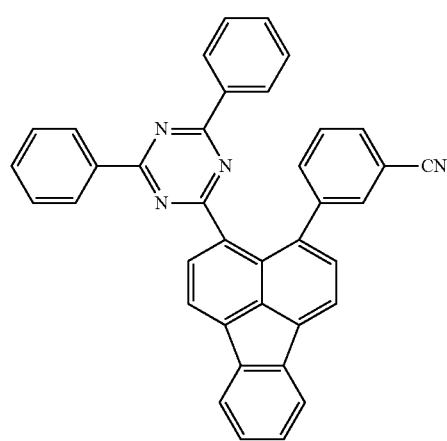

110
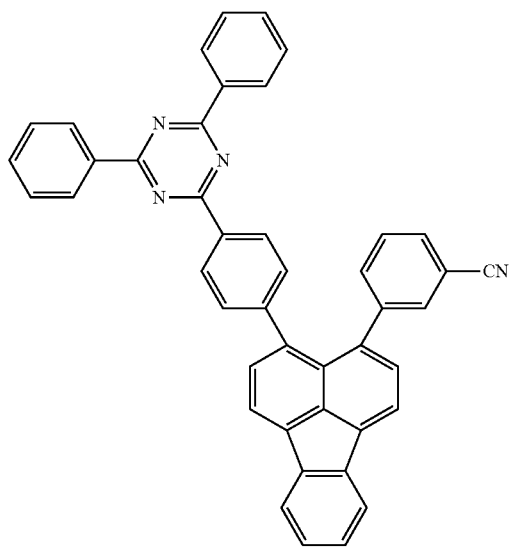
111
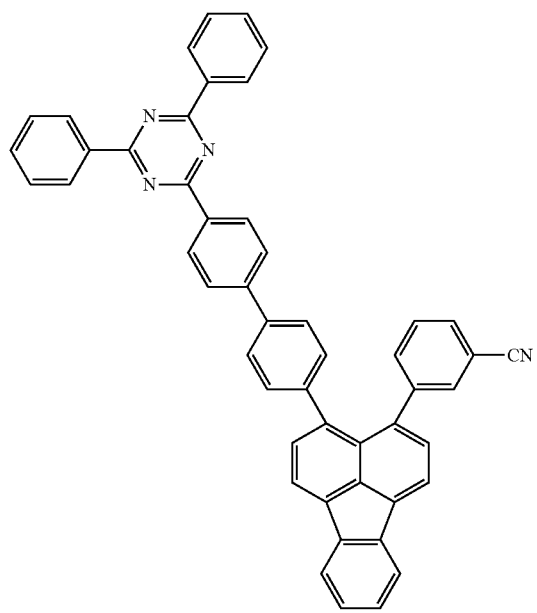
112
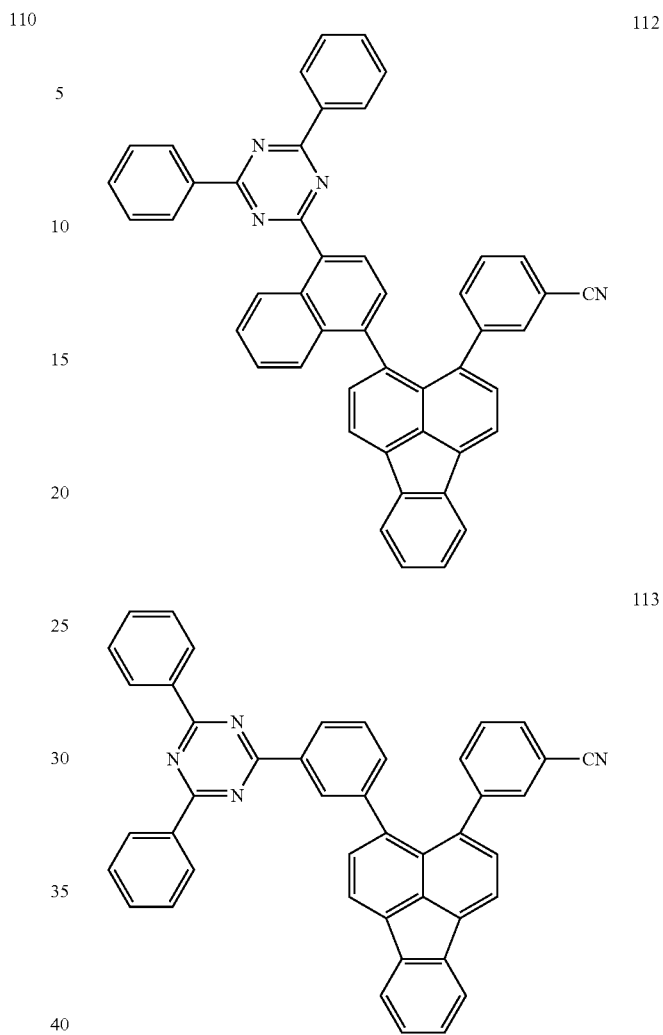
113
114
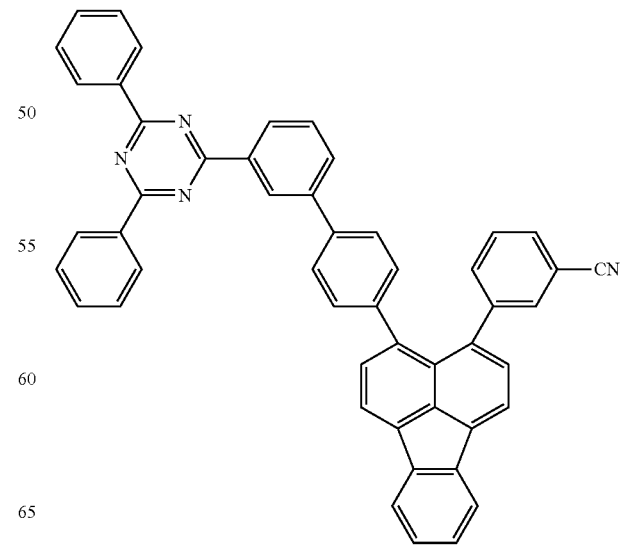

115
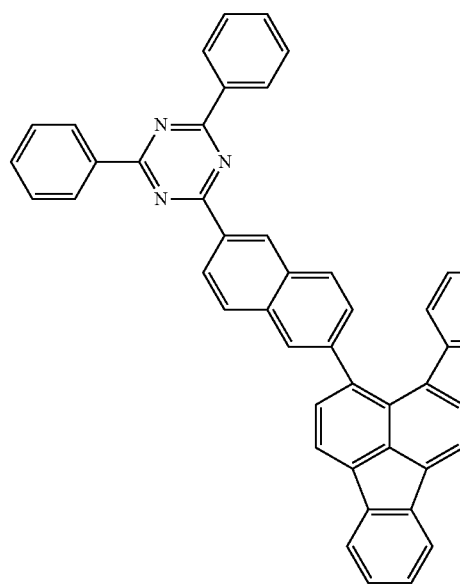
116
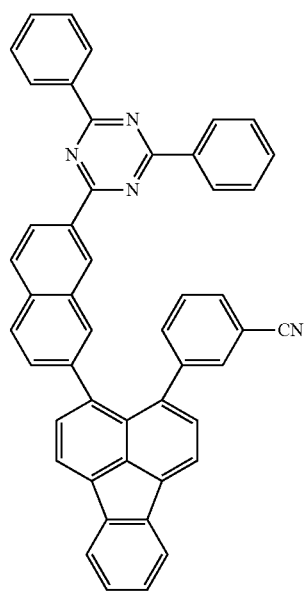
117
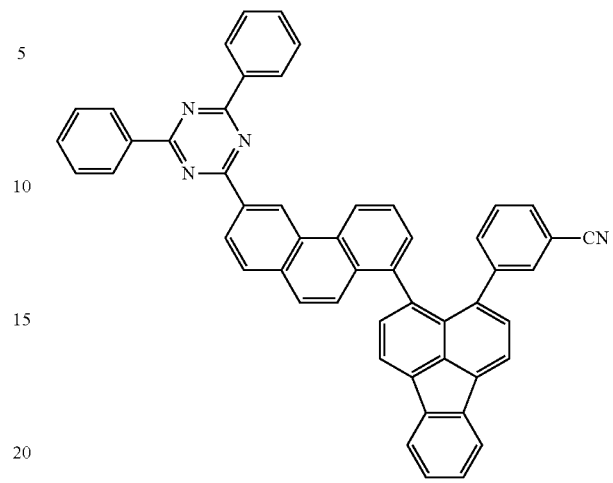
118
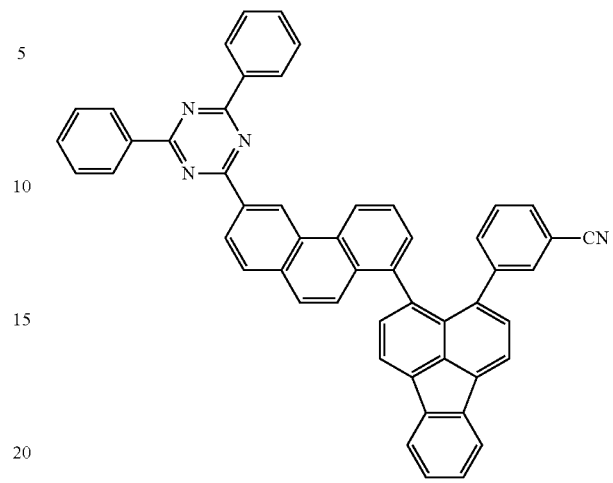
119
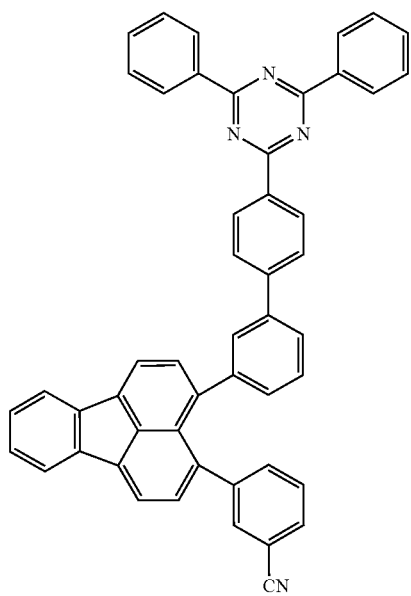

-continued
120
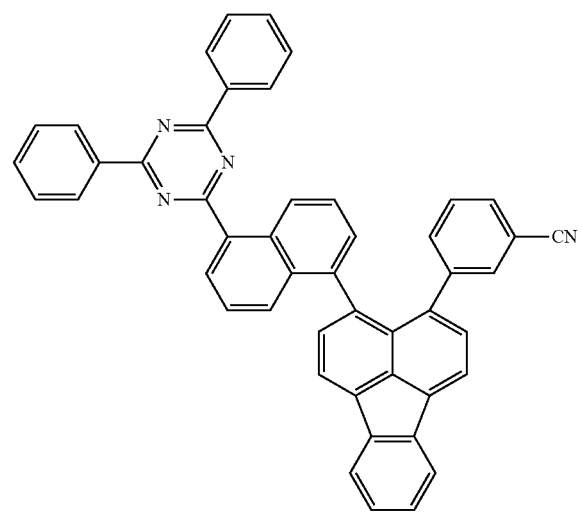
121
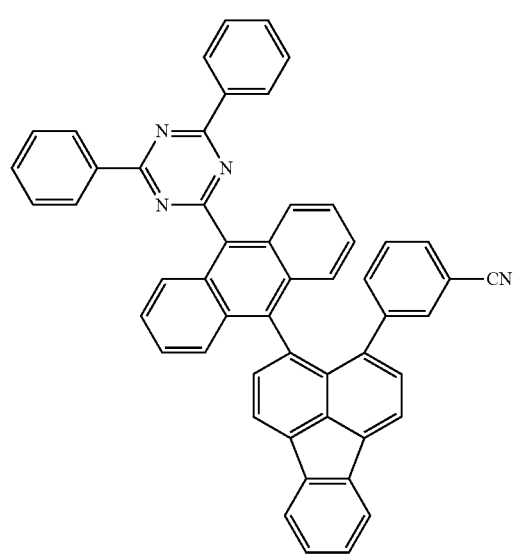
122
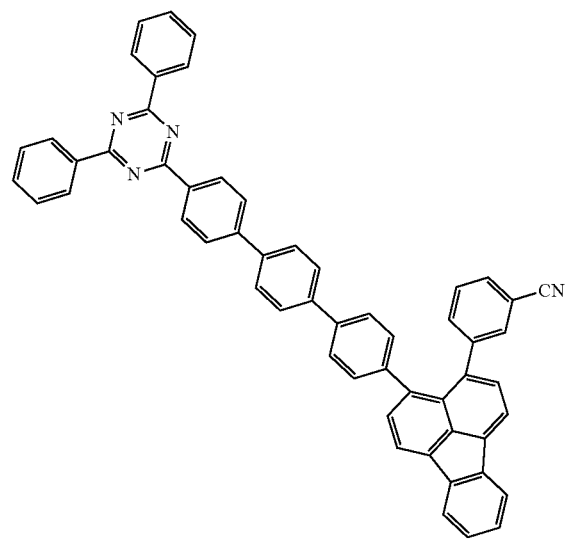
-continued
123
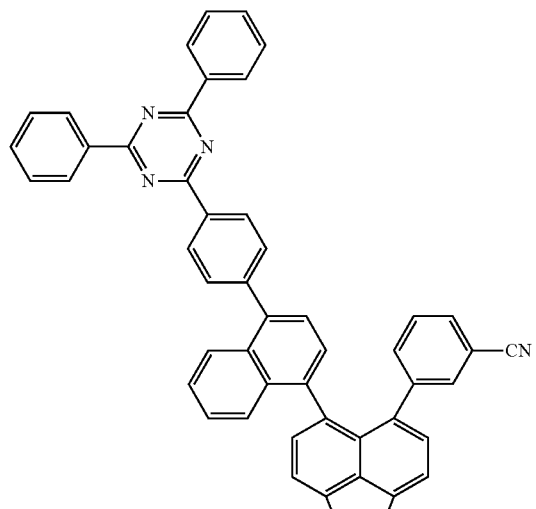
124
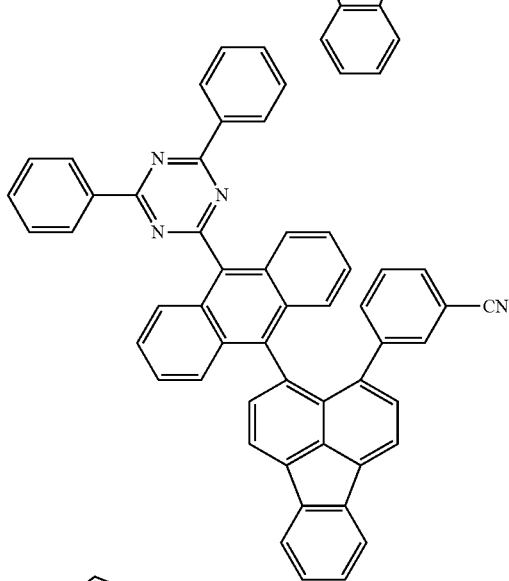
125
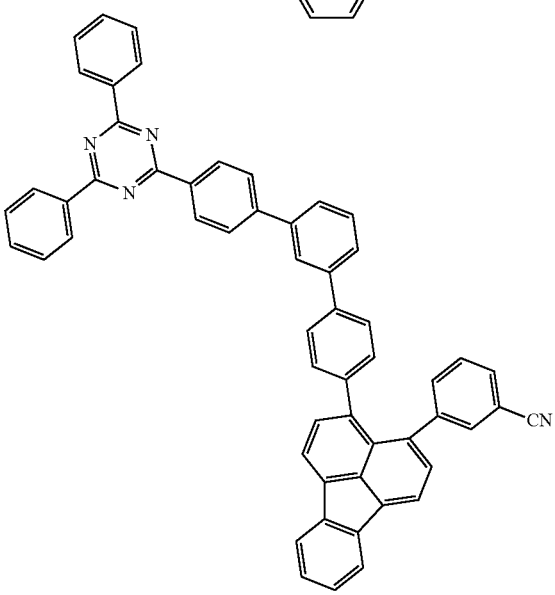

126
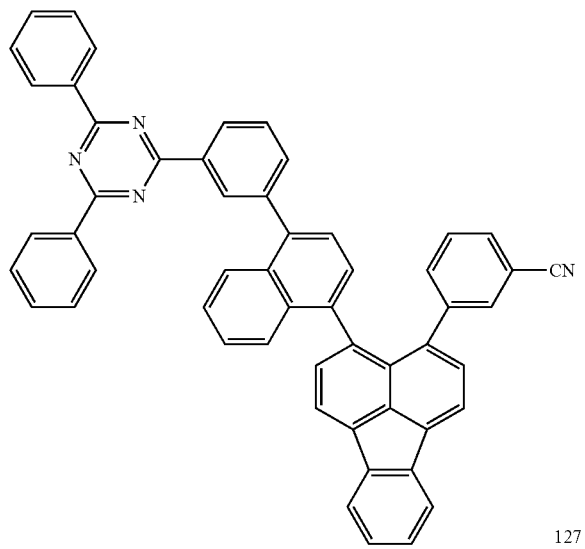
127
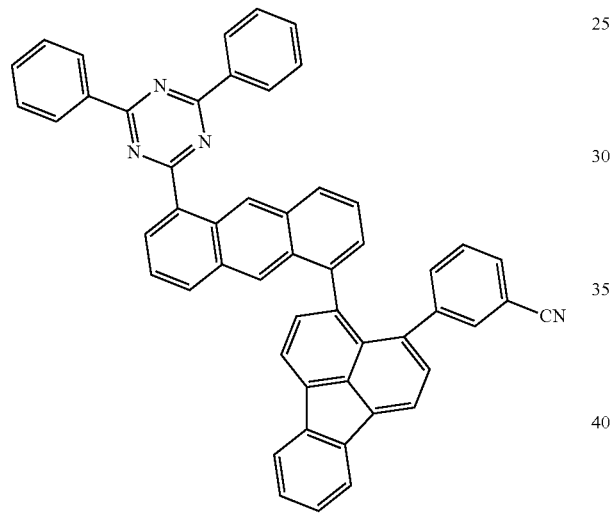
128
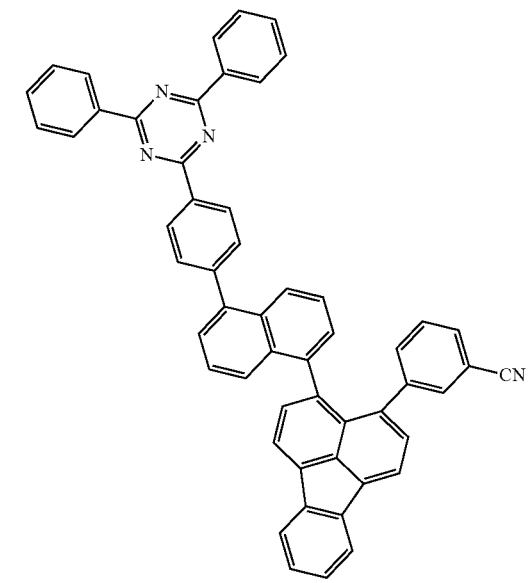
129
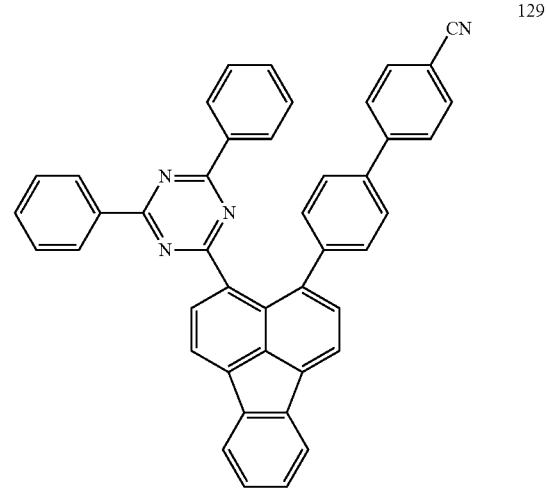
130
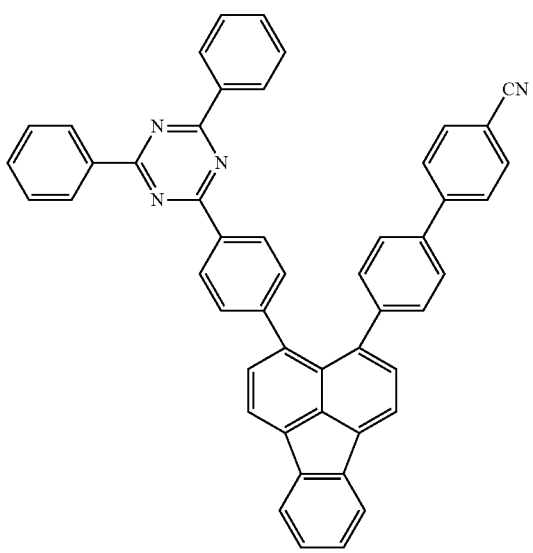
131
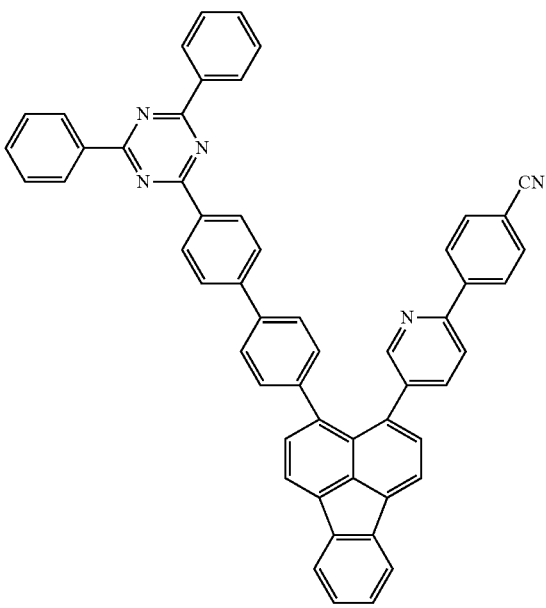

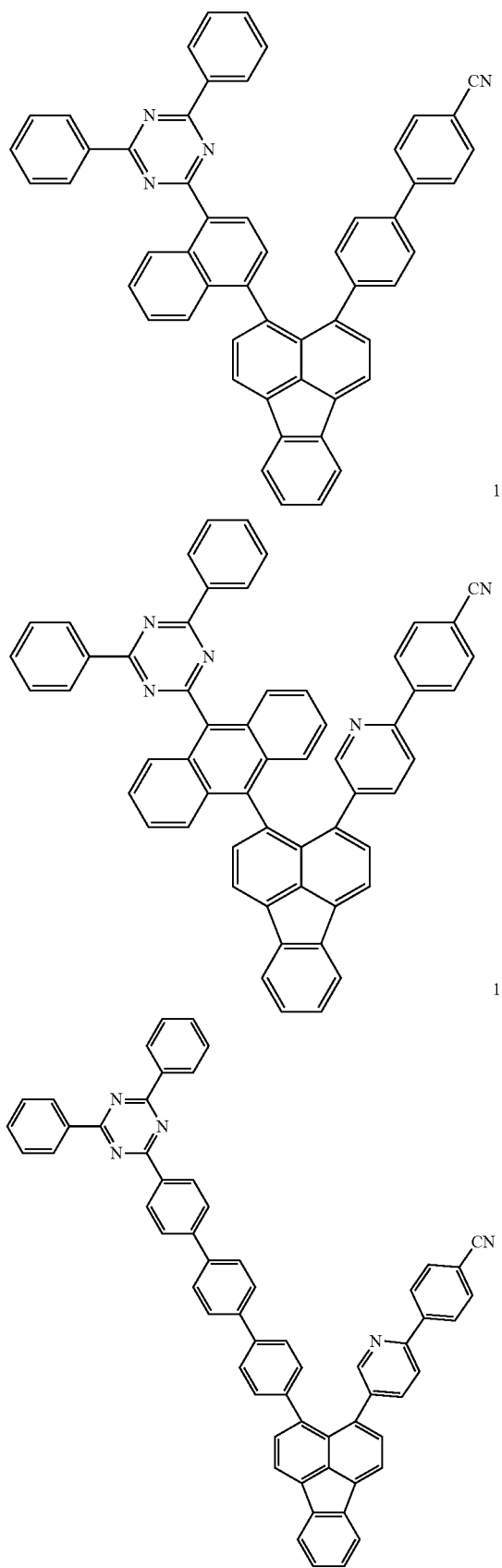
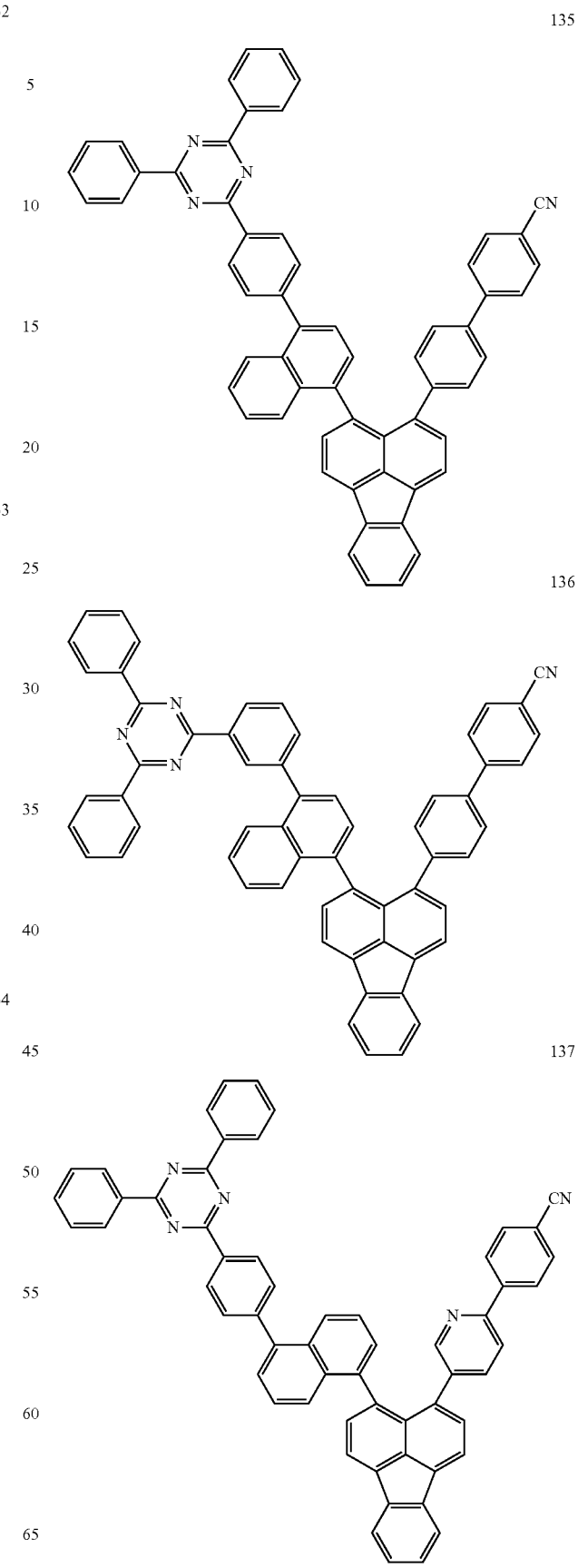

138
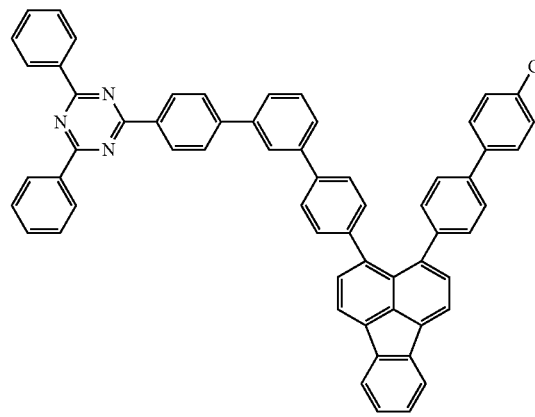
139
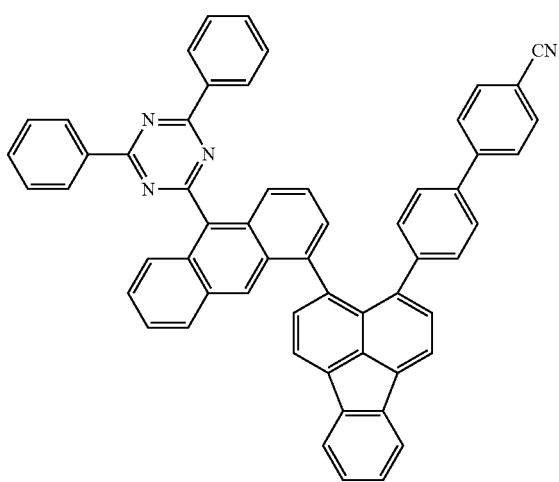
140
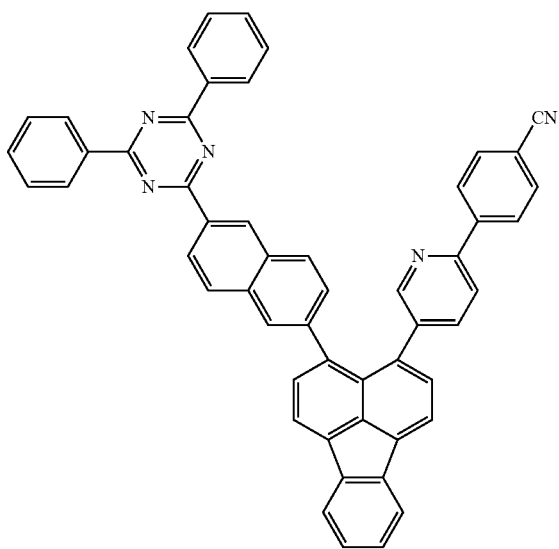
141
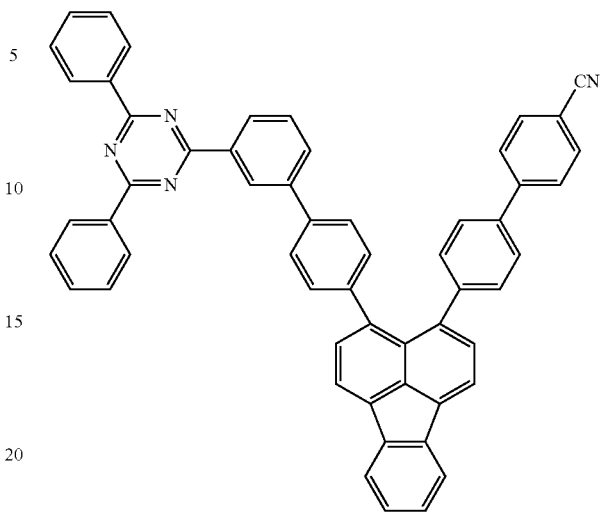
142
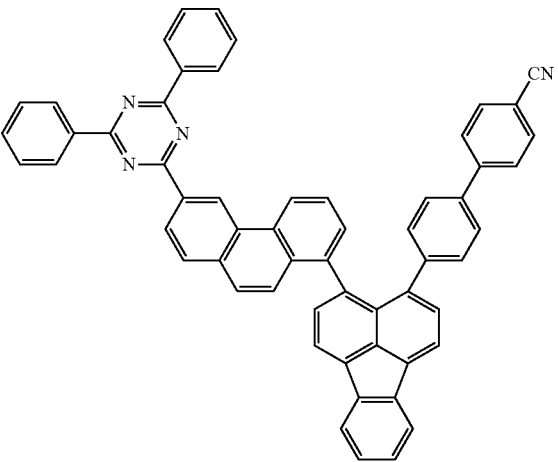
143

144
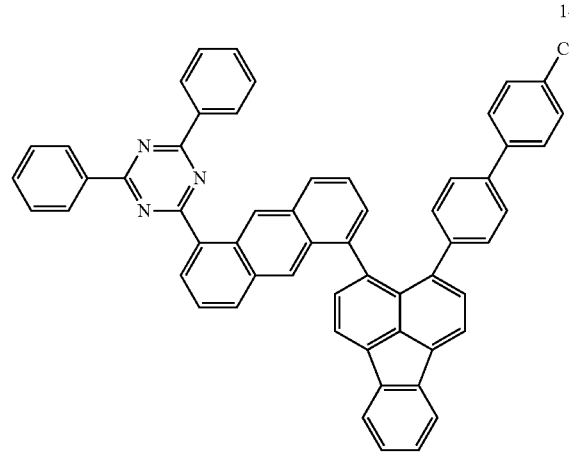
147
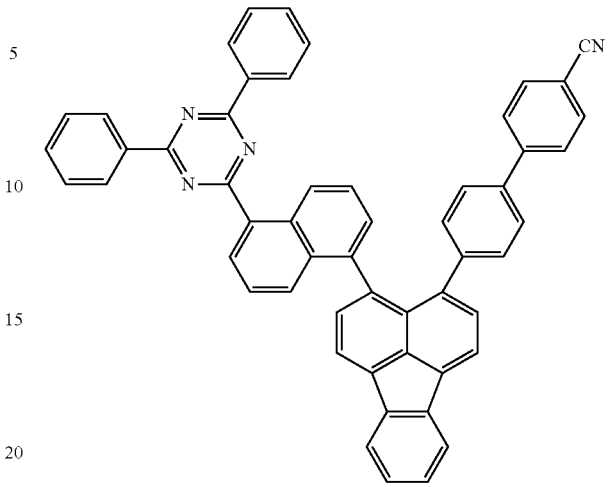
145
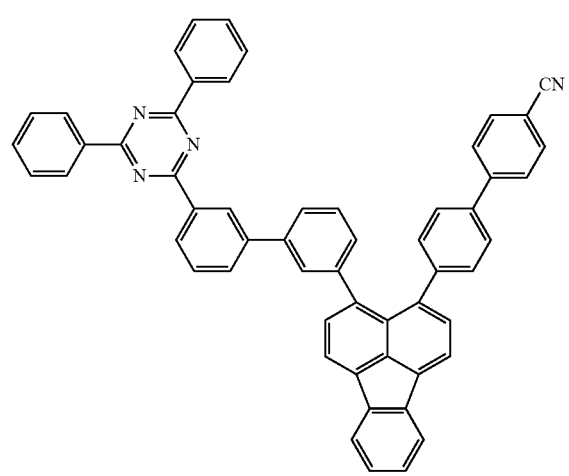
148
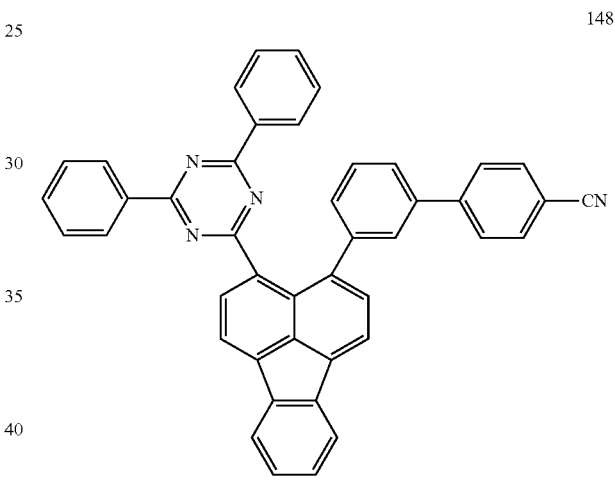
146
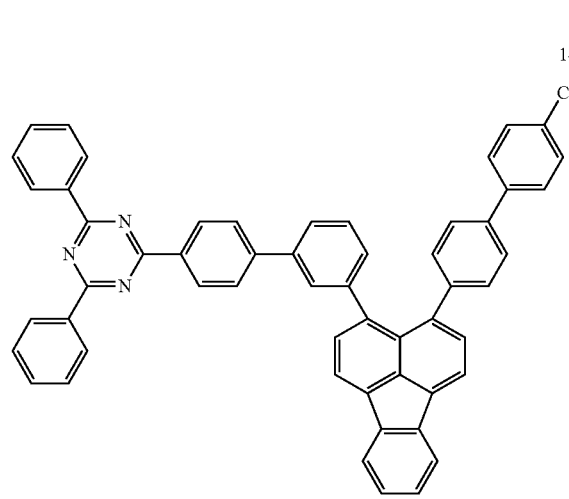
149
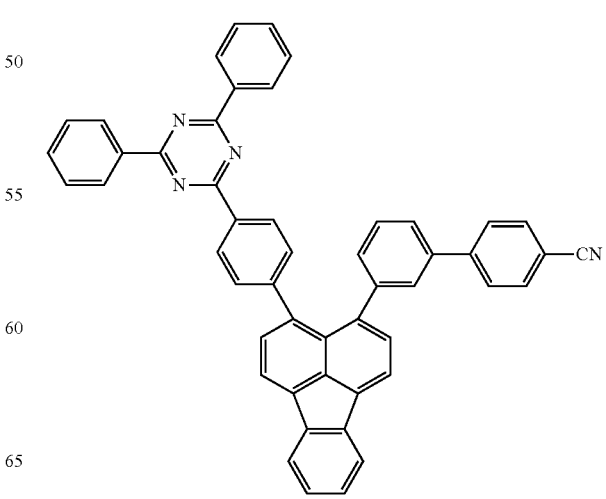

150
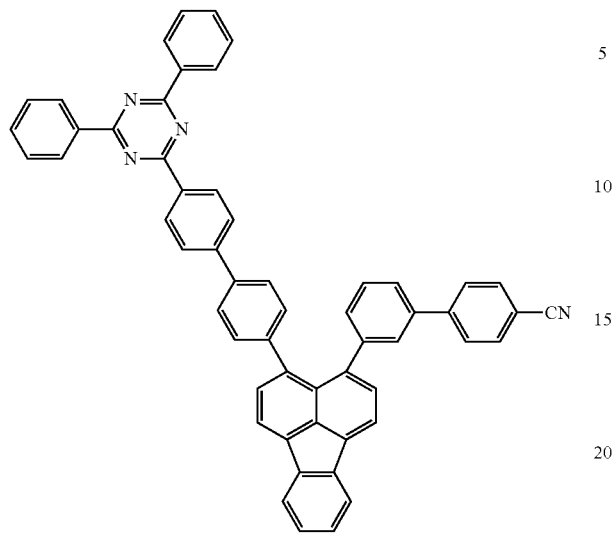
151

152
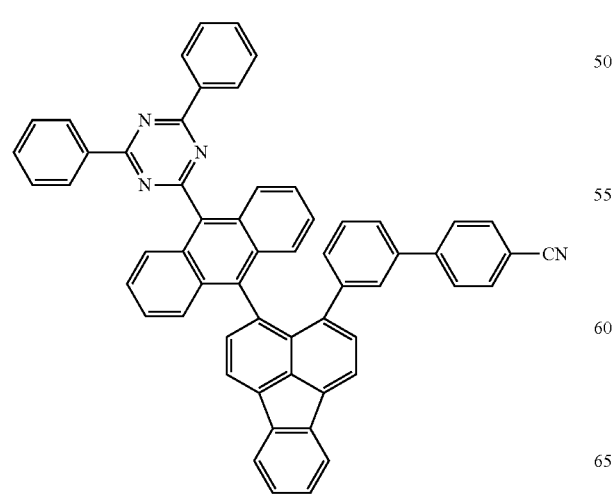
153
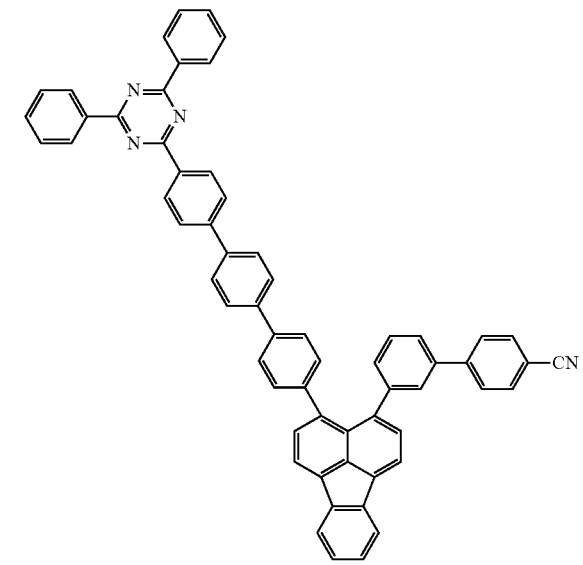
154
155

119
-continued
156
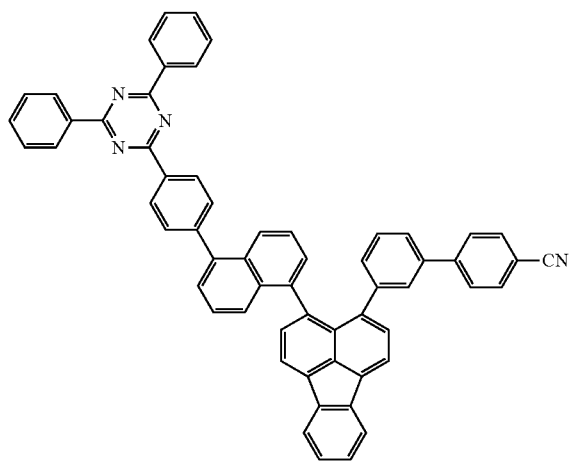
157
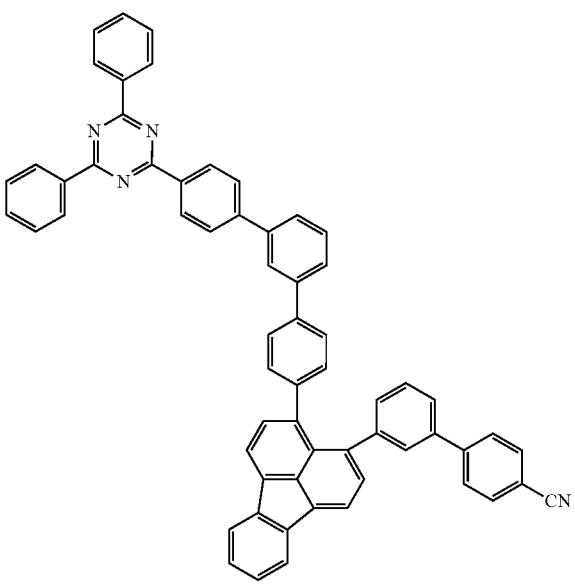
158
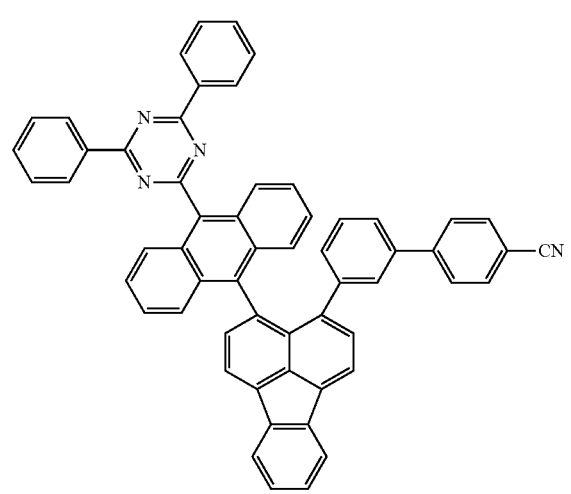
120
-continued
159
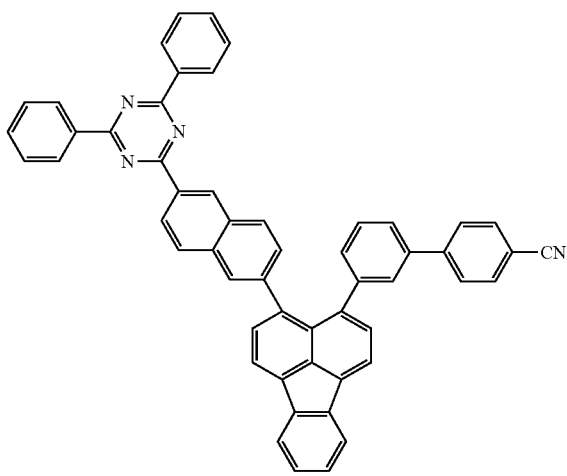
160
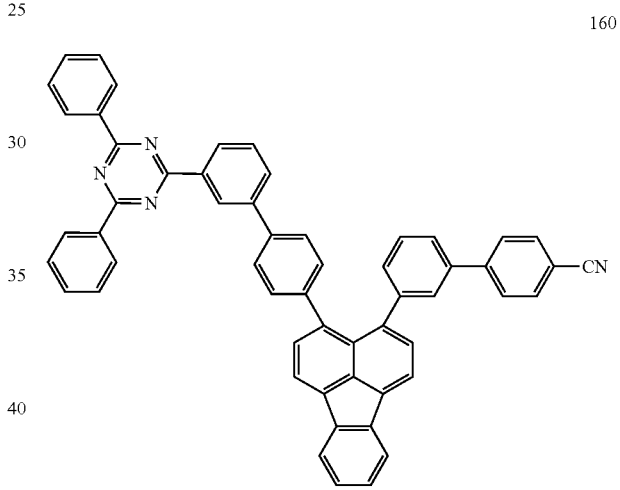
161
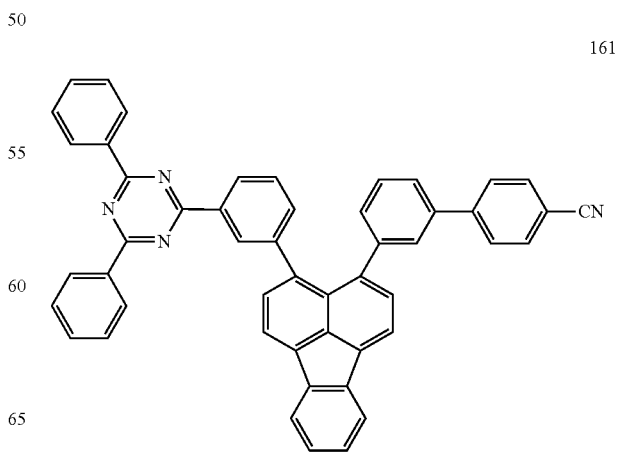

162
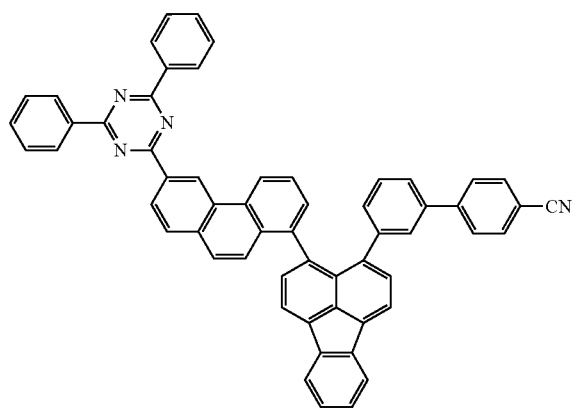
165
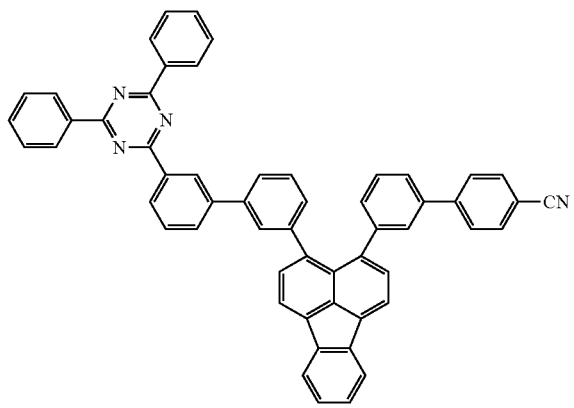
163
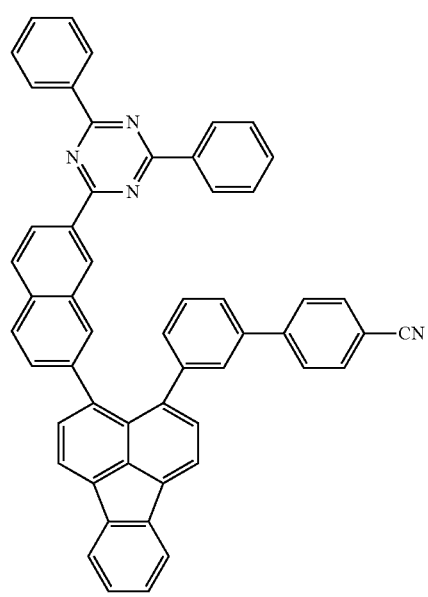
166
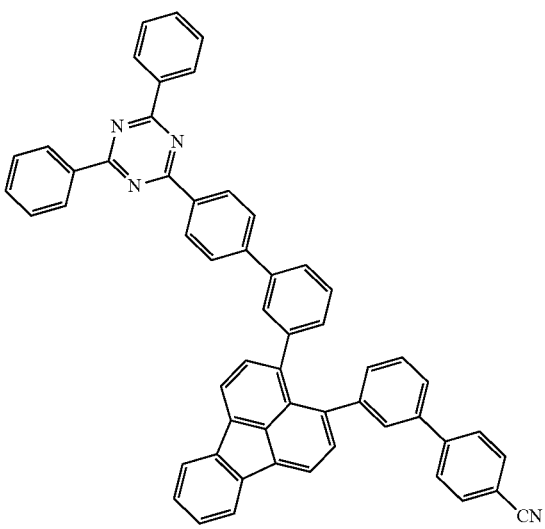
164
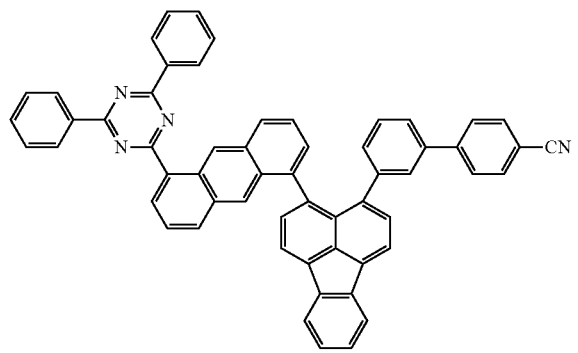
167
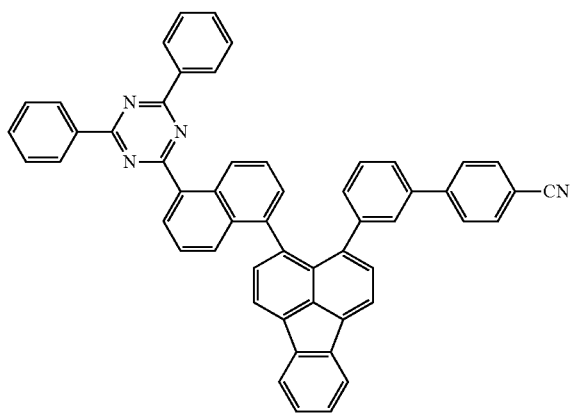

-continued
168
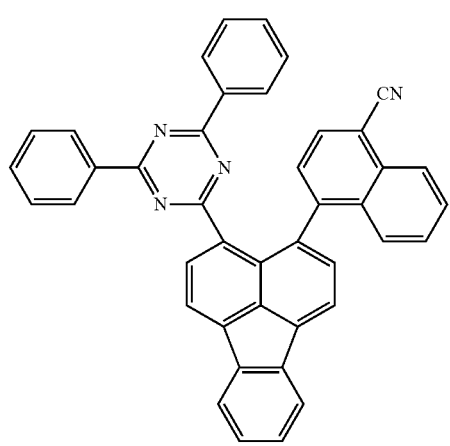
169
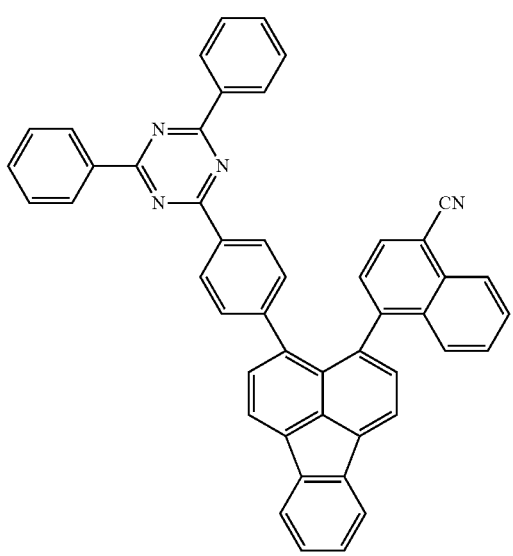
170
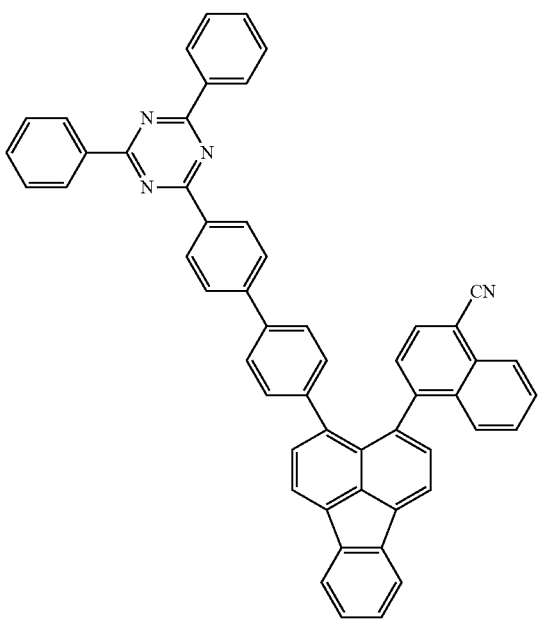
-continued
171
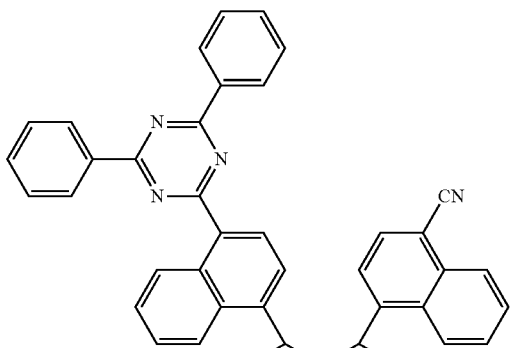
172
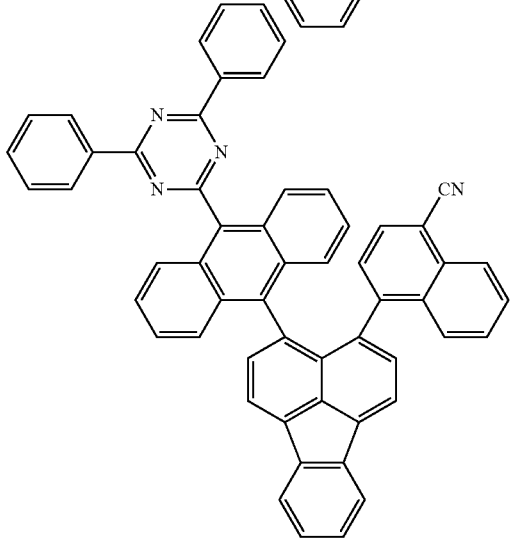
173
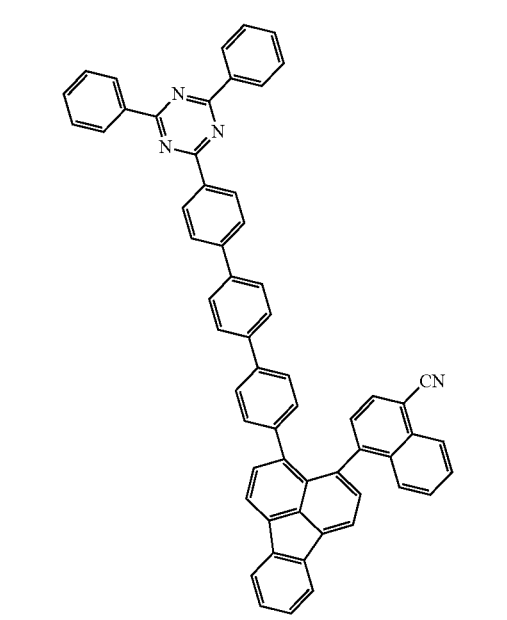

174
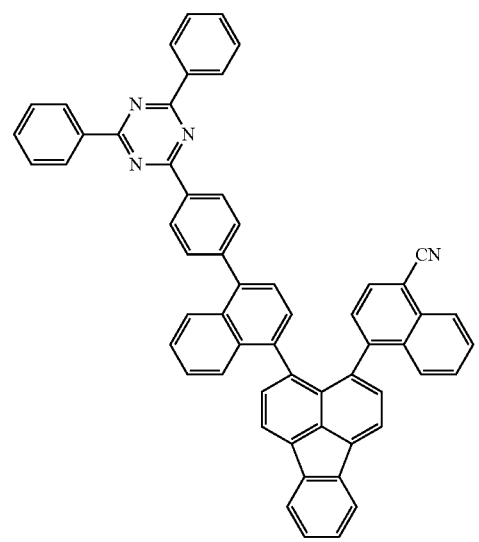
175
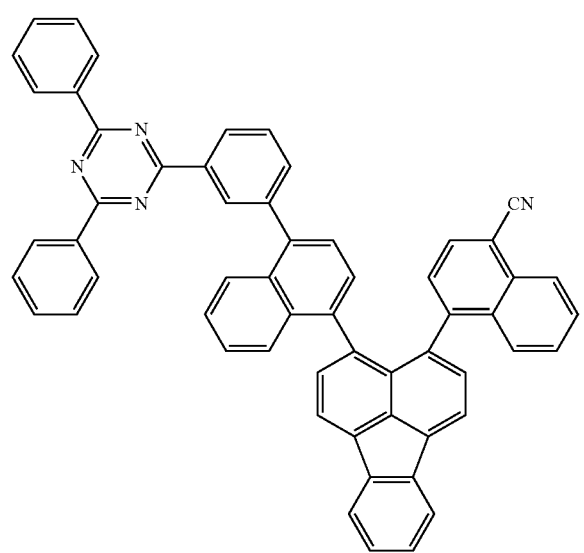
177
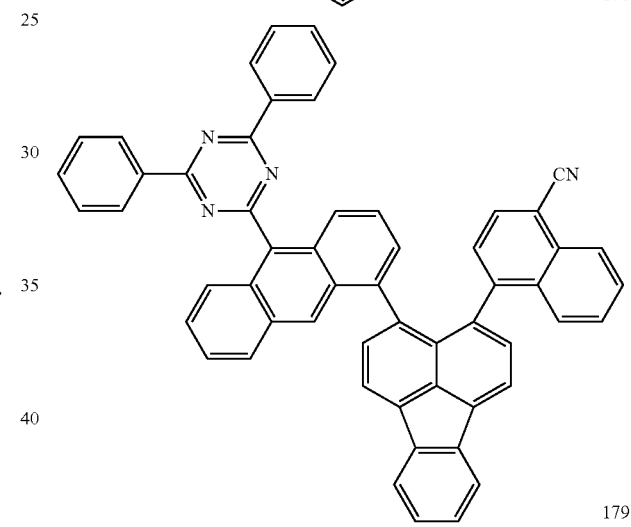
178
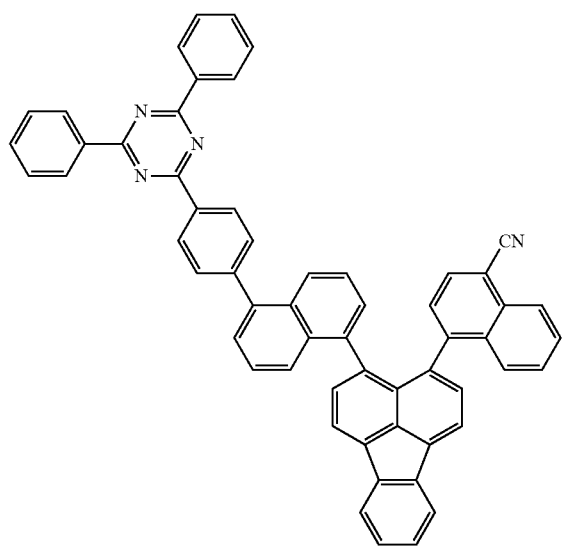
176
179
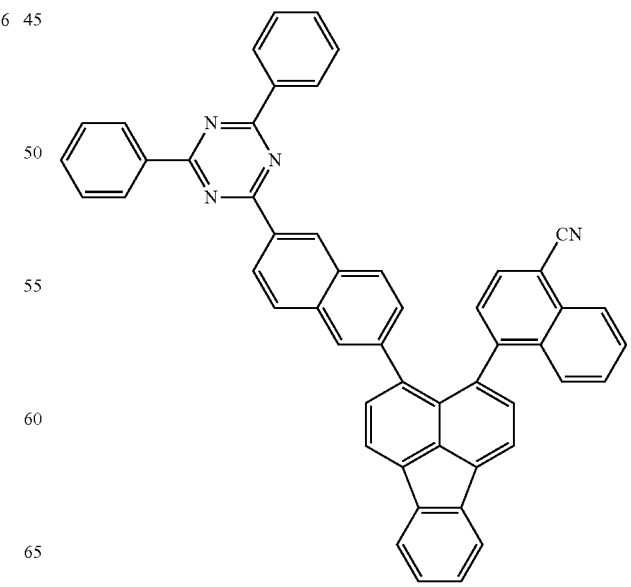

180
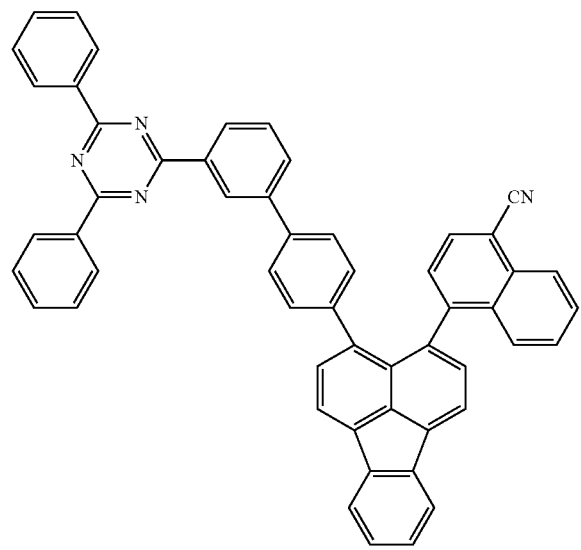
181
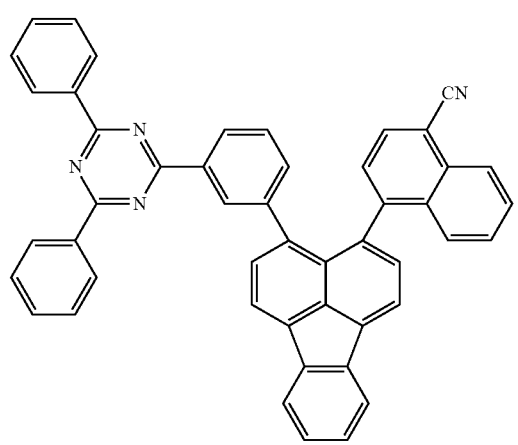
182
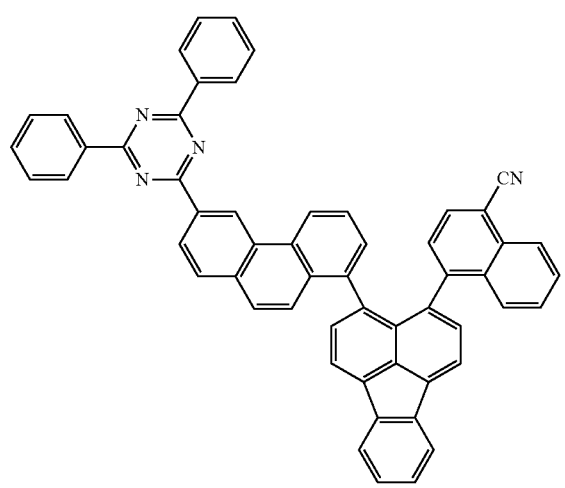
183
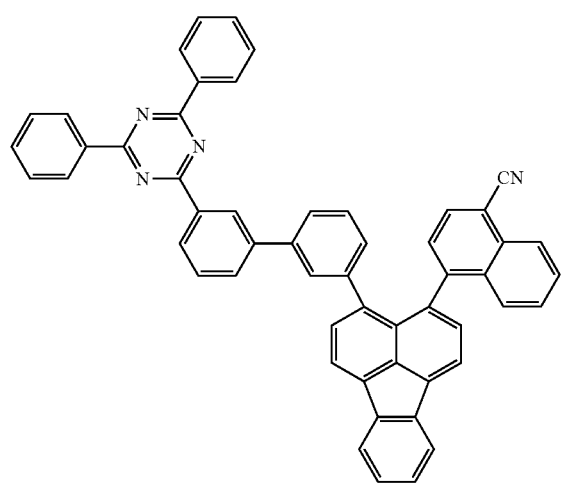
184
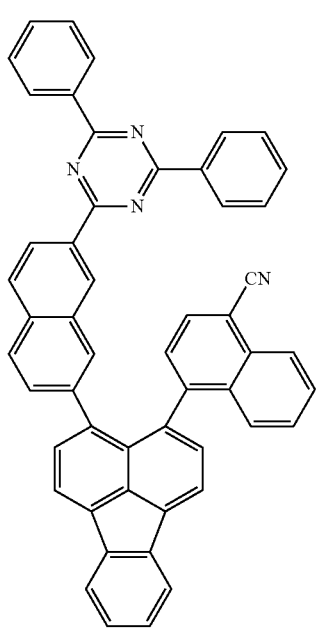
185
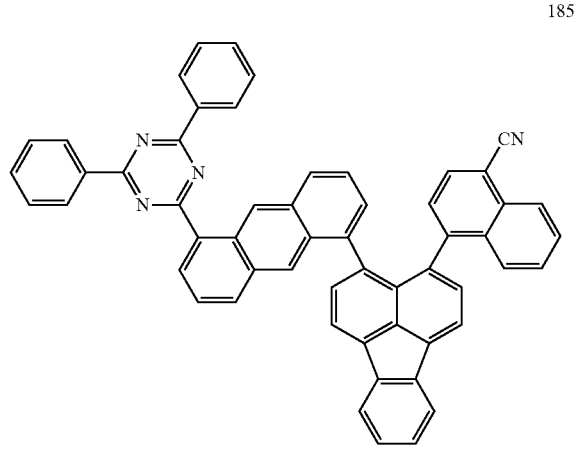

-continued
186
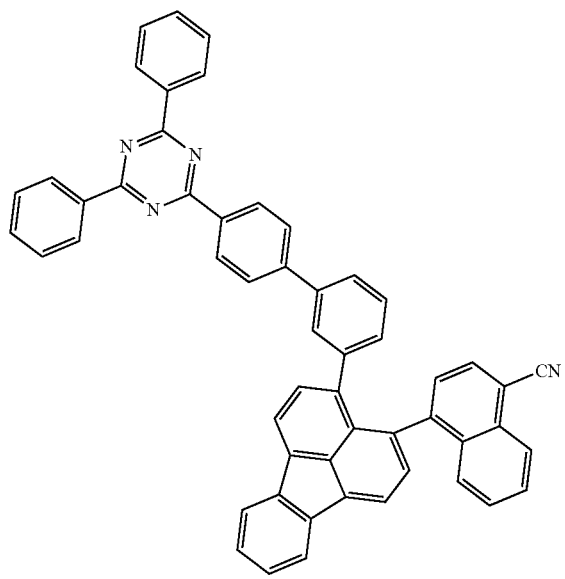
187
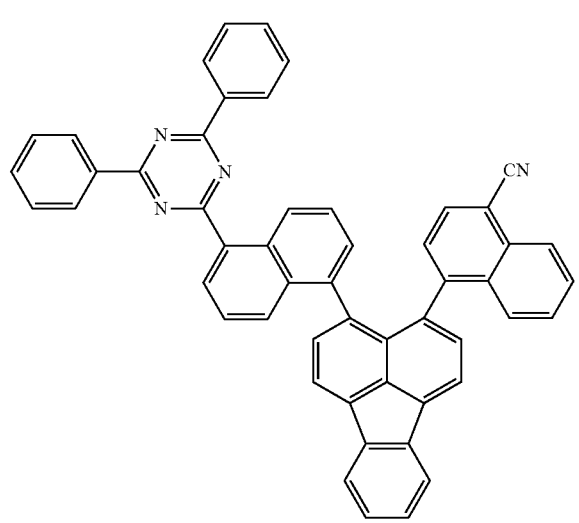
188
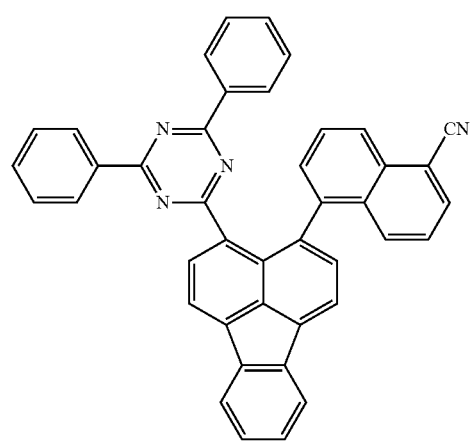
-continued
189
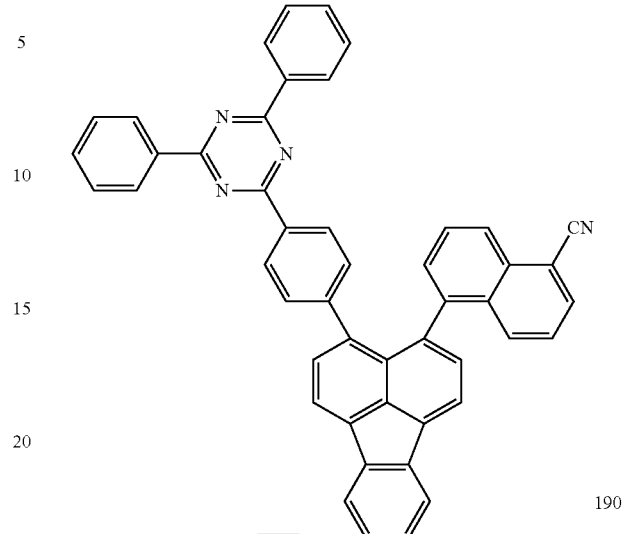
190
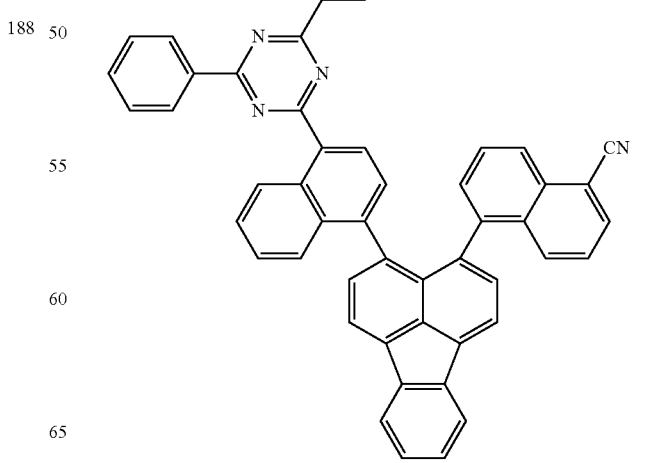
191

-continued
192
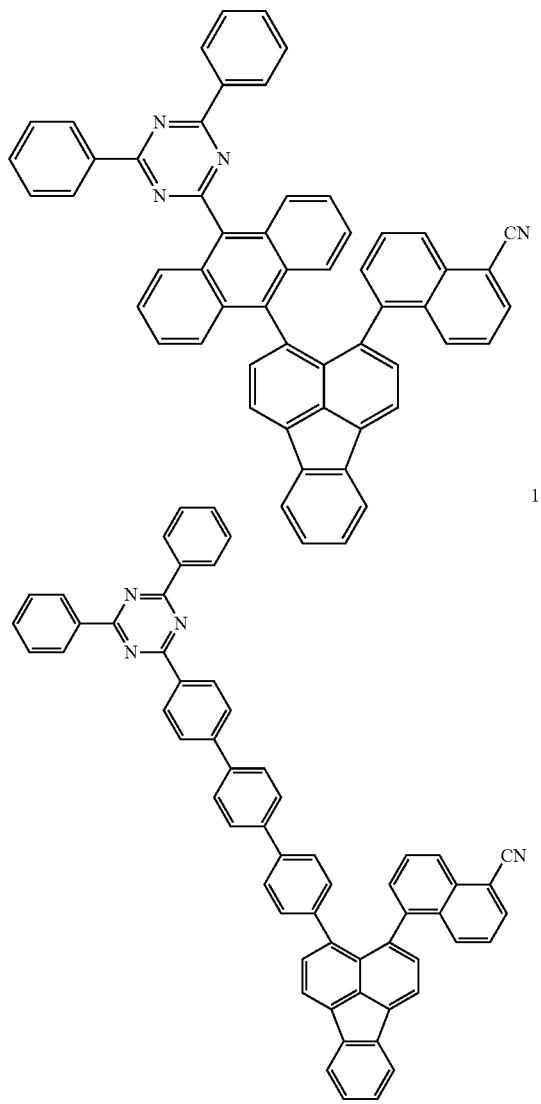
193
194
195
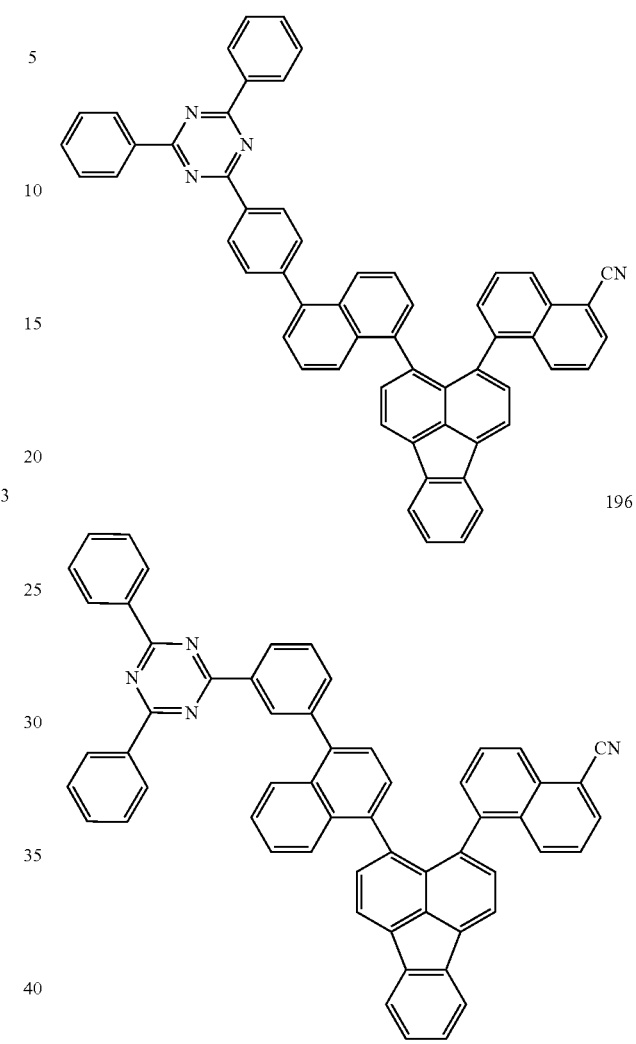
196
197
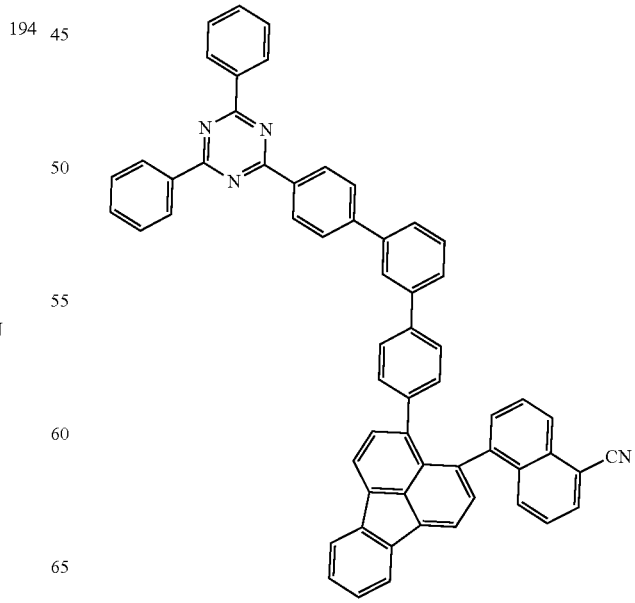
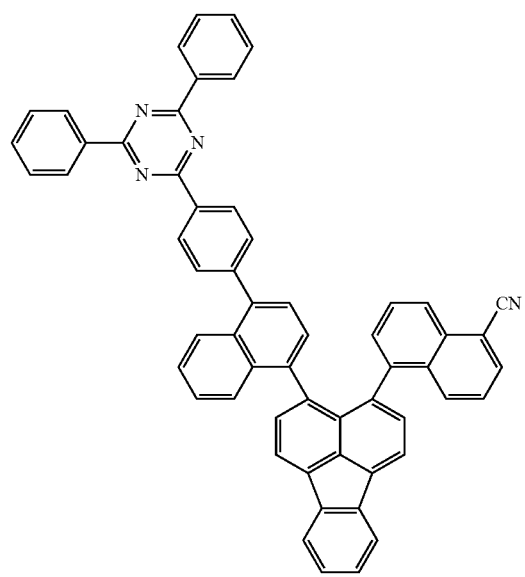

198
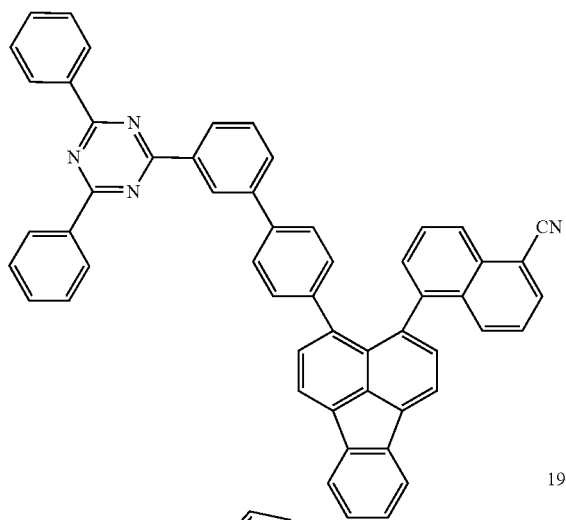
199
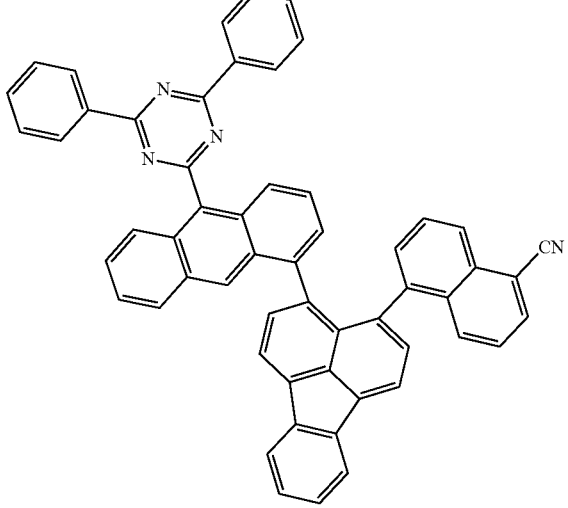
200
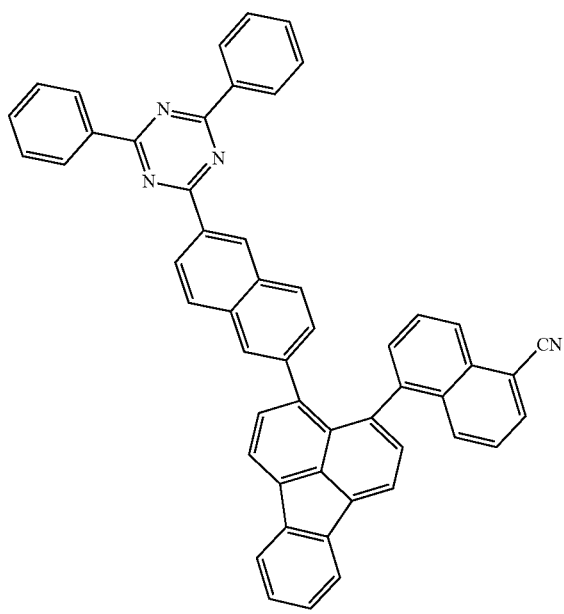
201
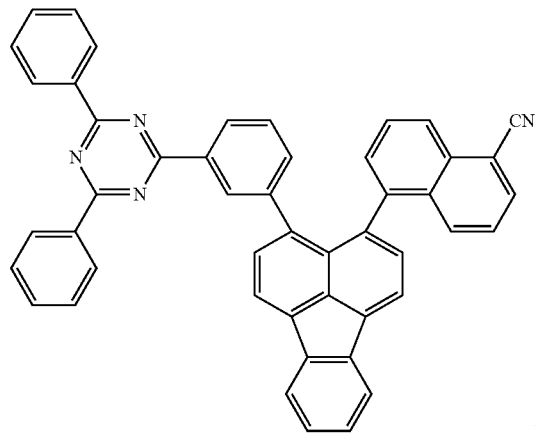
202
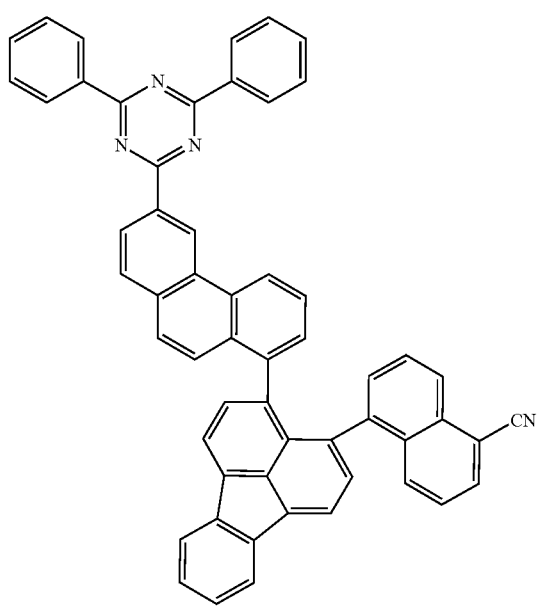
203
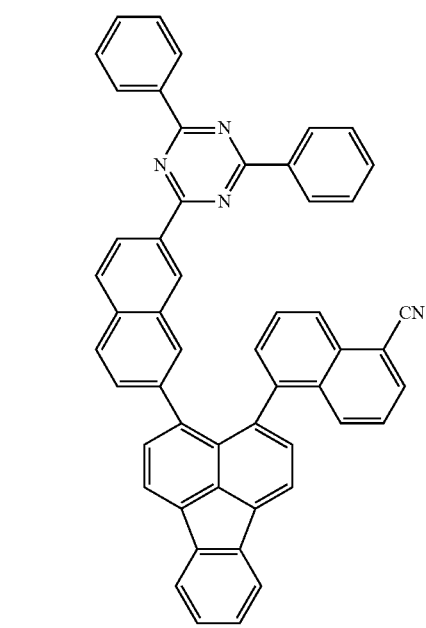

204
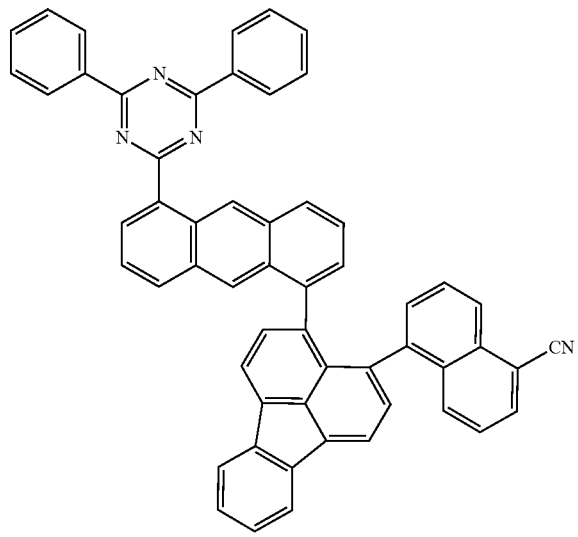
205
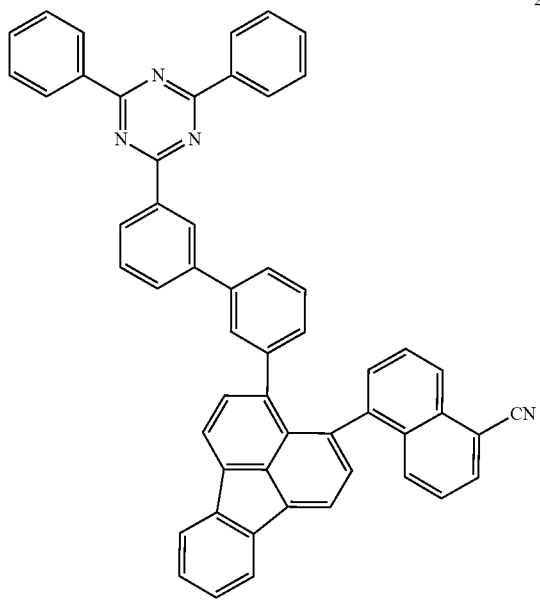
206
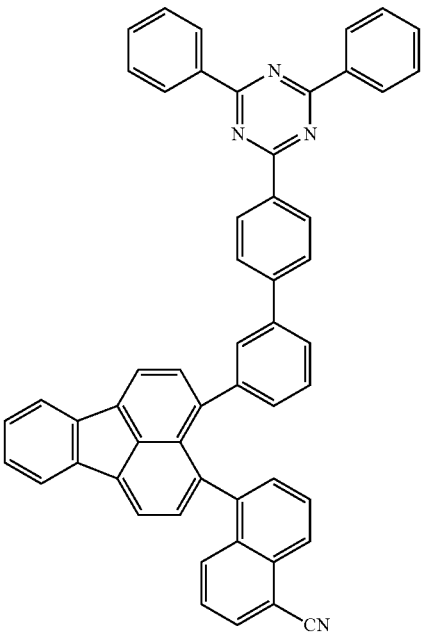
207
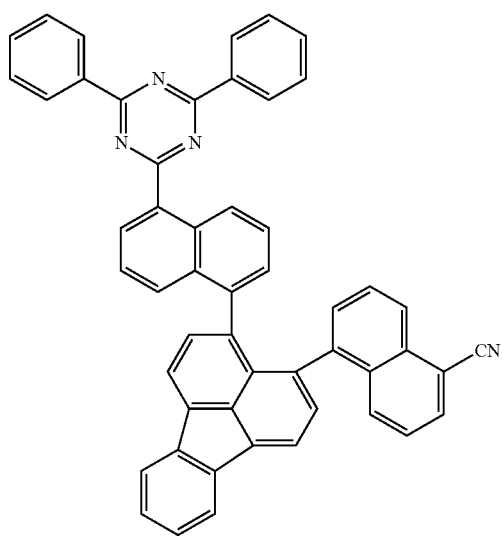
208
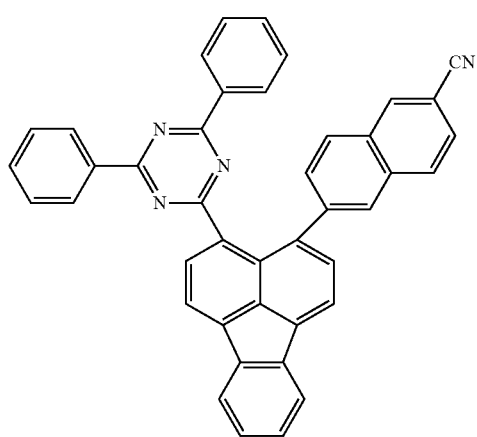

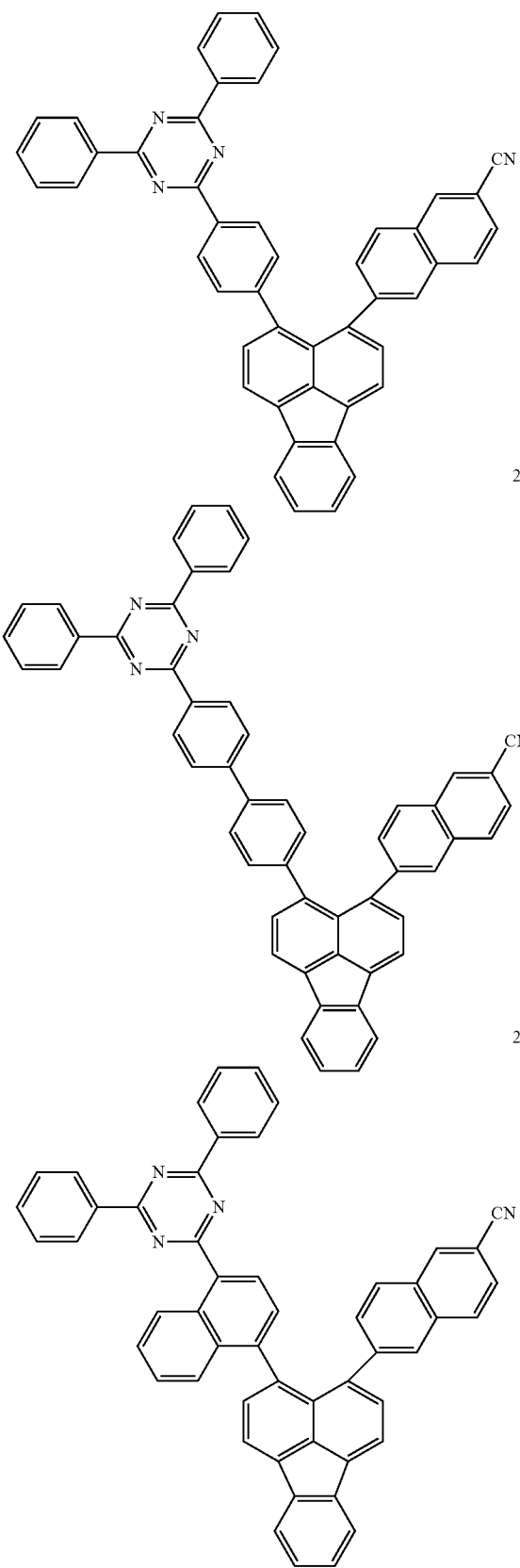
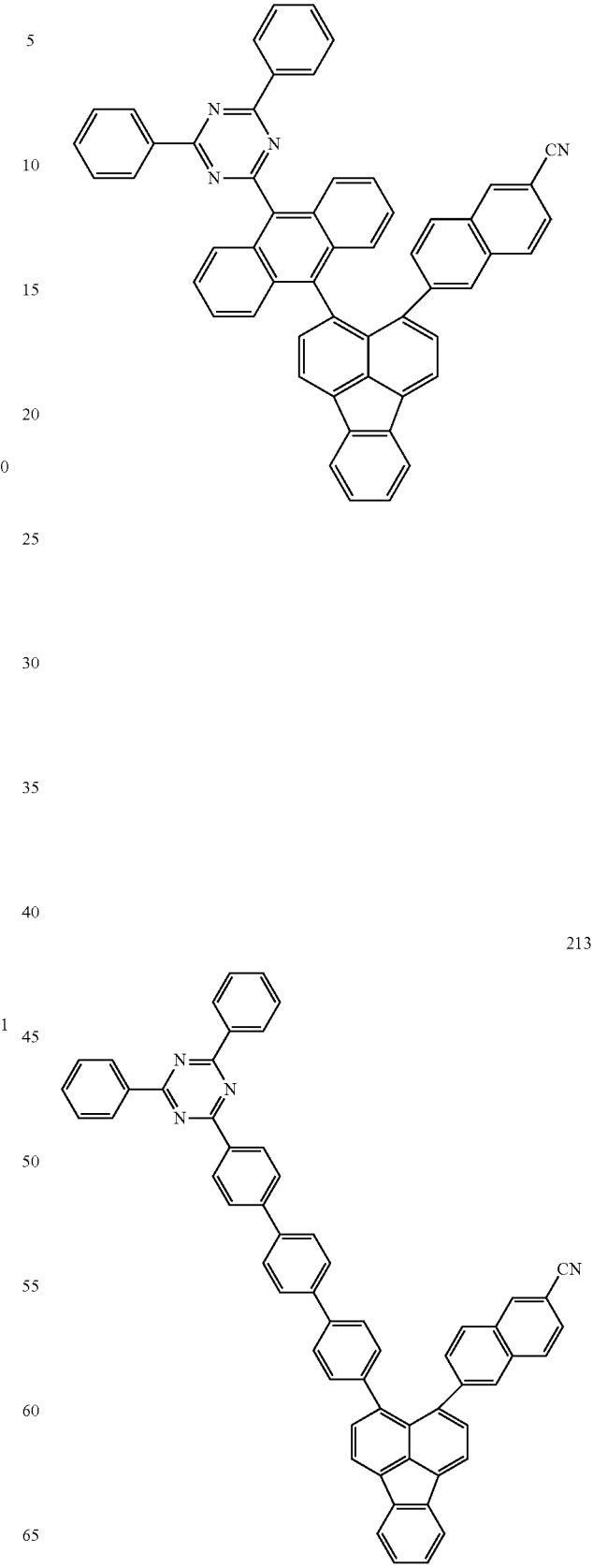

-continued
214
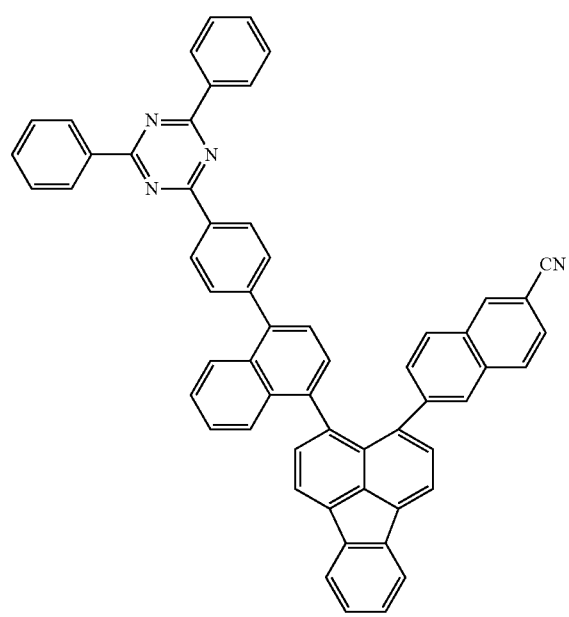
215
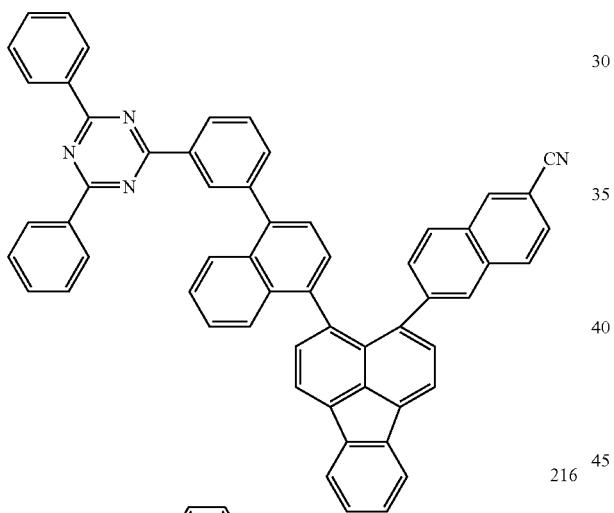
216
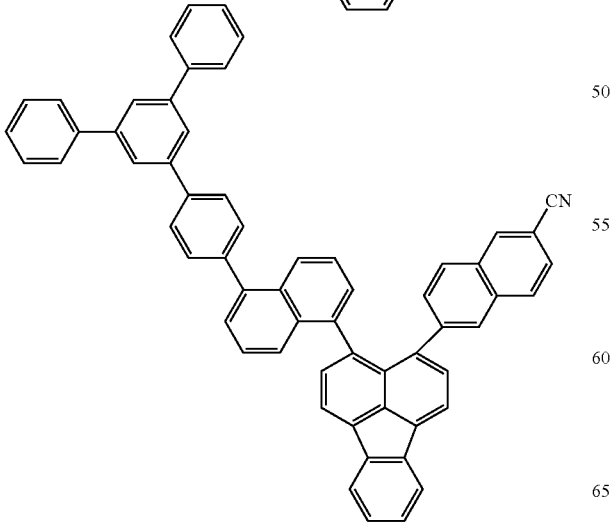
-continued
217
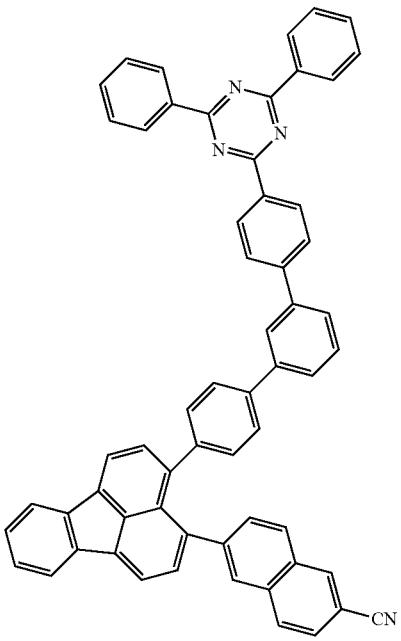
218
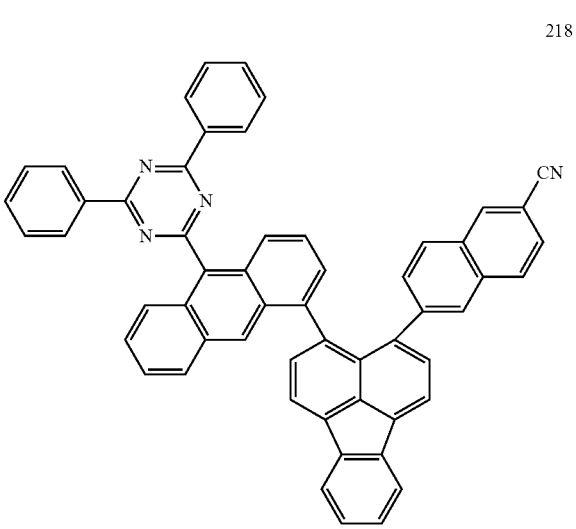

219
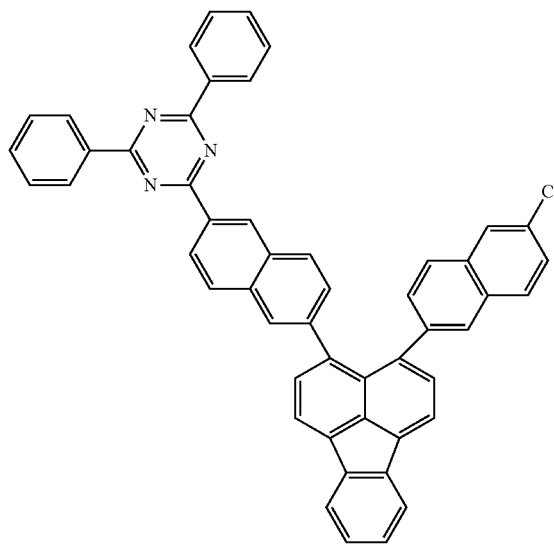
220
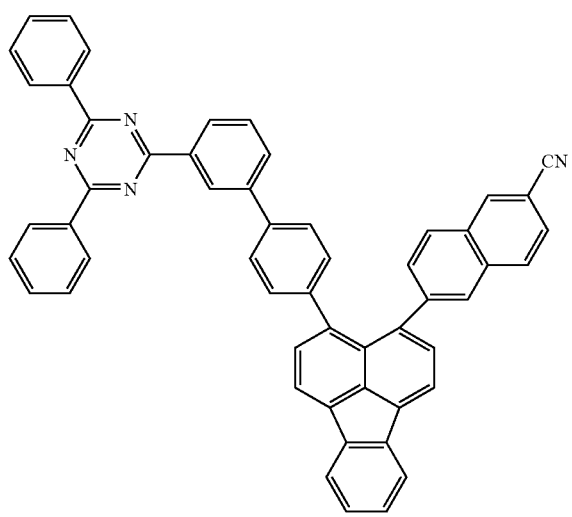
221
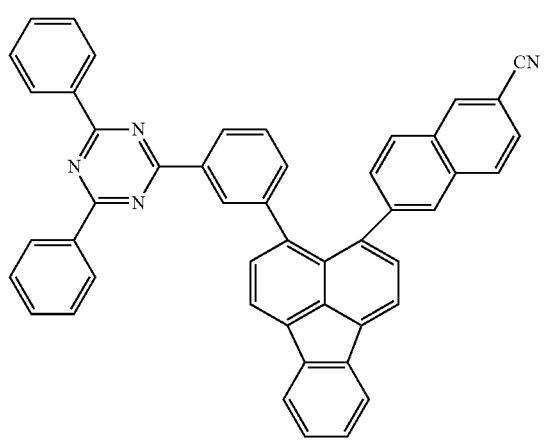
222
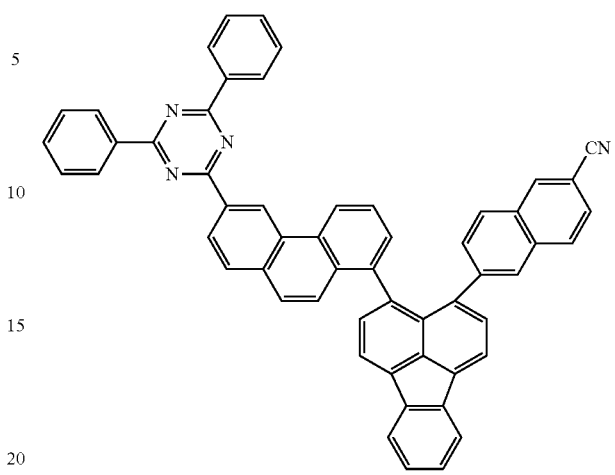
223
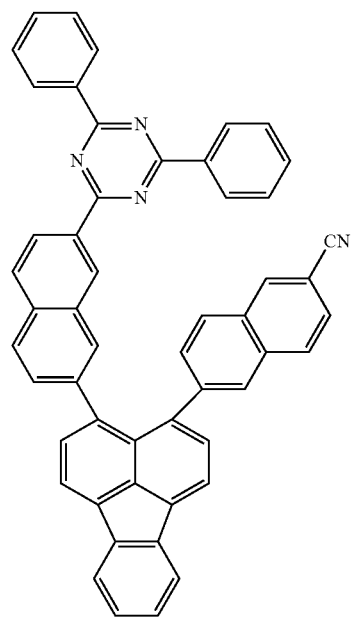
224
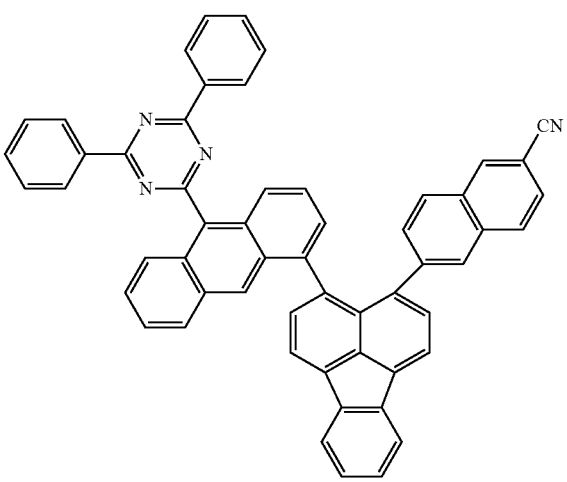

225
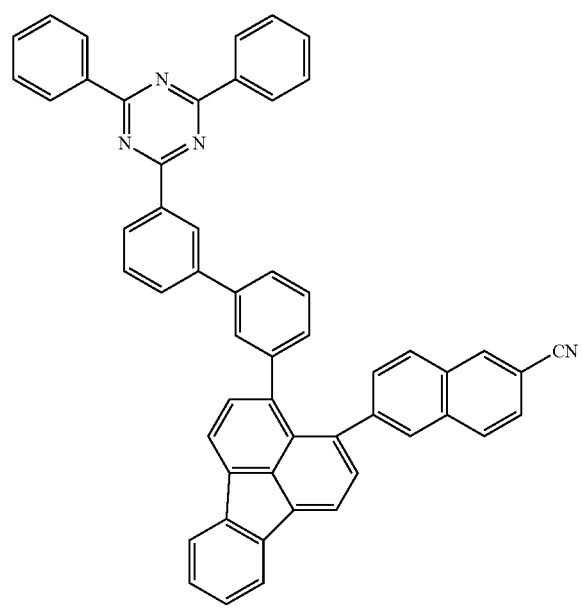
226
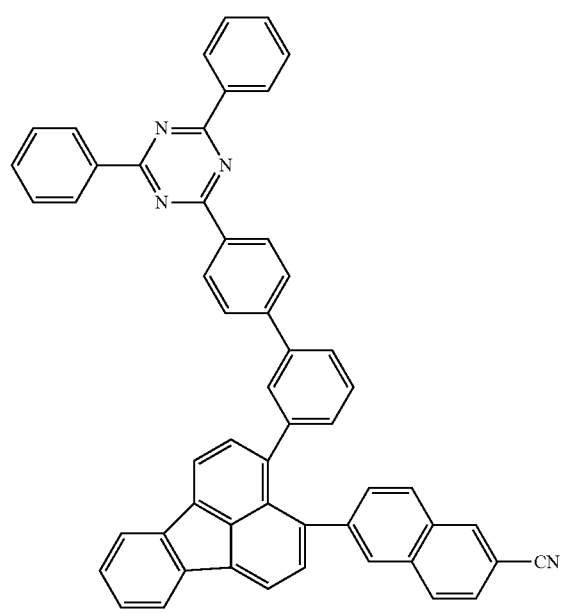
227
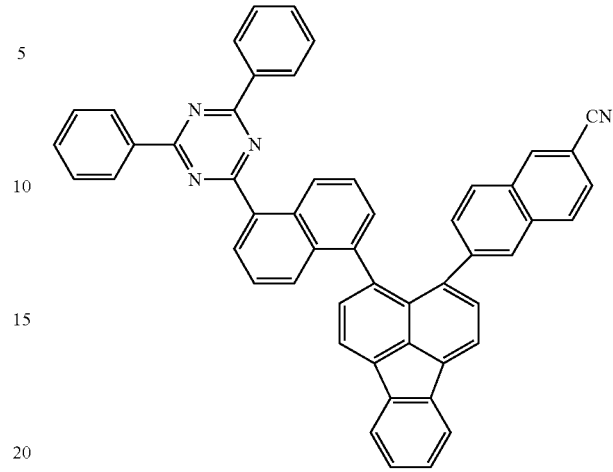
228
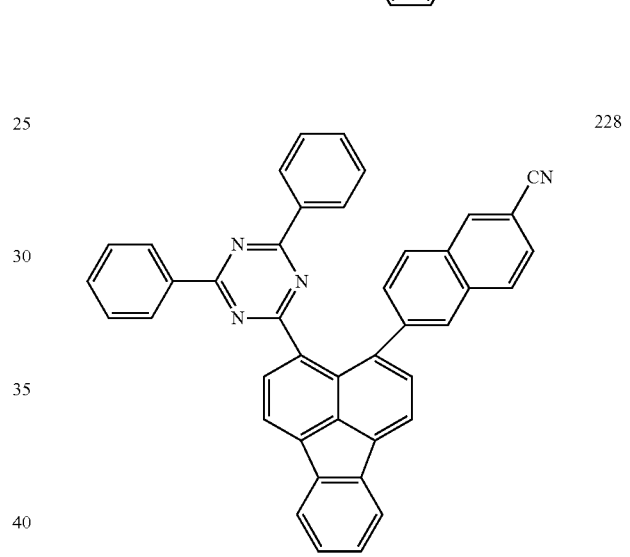
229
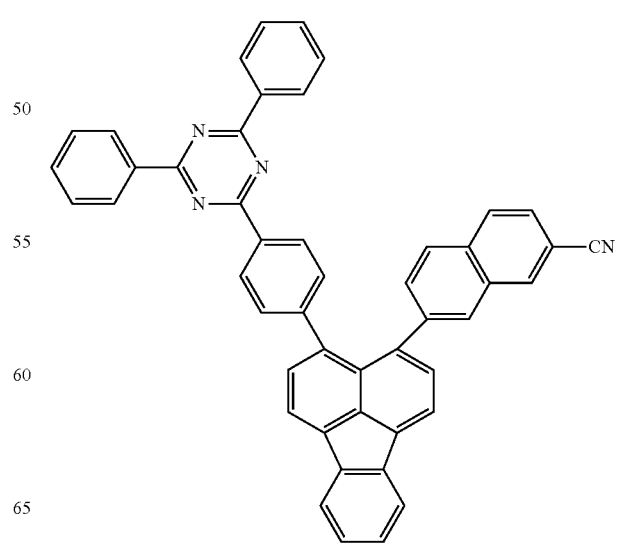

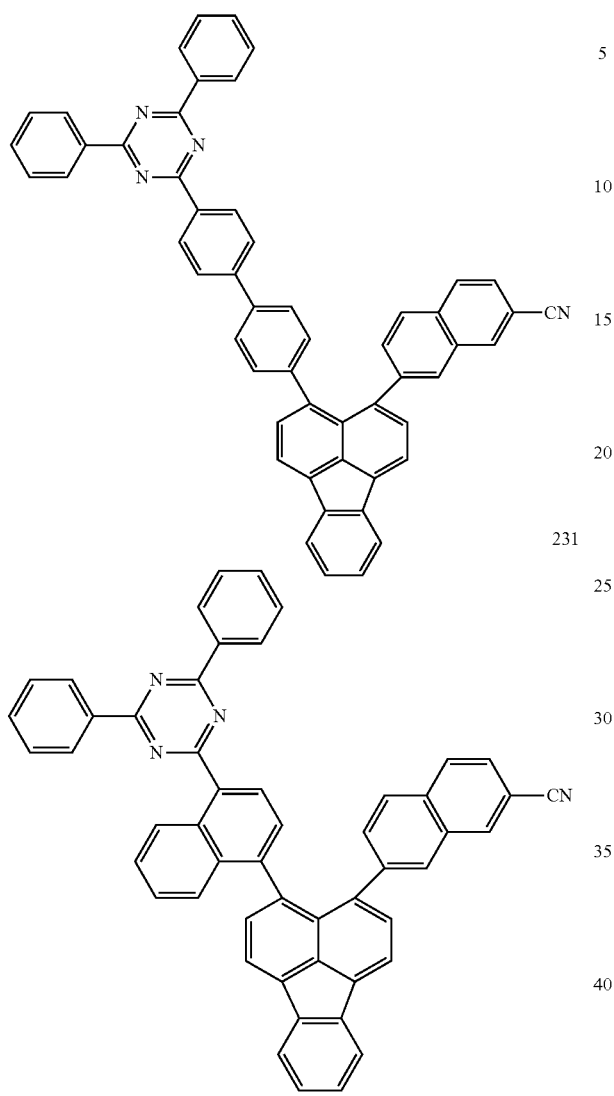
230
231
232
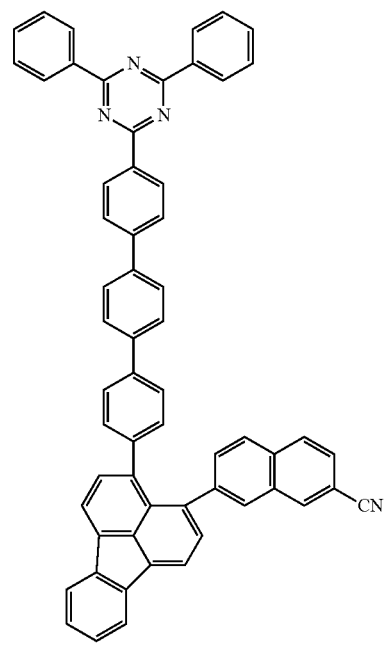
233
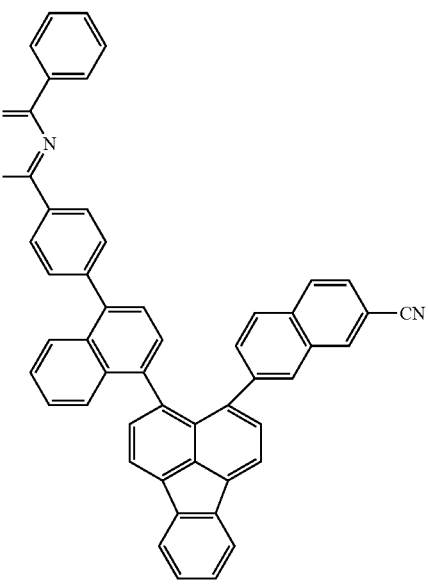
234

235
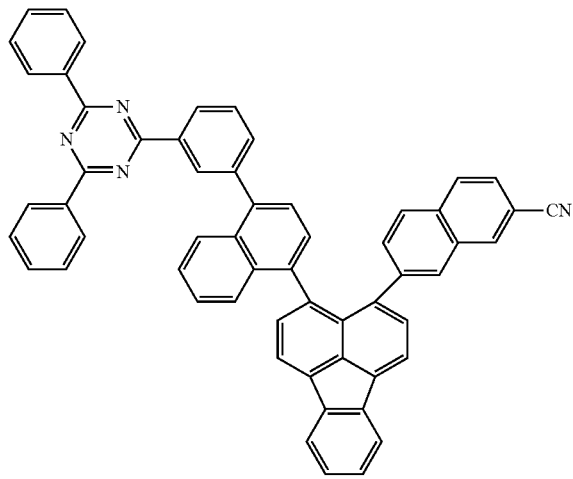
236
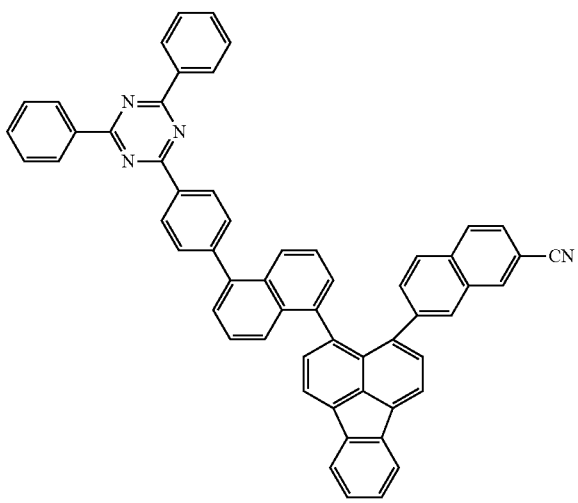
237
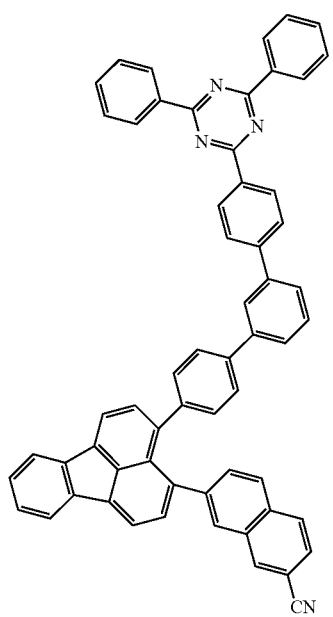
238
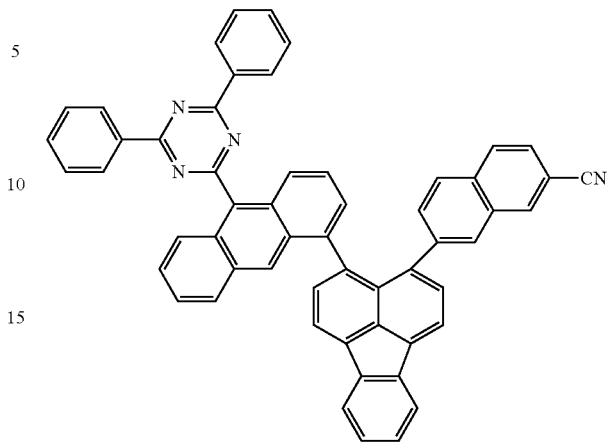
239
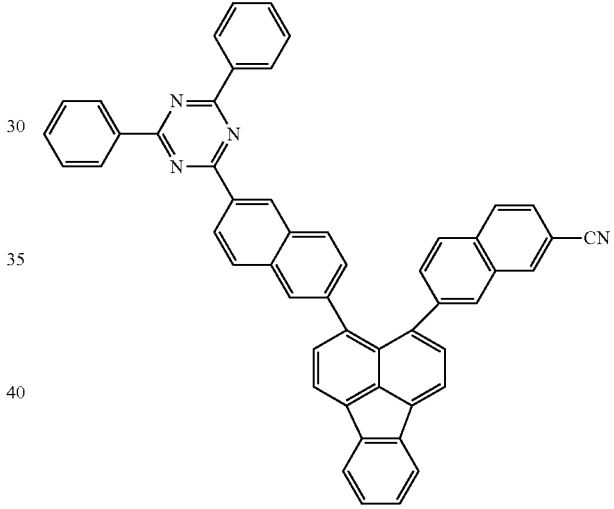
240
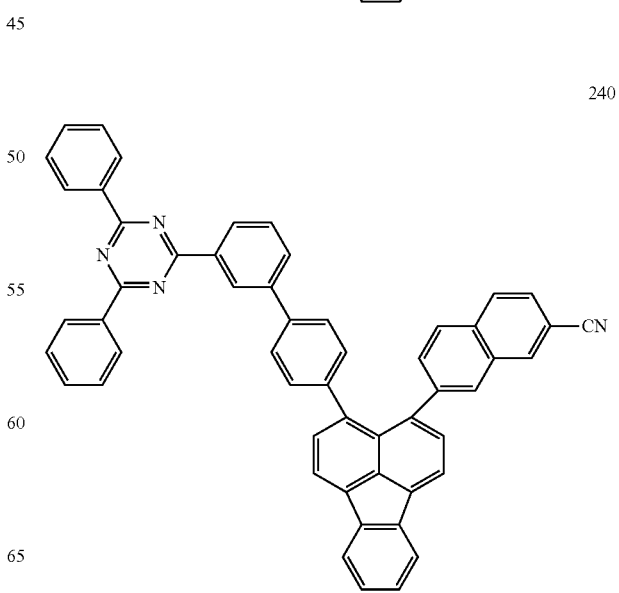

-continued
241
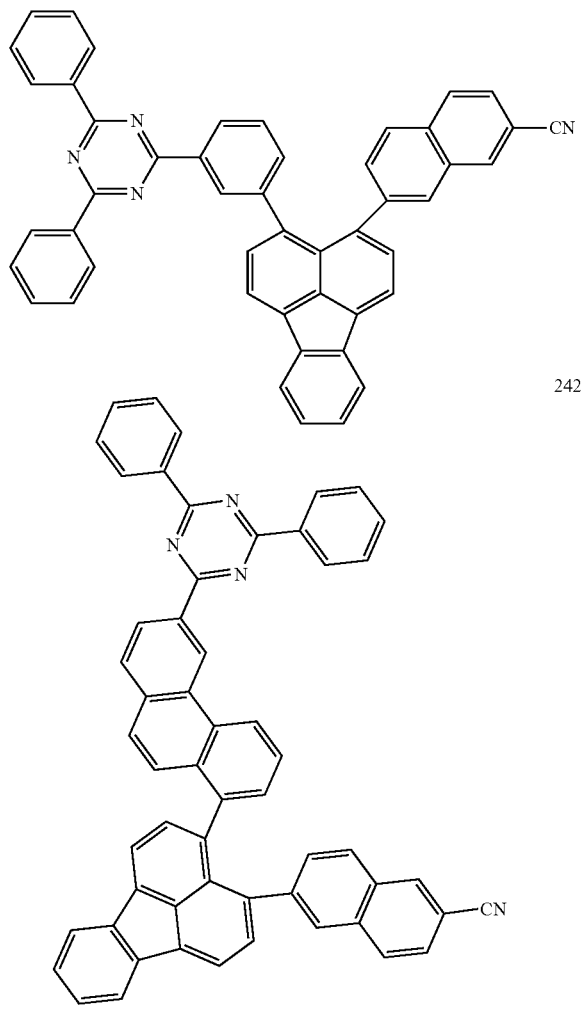
242
243
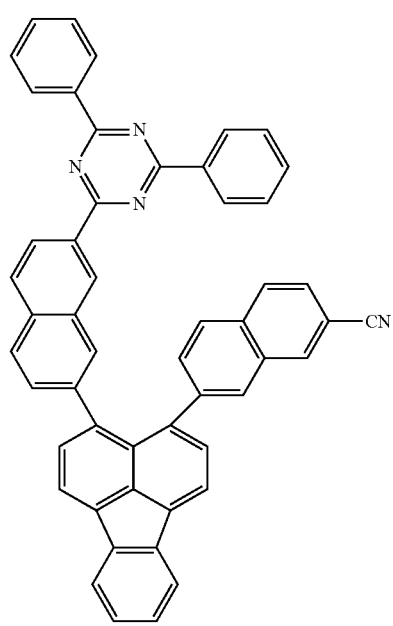
-continued
244
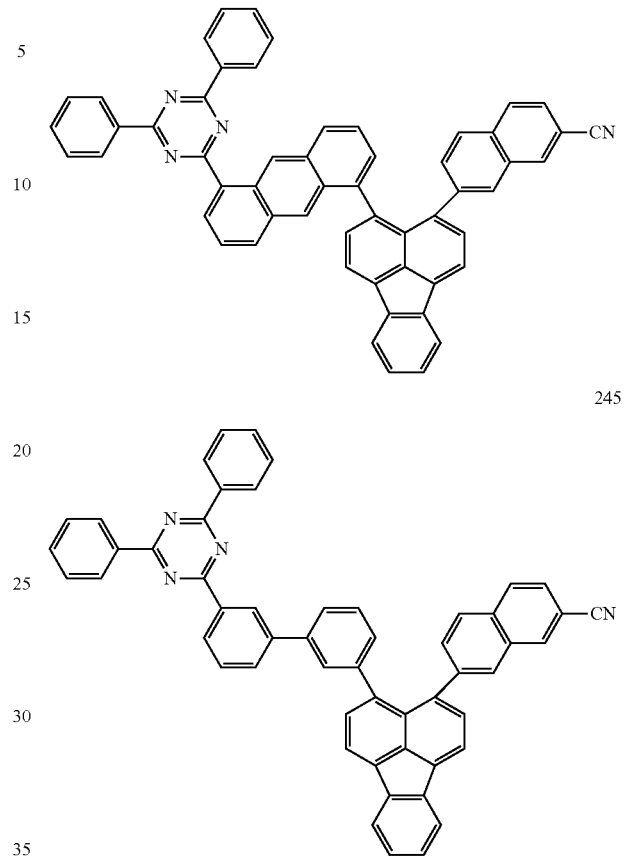
245
246
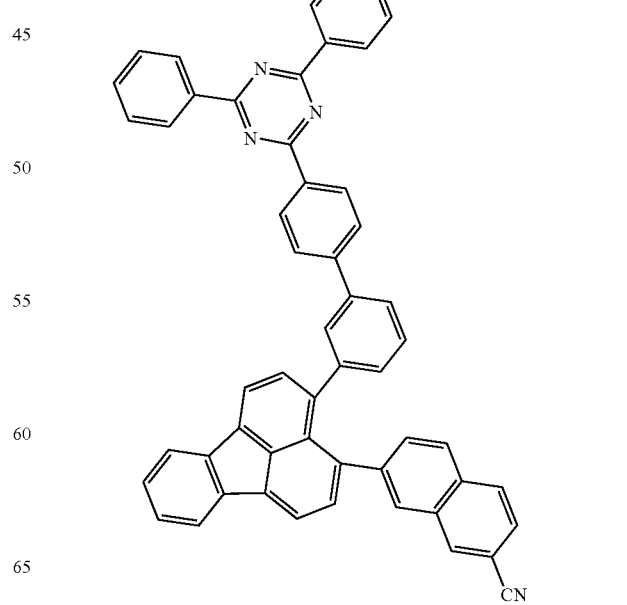

247
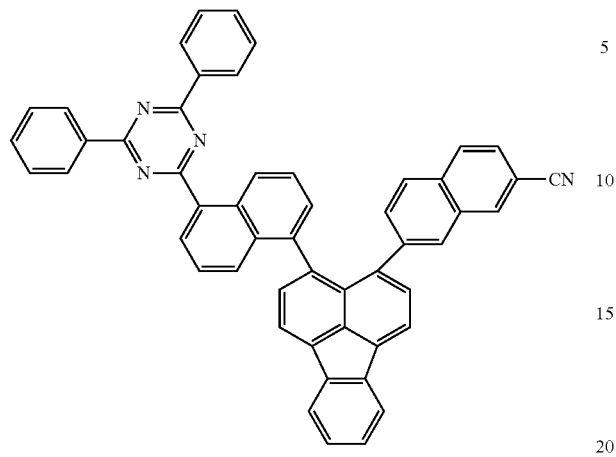
248
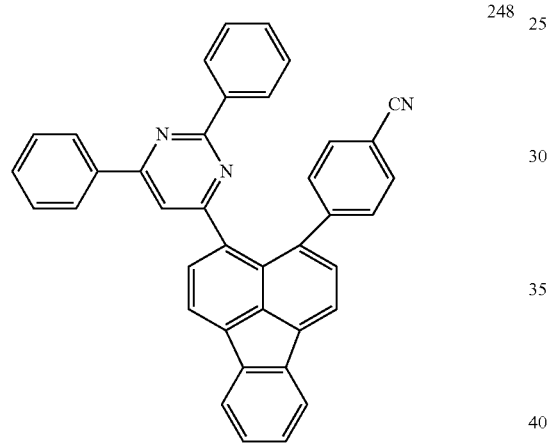
250
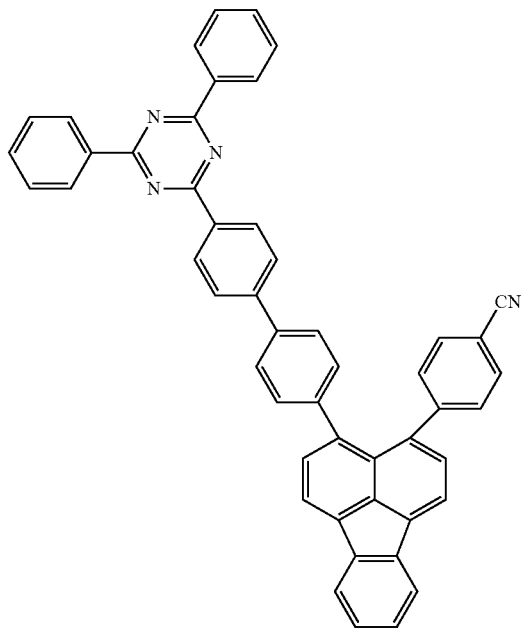
249
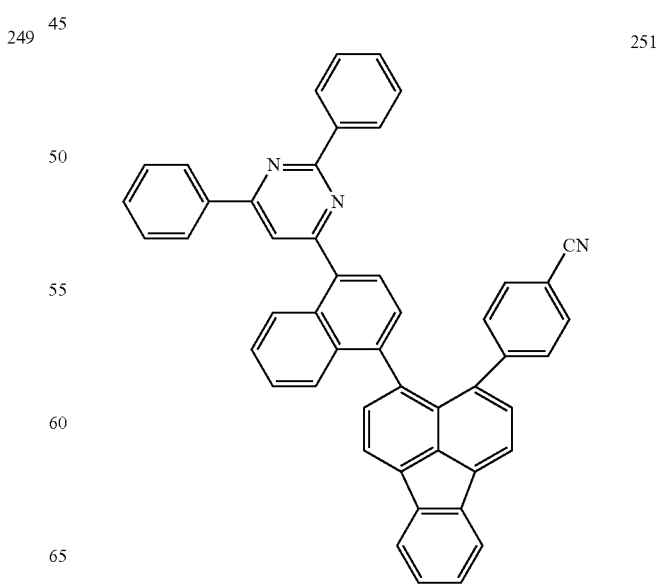
251

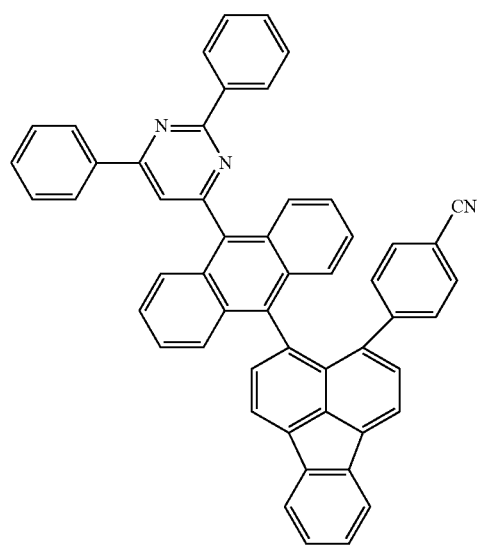
252
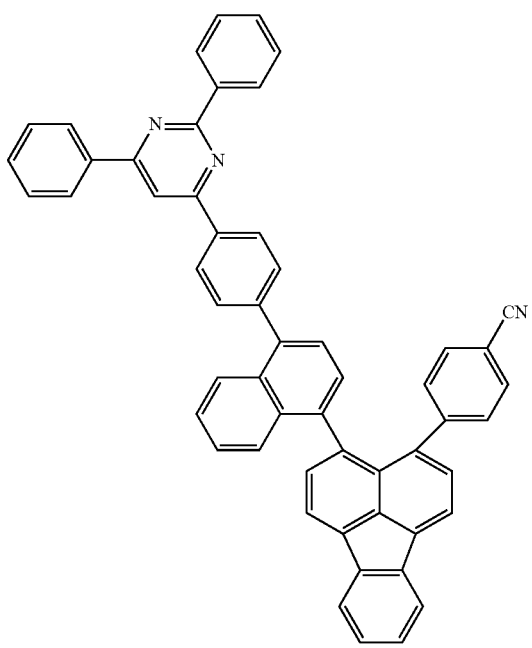
254
253
255

256
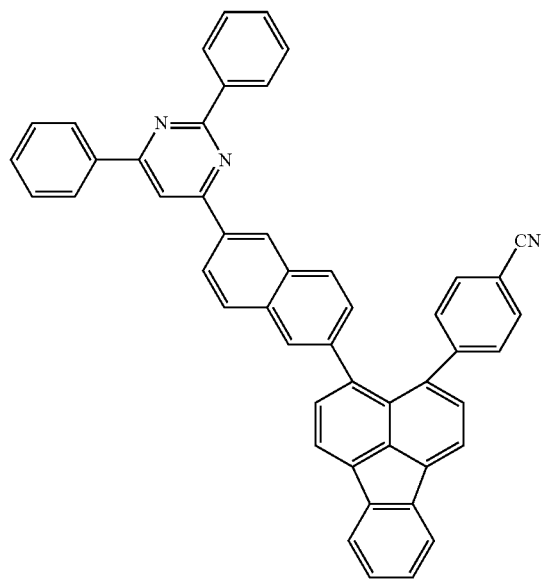
257
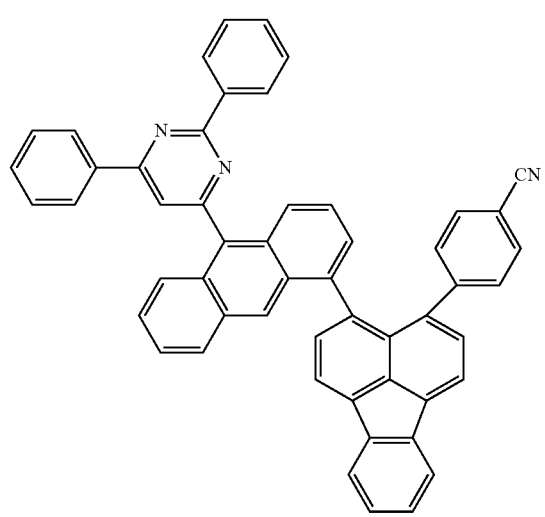
258
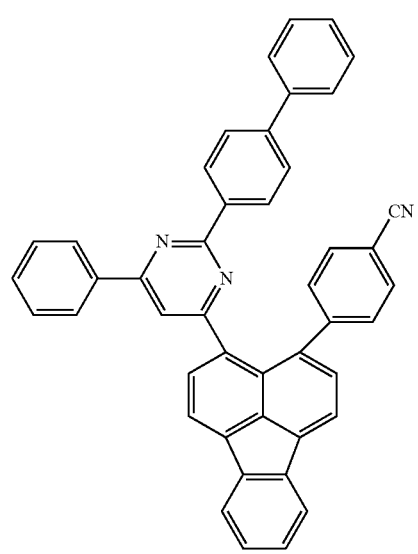
259
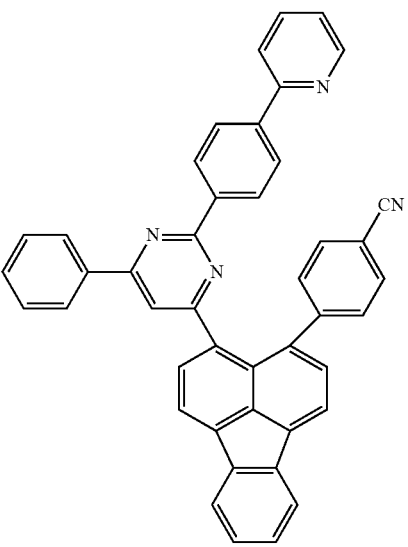
260
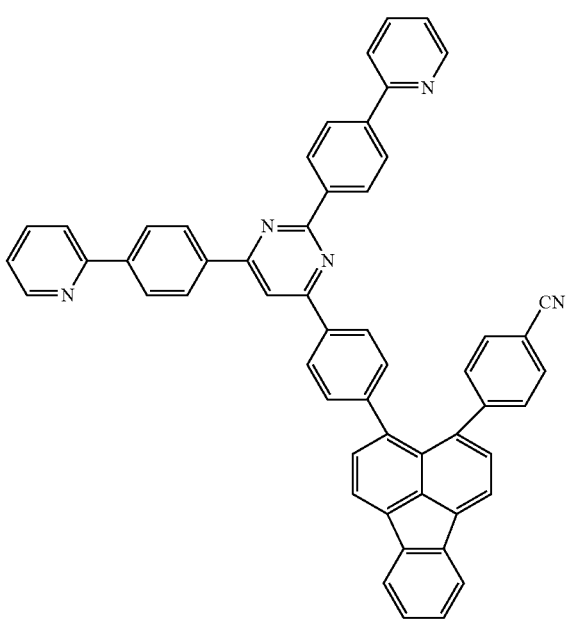

261
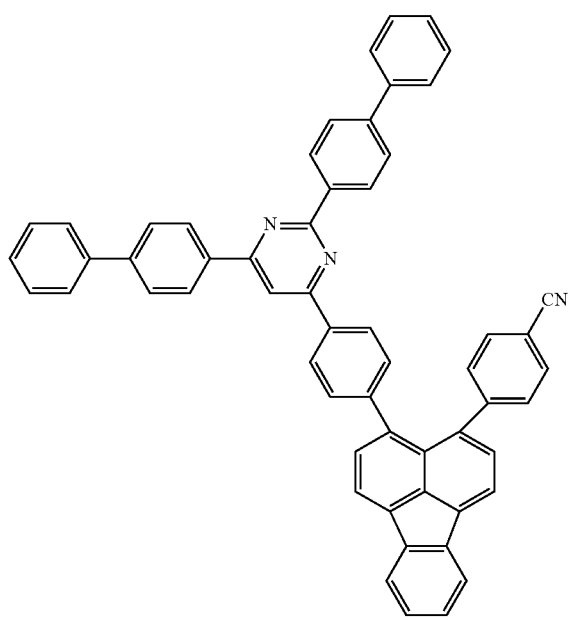
263
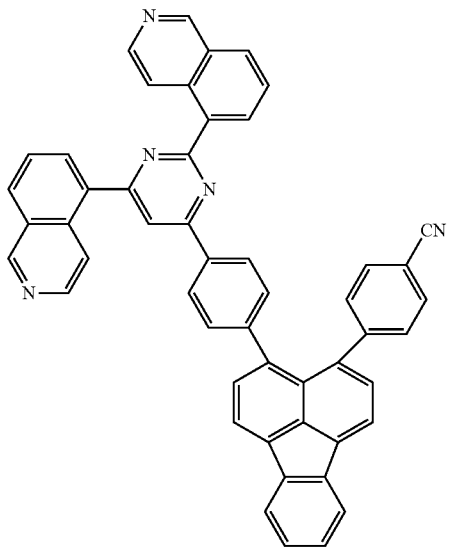
262
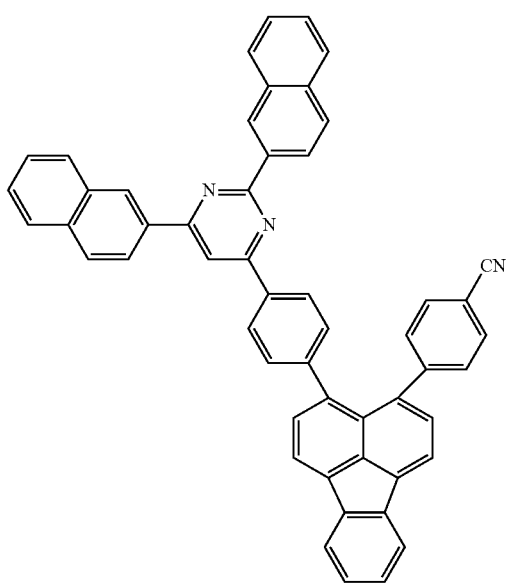
264
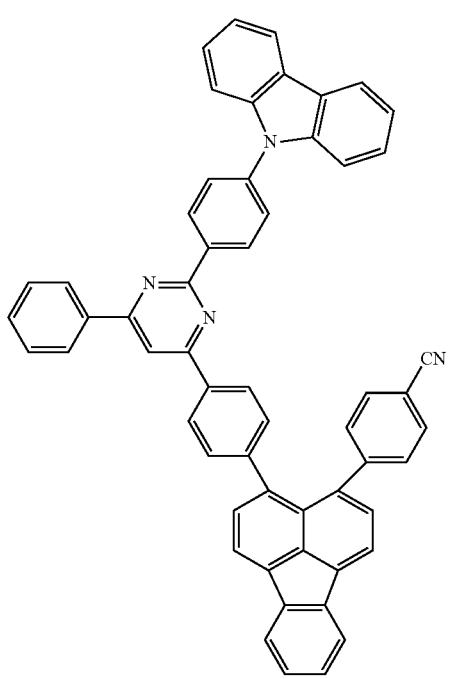

265
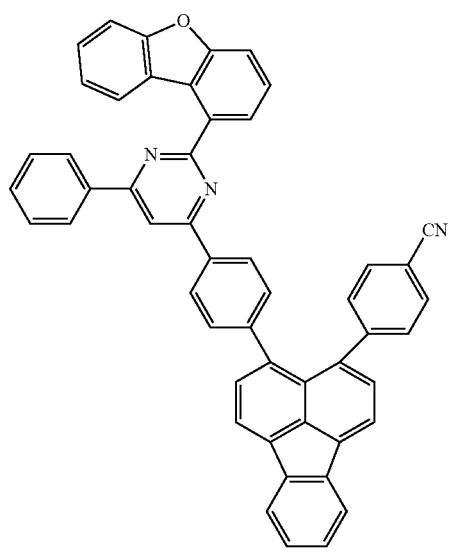
266
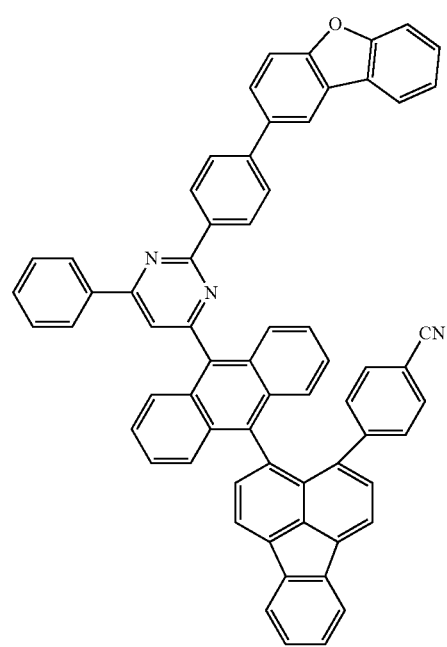
267
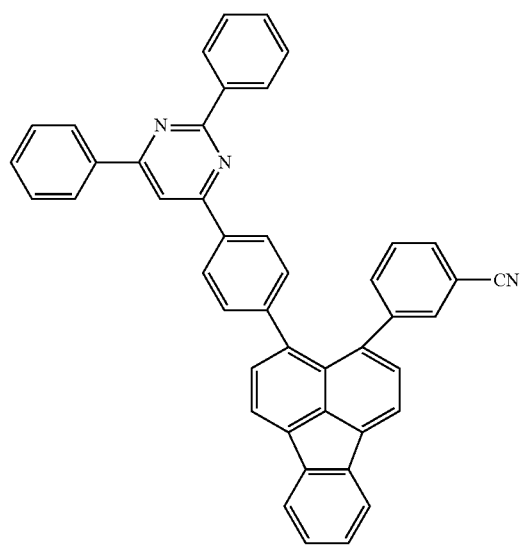
268
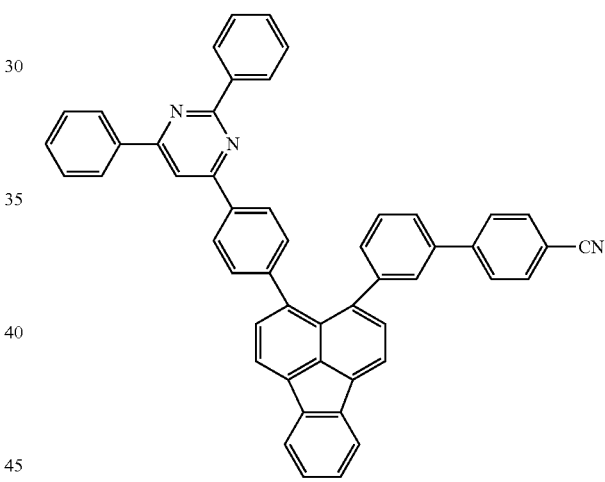
269
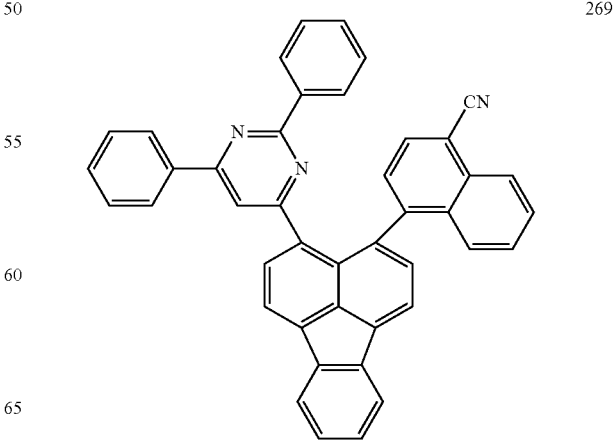

-continued
270
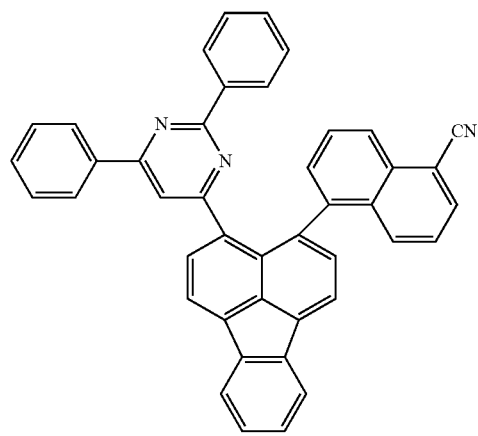
271
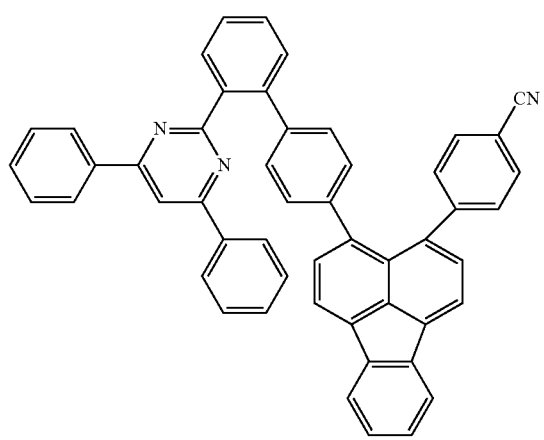
272
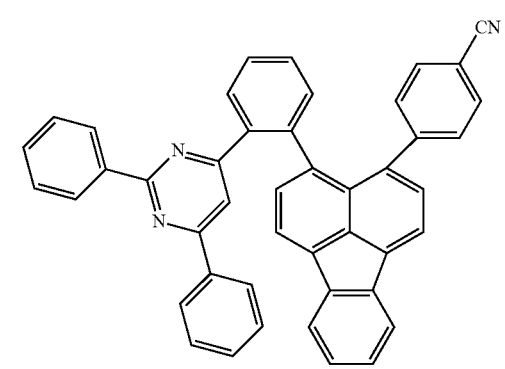
-continued
273
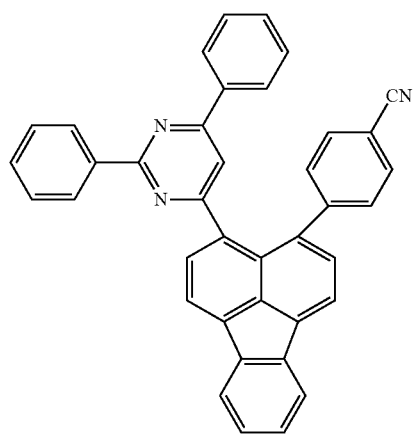
274
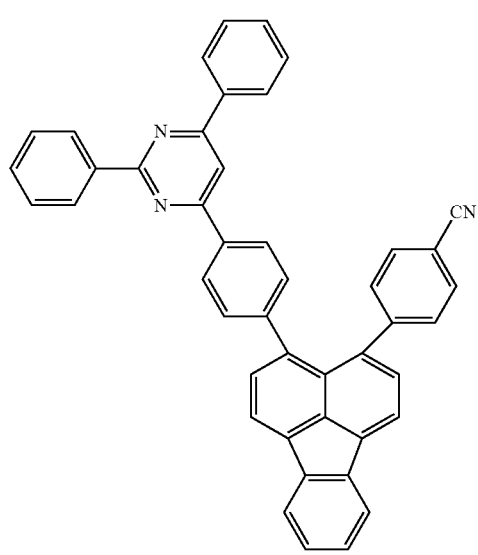
275
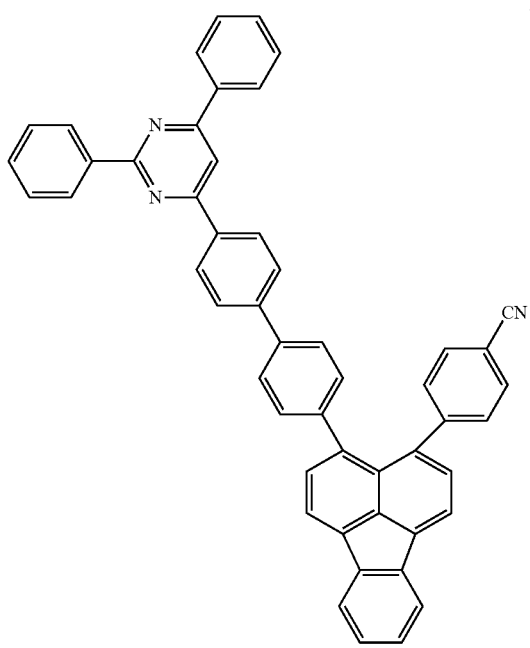

276
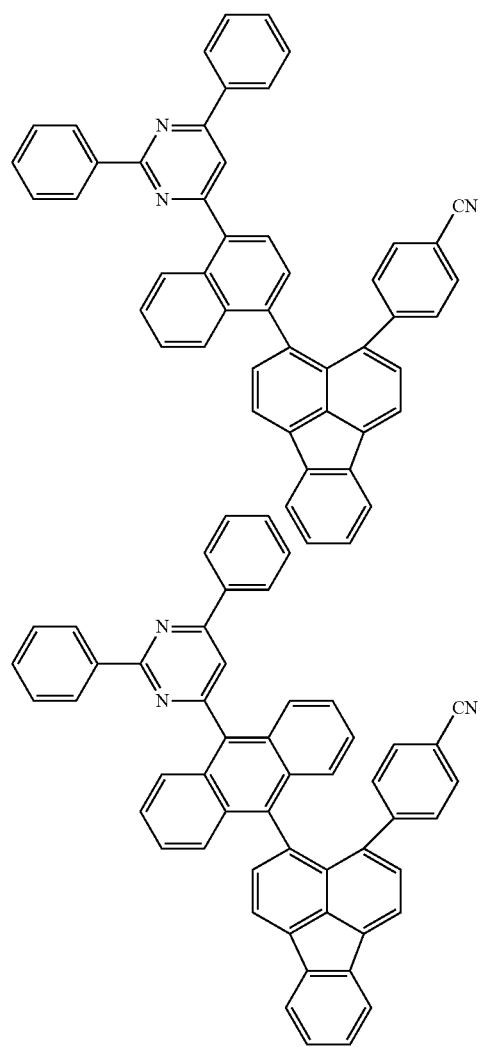
277
278
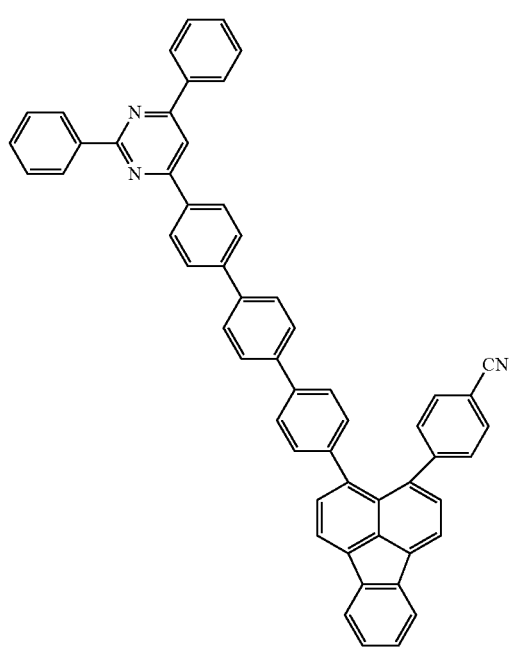
279
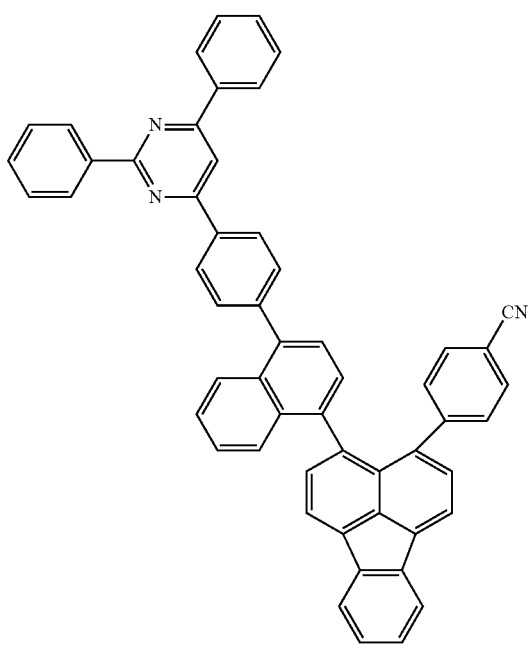
280
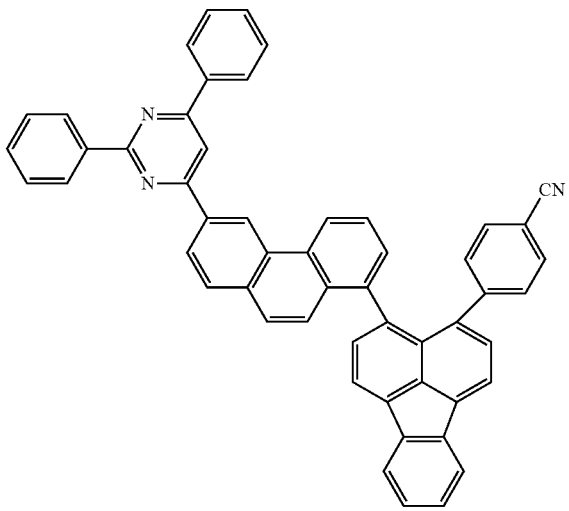

281
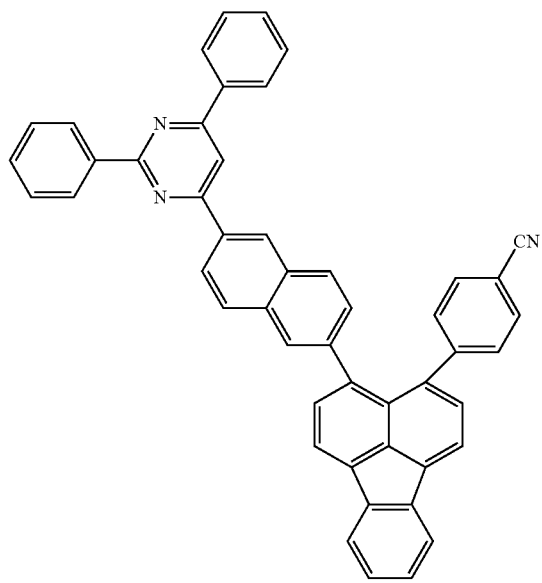
282
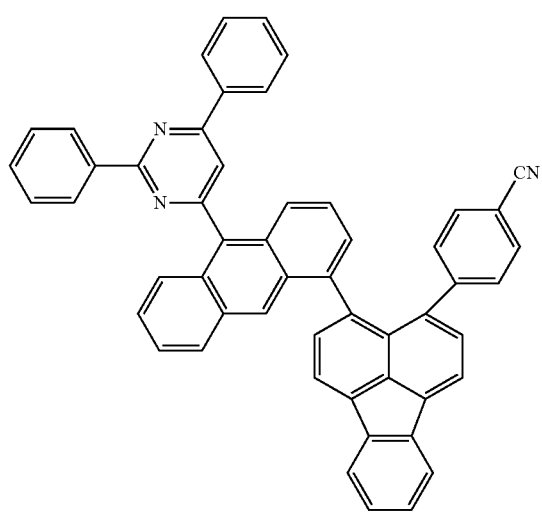
283
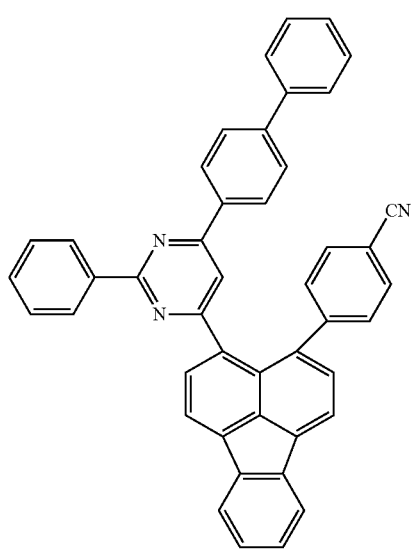
284
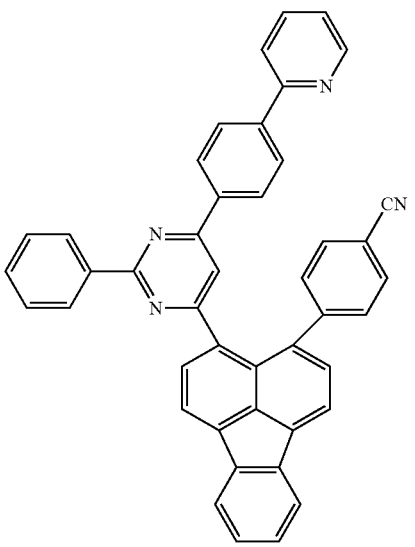
285
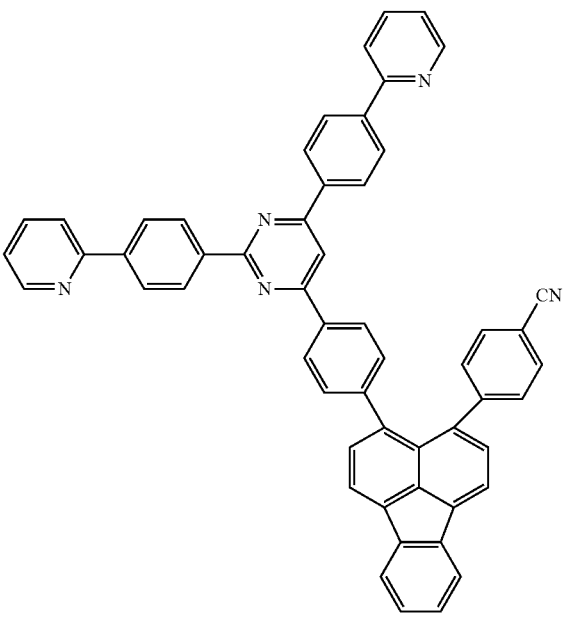

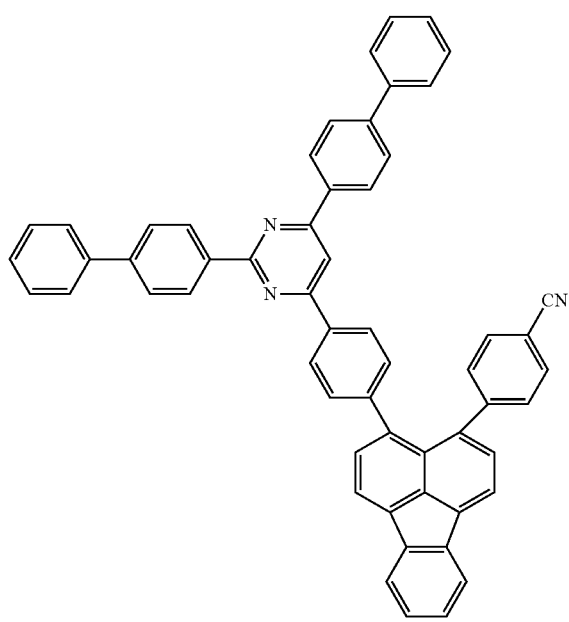
286
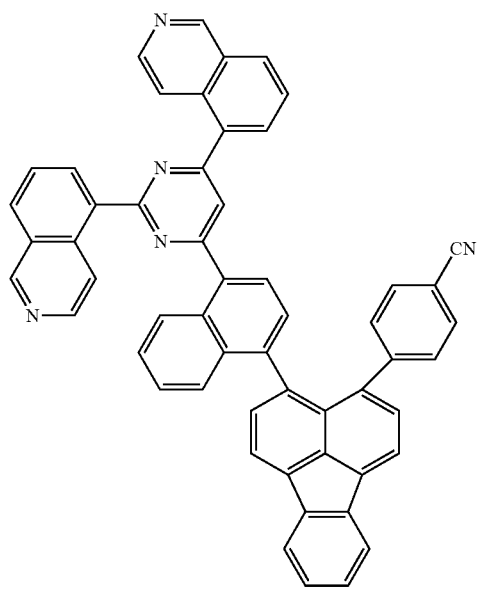
288
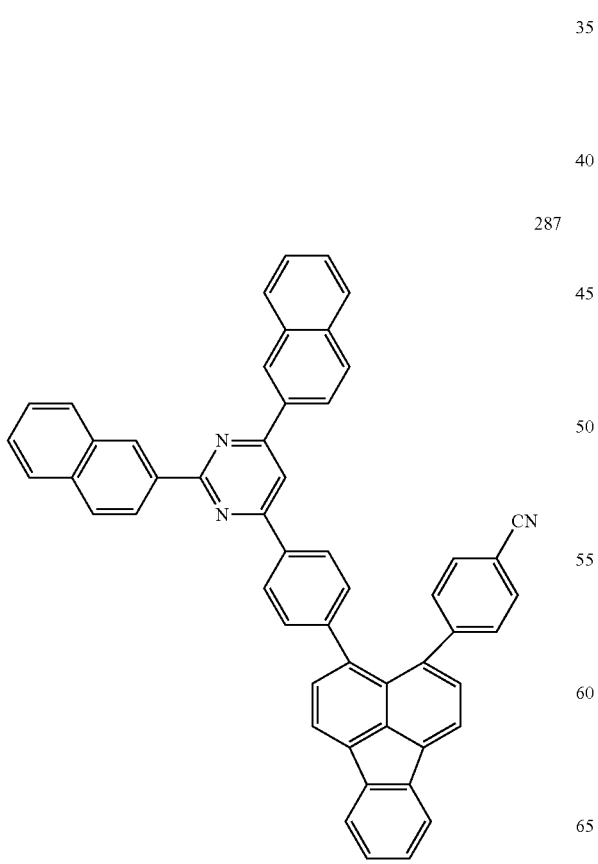
287
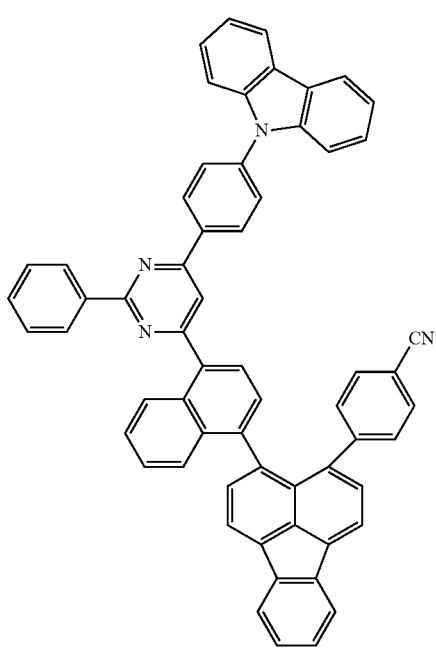
289

-continued
290
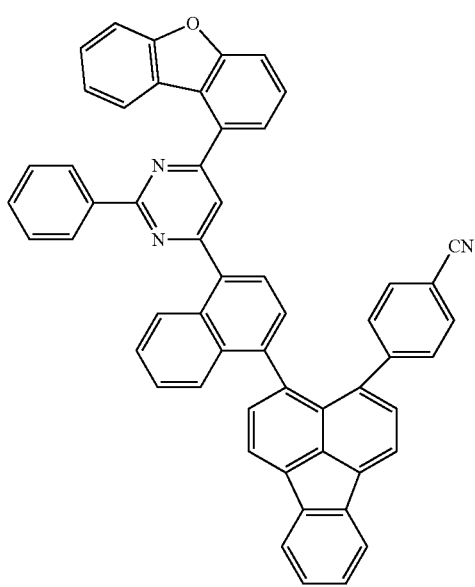
291
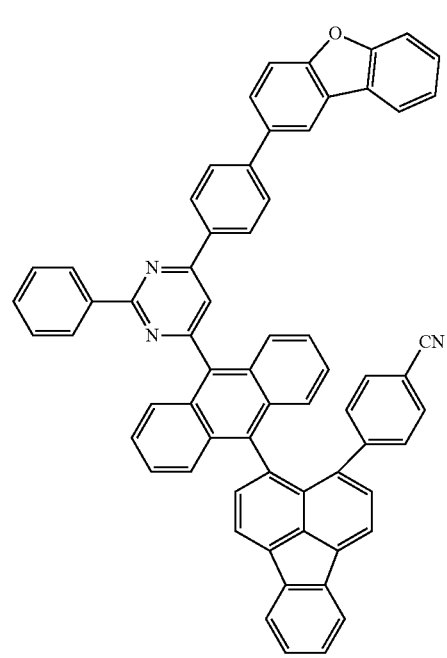
292
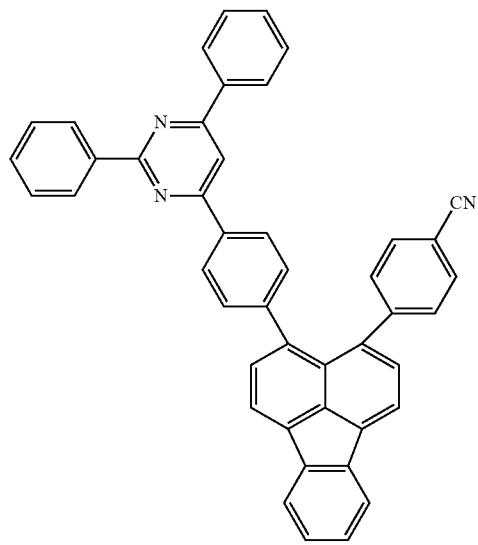
293
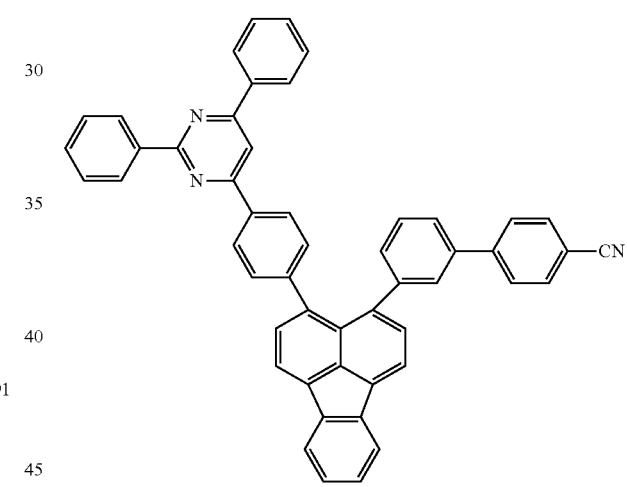
294
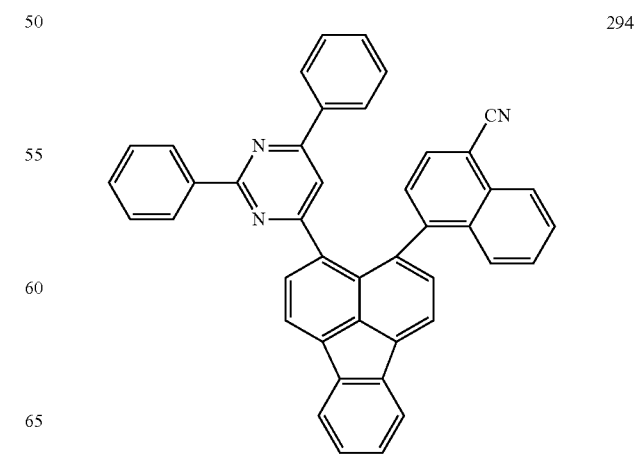

295
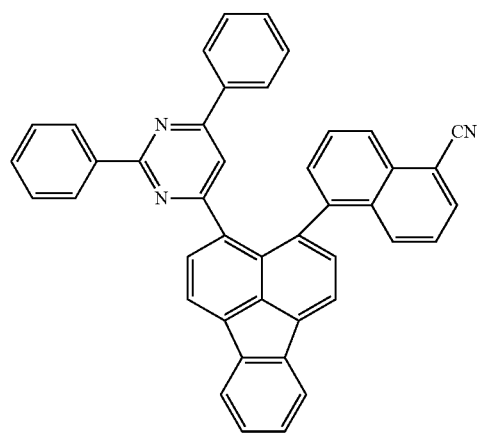
296
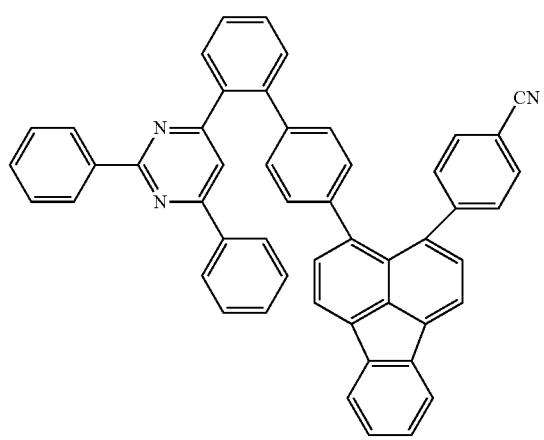
297
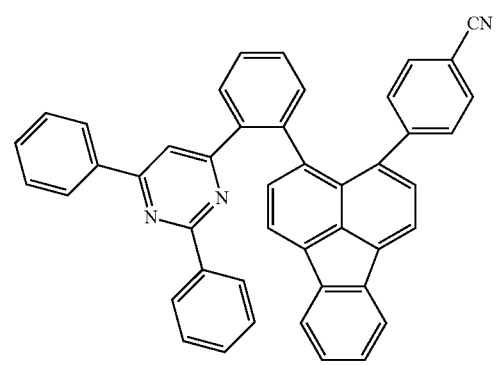
298
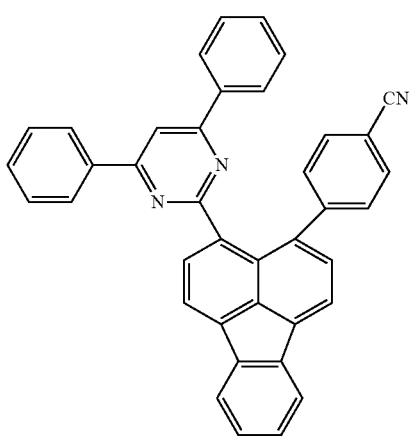
299
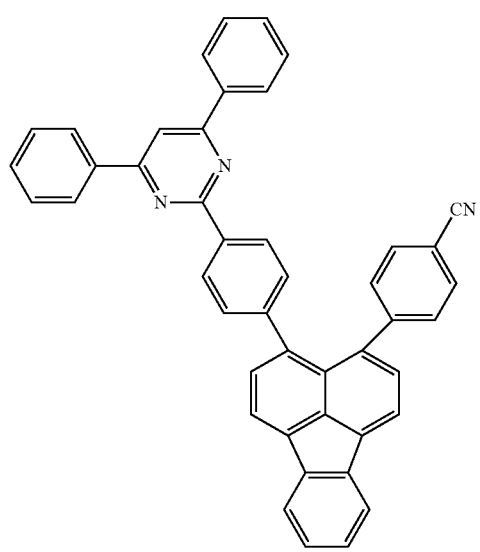
300
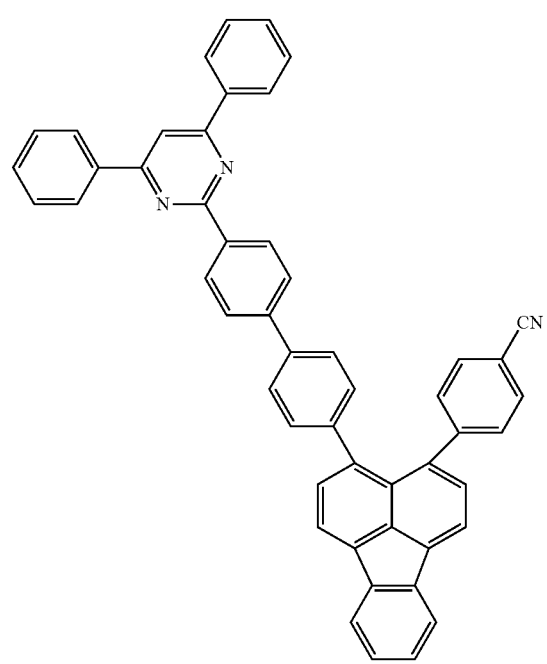

-continued
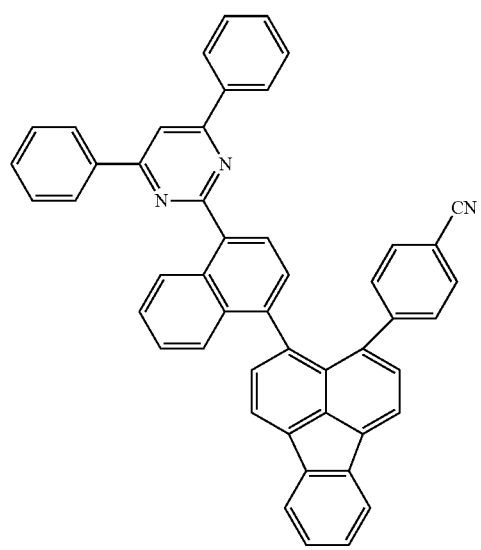
301
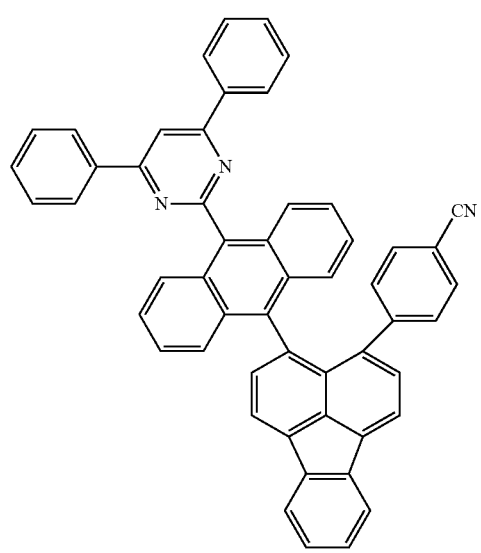
302
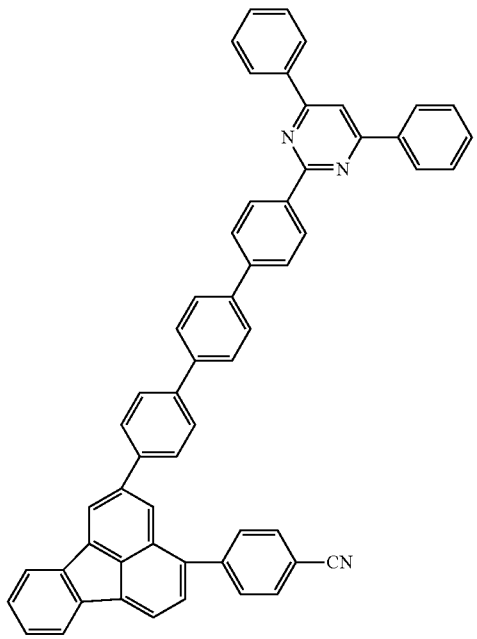
303
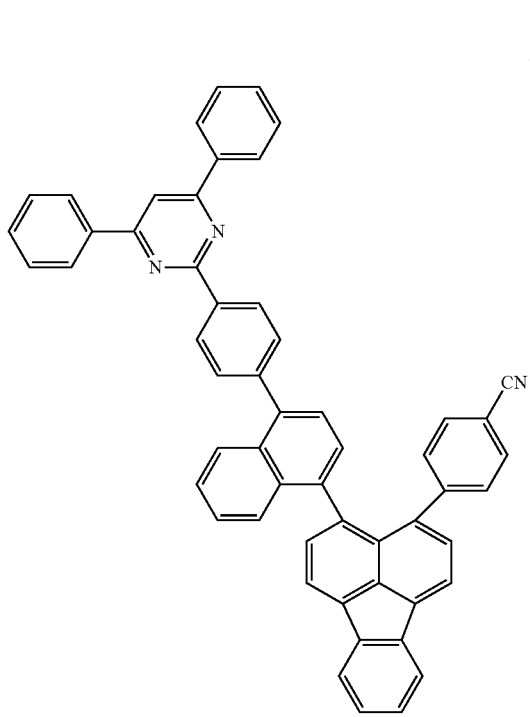
304

305
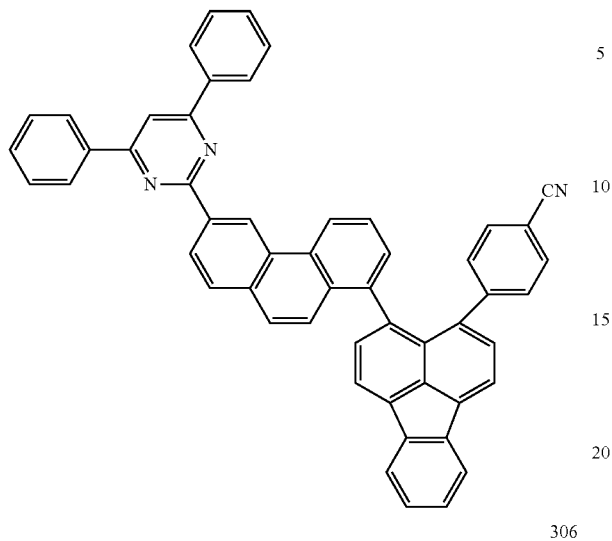
306
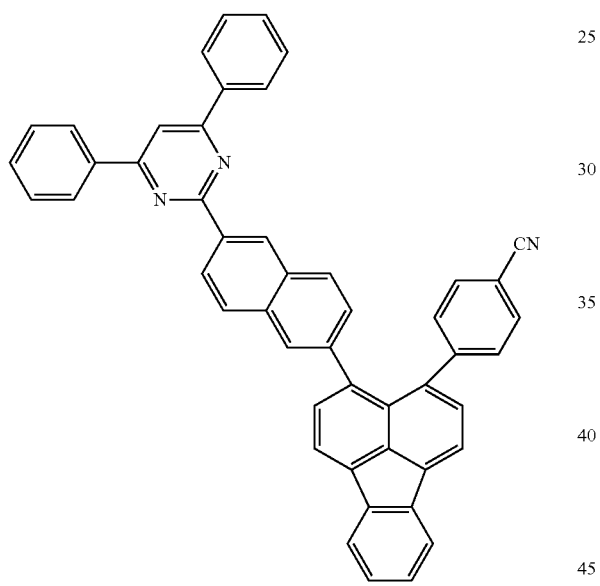
307
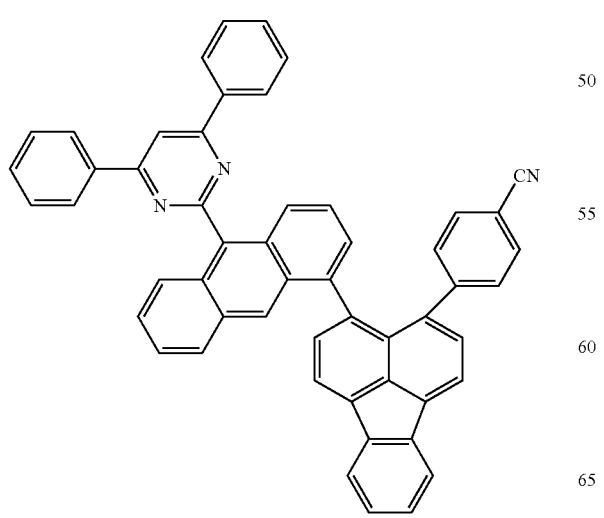
308
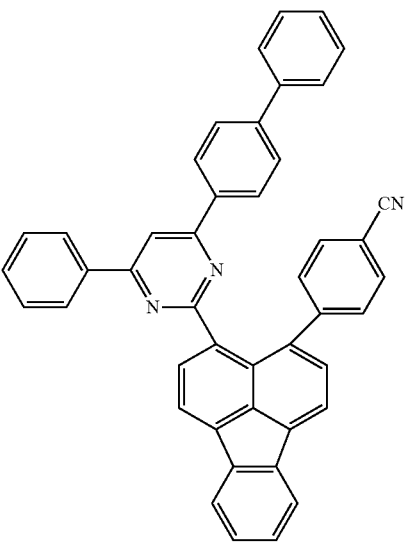
309
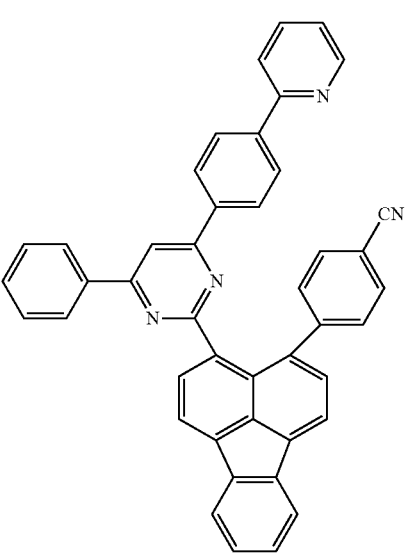

310
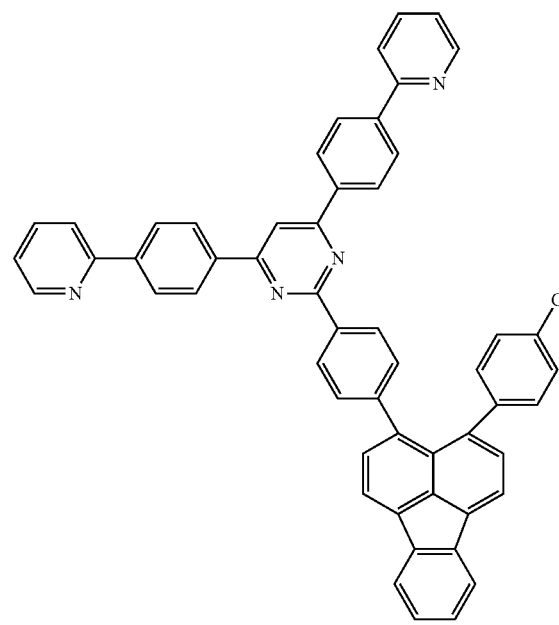
311
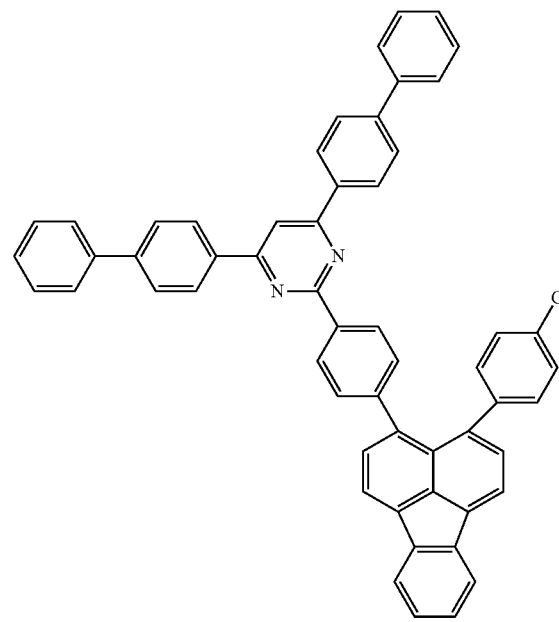
312
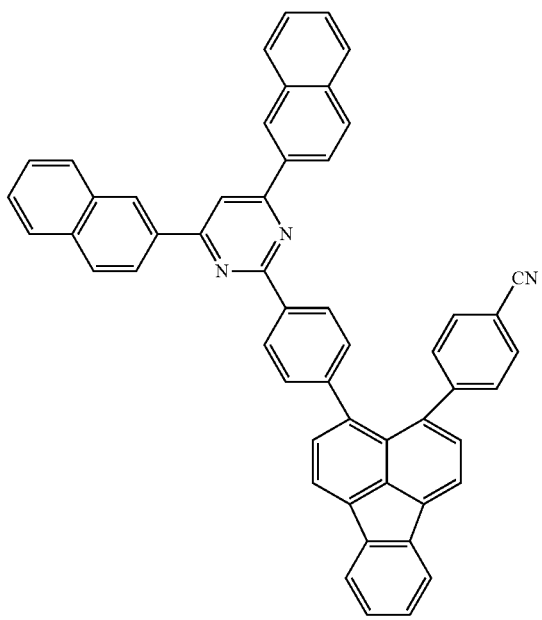
313
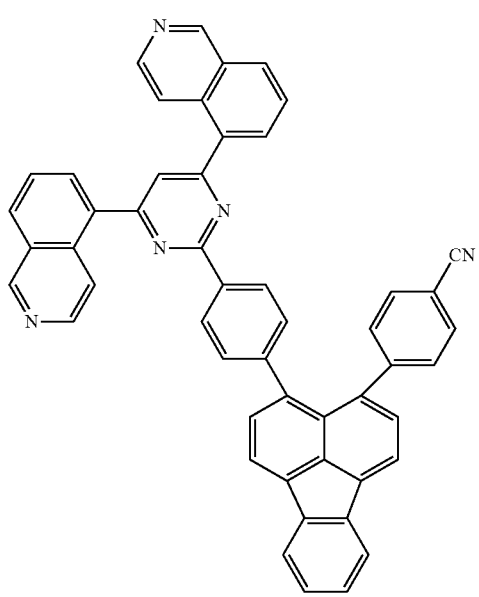

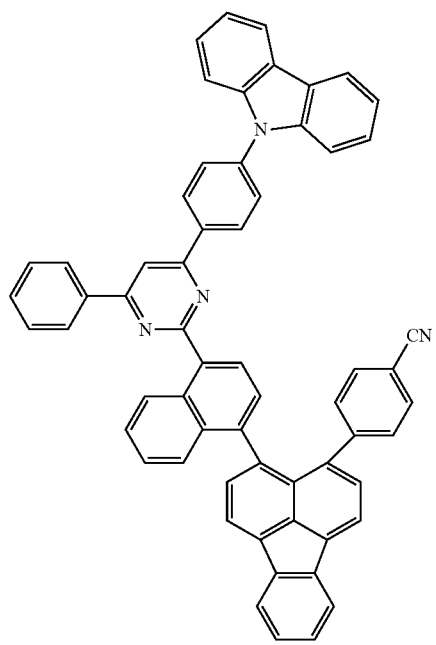
314
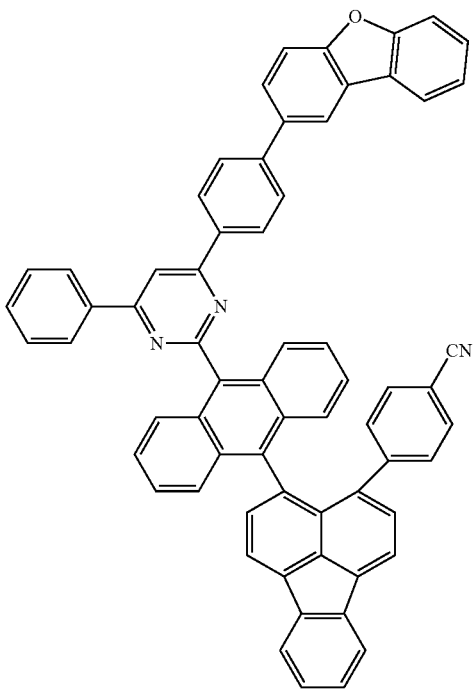
316
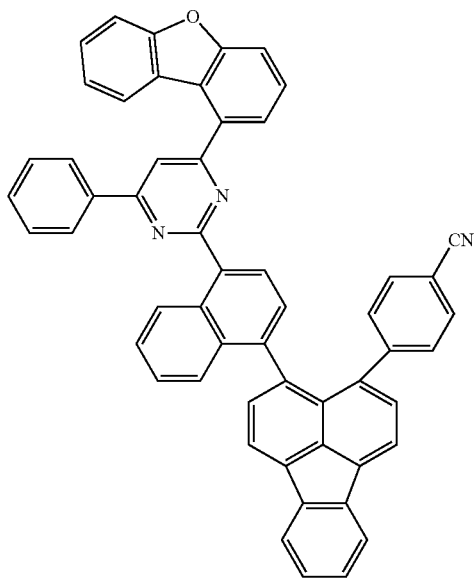
315

181
-continued
318
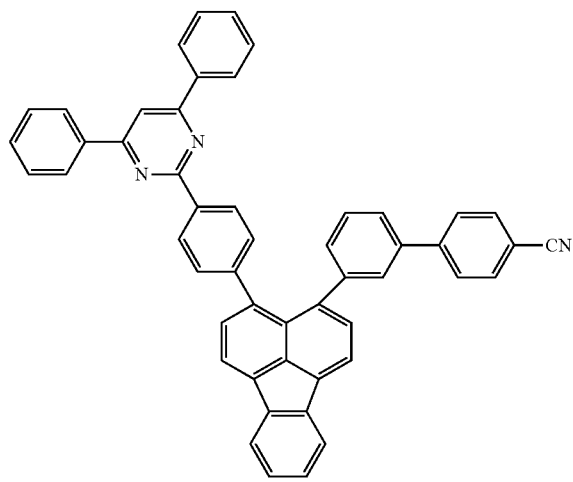
319
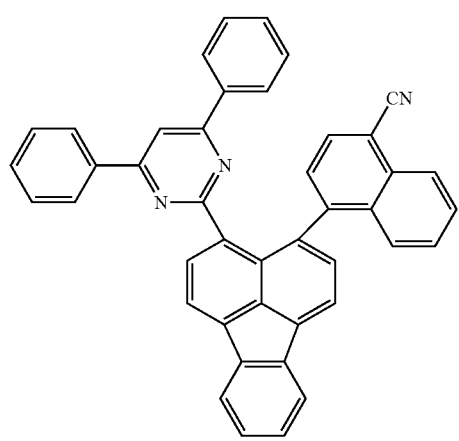
320
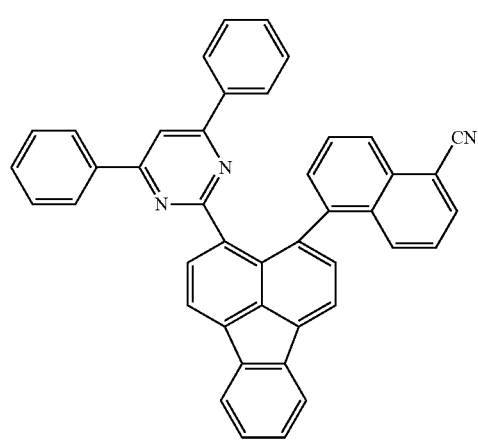
182
-continued
321
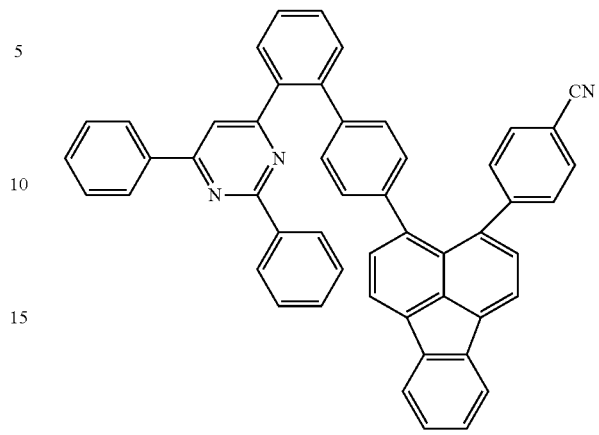
322
323
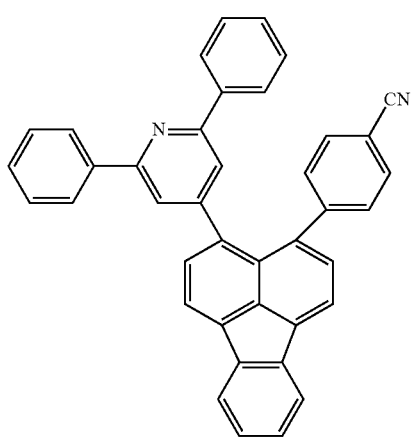

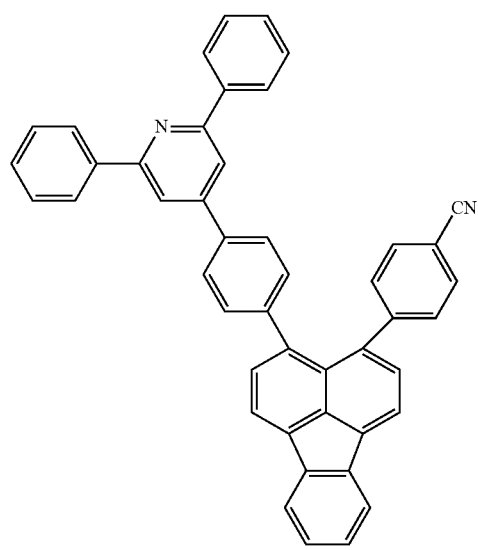
324
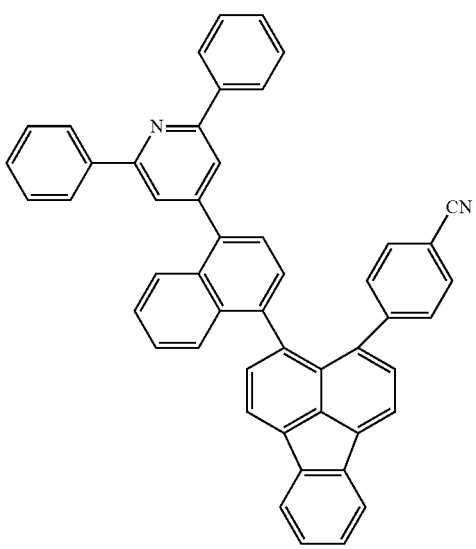
326
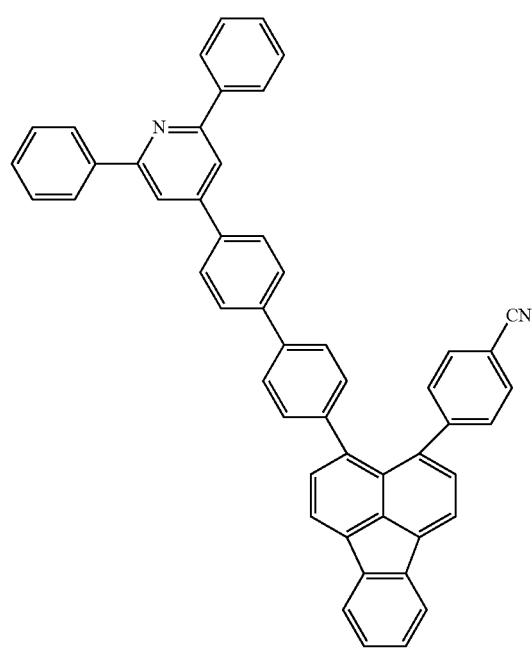
325
327

328
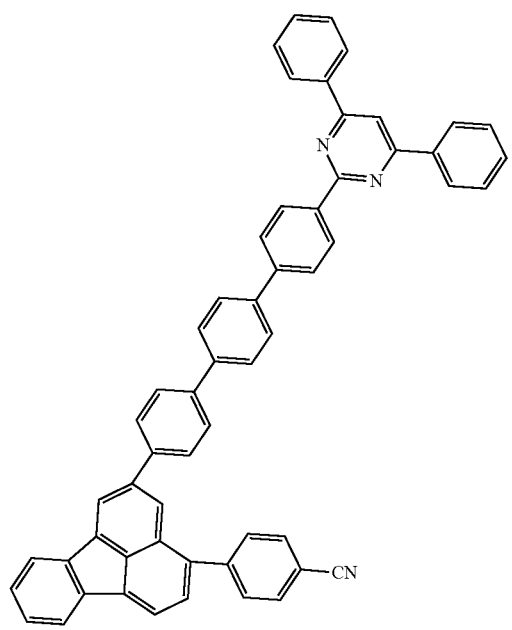
330
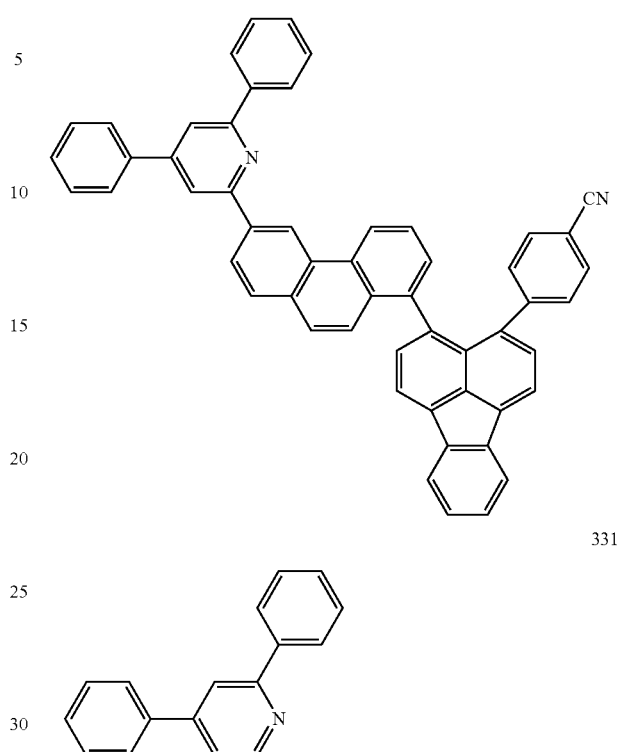
331
329
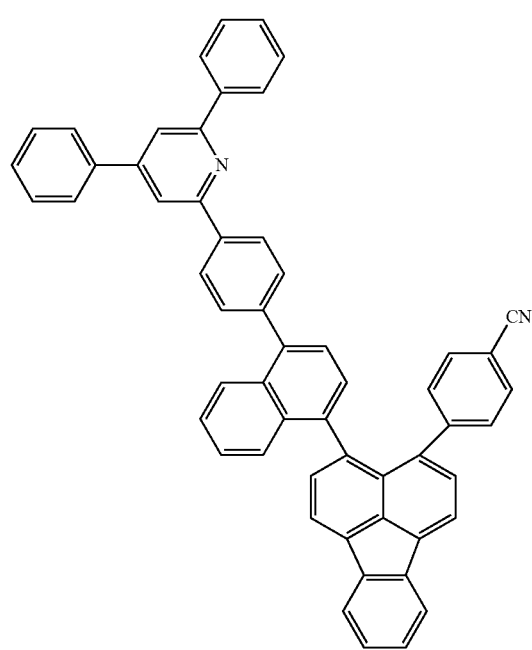
332
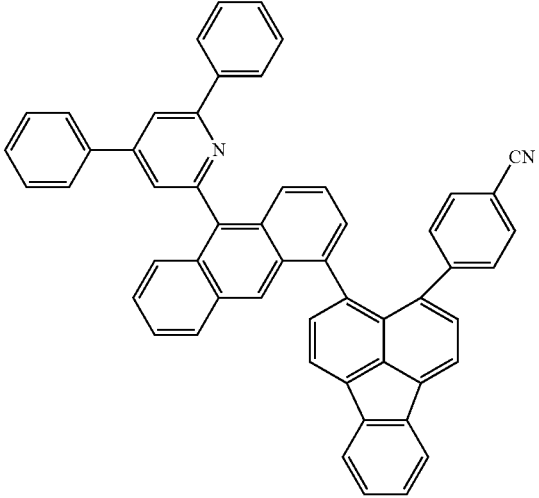

333
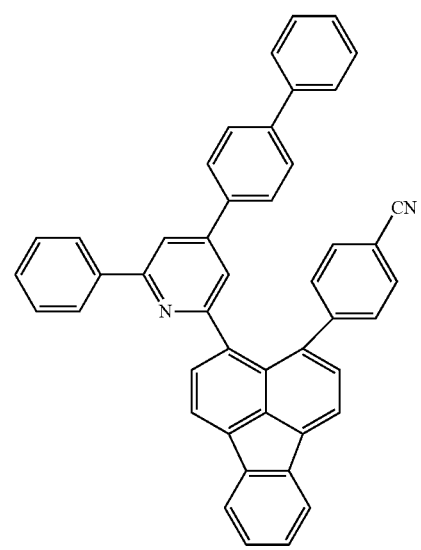
334
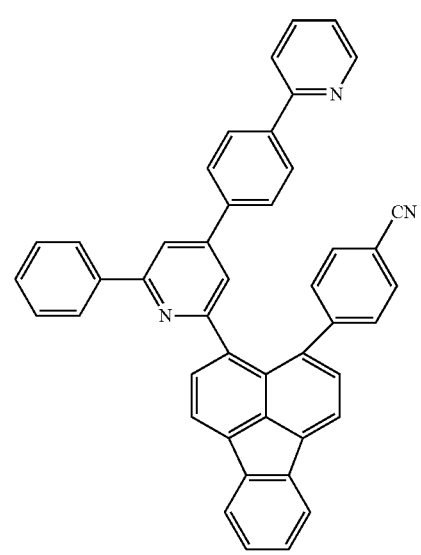
335
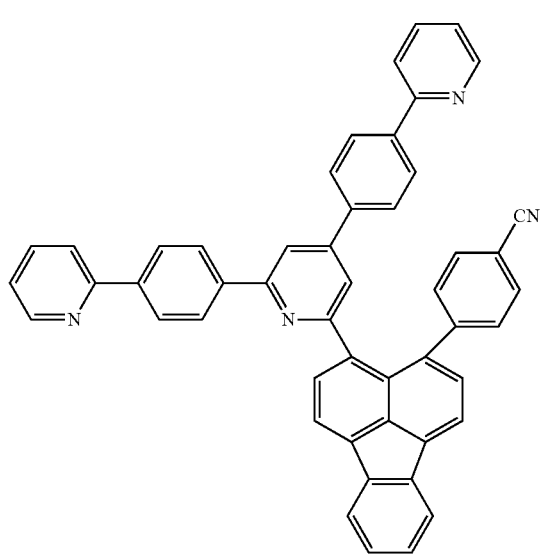
336
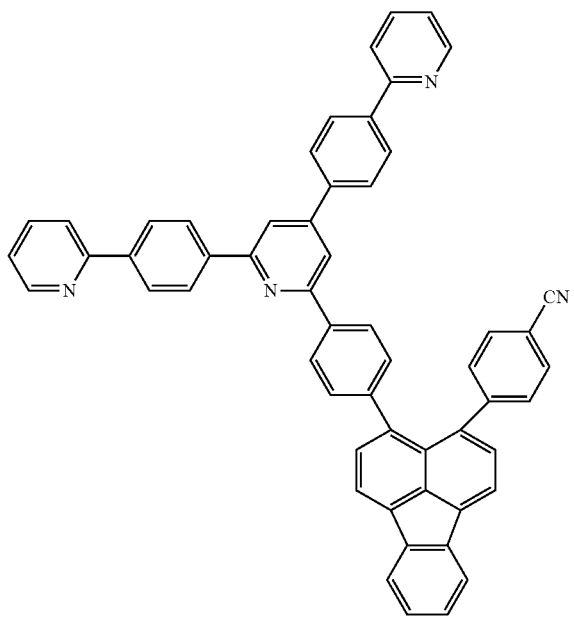
337
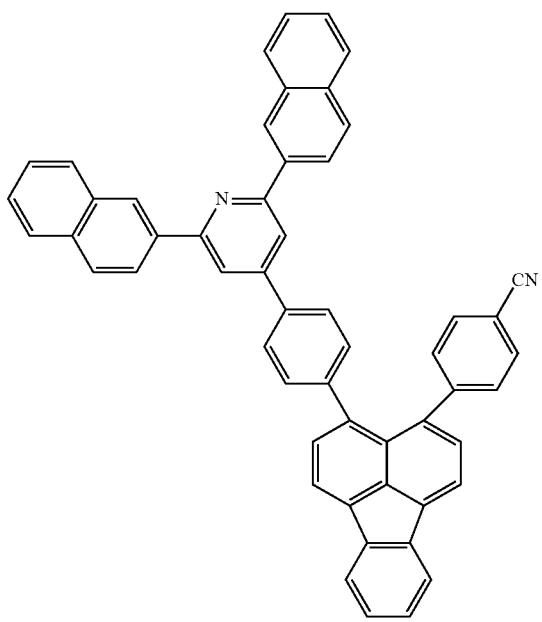

338
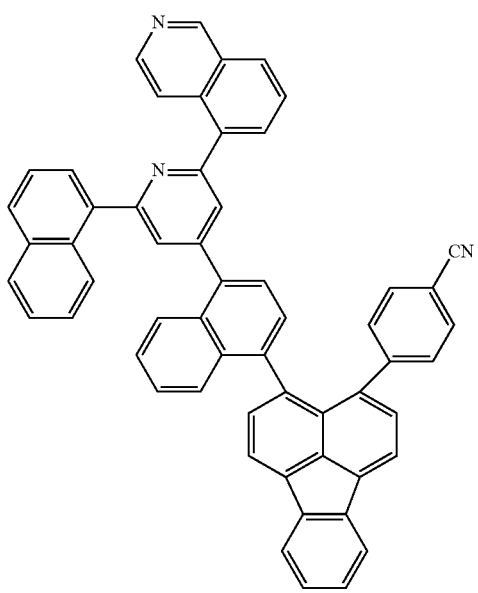
339
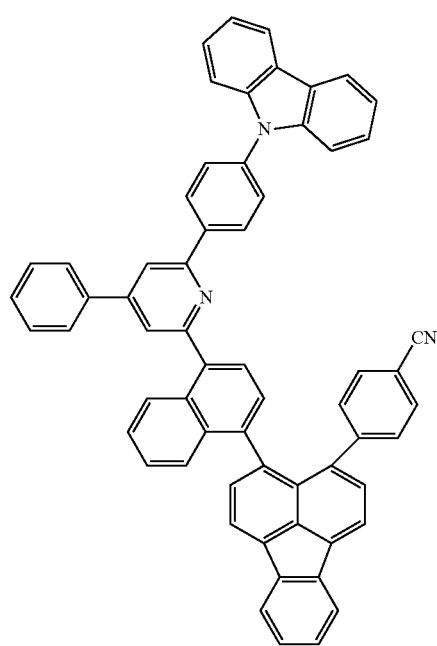
340
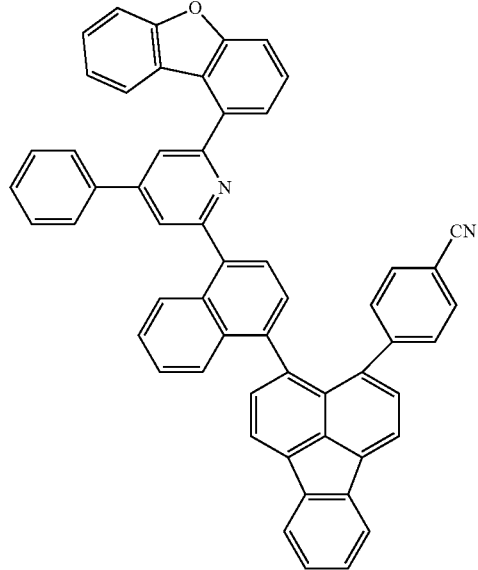
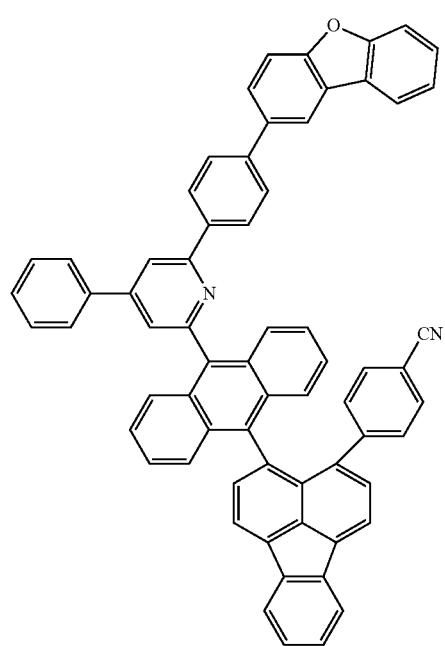

-continued
342
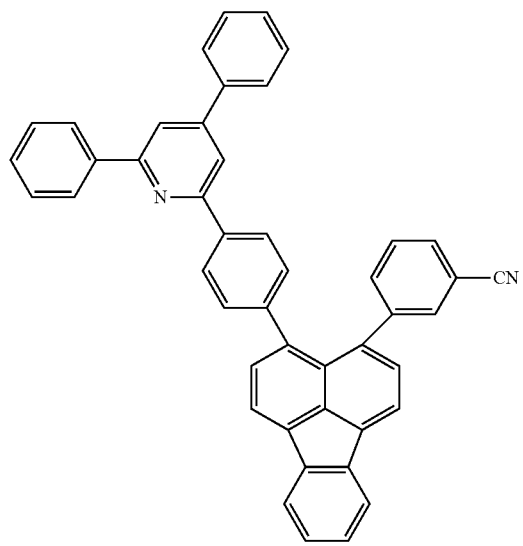
343
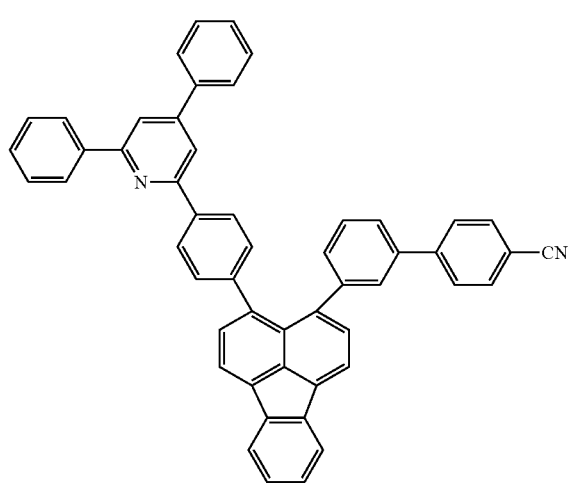
344
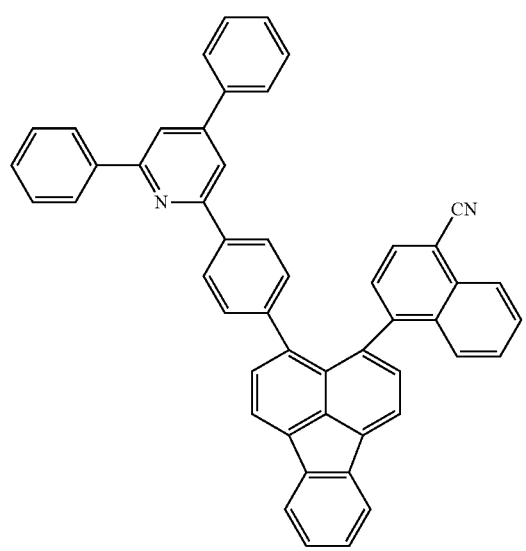
-continued
345
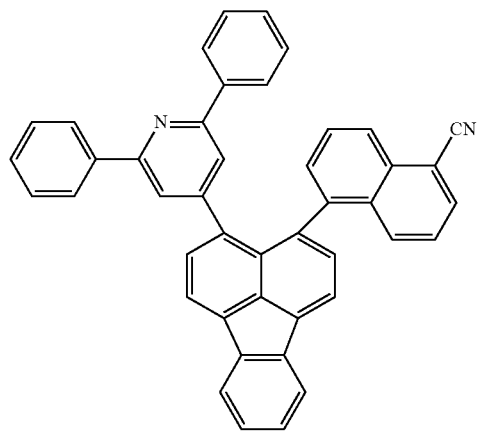
346
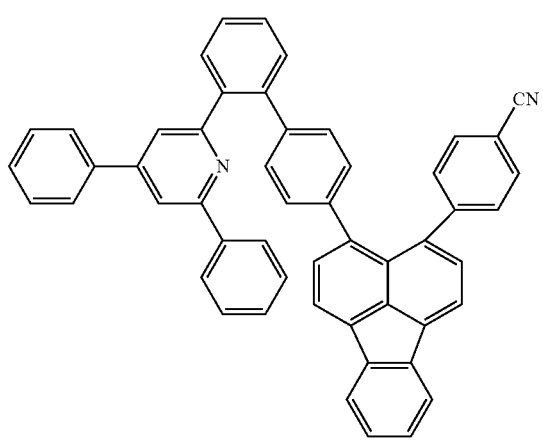
347
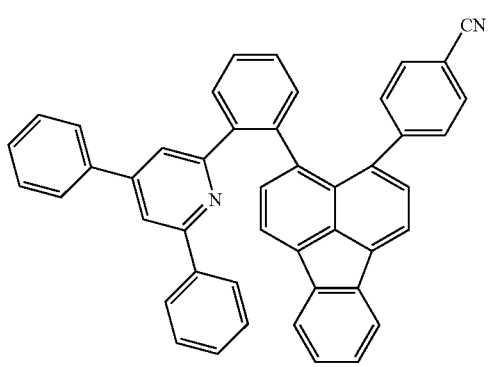

-continued
348
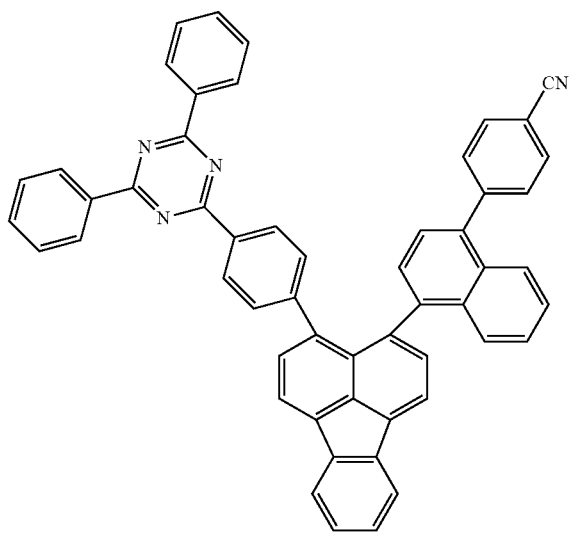
349
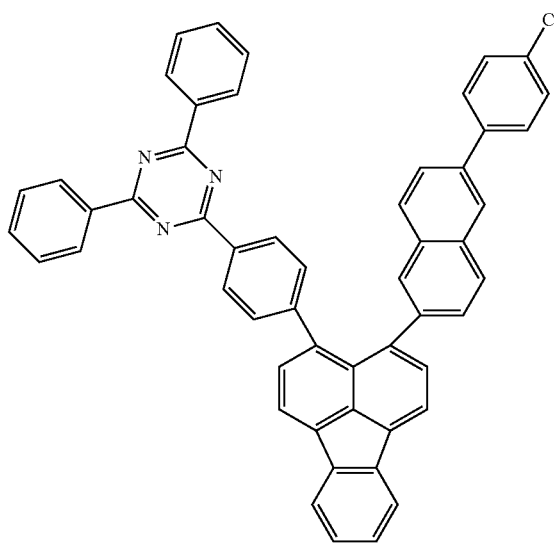
350
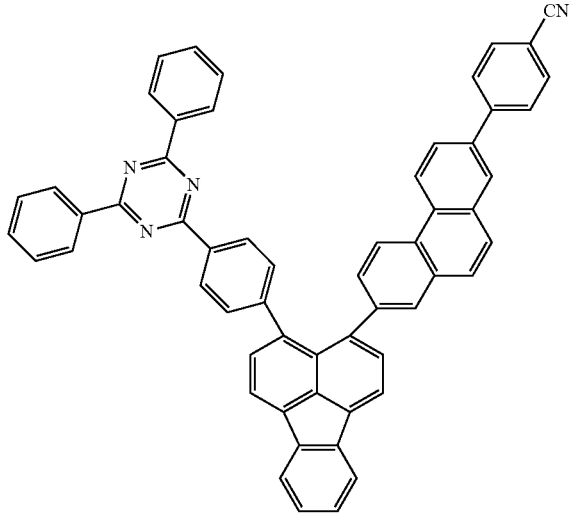
-continued
351
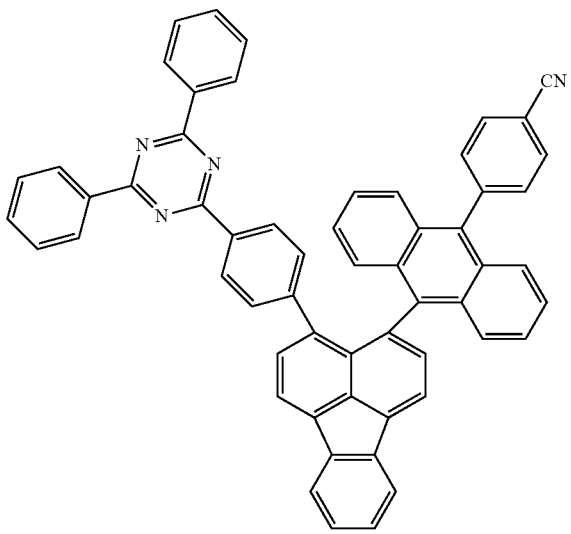
352
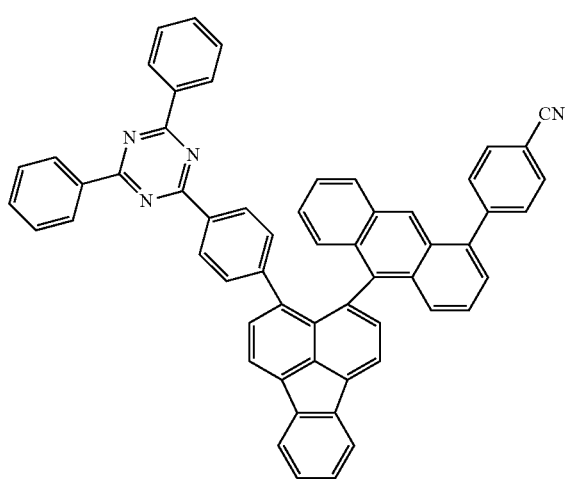
353
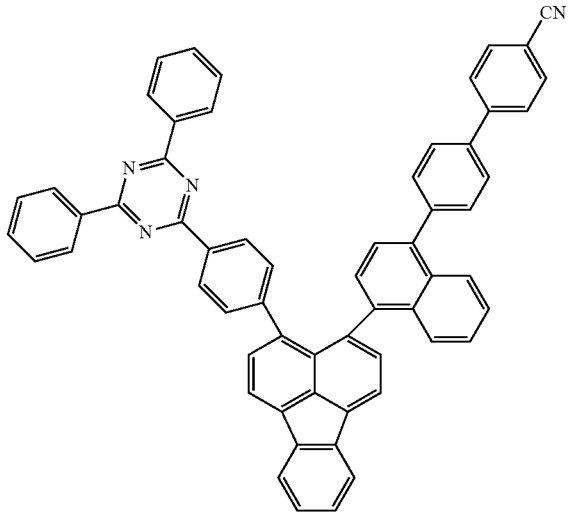

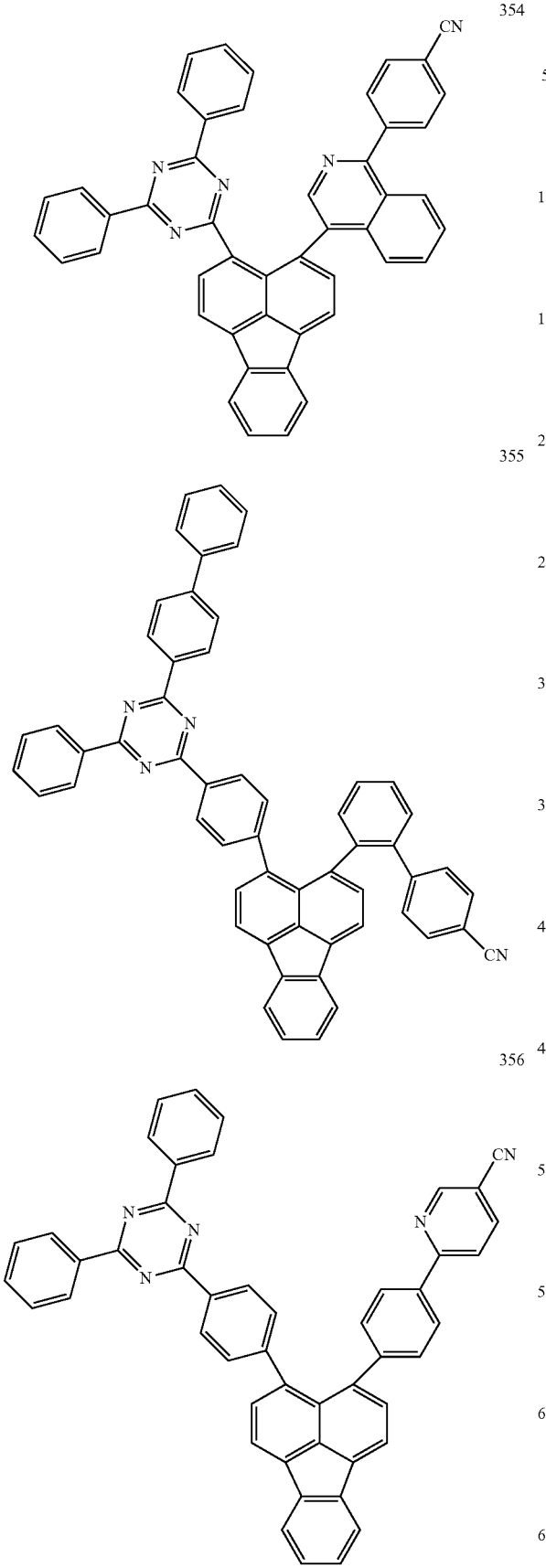
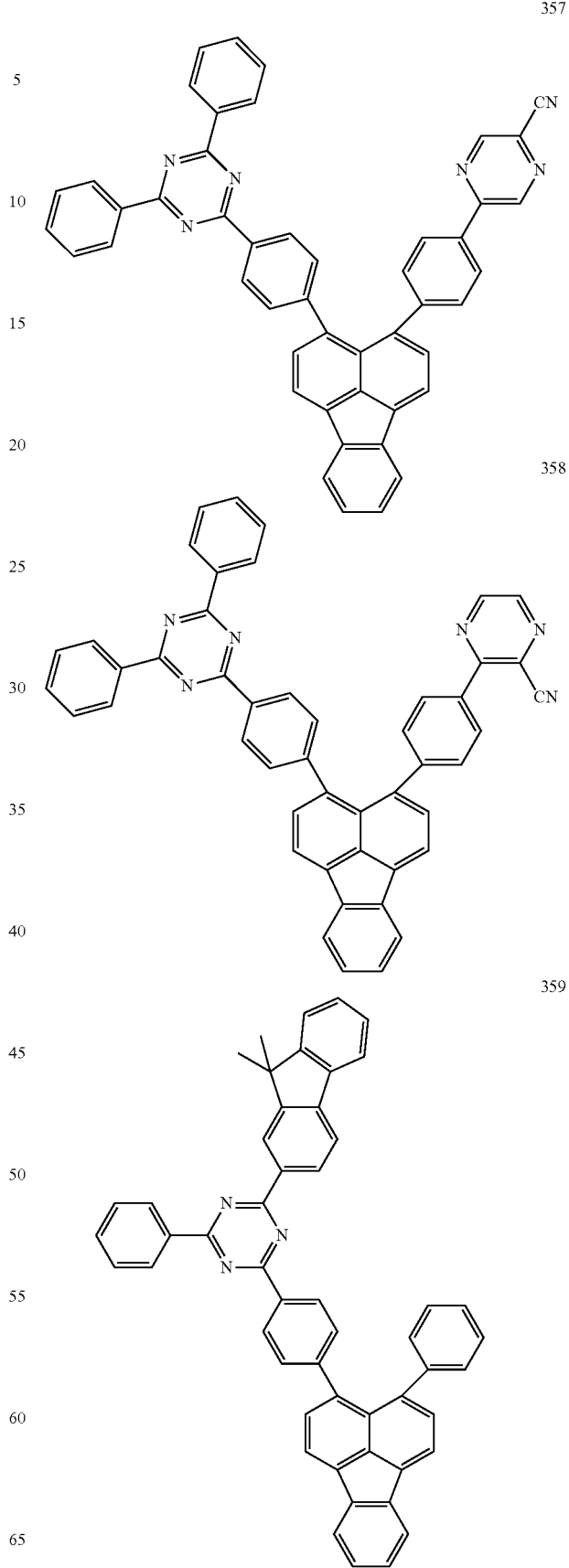

360
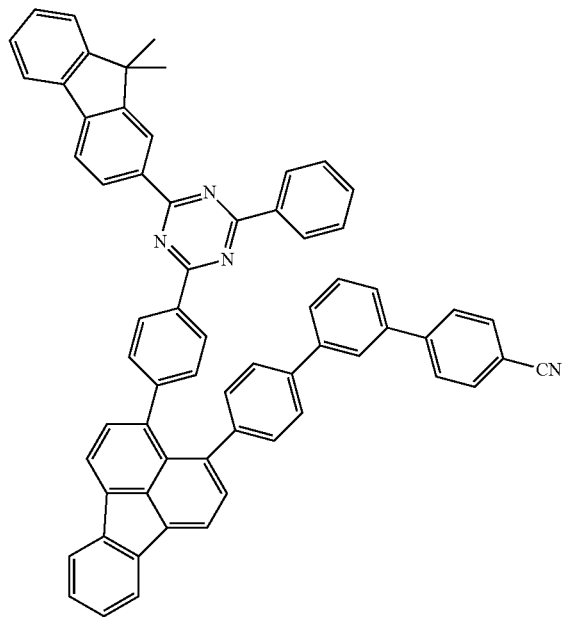
361
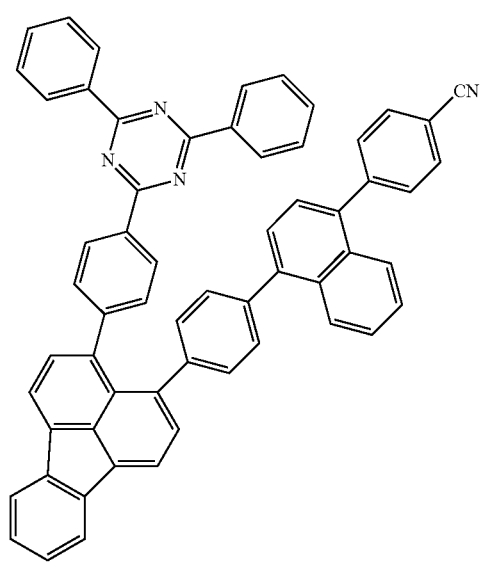
362
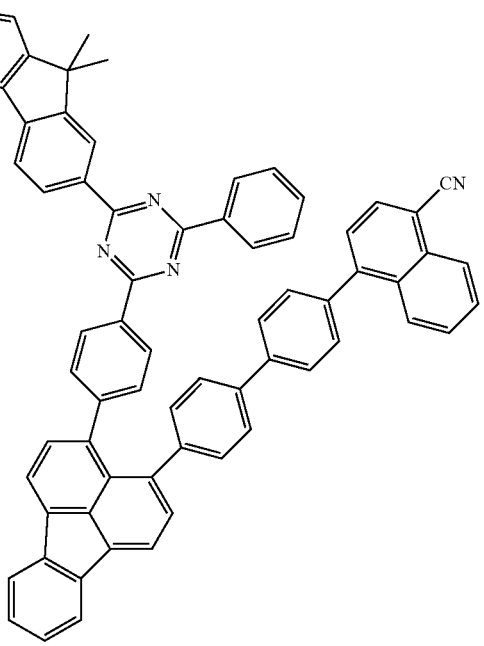
363
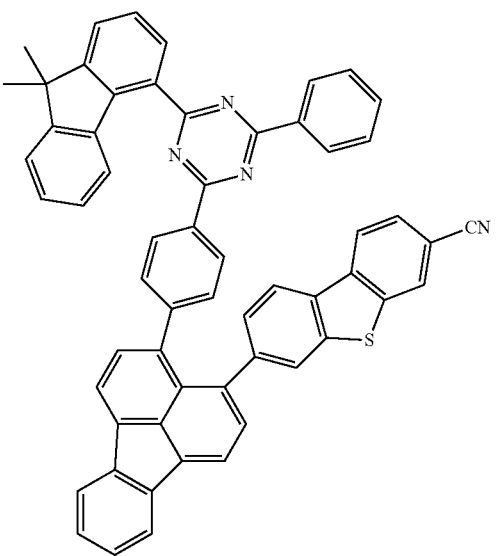

199
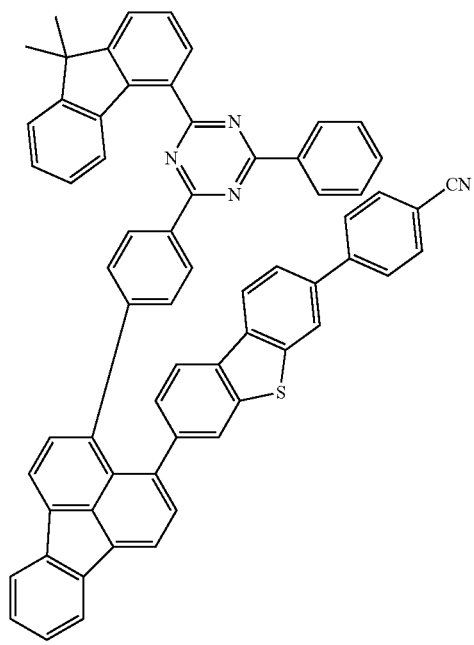
364
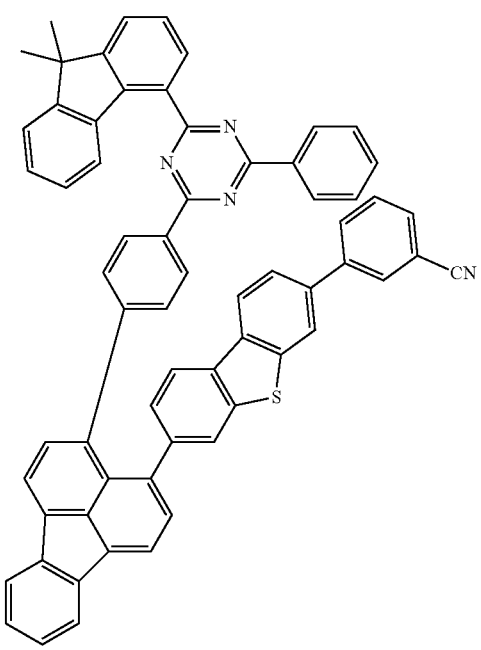
365
200
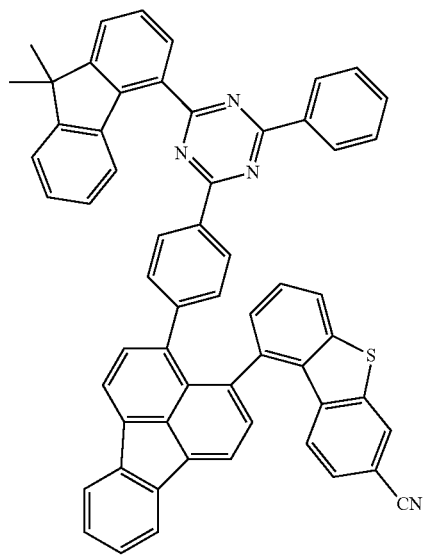
366
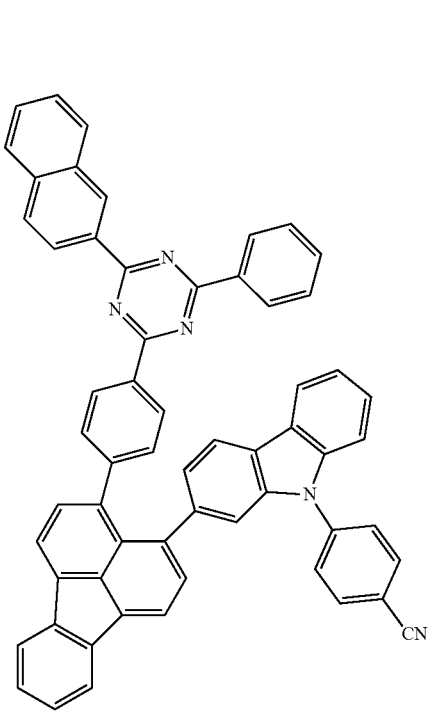
367

368
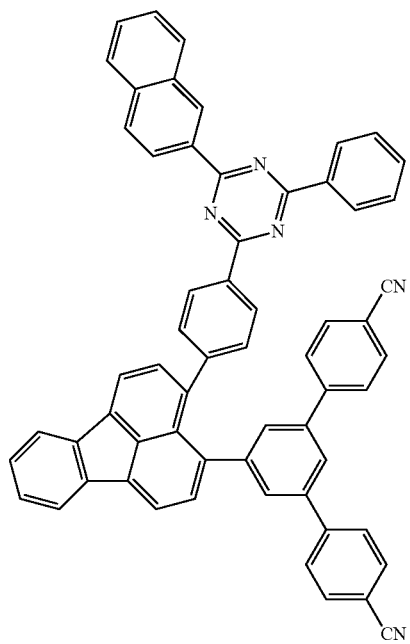
369
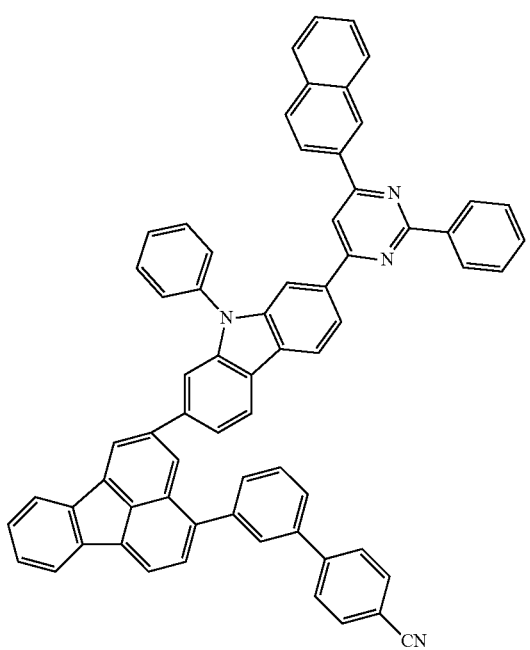
370
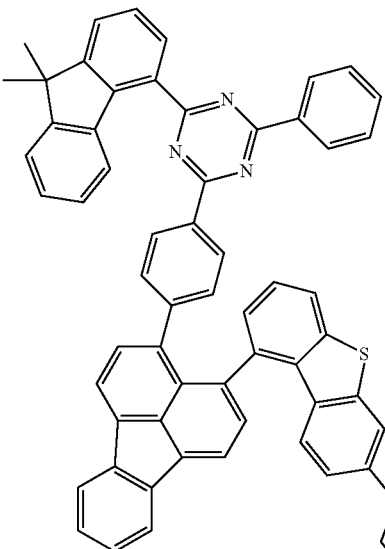
371
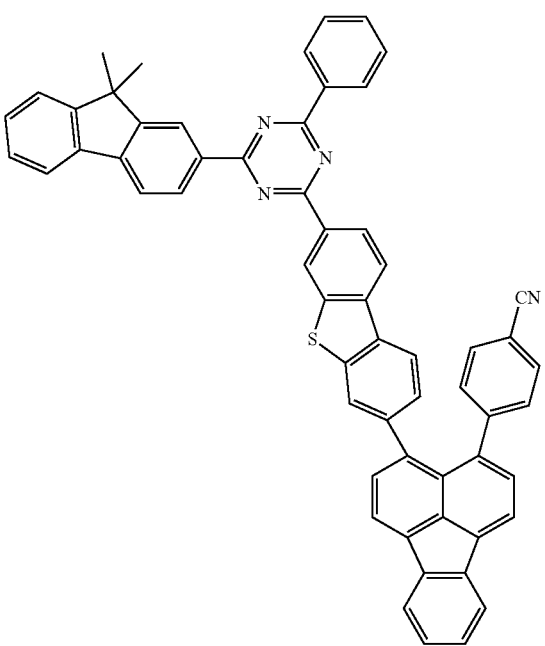

203
-continued
372
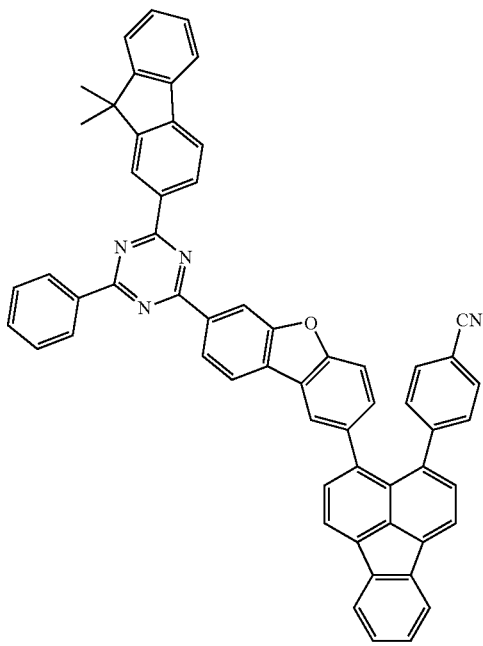
373
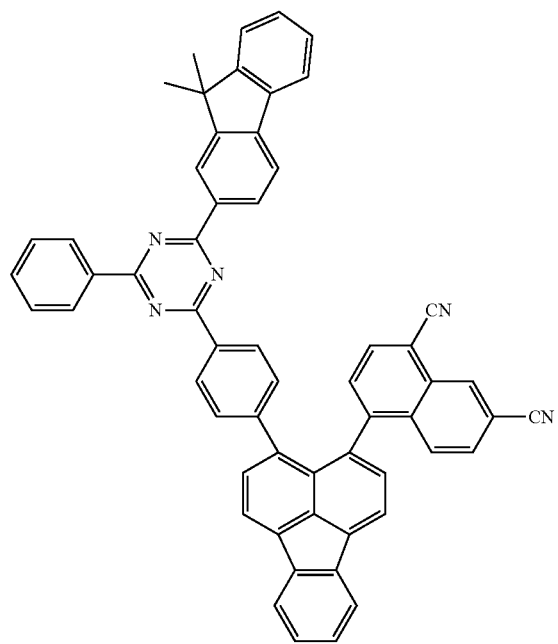
204
-continued
374
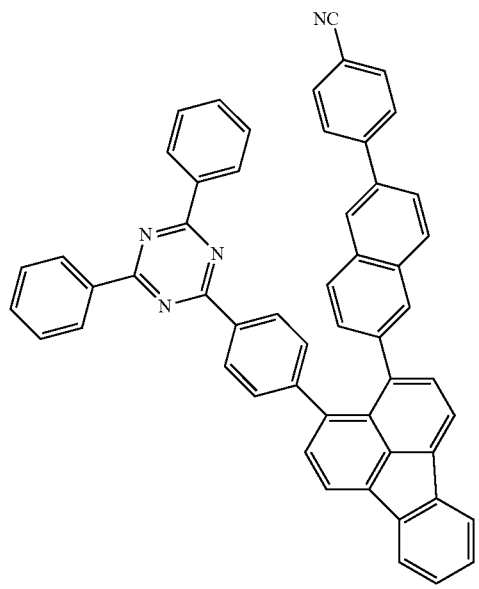
375
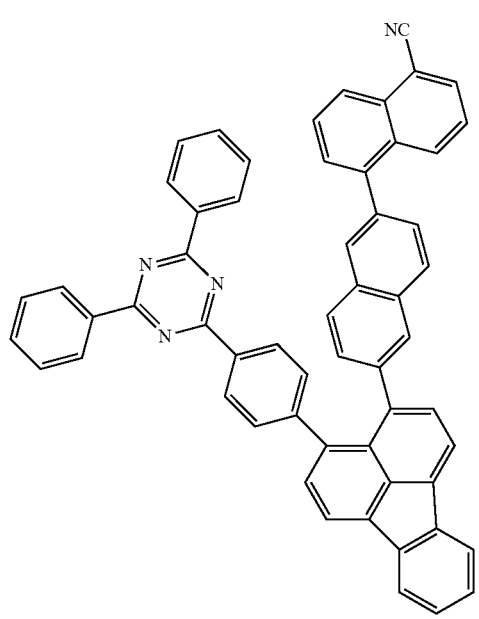

205
-continued
376
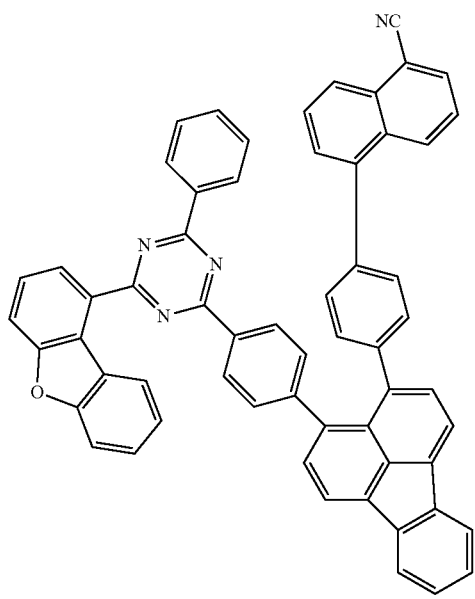
377
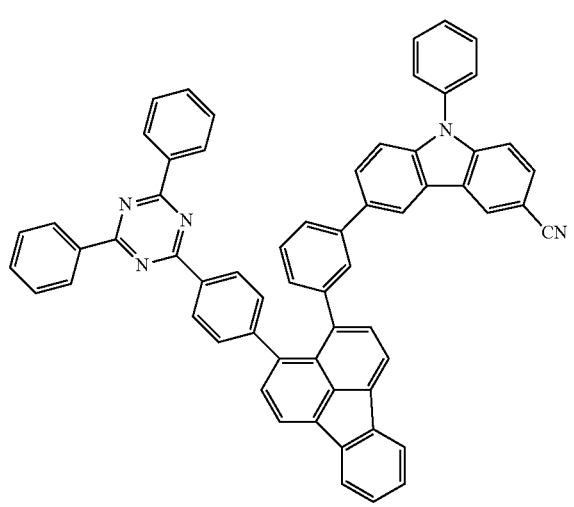
206
-continued
378
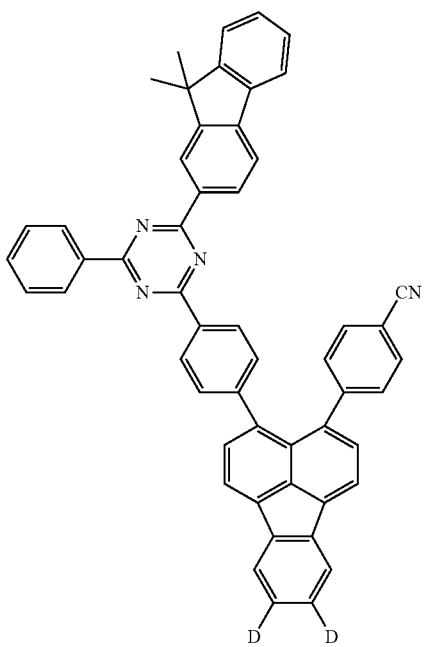
379
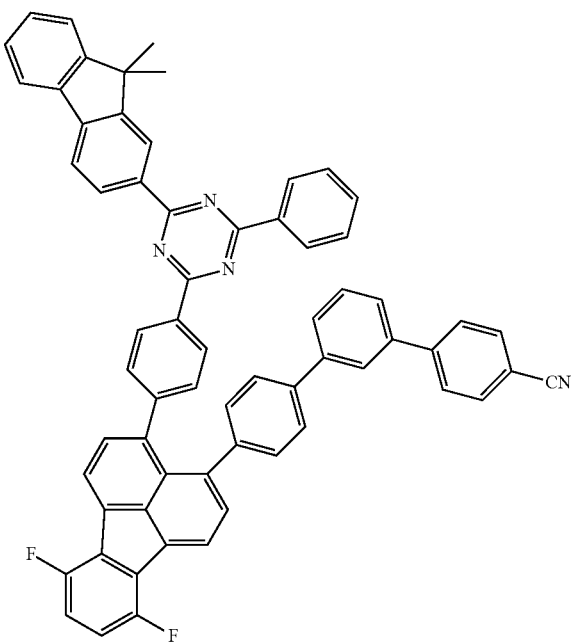

207
-continued
380
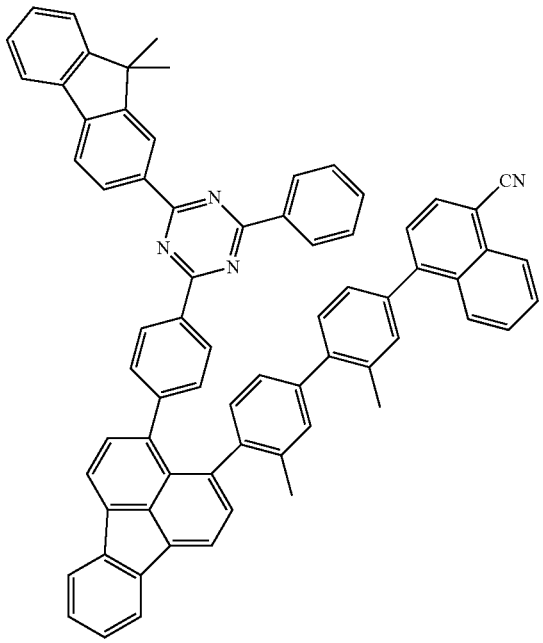
381
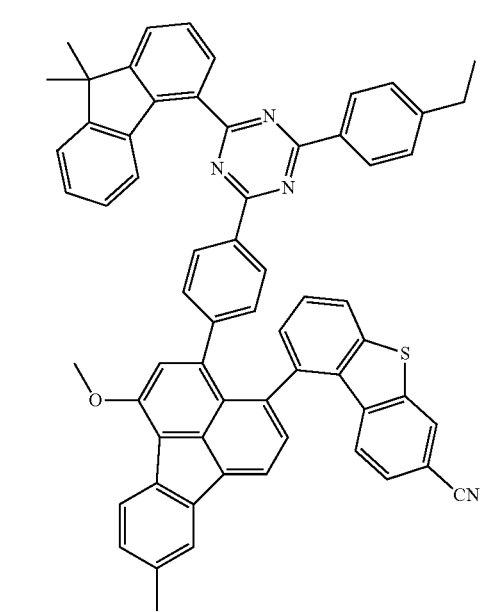
208
-continued
382
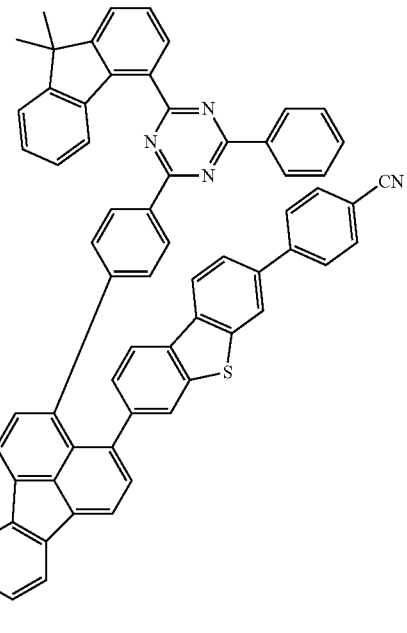
383

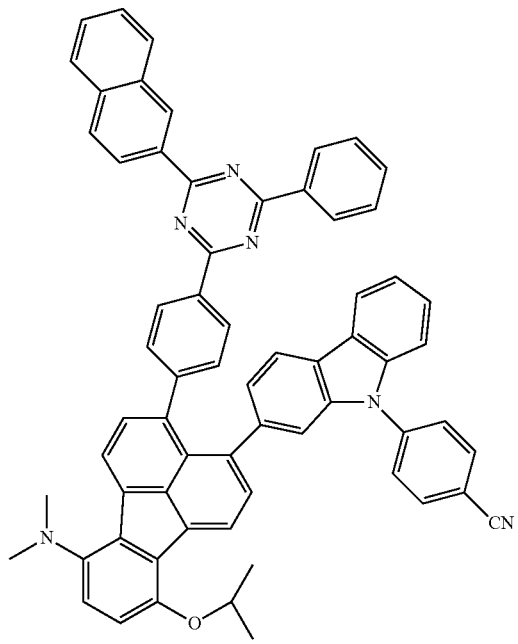
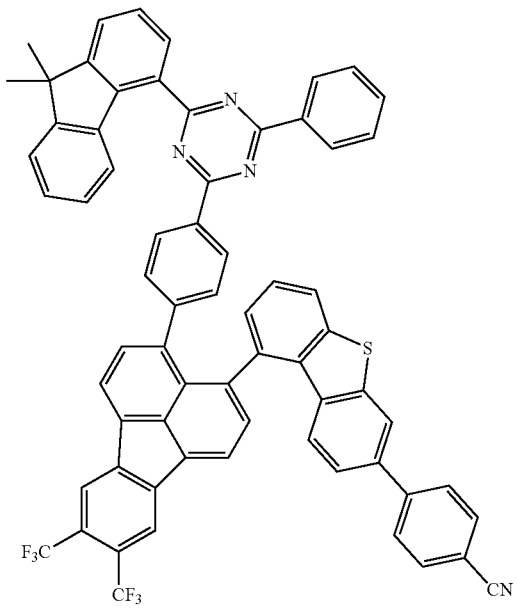
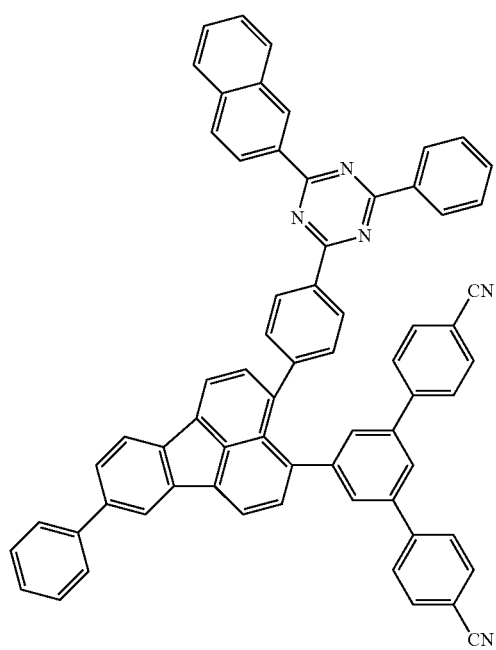
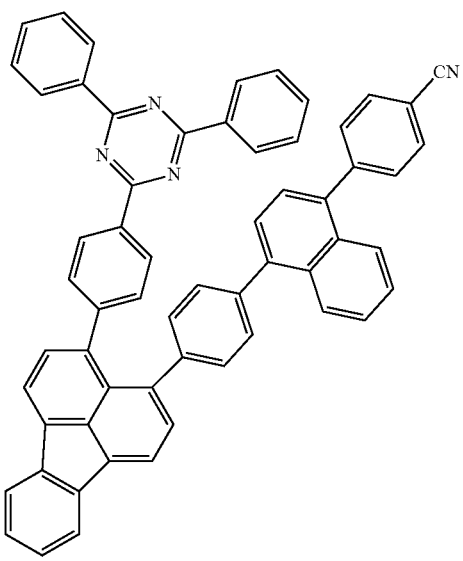

211
-continued
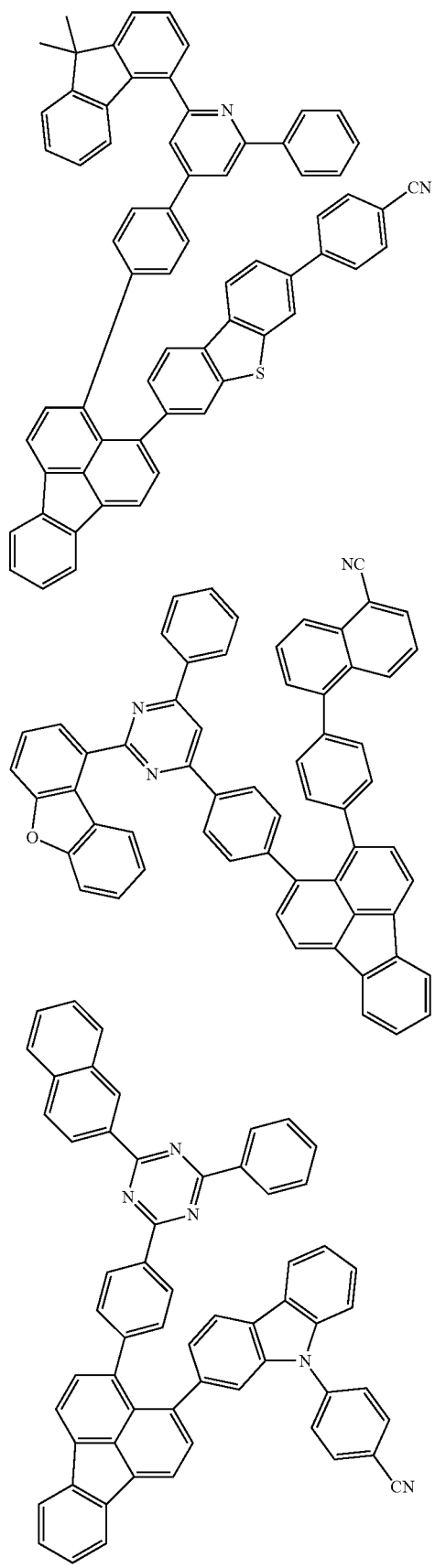
212
-continued
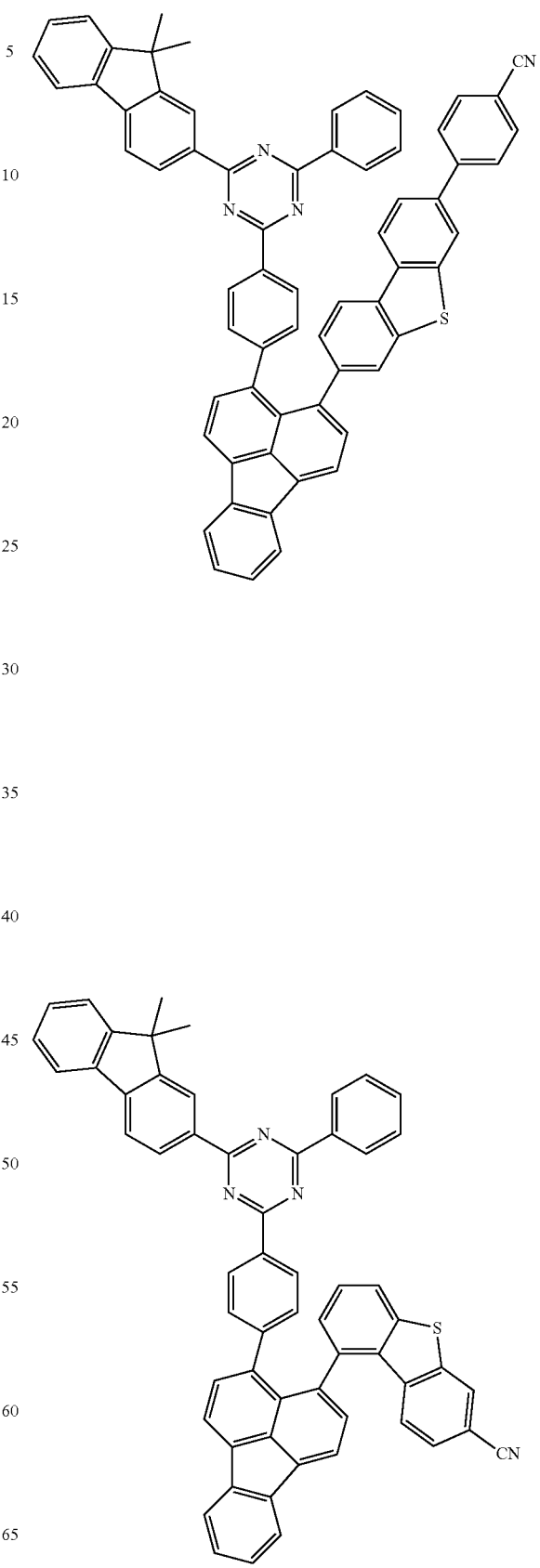

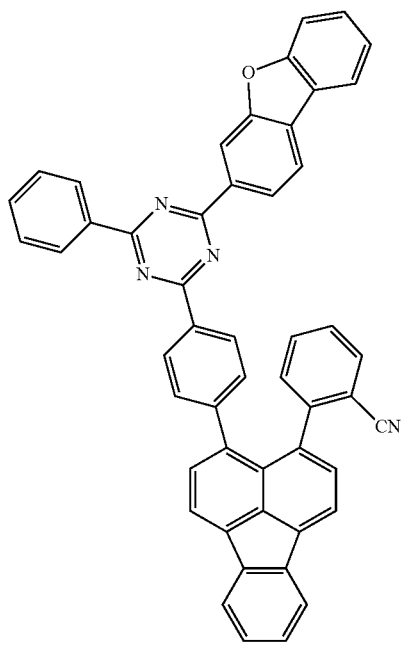
393
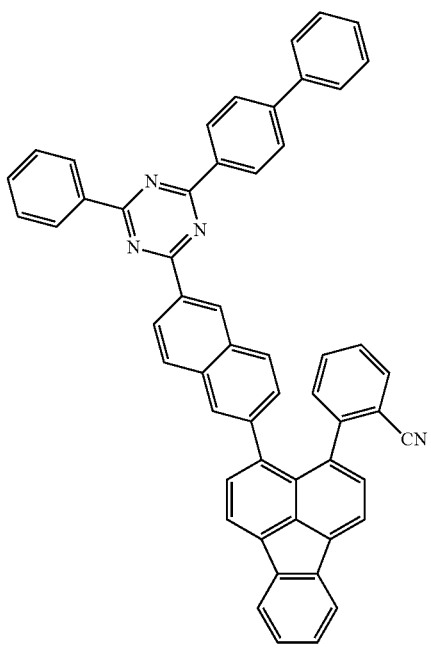
395
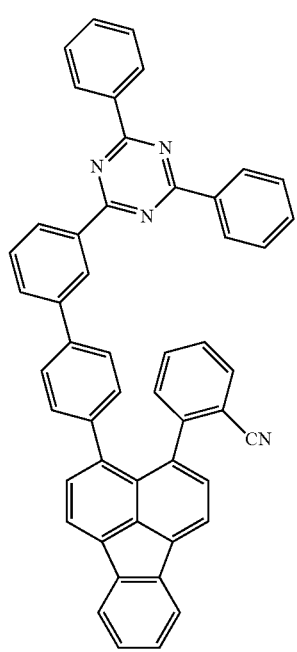
394
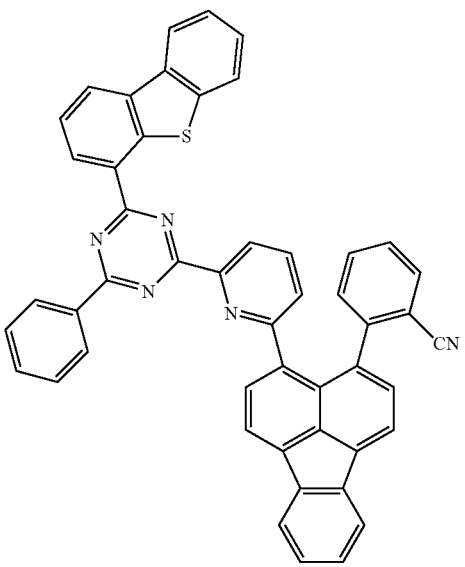
396

-continued

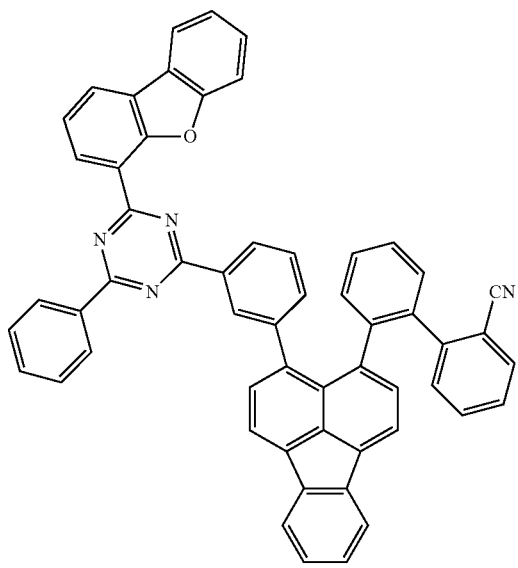
397

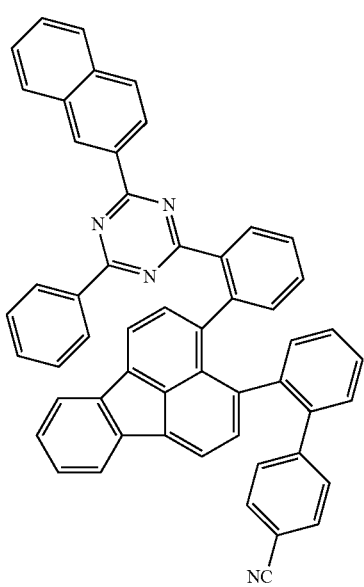
398

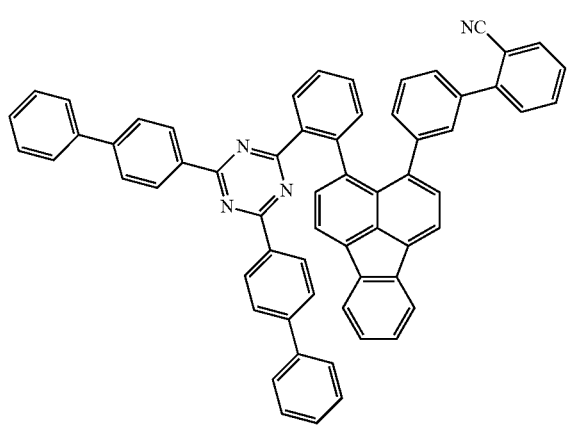
399

-continued

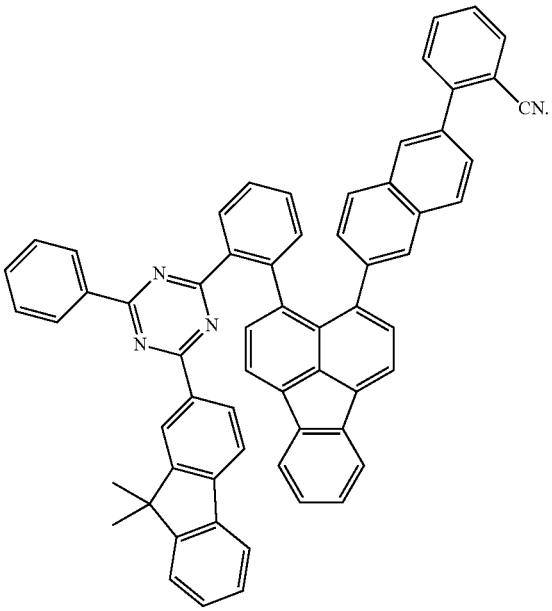
400

The present disclosure further provides an electronic device, used for achieving photoelectric conversion or electro-optical conversion. The electronic device includes an anode and a cathode disposed oppositely, and a functional layer disposed between the anode and the cathode; the functional layer contains the organic compound of the present disclosure.

For example, the electronic device is an organic electroluminescent device. As shown in FIG. 1, the organic electroluminescent device may include an anode 100, a cathode 200 and a functional layer 300, wherein, the anode 100 and the cathode 200 are disposed oppositely. The functional layer 300 is disposed between the anode 100 and the cathode 200. The functional layer 300 contains the compound in any one of the above embodiments.

As shown in FIG. 1, the anode 100 may be a metal, an alloy, or a metal oxide, and the like, for example, may be nickel, platinum, vanadium, chromium, copper, zinc, gold or alloys thereof, and may further be zinc oxide, indium oxide, indium tin oxide (ITO) and indium zincoxide (IZO); the anode 100 may further be other materials, for example, may be further a composition, such as: ZnO:Al, SnO$_2$:Sb, conducting polymer (poly(3-thiotolene), poly[3,4-(ethylidene-1,2-dioxy)thiophene](PEDT), polypyrrole and polyaniline); of course, the anode 100 is not limited to the above materials, and may further be other materials, but will be not enumerated one by one here. Optionally, the anode 100 may be indium tin oxide (ITO).

As shown in FIG. 1, the cathode 200 may be a metal or alloy material, for example, may be Mg, Ca, Na, K, Ti, Al, Ag, or alloys thereof, and may further be multilayer materials, such as, LiF/Al, Liq/Al, LiO2/Al, LiF/Ca, LiF/Al and BaF2/Ca; of course, the cathode 200 is not limited to the above materials, and may be further other materials, but will be not enumerated one by one here. Optionally, the cathode 200 may be Al.

As shown in FIG. 1, the functional layer 300 may include a hole transport layer 320, an luminescent layer 340 and an electron transport layer 350. The luminescent layer 340 is disposed one side of the hole transport layer 320 away from the anode 100. The electron transport layer 350 is disposed one side of the luminescent layer 340 close to the cathode 200.

As shown in FIG. 1, the luminescent layer 340 may consist of a single luminescent material, and may further includes a host material and an guest material. Optionally, the luminescent layer 340 consists of a host material and an guest material; holes injected into the luminescent layer 340 and electrons injected into the luminescent layer 340 may be composited in the luminescent layer 340 to form excitons; excitons transfer energy to the host material, and the host material transfers energy to the guest material, thereby enabling the guest material to emit light.

As shown in FIG. 1, the host material of the luminescent layer 340 may be a metal chelating compound, distyryl derivative, aromatic amine derivative, dibenzofuran derivative, or other types of materials; there is no special limitation to the host material in the present disclosure. In one embodiment of the present disclosure, the host material of the luminescent layer 340 may be CBP. In another embodiment of the present disclosure, the host material of the luminescent layer 340 may be $\alpha,\beta$-ADN.

As shown in FIG. 1, the guest material of the luminescent layer 340 may be a compound having a condensed aromatic ring or a derivative thereof, a compound having a heteroaryl ring or a derivative thereof, an aromatic amine derivative or other materials; there is no special limitation to the host material in the present disclosure. In one embodiment of the present disclosure, the guest material of the luminescent layer 340 may be Ir(piq)$_2$(acac). As shown in FIG. 1, the electron transport layer 350 may be a single layer structure, and may further be a multilayered structure; and the electron transport layer may include one or more electron transport materials, and the electron transport layer may contain the fluoranthene compound of the present disclosure.

As shown in FIG. 1, the functional layer 300 may further include a hole injection layer 310. The hole injection layer 310 may be disposed between the hole transport layer 320 and the anode 100.

As shown in FIG. 1, the functional layer 300 may further include an electron blocking layer 330. The electron blocking layer 330 may be disposed between the hole transport layer 320 and the luminescent layer 340.

As shown in FIG. 1, the functional layer 300 may further include an electron injection layer 360. The electron injection layer 360 may be disposed between the electron transport layer 350 and the cathode 200.

Further, as shown in FIG. 1, the functional layer 320 may include a first hole transport layer 3201 and a second hole transport layer 3202. Wherein, the first hole transport layer 3201 and the second hole transport layer 3202 contain the organic compound. The first hole transport layer 3201 covers on the hole transport layer 310, and the second hole transport layer 3202 is disposed on one side of the first hole transport layer 3201 away from the hole injection layer 310.

Figure 2:
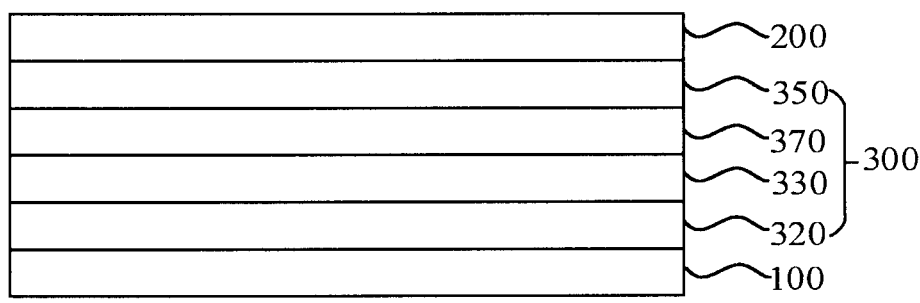
FIG. 2 is a structure diagram showing another specific embodiment (a solar cell) of an electronic device of the present disclosure.

In another embodiment, the electronic device is a solar cell. As shown in FIG. 2, the solar cell may include an anode 100, a cathode 200 and a functional layer 300, wherein,
 the cathode 100 and the cathode 200 are disposed oppositely. The functional layer 300 is disposed between the anode 100 and the cathode 200. The functional layer 300 contains the organic compound in any one of the above embodiments.

Components of the solar cell in the embodiment of the present disclosure will be described in detail below:

As shown in FIG. 2, the functional layer 300 may include a hole transport layer 320, a photoelectric conversion layer 370 and an electron transport layer 350. The photoelectric conversion layer 370 is disposed on one side of the hole transport layer 320 away from the anode 100. The electron transport layer 350 is disposed on one side of the photoelectric conversion layer 370 close to the cathode 200. The hole transport layer 320 contains the organic compound of the present disclosure.

As shown in FIG. 2, the functional layer 300 may include an electron blocking layer 330. The electron blocking layer 330 may be disposed between the hole transport layer 320 and the photoelectric conversion layer 370.

In one specific embodiment, the solar cell may be an organic thin-film solar cell.

Based on the excellent performance of the organic compound of the present disclosure, the electronic device that obtained by using the compound of the present disclosure as a material for a functional layer has higher luminous efficiency and extended lifetime.

Figure 3:
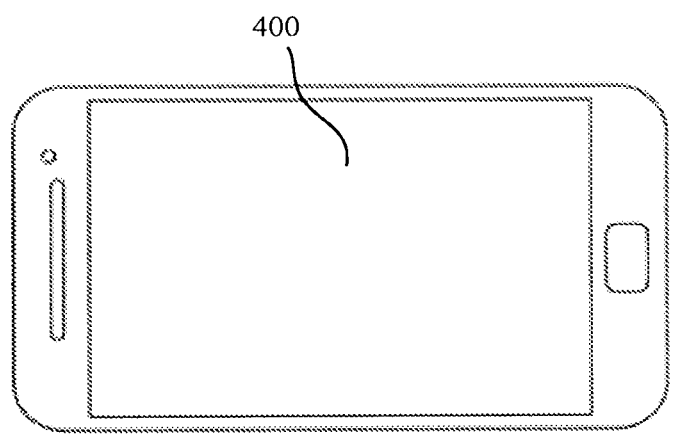
FIG. 3 is a structure diagram showing a third specific embodiment (an electronic apparatus) of an electronic device of the present disclosure.

For another example, as shown in FIG. 3, the present disclosure provides an electronic apparatus 400, and the electronic apparatus 400 includes any one photoelectric conversion device described in the embodiments of the photoelectric conversion device. The electronic apparatus 400 may be a solar power generation equipment, photodetector, fingerprint identification equipment, an optical module, CCD camera or other types of electronic apparatus. Since the electronic apparatus 400 has any one photoelectric conversion device described in the embodiments of the photoelectric conversion device, the electronic apparatus 400 has the same beneficial effects. There is no more detailed description in the present disclosure.

EXAMPLES

The present disclosure will be described specifically in combination with examples below. However, the examples based on the description may be amended into other various forms; and the scope of the description is not construed as being limited to the following examples. The examples of the description are provided to specify the description to a person skilled in the art more integrally.

A person skilled in the art will believe that the chemical reaction described in the present disclosure may be used for suitably preparing lots of other compounds of the present disclosure; and other methods for preparing the compound of the present disclosure will be regarded within the scope of the present disclosure. For example, the synthesis of non-exemplary compounds of the present disclosure may be successfully completed by a person skilled in the art by a modification method, such as, appropriate protection for interference groups, use of other known reagents except for the described in the present disclosure, and conventional amendments on the reaction conditions. Furthermore, the reaction applied in the present disclosure or known reaction conditions are also acknowledgedly suitable for the preparation of other compounds of the present disclosure.

In the following examples, unless otherwise specified, all the temperature are set degree centigrade. Reagents are purchased from commodity suppliers, such as, Aldrich Chemical Company, Arco Chemical Company and Alfa Chemical Company. There is no further purification step in use process, unless otherwise specified. Common reagents are purchased from Shantou Xilong Chemical Plant, Guangdong Guanghua Chemical Reagent Factory, Guangzhou Chemical Reagent Factory, Tianjin Haoyuyu Chemicals Co., Ltd., Tianjin Fuchen Chemical Reagent Factory, Wuhan Xinhuayuan Science & Technology Development Co., Ltd., Qingdao Tenglong Chemicals Co., Ltd., and Qingdao Marine Chemical Plant.

Reaction is generally performed under positive pressure of nitrogen or argon or by sleeving a dry tube on an anhydrous solvent (unless otherwise specified); the reaction flask is plugged with a suitable rubber plug, and substrate is pumped via an injector. All the glassware have been dried.

A silicagel column is used as a chromatographic column. Silicagel (300 to 400-mesh) is purchased from Qingdao Marine Chemical Plant.

Determination conditions of low-resolution mass spectrum (MS) data are as follows: Agilent 6120 quadrupole HPLC-M (column model: Zorbax SB-C18, 2.1×30 mm, 3.5 μm, 6 min, flow rate: 0.6 mL/min. Mobile phase: 5% to 95%, a ratio of ($CH_3CN$ containing 0.1% formic acid) in ($H_2O$ containing 0.1% formic acid); electrospray ionization (ESI) is used and UV detection is performed under 210 nm/254 nm.

Determination conditions of $^1HNMR$ are as follows: Bruker 400 MHz NMR equipment, at room temperature, $CD_2Cl_2$ serves as a solvent (unit: ppm), and TMS (0 ppm) serves as a reference standard. When multiplet appeared, the following abbreviation will be used: singlet (s), doublet (d), triplet (t) and multiplet (m).

The final compound of the present disclosure is denoted in the following chemical formula (M), and prepared by the reaction between intermediates (A-2) and (A-3), but not limited thereto.

The compound of the present disclosure may be prepared by the following general synthetic solutions; $Ar_1$, $Ar_2$, $Ar_3$, $X_1$, $X_2$, $X_3$, $L_1$ and $L_2$ of the following compound have the meanings in other parts of the description. In the above compound, X denotes halogen —I, —Br, or —Cl.

Reaction route is as follows:

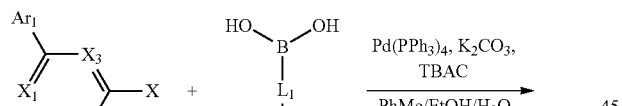

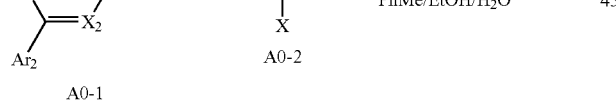

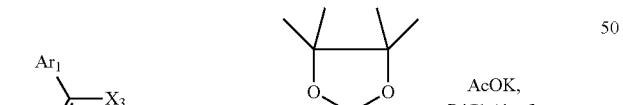

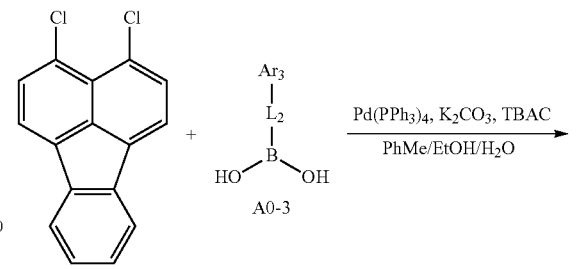

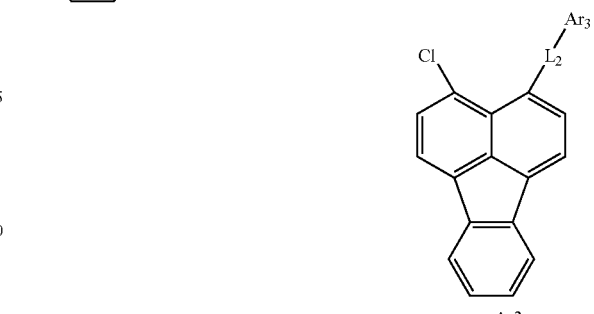

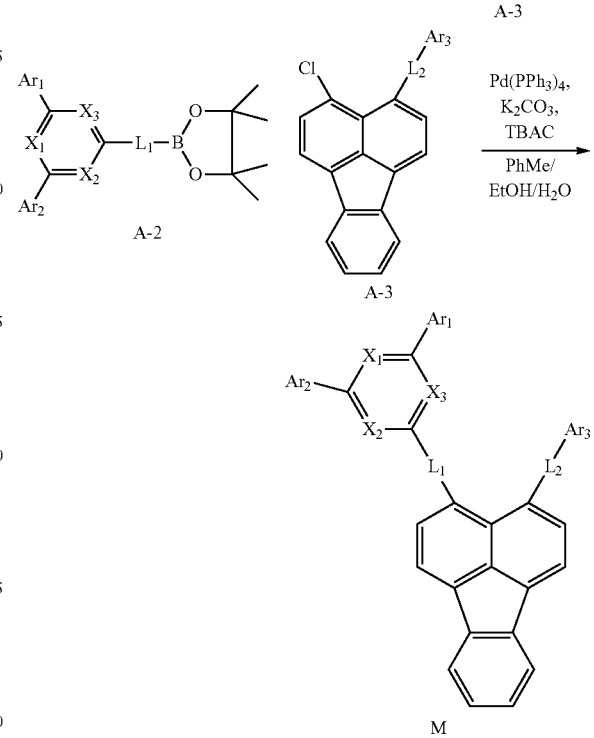

Synthetic solution: an aryl halide (A0-1) and aromatic boric acid (A0-2) are subjected to coupled reaction via a palladium catalyst under alkaline conditions to generate an intermediate (A-1); the intermediate (A-1) is reacted with bisdiboron via a palladium catalyst under alkaline conditions to generate a borate (A-2); 1,2-dichlorofluoranthene and boric acid (A0-3) are subjected to coupled reaction via a palladium catalyst under alkaline conditions to generate an intermediate (A-3); the borates (A-2) and (A-3) are subjected to coupled reaction via a palladium catalyst under alkaline conditions to generate the final compound (M).

The compound of the present disclosure may be prepared by the above general synthetic solution. For the convenience of understanding, the preparation process of a specific compound will be set as an example to exemplarily show the synthetic process of partial compounds of the present disclosure.

Intermediate Preparation Examples

Intermediates A-1-1 to A-1-20, A-2-1 to A-2-21, and A-3-1 to A-3-14 were prepared by the following steps:

Preparation of the intermediate A-1-1 was as follows:

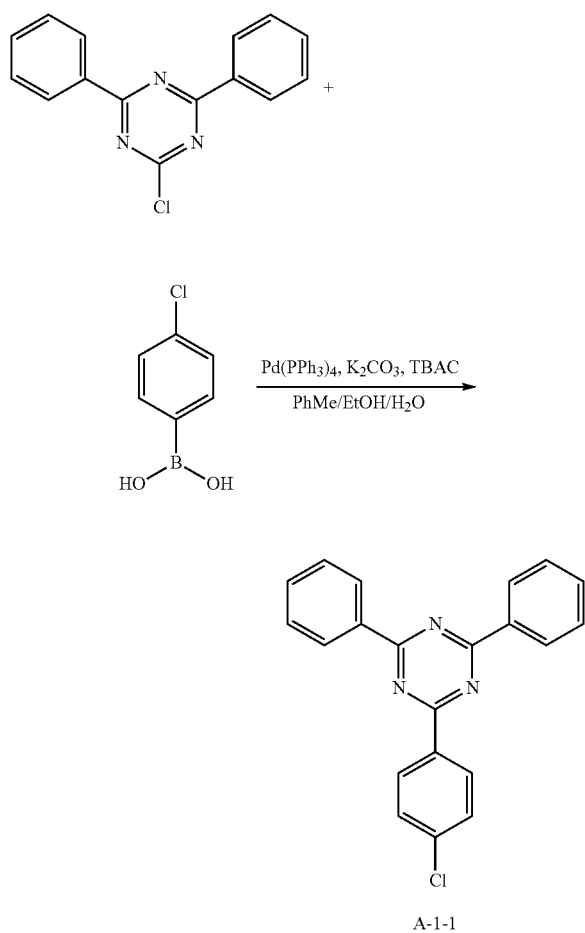

A-1-1

2-chloro-4,6-diphenyl-1,3,5-triazine (20 g, 74.40 mmol), p-chlorophenylboronic acid (11.68 g, 74.70 mmol), tetrakis (triphenylphosphine)palladium (1.72 g, 1.49 mmol), potassium carbonate (22.71 g, 164.35 mmol), and tetrabutylammonium chloride (TBAC) (1.03 g, 3.73 mmol) were respectively added to a three-necked flask; then methylbenzene (160 mL), ethanol (80 mL), and water (40 mL) were added to the flask, and the mixture was heated to reflux and stirred for 12 h at 80° C. After the reaction is completed, CH$_2$Cl$_2$ and water were used for extraction; the combined organic phases were dried over anhydrous MgSO$_4$ and filtered. The filtrate was concentrated in vacuo to obtain a crude product. The crude product was purified by silica gel column chromatography to obtain an intermediate A-1-1 (16.69 g, yield 65%).

Preparation method of the intermediate A-1-5 was as follows:

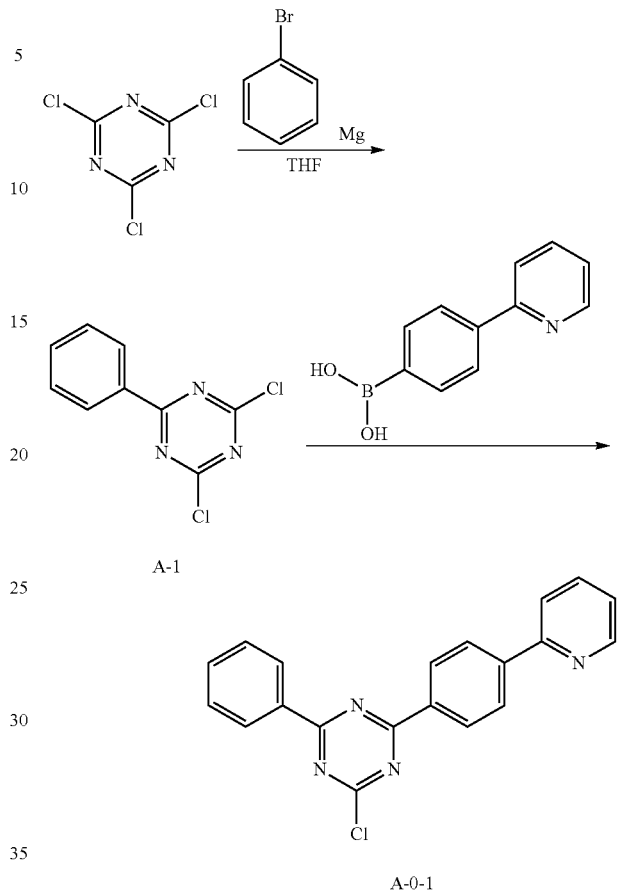

A-0-1

(i) Preparation of the Intermediate A-1

2,4,6-trichloro-1,3,5-triazine (100 g, 542.27 mmol) and 800 mL anhydrous tetrahydrofuran were added into a 3 L reaction flask, and stirred under nitrogen atmosphere at 0° C. 650 mL (1 mol/L) phenylmagnesium bromide (obtained by reacting bromobenzene with metal magnesium) was added dropwise, and the resulted mixture was warmed naturally to room temperature, and stirred for 1 h. 2 mol/L aqueous hydrochloric acid solution was added to the above solution, and then washed by dichloromethane and ultrapure water. The separated organic phase was wasted with water and dried over anhydrous magnesium sulfate, and then concentrated in vacuo to obtain a crude product. The crude product was purified by silica gel column chromatography, and then purified by recrystallization using a mixture of dichloromethane and n-heptane to obtain intermediate A-1 (98 g, yield 80%).

(ii) Preparation of the Intermediate A-0-1:

The intermediate A-1 (98 g, 433.44 mmol), 4-(2pyridyl) phenylboronic acid (86.27 g, 433.44 mmol), 1000 ml anhydrous tetrahydrofuran, palladium acetate (2.92 g, 13.0 mmol), 2-dicyclohexyl phosphorus-2,4,6-triisopropyl biphenyl (12.39 g, 26.00 mmol) and potassium acetate (127.61 g, 1300.31 mmol) were added into a 3 L reaction flask, and reflux stirred for 2 h under nitrogen atmosphere. The reaction solution was cooled to room temperature, and extracted with dichloromethane and ultrapure water. The separated organic phase was wasted with water and dried over anhydrous magnesium sulfate, and then concentrated in vacuo to obtain a crude product.

The crude product was purified by silica gel column chromatography and eluted with a mixture of dichloromethane and n-heptane to obtain an intermediate A-0-1 (119.2 g, yield 80%).

(iii) Preparation of the Intermediate A-1-5

The intermediate A-0-1 (25.8 g, 74.40 mmol), p-chlorophenylboronic acid (11.58 g, 74.60 mmol), tetrakis(triphenylphosphine)palladium (1.70 g, 1.45 mmol), potassium carbonate (22.71 g, 164.35 mmol), and tetrabutylammonium chloride (TBAC) (1.03 g, 3.73 mmol) were respectively added to a three-necked flask; then methylbenzene (160 mL), ethanol (80 mL), and water (40 mL) were added to the flask, and the mixture was heated to reflux and stirred for 12 h at 80° C. After the reaction is completed, $CH_2Cl_2$ and water were used for extraction; the separated organic phase was dried over anhydrous $MgSO_4$ and filtered. The filtrate was concentrated in vacuo to obtain a crude product. The crude product was purified by silica gel column chromatography to obtain intermediate A-1-5 (21.5 g, yield 68.7%).

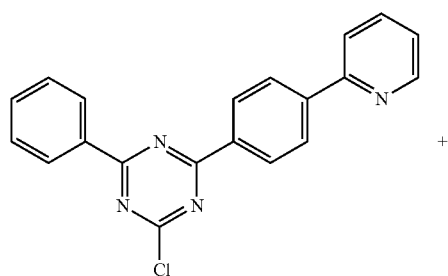

+

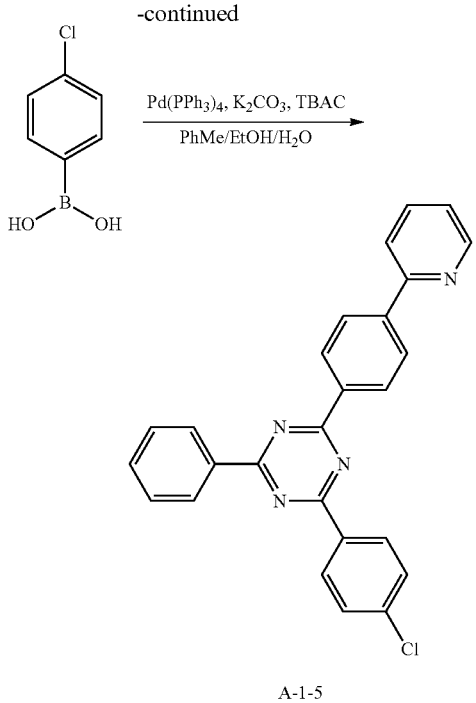

A-1-5

Referring to the steps in the preparation method of the intermediate A-1-1 of the compound 1, the intermediates A-1-2 to A-1-4, A-1-6 to A-1-18 and A-1-20 were prepared by replacing 2-chloro-4,6-diphenyl-1,3,5-triazine with the raw material 1 in Table 1, and replacing p-chlorophenylboronic acid with the raw material 2 in Table 1.

TABLE 1

| Preparation example | Raw material 1 | Raw material 2 | Intermediate A-1 | Yield |
|---|---|---|---|---|
| A-1-2 | | | | 60% |
| A-1-3 | | | | 59% |

TABLE 1-continued

| Preparation example | Raw material 1 | Raw material 2 | Intermediate A-1 | Yield |
|---|---|---|---|---|
| A-1-4 | | | | 61% |
| A-1-6 | | | | 62% |
| A-1-7 | | | | 59% |

TABLE 1-continued
| Preparation example | Raw material 1 | Raw material 2 | Intermediate A-1 | Yield |
|---|---|---|---|---|
| A-1-8 | 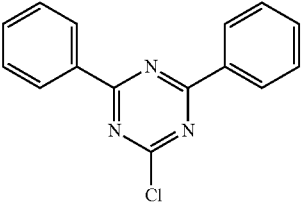 | 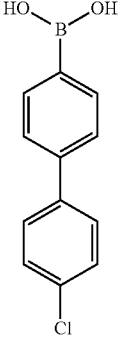 | 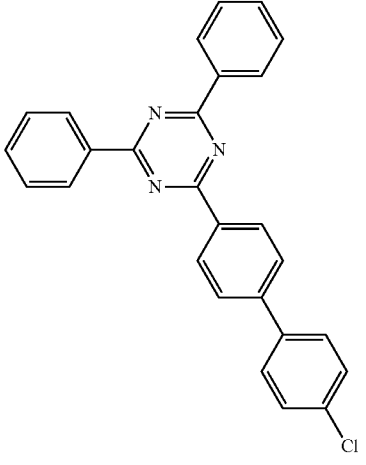 [SMILES: Clc1ccc(-c2ccc(-c3nc(-c4ccccc4)nc(-c4ccccc4)n3)cc2)cc1] | 58% |
| A-1-9 | 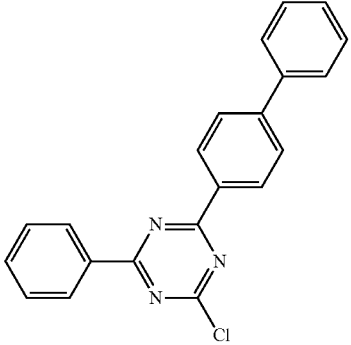 [SMILES: Clc1nc(-c2ccccc2)nc(-c2ccc(-c3ccccc3)cc2)n1] | 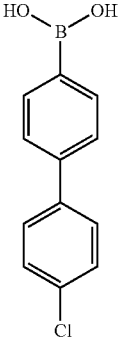 | 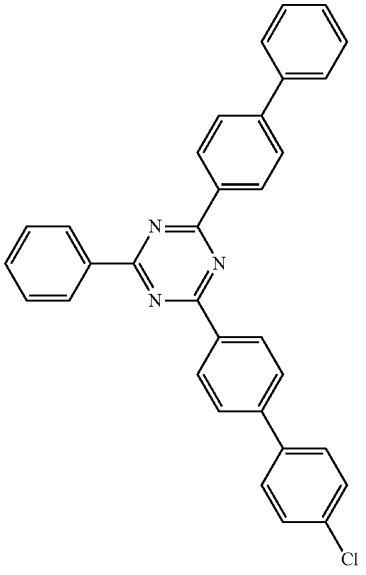 [SMILES: Clc1ccc(-c2ccc(-c3nc(-c4ccccc4)nc(-c4ccc(-c5ccccc5)cc4)n3)cc2)cc1] | 60% |
| A-1-10 | 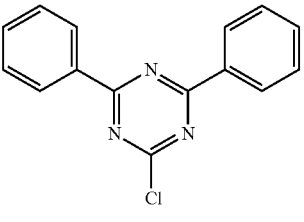 [SMILES: Clc1nc(-c2ccccc2)nc(-c2ccccc2)n1] | 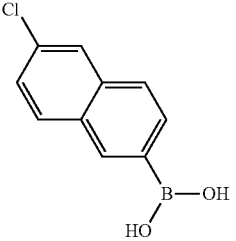 [SMILES: OB(O)c1ccc2cc(Cl)ccc2c1] | 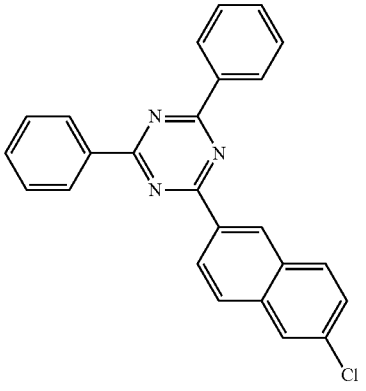 [SMILES: Clc1ccc2cc(-c3nc(-c4ccccc4)nc(-c4ccccc4)n3)ccc2c1] | 58% |

TABLE 1-continued

| Preparation example | Raw material 1 | Raw material 2 | Intermediate A-1 | Yield |
|---|---|---|---|---|
| A-1-11 | | | | 60% |
| A-1-12 | | | | 60% |
| A-1-13 | CAS: 1618106-98-1 | | | 61% |
| A-1-14 | | | | 63% |

TABLE 1-continued

| Preparation example | Raw material 1 | Raw material 2 | Intermediate A-1 | Yield |
|---|---|---|---|---|
| A-1-15 | | | | 60% |
| A-1-16 | | | | 58% |
| A-1-17 | | | | 60% |
| A-1-18 | | | | 61% |

TABLE 1-continued

| Preparation example | Raw material 1 | Raw material 2 | Intermediate A-1 | Yield |
|---|---|---|---|---|
| A-1-20 | 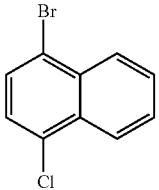 [SMILES: Clc1ccc(Br)c2ccccc12] | 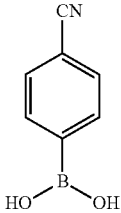 | 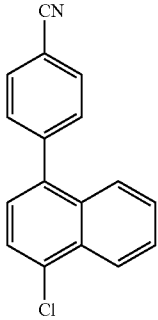 [SMILES: N#Cc1ccc(-c2ccc(Cl)c3ccccc23)cc1] | 62% |

Preparation of the Intermediate A-1-19

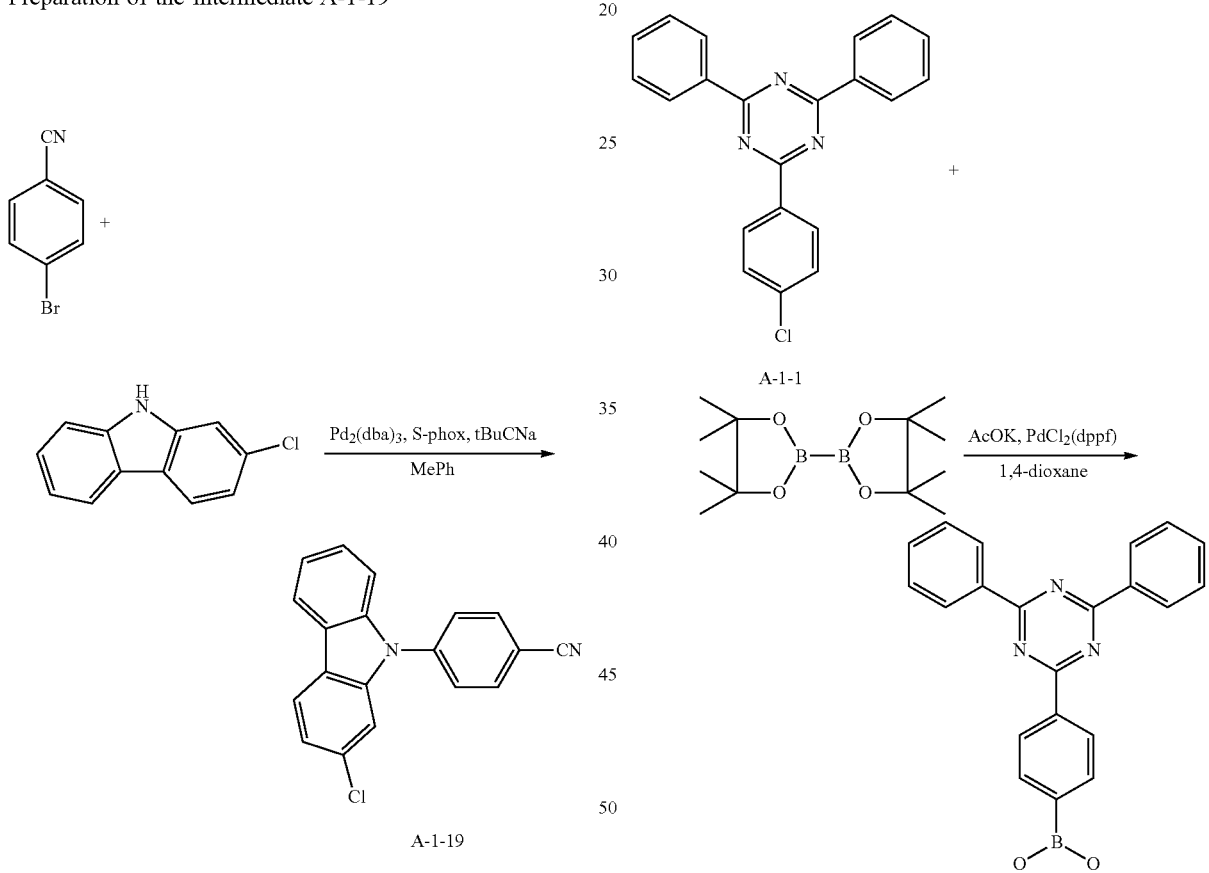

A-1-19

A-1-1

A-2-1 p-bromobenzonitrile (20 g, 109.87 mmol), 3-chlorocarbazole (22.15 g, 109.87 mmol), tris(dibenzylideneacetone) dipalladium (1 g, 1.098 mmol), 2-dicyclohexyl phosphorus-2',6'-dimethoxy biphenyl (0.90 g, 2.197 mmol) and sodium tert-butoxide (23.23 g, 241.73 mmol) were added to methylbenzene (200 mL), the mixture was heated to 108° C. under nitrogen atmosphere and stirred for 3 h and then cooled to room temperature. The reaction solution was washed with water and the separated organic phase was wasted with water and dried over anhydrous magnesium sulfate, and then concentrated in vacuo to obtain a crude product. The crude product was purified by recrystallization using methylbenzene, to obtain intermediate A-1-19 (23.28 g, yield 70%).

A-1-1 (16 g, 46.53 mmol), bisdiboron (14.18 g, 55.84 mmol), 1,1'-bis(diphenylphosphino)ferrocene)palladium $PdCl_2(dppf)$ (0.68 g, 0.93 mmol), potassium acetate (13.7 g, 139.61 mmol) and 1,4-dioxane (160 mL) were added to three-necked flask, and the mixture was subjected to reflux and stirred for 12 h at 80° C. After the reaction is completed, $CH_2Cl_2$ and water were used for extraction, the combined organic phases were dried over anhydrous $MgSO_4$ and filtered. The filtrate was concentrated in vacuo to obtain a (2) Preparation of the Intermediates A-2-1 to A-2-21 crude product. The crude product was purified by silica gel column chromatography to obtain intermediate A-2-1 (12.15 g, yield 60%).

Referring to the preparation method of the intermediate A-2-1, intermediates A-2-2 to A-2-21 were prepared by replacing A-1-1 with the intermediate A-1 in Table 2.

TABLE 2

| Preparation example | Intermediate A-1 | Intermediate A-2 | Yield |
|---|---|---|---|
| A-2-2 | A-1-2 | | 51% |
| A-2-3 | A-1-3 | | 52% |
| A-2-4 | A-1-4 | | 60% |

TABLE 2-continued
| Preparation example | Intermediate A-1 | Intermediate A-2 | Yield |
|---|---|---|---|
| A-2-5 | 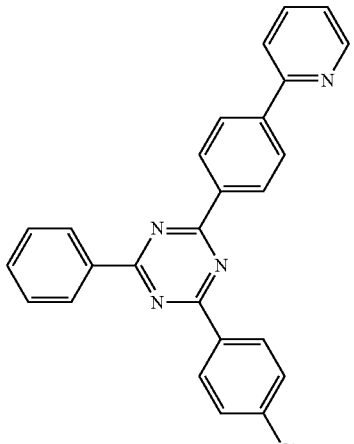<br>A-1-5 | 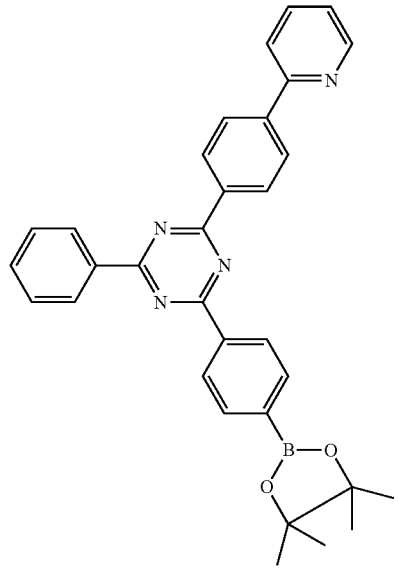 | 55% |
| A-2-6 | 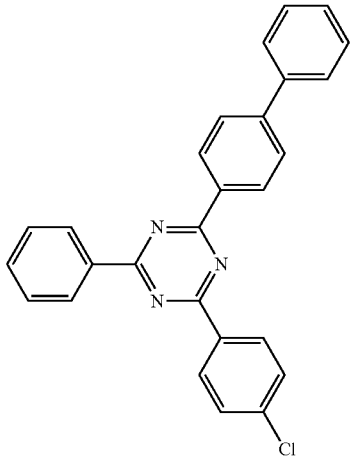<br>A-1-6 | 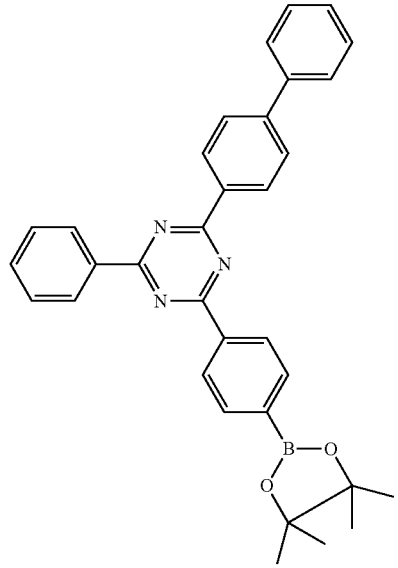 [SMILES: CC1(C)OB(c2ccc(-c3nc(-c4ccccc4)nc(-c4ccc(-c5ccccn5)cc4)n3)cc2)OC1(C)C] | 54% |
| A-2-7 | 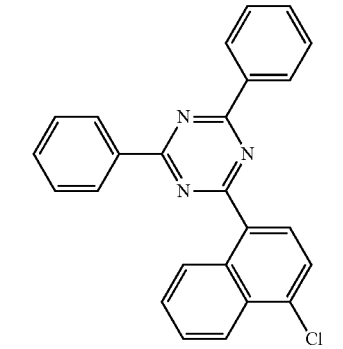<br>A-1-7 | 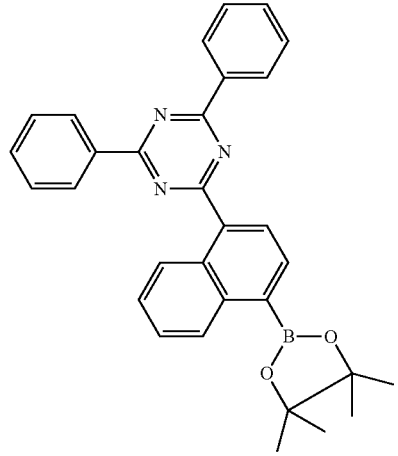 [SMILES: CC1(C)OB(c2ccc(-c3nc(-c4ccccc4)nc(-c4ccccc4)n3)c3ccccc23)OC1(C)C] | 59% |

TABLE 2-continued
| Preparation example | Intermediate A-1 | Intermediate A-2 | Yield |
|---|---|---|---|
| A-2-8 | 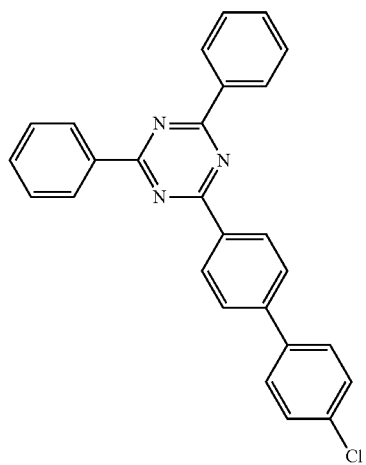<br>A-1-8 | 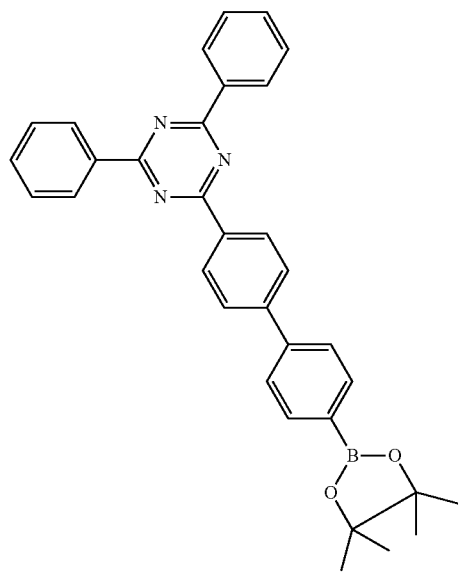 [SMILES: CC1(C)OB(c2ccc(-c3ccc(-c4nc(-c5ccccc5)nc(-c5ccccc5)n4)cc3)cc2)OC1(C)C] | 58% |
| A-2-9 | 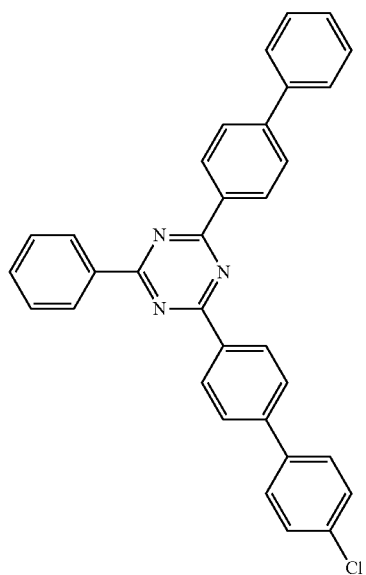<br>A-1-9 | 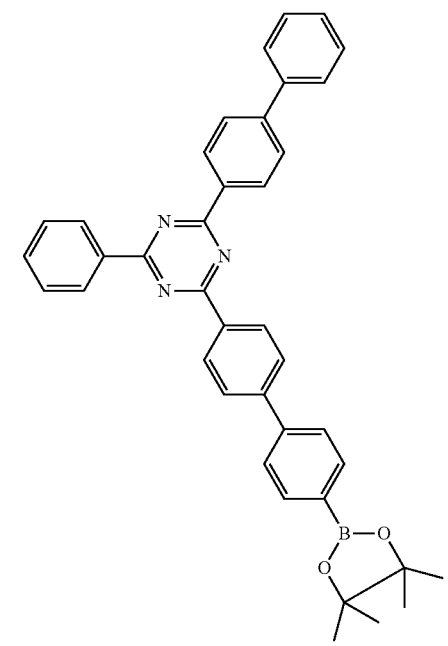 [SMILES: CC1(C)OB(c2ccc(-c3ccc(-c4nc(-c5ccccc5)nc(-c5ccc(-c6ccccc6)cc5)n4)cc3)cc2)OC1(C)C] | 53% |

TABLE 2-continued

| Preparation example | Intermediate A-1 | Intermediate A-2 | Yield |
|---|---|---|---|
| A-2-10 | A-1-10 | | 58% |
| A-2-11 | A-1-11 | | 55% |
| A-2-12 | A-1-12 | | 52% |

TABLE 2-continued

| Preparation example | Intermediate A-1 | Intermediate A-2 | Yield |
|---|---|---|---|
| A-2-13 | A-1-13 | | 53% |
| A-2-14 | A-1-14 | | 60% |
| A-2-15 | A-1-15 | | 55% |

TABLE 2-continued
| Preparation example | Intermediate A-1 | Intermediate A-2 | Yield |
|---|---|---|---|
| A-2-16 | 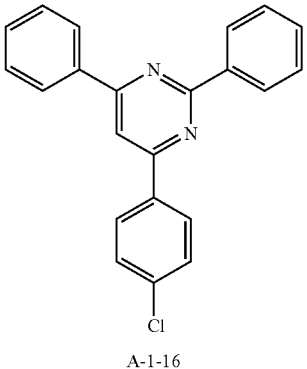 [SMILES: Clc1ccc(-c2cc(-c3ccccc3)nc(-c3ccccc3)n2)cc1]<br>A-1-16 | 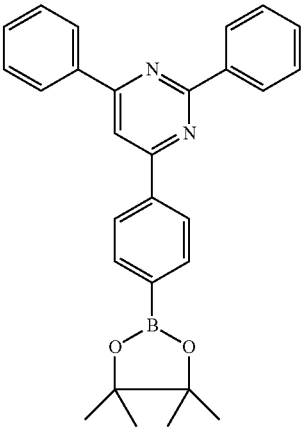 [SMILES: CC1(C)OB(c2ccc(-c3cc(-c4ccccc4)nc(-c4ccccc4)n3)cc2)OC1(C)C] | 52% |
| A-2-17 | 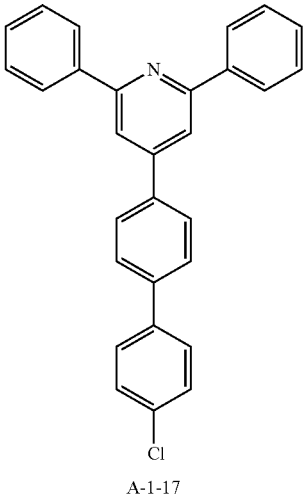 [SMILES: Clc1ccc(-c2ccc(-c3cc(-c4ccccc4)nc(-c4ccccc4)c3)cc2)cc1]<br>A-1-17 | 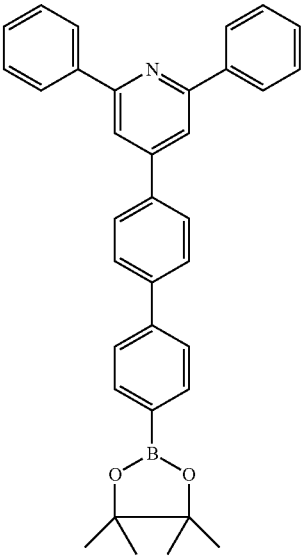 [SMILES: CC1(C)OB(c2ccc(-c3ccc(-c4cc(-c5ccccc5)nc(-c5ccccc5)c4)cc3)cc2)OC1(C)C] | 54% |
| A-2-18 | 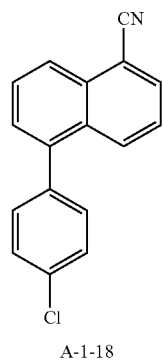 [SMILES: N#Cc1cccc2c(-c3ccc(Cl)cc3)cccc12]<br>A-1-18 | 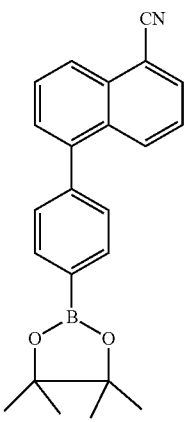 [SMILES: CC1(C)OB(c2ccc(-c3cccc4c(C#N)cccc34)cc2)OC1(C)C] | 53% |

247 248
TABLE 2-continued
| Preparation example | Intermediate A-1 | Intermediate A-2 | Yield |
|---|---|---|---|
| A-2-19 | A-1-19 | | 50% |
| A-2-20 | A-1-20 | | 53% |
| A-2-21 | CAS: 885227-79-2 | | 52% |
(3) Preparation of the Intermediates A-3-1 to A-3-14
-continued
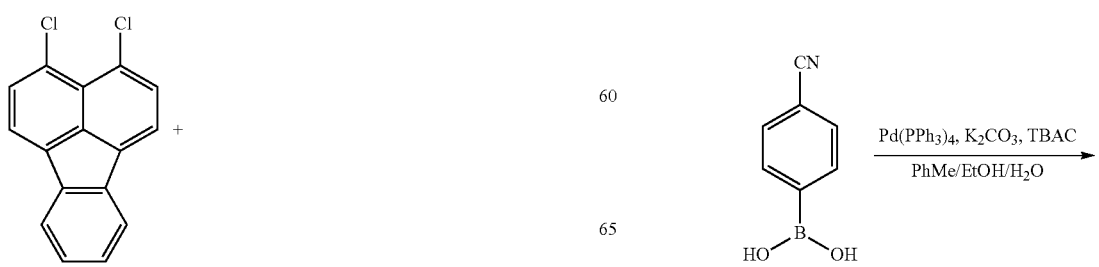

-continued

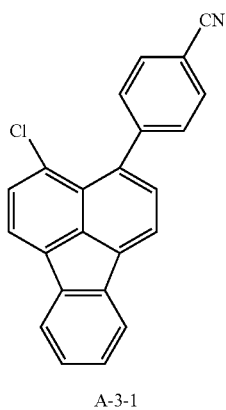
A-3-1

3,4-dichlorofluoranthene (20 g, 73.76 mmol), 4-cyanophenylboronic acid (9.03 g, 61.46 mmol), $K_2CO_3$ (25.48 g, 184.4 mmol), tetrabutylammonium chloride (TBAC) (17.08 g, 61.46 mmol) were added to a three-necked flask; then methylbenzene (160 mL), ethanol (80 mL), and water (40 mL) were added, then tetrakis(triphenylphosphine)palladium $Pd(PPh_3)_4$ (1.42 g, 1.23 mmol) was added too. The mixture was heated to reflux and stirred for 12 h at 80° C. After the reaction is completed, dichloromethane and water were added for extraction; the separated organic phase was dried over anhydrous $MgSO_4$ and filtered. The filtrate was concentrated in vacuo to obtain a crude product. The crude product was purified by silica gel column chromatography to obtain intermediate A-3-1 (11.41 g, yield 55%).

Referring to the preparation method of the intermediate A-3-1, intermediates A-3-2 to A-3-14 were prepared by replacing 4-cyanophenylboronic acid with the raw material 3 in Table 3.

TABLE 3

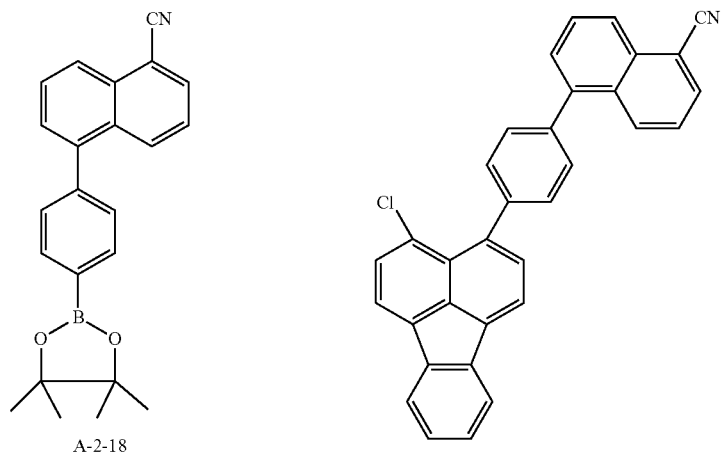

| Preparation example | Raw material 3 | Intermediate A-3 | Yield |
|---|---|---|---|
| A-3-2 | | | 60% |
| A-3-3 | A-2-18 | | 59% |

TABLE 3-continued

| Preparation example | Raw material 3 | Intermediate A-3 | Yield |
|---|---|---|---|
| A-3-4 | | | 61% |
| A-3-5 | | | 60% |
| A-3-6 | A-2-21 | | 62% |

TABLE 3-continued

| Preparation example | Raw material 3 | Intermediate A-3 | Yield |
|---|---|---|---|
| A-3-7 | | | 59% |
| A-3-8 | | | 56% |
| A-3-9 | A-2-20 | | 53% |

TABLE 3-continued

| Preparation example | Raw material 3 | Intermediate A-3 | Yield |
|---|---|---|---|
| A-3-10 | | | 51% |
| A-3-11 | A-2-11 | | 52% |
| A-3-12 | | | 51% |

TABLE 3-continued
| Preparation example | Raw material 3 | Intermediate A-3 | Yield |
|---|---|---|---|
| A-3-13 | 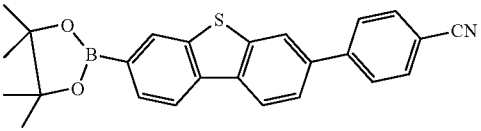<br>A-2-12 | 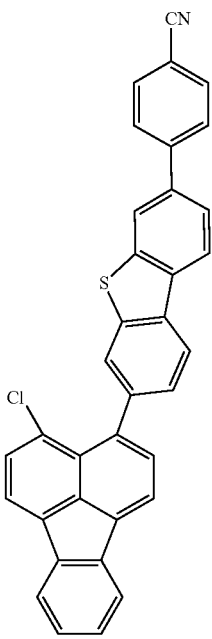 | 54% |
| A-3-14 | 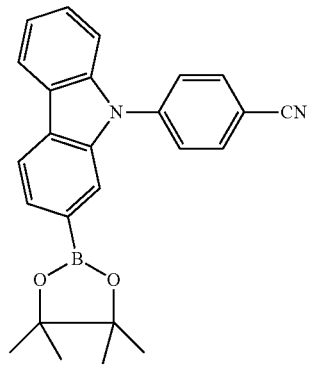 [SMILES: CC1(C)OB(c2ccc3c4ccccc4n(-c4ccc(C#N)cc4)c3c2)OC1(C)C]<br>A-2-19 | 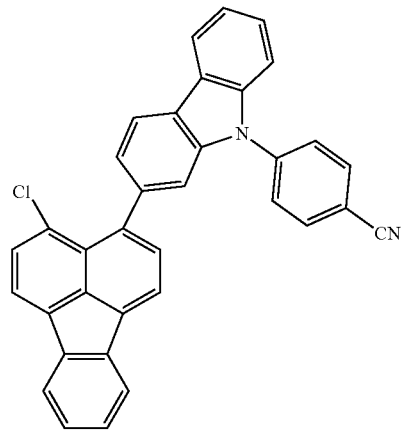 | 53% |

Compound Preparation Example 1

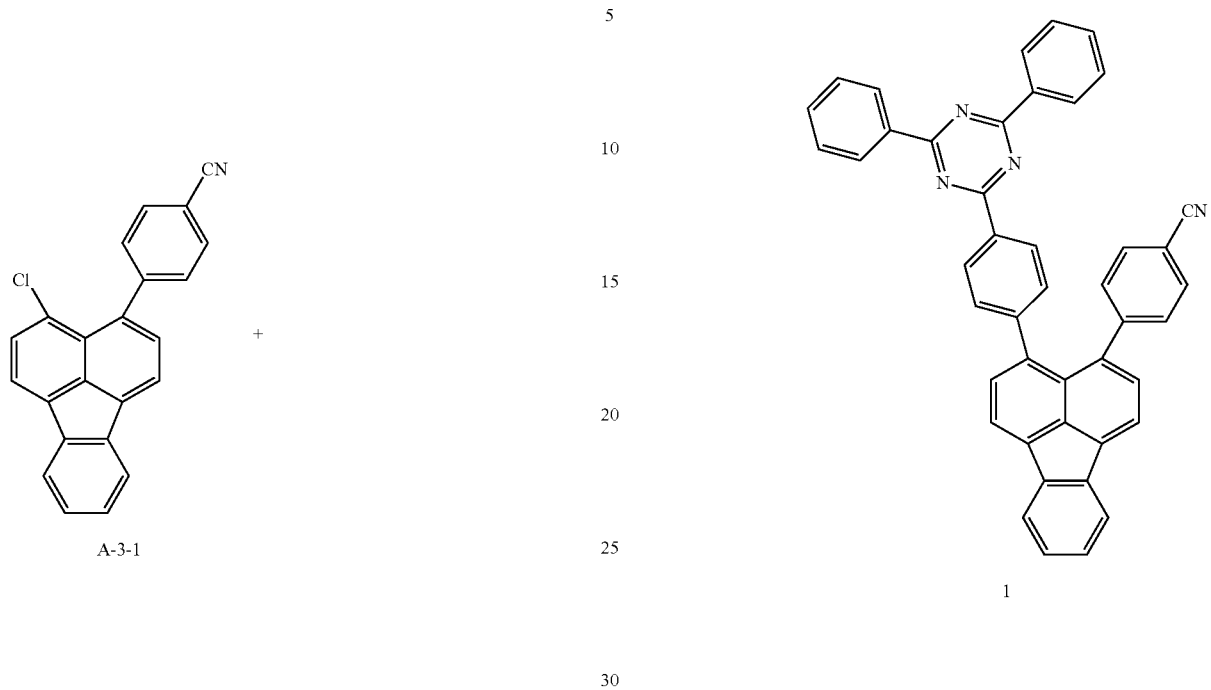

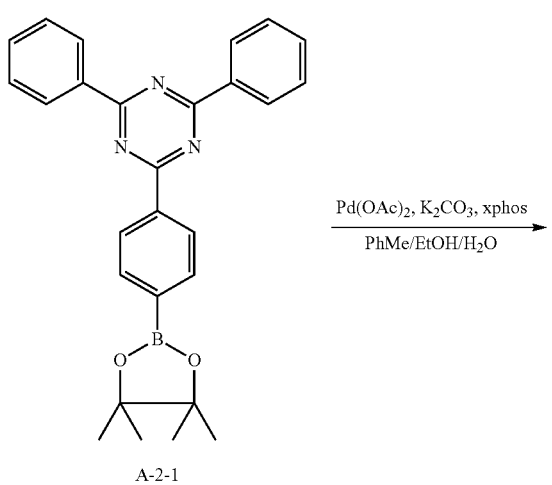

A-2-1 (12 g, 27.56 mmol), A-3-1 (7.75 g, 22.97 mmol), Pd(OAc)$_2$ (0.25 g, 1.14 mmol), K$_2$CO$_3$ (6.98 g, 50.53 mmol), 2-dicyclohexylphosphorus-2',4',6'-triisopropyl biphenyl (x-phos)(0.54 g, 1.14 mmol), methylbenzene (96 mL), absolute ethanol (48 mL), and deionized water (24 mL) were added to a three-necked flask, and the mixture was heated to reflux and stirred for 12 h at 78° C. After the reaction is completed, dichloromethane and water were used for extraction; the separated organic phase was dried over anhydrous MgSO$_4$ and filtered. The filtrate was concentrated in vacuo to obtain a crude product. The crude product was purified by silica gel column chromatography to obtain compound 1 (8.41 g, yield 60%) (LC-MS(ESI,pos.ion) m/z: 611.22[M+H]$^+$).

$^1$HNMR (CD$_2$Cl$_2$, 400 MHz), δ(ppm): 8.80 (d, 4H), 8.28 (d, 2H), 8.03-7.96 (m, 4H), 7.79-7.74 (m, 4H), 7.6 (t, 4H), 7.59-7.51 (m, 5H), 7.37 (d, 1H), 7.12-7.10 (m, 2H).

Compound Preparation Examples 2 to 28

Referring to the preparation method of the compound 1, the following compounds were prepared by replacing A-2-1 with the intermediates in column A-2 of Table 4 and replacing A-3-1 with the intermediates in column A-3.

TABLE 4
| Preparation example | Compound No. | Intermediate A-2 | Intermediate A-3 |
|---|---|---|---|
| 2 | 3 | 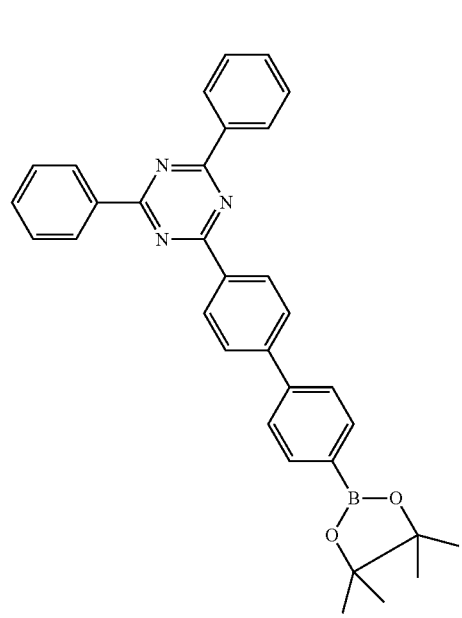<br>A-2-8 | 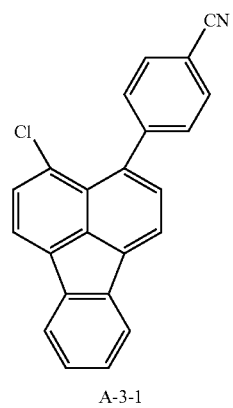<br>A-3-1 |
| 3 | 4 | 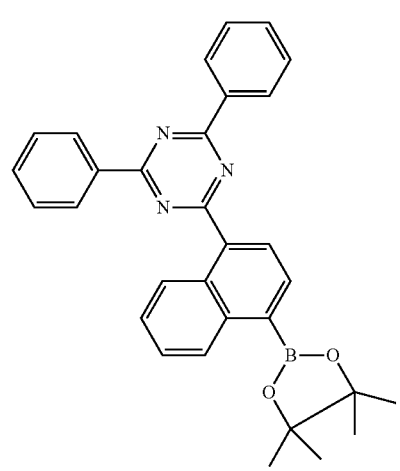<br>A-2-7 | 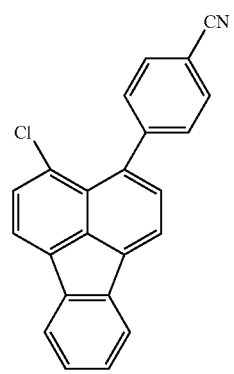<br>A-3-1 |

TABLE 4-continued
| | | | |
|---|---|---|---|
| 4 | 34 | 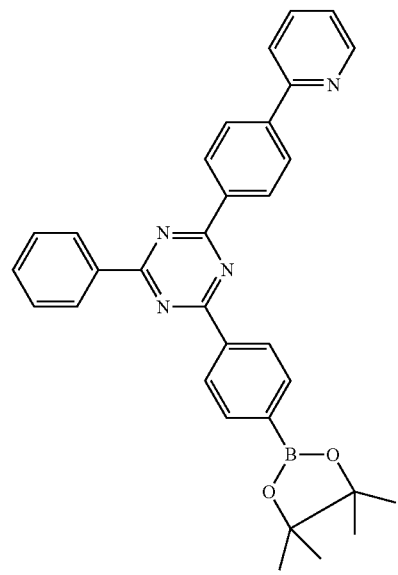<br>A-2-5 | 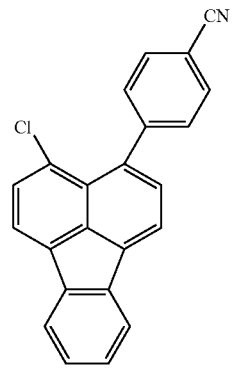<br>A-3-1 |
| 5 | 49 | 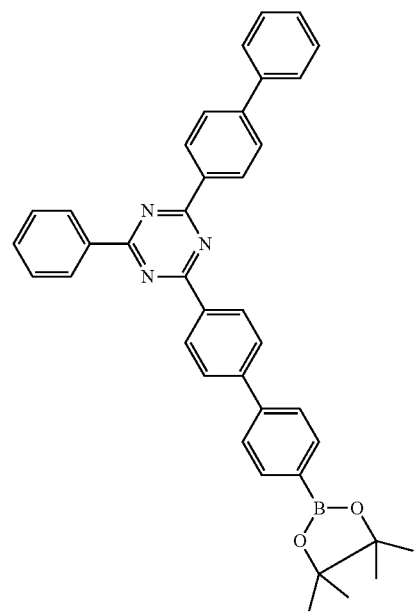<br>A-2-9 | 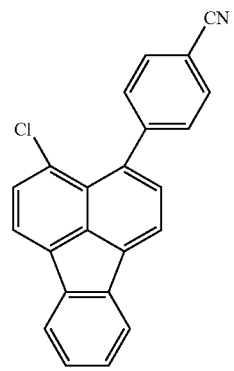<br>A-3-1 |
| 6 | 113 | 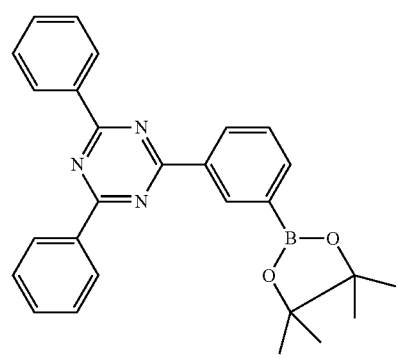<br>A-2-2 | 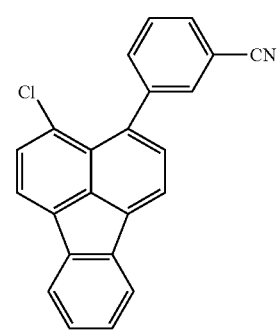<br>A-3-2 |

TABLE 4-continued
| | | | |
|---|---|---|---|
| 7 | 130 | 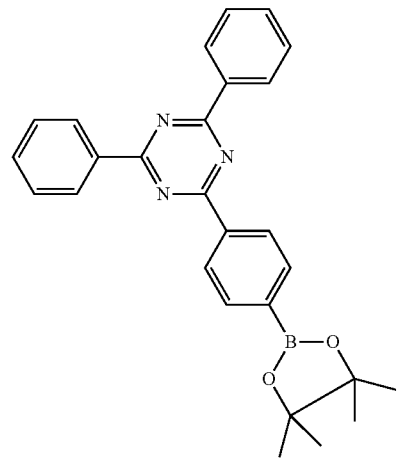<br>A-2-1 | 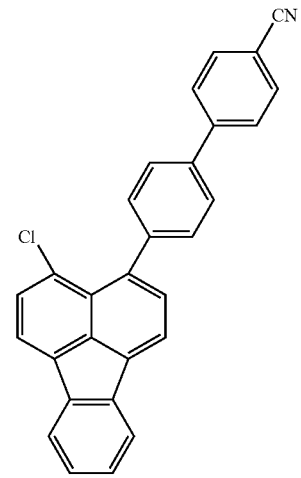<br>A-3-7 |
| 8 | 38 | 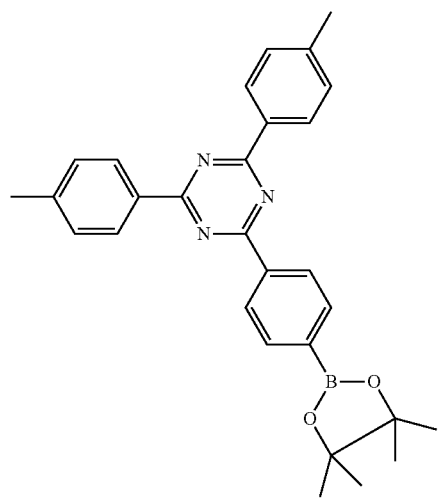<br>A-2-4 | 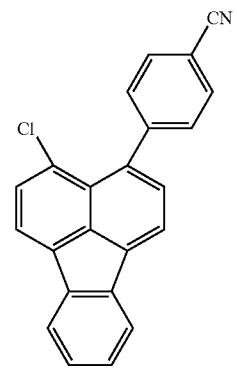<br>A-3-1 |
| 9 | 115 | 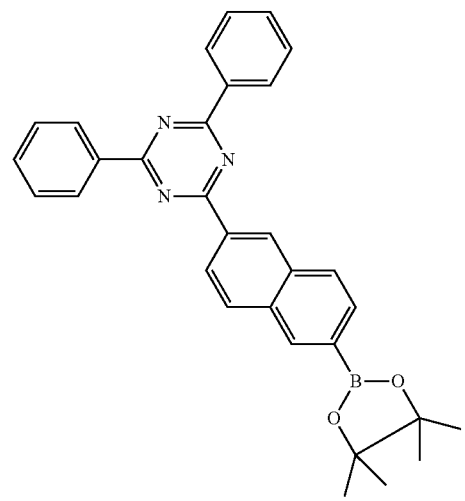<br>A-2-10 | 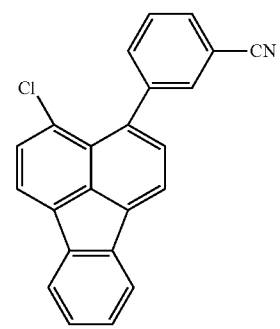 [SMILES: N#Cc1cccc(-c2ccc3c4c(ccc(Cl)c24)-c2ccccc2-3)c1]<br>A-3-2 |

TABLE 4-continued
| | | | |
|---|---|---|---|
| 10 | 132 | 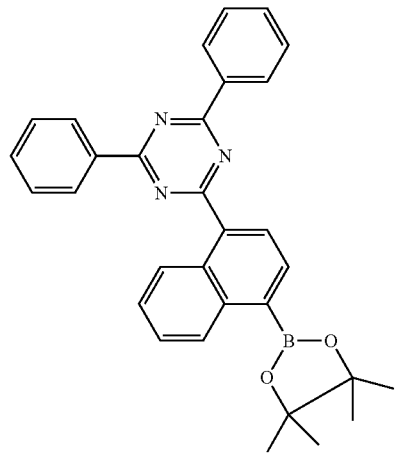<br>A-2-7 | 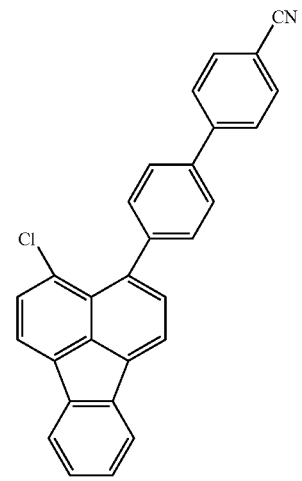 [SMILES: N#Cc1ccc(-c2ccc(-c3ccc4c5c(ccc(Cl)c35)-c3ccccc3-4)cc2)cc1]<br>A-3-7 |
| 11 | 161 | 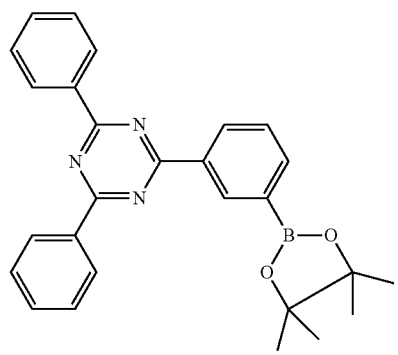<br>A-2-2 | 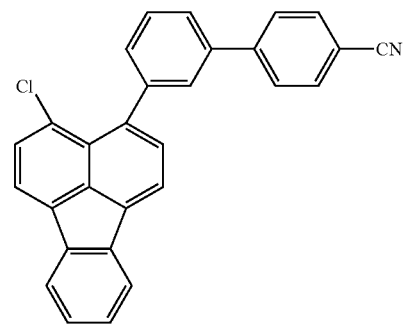 [SMILES: N#Cc1ccc(-c2cccc(-c3ccc4c5c(ccc(Cl)c35)-c3ccccc3-4)c2)cc1]<br>A-3-8 |
| 12 | 171 | 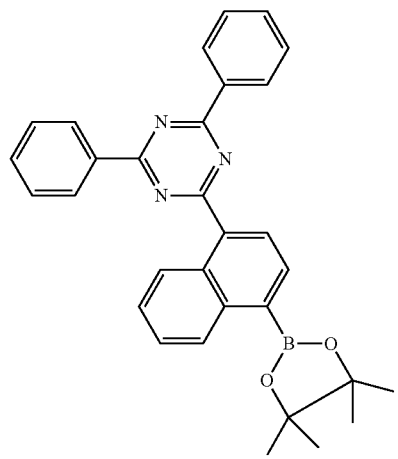<br>A-2-7 | 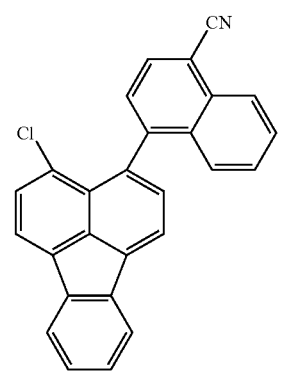<br>A-3-4 |

TABLE 4-continued
| 13 | 209 | 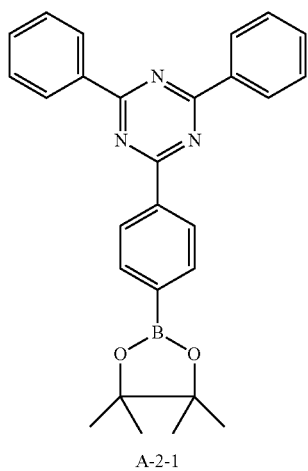 [SMILES: CC1(C)OB(c2ccc(-c3nc(-c4ccccc4)nc(-c4ccccc4)n3)cc2)OC1(C)C]<br>A-2-1 | 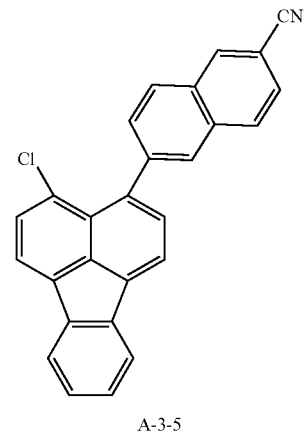 [SMILES: N#Cc1ccc2cc(-c3ccc4c5c(ccc(Cl)c35)-c3ccccc3-4)ccc2c1]<br>A-3-5 |
| 14 | 219 | 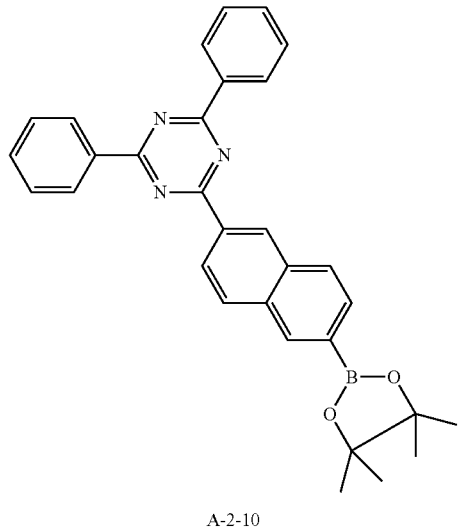 [SMILES: CC1(C)OB(c2ccc3cc(-c4nc(-c5ccccc5)nc(-c5ccccc5)n4)ccc3c2)OC1(C)C]<br>A-2-10 | 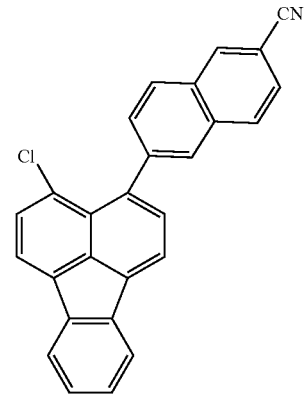<br>A-3-5 |
| 15 | 33 | 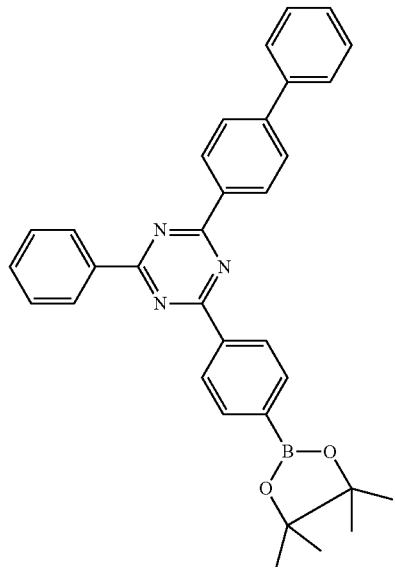<br>A-2-6 | 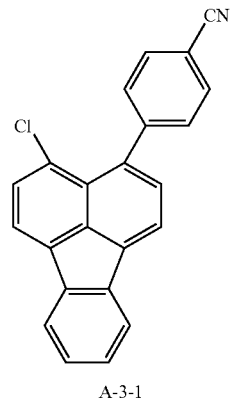 [SMILES: N#Cc1ccc(-c2ccc3c4c(ccc(Cl)c24)-c2ccccc2-3)cc1]<br>A-3-1 |

TABLE 4-continued
| 16 | 39 | 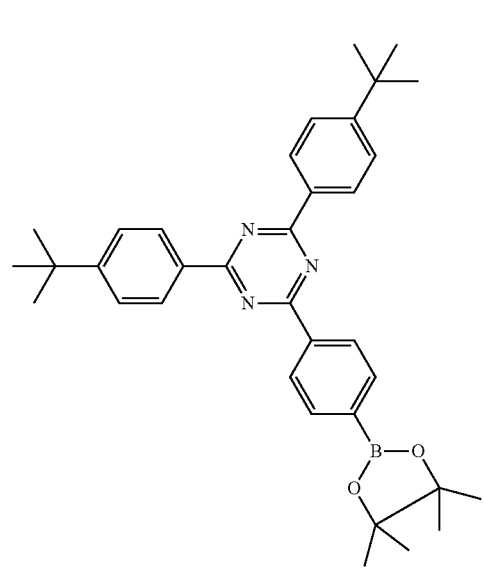 | 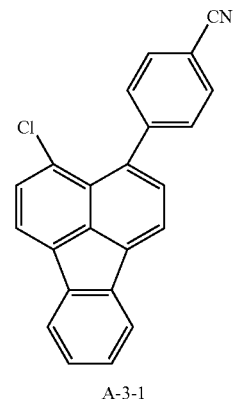 [SMILES: N#Cc1ccc(-c2ccc3c4c(ccc(Cl)c24)-c2ccccc2-3)cc1] |
A-2-3
A-3-1
| 17 | 348 | 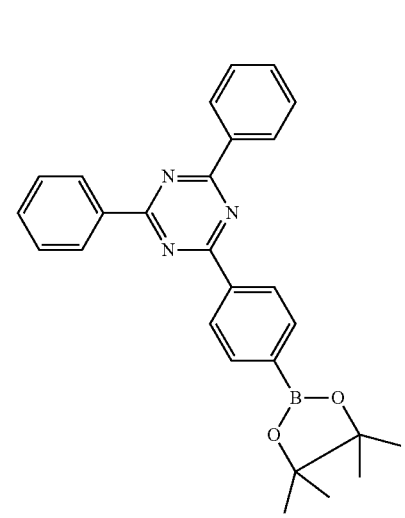 | 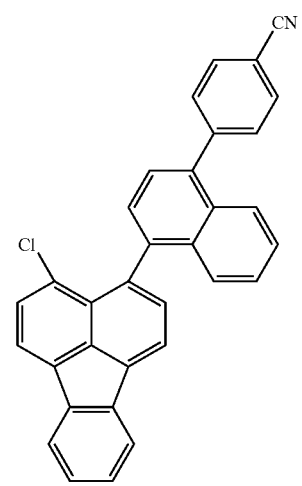 |
A-2-1
A-3-9

TABLE 4-continued
| 18 | 355 | | |
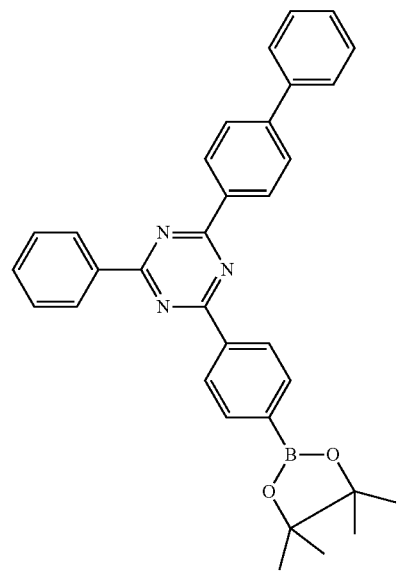
A-2-6
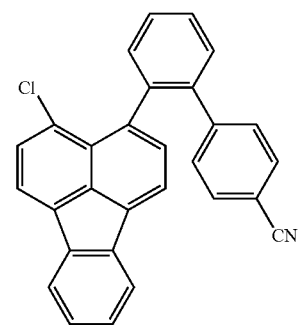
A-3-10
| 19 | 391 | | |
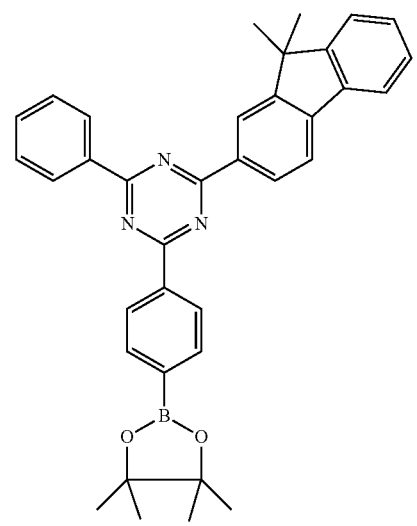
A-2-13
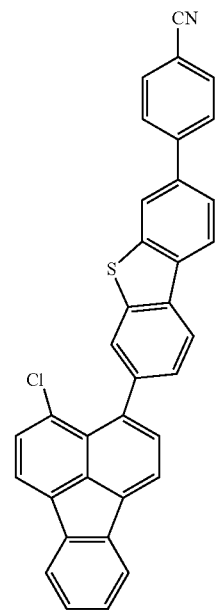
A-3-13

TABLE 4-continued
| 20 | 392 | 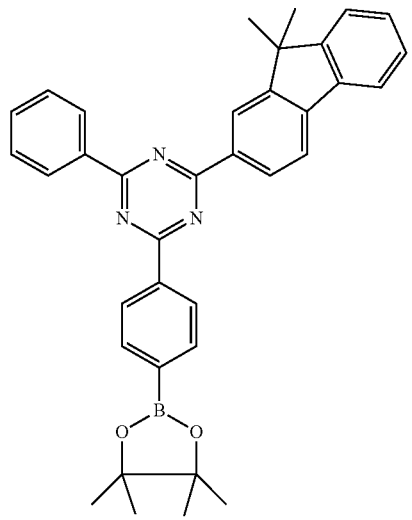<br>A-2-13 | 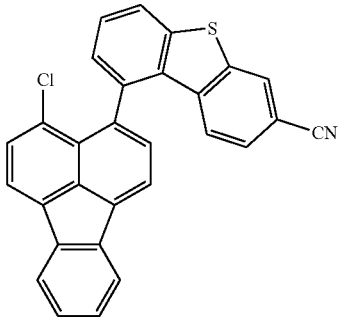<br>A-3-12 |
| 21 | 359 | 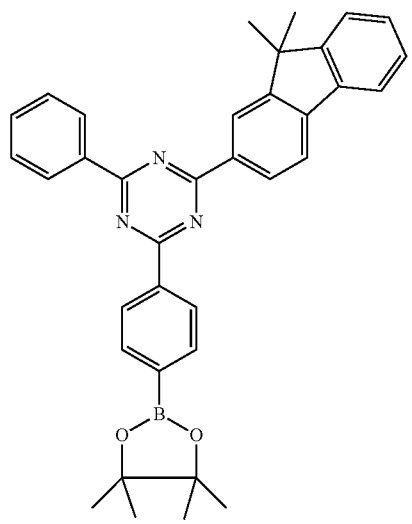<br>A-2-13 | 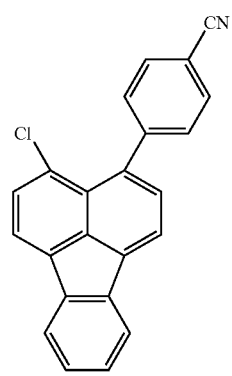<br>A-3-1 |

TABLE 4-continued
| | | | |
|---|---|---|---|
| 22 | 361 | 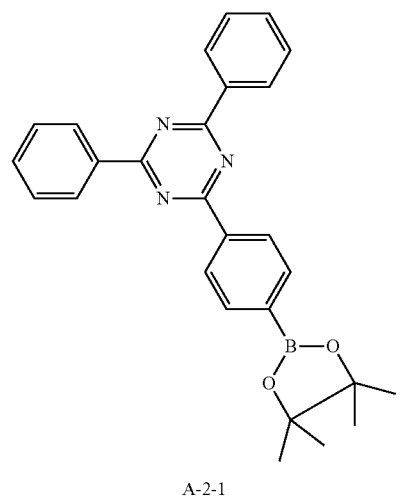 [SMILES: CC1(C)OB(c2ccc(-c3nc(-c4ccccc4)nc(-c4ccccc4)n3)cc2)OC1(C)C]<br>A-2-1 | 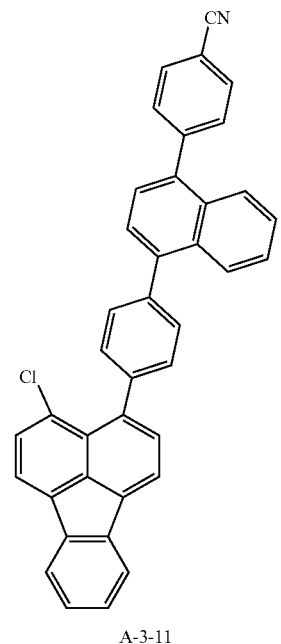 [SMILES: N#Cc1ccc(-c2ccc(-c3ccc(-c4ccc5c6c(ccc(Cl)c46)-c4ccccc4-5)cc3)c3ccccc23)cc1]<br>A-3-11 |
| 23 | 367 | 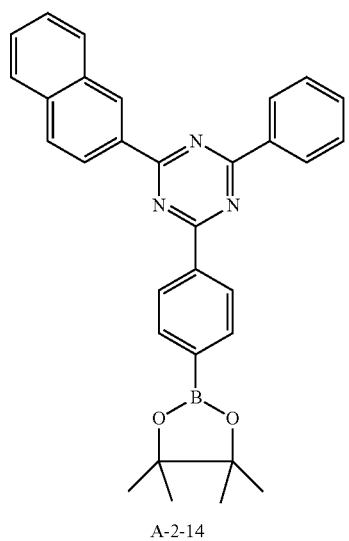 [SMILES: CC1(C)OB(c2ccc(-c3nc(-c4ccccc4)nc(-c4ccc5ccccc5c4)n3)cc2)OC1(C)C]<br>A-2-14 | 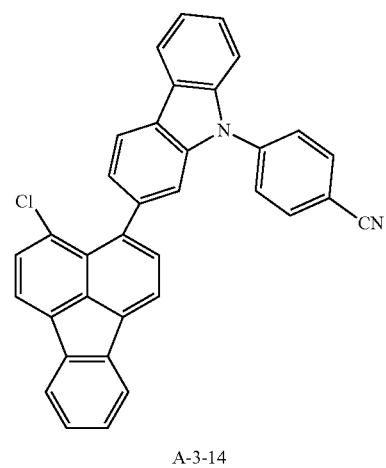 [SMILES: N#Cc1ccc(-n2c3ccccc3c3ccc(-c4ccc5c6c(ccc(Cl)c46)-c4ccccc4-5)cc32)cc1]<br>A-3-14 |
| 24 | 376 | 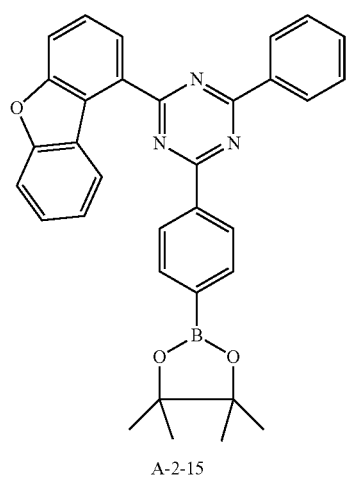 [SMILES: CC1(C)OB(c2ccc(-c3nc(-c4ccccc4)nc(-c4cccc5oc6ccccc6c45)n3)cc2)OC1(C)C]<br>A-2-15 | 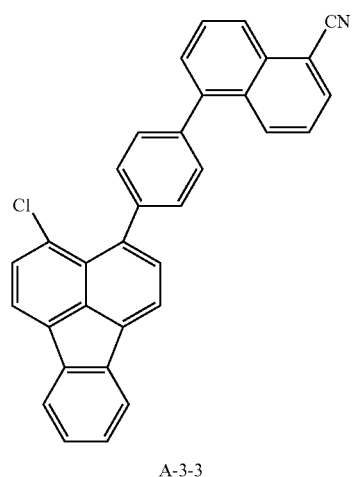 [SMILES: N#Cc1cccc2c(-c3ccc(-c4ccc5c6c(ccc(Cl)c46)-c4ccccc4-5)cc3)cccc12]<br>A-3-3 |

TABLE 4-continued
| 25 | 249 | 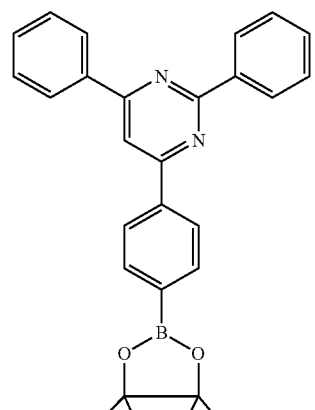<br>A-2-16 | 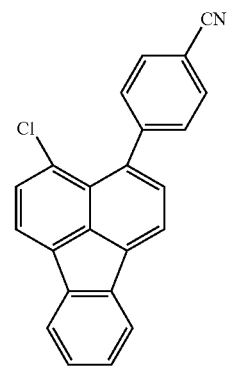<br>A-3-1 |
| 26 | 292 | 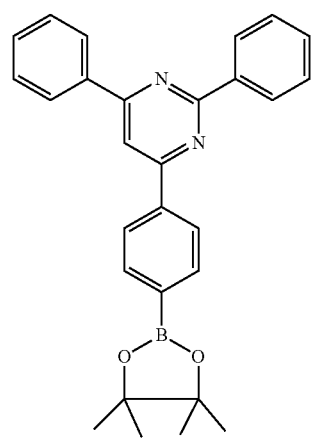<br>A-2-16 | 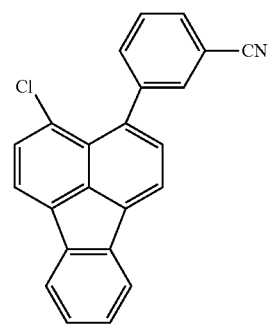<br>A-3-2 |
| 27 | 325 | 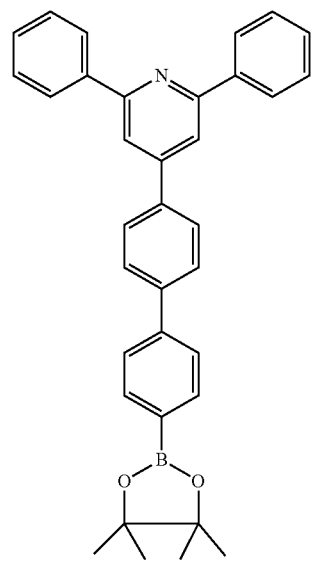<br>A-2-17 | 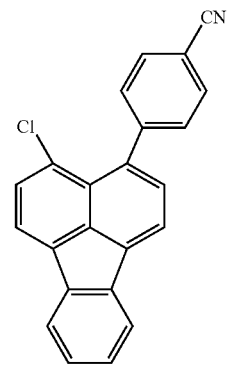<br>A-3-1 |

TABLE 4-continued
| | | | | | |
|---|---|---|---|---|---|
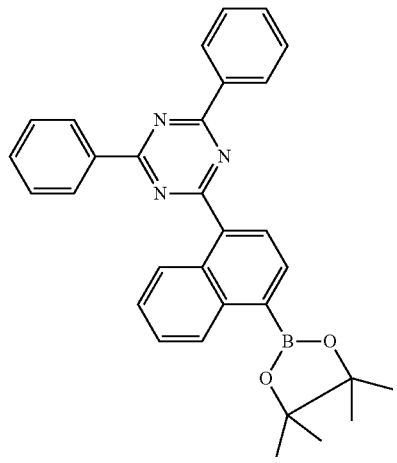
A-2-7
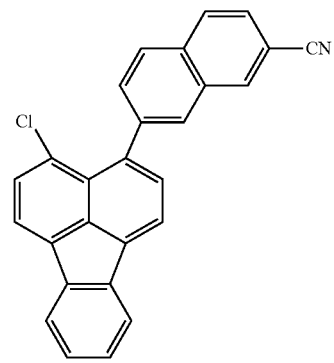
A-3-6
| Preparation example | Compound No. | Structural formula of the compound | Yield/g | Productive rate/% | Mass spectrum LC-MS (ESI, pos.ion) m/z |
|---|---|---|---|---|---|
| 2 | 3 | | 11.1 | 59 | 687.25 |
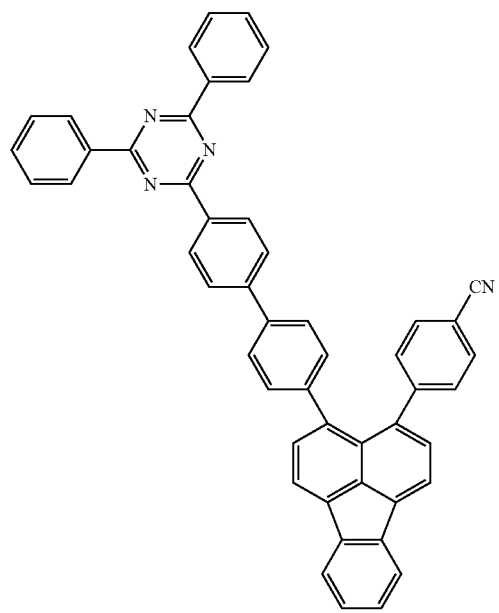
3

TABLE 4-continued
| | | | | | |
|---|---|---|---|---|---|
| 3 | 4 | | 10.1 | 56 | 660.82 |
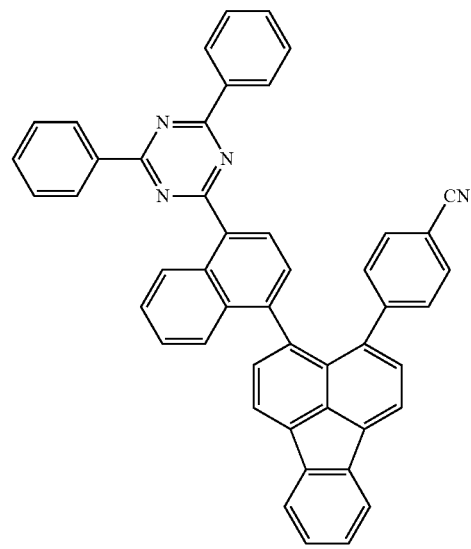
4
| | | | | | |
|---|---|---|---|---|---|
| 4 | 34 | | 9.8 | 55 | 688.24 |
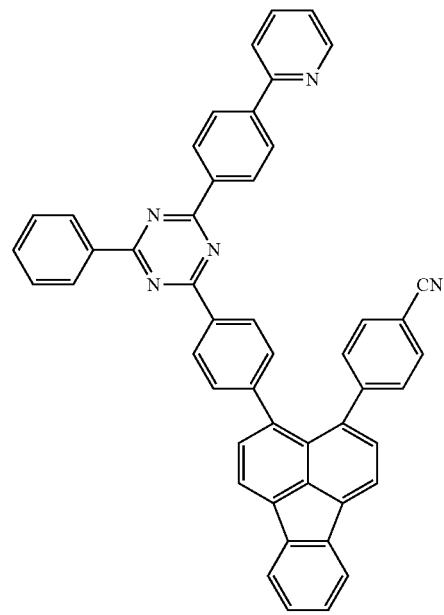
34

TABLE 4-continued
| | | | | | |
|---|---|---|---|---|---|
| 5 | 49 | 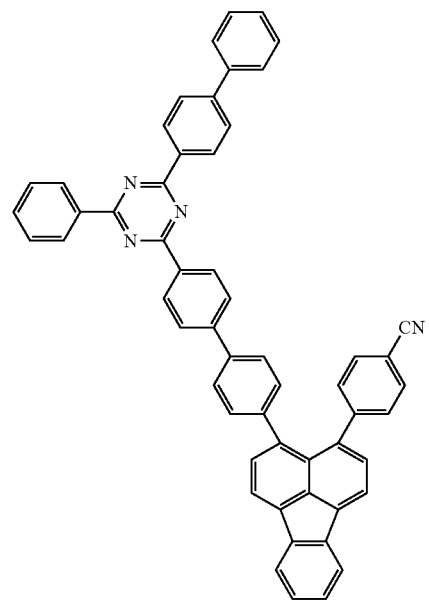 49 | 10.9 | 52 | 763.08 |
| 6 | 113 | 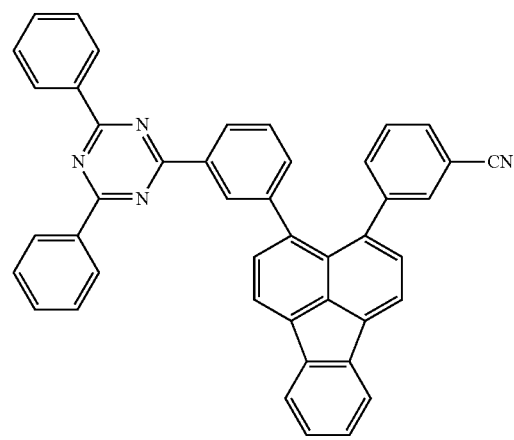 113 | 9.4 | 56 | 611.22 |

TABLE 4-continued
| 7 | 130 | | 10.7 | 57 | 687.25 |
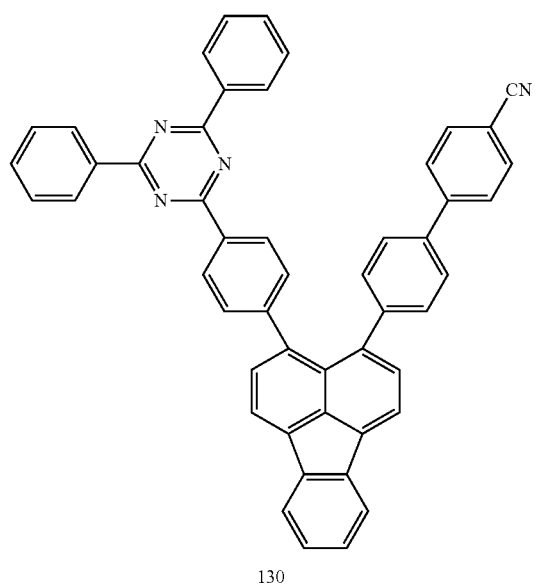 [SMILES: N#Cc1ccc(-c2ccc(-c3ccc4c5c(ccc(-c6ccc(-c7nc(-c8ccccc8)nc(-c8ccccc8)n7)cc6)c35)-c3ccccc3-4)cc2)cc1]
130
| 8 | 38 | | 9.5 | 54 | 639.25 |
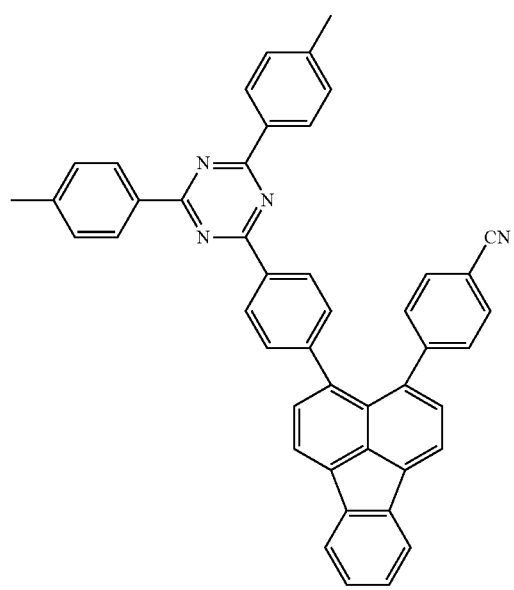
38

TABLE 4-continued
| | | | | | |
|---|---|---|---|---|---|
| 9 | 115 | | 10.5 | 58 | 661.23 |
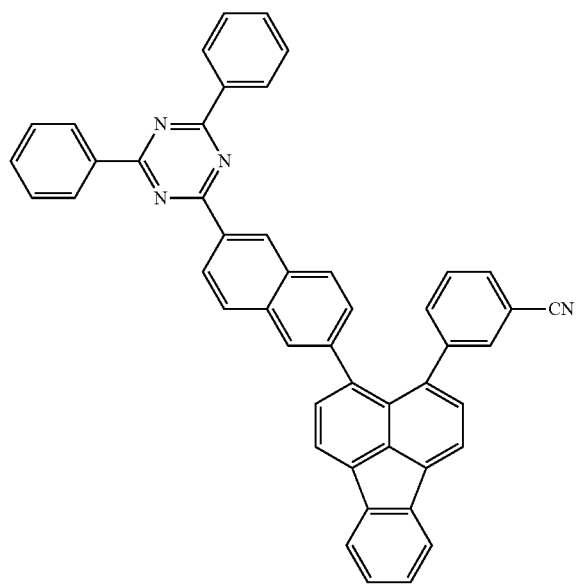
115
| | | | | | |
|---|---|---|---|---|---|
| 10 | 132 | | 10.5 | 52 | 737.23 |
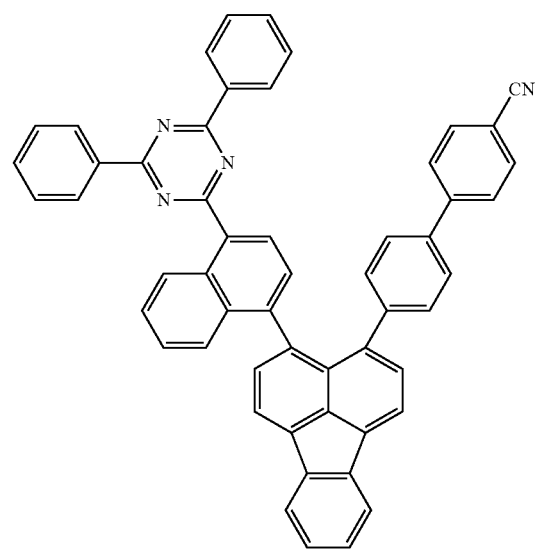
132

TABLE 4-continued

| 11 | 161 | | 9.8 | 53 | 687.25 |
|---|---|---|---|---|---|
| 12 | 171 | | 10.7 | 55 | 711.23 |
| 13 | 209 | | 10.1 | 56 | 661.23 |

TABLE 4-continued
| | | | | | |
|---|---|---|---|---|---|
| 14 | 219 | | 10.5 | 54 | 711.25 |
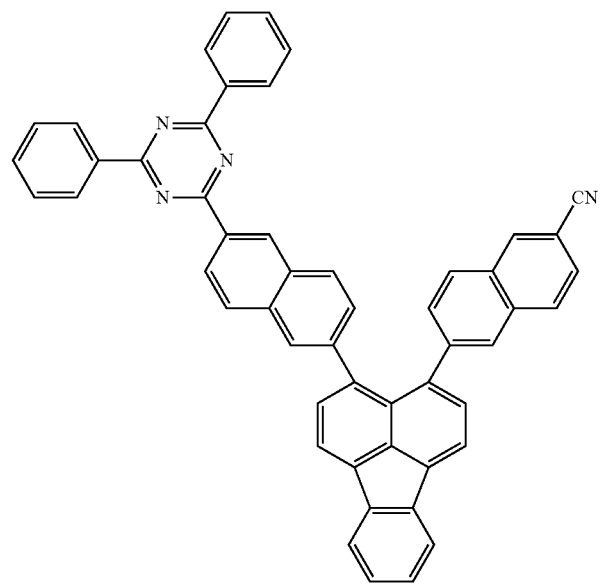
219
| | | | | | |
|---|---|---|---|---|---|
| 15 | 33 | | 11.3 | 60 | 687.59 |
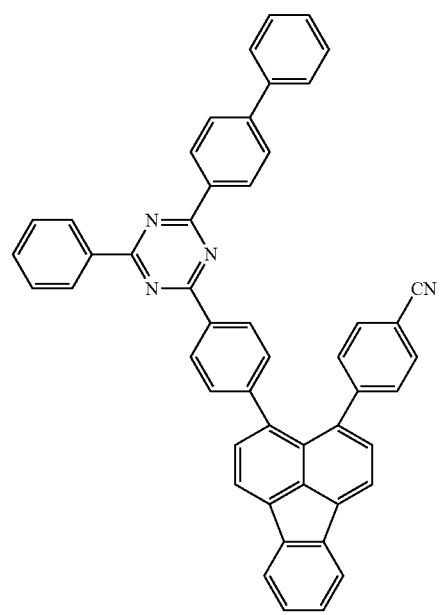
33

TABLE 4-continued
| 16 | 39 | | 11.5 | 58 | 723.92 |
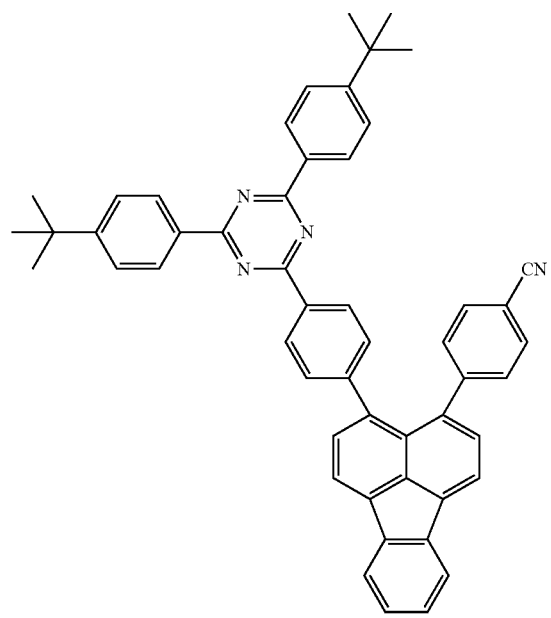
39
| 17 | 348 | | 11.0 | 50 | 801.28 |
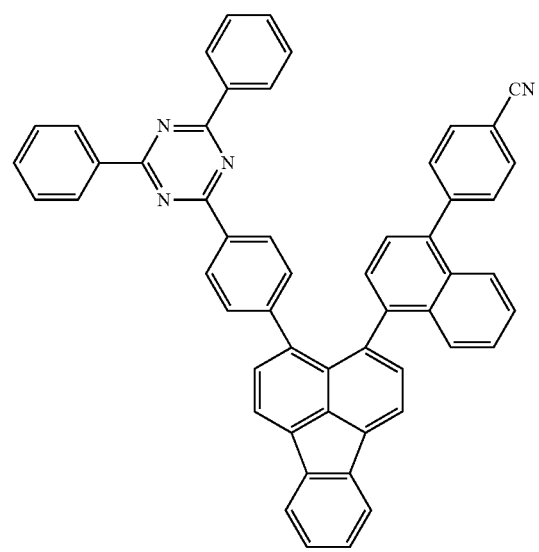
348

TABLE 4-continued
| 18 | 355 | | 10.7 | 51 | 763.28 |
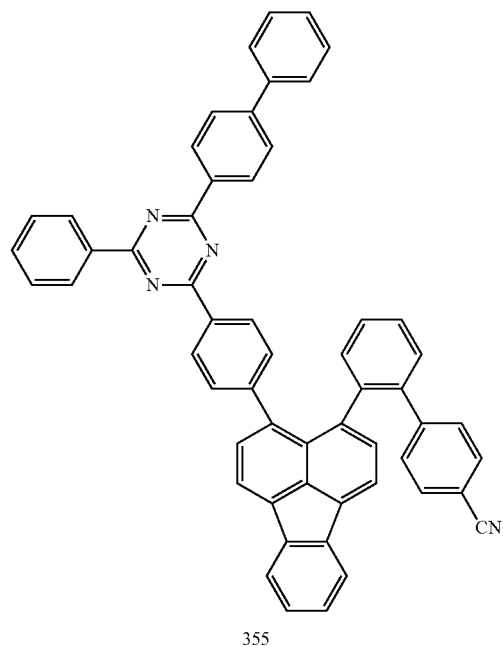 [SMILES: N#Cc1ccc(-c2ccccc2-c2ccc3c4c(ccc(-c5ccc(-c6nc(-c7ccccc7)nc(-c7ccc(-c8ccccc8)cc7)n6)cc5)c24)-c2ccccc2-3)cc1]
355
| 19 | 391 | | 10.6 | 51 | 908.29 |
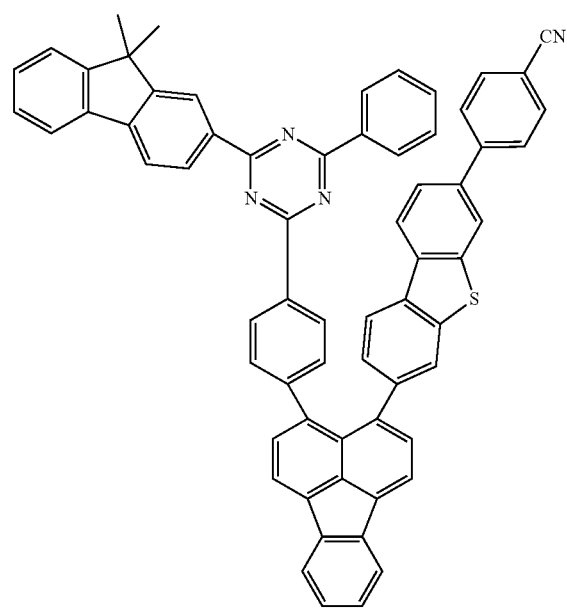
391

TABLE 4-continued
| 20 | 392 | | 10.3 | 52 | 832.26 |
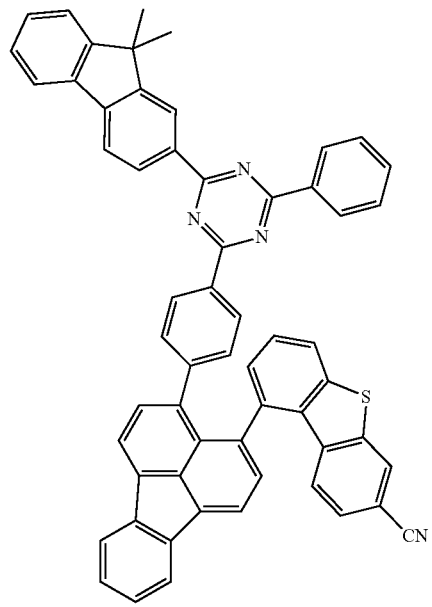
392
| 21 | 359 | | 11.0 | 55 | 726.27 |
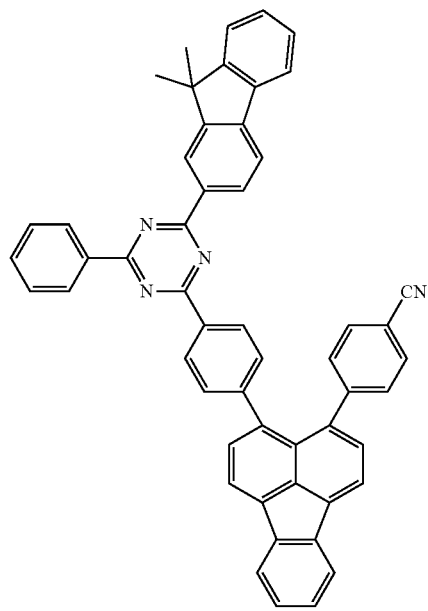
359

TABLE 4-continued
| 22 | 361 | 10.5 | 52 | 812.29 |
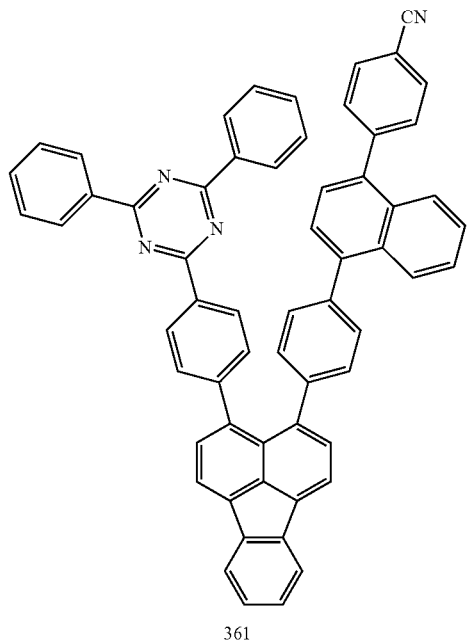 [SMILES: N#Cc1ccc(-c2ccc(-c3ccc(-c4ccc5c6c(ccc(-c7ccc(-c8nc(-c9ccccc9)nc(-c9ccccc9)n8)cc7)c46)-c4ccccc4-5)cc3)c3ccccc23)cc1]
361
| 23 | 367 | 10.4 | 56 | 825.28 |
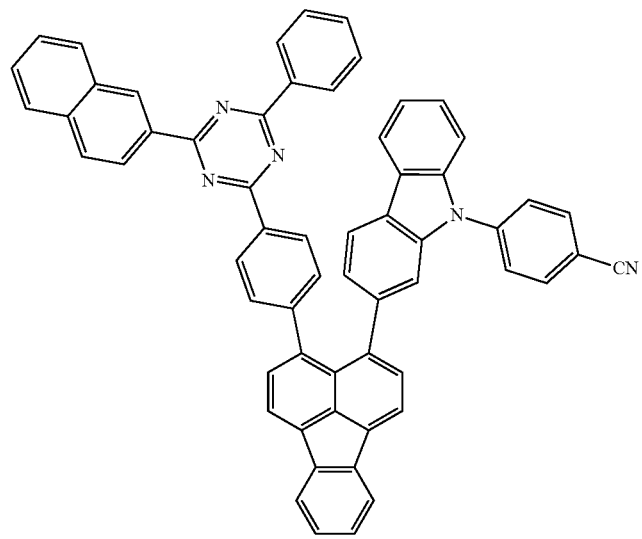
367

| | | | | | |
|---|---|---|---|---|---|
| 24 | 376 | | 10.1 | 52 | 826.27 |
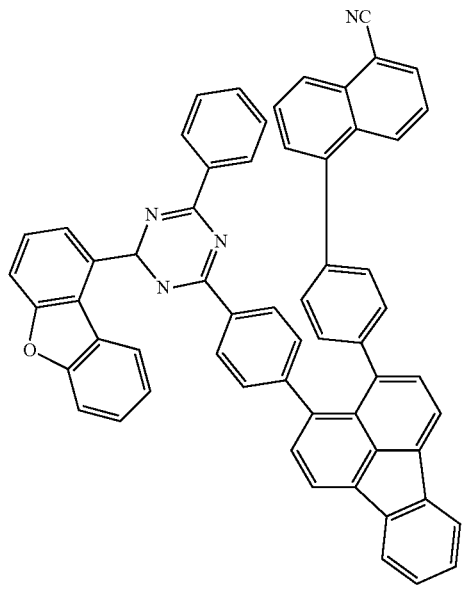
376
| | | | | | |
|---|---|---|---|---|---|
| 25 | 249 | | 10.8 | 53 | 609.22 |
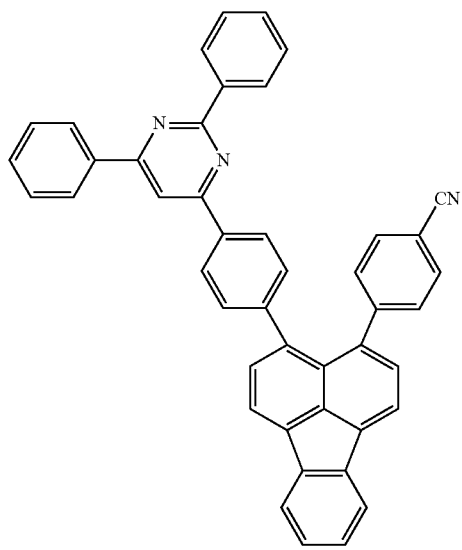
249

TABLE 4-continued
| 26 | 292 | | 10.5 | 54 | 609.23 |
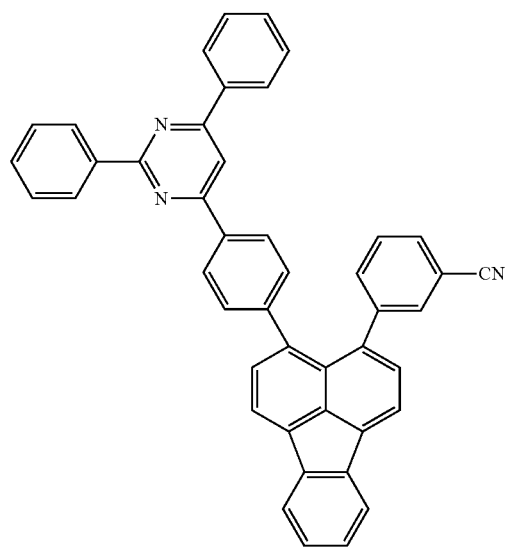
292
| 27 | 325 | | 10.6 | 53 | 684.25 |
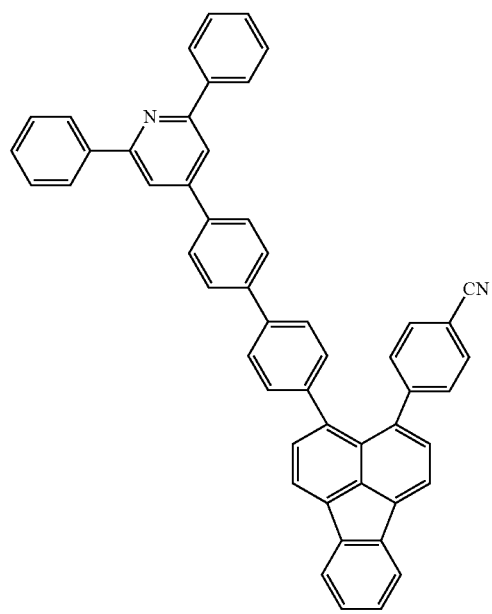
325

| 28 | 231 | | | | 10.4 | 52 | 711.15 |

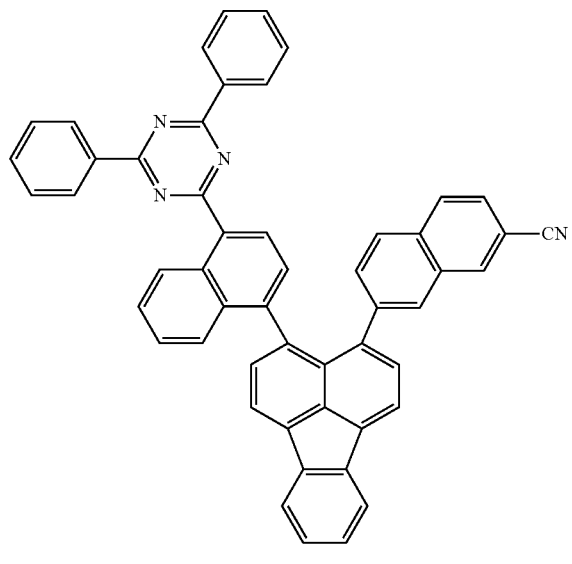

231

NMR data of compounds in the above partial embodiments:

Compound 113: ¹HNMR (CD$_2$Cl$_2$, 400 MHz) δ (ppm): 8.92 (d, 1H), 8.79 (d, 4H), 8.58 (d, 1H), 8.20 (s, 1H), 7.93 (d, 11H), 7.87-7.82 (m, 2H), 7.79-7.72 (m, 6H), 7.68-7.62 (m, 5H), 7.60-7.55 (m, 3H), 7.13-7.09 (m, 2H).

Compound 130: ¹HNMR (CD$_2$Cl$_2$, 400 MHz) δ (ppm): 8.81 (d, 4H), 8.30 (d, 2H), 8.02 (d, 2H), 7.92 (d, 2H), 7.81-7.76 (m, 8H), 7.66-7.56 (m, 8H), 7.38 (d, 2H), 7.13-7.09 (m, 2H).

Compound 33: ¹HNMR (CD$_2$Cl$_2$, 400 MHz) δ (ppm): 8.79 (d, 2H), 8.28 (d, 2H), 8.19 (d, 2H), 8.03-7.96 (m, 4H), 7.86 (d, 2H), 7.78-7.84 (m, 4H), 7.64 (t, 2H), 7.60-7.51 (m, 8H), 7.43-7.36 (m, 2H), 7.13-7.10 (m, 2H).

Device Example 1

A blue organic electroluminescent device was prepared by the following method:

an anode was prepared by the following process: an ITO substrate having an ITO thickness of 1500 Å was cut into a size of 40 mm (length)×40 mm (width)×0.7 mm (thickness), and prepared into an experimental substrate with a cathode, anode and insulating layer pattern by a photoetching process; then the experimental substrate was subjected to surface treatment with ultraviolet ozone, O$_2$:N$_2$ plasma to increase the work function of the anode; the surface of the ITO substrate was cleaned by an organic solvent to remove impurities and greasy dirt on the surface of the ITO substrate. It should be indicated that the ITO substrate may be further cut into other sizes according to the actual demands; there is no special limitation to the size of the ITO substrate in the present disclosure.

m-MTDATA(4,4',4"-tris(N-3-methylphenyl-N-phenylamino)triphenylamine) (referring to following structural formula) was vacuum evaporated on the experimental substrate (anode) to form a hole injection layer (HIL) with a thickness of 100 Å; and NPB (referring to following structural formula) was vacuum evaporated on the hole injection layer (HIL) to form a hole transport layer (HTL) with a thickness of 1000 Å.

TCTA(4,4',4"-tris(carbazole-9-yl)triphenylamine) was evaporated on the hole transport layer (HTL) to form an electron blocking layer (EBL) with a thickness of 150 Å.

α,β-ADN (referring to following structural formula) served as a host and was doped with BD-1 (referring to following structural formula) according to a film thickness ratio of 100:3 to form an luminescent layer (EML) with a thickness of 220 Å.

The compound 1 served as an electron transport layer (referring to above structural formula) and was mixed with LiQ (referring to following structural formula) according to a weight ratio of 1:1, thus forming an electron transport layer (ETL) with a thickness of 300 Å by evaporation. Afterwards, the metal Yb was evaporated on the electron transport layer to form an electron injection layer (EIL) with a thickness of 10 Å, and then, Mg and Ag were mixed according to an evaporation rate of 1:9, and vacuum evaporated on the electron injection layer (EIL), thus forming a cathode having a thickness of 120 Å.

In addition, the above cathode was evaporated with CP-1 with a thickness of 650 Å (referring to following structural formula) to form a covering layer (CPL), thus completing the manufacture of the organic electroluminescent device.

The structural formulae of the m-MTDATA, NPB, TCTA, α,β-ADN, BD-1, LiQ, and CP-1 were as shown below:

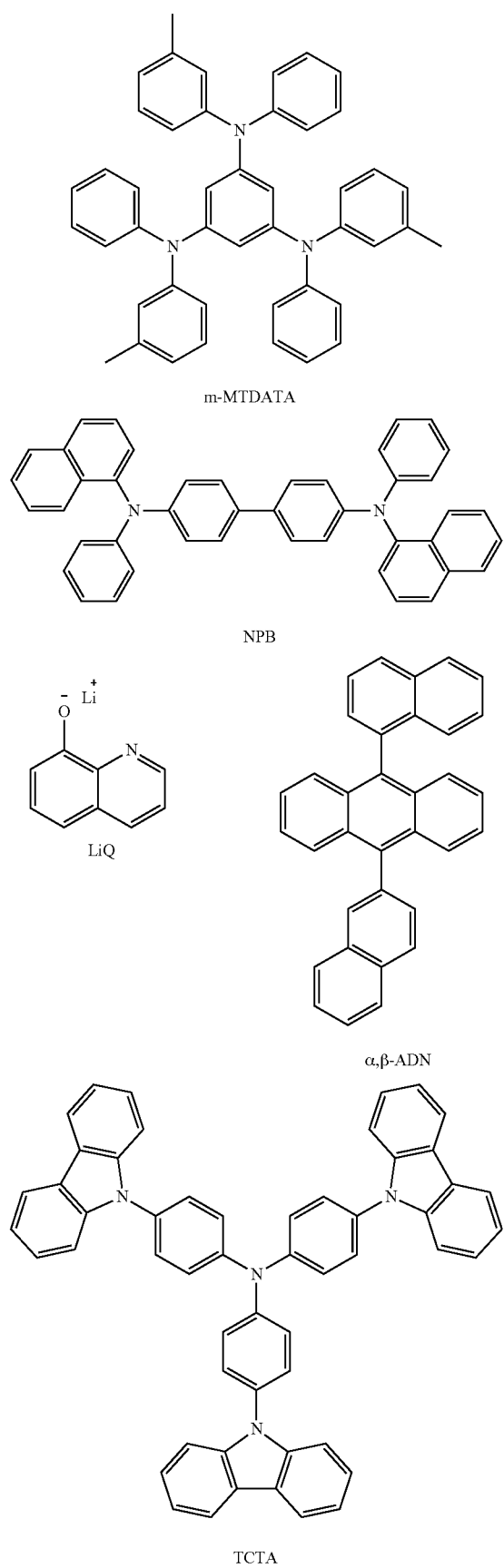

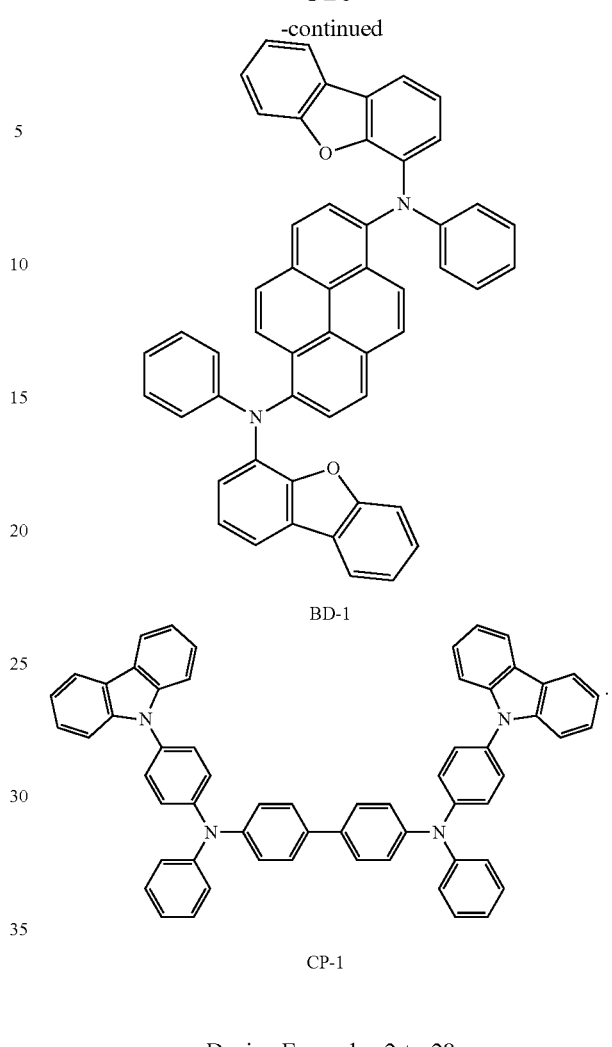

Device Examples 2 to 28

The organic electroluminescent devices were manufactured by a method the same as that in Example 1 except for using the compounds as shown in the table below respectively during the formation of an electron transport layer.

That is, the organic electroluminescent device was prepared in Example 2 using the compound 3; the organic electroluminescent device was prepared in Example 3 using the compound 4; the rest organic electroluminescent devices in Examples 4 to 28 were prepared according to the sequence of the compounds enumerated in Table 1; IVL (current, voltage, and luminance) and Lifetime (T95) data of the organic electroluminescent device will be enumerated in the Table one by one.

Device Comparative Examples 1 to 5

Comparative Example 1: the organic electroluminescent device was prepared by a method the same as that in Example 1 except for using the compound A (the structure was shown below) as an electron transport layer to replace the compound 1.

Comparative Example 2: the organic electroluminescent device was prepared by a method the same as that in Example 1 except for using the compound B (the structure was shown below) as an electron transport layer to replace the compound 1.

Comparative Example 3: the organic electroluminescent device was prepared by a method the same as that in Example 1 except for using the compound C (the structure was shown below) as an electron transport layer to replace the compound 1.

Comparative Example 4: the organic electroluminescent device was prepared by a method the same as that in Example 1 except for using the compound D (the structure was shown below) as an electron transport layer to replace the compound 1.

Comparative Example 5: the organic electroluminescent device was prepared by a method the same as that in Example 1 except for using the compound E (the structure was shown below) as an electron transport layer to replace the compound 1:

wherein, the compounds A, B, C, D, and E have the following structures:

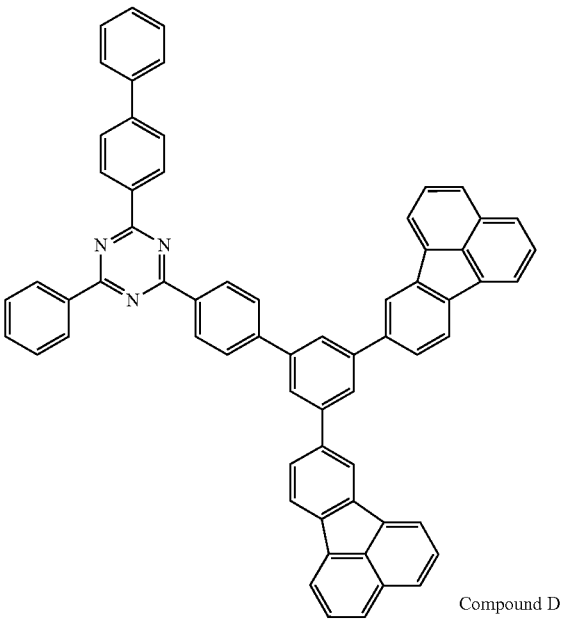

Compound C

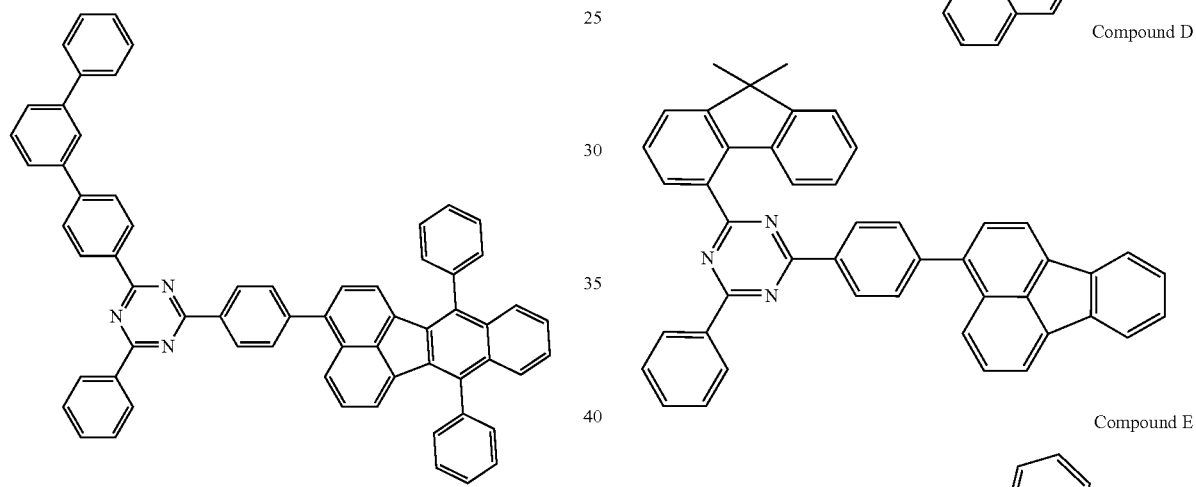

Compound A

Compound D

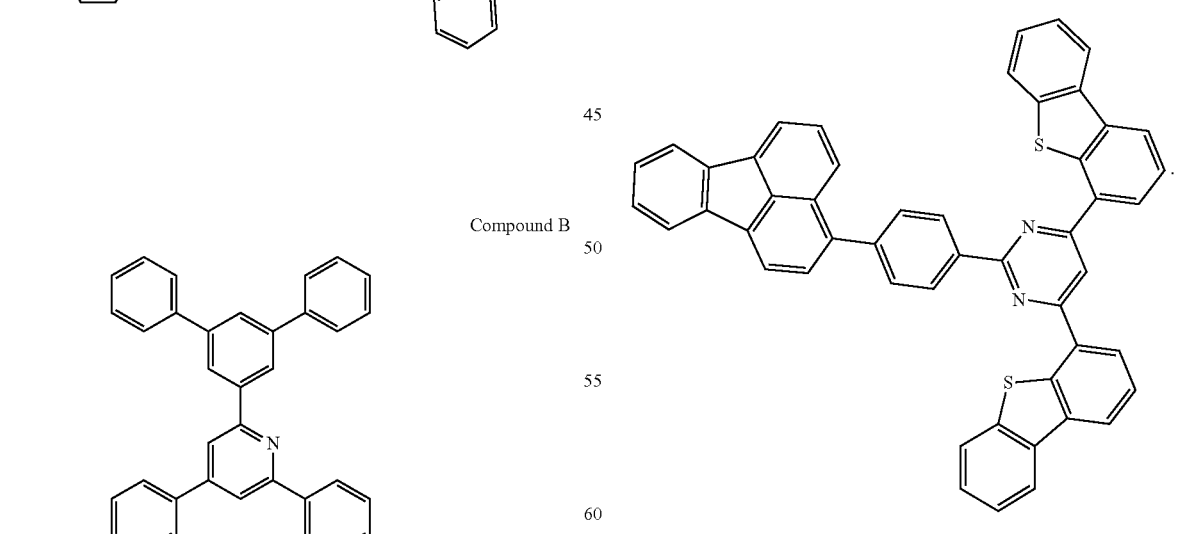

Compound B

Compound E

For the blue organic electroluminescent devices prepared in Device Examples 1 to 28 and Comparative Examples 1 to 5, IVL (current, voltage, and luminance) data comparison indicates the test results at 15 mA/cm$^2$; T95 lifetime is the test result at a current density of 20 mA/cm$^2$; and the specific performance comparison is specifically as shown in Table 5.

TABLE 5

Performance of organic electroluminescent devices in the Examples 1 to 28 and Comparative Examples 1 to 5

| Example | Compound | Working voltage Volt(V) | Luminous efficiency (Cd/A) | External quantum efficiency EQE (%) | T95 device lifetime (h) | Chromaticity coordinate CIEy |
|---|---|---|---|---|---|---|
| Example 1 | 1 | 3.81 | 6.4 | 12.4 | 144 | 0.050 |
| Example 2 | 3 | 3.83 | 6.8 | 13.1 | 146 | 0.050 |
| Example 3 | 4 | 3.81 | 6.6 | 12.7 | 149 | 0.050 |
| Example 4 | 34 | 3.85 | 6.7 | 12.9 | 139 | 0.050 |
| Example 5 | 49 | 3.84 | 6.6 | 12.7 | 145 | 0.050 |
| Example 6 | 113 | 3.83 | 6.8 | 13.1 | 152 | 0.050 |
| Example 7 | 130 | 3.80 | 6.7 | 13.0 | 142 | 0.050 |
| Example 8 | 38 | 3.78 | 6.6 | 12.7 | 152 | 0.050 |
| Example 9 | 115 | 3.74 | 6.6 | 12.7 | 152 | 0.050 |
| Example 10 | 132 | 3.80 | 6.8 | 13.1 | 151 | 0.050 |
| Example 11 | 161 | 3.75 | 6.7 | 13.0 | 151 | 0.050 |
| Example 12 | 171 | 3.81 | 6.4 | 12.4 | 139 | 0.050 |
| Example 13 | 209 | 3.77 | 6.8 | 13.1 | 142 | 0.050 |
| Example 14 | 219 | 3.76 | 6.7 | 12.9 | 141 | 0.050 |
| Example 15 | 33 | 3.82 | 6.4 | 12.4 | 140 | 0.050 |
| Example 16 | 39 | 3.77 | 6.8 | 13.2 | 149 | 0.050 |
| Example 17 | 348 | 3.79 | 6.6 | 12.8 | 150 | 0.050 |
| Example 18 | 355 | 3.80 | 6.5 | 12.6 | 148 | 0.050 |
| Example 19 | 391 | 3.75 | 6.6 | 12.7 | 151 | 0.049 |
| Example 20 | 392 | 3.79 | 6.8 | 13.1 | 155 | 0.050 |
| Example 21 | 359 | 3.76 | 6.8 | 13.1 | 156 | 0.050 |
| Example 22 | 361 | 3.80 | 6.4 | 12.4 | 149 | 0.048 |
| Example 23 | 367 | 3.75 | 6.7 | 13.0 | 152 | 0.050 |
| Example 24 | 376 | 3.74 | 6.7 | 12.9 | 146 | 0.049 |
| Example 25 | 249 | 3.78 | 6.2 | 12.8 | 120 | 0.050 |
| Example 26 | 292 | 3.75 | 6.1 | 12.6 | 122 | 0.050 |
| Example 27 | 325 | 3.85 | 6.0 | 12.7 | 119 | 0.049 |
| Example 28 | 231 | 3.82 | 6.5 | 12.7 | 142 | 0.048 |
| Comparative Example 1 | Compound A | 3.89 | 5.3 | 12.0 | 102 | 0.050 |
| Comparative Example 2 | Compound B | 3.90 | 5.1 | 11.4 | 98 | 0.050 |
| Comparative Example 3 | Compound C | 3.88 | 5.3 | 12.1 | 87 | 0.050 |
| Comparative Example 4 | Compound D | 3.90 | 5.3 | 12.1 | 102 | 0.050 |
| Comparative Example 5 | Compound E | 3.88 | 5.2 | 12.0 | 95 | 0.050 |

It can be seen from Table 5 that compared with the organic electroluminescent devices in Comparative Examples 1 to 5, the organic electroluminescent devices in Examples 1 to 28 have greatly improved performances, mainly reflected as follows: the devices in Examples 1 to 28 have a luminous efficiency of 6.0 to 6.8 Cd/A, while Comparative Examples 1 to 5 have a luminous efficiency of 5.1 to 5.3 Cd/A, that is, the luminous efficiency of the devices in Examples 1 to 28 increases by at least 13.2%; the T95 lifetime at current density of 20 mA/cm$^2$ of the devices in Examples 1 to 28 is up to 119~152 h, while the T95 lifetime in the Comparative Examples 1 to 5 is 87~102 h, that is, the T95 lifetime of the devices in Examples 1 to 28 increases by at least 16.67%.

Thus, it can be seen that the presence of fluoranthene in a compound improves the heat stability of the compound and prolongs the lifetime of the device; the presence of a nitrogen-containing heteroaromatic cyclic group and cyano improves the dipole moment of molecules, promotes electron transport efficiency and improves the electronic mobility of electron transport materials, thereby improving the luminous efficiency of the device and reducing the driving voltage of the device.

Therefore, the compound of the present disclosure may be applied in the electron transport layer of an organic electroluminescent device to significantly promote the organic electroluminescent efficiency and effectively extend the lifetime of the organic electroluminescent device.

Optional embodiments of the present disclosure are described with reference to the accompanying drawings, but the present disclosure is not limited to the specific details in the above embodiments. Various simple modifications may be made to the technical solution of the present disclosure within the scope of the technical idea of the present disclosure, and these fall within the protection scope of the present disclosure.

It should be additionally indicated that each specific technical feature described in the above specific embodiments may be combined with each other by any suitable way. For the purpose of avoiding unnecessary repetition, various possible ways of combination of the present disclosure will be not described any more.

Further, various different embodiments of the present disclosure may be also in any combination, and the combination shall be regarded as the disclosure of the present disclosure as long as it falls within the idea of the present disclosure.

What is claimed is:

1. An organic compound, wherein the organic compound has a structure as shown in the following Formula (1):

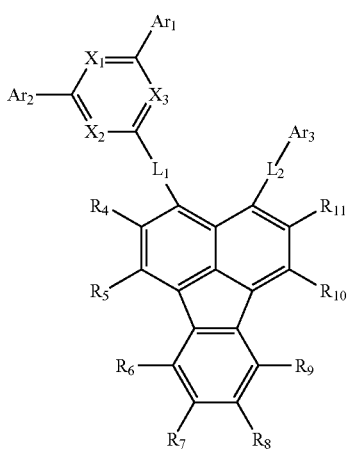

Formula (1)

wherein, $X_1$, $X_2$ and $X_3$ are the same or different; $X_1$ is $C(R^1)$ or N, $X_2$ is $C(R^2)$ or N, $X_3$ is $C(R^3)$ or N, and at least one of $X_1$, $X_2$ and $X_3$ is N;

$R^1$, $R^2$ and $R^3$ are the same as or different from each other, and are each independently selected from the group consisting of hydrogen, deuterium, fluorine, chlorine, alkyl with 1 to 12 carbon atoms, haloalkyl with 1 to 12 carbon atoms, alkoxy with 1 to 12 carbon atoms, cycloalkyl with 3 to 10 carbon atoms, aryl with 6 to 20 carbon atoms, and heteroaryl with 3 to 20 carbon atoms;

$L_1$ and $L_2$ are the same as or different from each other, and are each independently selected from the group consisting of a single bond, substituted or unsubstituted arylene with 6 to 30 carbon atoms, and substituted or unsubstituted heteroarylene with 1 to 30 carbon atoms;

$Ar_1$ and $Ar_2$ are the same as or different from each other, and are each independently selected from the group consisting of substituted or unsubstituted alkyl with 1 to 12 carbon atoms, substituted or unsubstituted cycloalkyl with 3 to 10 carbon atoms, substituted or unsubstituted aralkyl with 7 to 30 carbon atoms, substituted or unsubstituted heteroaralkyl with 2 to 30 carbon atoms, substituted or unsubstituted aryl with 6 to 30 carbon atoms, and substituted or unsubstituted heteroaryl with 3 to 30 carbon atoms;

wherein, $Ar_3$ is selected from the group consisting of substituted aryl with 6 to 30 carbon atoms, and substituted heteroaryl with 3 to 30 carbon atoms;

$R_4$ to $R_{11}$ are the same or different, and are each independently selected from the group consisting of hydrogen, deuterium, halogen, cyano, substituted or unsubstituted alkyl with 1 to 10 carbon atoms, substituted or unsubstituted alkenyl with 2 to 10 carbon atoms, haloalkyl with 1 to 12 carbon atoms, alkoxy with 1 to 12 carbon atoms, alkylthio with 1 to 12 carbon atoms, alkylsilyl with 1 to 12 carbon atoms, substituted or unsubstituted cycloalkyl with 3 to 20 carbon atoms, substituted or unsubstituted heterocycloalkyl with 3 to 20 carbon atoms, alkylamino with 1 to 12 carbon atoms, aryl with 6 to 30 carbon atoms and heteroaryl with 1 to 30 carbon atoms;

substituents in $L_1$, $L_2$, $Ar_1$, $Ar_2$, $Ar_3$ and $R_4$ to $R_1$ are the same as or different from each other, and are each independently selected from the group consisting of deuterium; halogen; cyano; alkyl with 1 to 10 carbon atoms; haloalkyl with 1 to 10 carbon atoms; aryl with 6 to 20 carbon atoms, which can be optionally substituted by 0, 1, 2 or 3 substituents selected from deuterium, fluorine, chlorine, bromine, cyano, alkyl with 1 to 5 carbon atoms, aryl with 6 to 12 carbon atoms and heteroaryl with 5 to 12 carbon atoms; heteroaryl with 3 to 20 carbon atoms, which can be optionally substituted by 0, 1, 2 or 3 substituents selected from deuterium, fluorine, chlorine, bromine, cyano, alkyl with 1 to 5 carbon atoms, aryl with 6 to 12 carbon atoms and heteroaryl with 5 to 12 carbon atoms; aryloxy with 6 to 20 carbon atoms; arylthio with 6 to 20 carbon atoms; alkylsilyl with 3 to 12 carbon atoms; alkylamino with 1 to 10 carbon atoms and cycloalkyl with 3 to 10 carbon atoms; and at least one of substituents of the $Ar_3$ is cyano; optionally, any two adjacent substituents form a ring.

2. The organic compound according to claim 1, wherein the substituents in $L_1$, $L_2$, $Ar_1$, $Ar_2$, $Ar_3$ and $R_4$ to Ru are the same as or different from each other, and are each independently selected from the group consisting of deuterium, halogen; cyano, alkyl with 1 to 10 carbon atoms, haloalkyl with 1 to 10 carbon atoms, aryl with 6 to 20 carbon atoms, heteroaryl with 3 to 20 carbon atoms, aryloxy with 6 to 20 carbon atoms, arylthio with 6 to 20 carbon atoms, alkylsilyl with 3 to 12 carbon atoms, alkylamino with 1 to 10 carbon atoms and cycloalkyl with 3 to 10 carbon atoms; and at least one of substituents in the $Ar_3$ is cyano.

3. The organic compound according to claim 1, wherein $Ar_1$, $Ar_2$, and $Ar_3$ are the same as or different from each other, and are each independently selected from the group consisting of substituted or unsubstituted aryl with 6 to 25 carbon atoms, substituted or unsubstituted heteroaryl with 3 to 18 carbon atoms; and the substituents in the $Ar_1$, $Ar_2$, and $Ar_3$ are the same as or different from each other, and are each independently selected from the group consisting of deuterium, fluorine, chlorine, bromine, cyano, alkyl with 1 to 10 carbon atoms, haloalkyl with 1 to 10 carbon atoms, alkoxy with 1 to 10 carbon atoms, alkylthio with 1 to 10 carbon atoms, aryl with 6 to 20 carbon atoms, heteroaryl with 3 to 20 carbon atoms, aryloxy with 6 to 20 carbon atoms, arylthio with 6 to 20 carbon atoms, alkylsilyl with 3 to 12 carbon atoms, alkylamino with 1 to 10 carbon atoms and cycloalkyl with 3 to 10 carbon atoms; and the $Ar_3$ is substituted by at least one cyano.

4. The organic compound according to claim 1, wherein the $Ar_1$ and $Ar_2$ are the same as or different from each other, and are each independently selected from a substituted or unsubstituted group $Y_1$; and the group $Y_1$ is selected from the following groups:

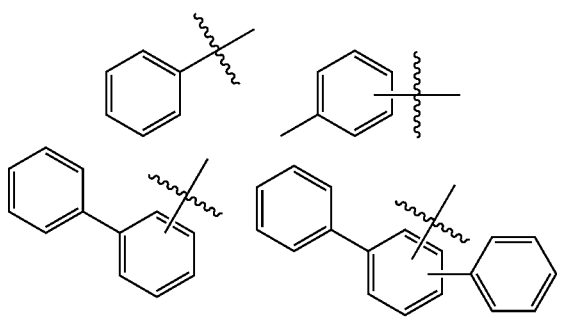

317
-continued
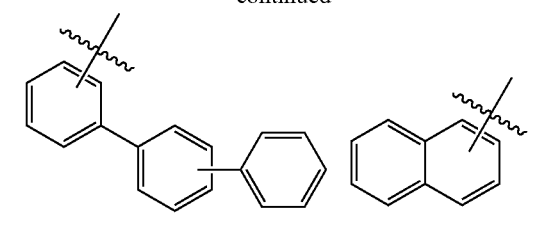
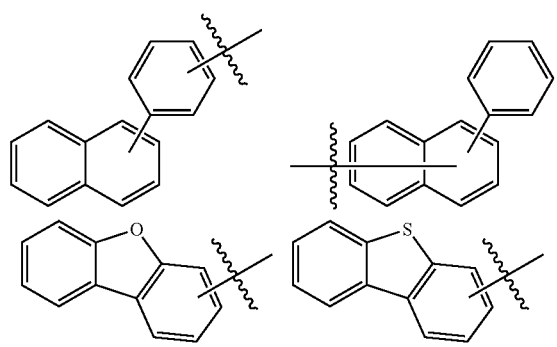
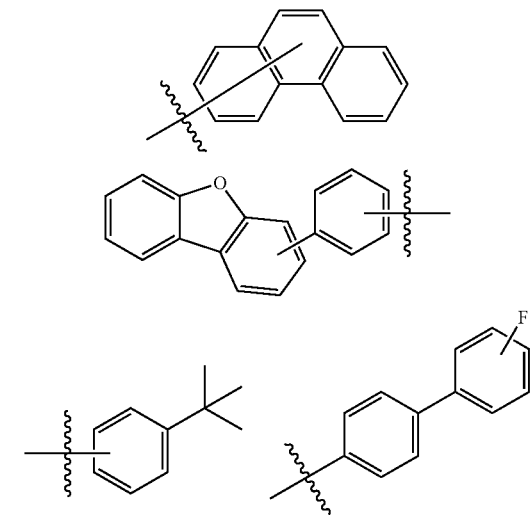
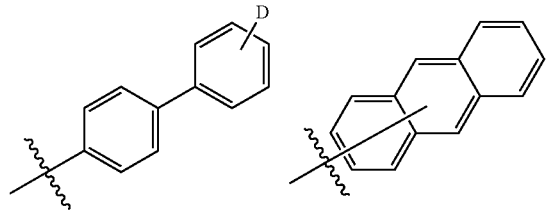
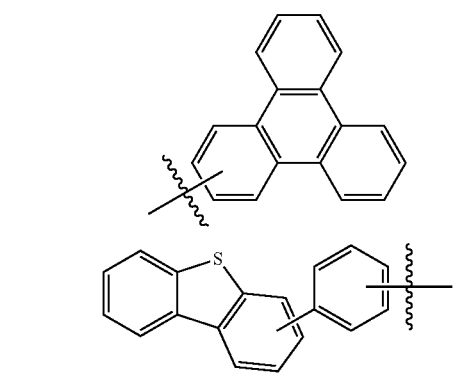
318
-continued
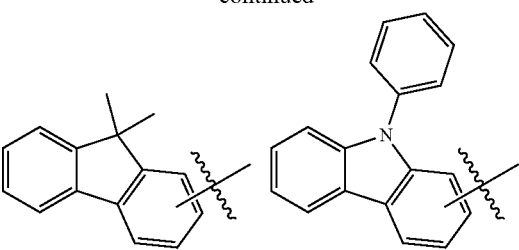
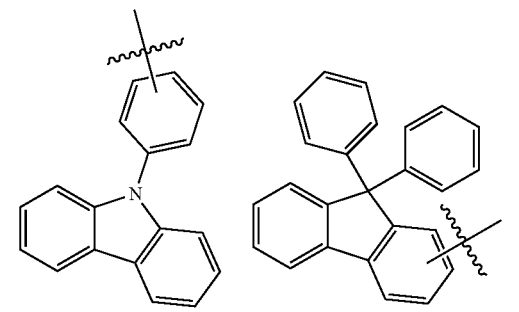
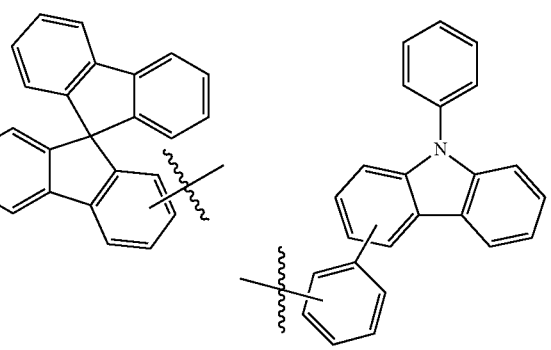
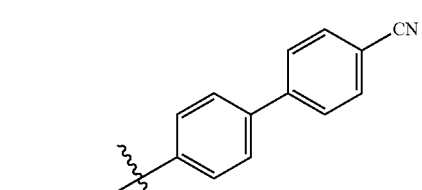
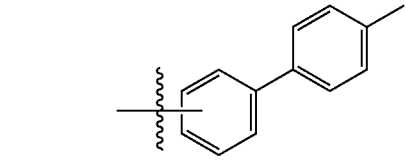
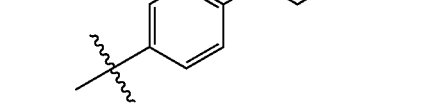

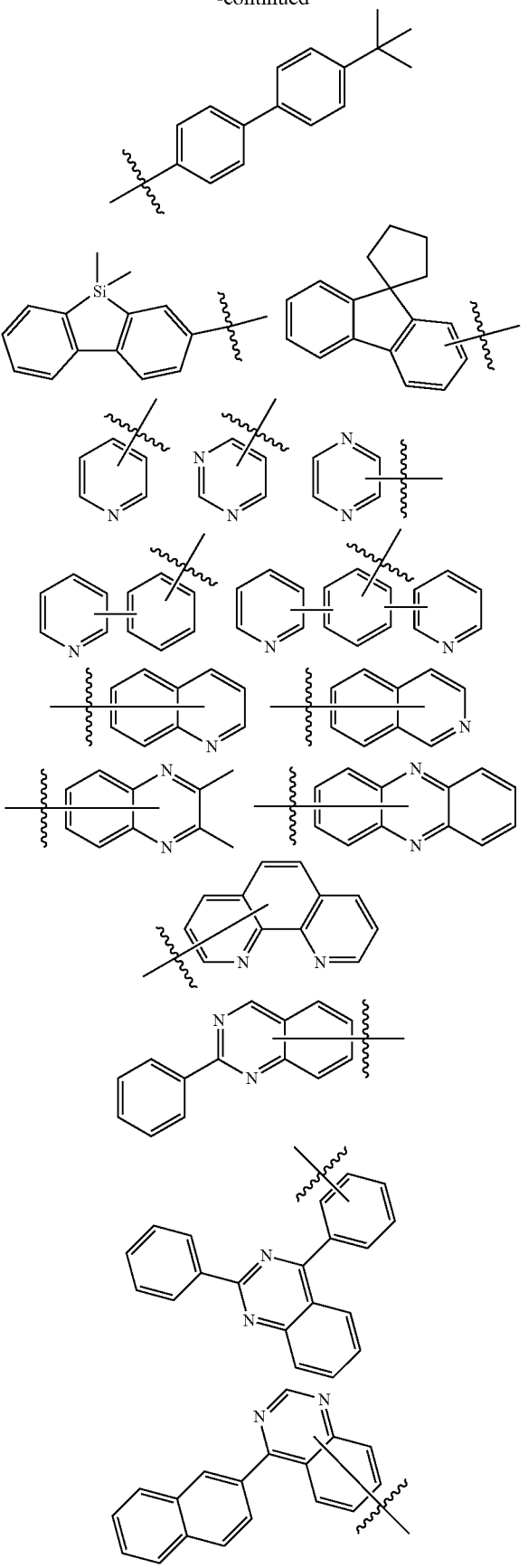
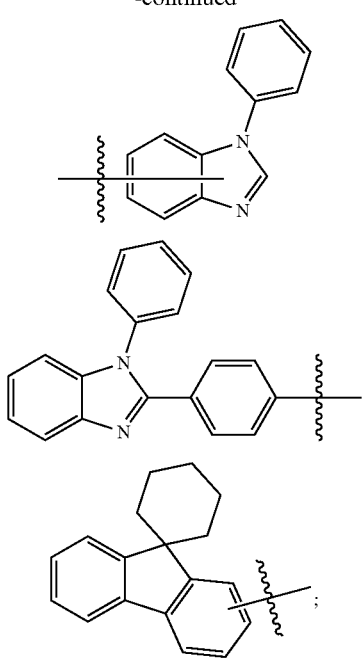
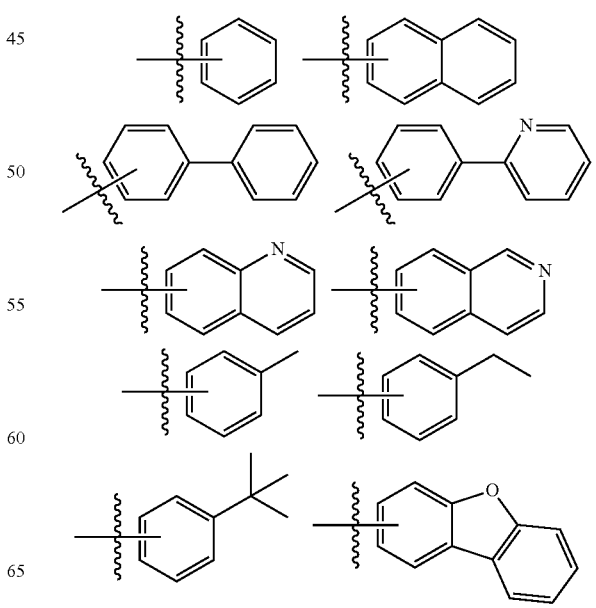

when the group $Y_1$ is substituted, the substituent of the $Y_1$ is selected from deuterium, fluorine, chlorine, bromine, cyano, alkyl with 1 to 4 carbon atoms, alkoxy with 1 to 4 carbon atoms, haloalkyl with 1 to 4 carbon atoms, alkylsilyl with 3 to 9 carbon atoms, cycloalkyl with 3 to 10 carbon atoms, aryl with 6 to 12 carbon atoms, and heteroaryl with 3 to 12 carbon atoms; when the $Y_1$ has a plurality of substituents, the plurality of the substituents are the same or different.

5. The organic compound according to claim 1, wherein the $Ar_1$ and $Ar_2$ are the same as or different from each other, and are each independently selected from the following groups:

321
-continued
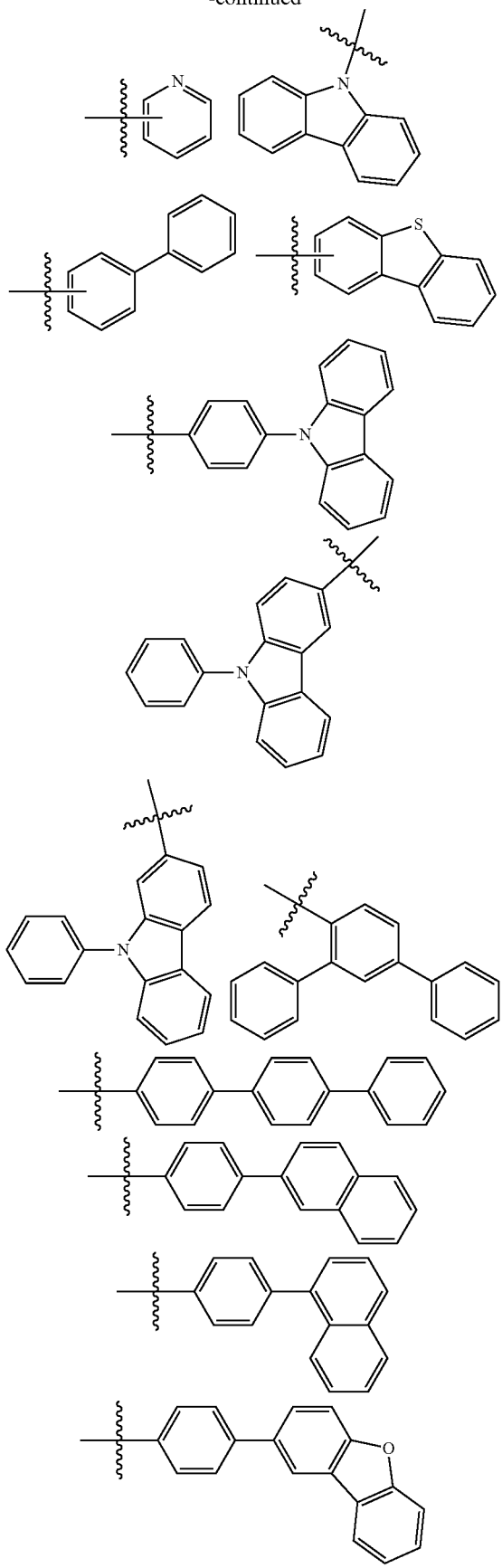
322
-continued
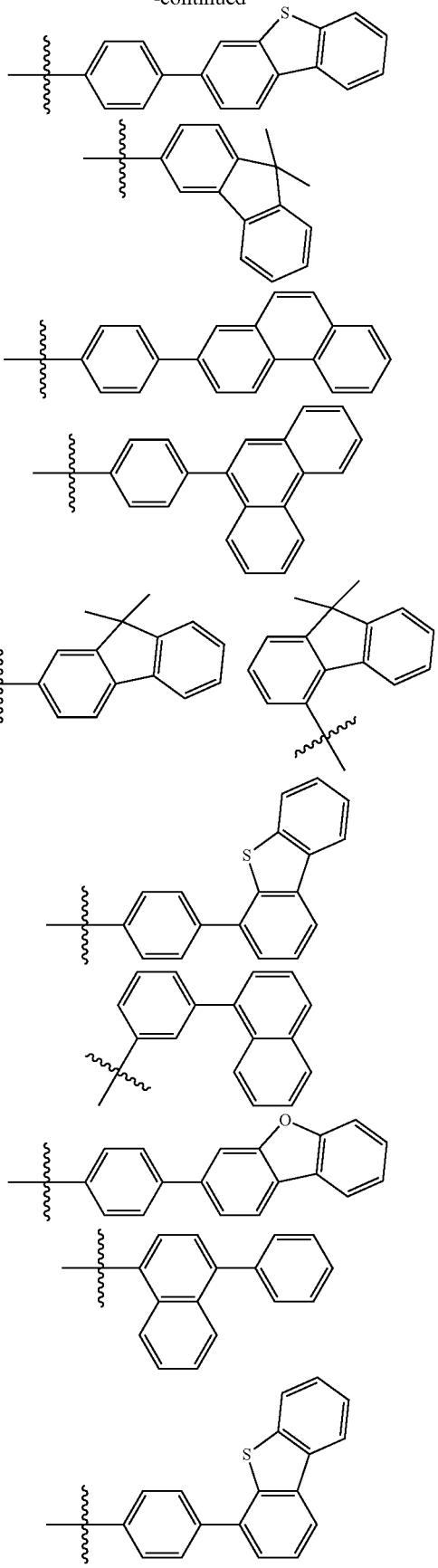

-continued
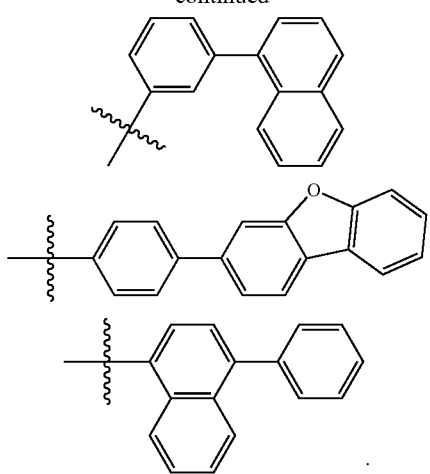
6. The organic compound according to claim 1, wherein the $Ar_3$ is selected from a substituted or unsubstituted group $Z_1$; and the group $Z_1$ is selected from the following the groups:
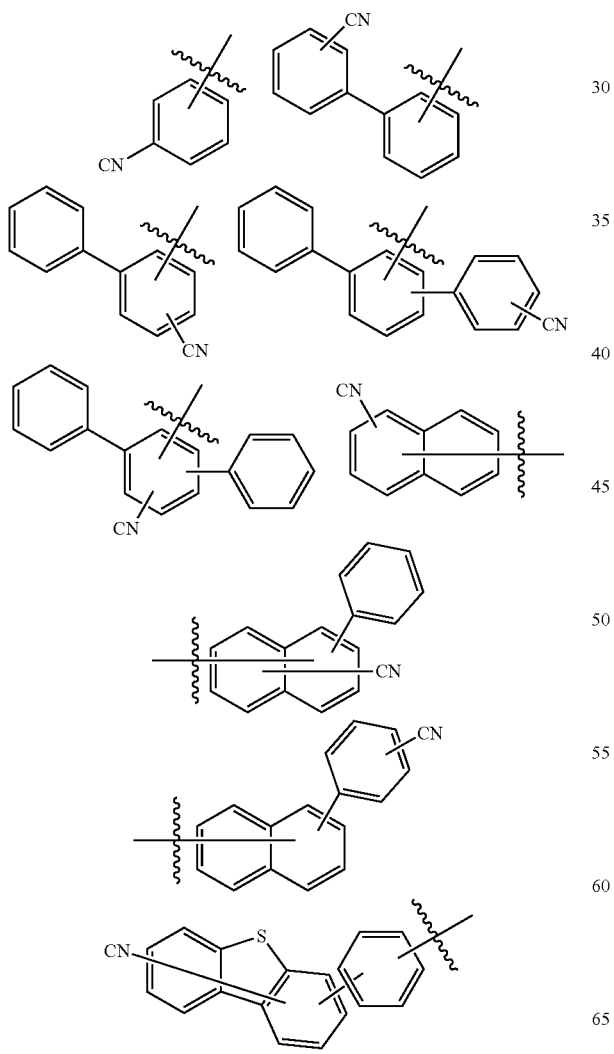
-continued
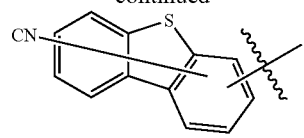
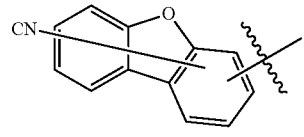
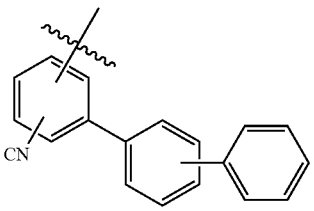
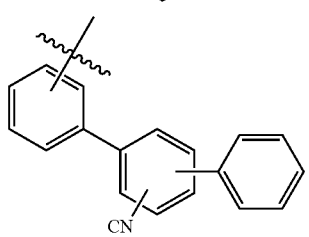
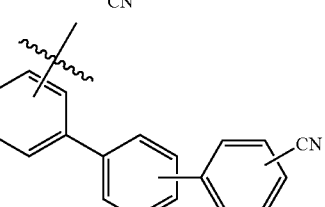
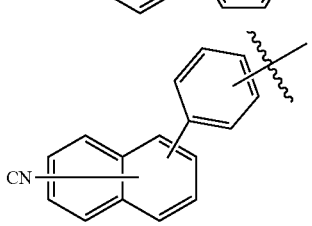
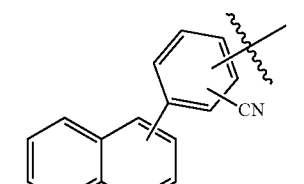
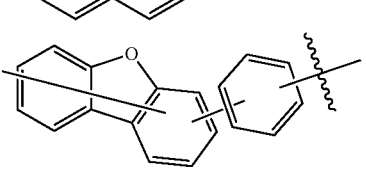
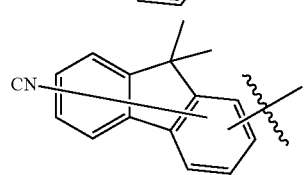

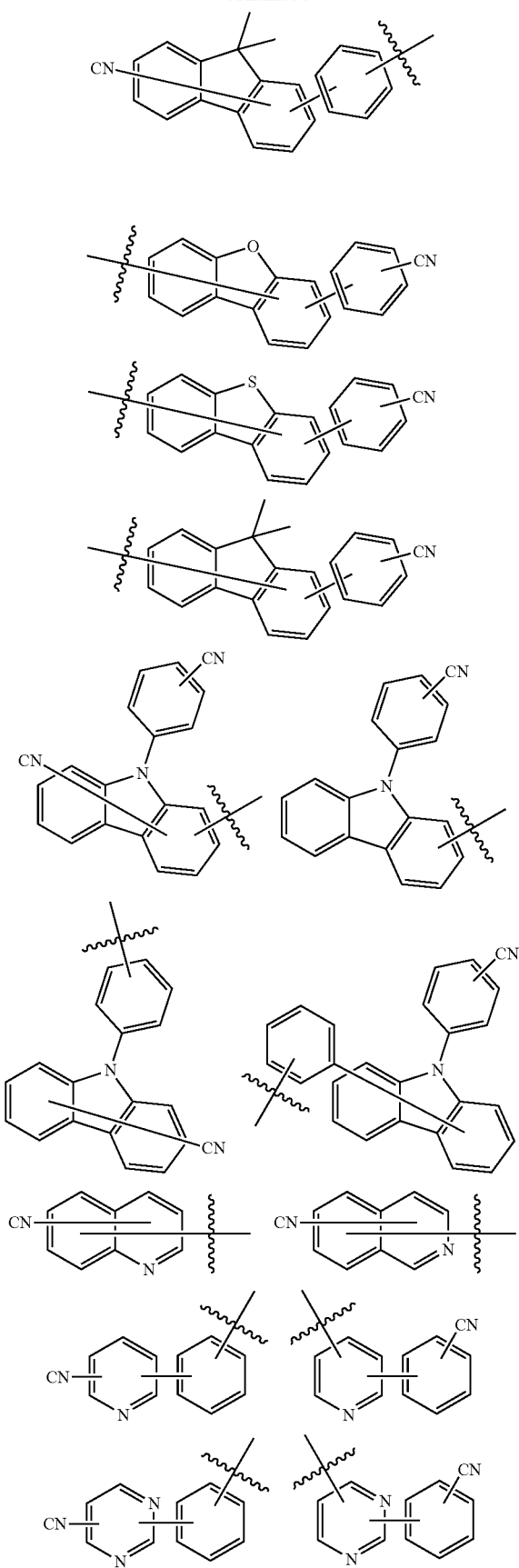
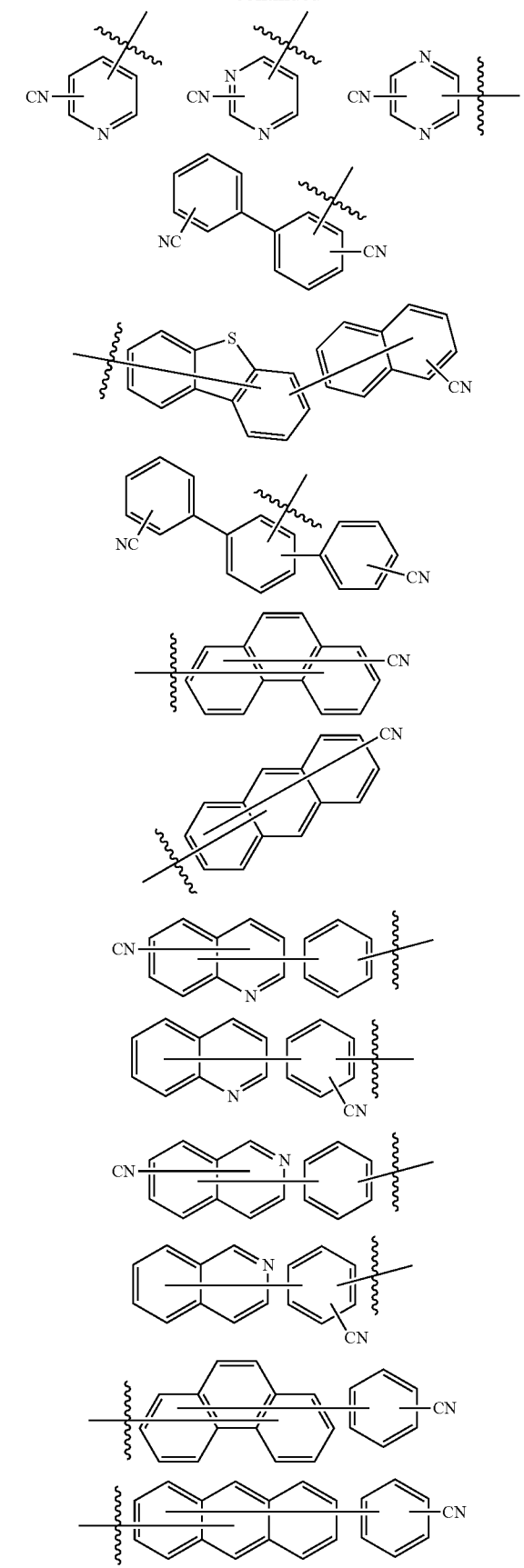

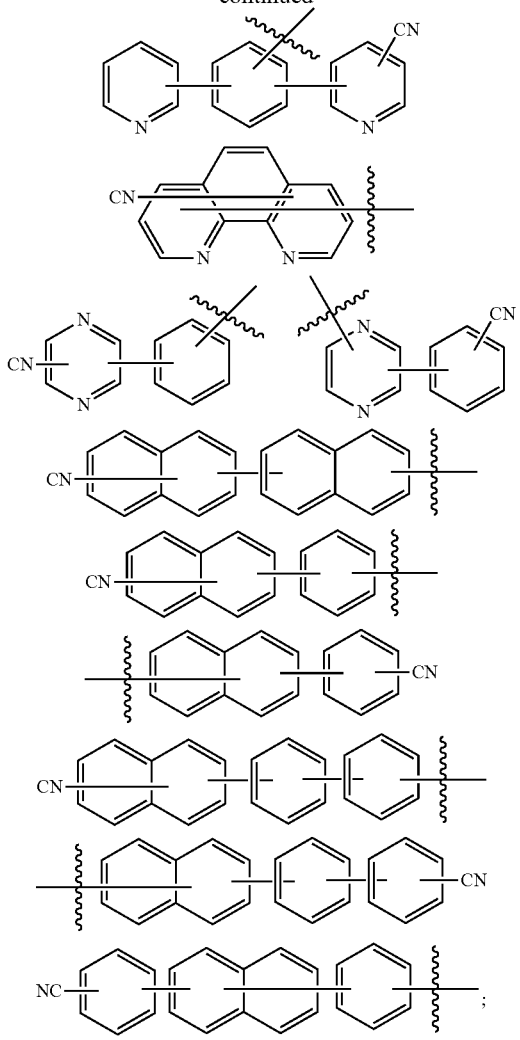

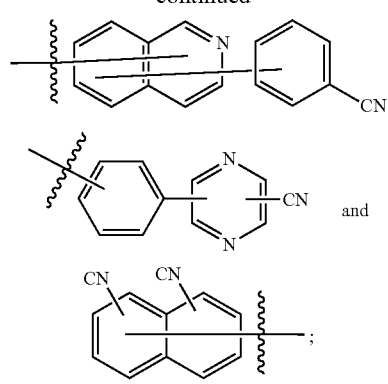

when the group $Z_1$ is substituted, the substituent of the $Z_1$ is selected from deuterium, fluorine, chlorine, bromine, cyano, alkyl with 1 to 4 carbon atoms, alkoxy with 1 to 4 carbon atoms, haloalkyl with 1 to 4 carbon atoms, alkylsilyl with 3 to 9 carbon atoms, cycloalkyl with 3 to 10 carbon atoms, aryl with 6 to 12 carbon atoms, and heteroaryl with 3 to 12 carbon atoms; when the $Z_1$ has a plurality of substituents, the plurality of the substituents are the same or different.

7. The organic compound according to claim 1, wherein the $Ar_3$ is selected from a substituted or unsubstituted group $Z_2$; and the group $Z_2$ is selected from the following groups:

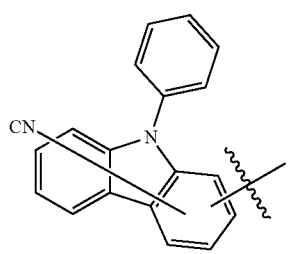

when the group $Z_2$ is substituted, the substituent of the $Z_2$ is selected from deuterium, fluorine, chlorine, bromine, cyano, alkyl with 1 to 4 carbon atoms, alkoxy with 1 to 4 carbon atoms, haloalkyl with 1 to 4 carbon atoms, alkylsilyl with 3 to 9 carbon atoms, cycloalkyl with 3 to 10 carbon atoms, aryl with 6 to 12 carbon atoms, and heteroaryl with 3 to 12 carbon atoms; when the $Z_2$ has a plurality of substituents, the plurality of the substituents are the same or different.

8. The organic compound according to claim 1, wherein the $Ar_3$ is selected from the following groups:

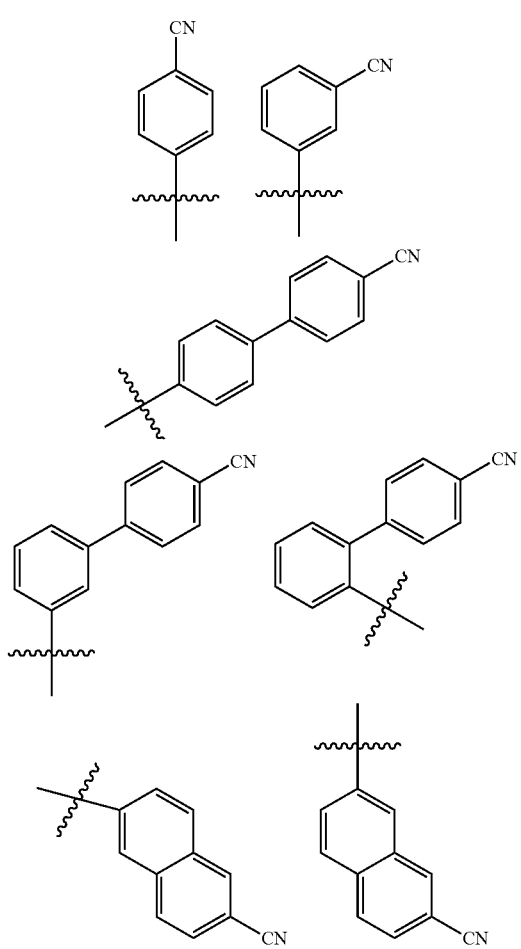

329
-continued
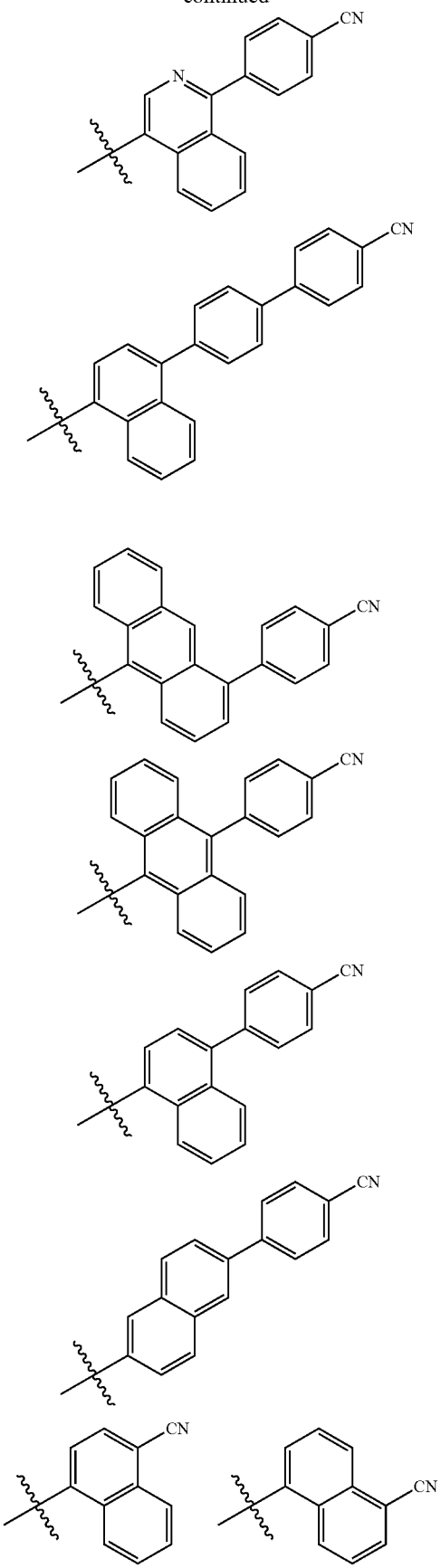
330
-continued
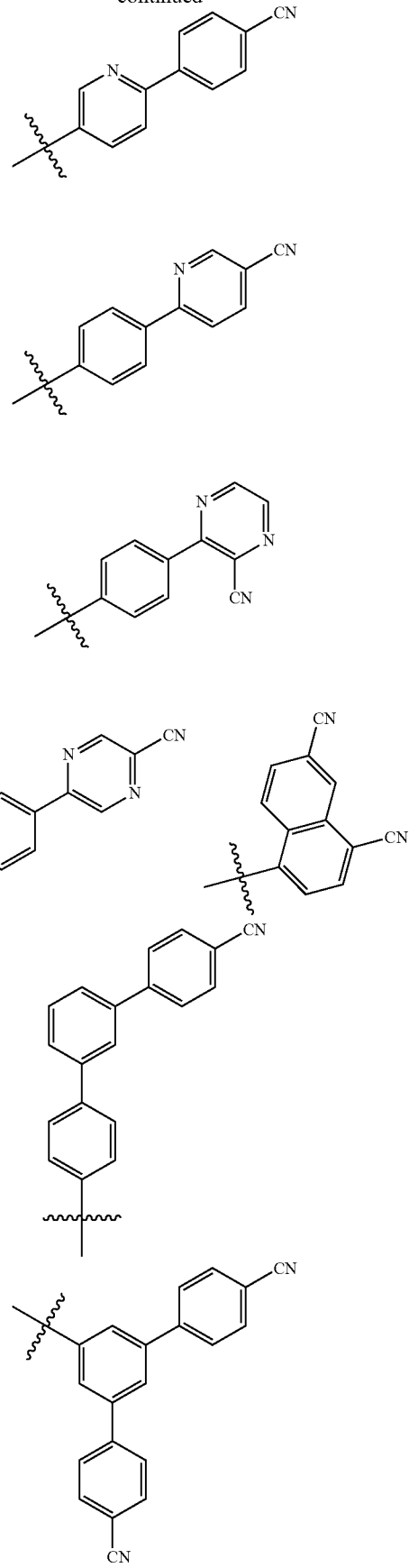

331
-continued
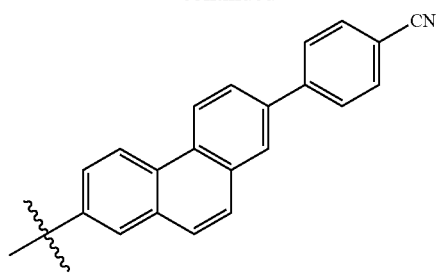
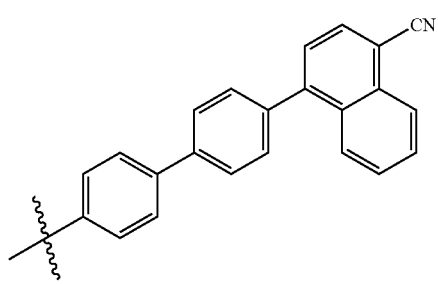
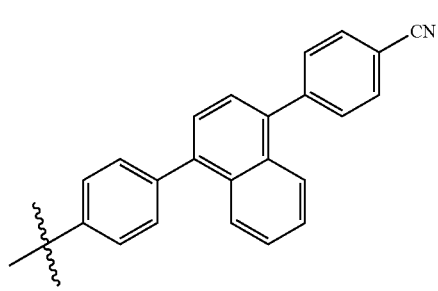
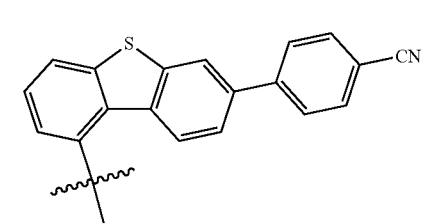
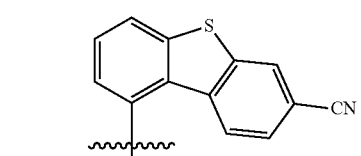
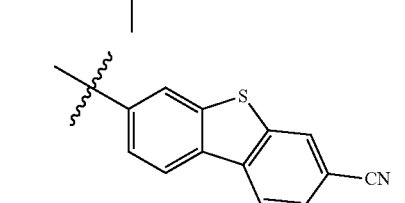
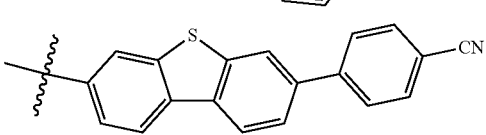
332
-continued
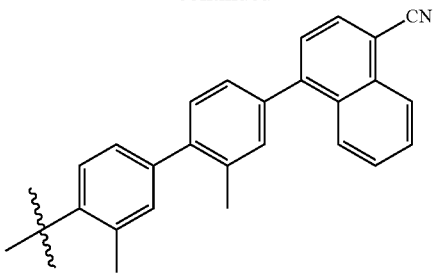
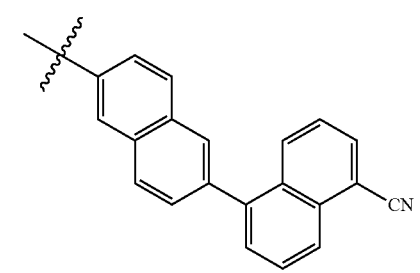
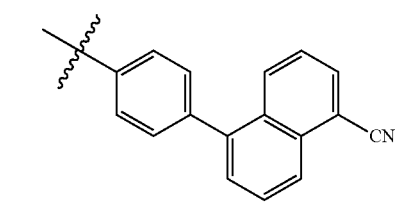
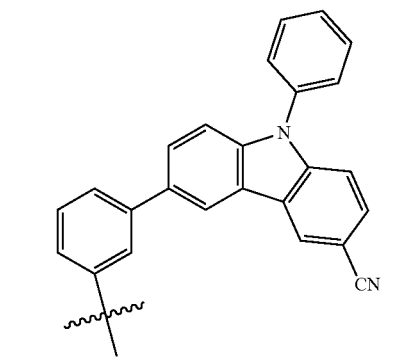
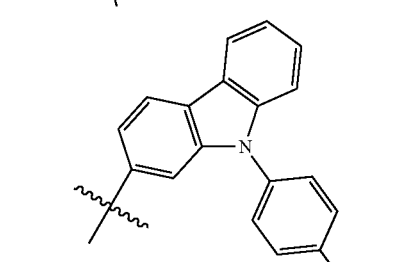
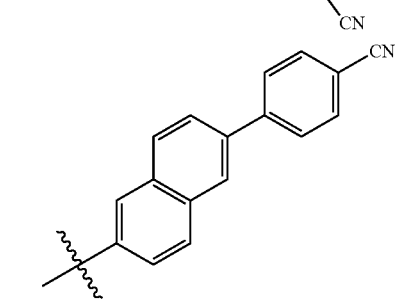

333
-continued
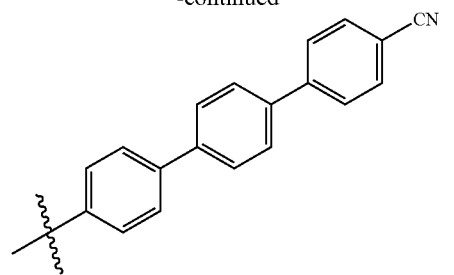
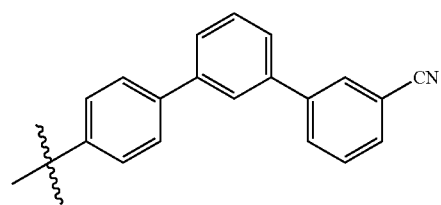
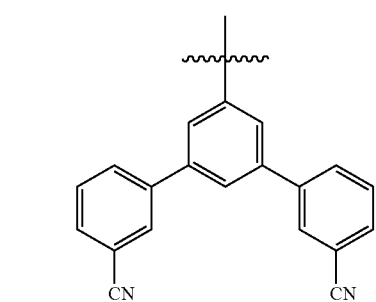
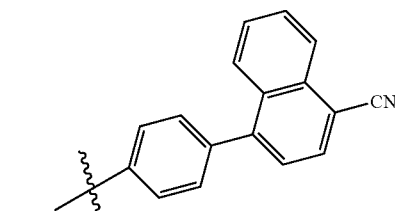
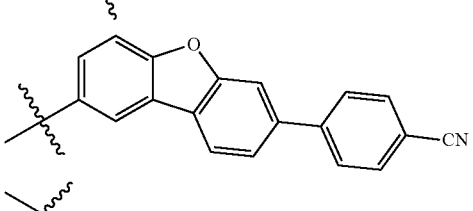
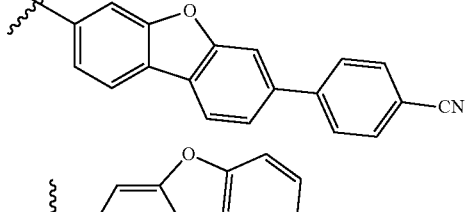
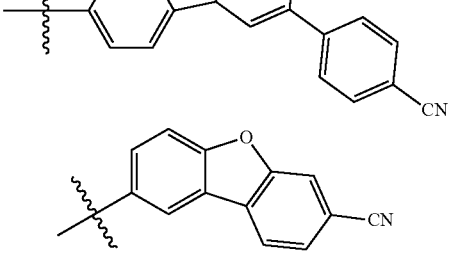
334
-continued
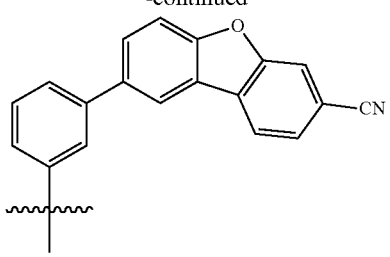
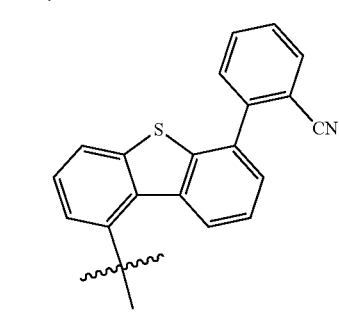
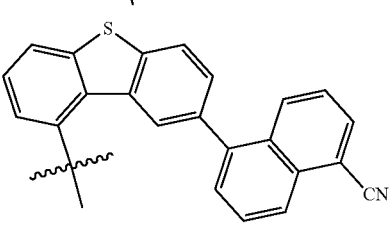
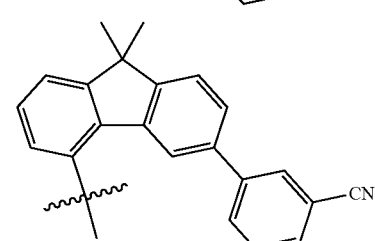
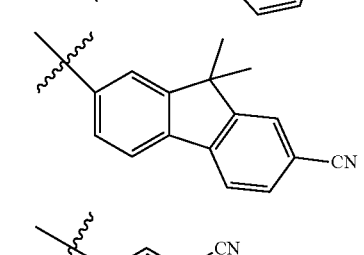
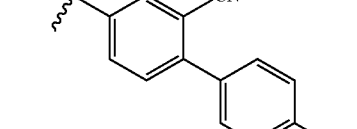
9. The organic compound according to claim 1, wherein the $Ar_3$ is selected from the following groups:
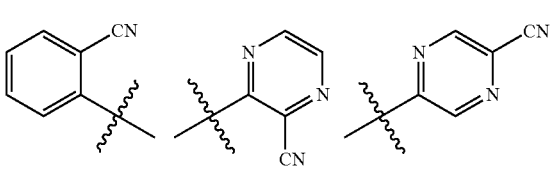

-continued

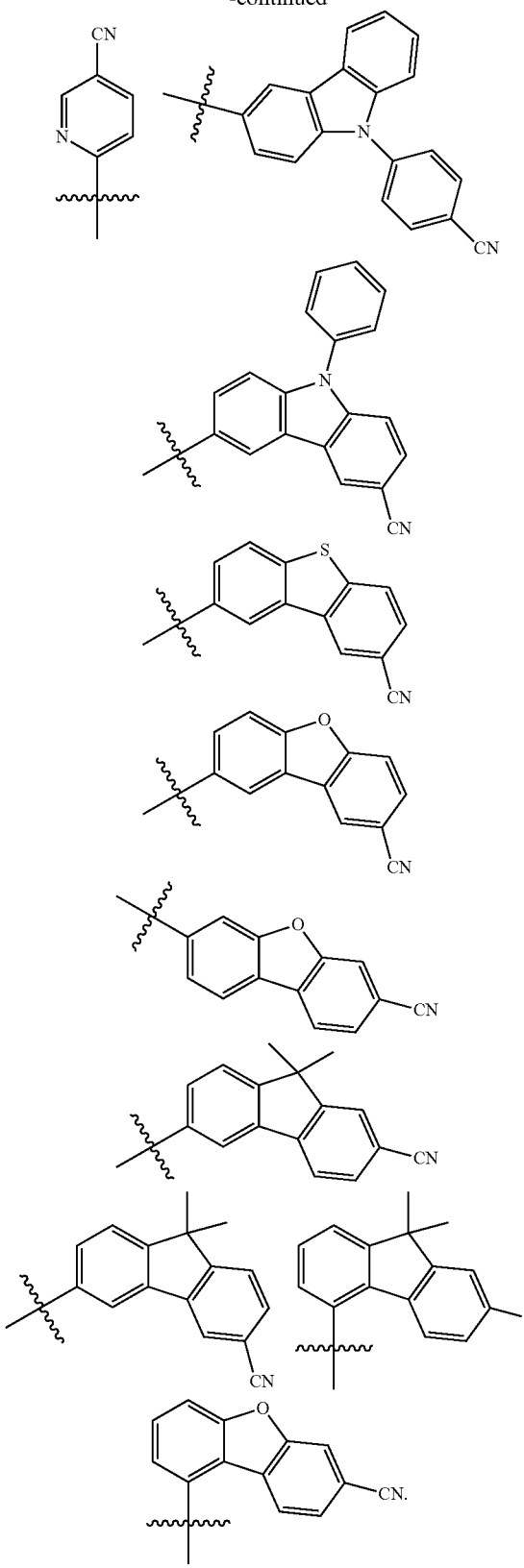

10. The organic compound according to claim 1, wherein the $L_1$ and $L_2$ are the same as or different from each other, and are each independently selected from the group consisting of single bond, substituted or unsubstituted arylene with 6 to 25 carbon atoms, and substituted or unsubstituted heteroarylene with 1 to 18 carbon atoms; the substituents in the $L_1$ and $L_2$ are the same as or different from each other, and are each independently selected from the group consisting of deuterium, halogen, cyano, alkyl with 1 to 6 carbon atoms, haloalkyl with 1 to 6 carbon atoms, aryl with 6 to 15 carbon atoms, heteroaryl with 3 to 15 carbon atoms, aryloxy with 6 to 12 carbon atoms, arylthio with 6 to 12 carbon atoms, alkylsilyl with 3 to 8 carbon atoms, alkylamino with 1 to 6 carbon atoms and cycloalkyl with 3 to 8 carbon atoms; and the $Ar_3$ is substituted by at least one cyano.

11. The organic compound according to claim 1, wherein the $L_1$ and $L_2$ are the same or different, and are each independently selected from a single bond, or selected from the group consisting of substituted or unsubstituted group $W_1$; and the group $W_1$ is selected from the group consisting of the following groups:

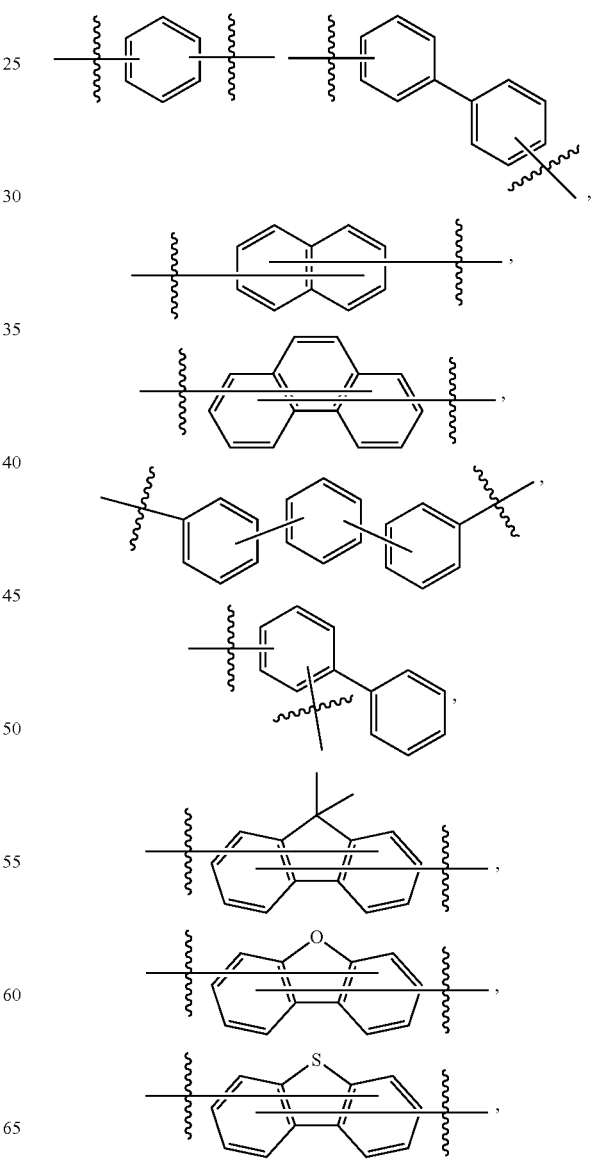

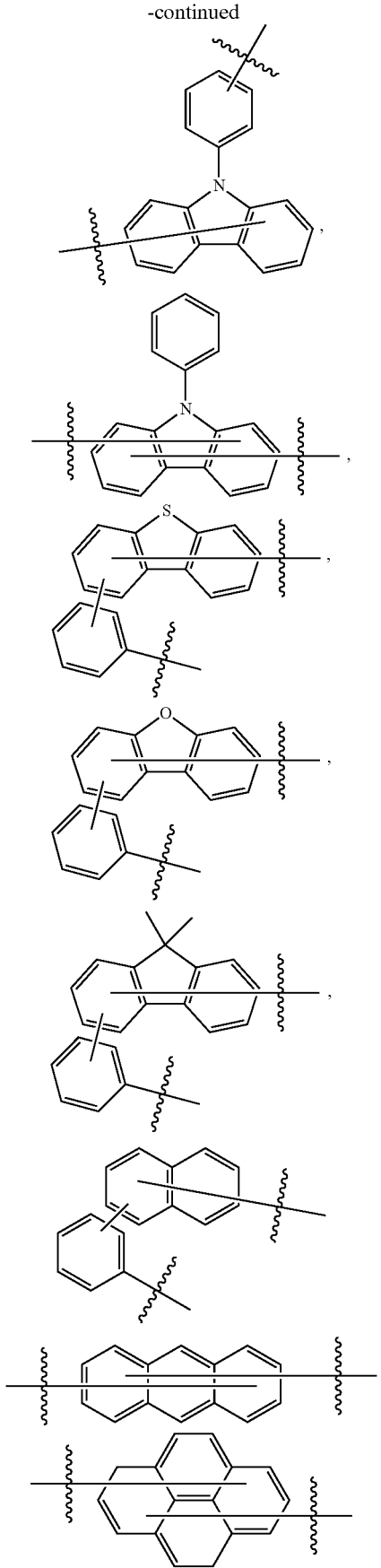
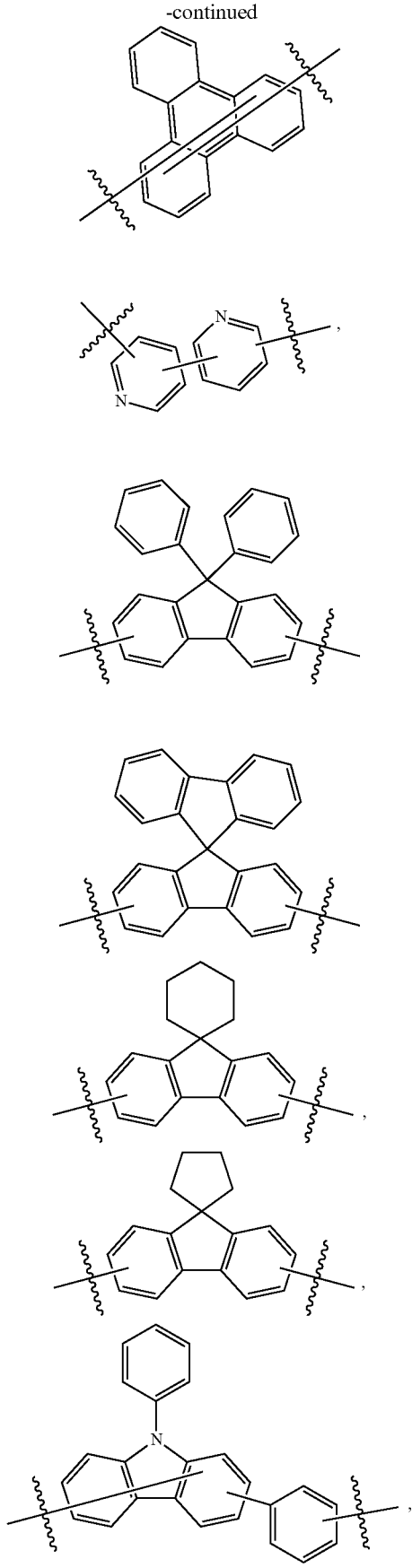

339
-continued

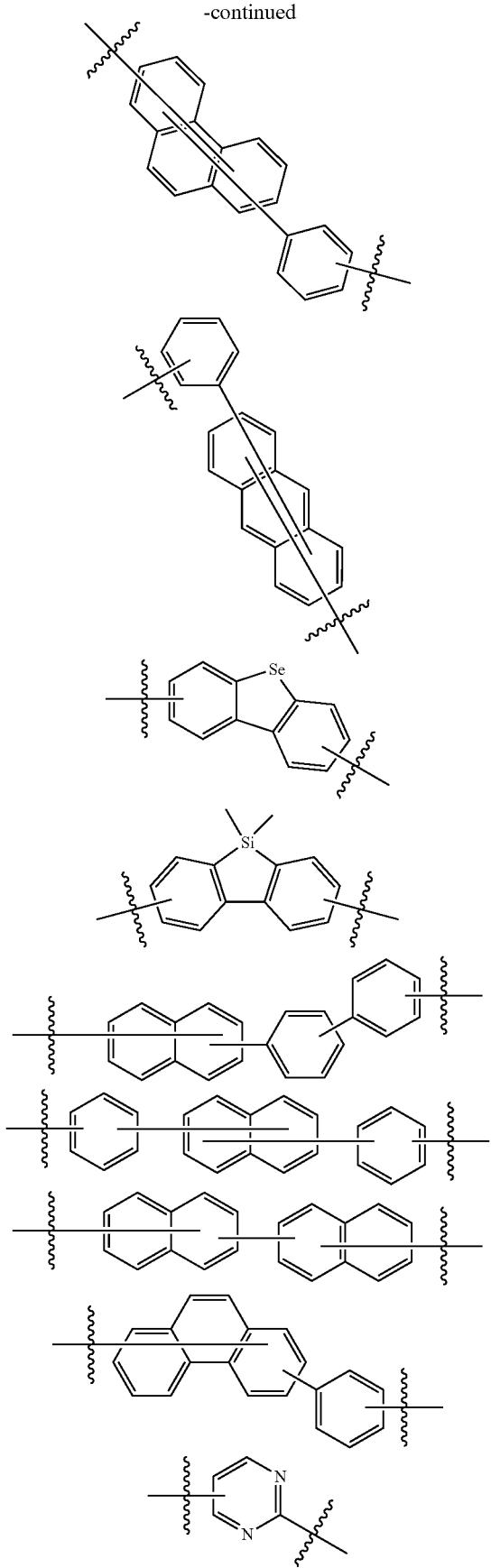

340
-continued

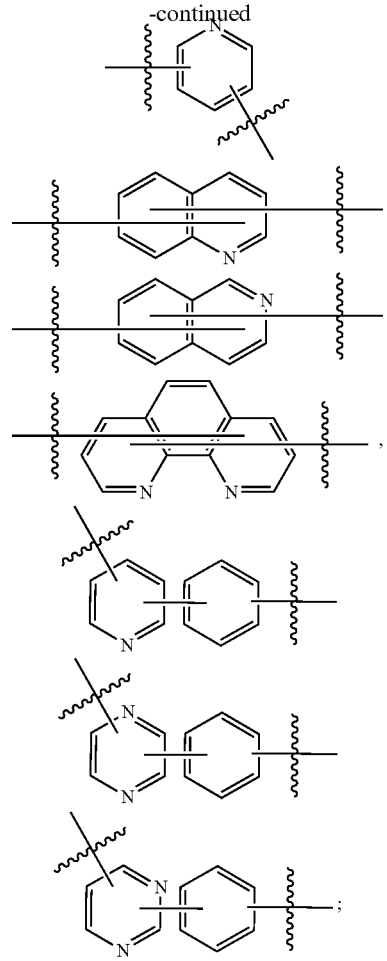

when the group $W_1$ is substituted, substituent of the $W_1$ is selected from the group consisting of deuterium, fluorine, chlorine, bromine, cyano, alkyl with 1 to 6 carbon atoms, alkoxy with 1 to 4 carbon atoms, haloalkyl with 1 to 4 carbon atoms, alkylsilyl with 3 to 9 carbon atoms, cycloalkyl with 3 to 10 carbon atoms, aryl with 6 to 13 carbon atoms, and heteroaryl with 3 to 12 carbon atoms; when the $W_1$ has a plurality of substituents, the plurality of the substituents are the same or different.

12. The organic compound according to claim 1, wherein the $L_1$ and $L_2$ are the same or different, and are each independently selected from a substituted or unsubstituted group $W_2$; the unsubstituted group $W_2$ has a structure shown

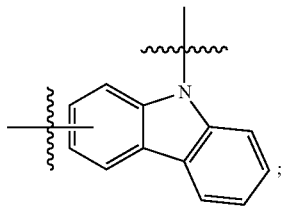

and the substituted group $W_2$ is optionally substituted by 1, 2, or 3 groups selected from deuterium, fluorine, chlorine, bromine, cyano, and alkyl with 1 to 4 carbon atoms.

13. The organic compound according to claim 1, wherein the $L_1$ and $L_2$ are the same or different, and are each independently selected from a single bond, or selected from the group consisting of the following groups:
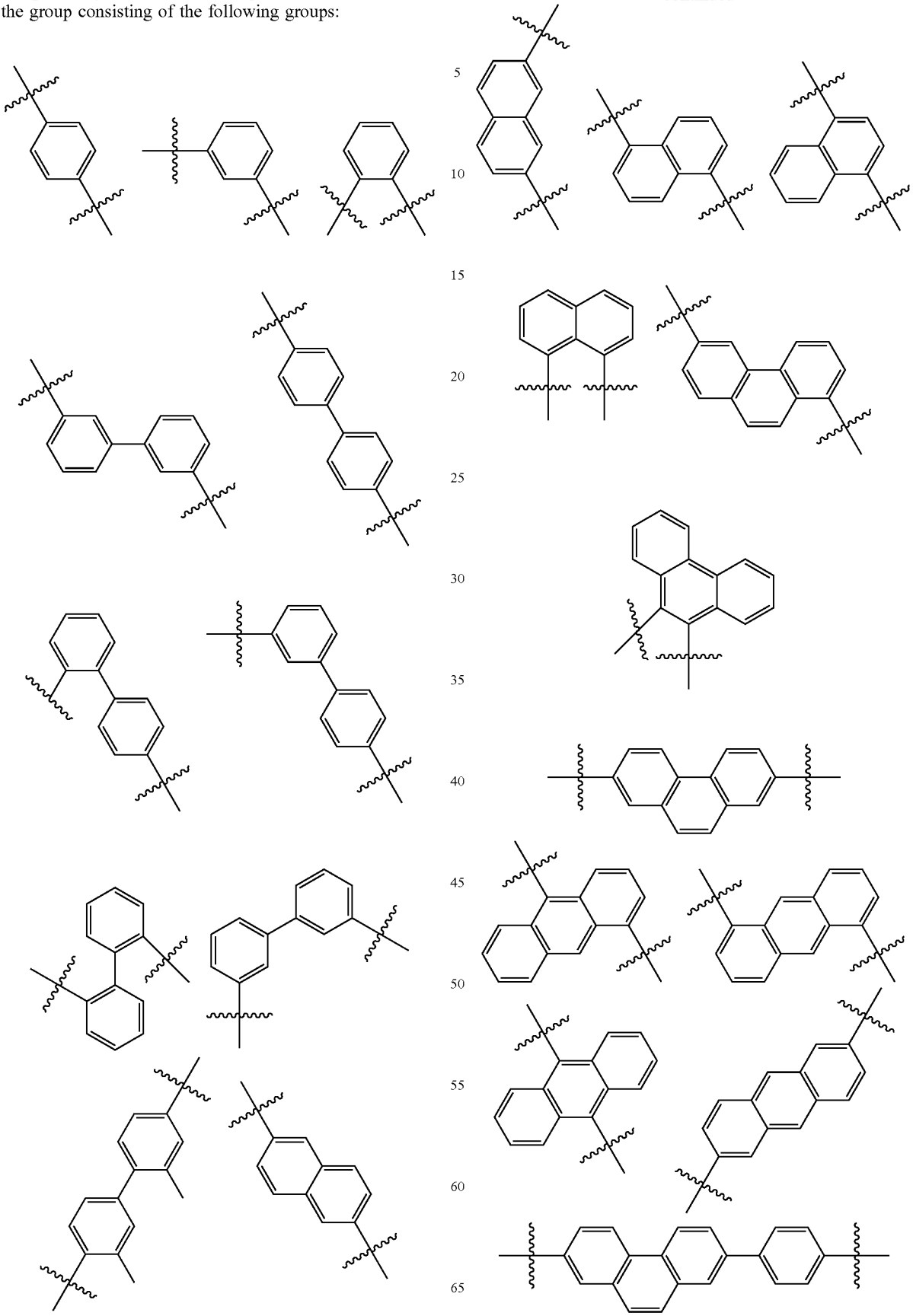

343
-continued
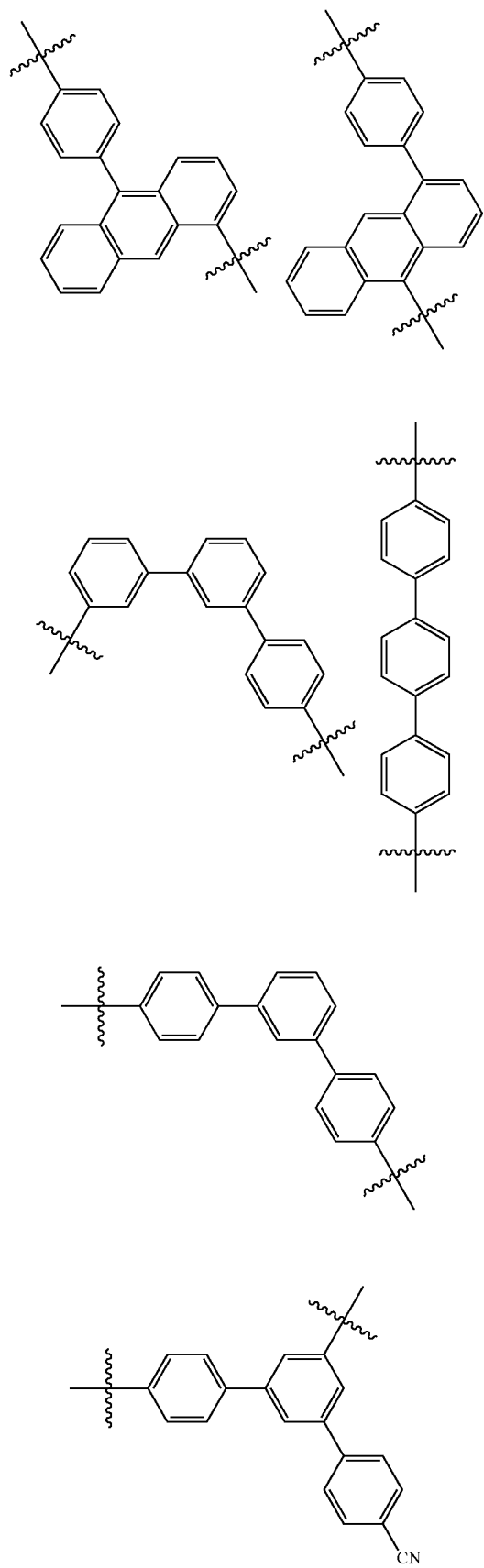
344
-continued
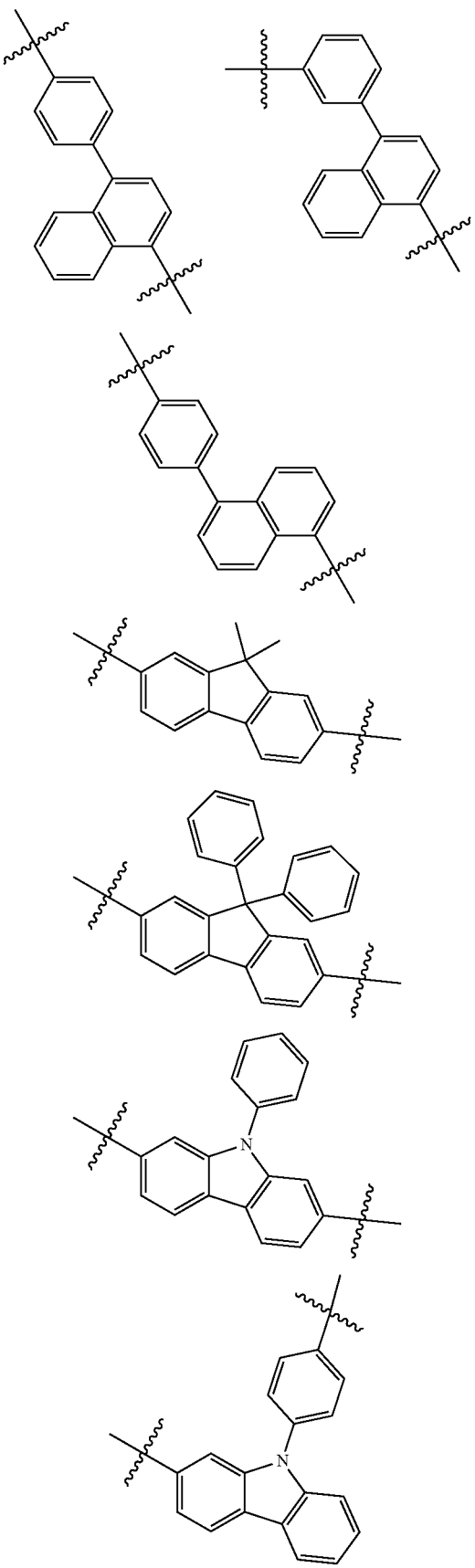

345
-continued
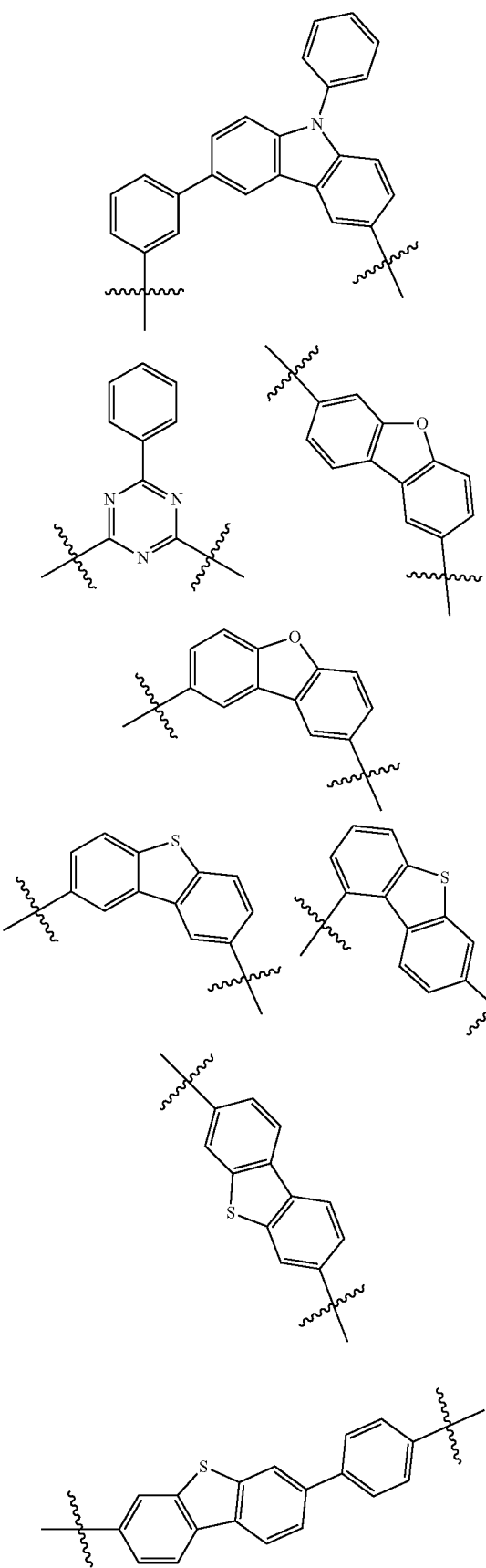
346
-continued
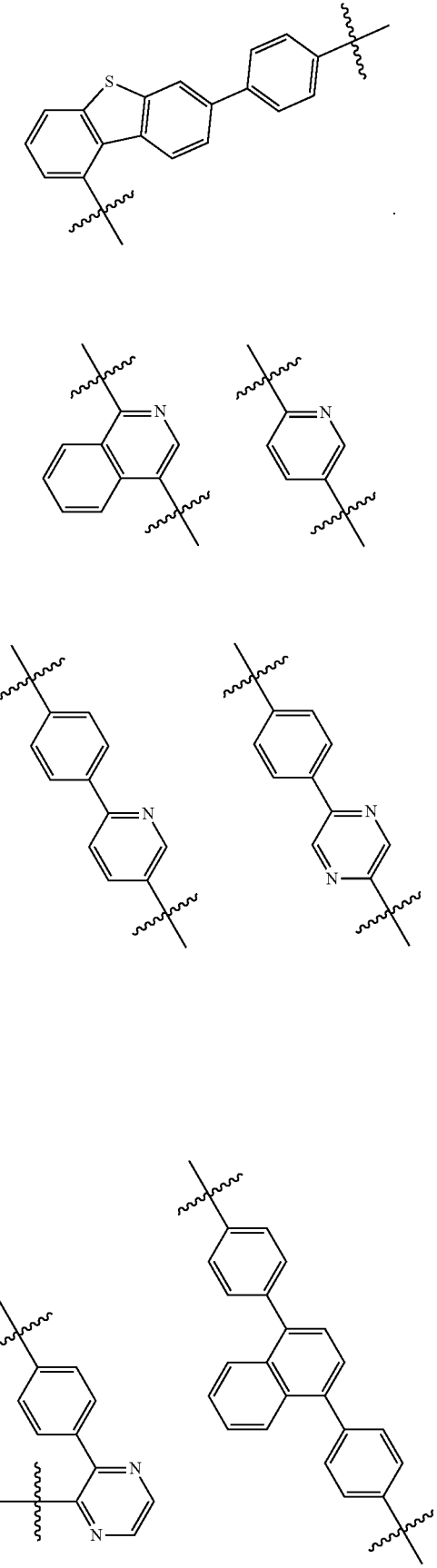

-continued
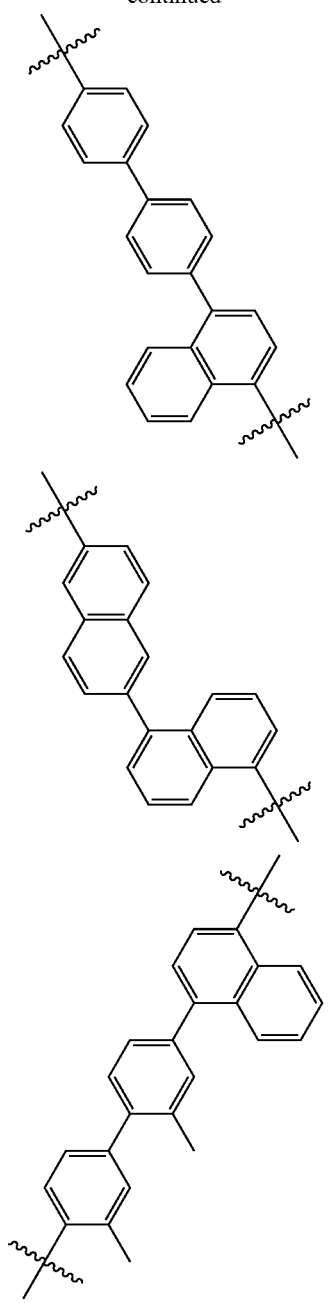
-continued
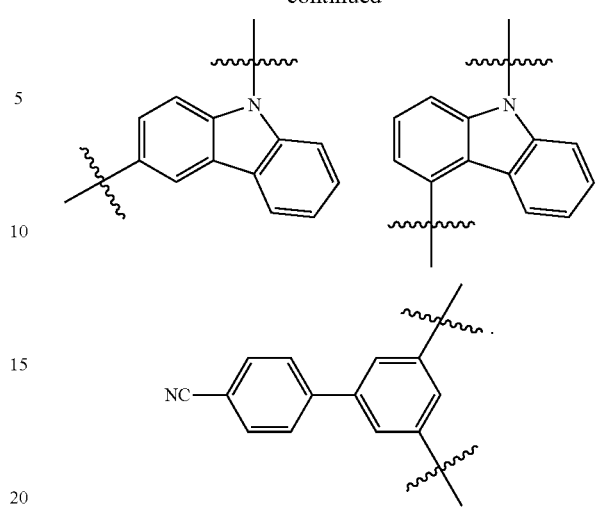
15. The organic compound according to claim 1, wherein the organic compound is selected from one or more of the following compounds:
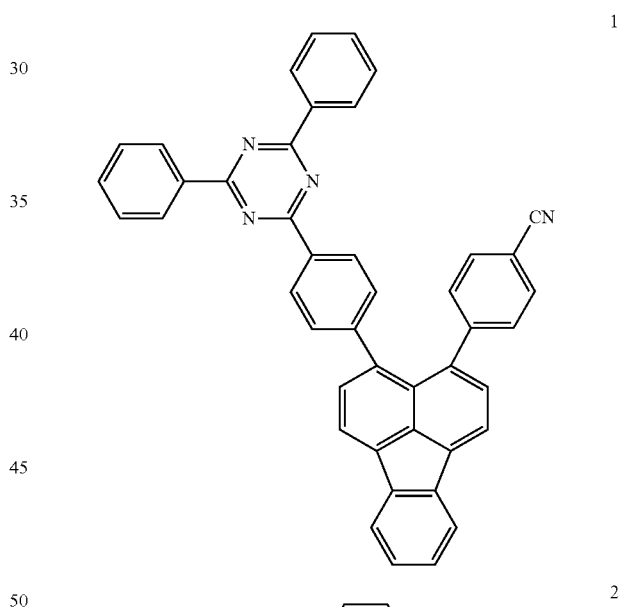
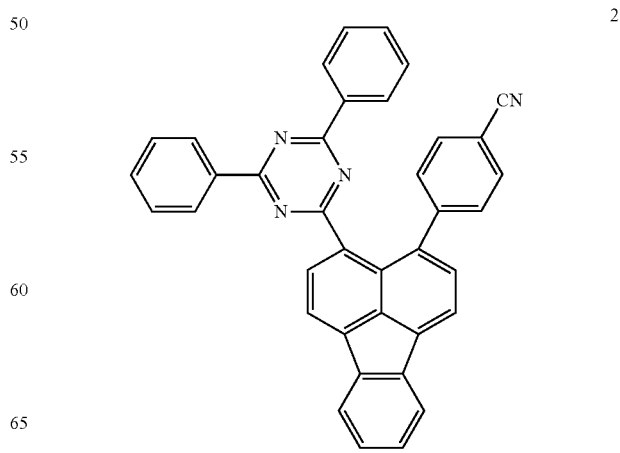
14. The organic compound according to claim 1, wherein the $L_1$ and $L_2$ are the same or different, and are each independently selected from the group consisting of the following groups:
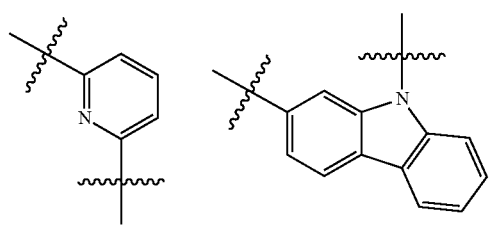

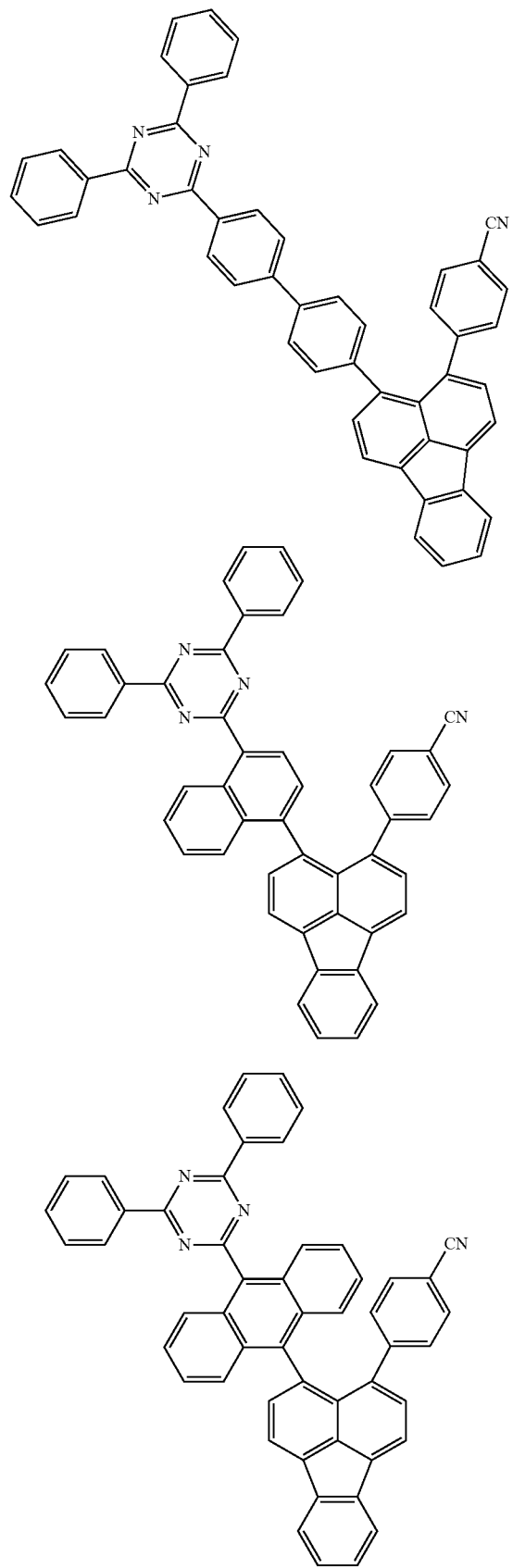
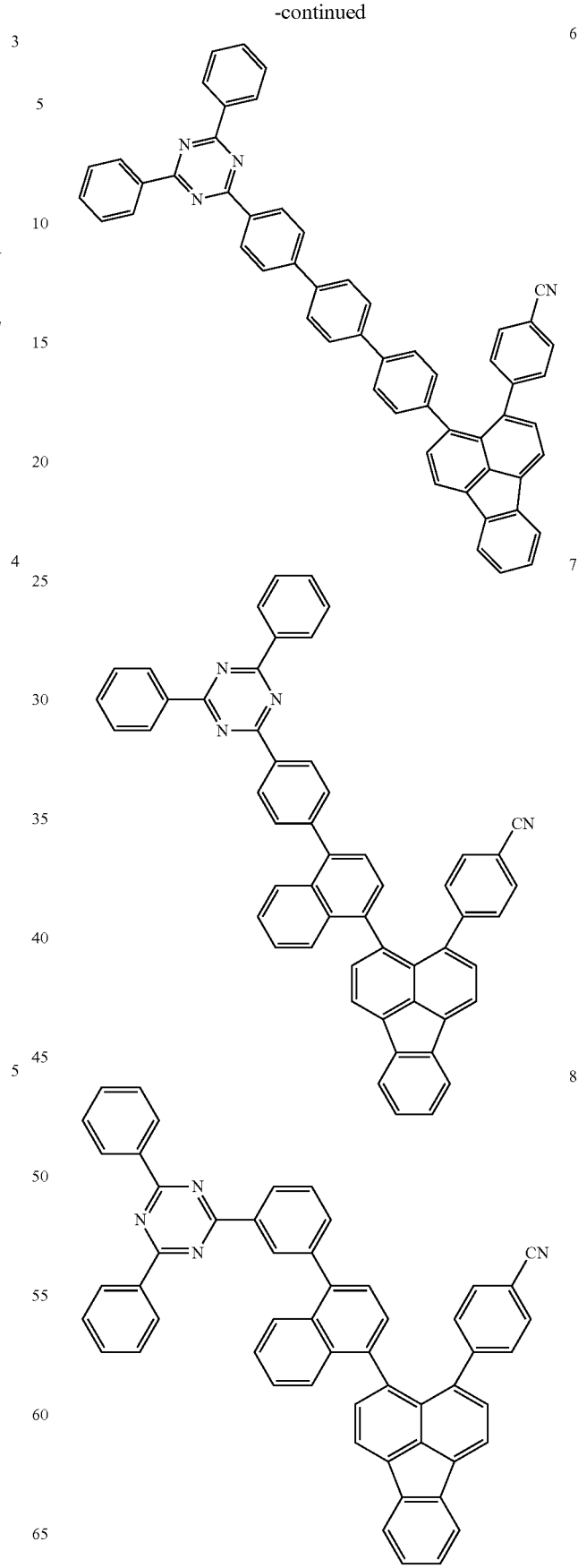

9
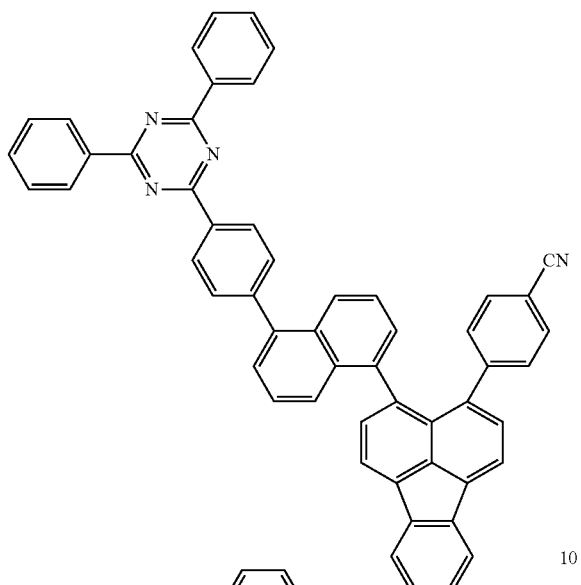
10
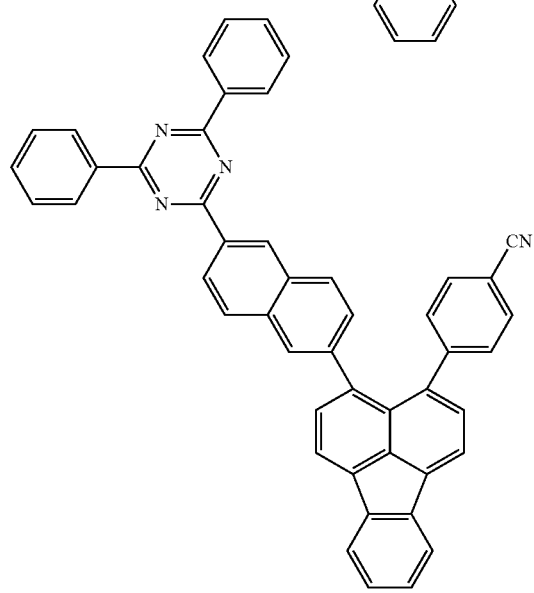
11
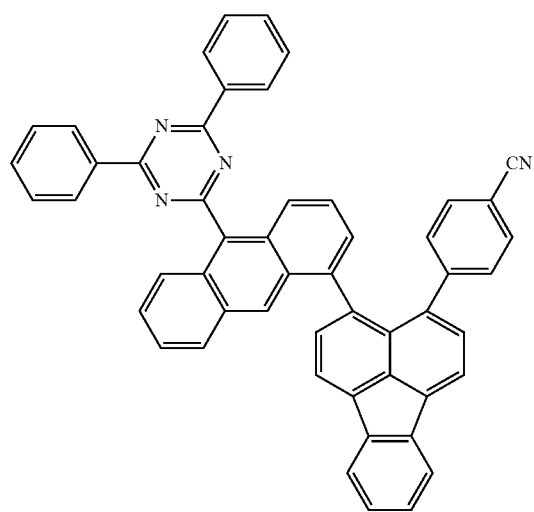
12
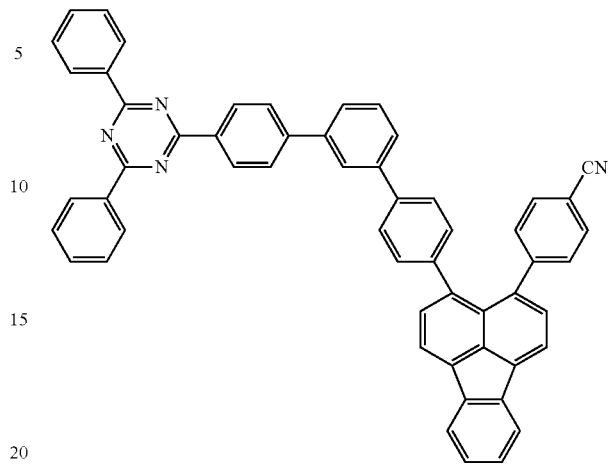
13
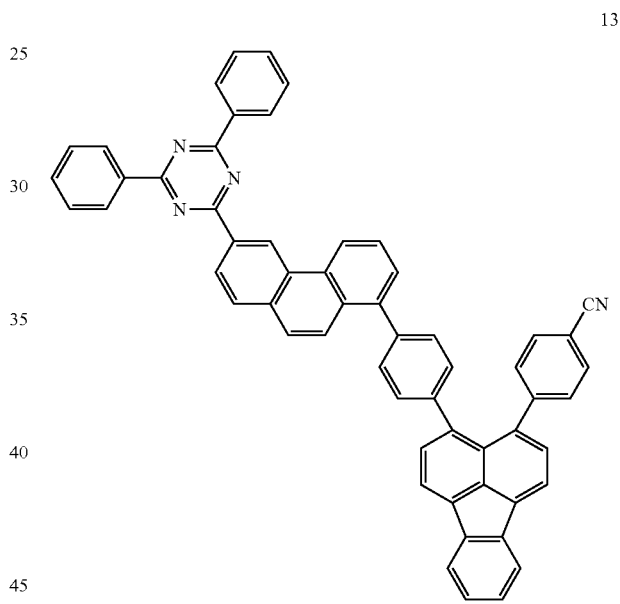
14
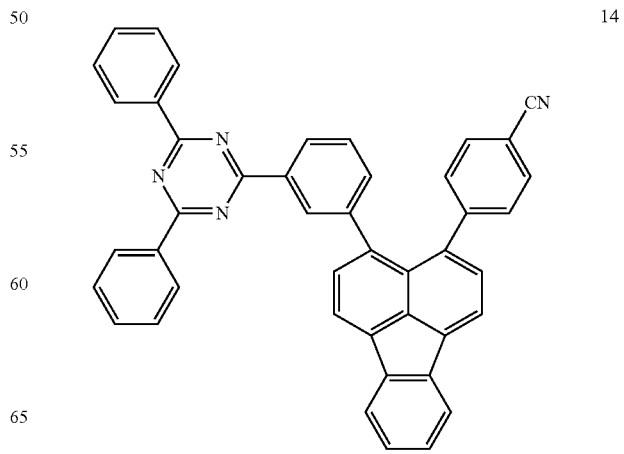

353
-continued
15
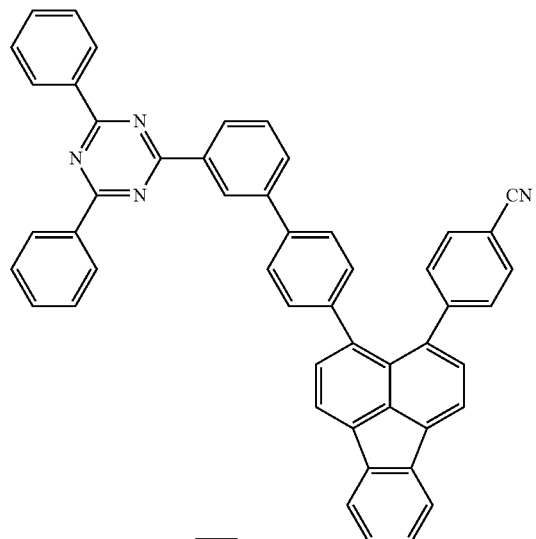
16
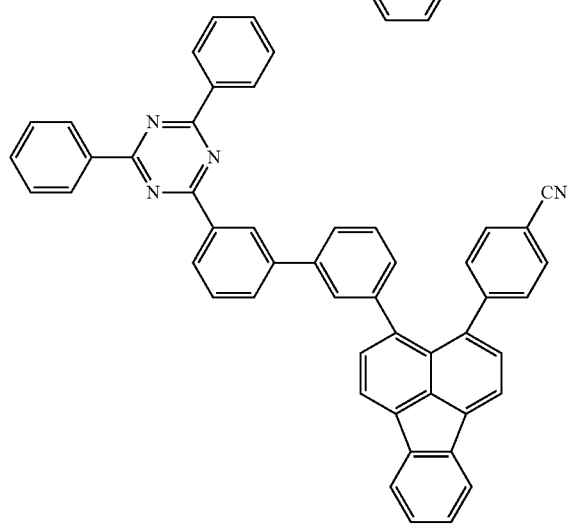
17
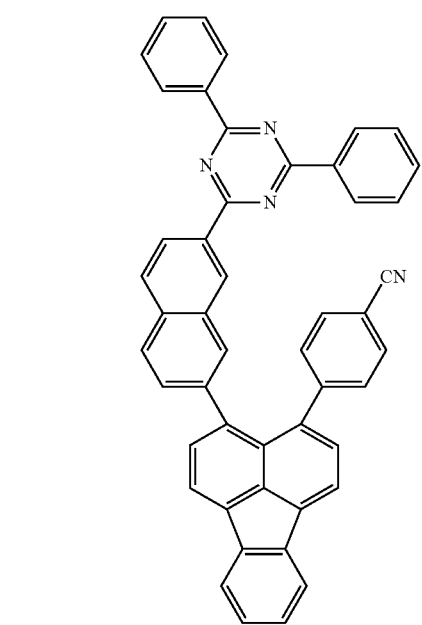
354
-continued
18
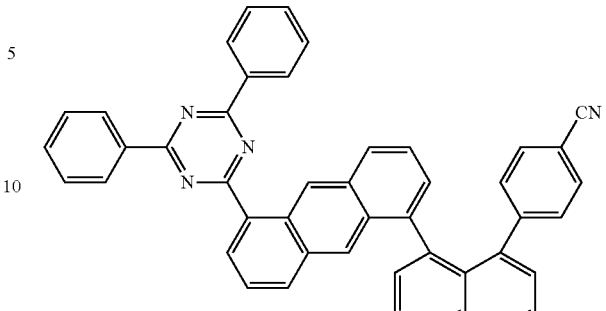
19
20
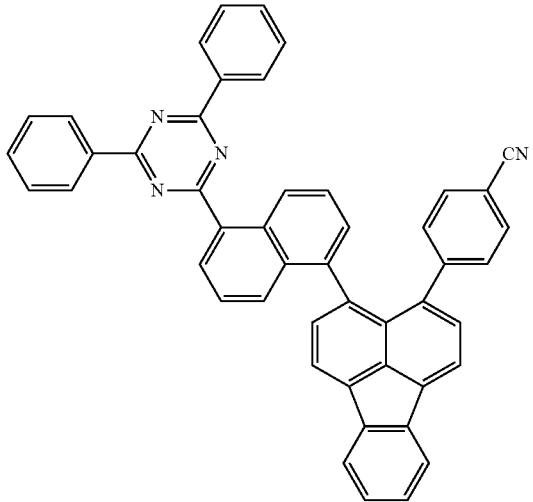

21
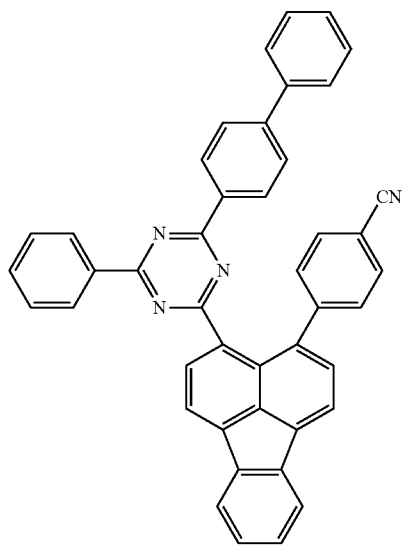
22
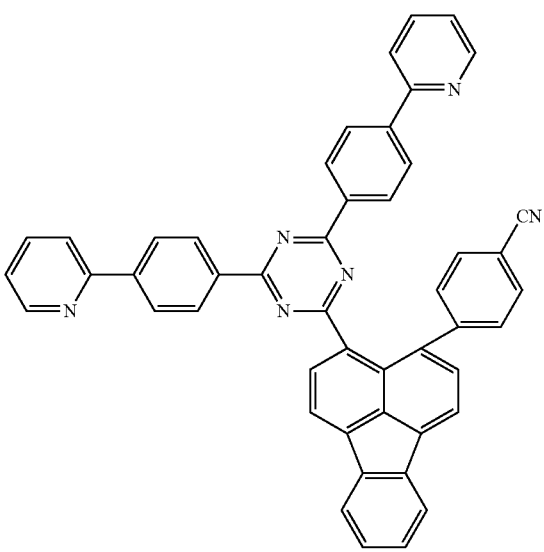
23
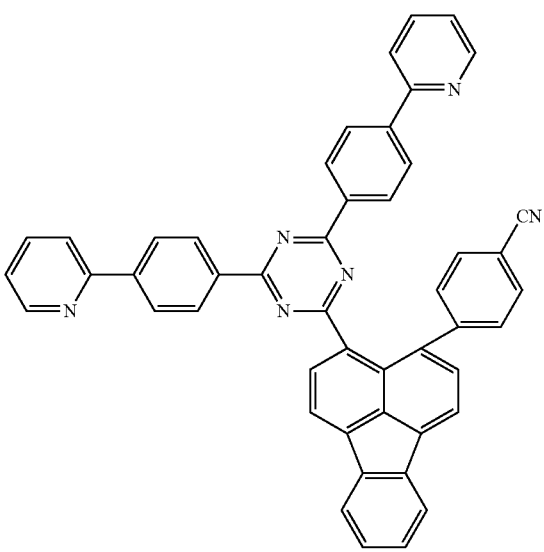
24
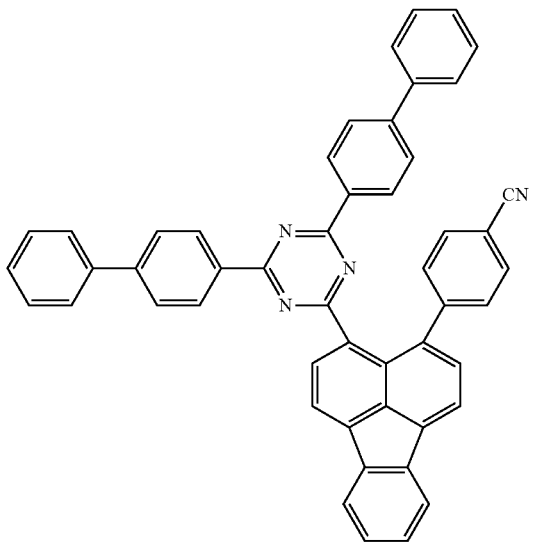
25
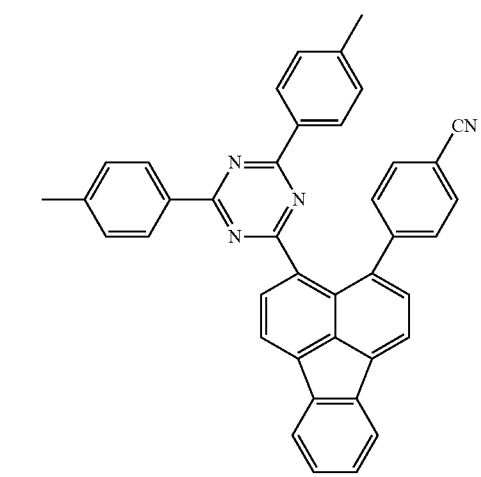
26
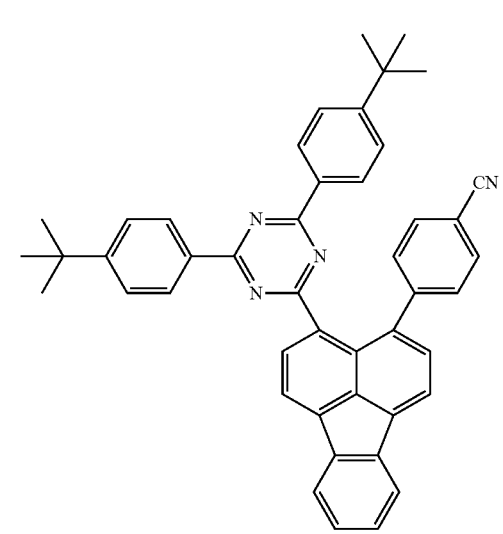

-continued
27
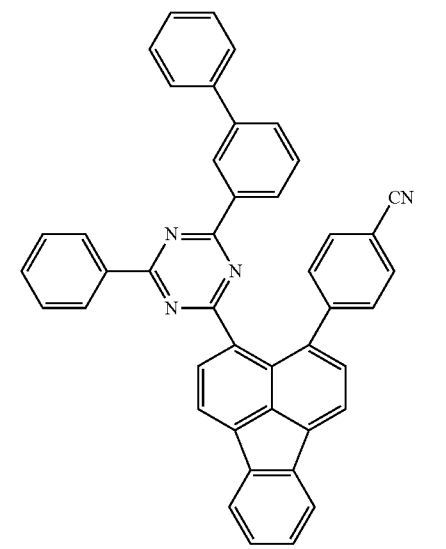
28
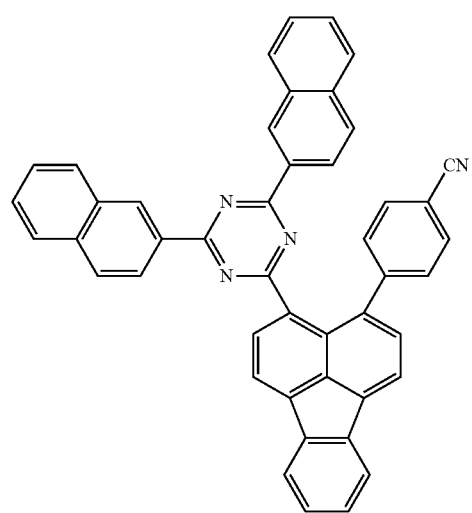
29
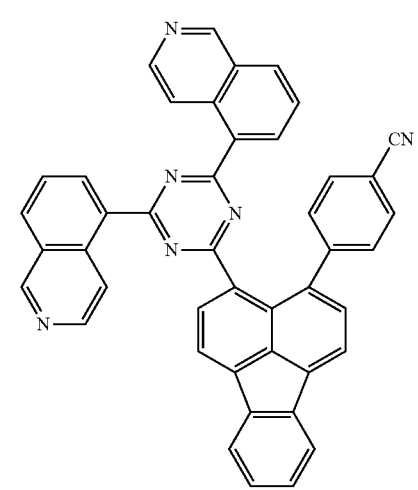
-continued
30
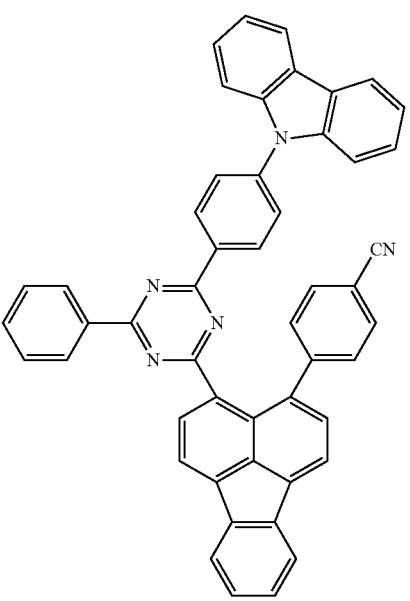
31
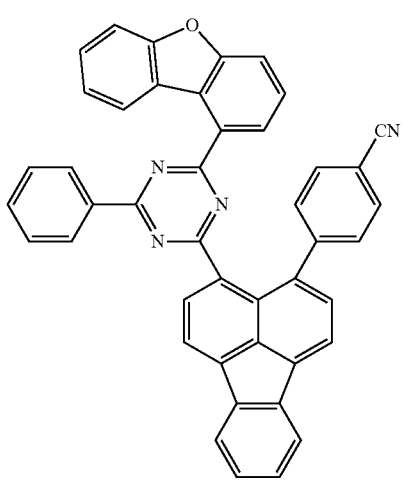
32
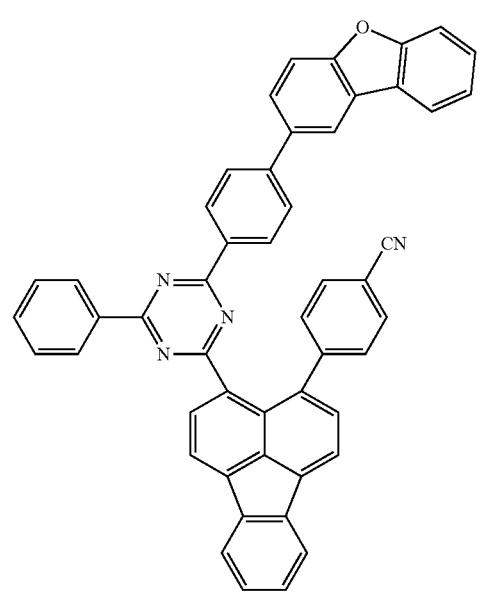

359
-continued
33
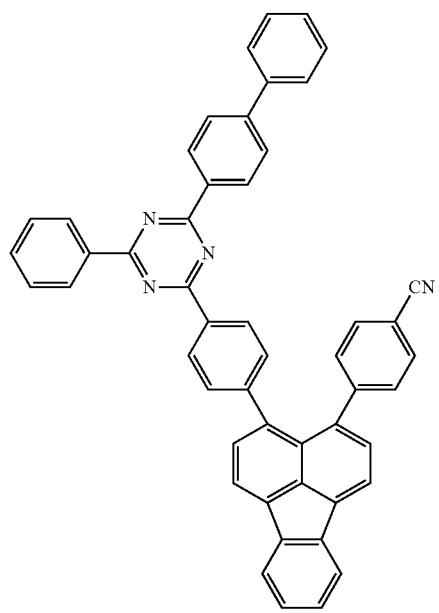
34
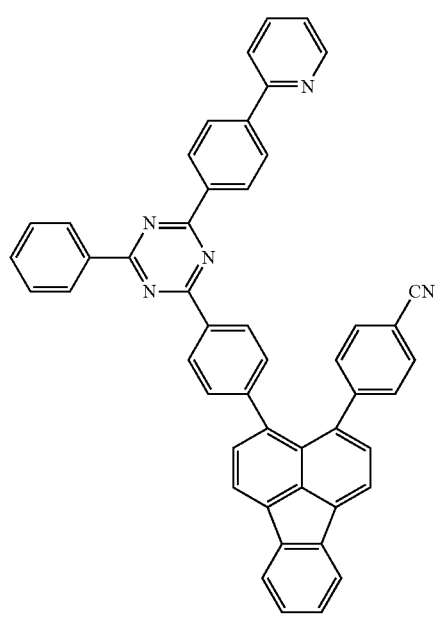
360
-continued
35
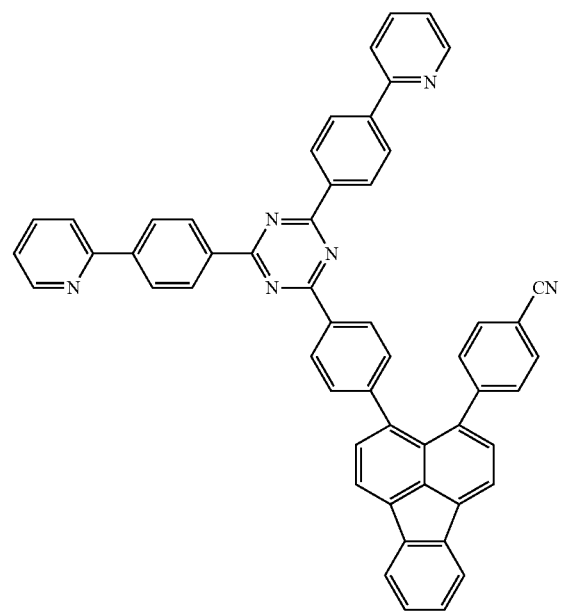
36
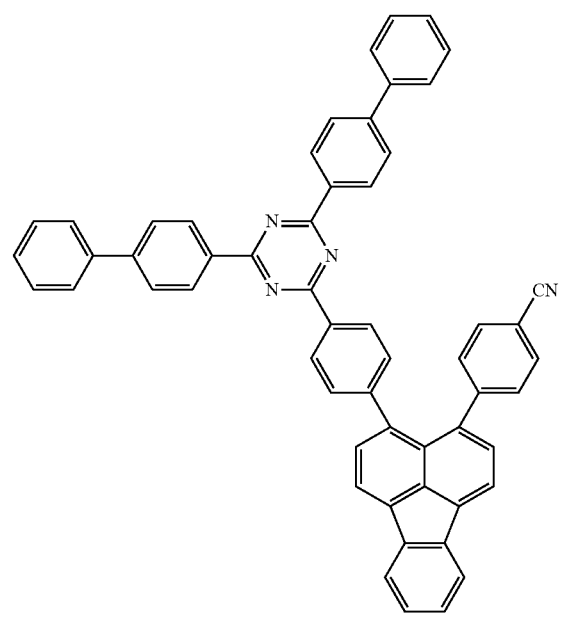

37
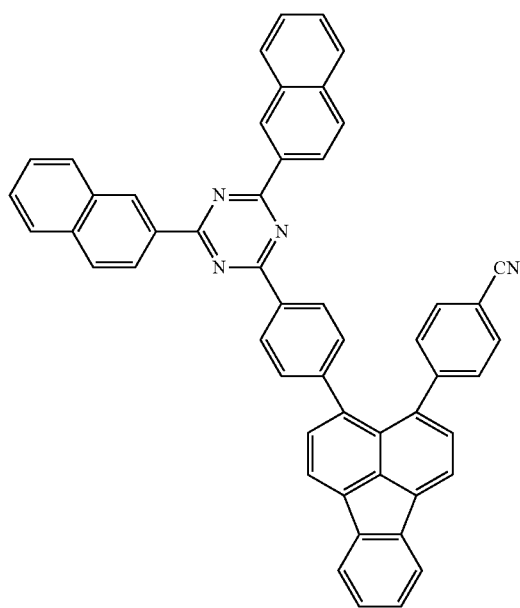
38
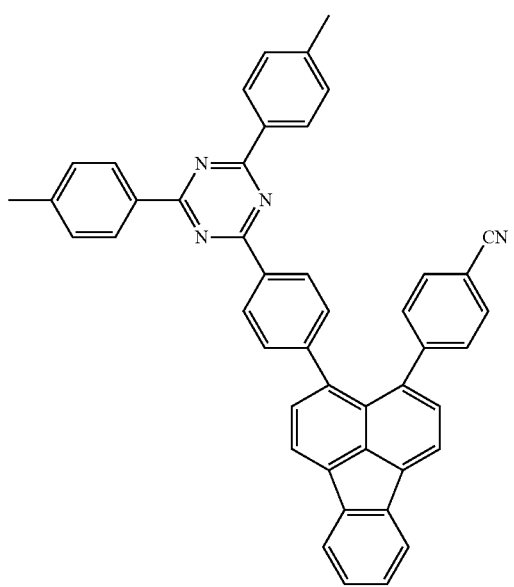
39
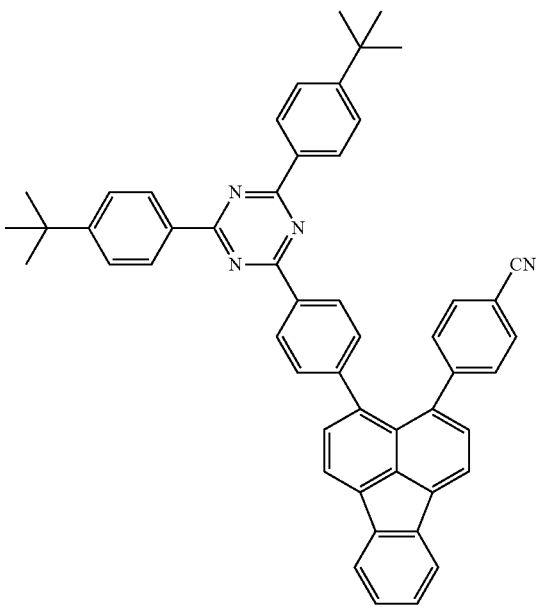
40
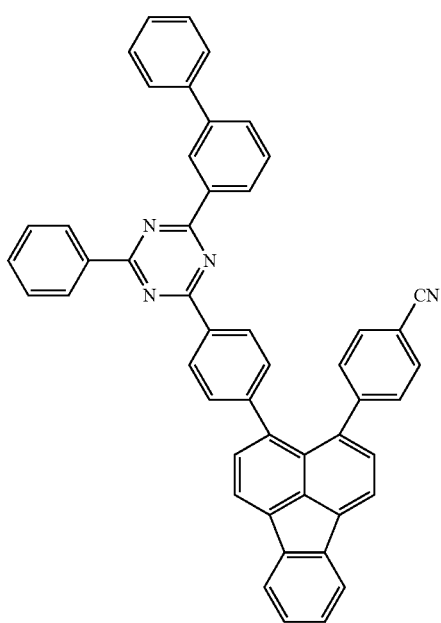

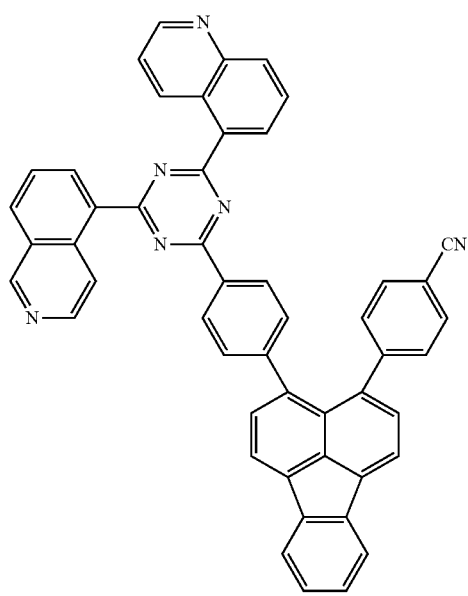
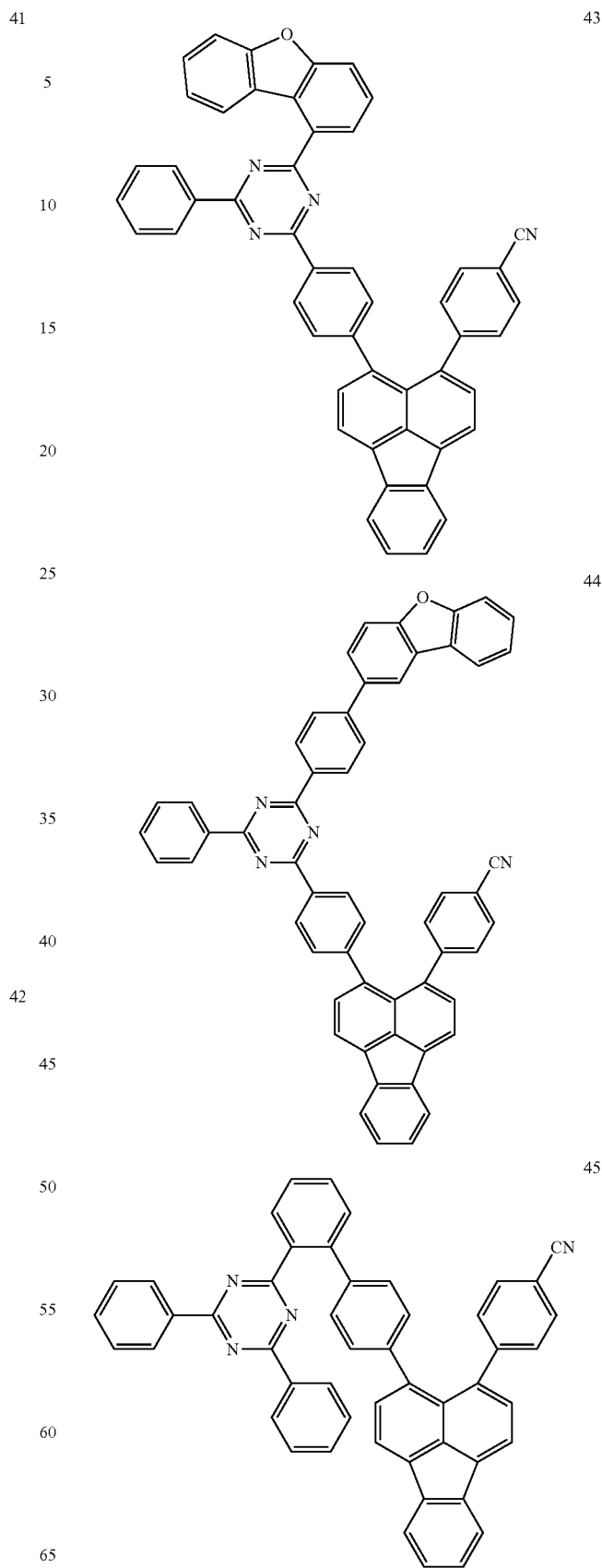

46
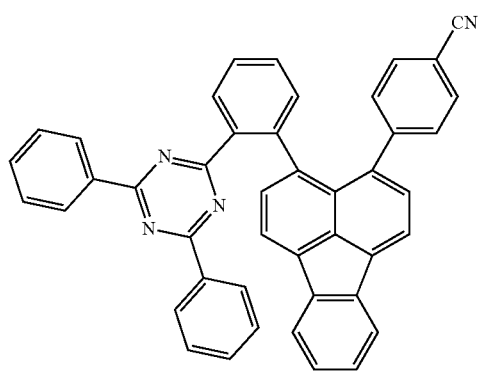
47
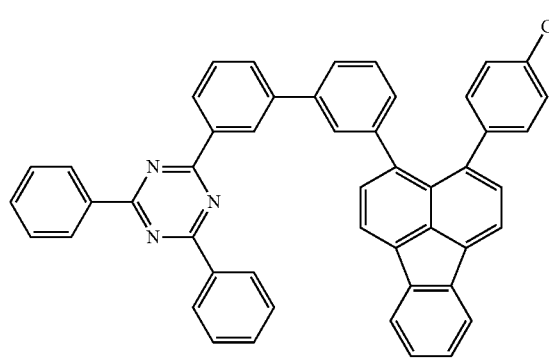
48
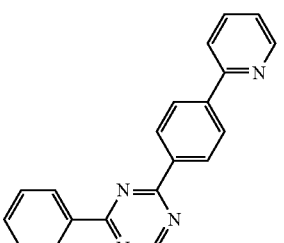
49
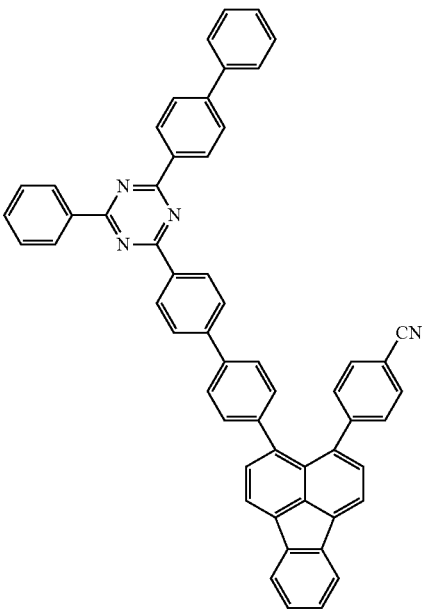
50
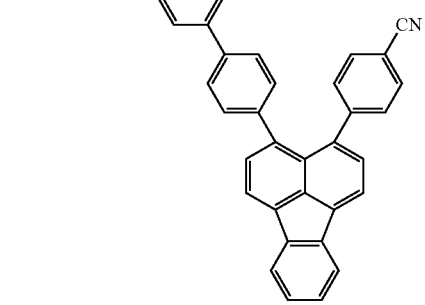

367
-continued
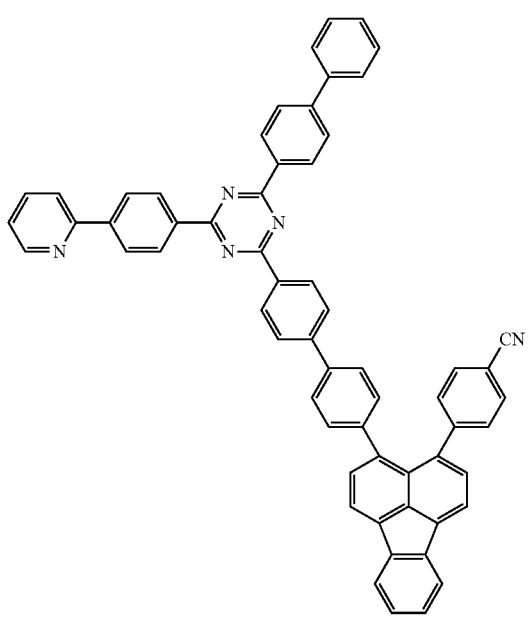
51
368
-continued
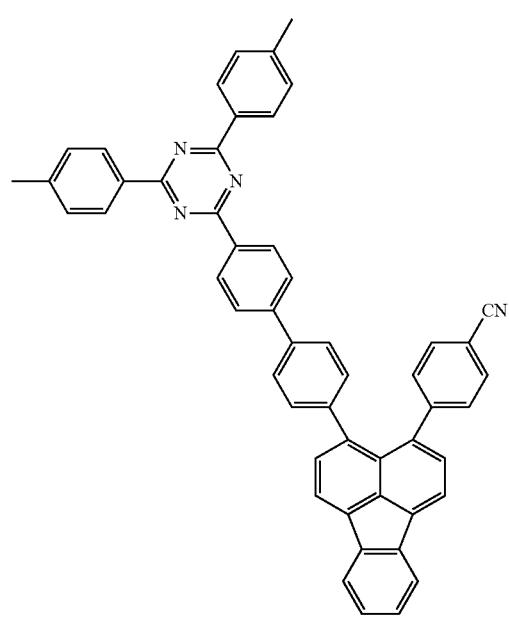
53
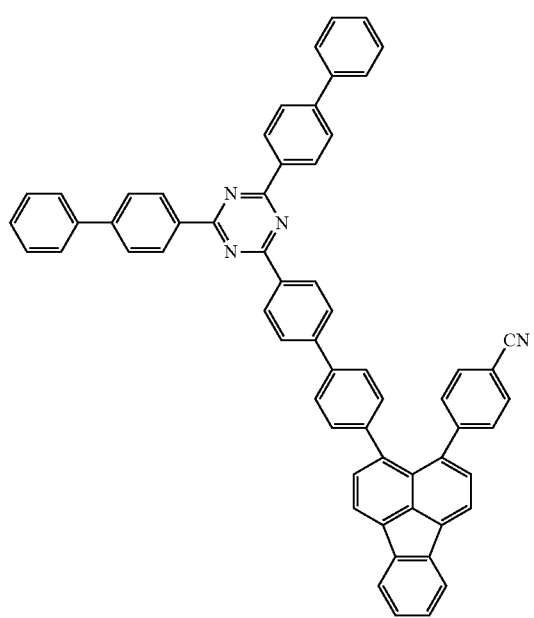
52
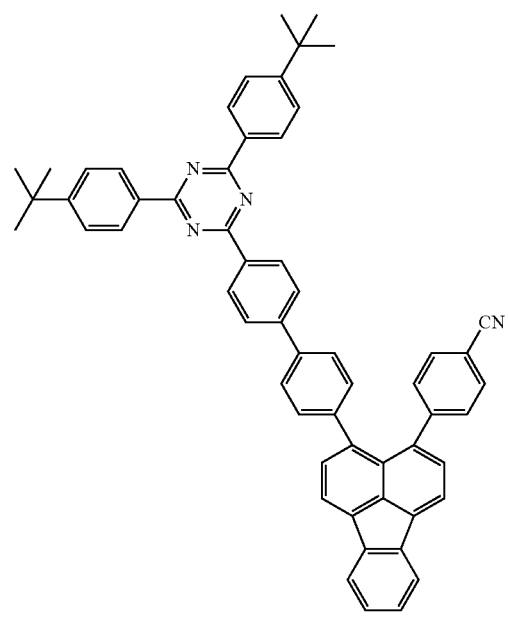
54

369
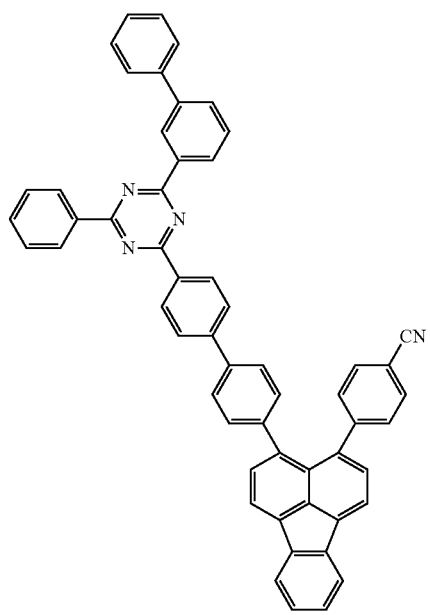
56
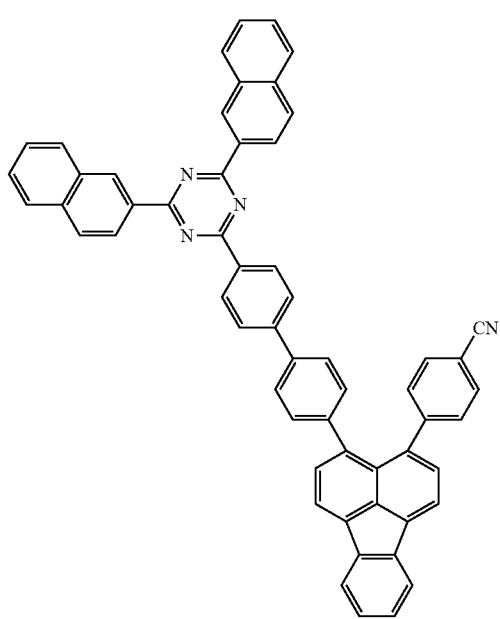
370
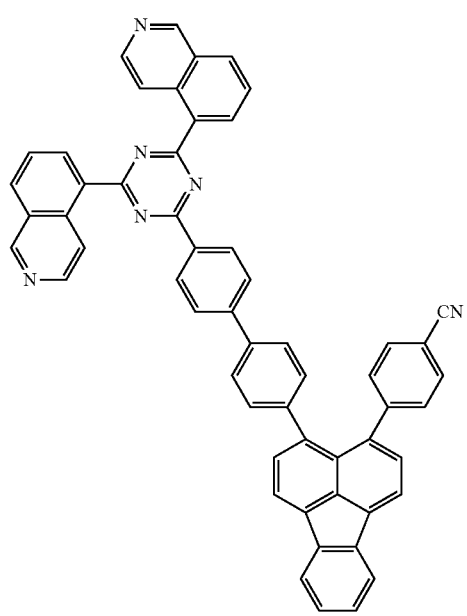
58
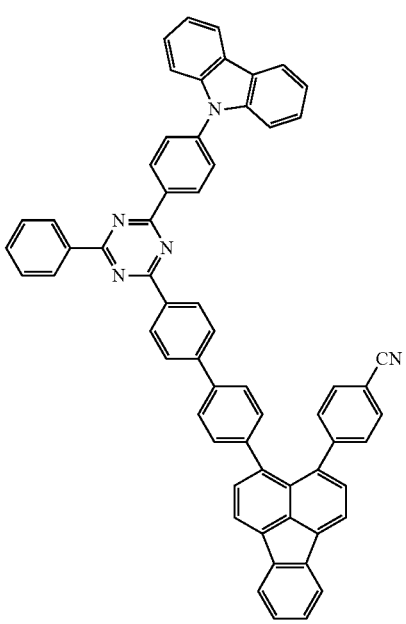

-continued
371
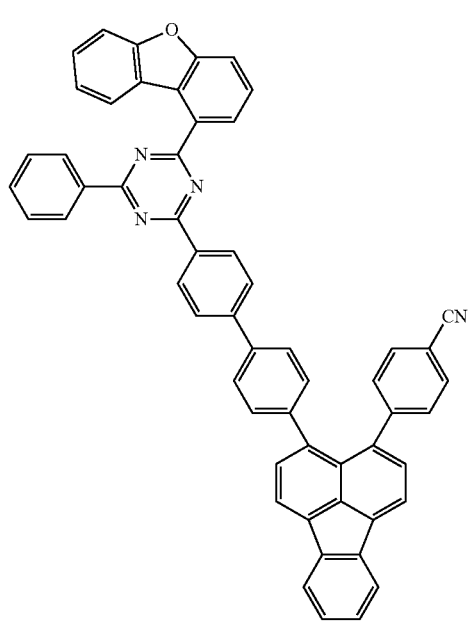
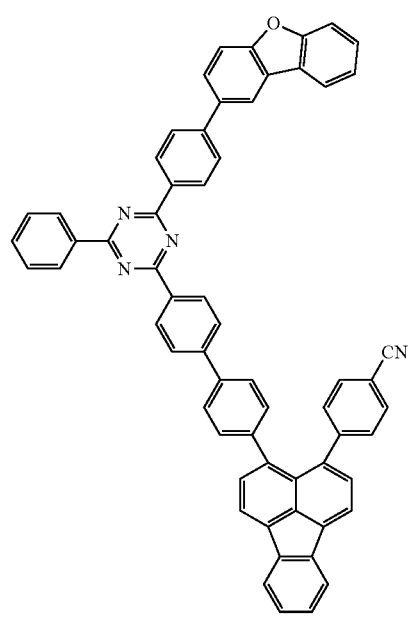
-continued
372
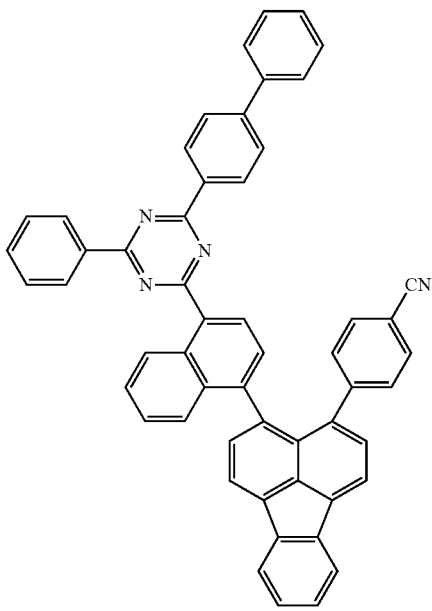
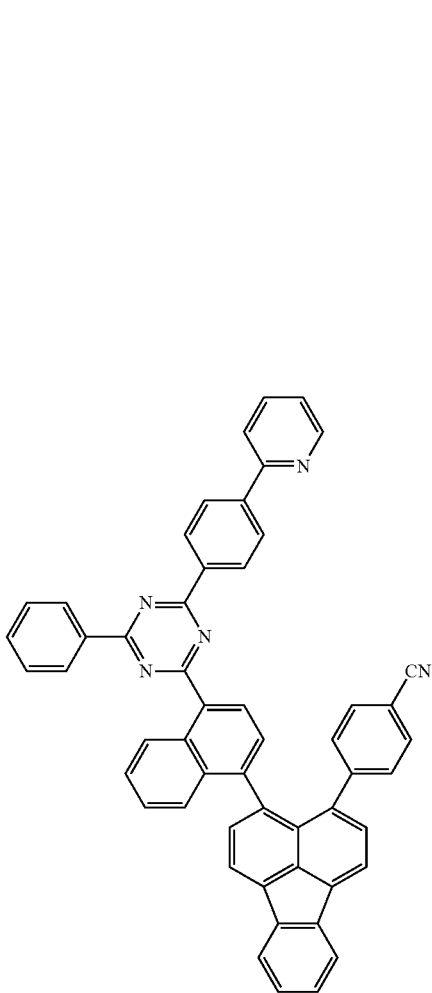

373
-continued
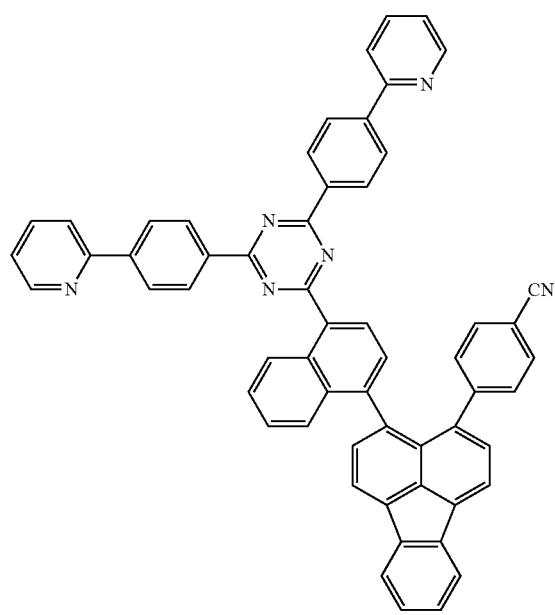
374
-continued
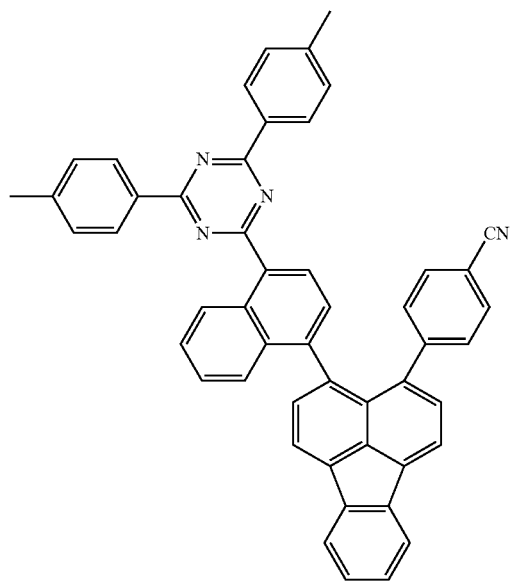
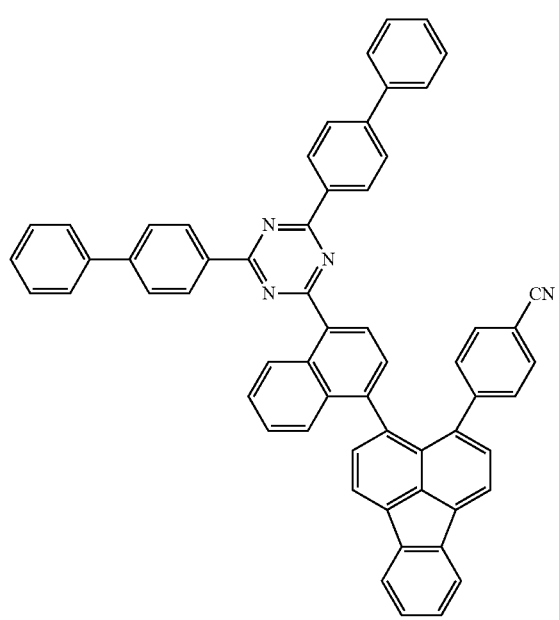
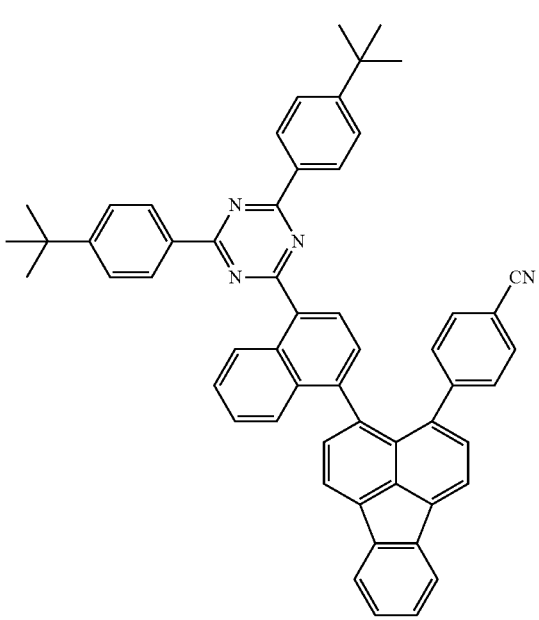

375
-continued
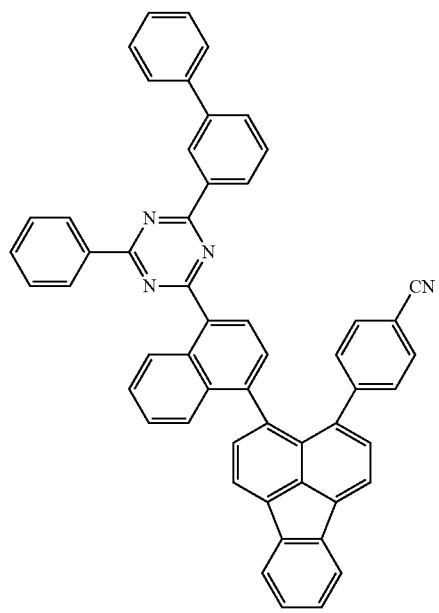
376
-continued
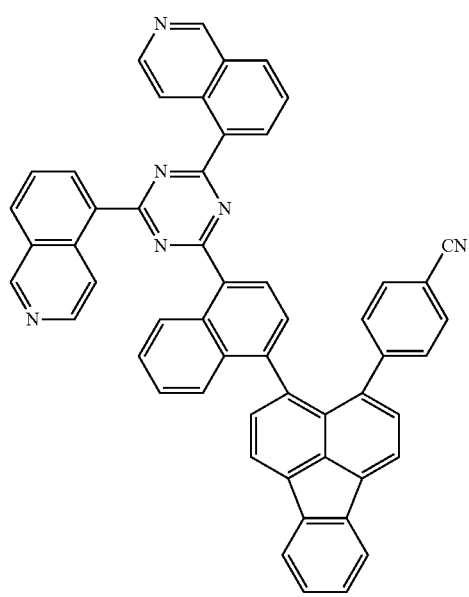
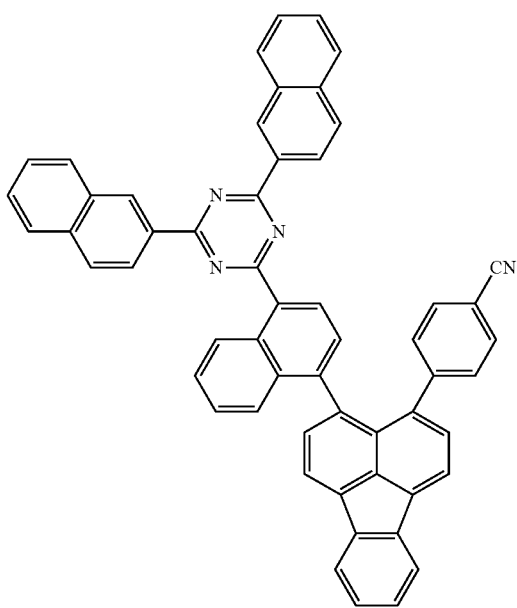
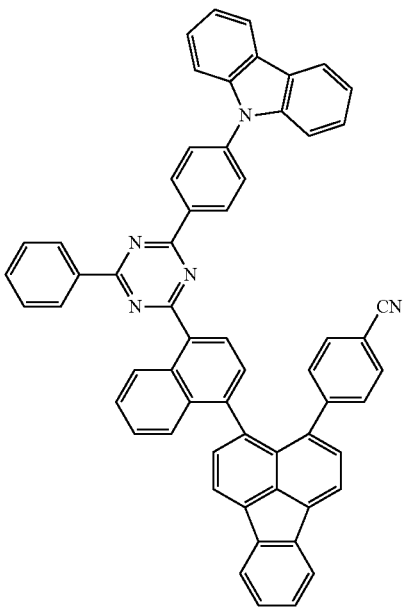

377
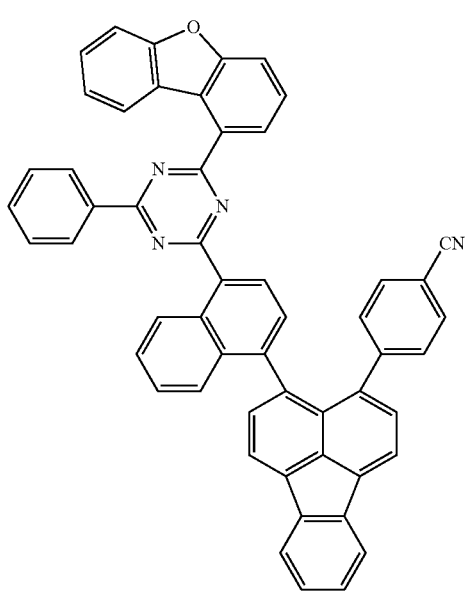
378
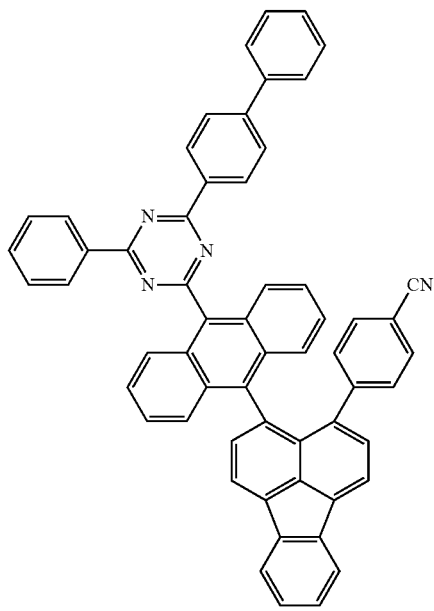
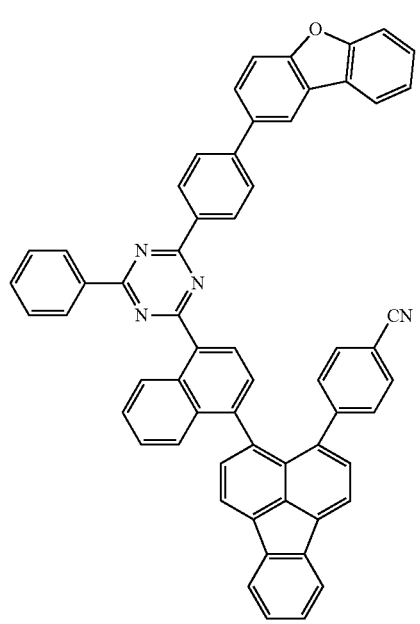
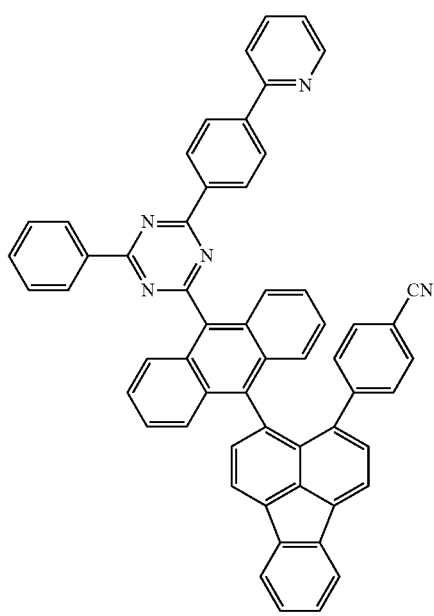

379
75
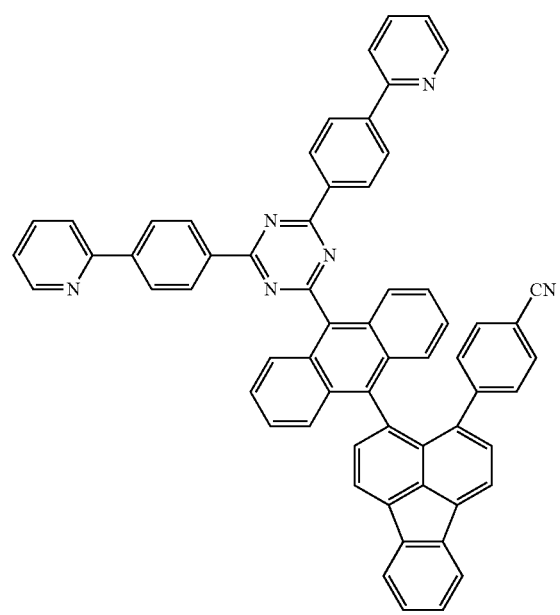
380
77
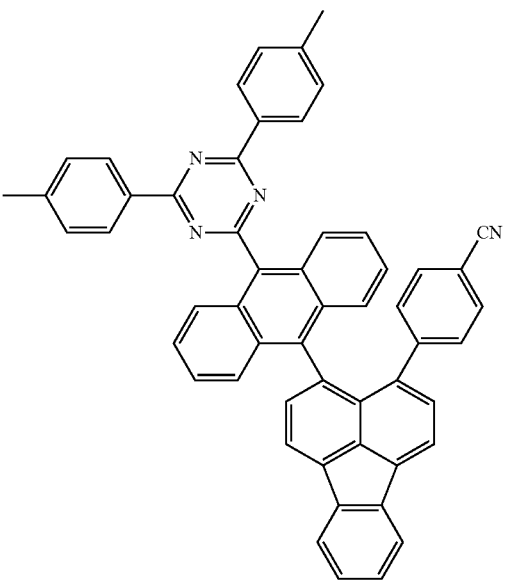
76
78
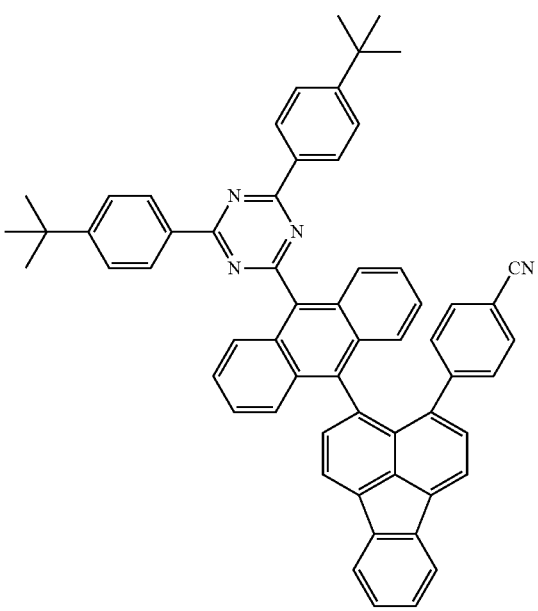

381
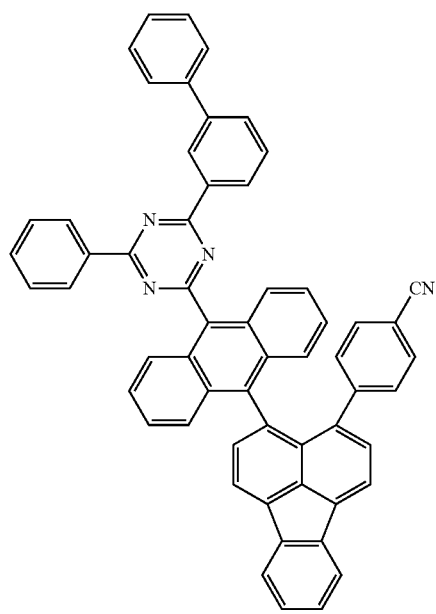
382
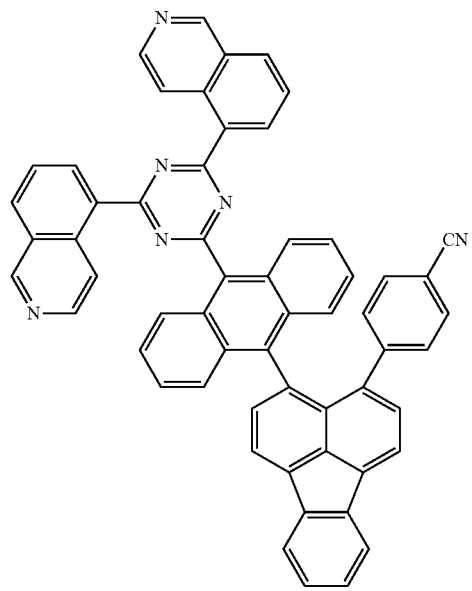
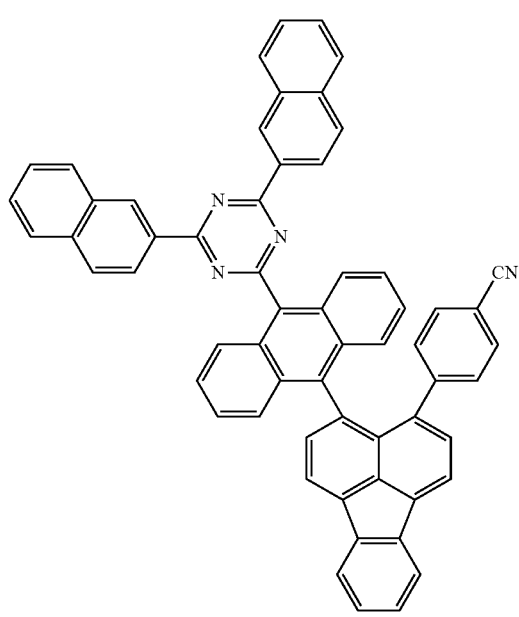
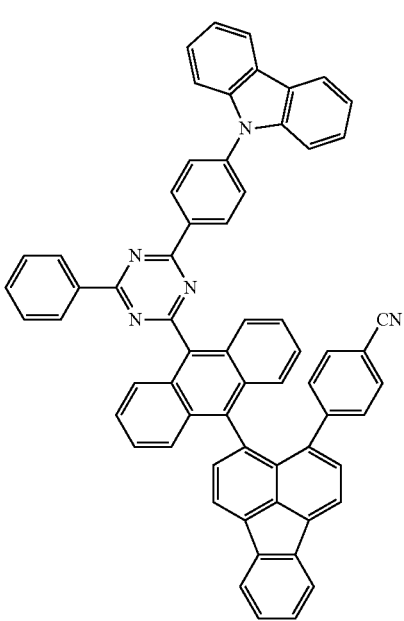

383
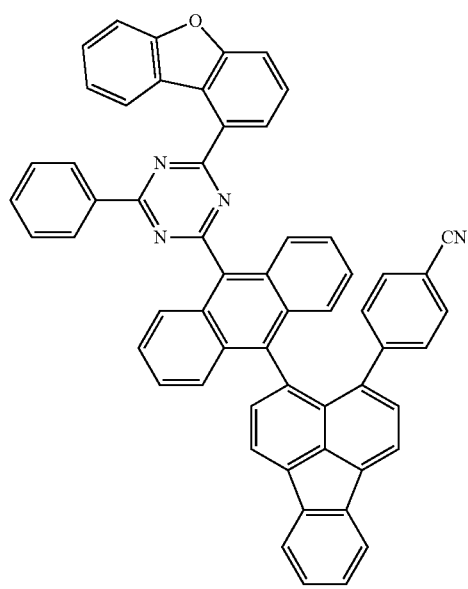
384
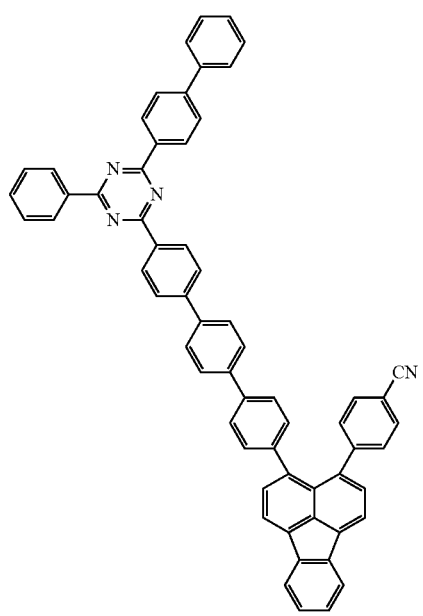

385
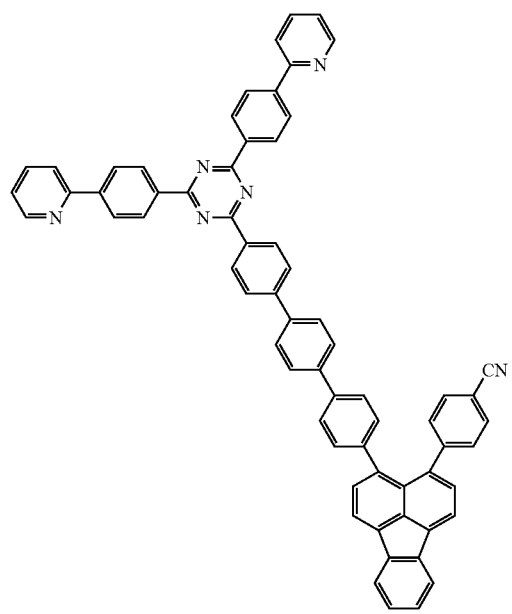
87
386
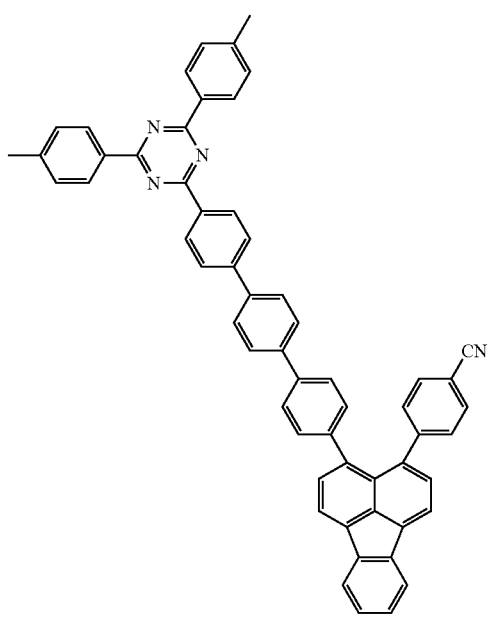
89
88
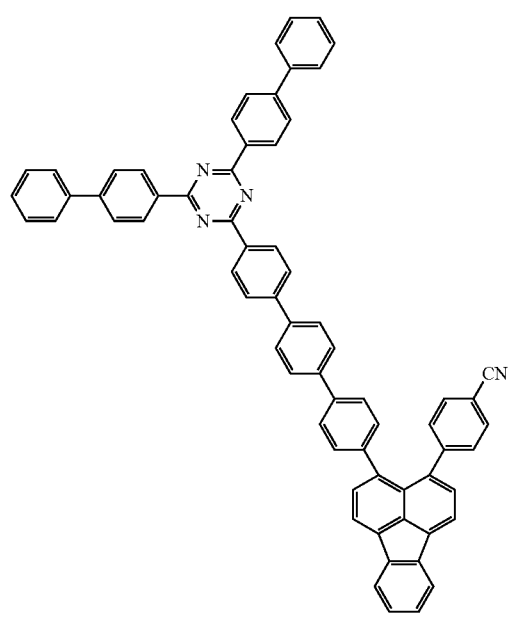
90
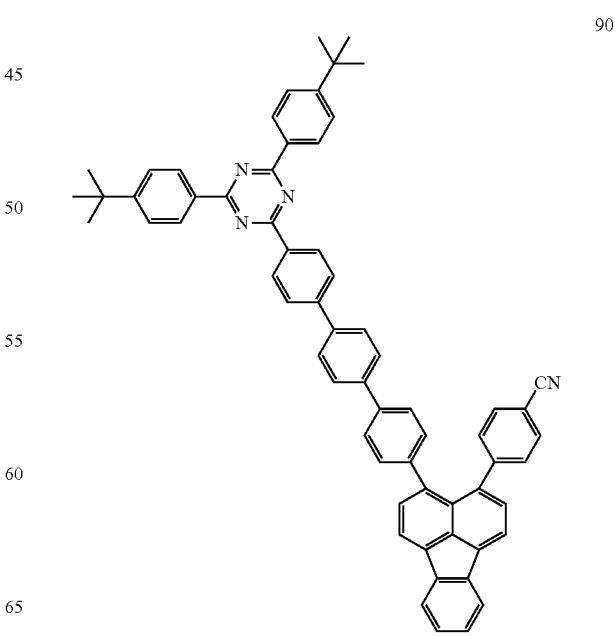

387
-continued
388
-continued
91
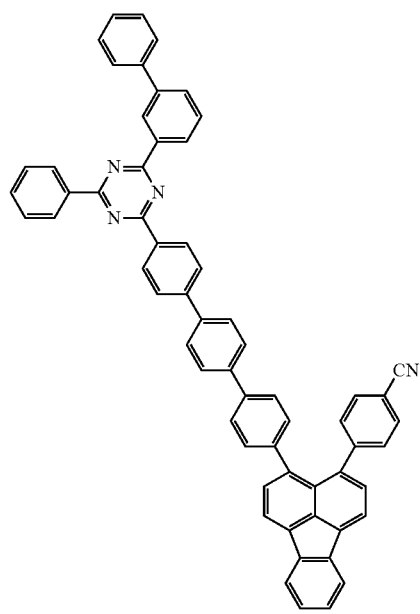
93
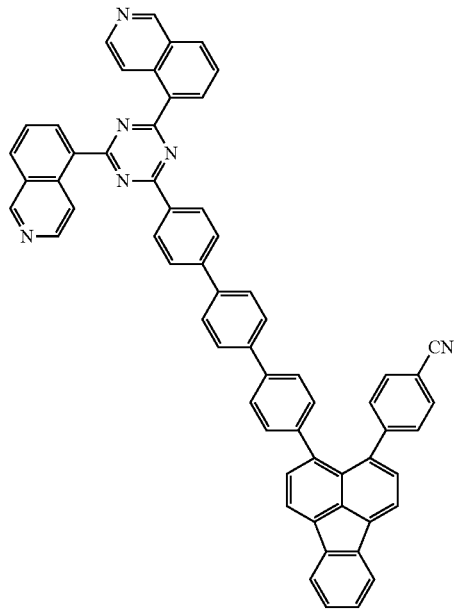
92
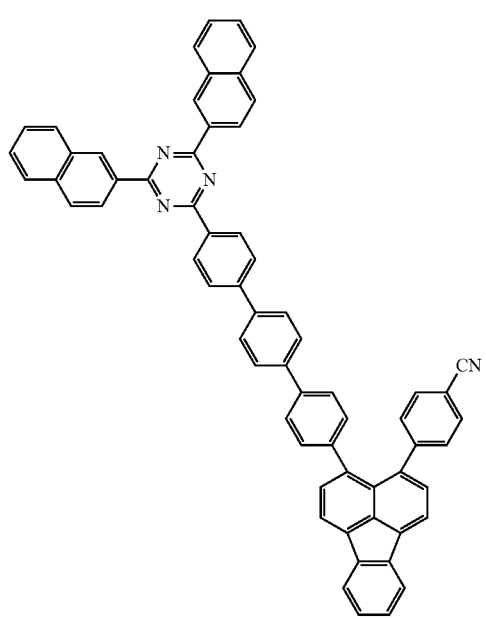
94
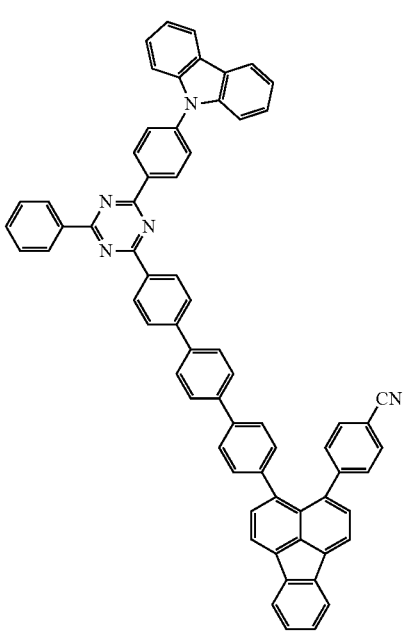

389
-continued
95
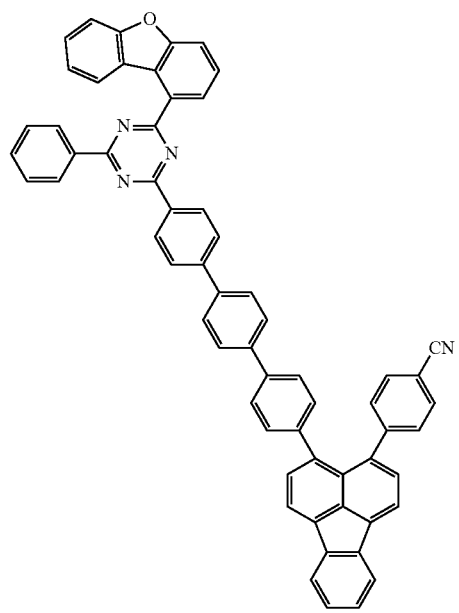
96
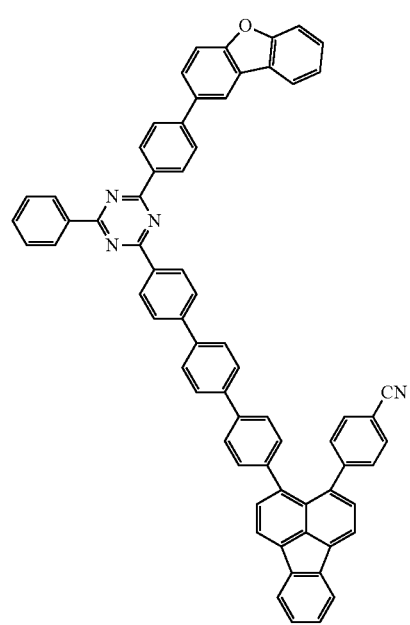
390
-continued
97
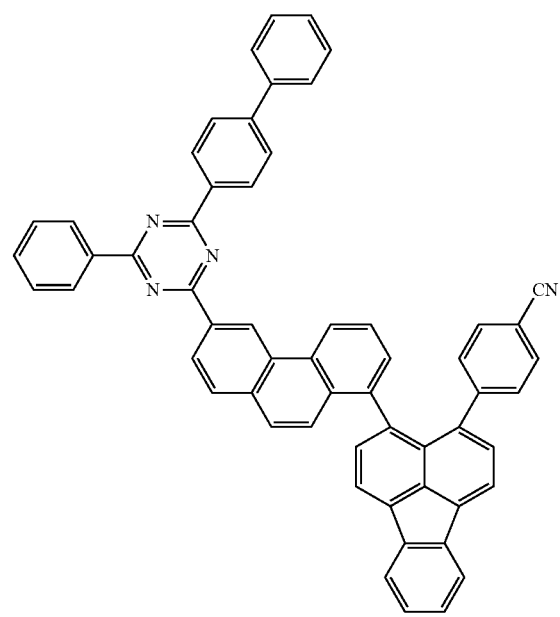
98
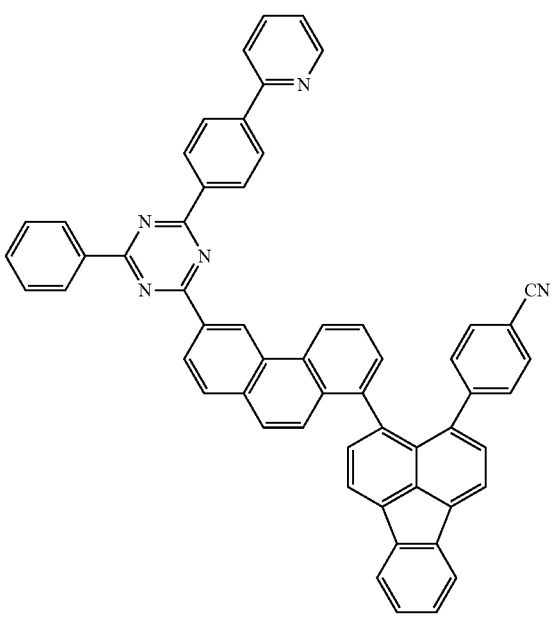

391
-continued
99
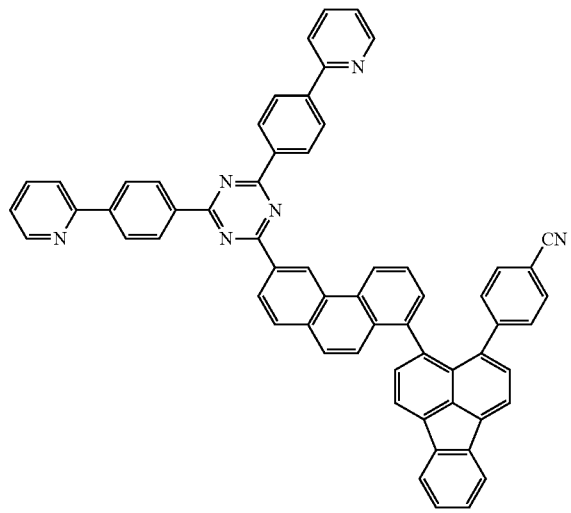
100
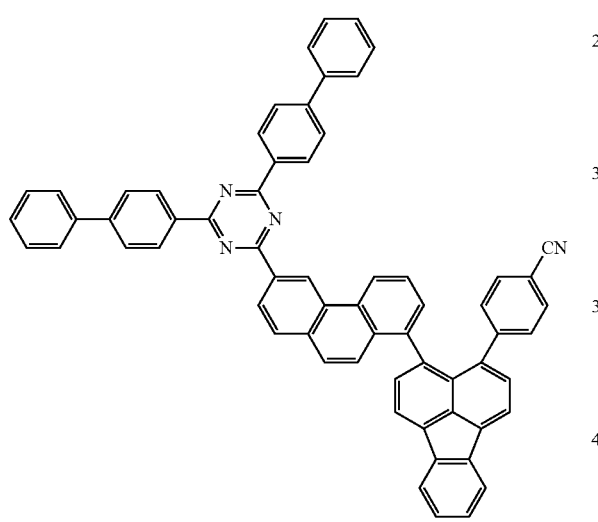
101
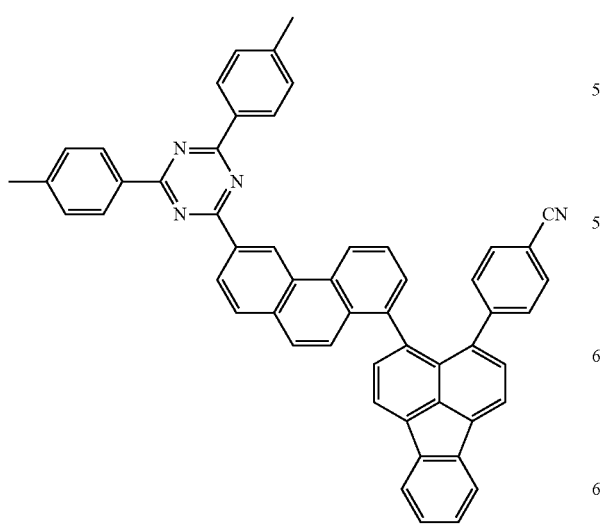
392
-continued
102
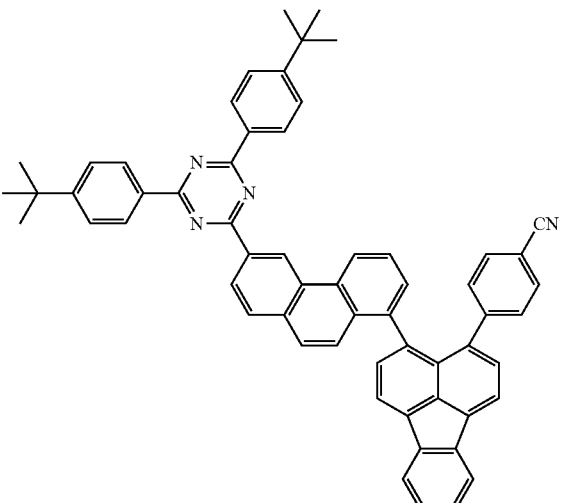
103
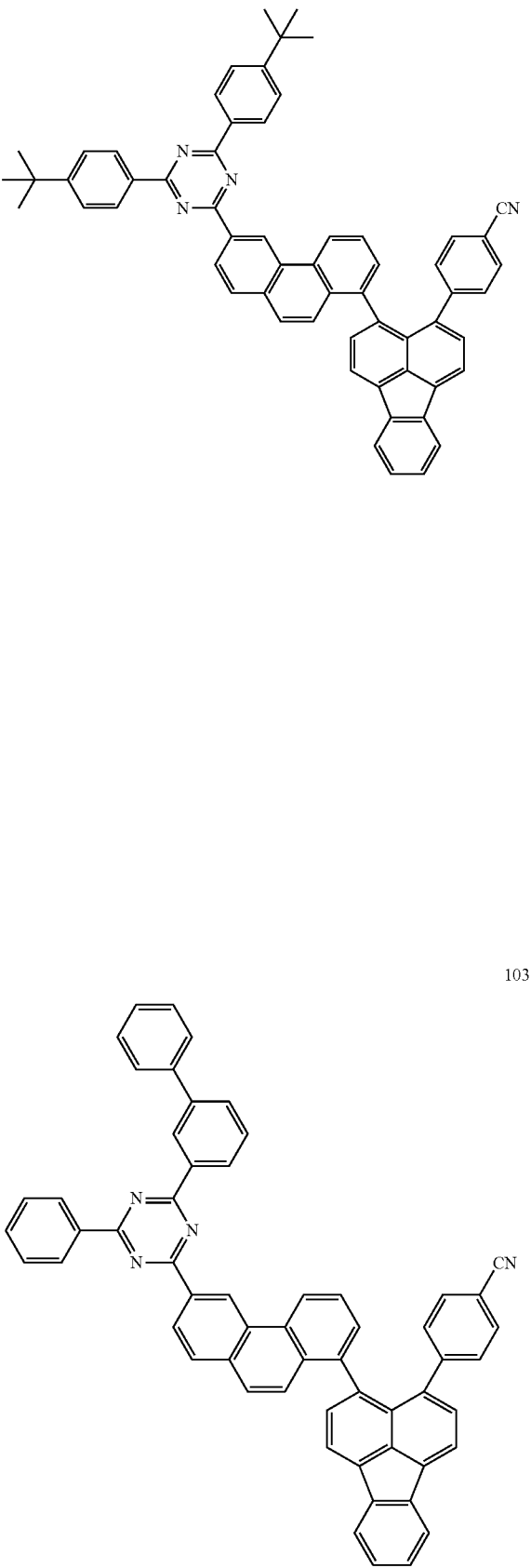

104
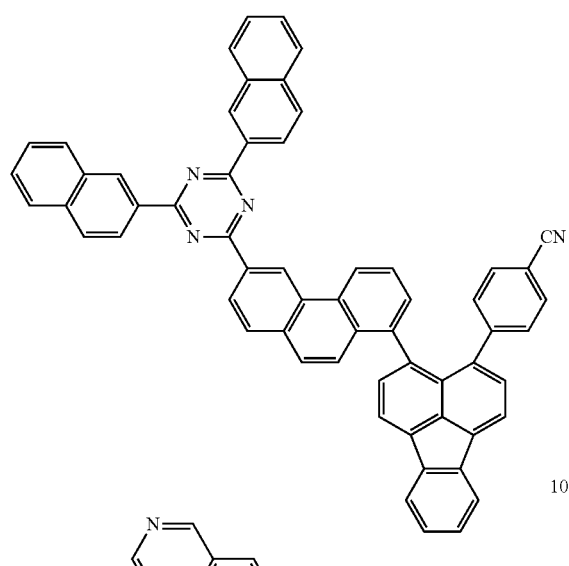
107
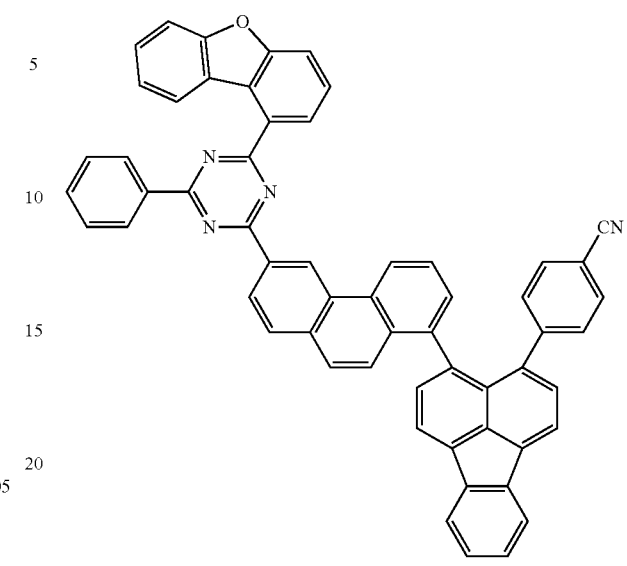
105
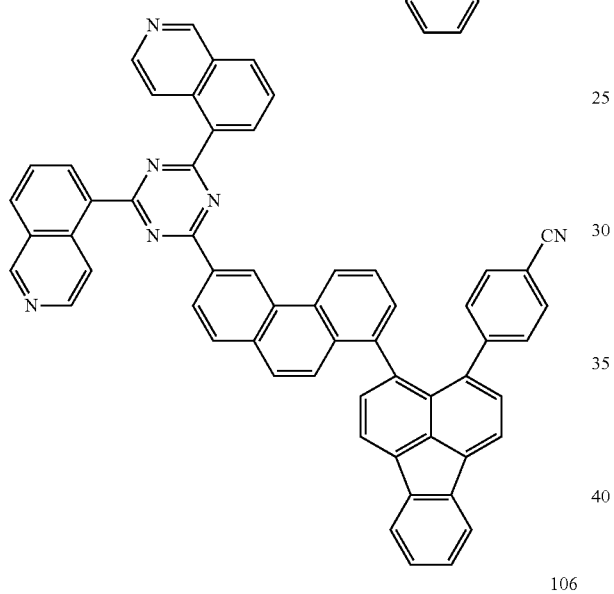
106
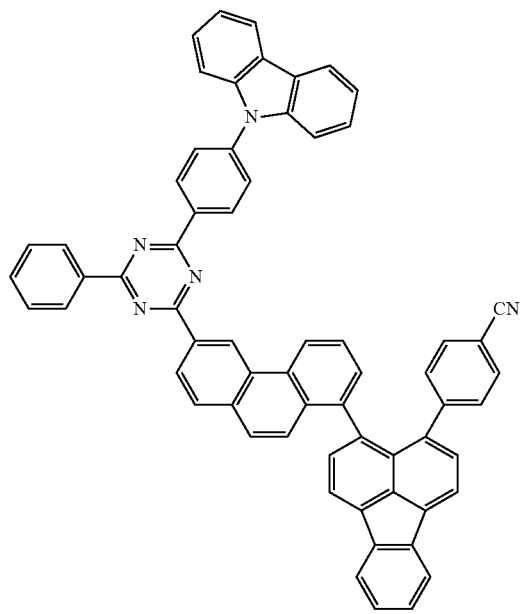
108
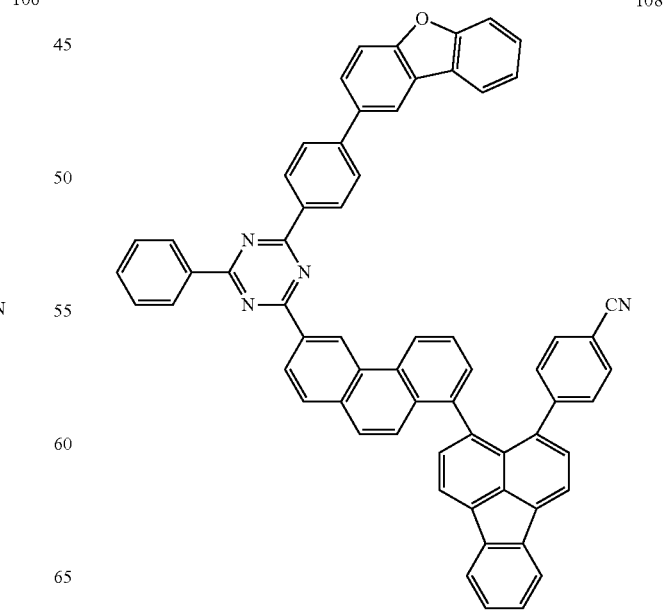

395
-continued
110
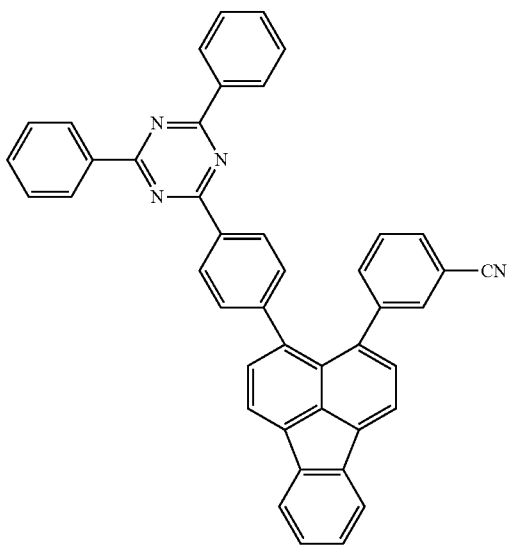
111
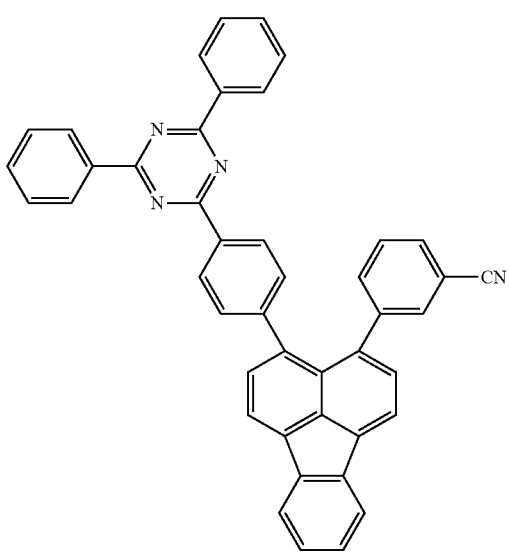
112
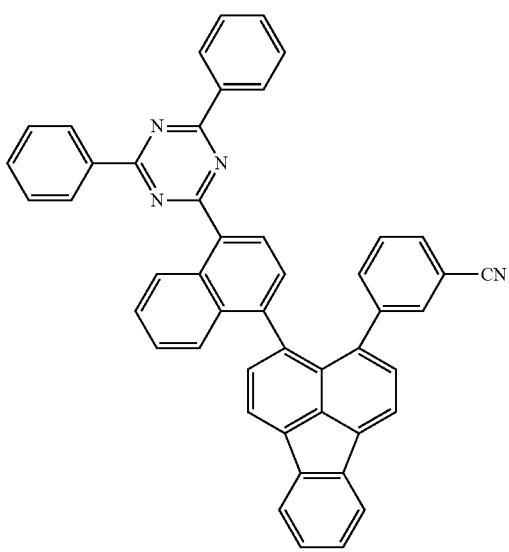
396
-continued
113
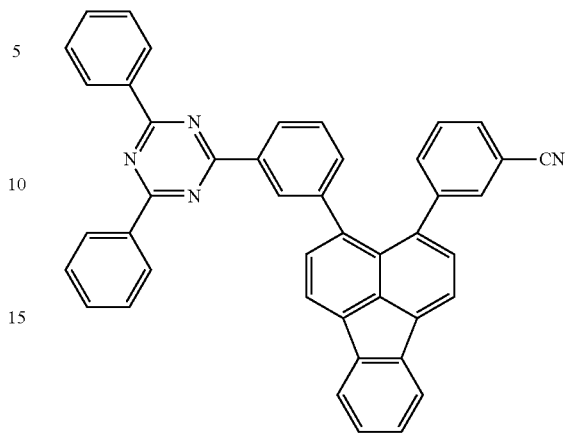
114
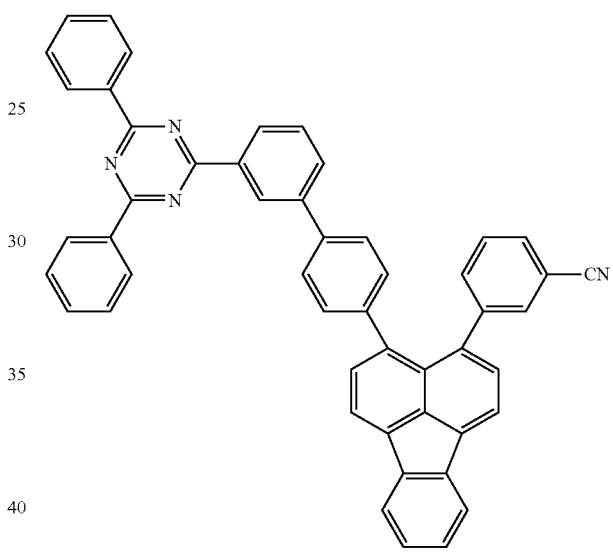
115
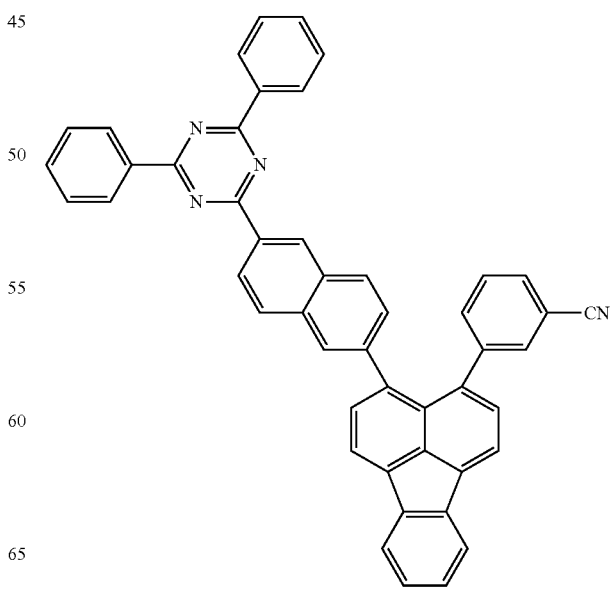

397
-continued
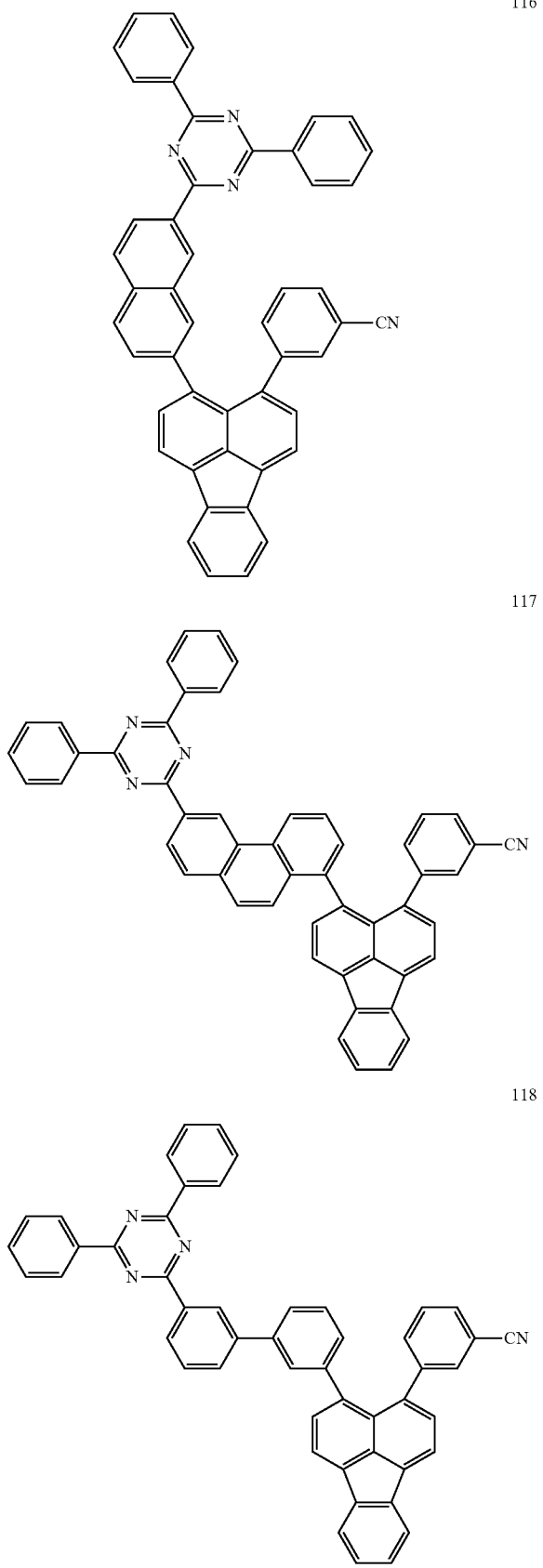 [SMILES: N#Cc1cccc(-c2ccc3c4c(ccc(-c5ccc6ccc(-c7nc(-c8ccccc8)nc(-c8ccccc8)n7)cc6c5)c24)-c2ccccc2-3)c1 ; N#Cc1cccc(-c2ccc3c4c(ccc(-c5cccc6c5ccc5ccc(-c7nc(-c8ccccc8)nc(-c8ccccc8)n7)cc56)c24)-c2ccccc2-3)c1 ; N#Cc1cccc(-c2ccc3c4c(ccc(-c5cccc(-c6cccc(-c7nc(-c8ccccc8)nc(-c8ccccc8)n7)c6)c5)c24)-c2ccccc2-3)c1]
398
-continued
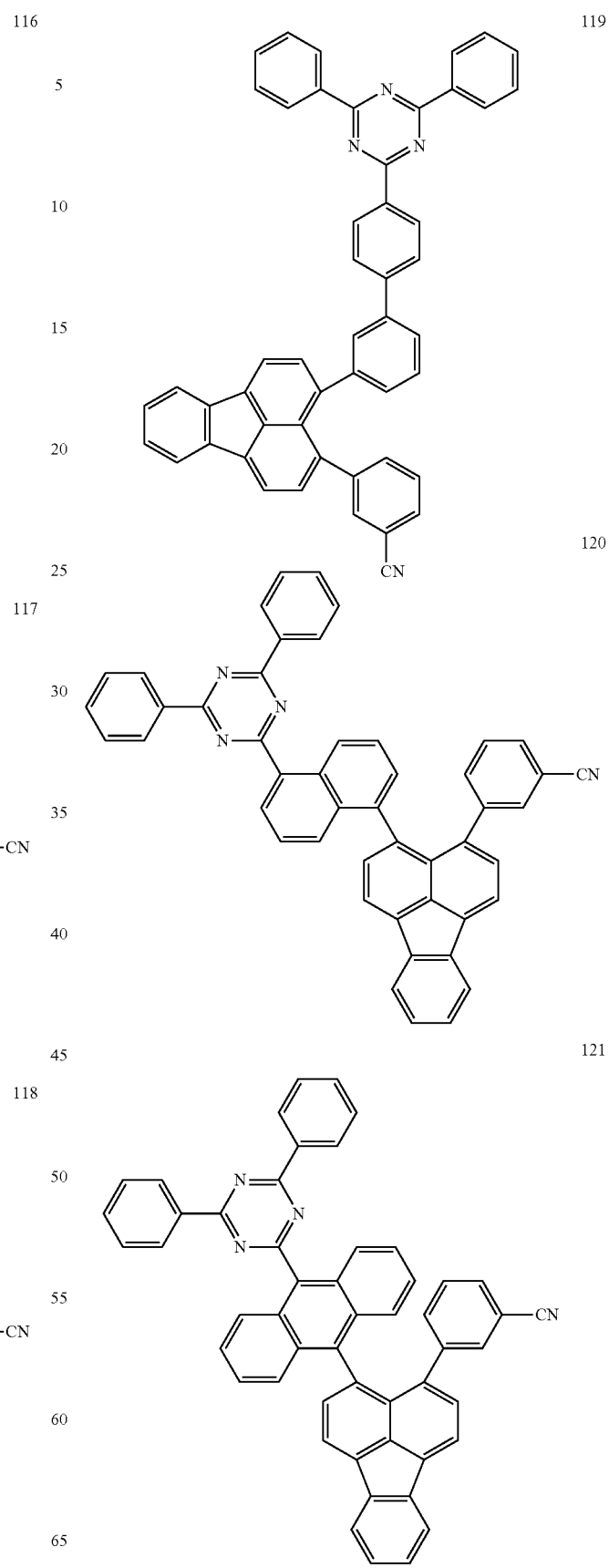

122
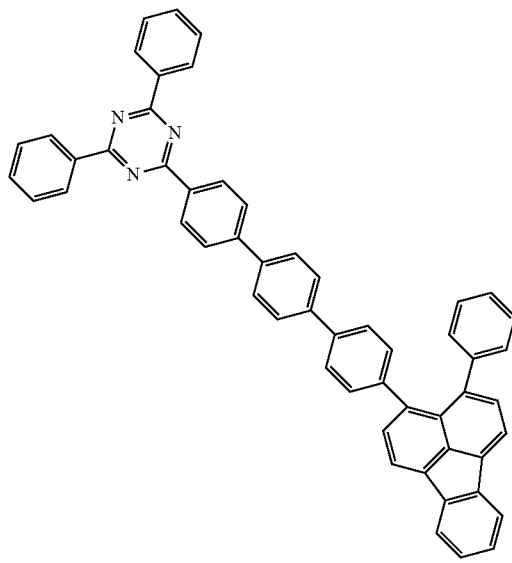
123
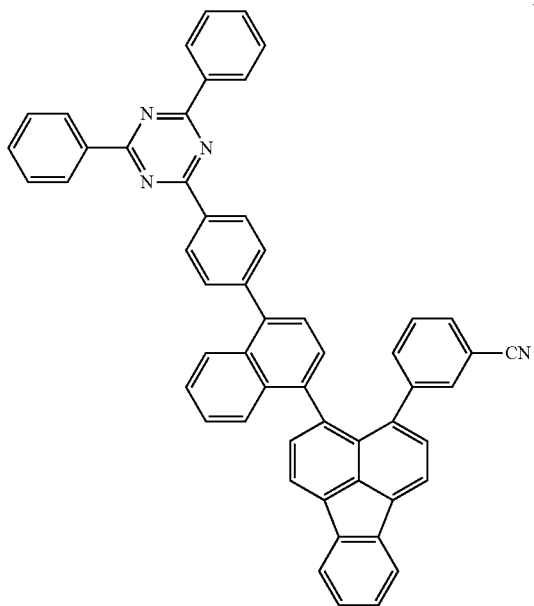
124
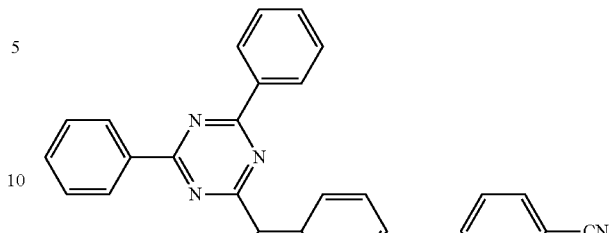
125
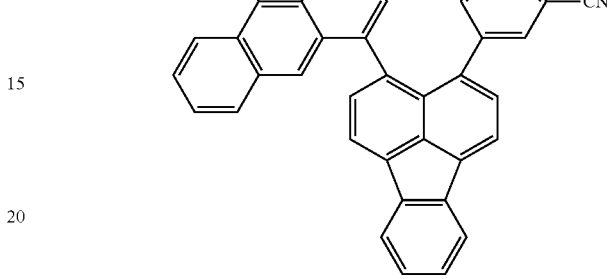
126
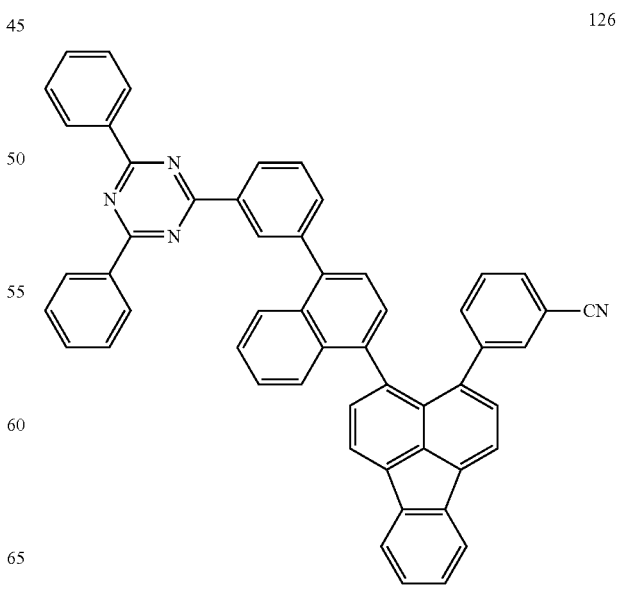

401
-continued
127
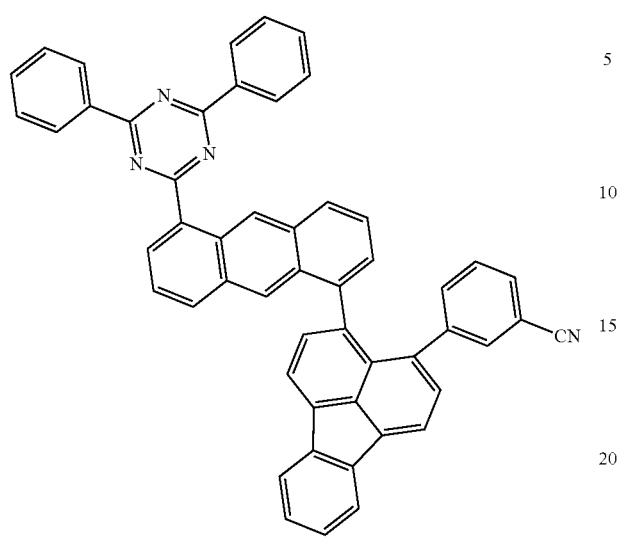
128
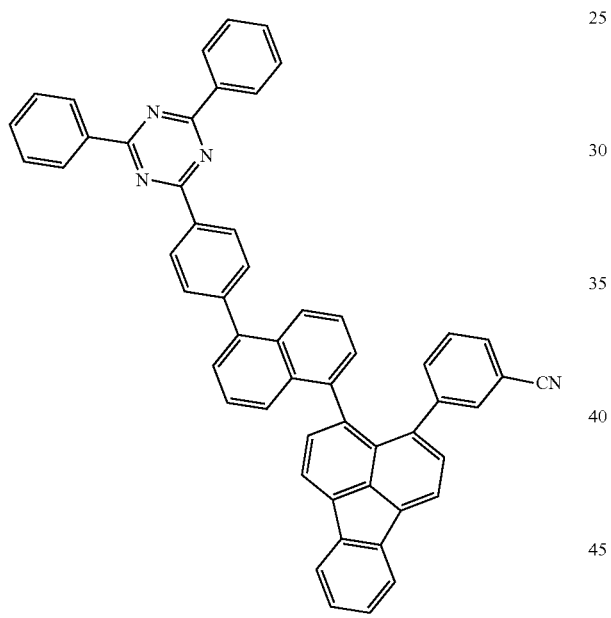
129
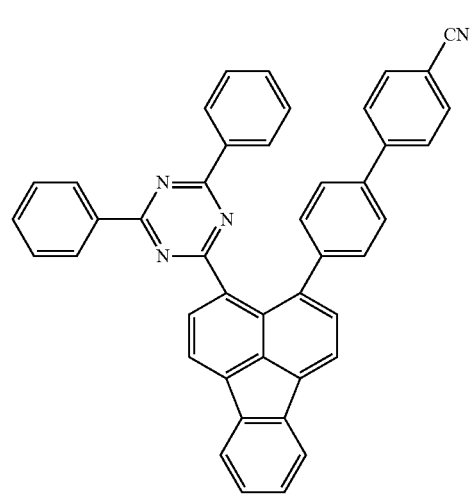
402
-continued
130
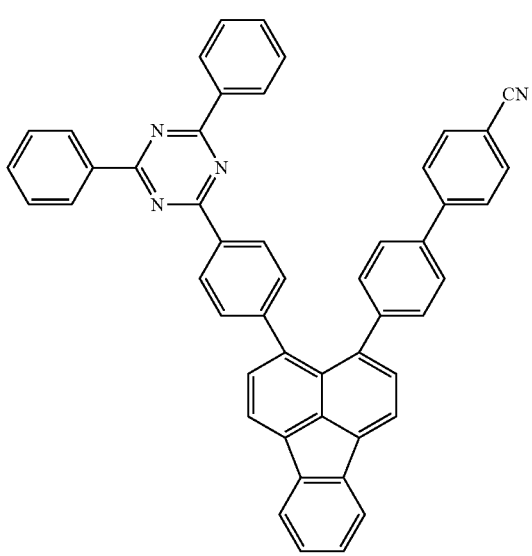
131
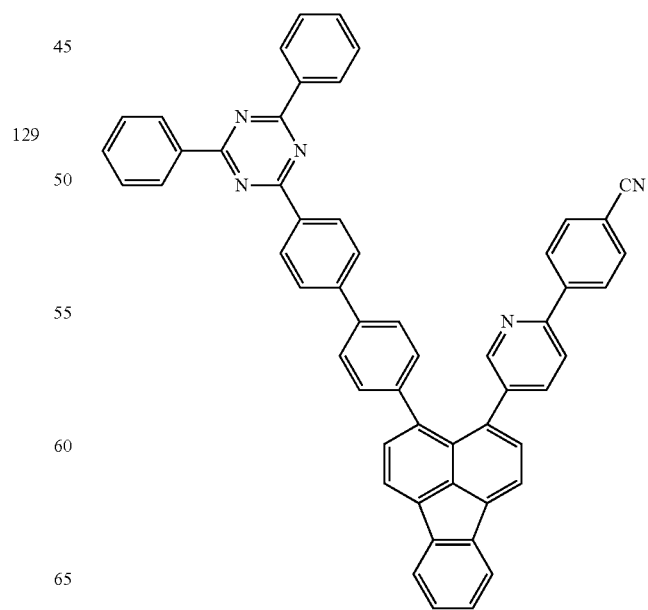

132
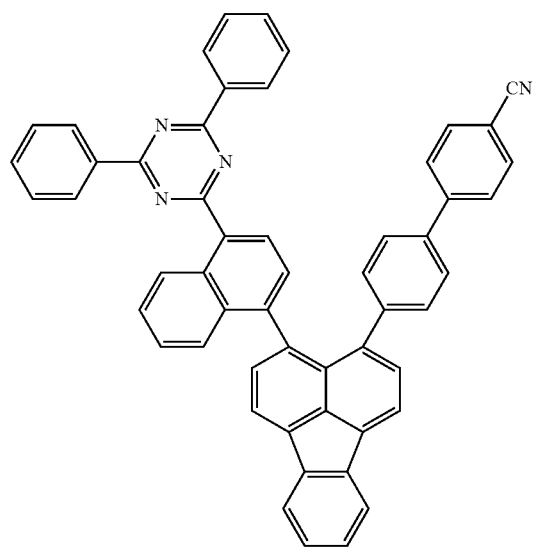
133
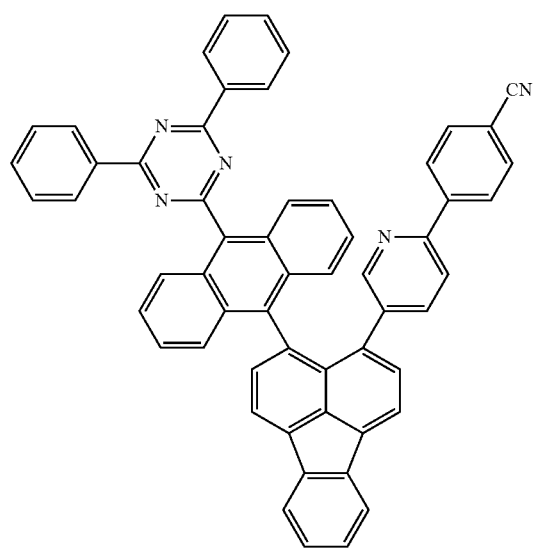
134
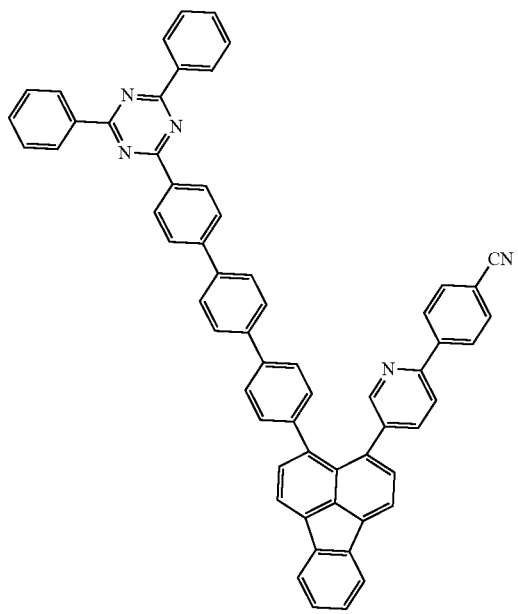
135
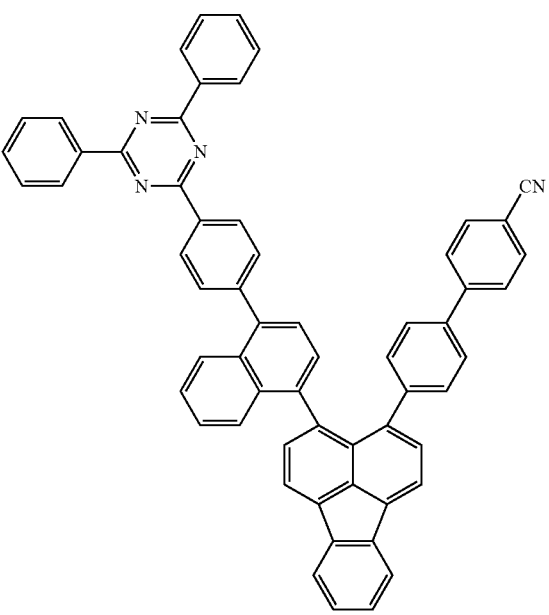

136
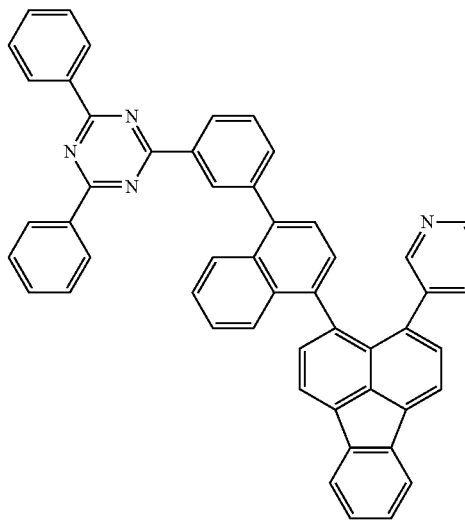
137
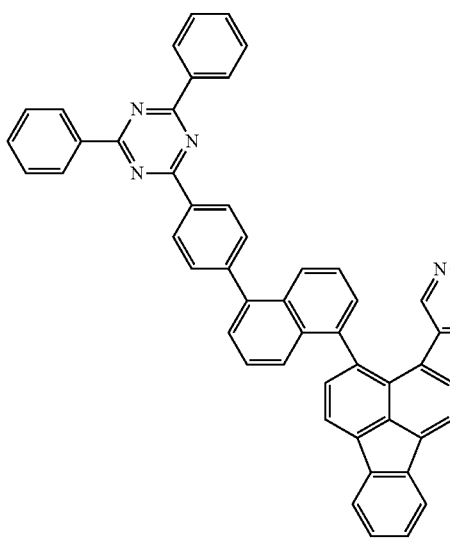
138
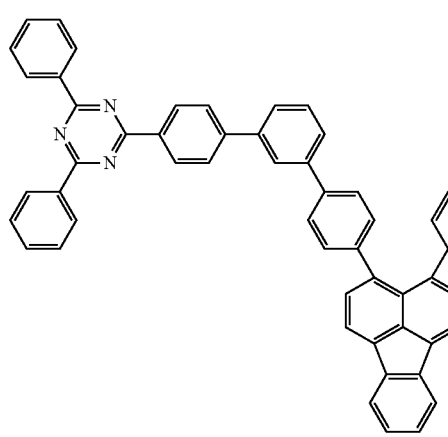
139
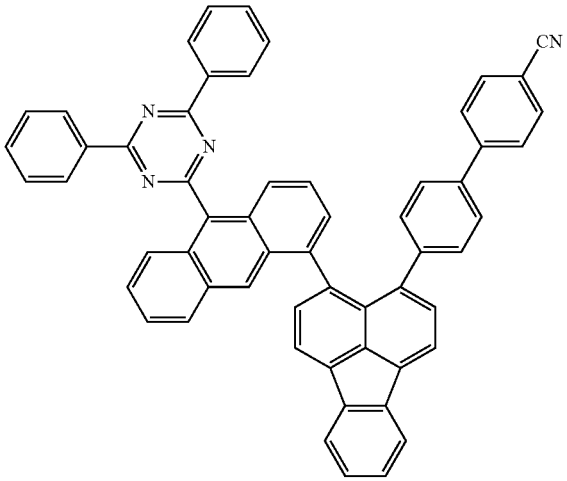
140
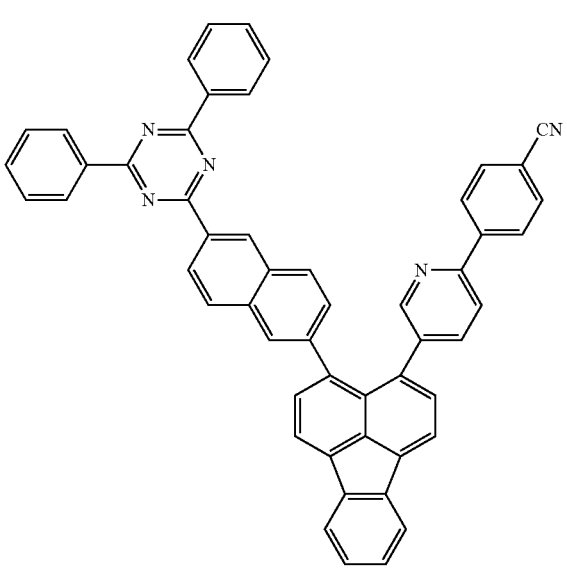
141
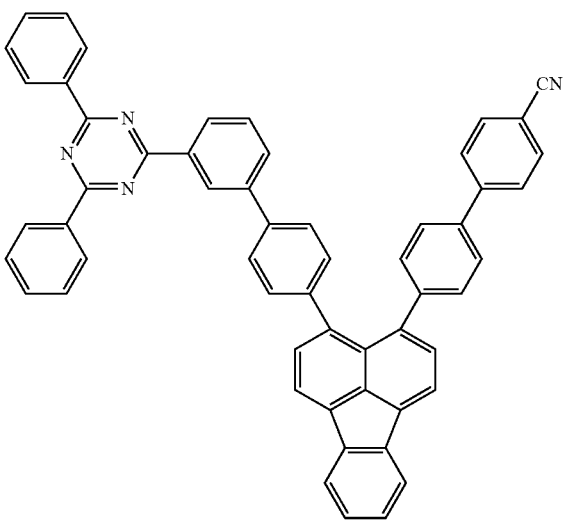

407
-continued
408
-continued
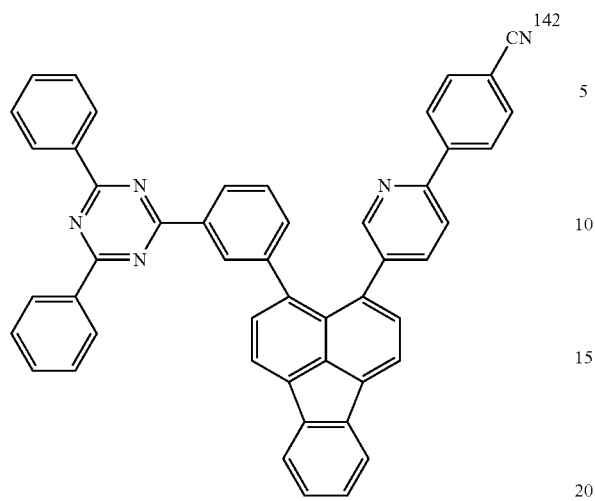
142
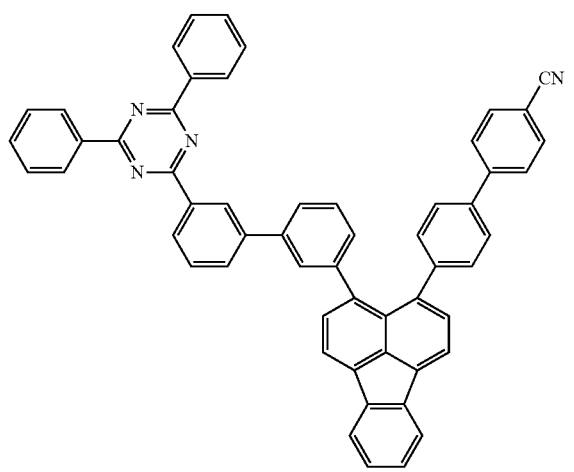
145
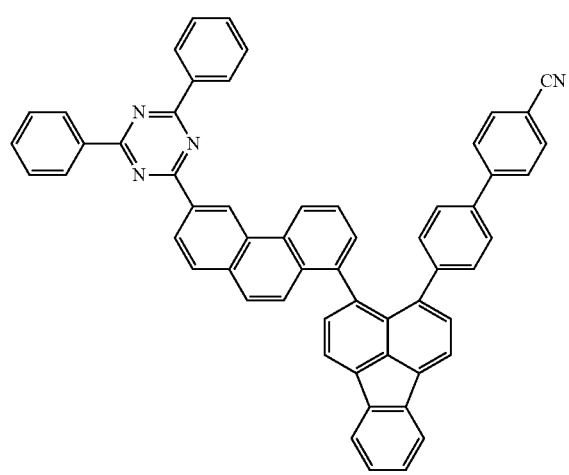
143
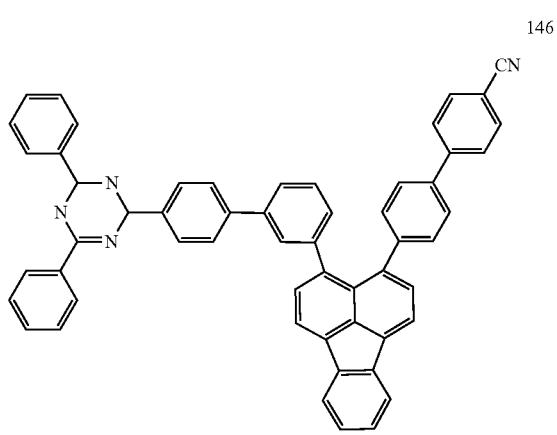
146
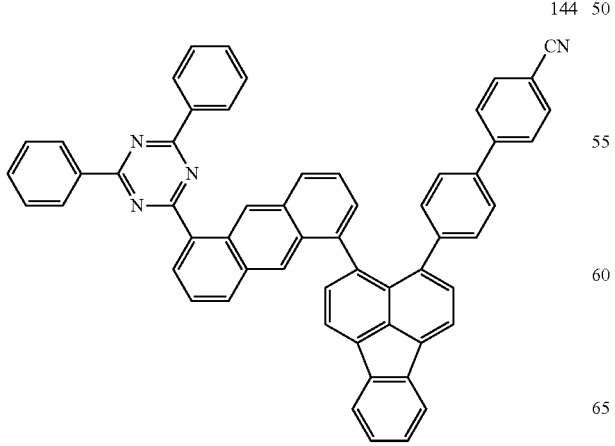
144
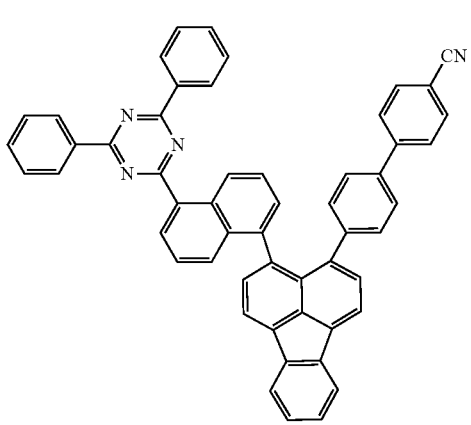
147

-continued
148
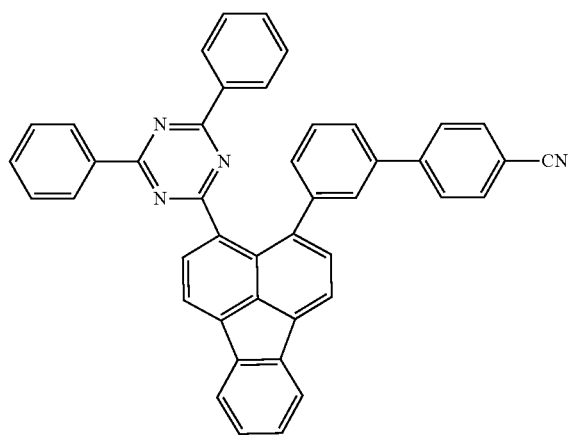
149
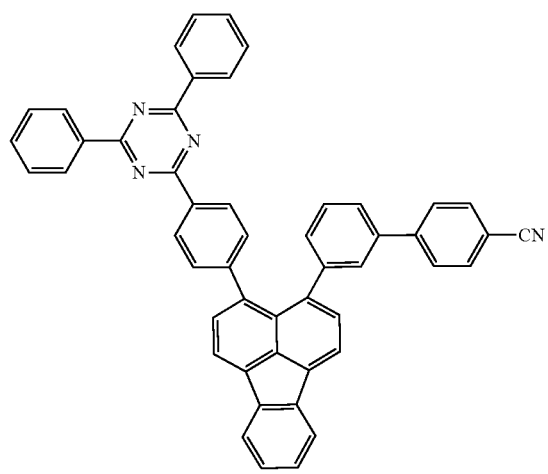
150
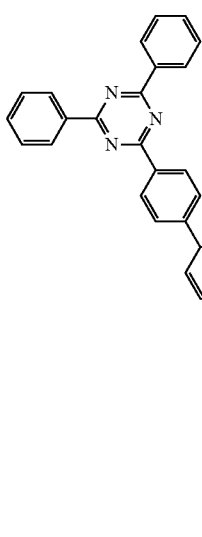
-continued
151
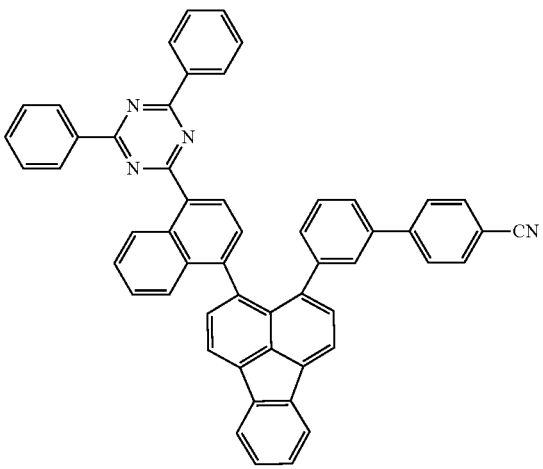
152
153

411
-continued
154
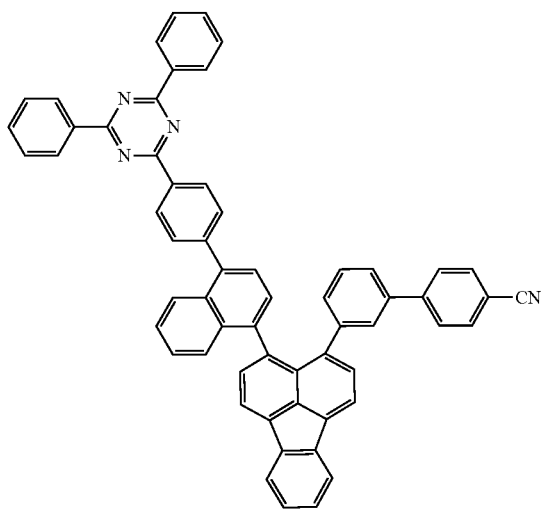
155
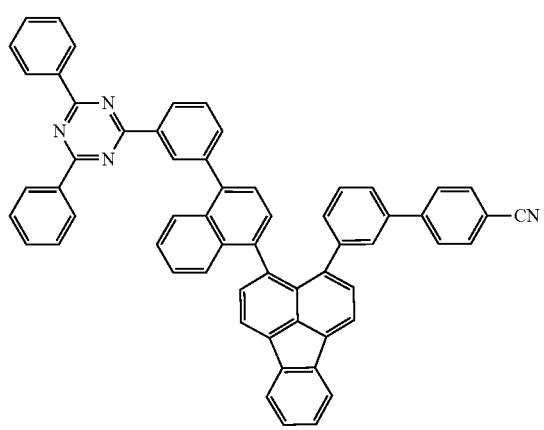
156
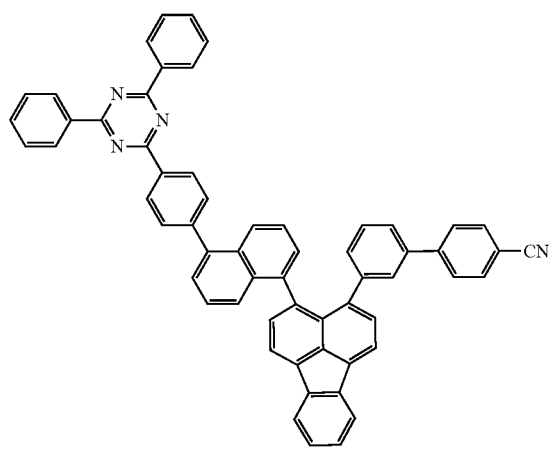
412
-continued
157
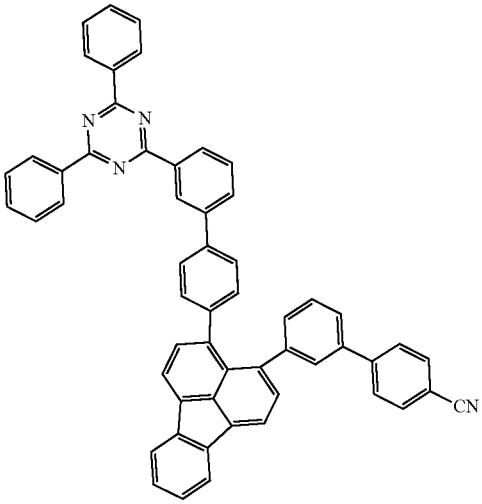
158
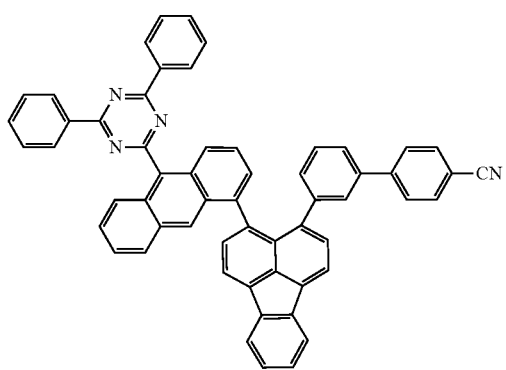
159
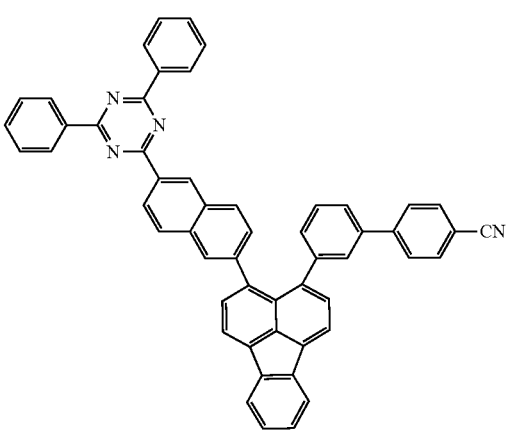

413
-continued
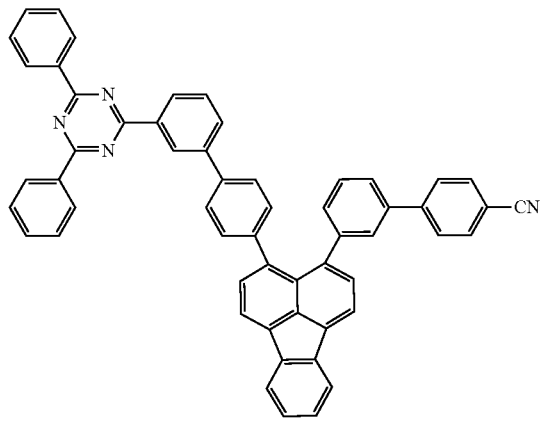
160
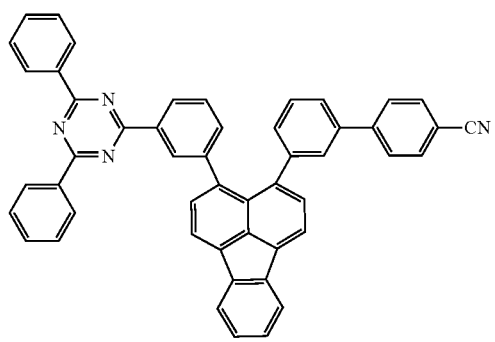
161
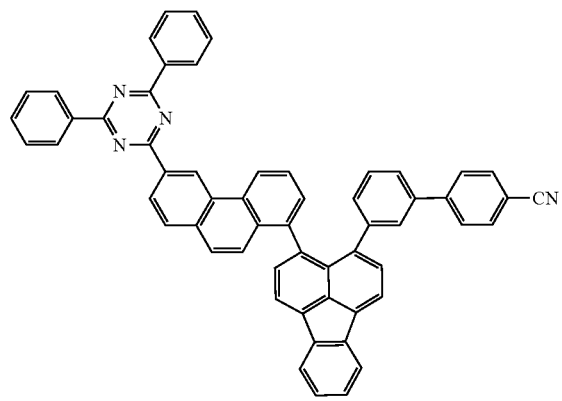
162
414
-continued
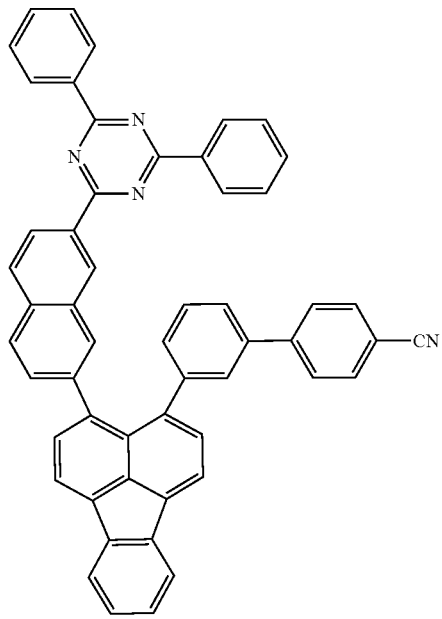
163
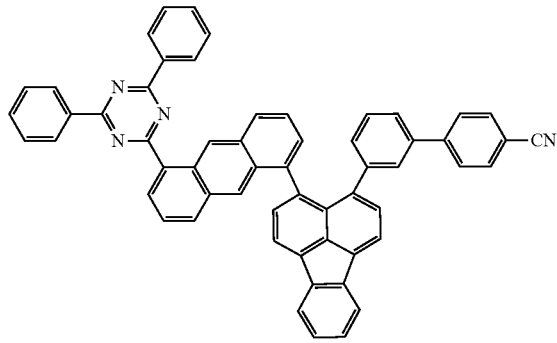
164
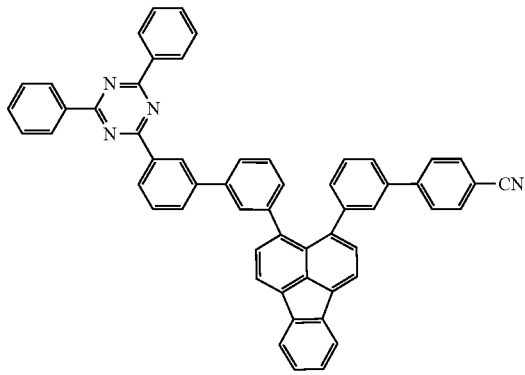
165

415
-continued
166
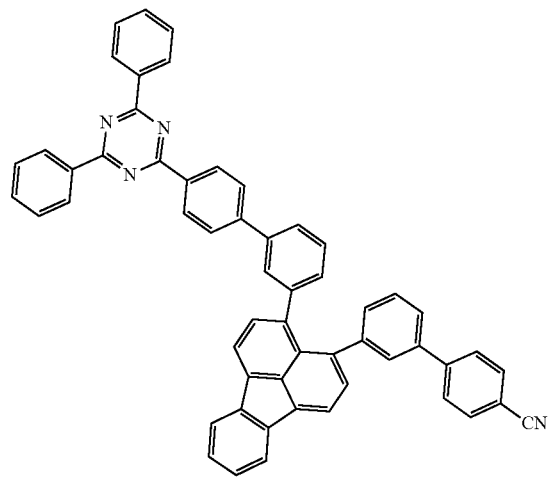
167
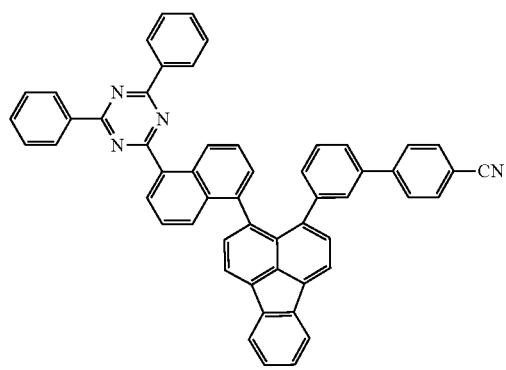
168
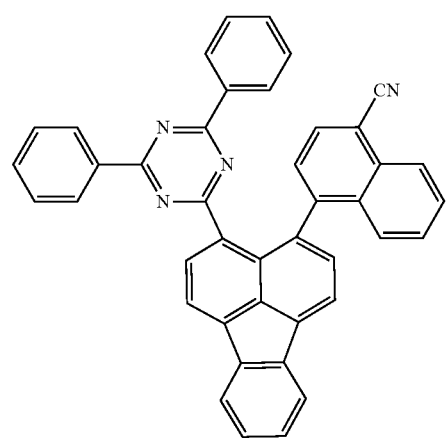
416
-continued
169
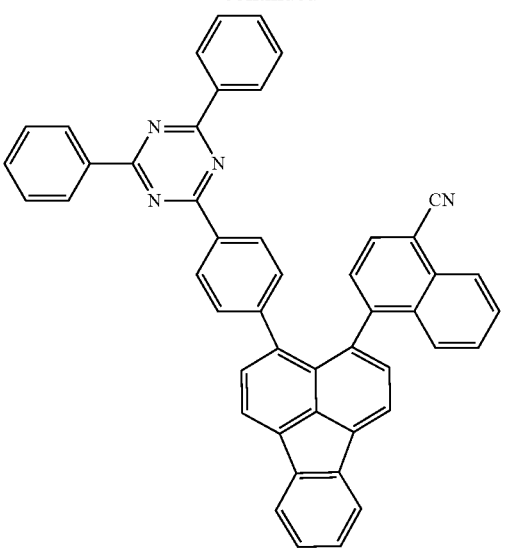
170
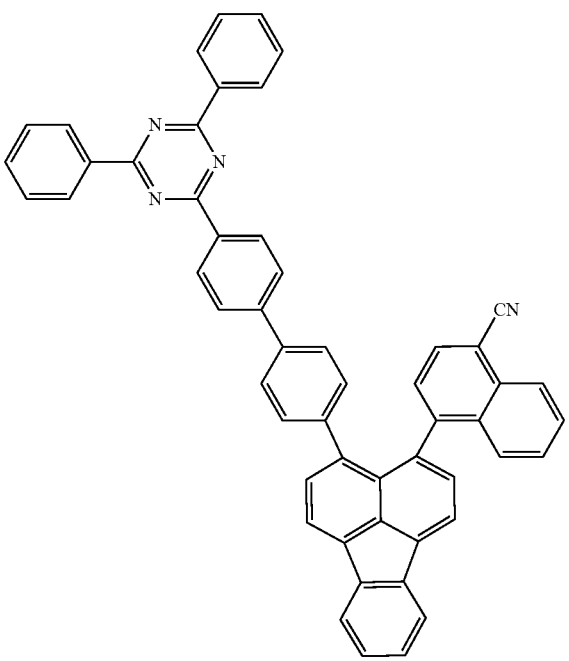

417
-continued
171
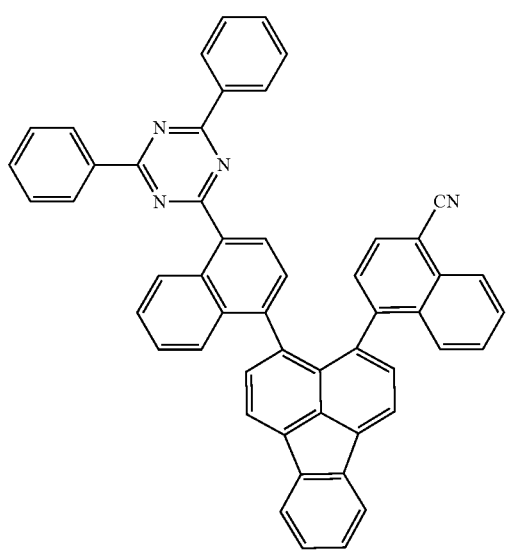
172
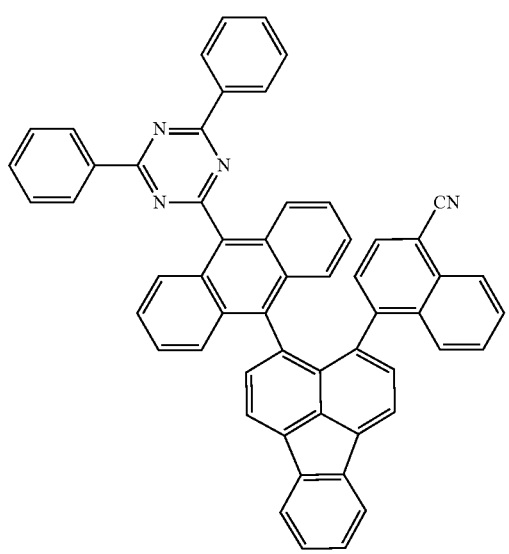
418
-continued
173
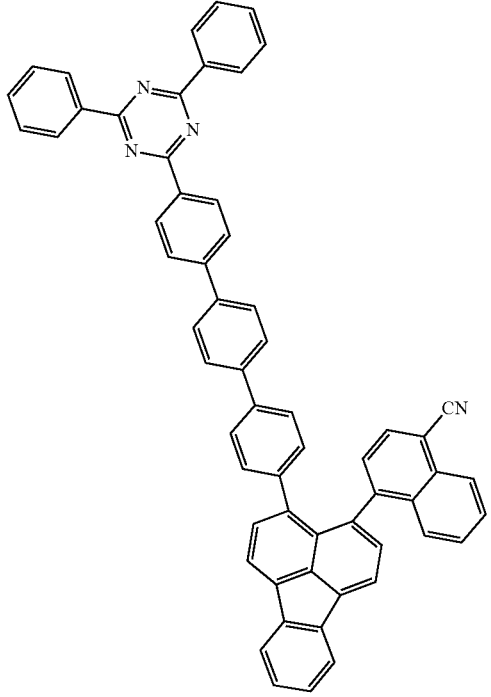
174
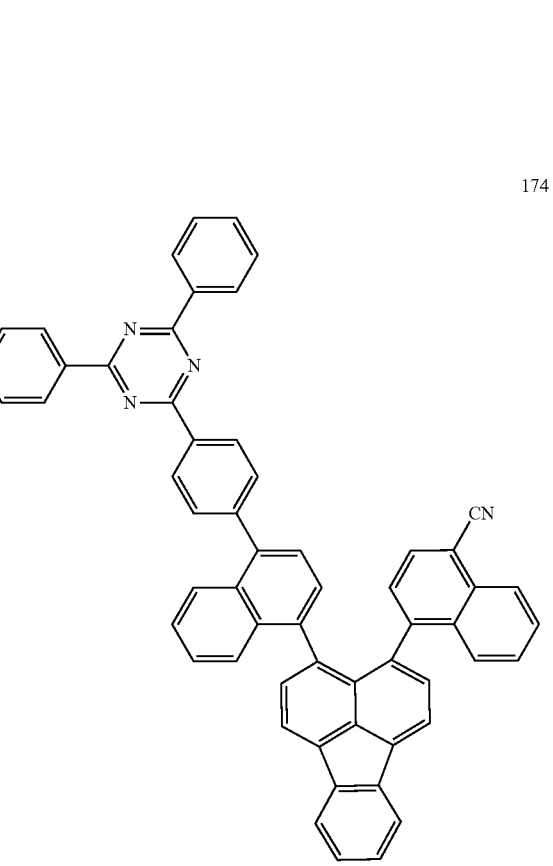

-continued
175
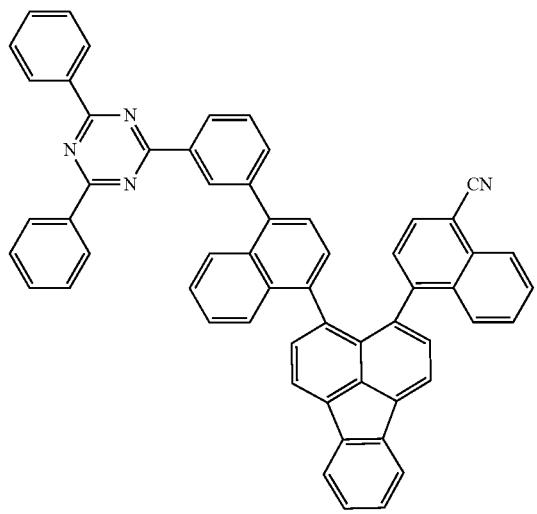
176
177
-continued
178
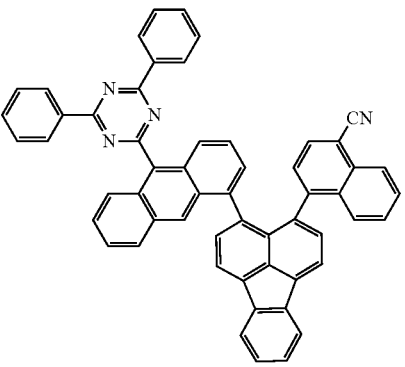
179
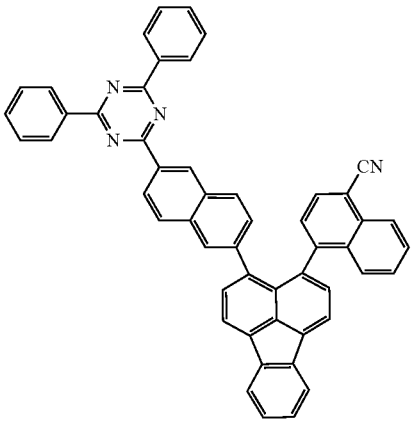
180
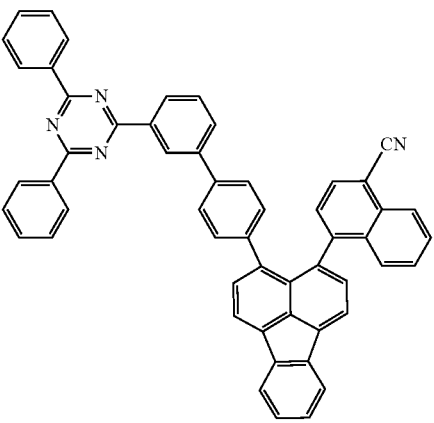
181
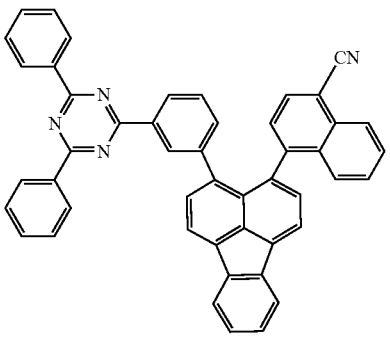

182
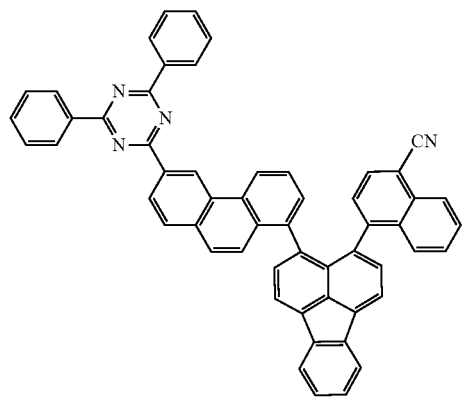
183
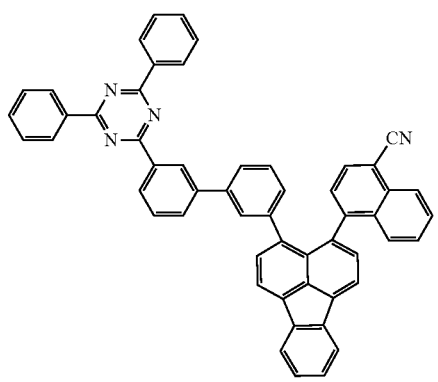
184
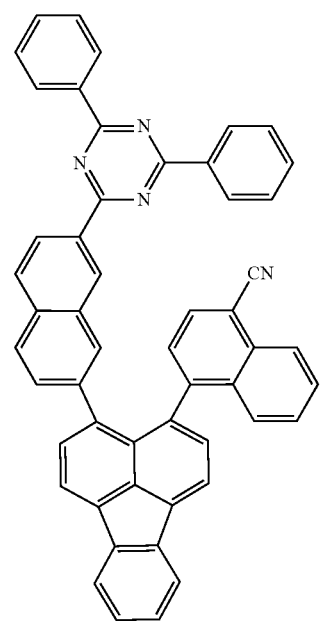
185
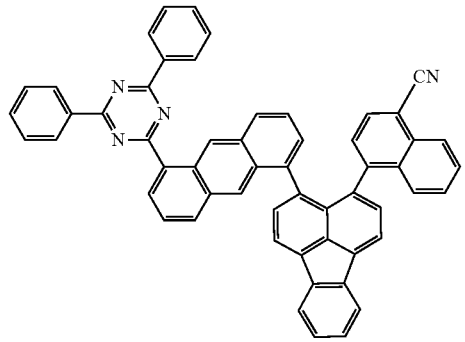
186
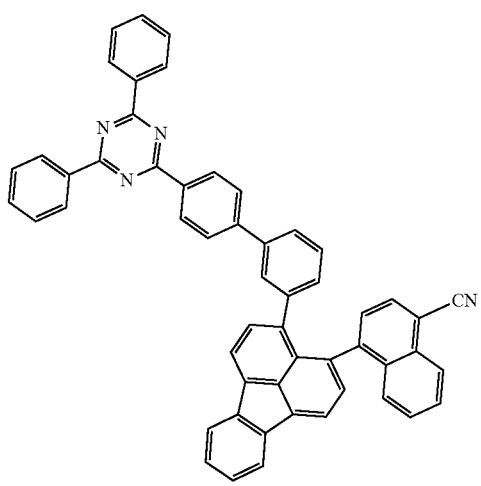
187
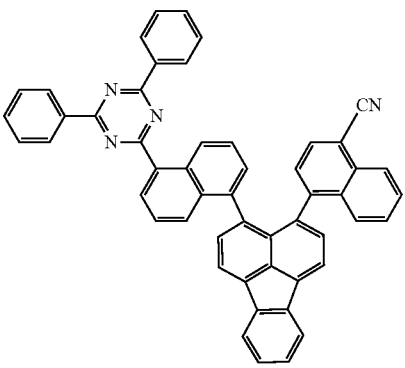
188
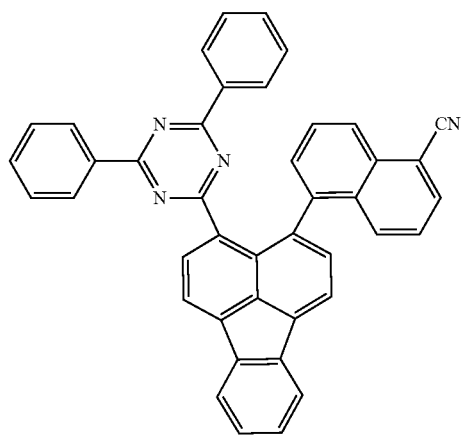

189
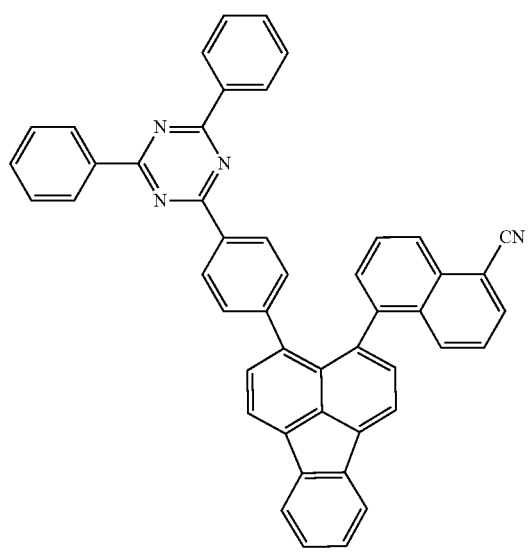
190
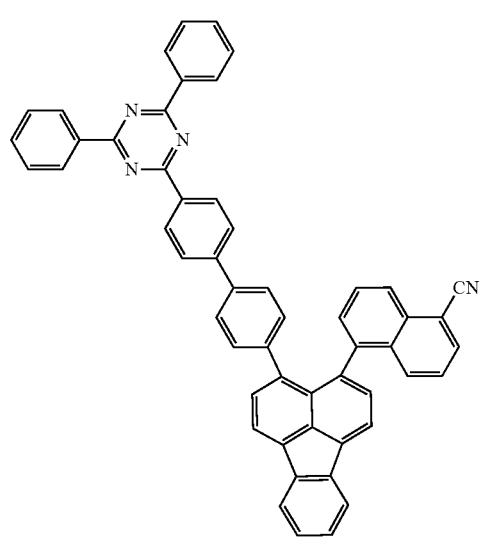
191
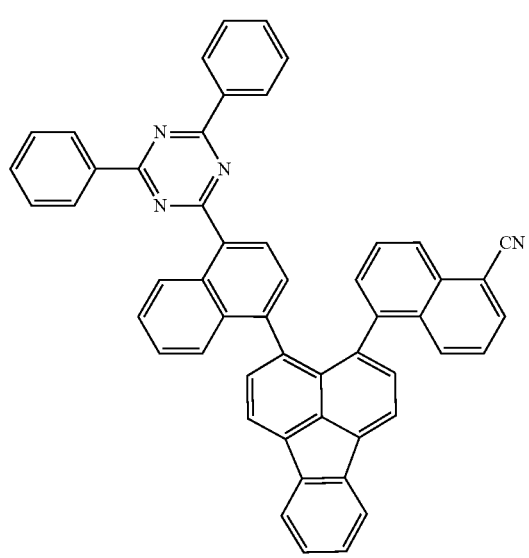
192
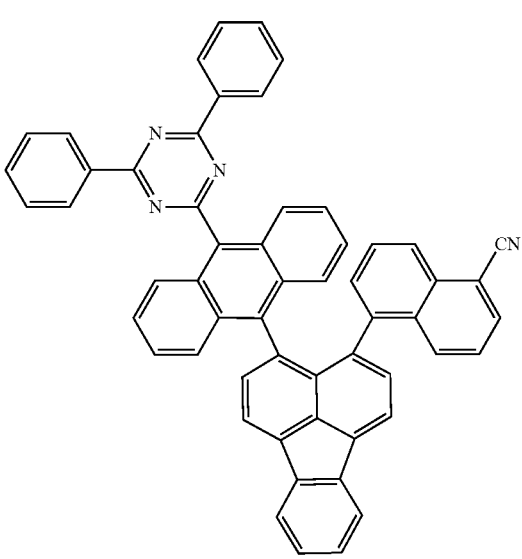
193
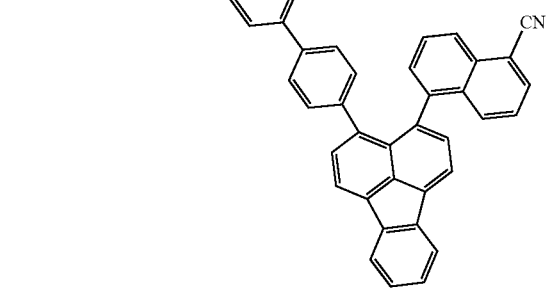

-continued
194
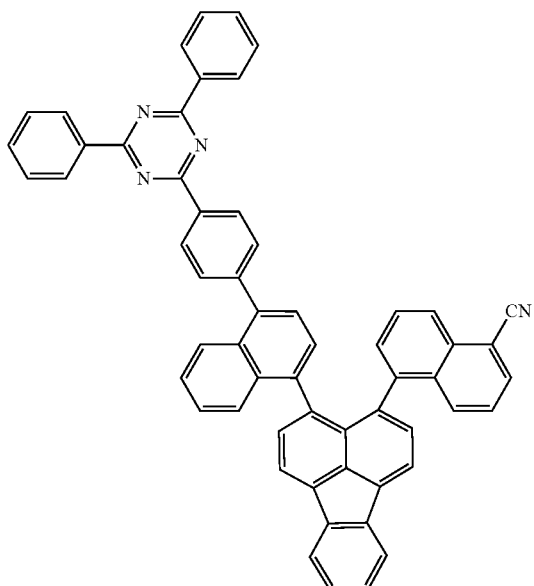
195
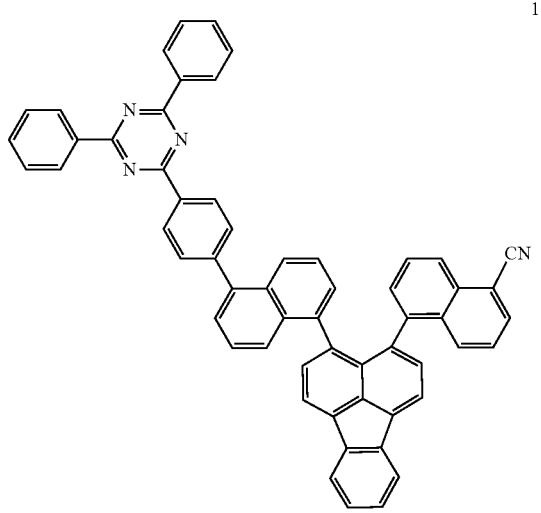
196
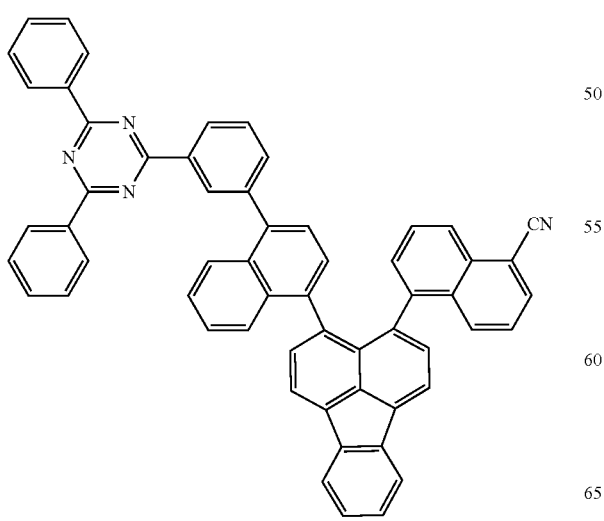
-continued
197
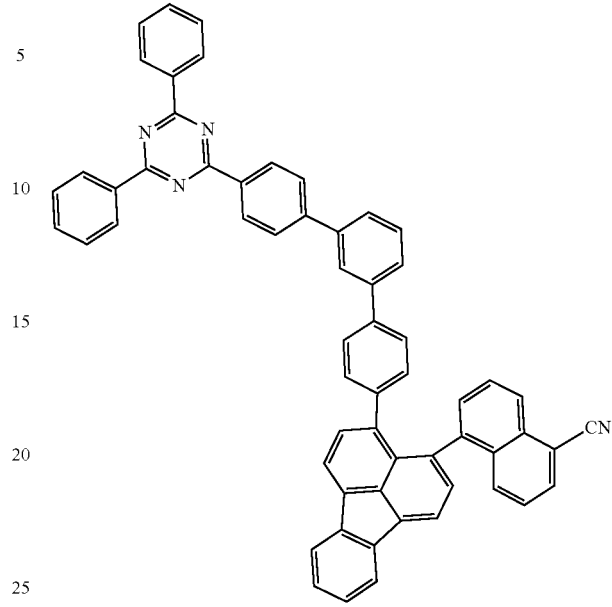
198
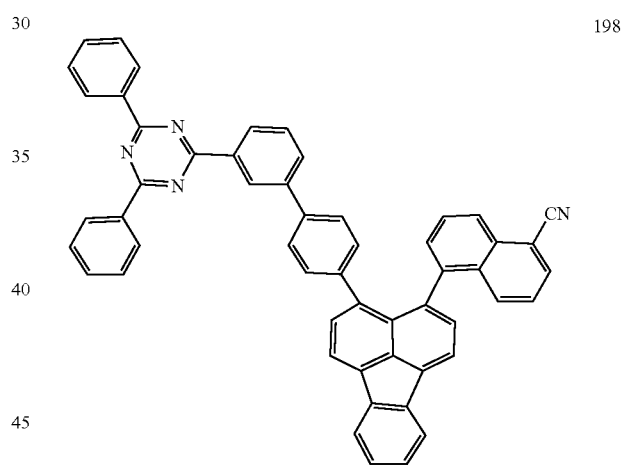
199
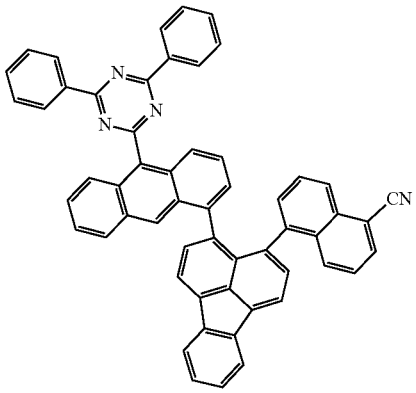

427
-continued
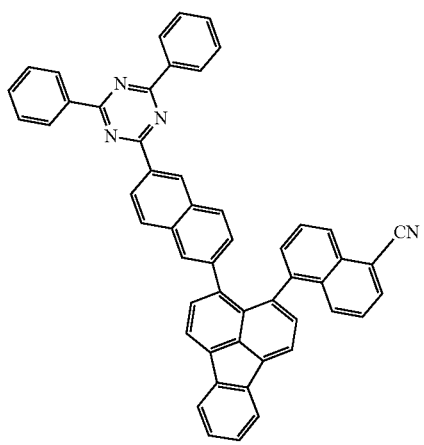
200
201
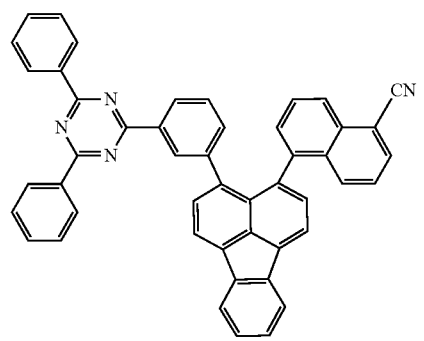
202
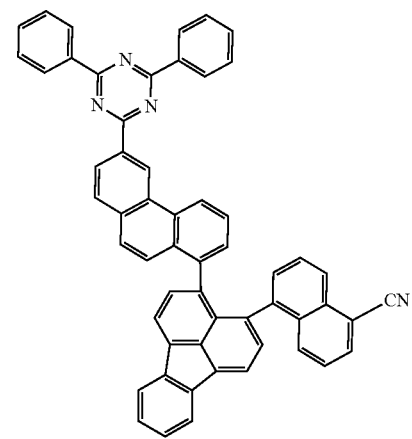
428
-continued
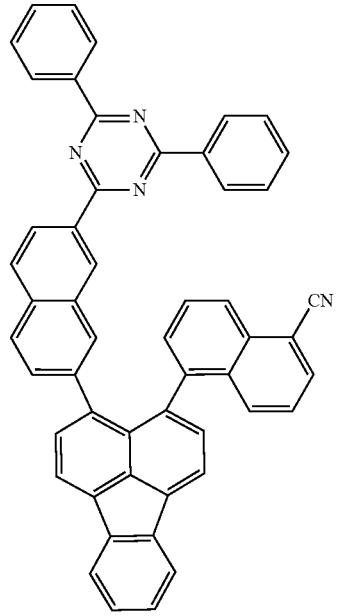
203
204
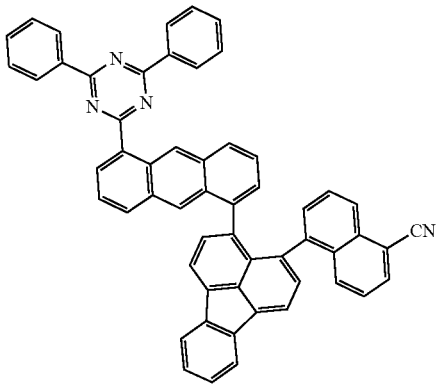
205
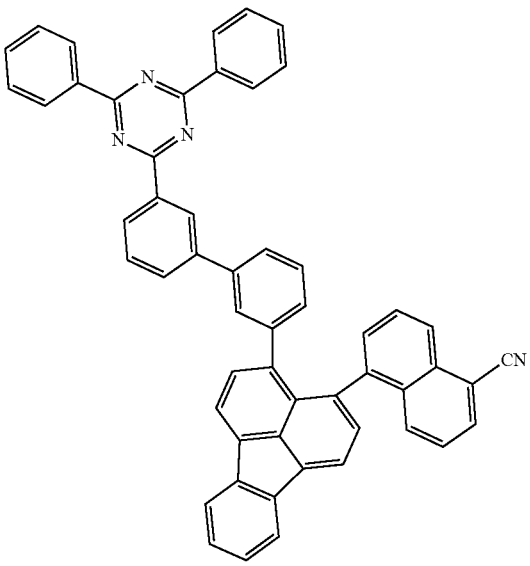

429
191
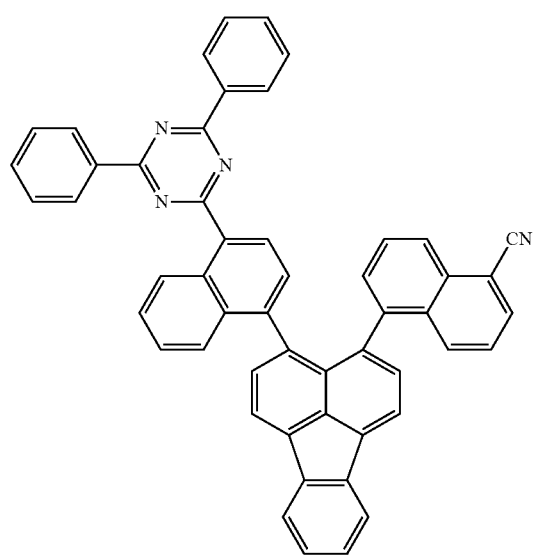
192
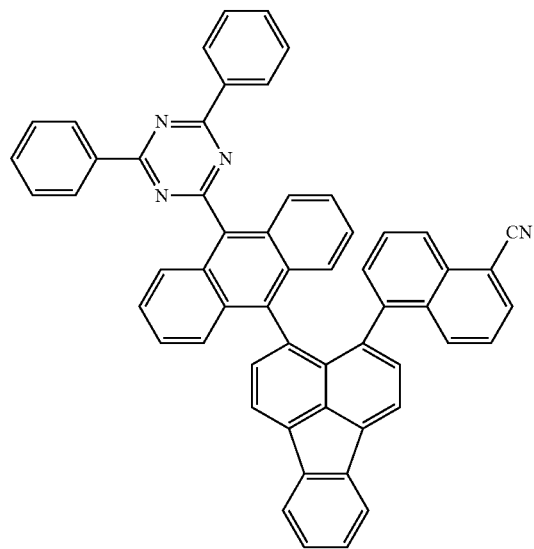
430
-continued
193
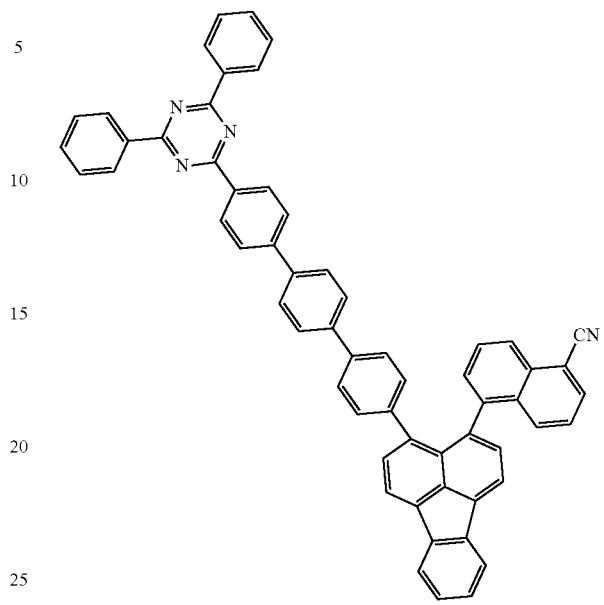
194
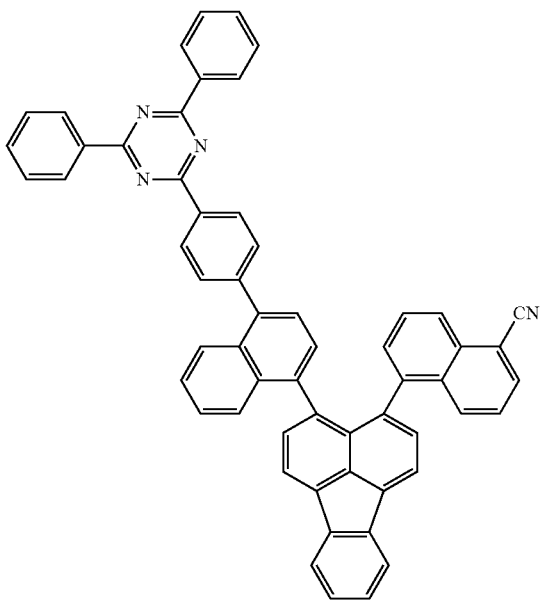

195
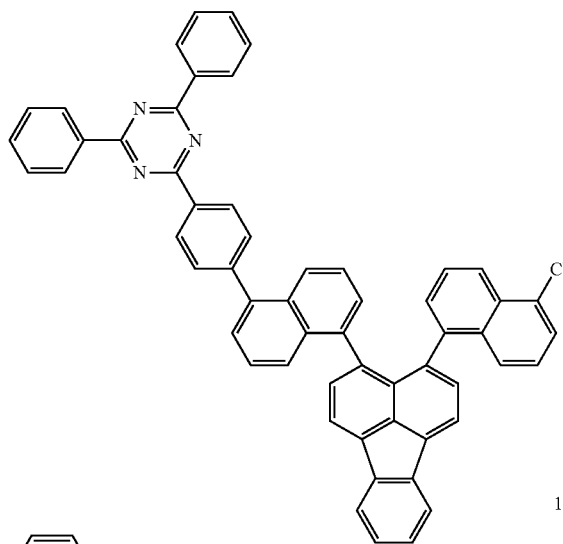
196
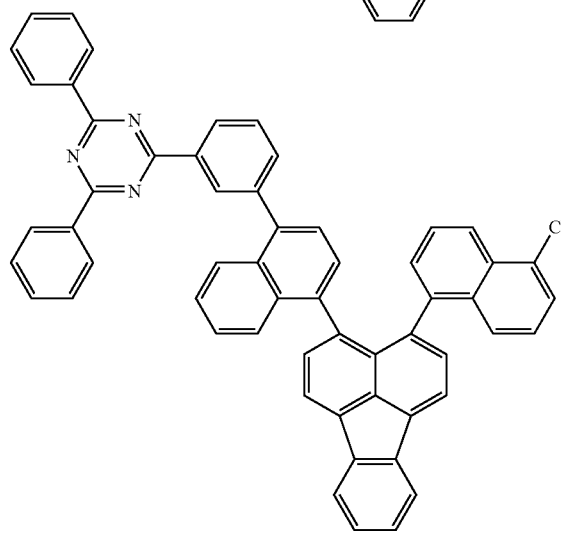
197
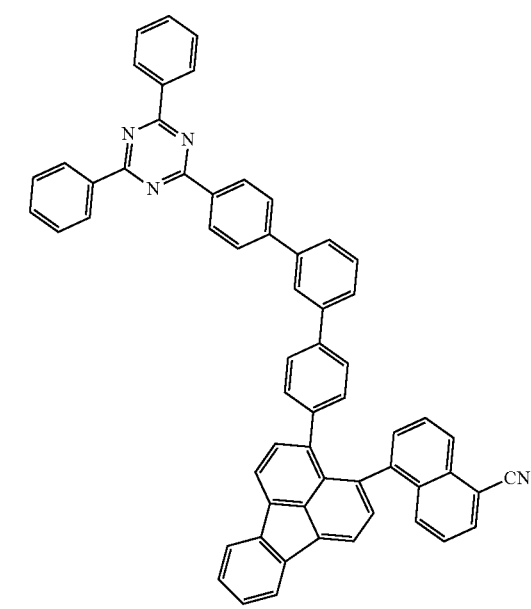
198
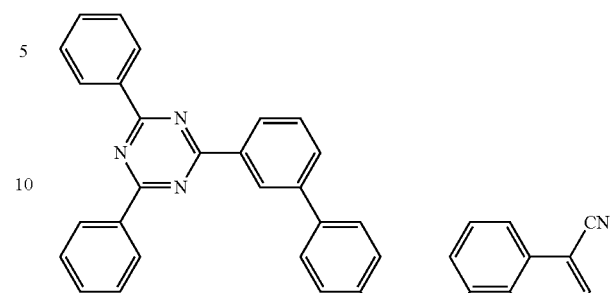
199
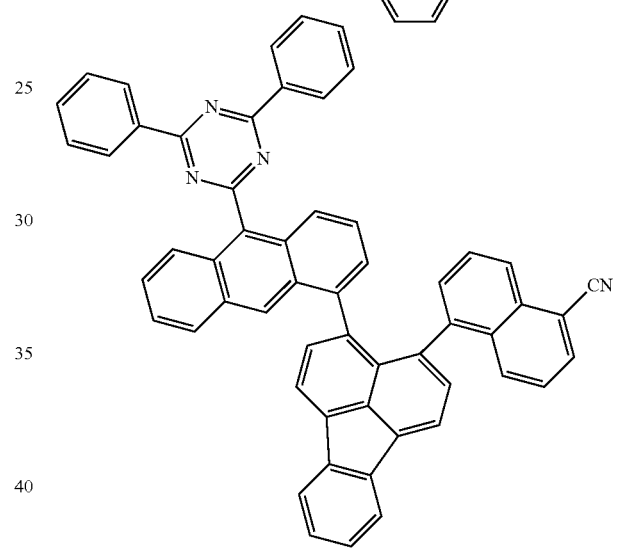
200
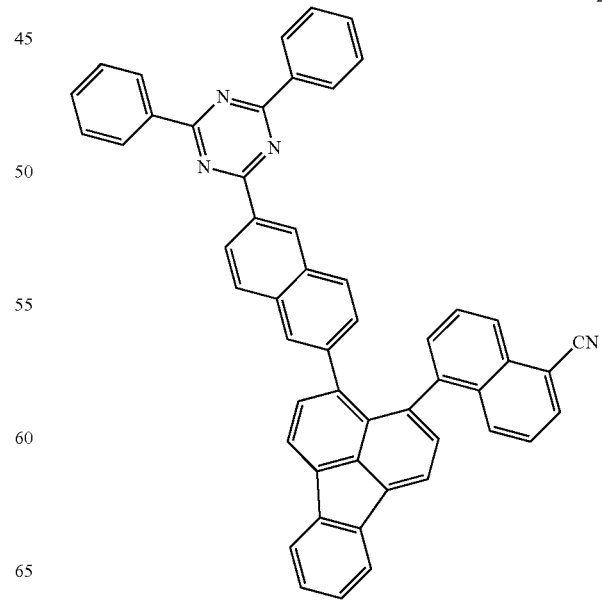

433
-continued
201
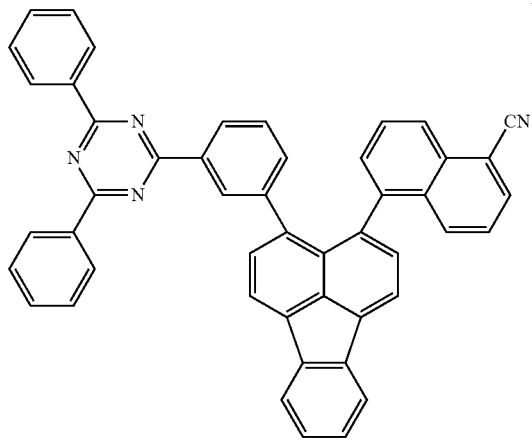
202
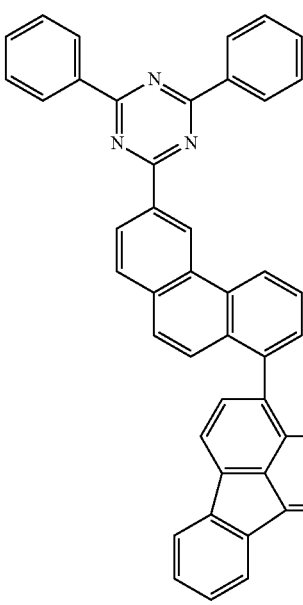
203
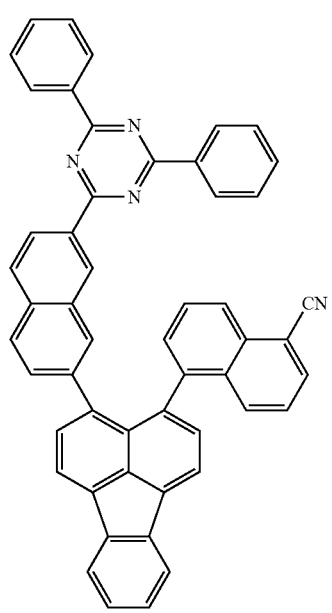
434
-continued
204
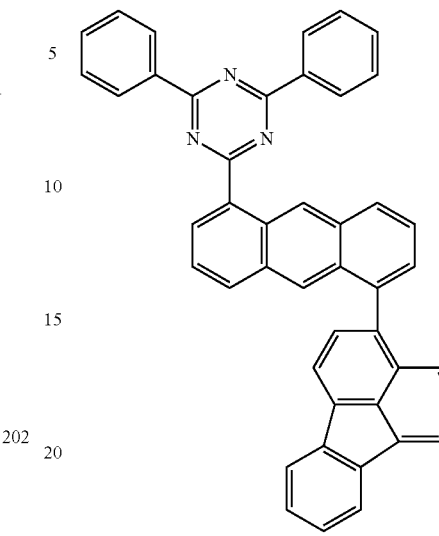
205
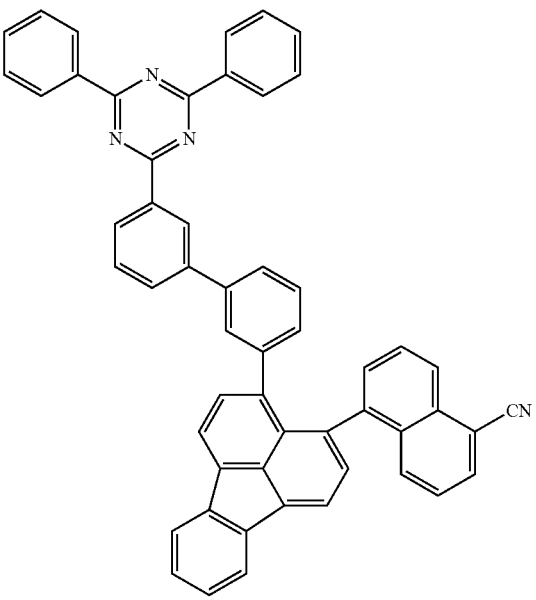

435
-continued
206
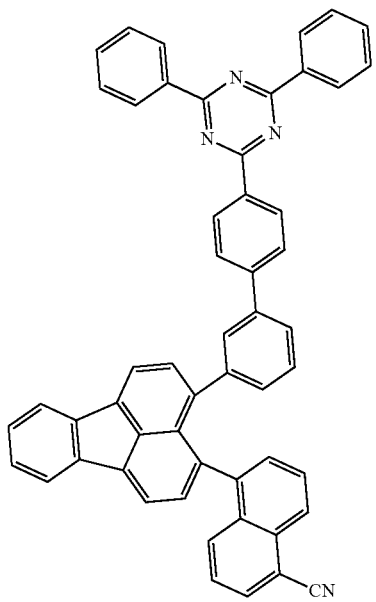
436
-continued
209
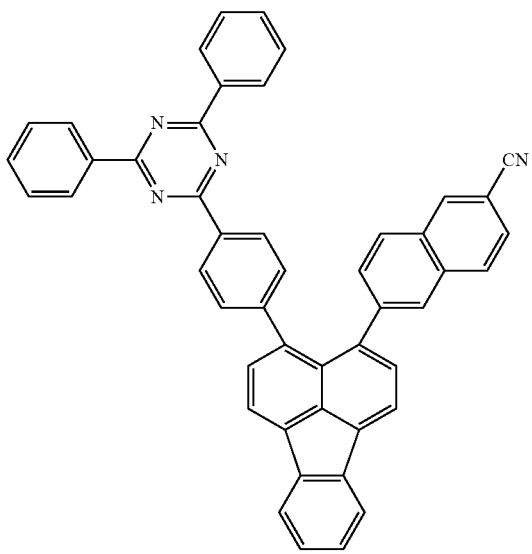
207
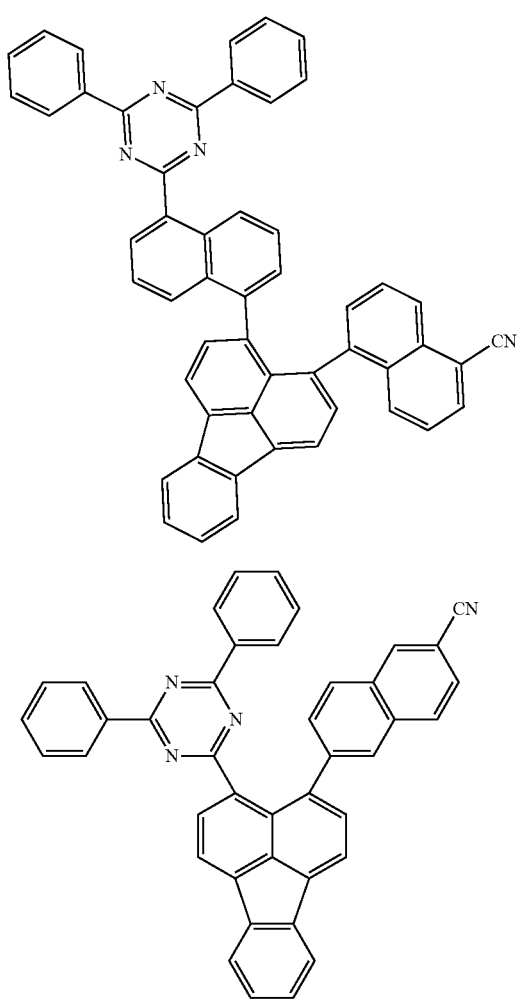
208
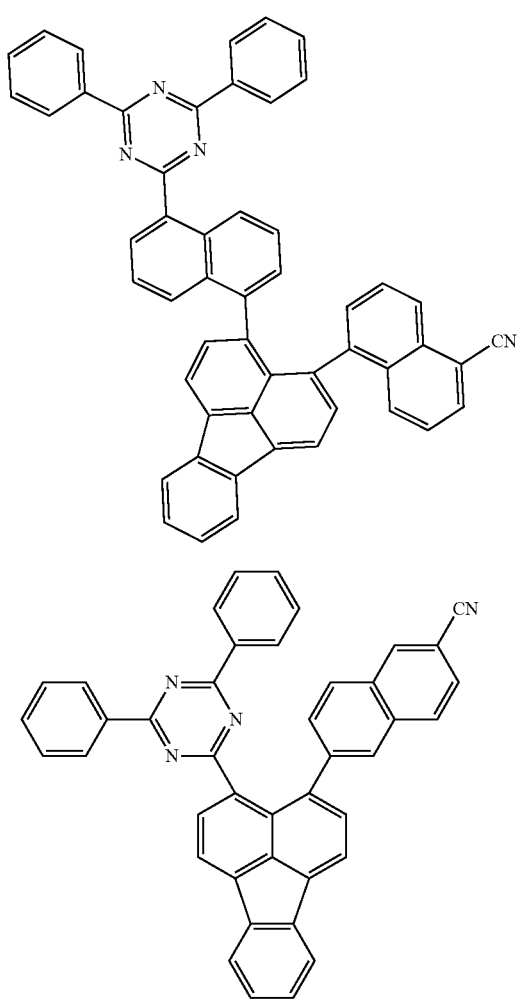
210
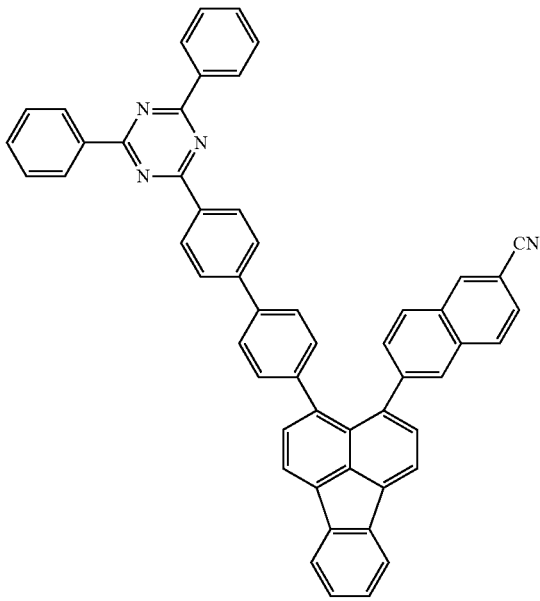

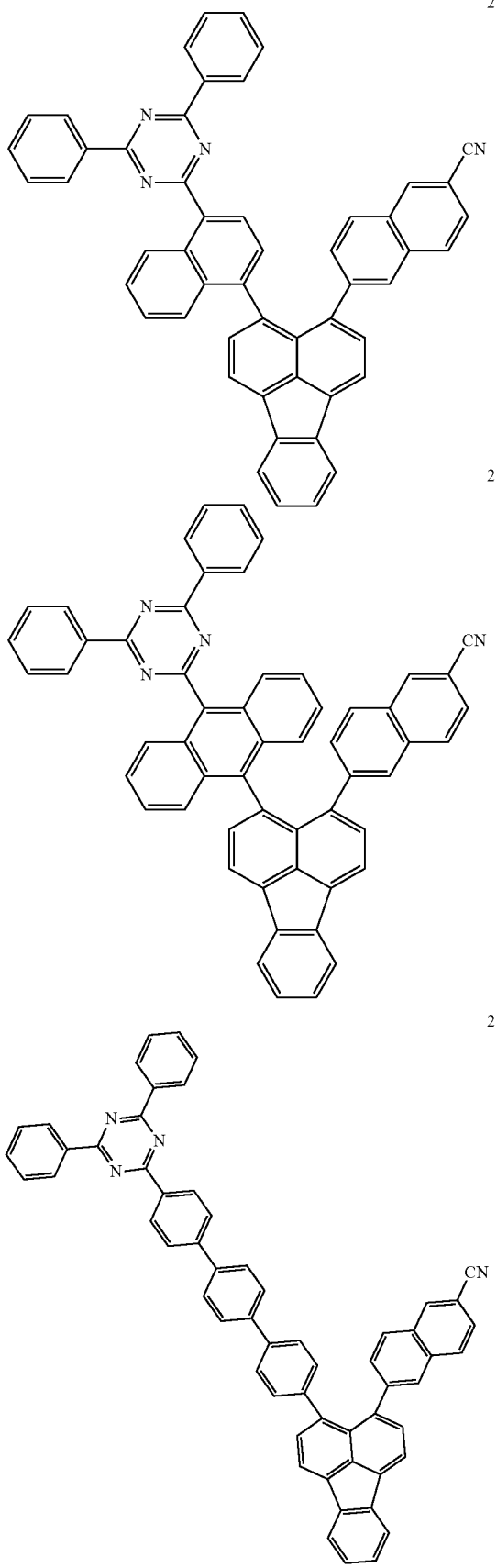
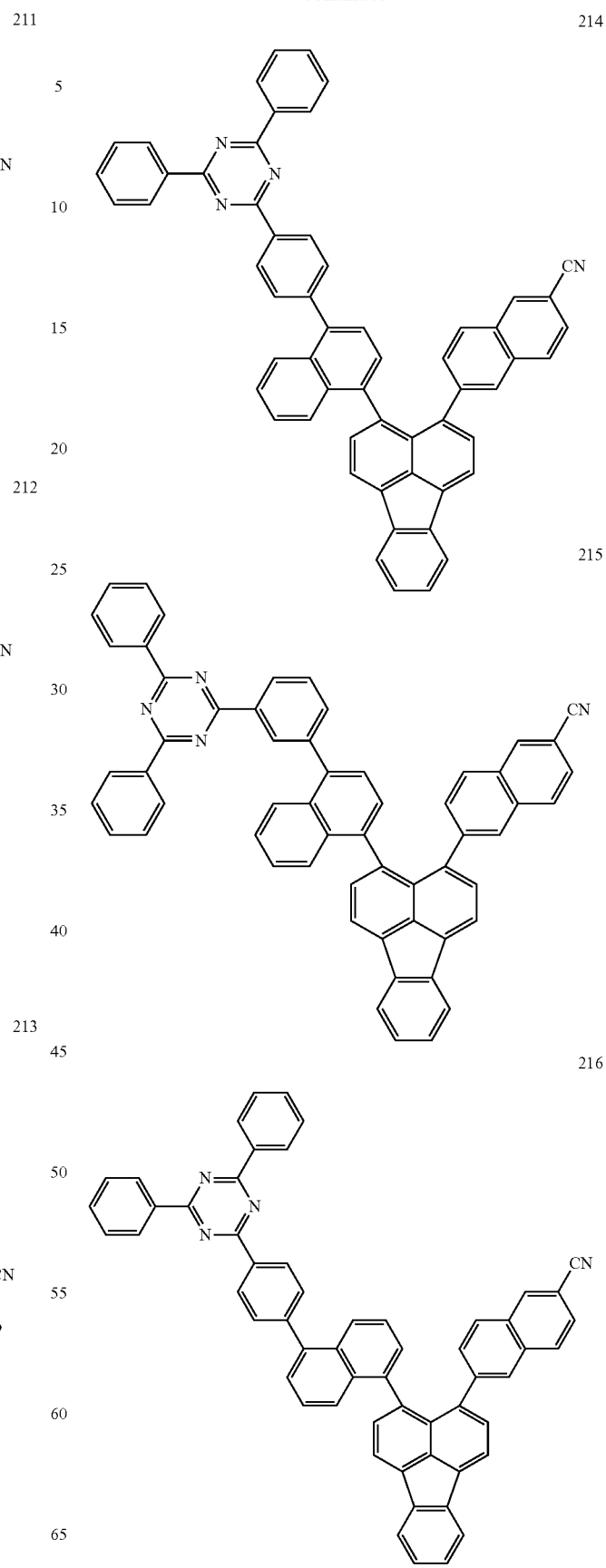

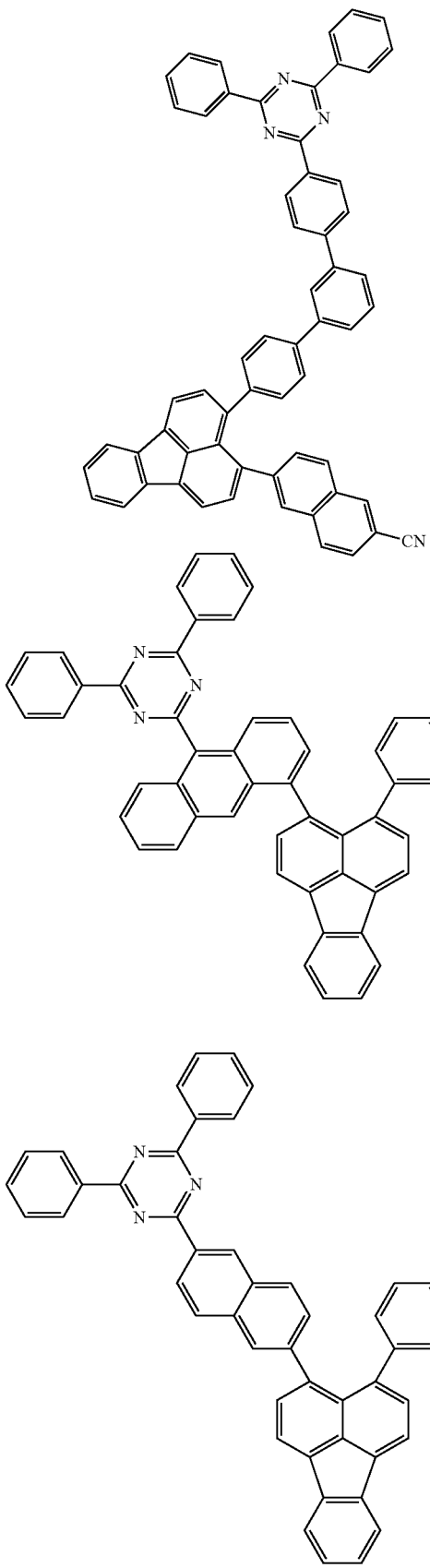
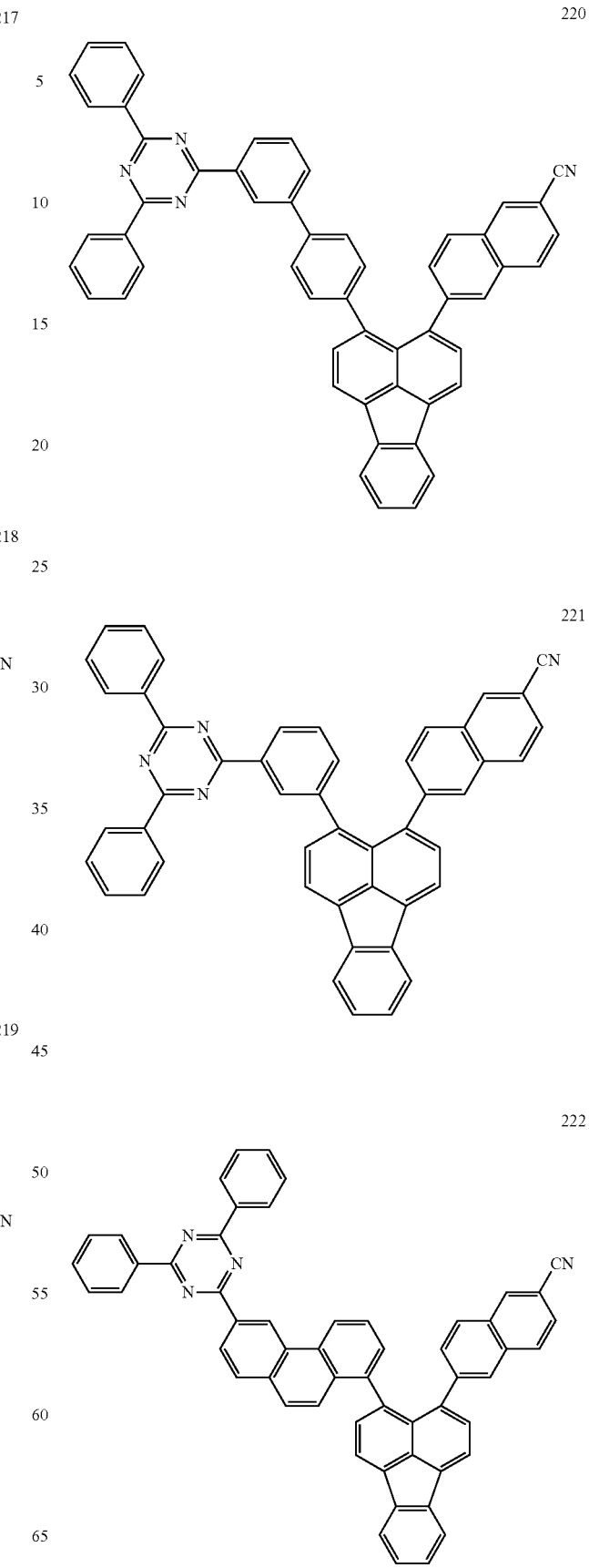

-continued
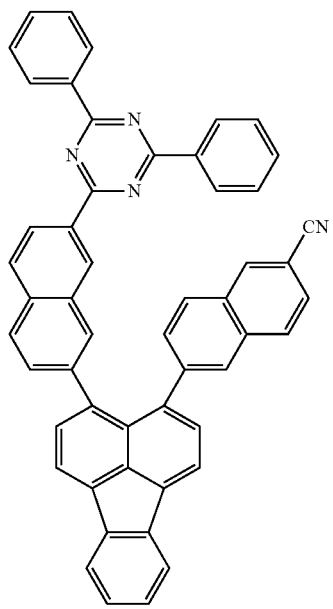
223
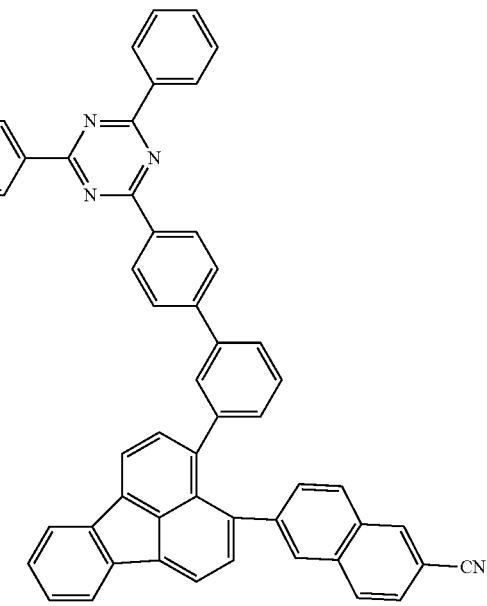
226
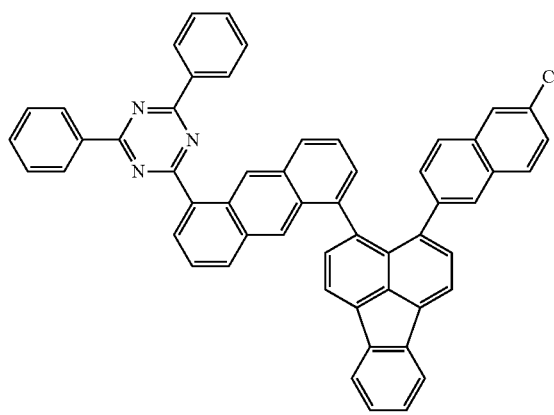
224
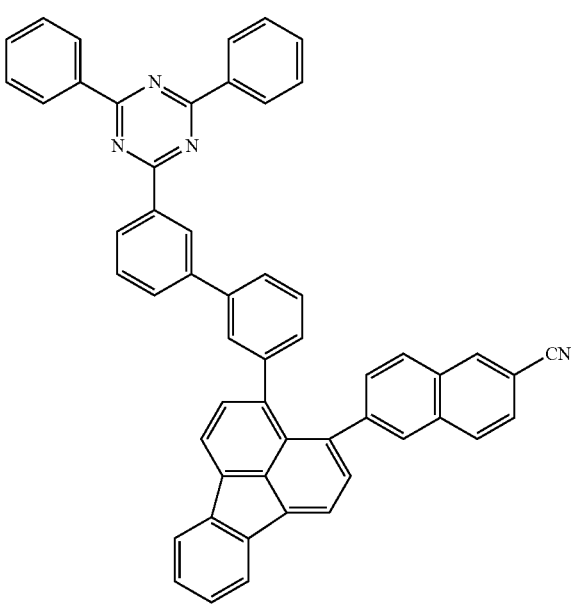
225
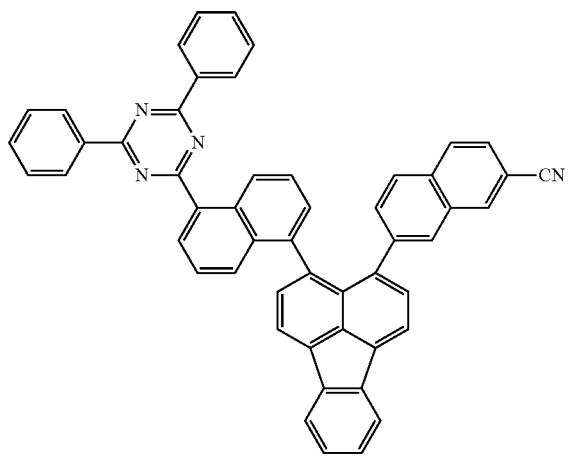
227
228

443
-continued
229
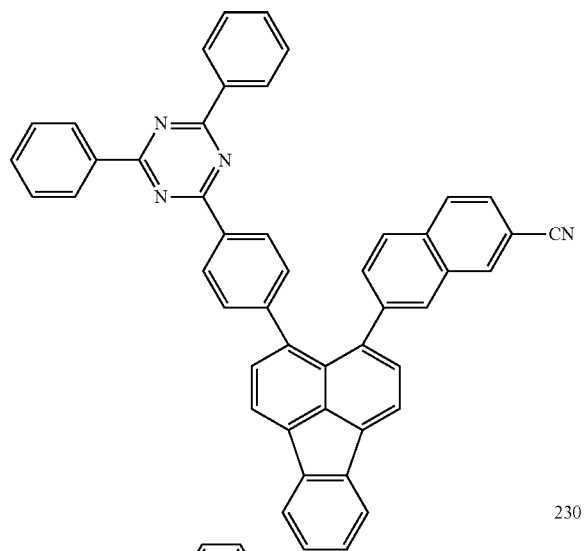
230
231
444
-continued
232
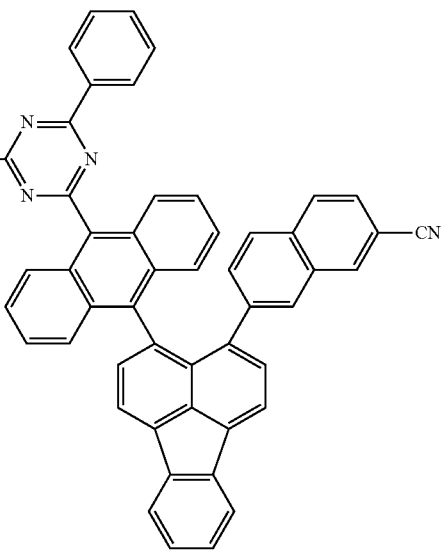
233
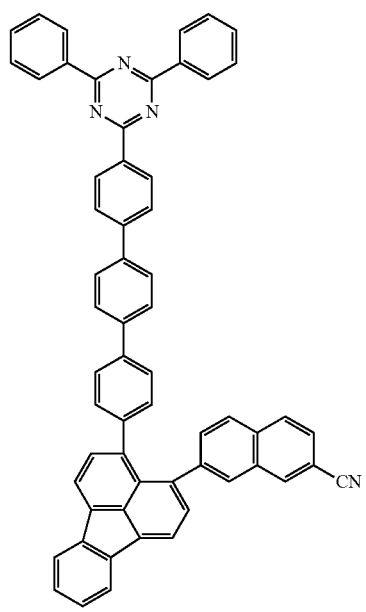

234
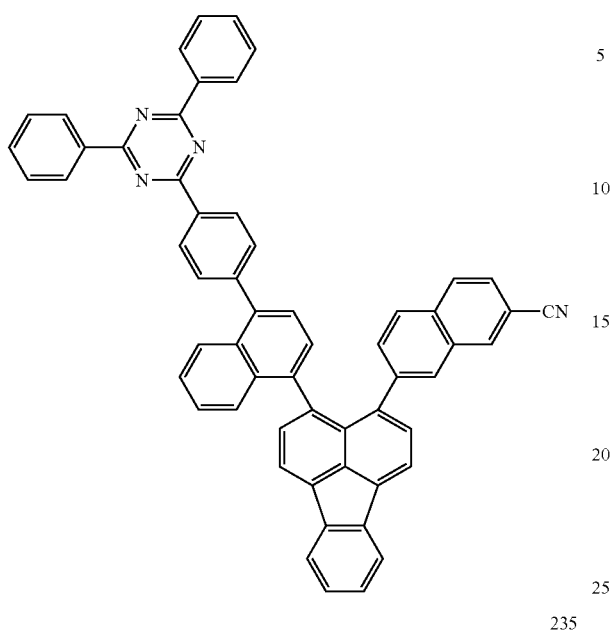
235
237
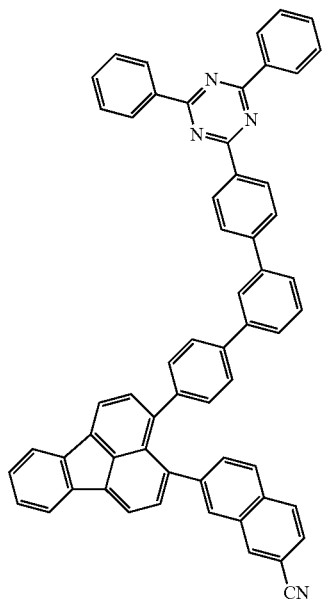
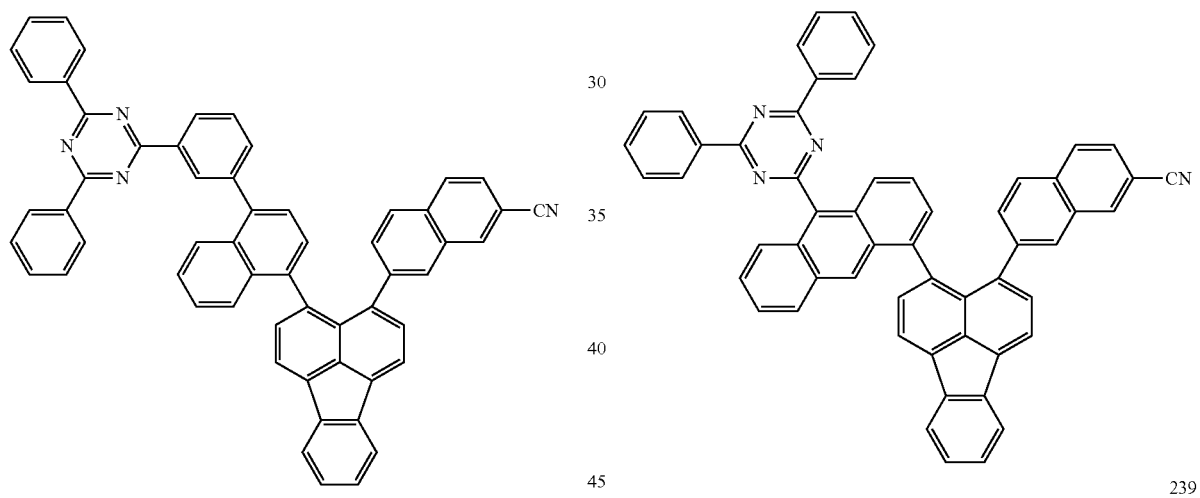
236
238
239
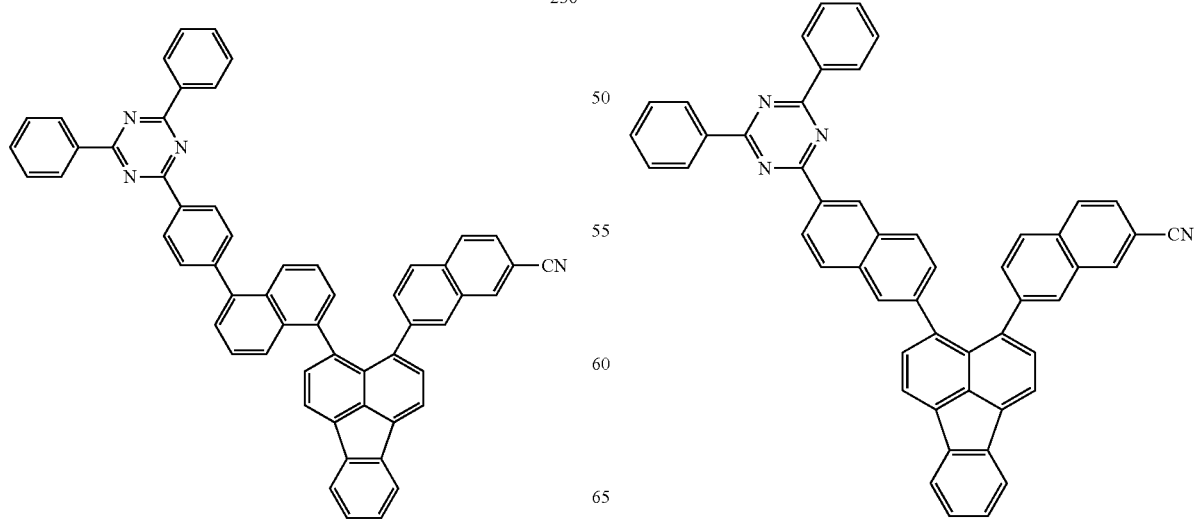

240
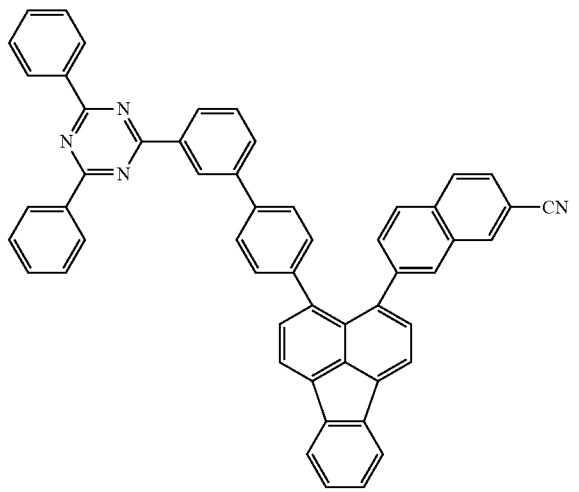
241
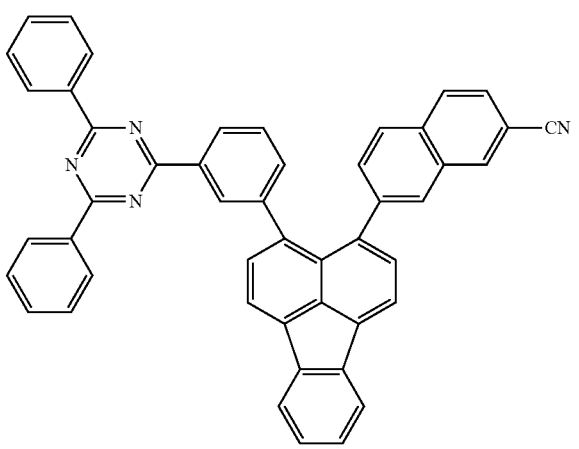
242
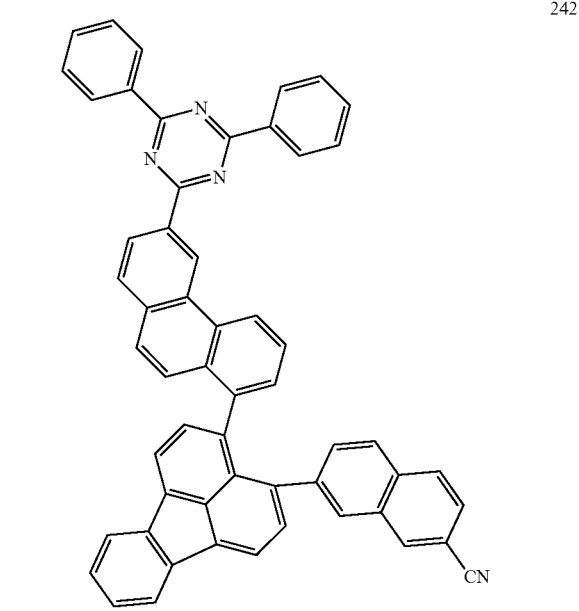
243
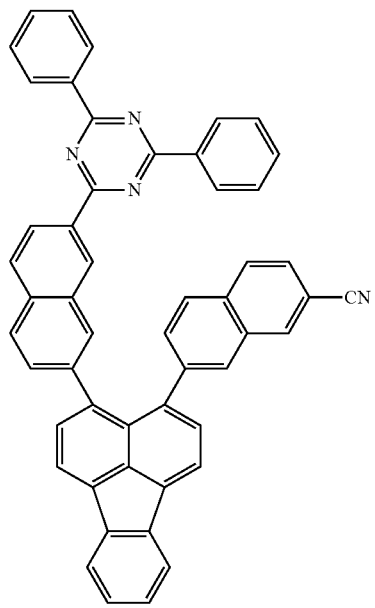
244
245
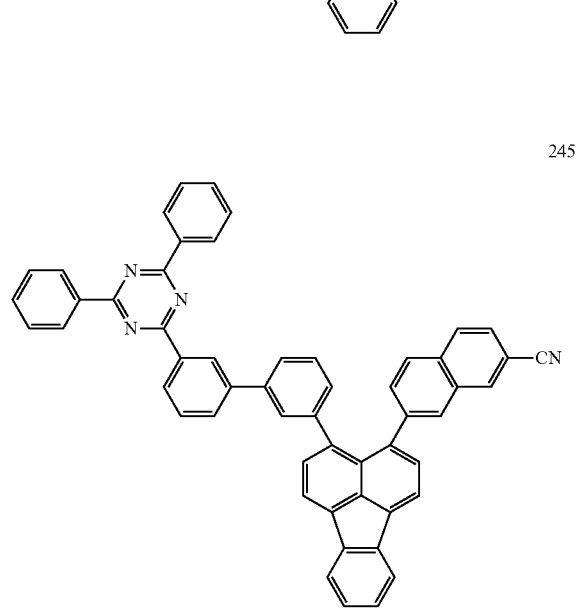

449
-continued
246
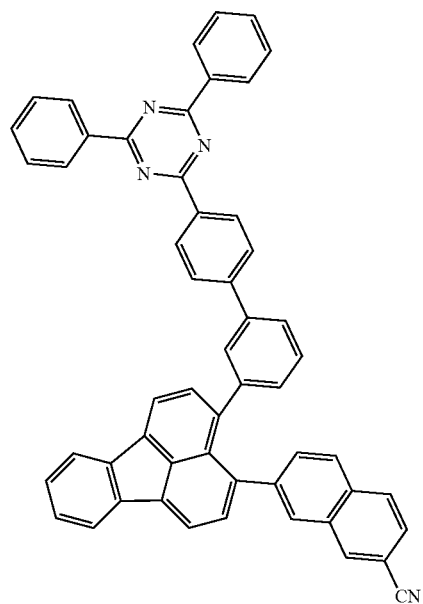
247
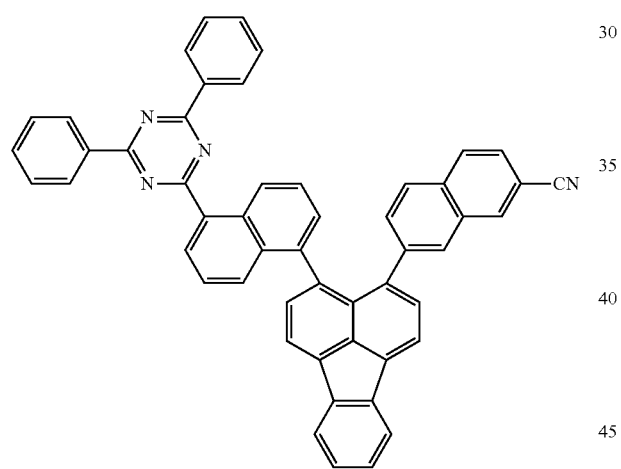
248
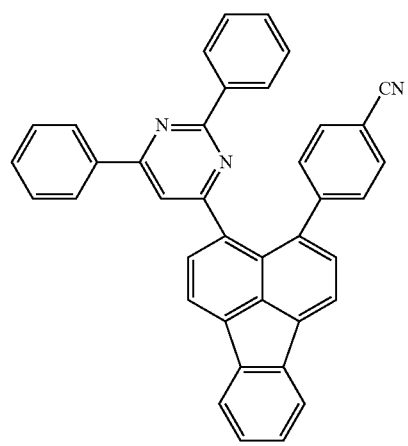
450
-continued
249
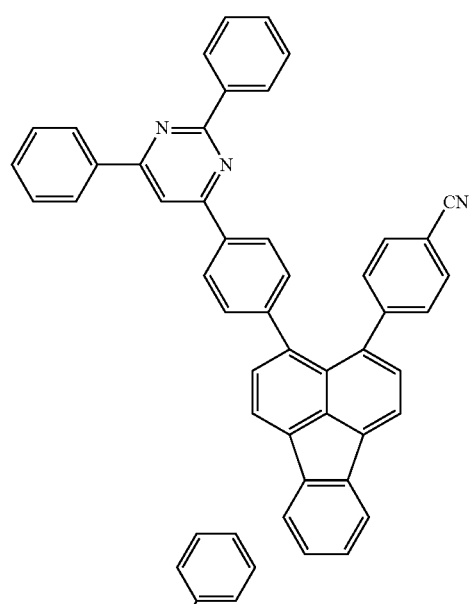
250
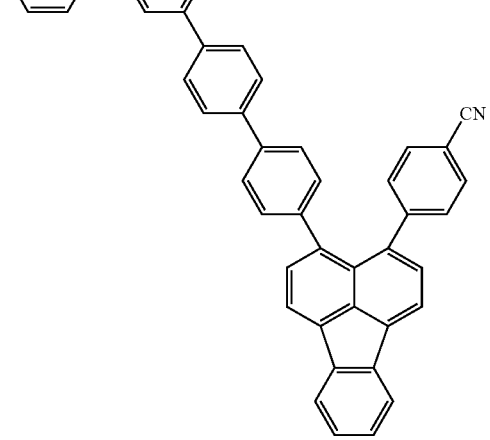
251
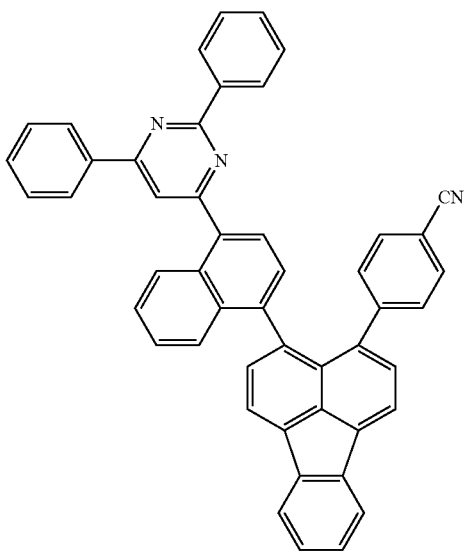

451
-continued
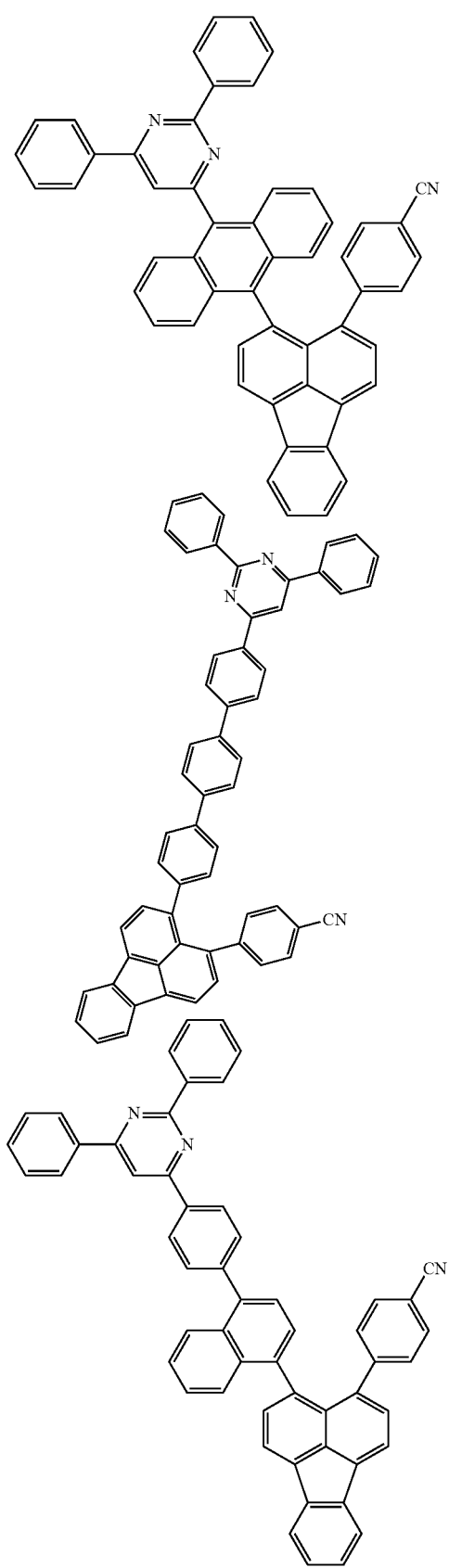
452
-continued
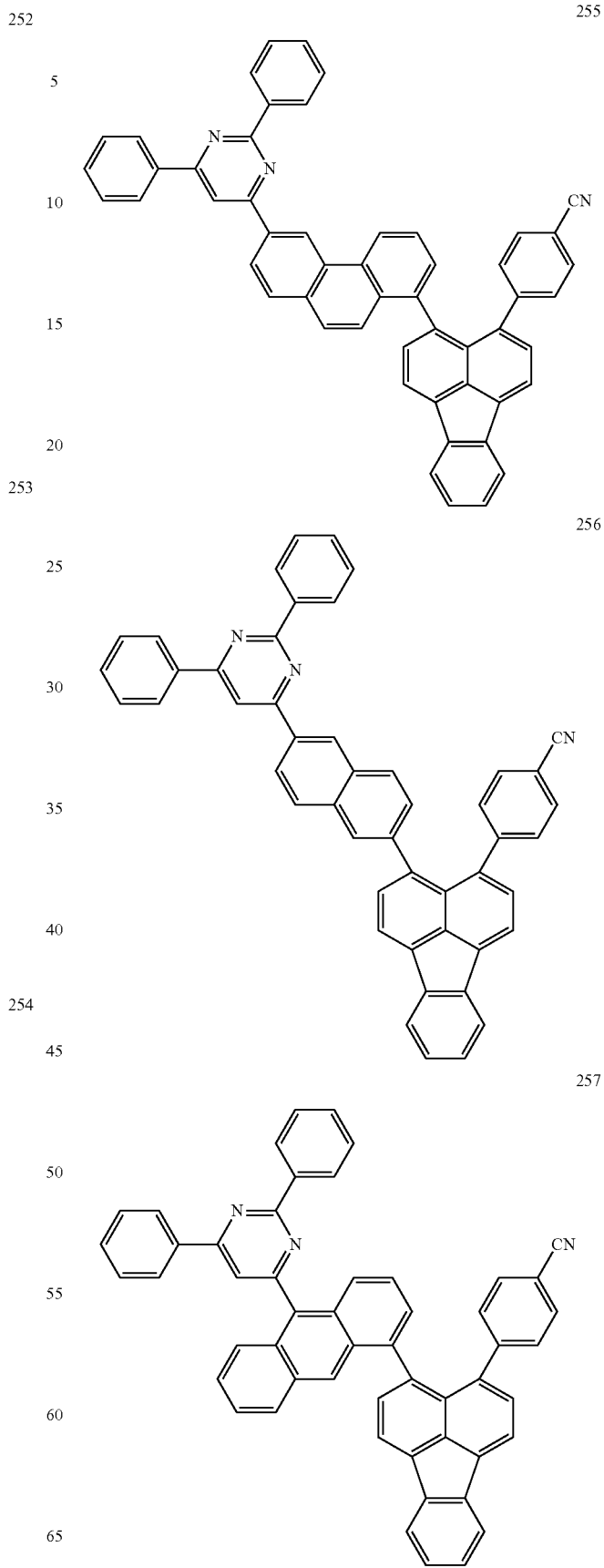

258
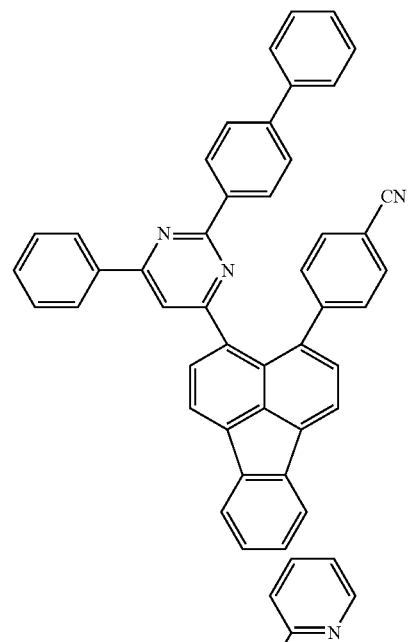
259
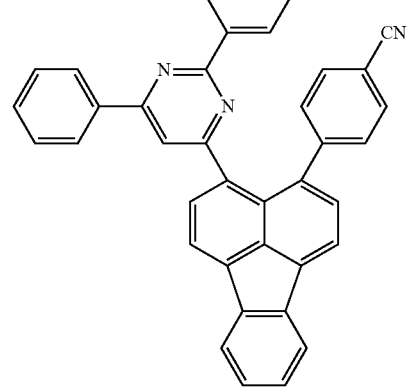
260
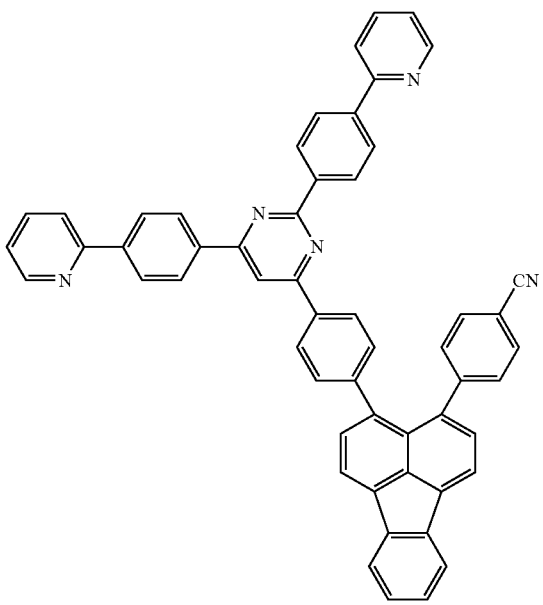
261
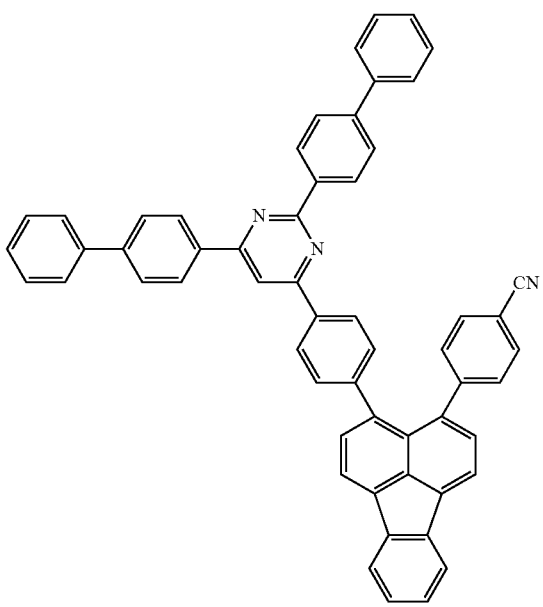
262
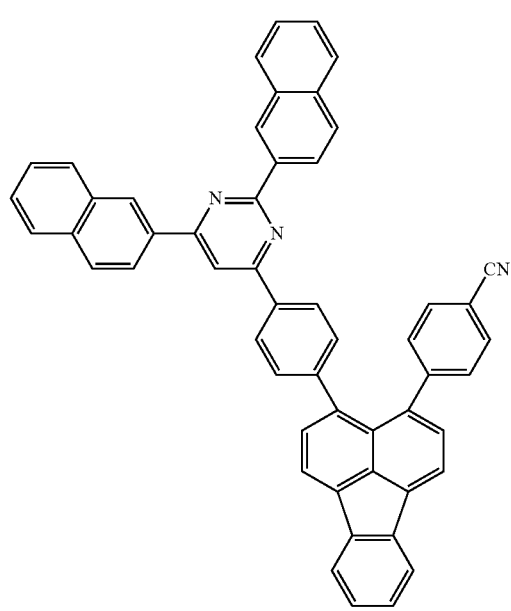

455 -continued
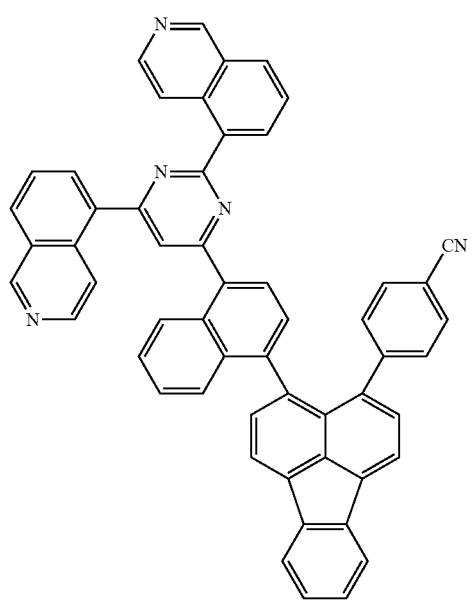
263
456 -continued
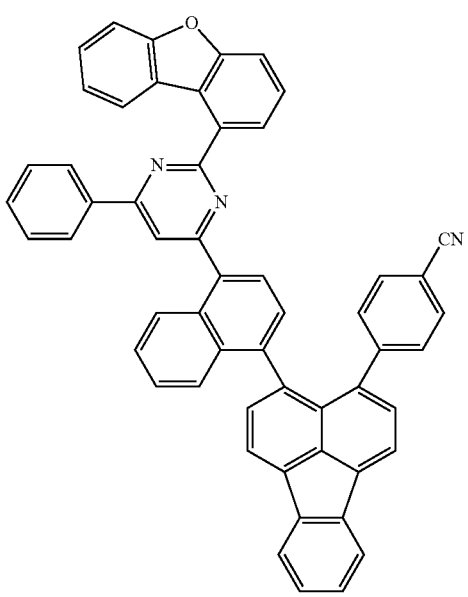
265
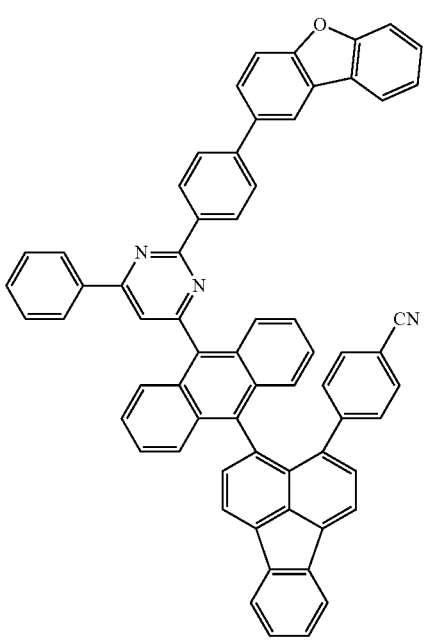
264
266

267
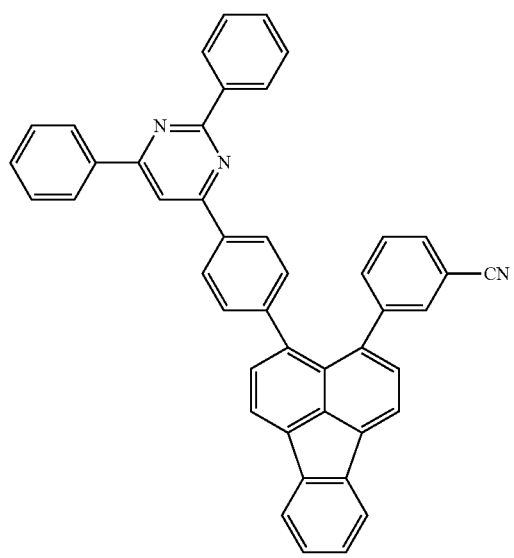
268
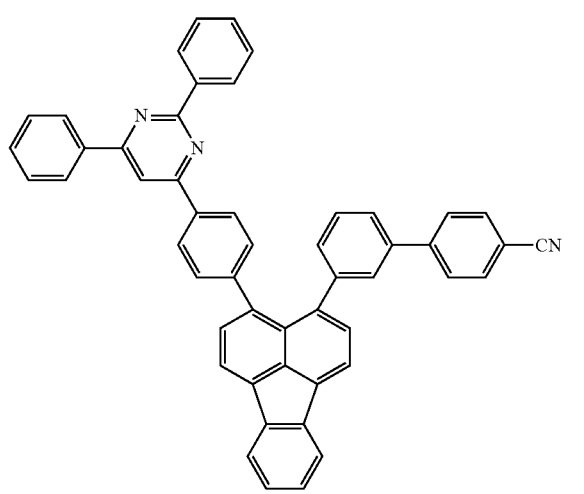
269
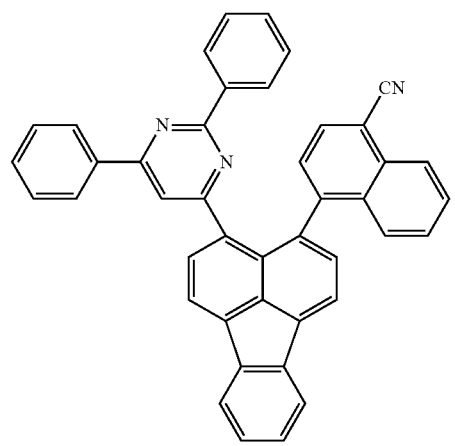
270
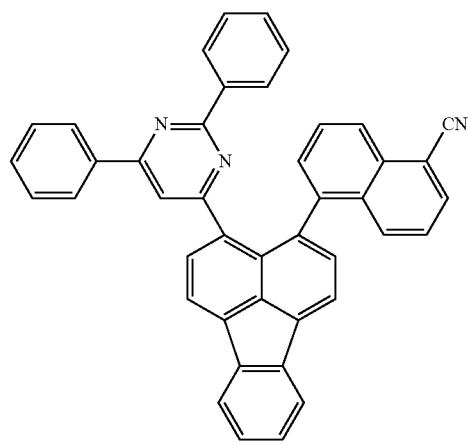
271
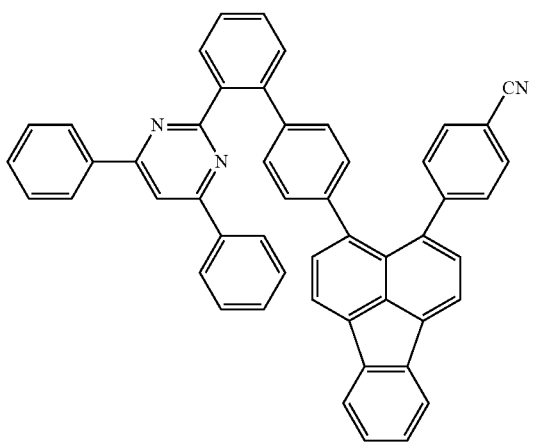
272
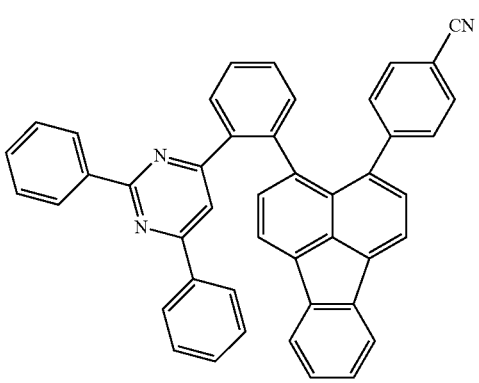

459
-continued
273
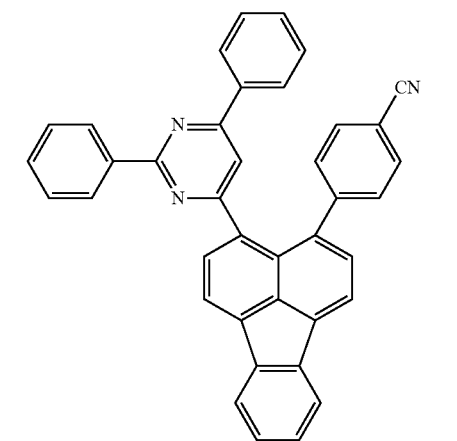
274
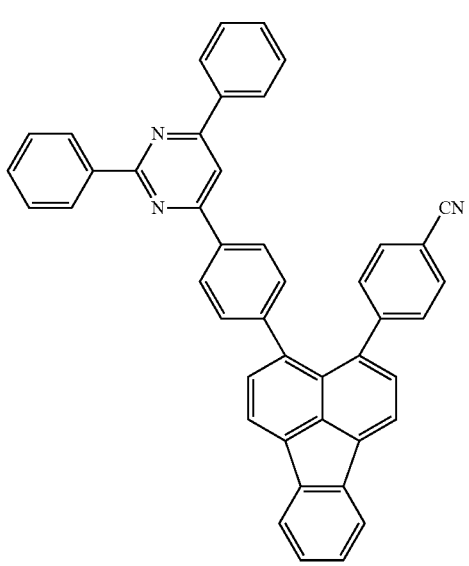
275
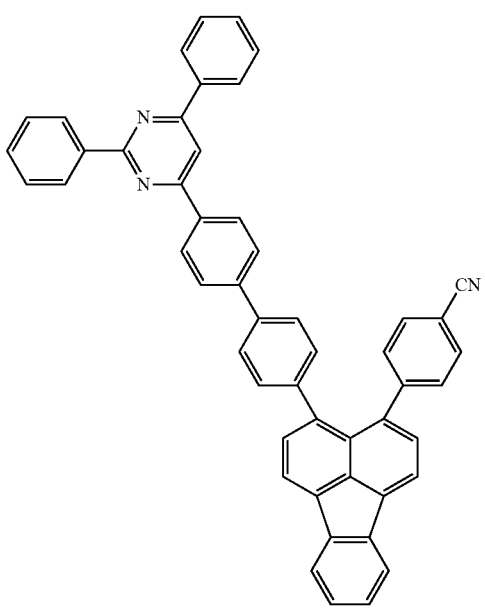
460
-continued
276
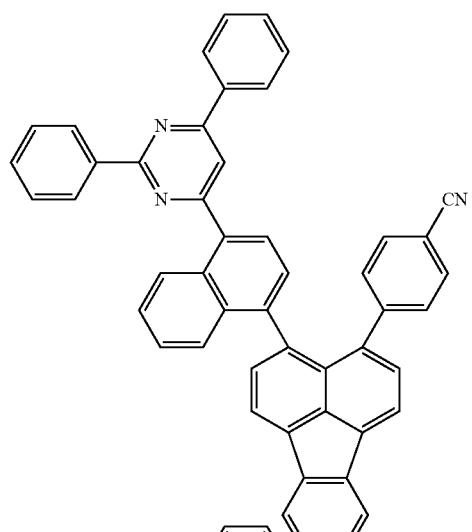
277
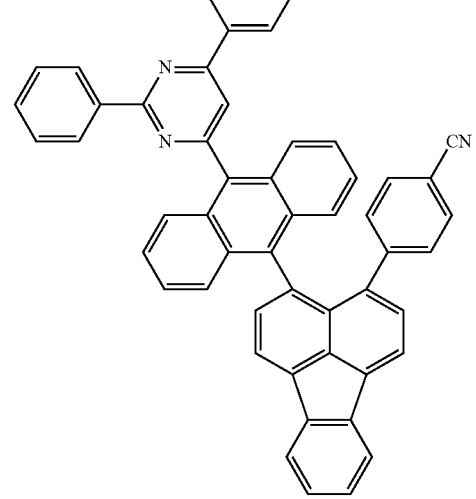
278
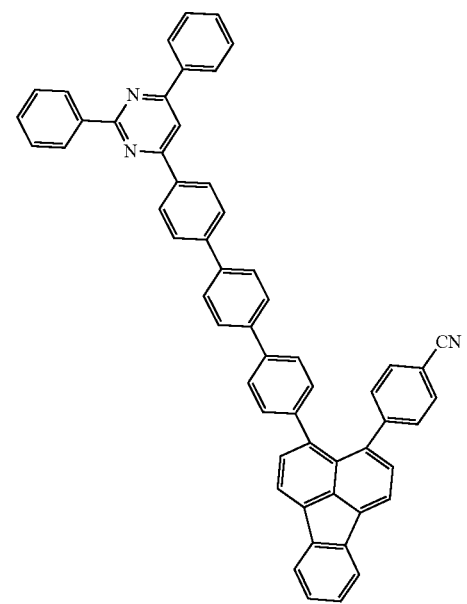

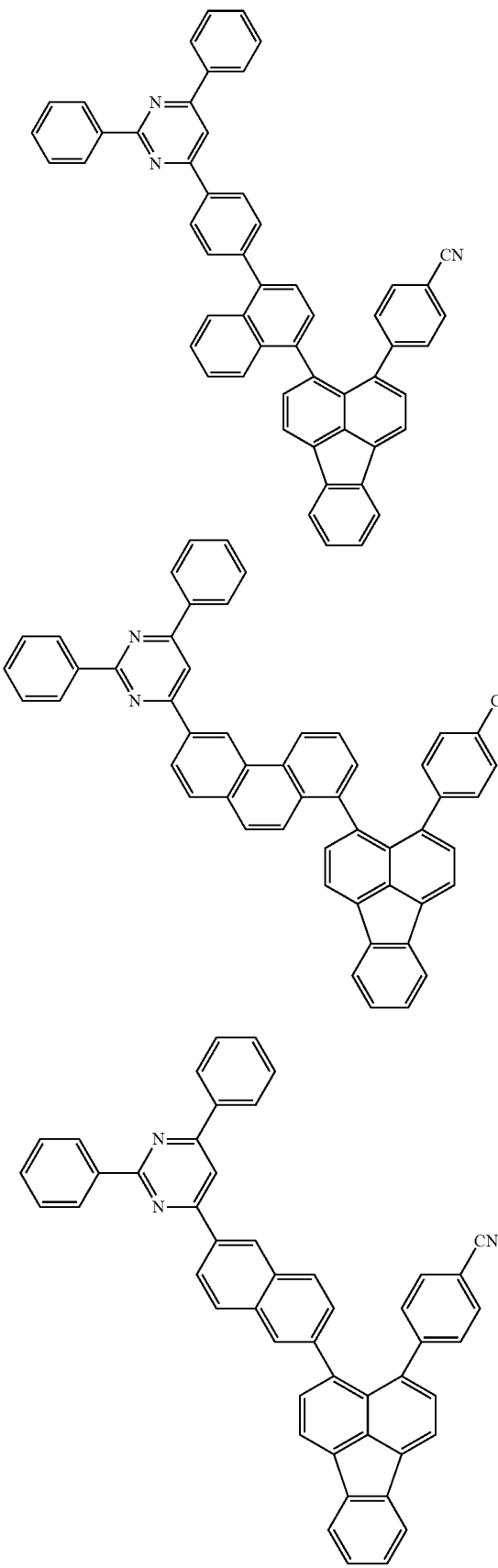
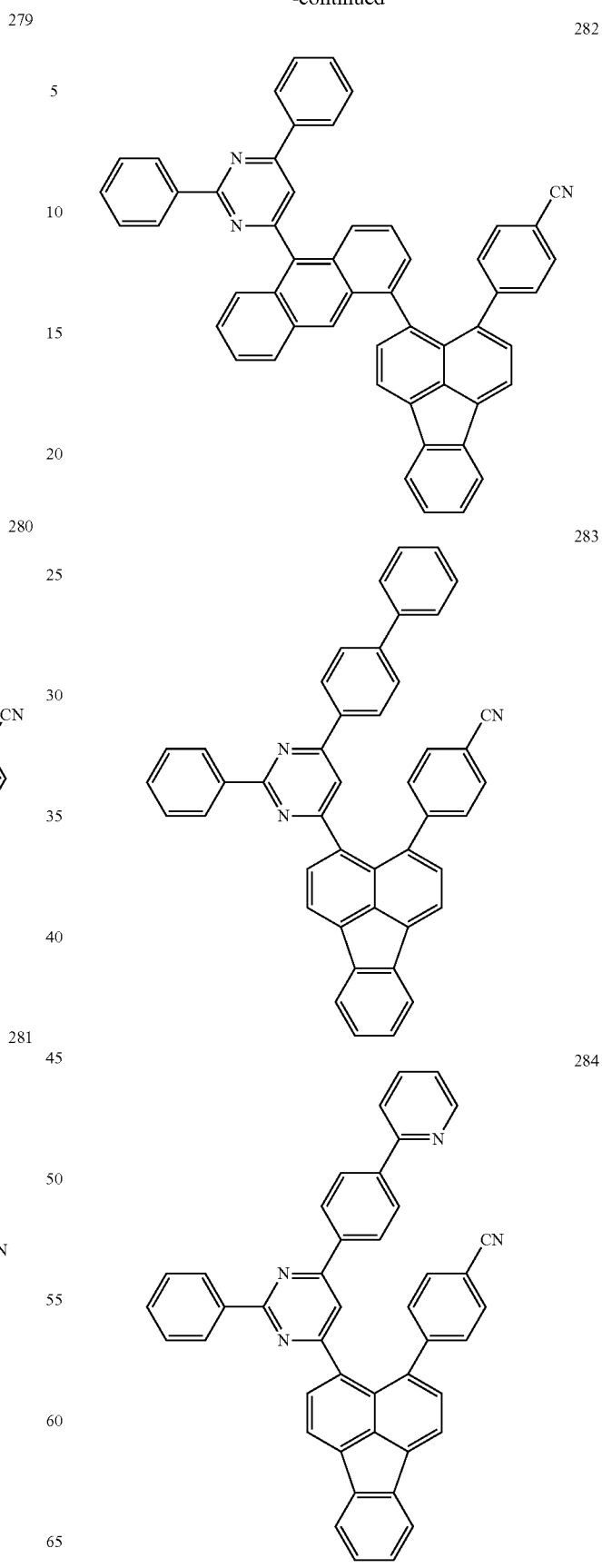

463
-continued
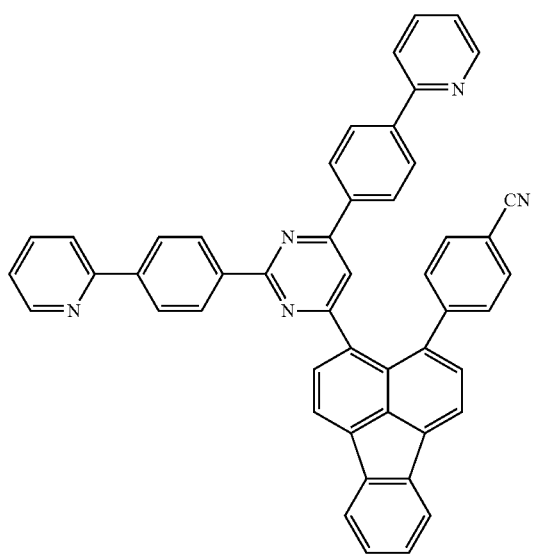
285
464
-continued
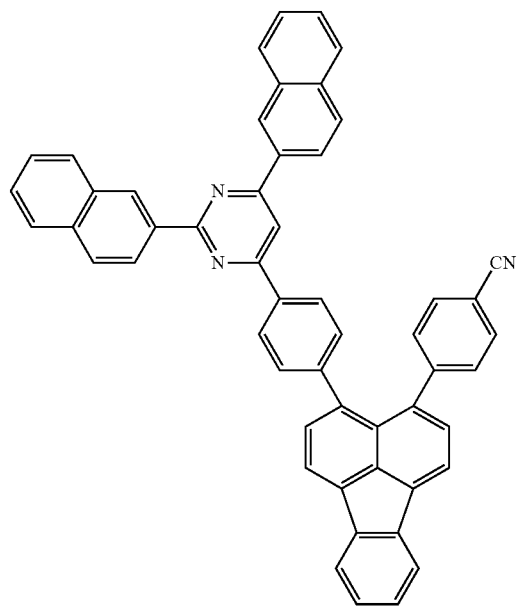
287
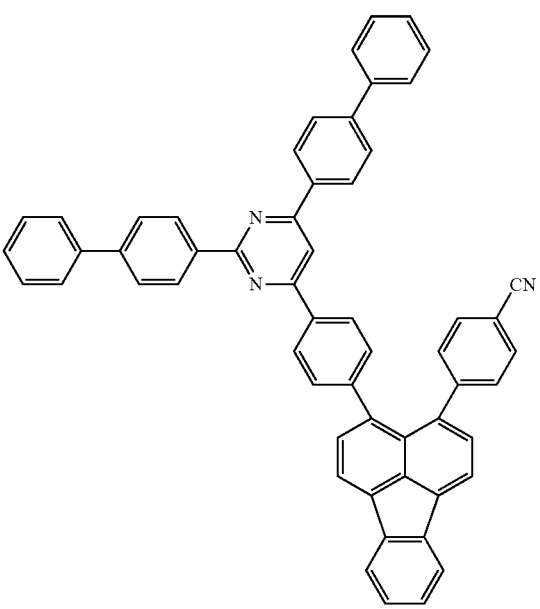
286
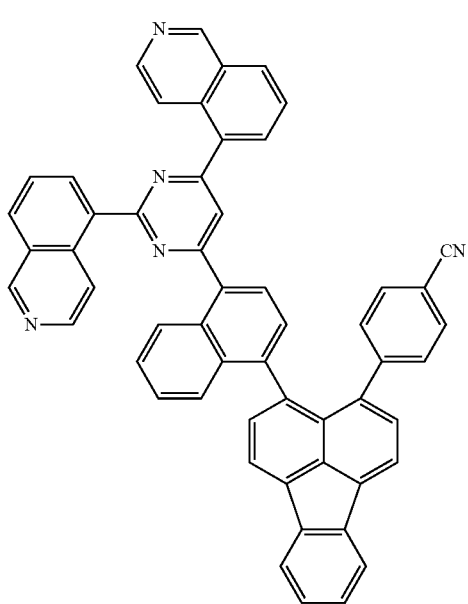
288

-continued
289
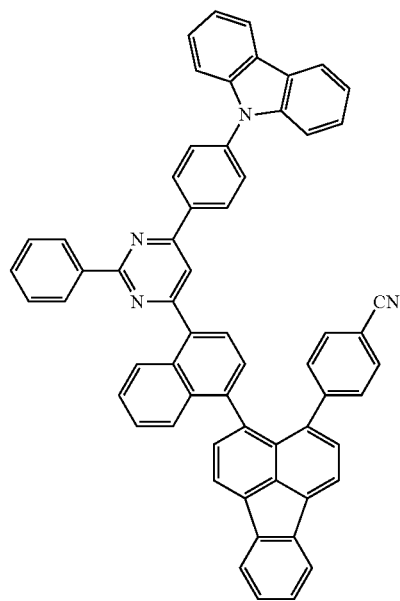
290
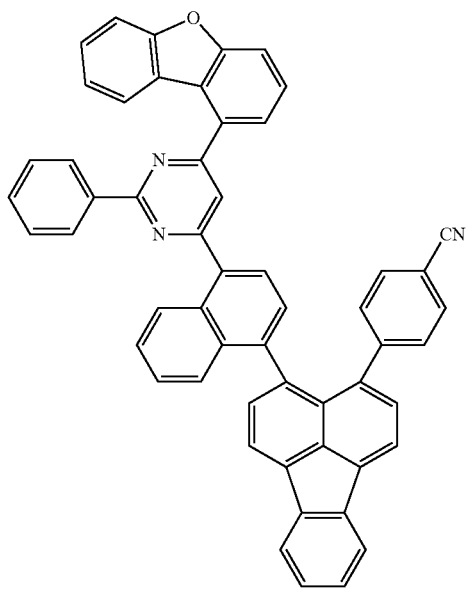
-continued
291
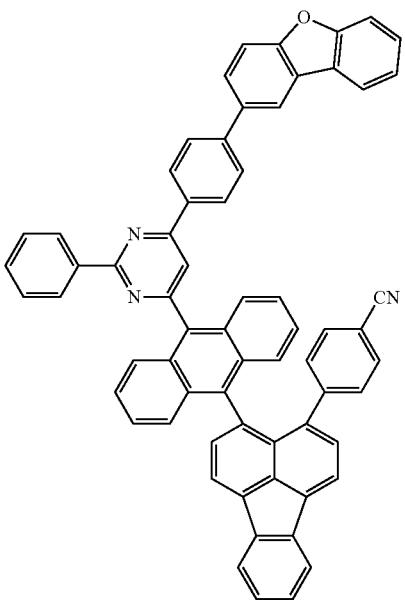
292
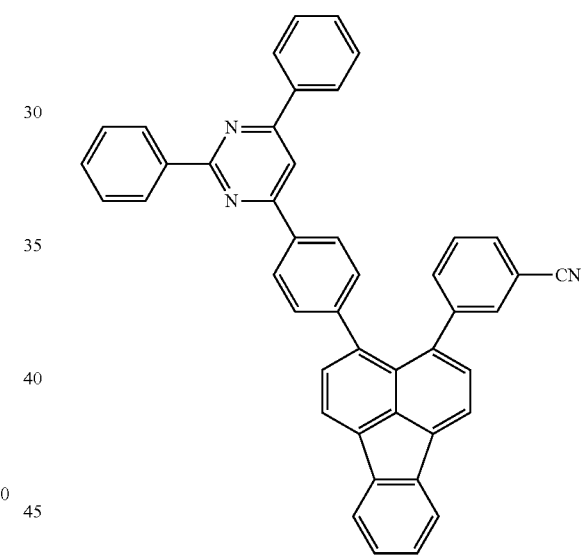
293
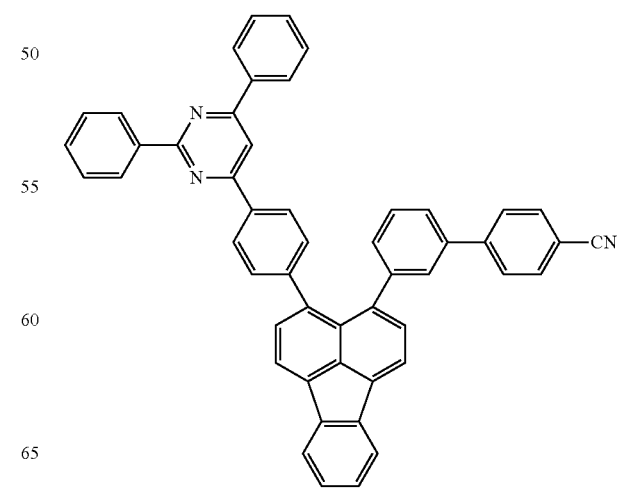

-continued
294
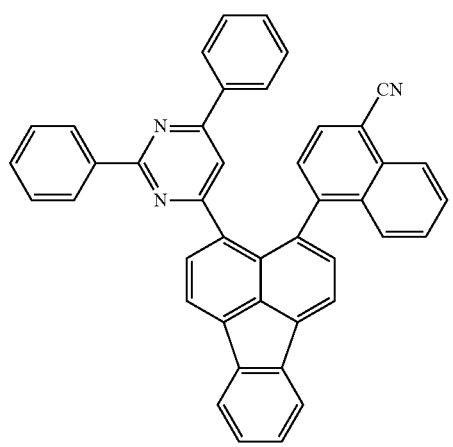
295
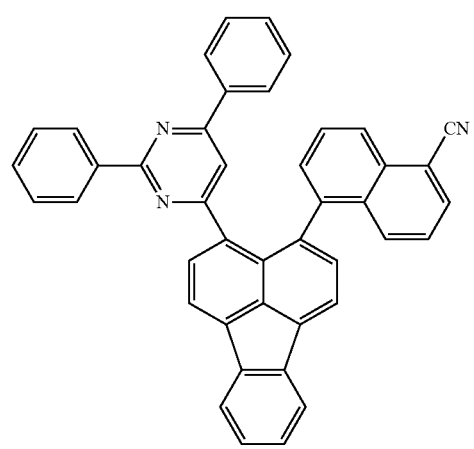
296
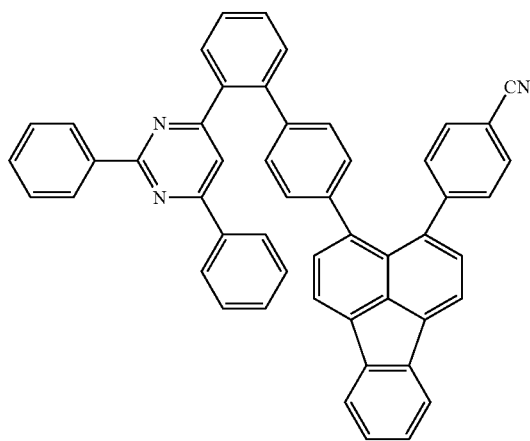
-continued
297
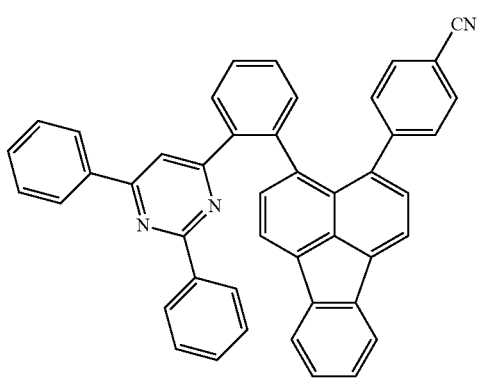
298
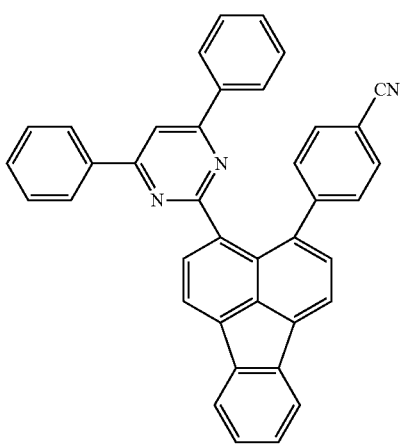
299
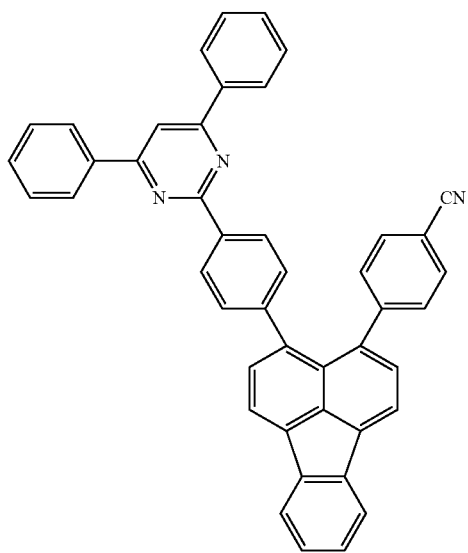

469
-continued
470
-continued
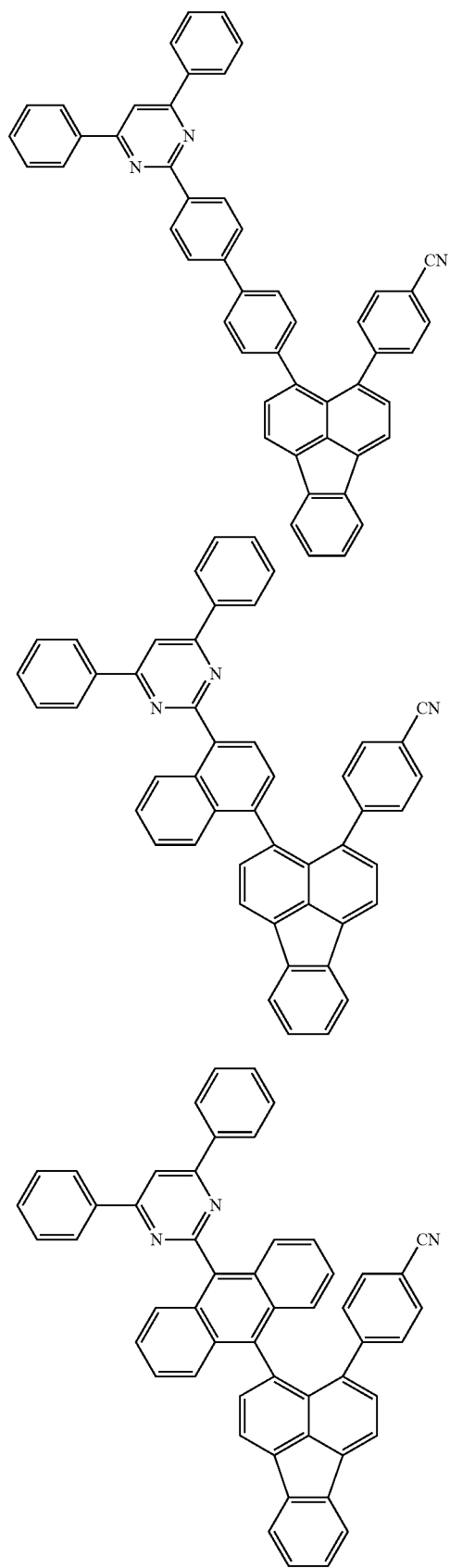
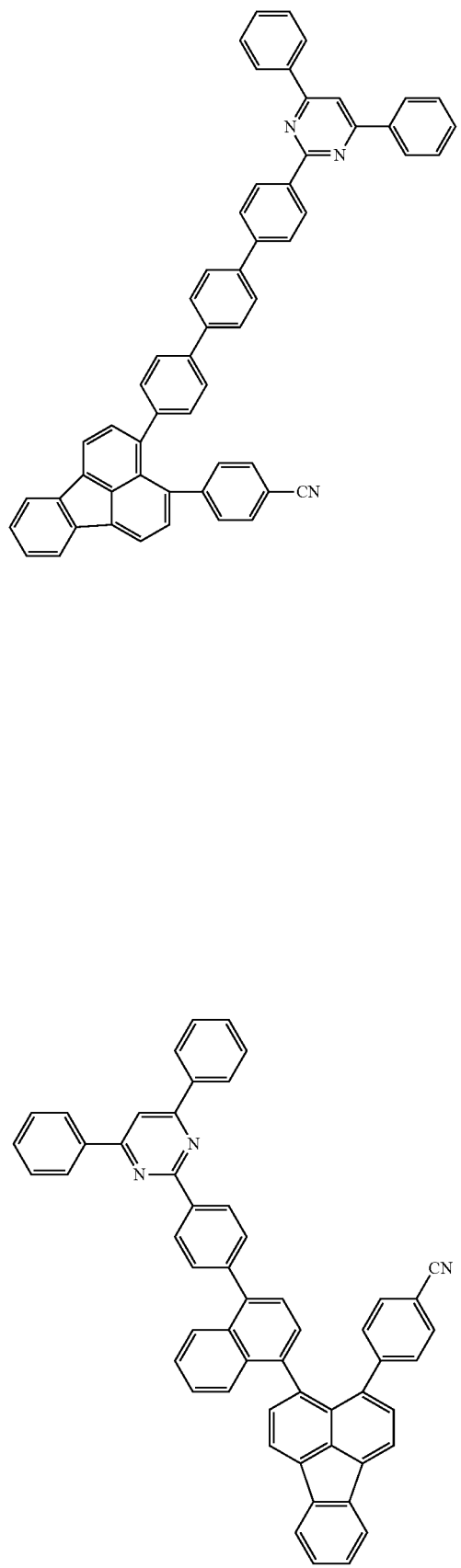

-continued
305
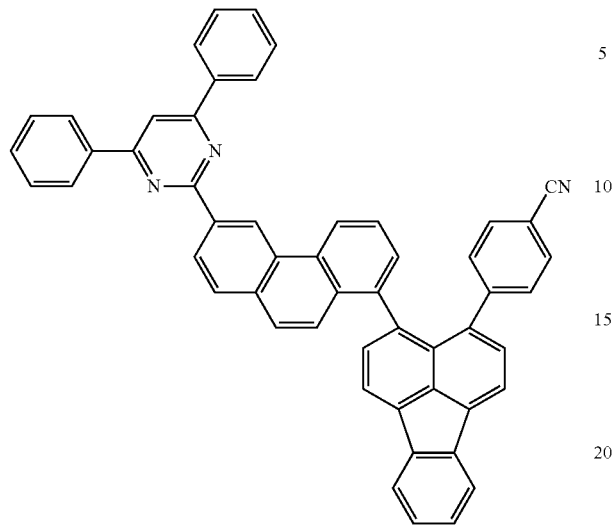
306
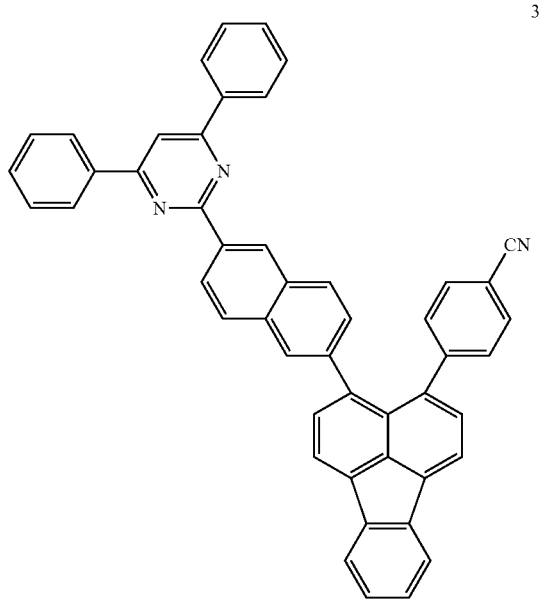
307
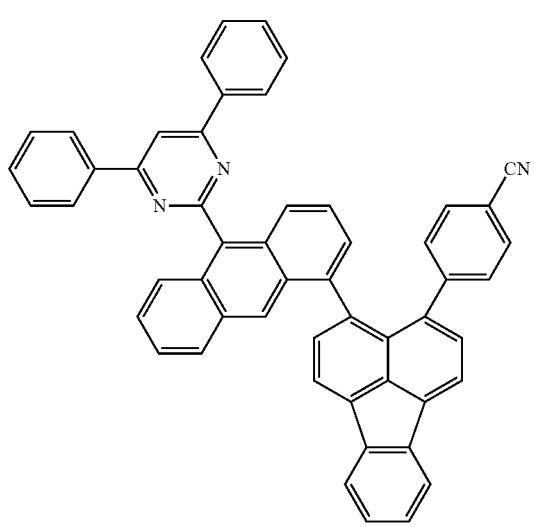
-continued
308
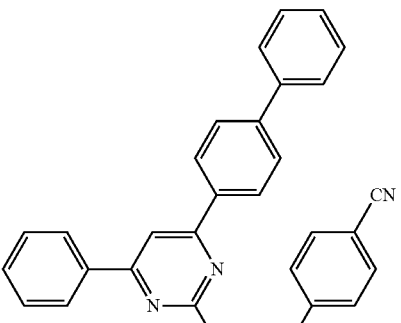
309
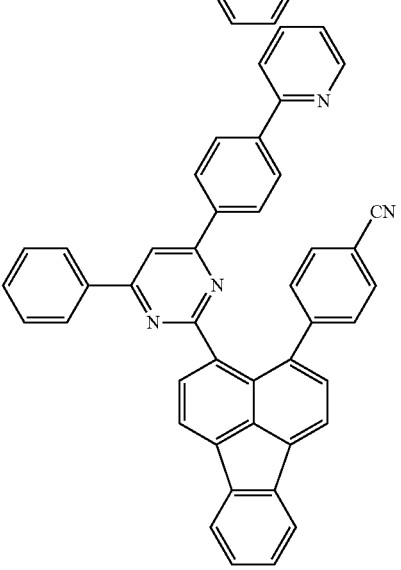
310
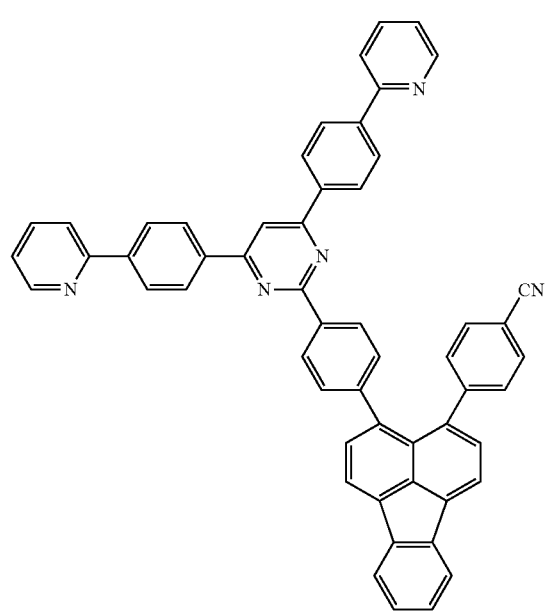

473
-continued
474
-continued
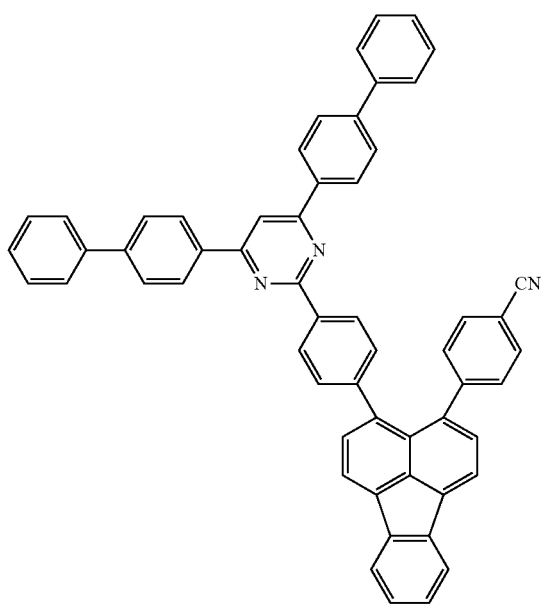
311
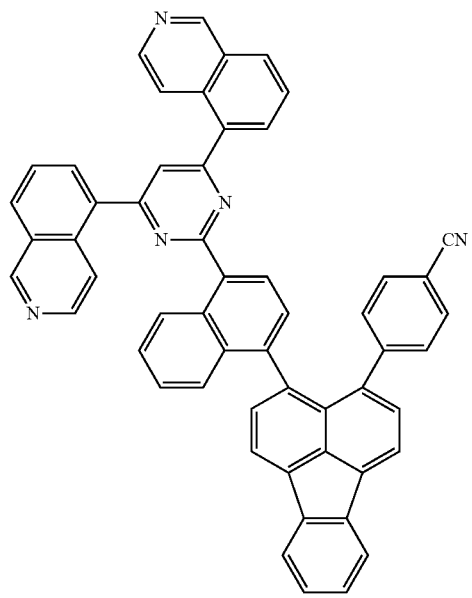
313
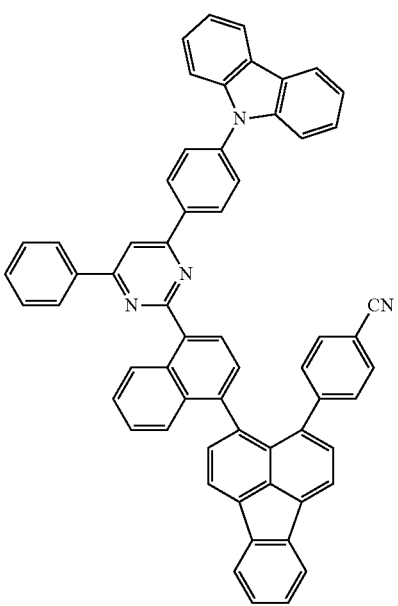
314
312

475
-continued
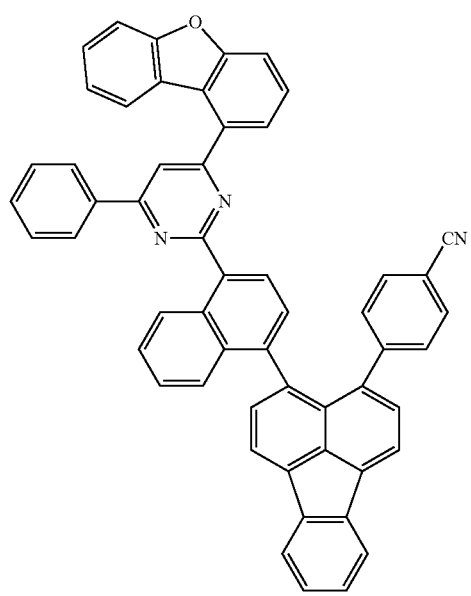
315
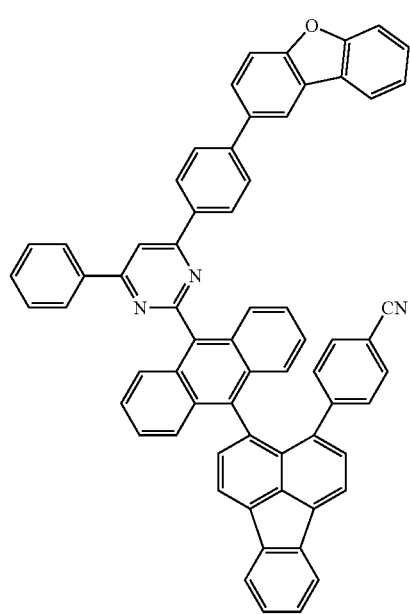
316
476
-continued
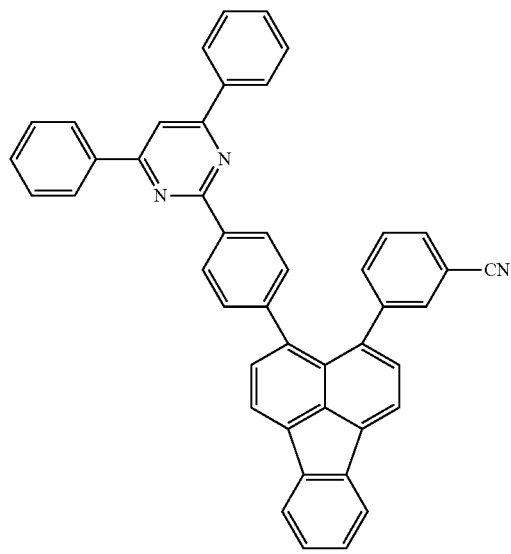
317
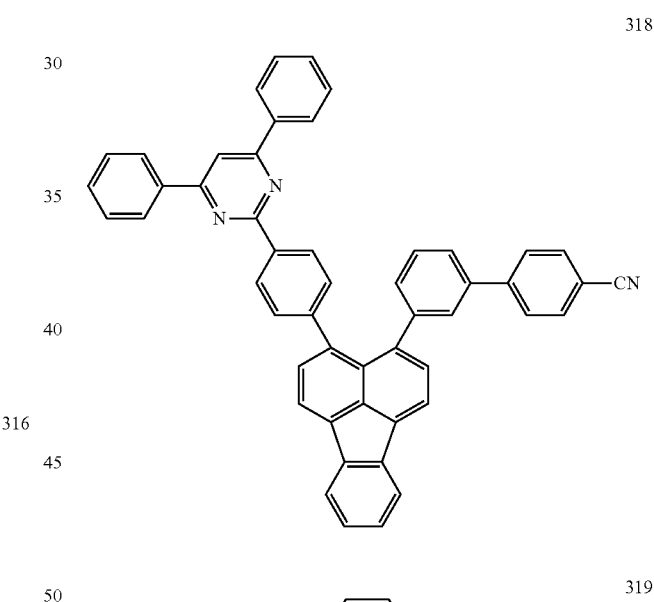
318
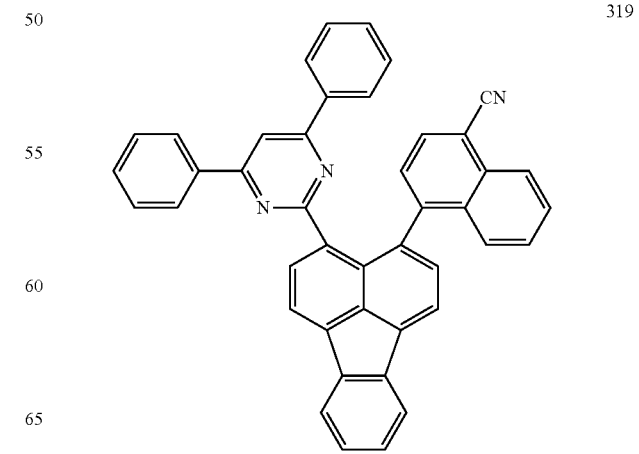
319

477
-continued
320
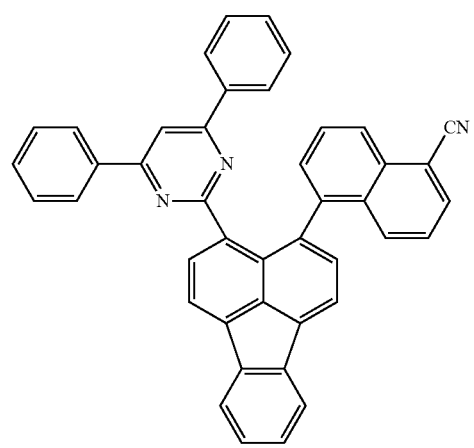
321
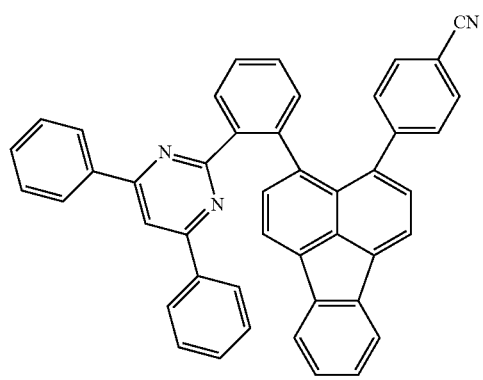
322
478
-continued
323
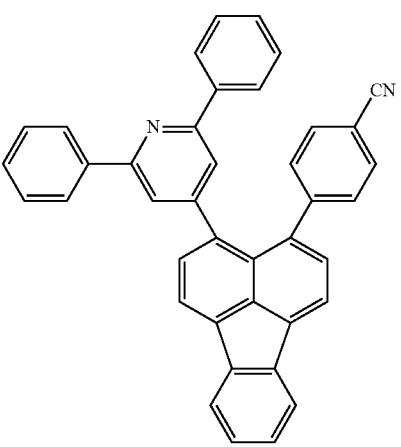
324
325
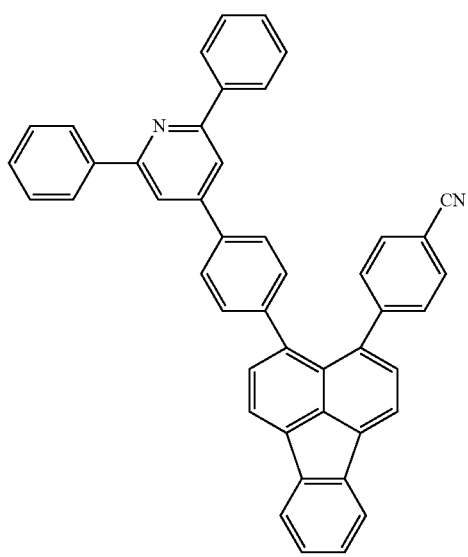

-continued
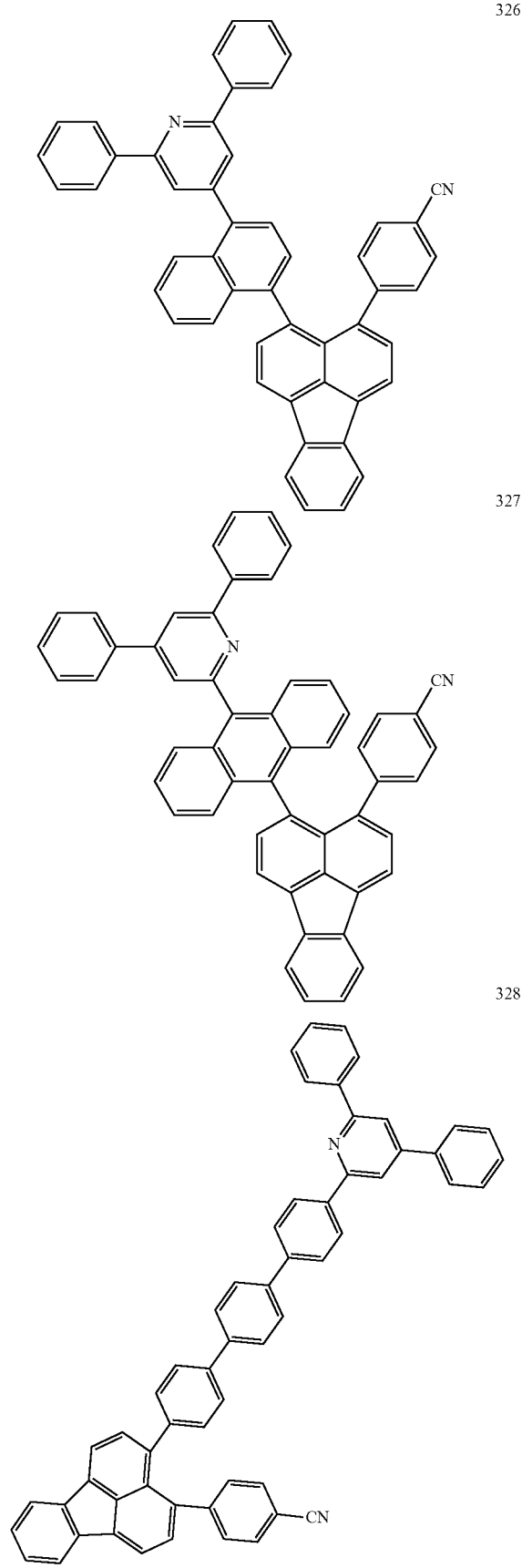
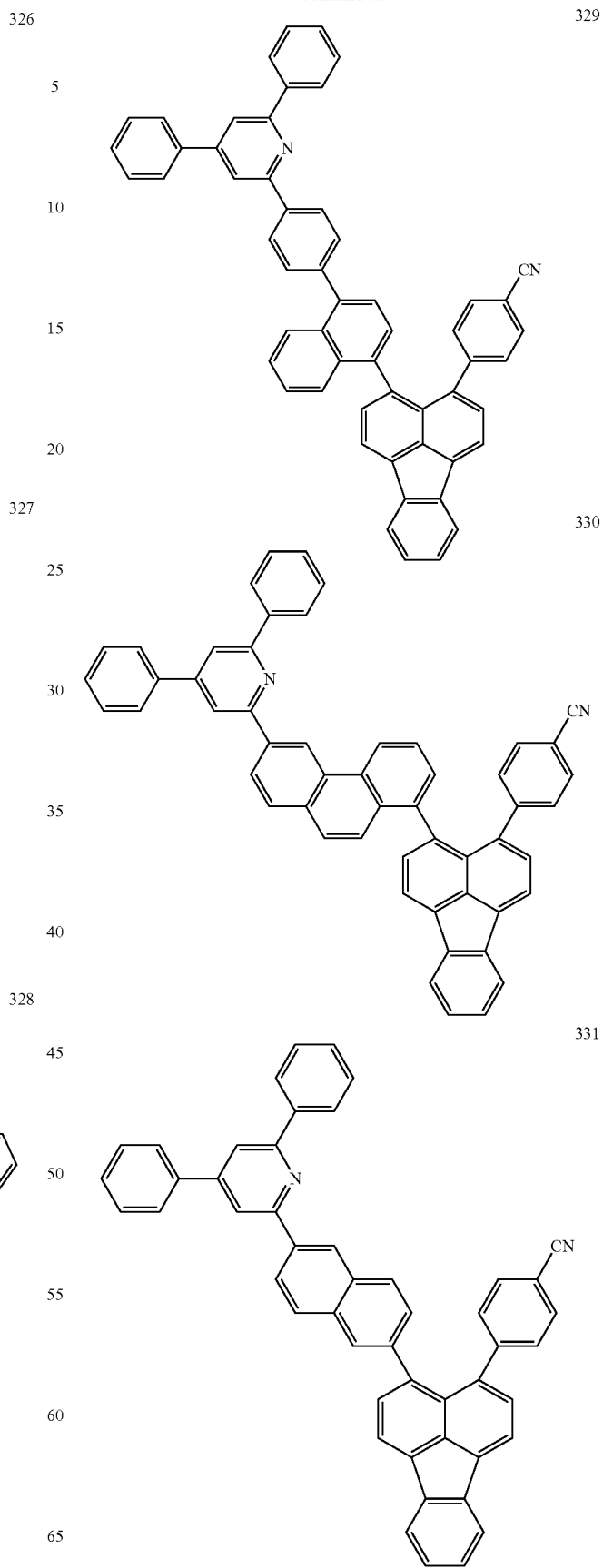

-continued
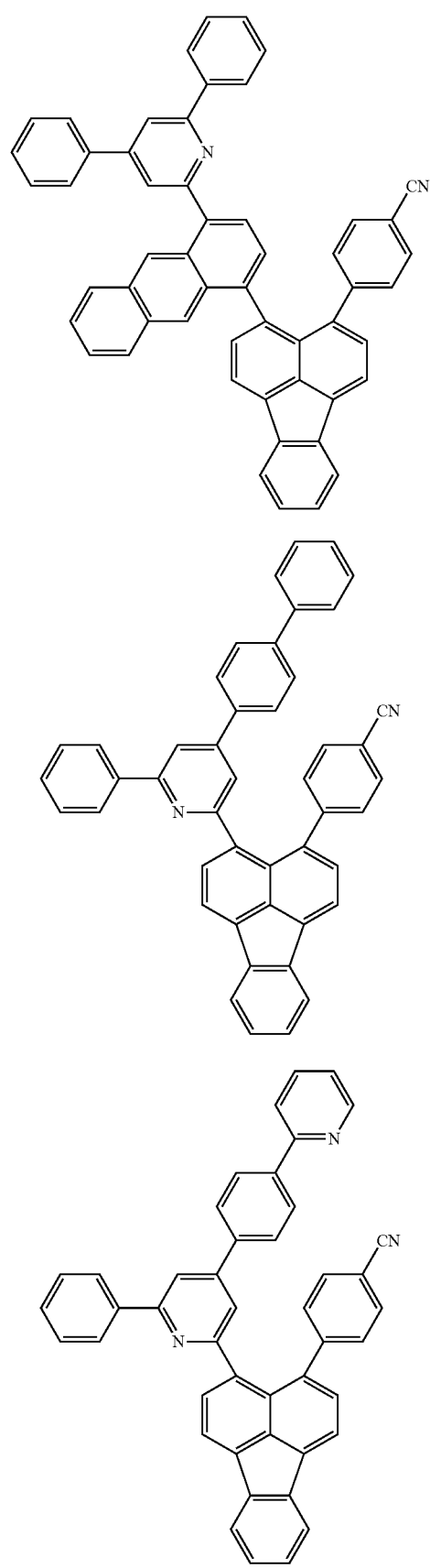
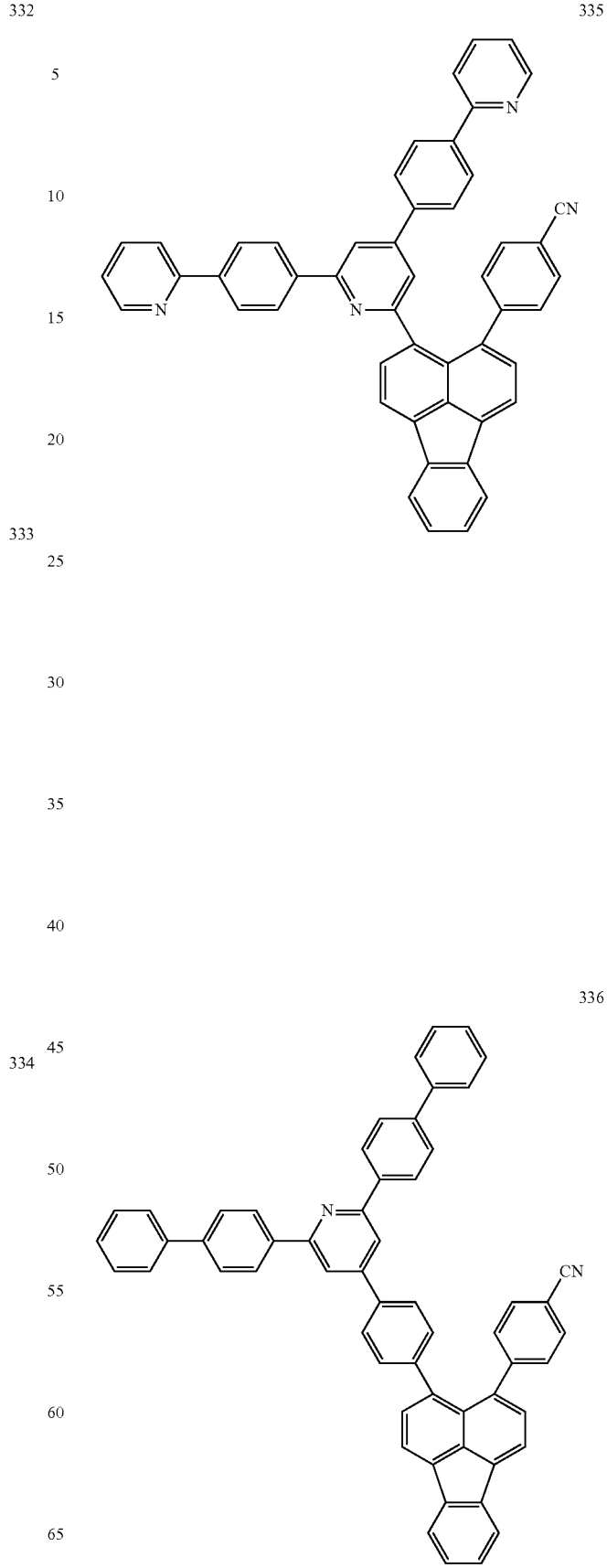

483
-continued
337
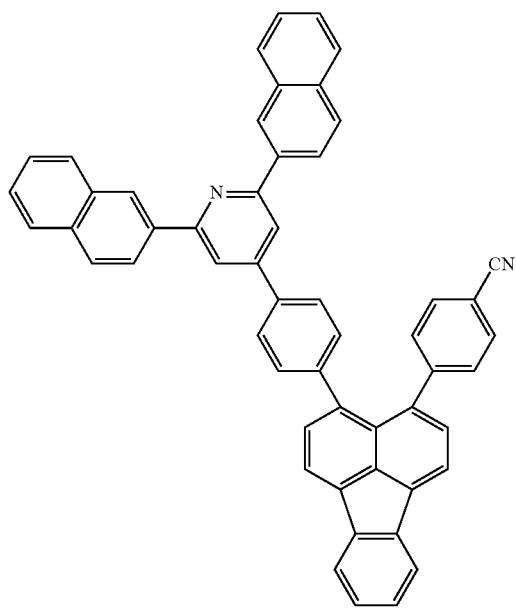
338
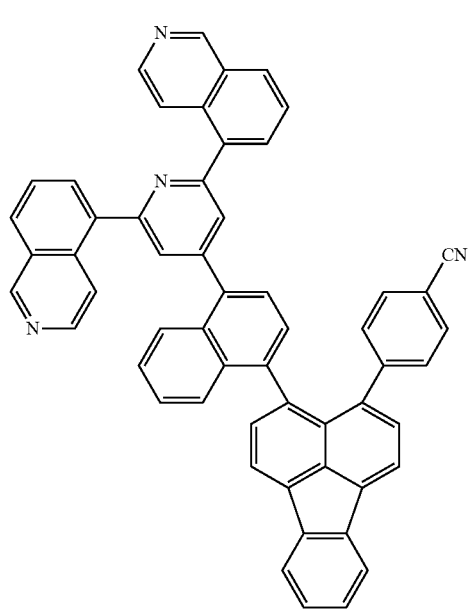
484
-continued
339
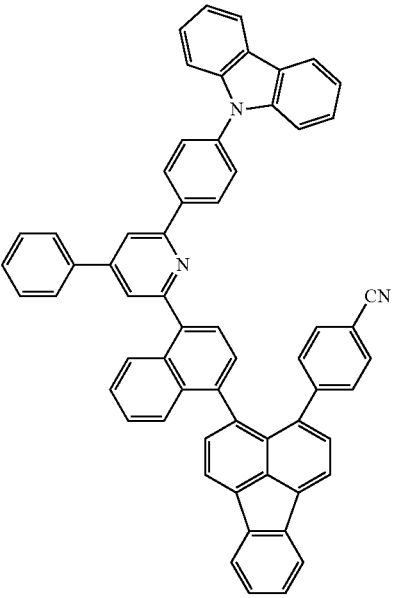
340
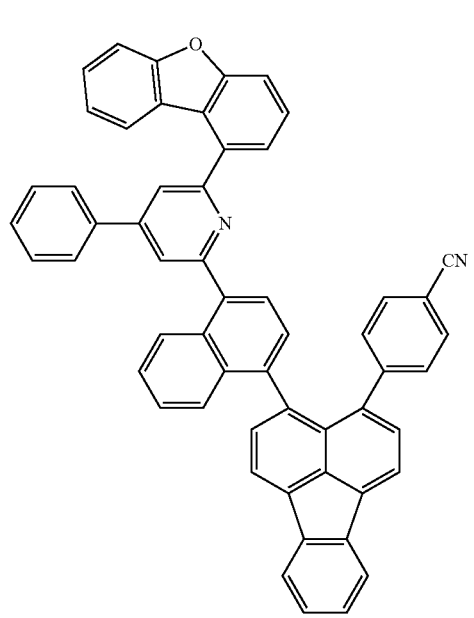

485
-continued
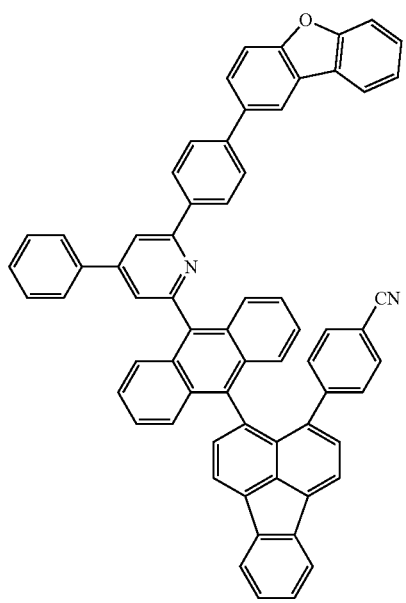
342
343
486
-continued
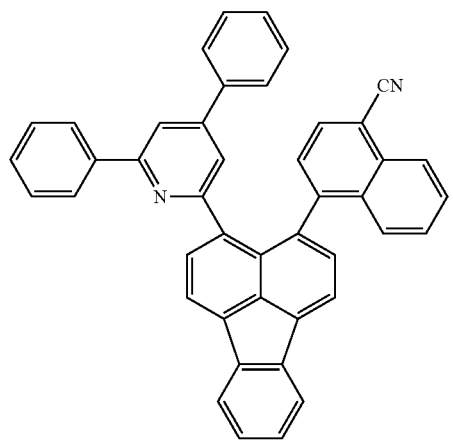
344
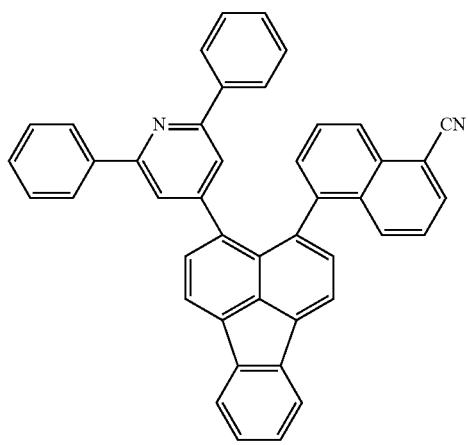
345
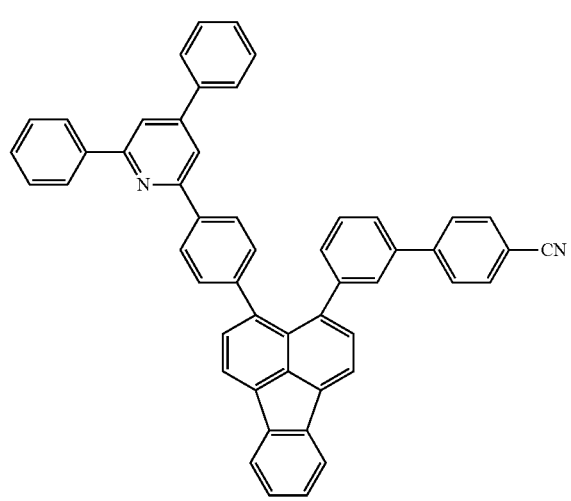
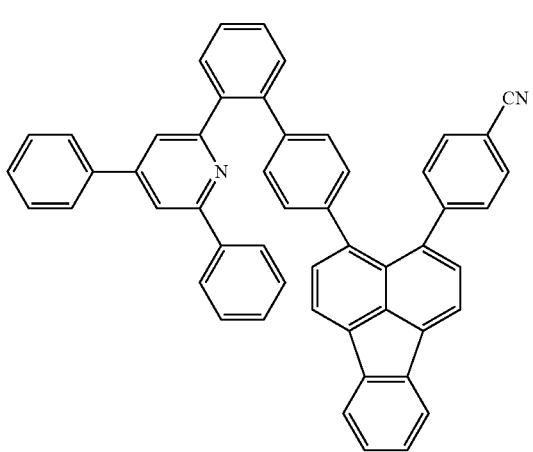
346

487
-continued
347
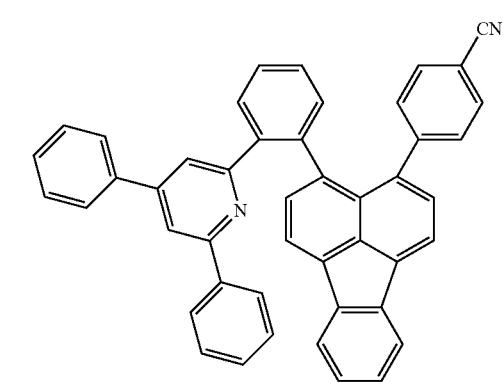
348
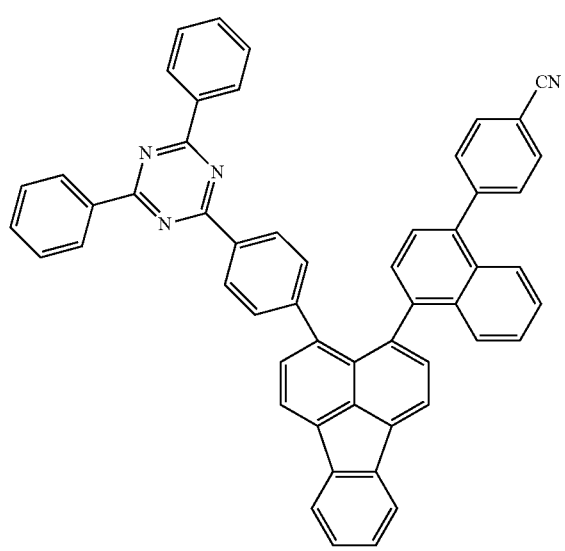
349
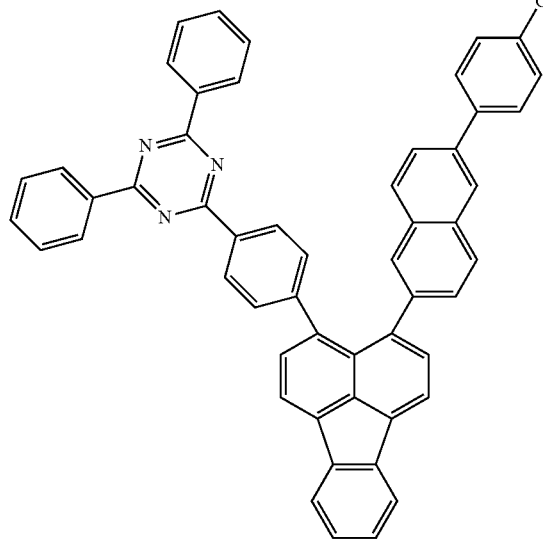
488
-continued
350
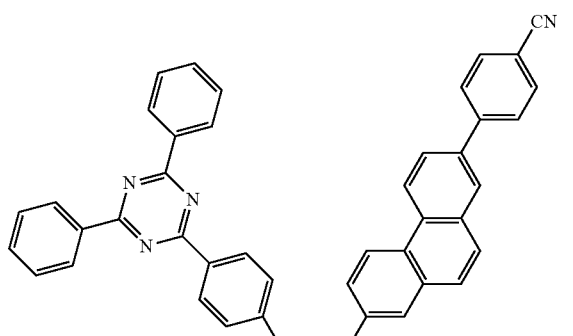
351
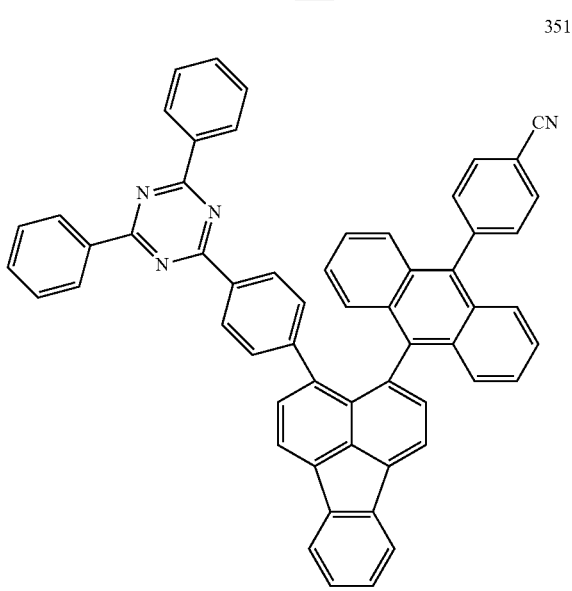
352
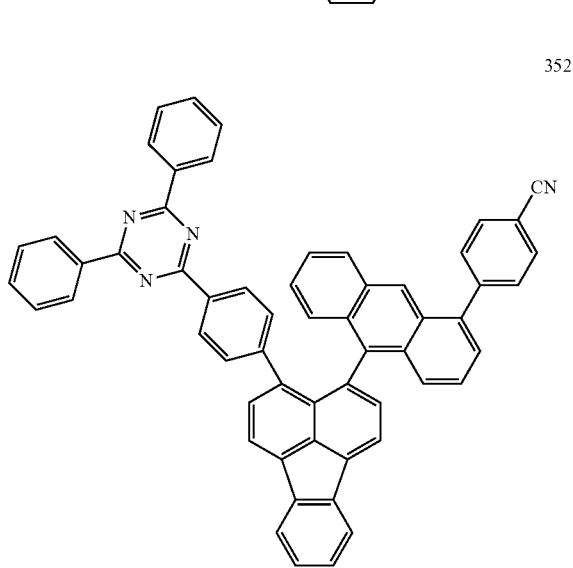

489
-continued
353
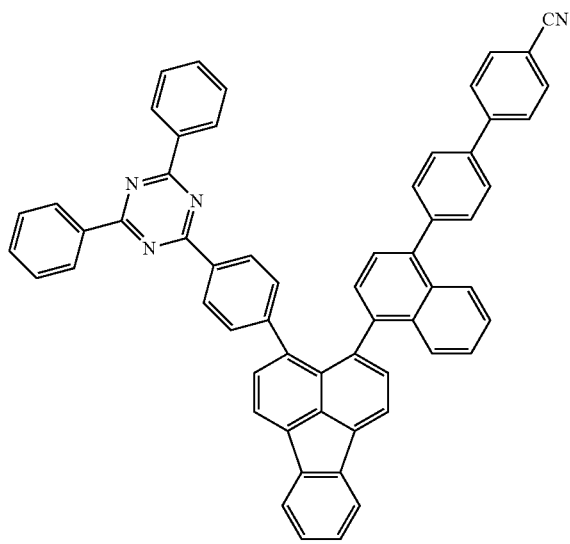
354
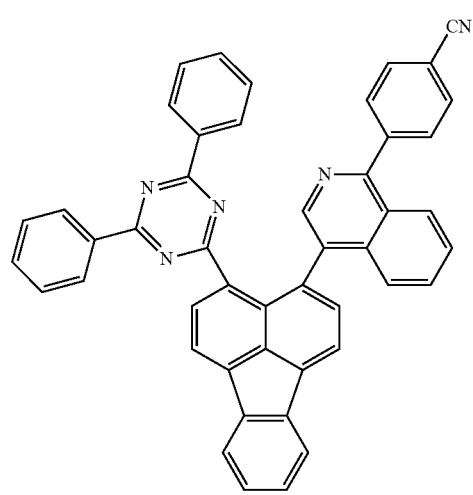
355
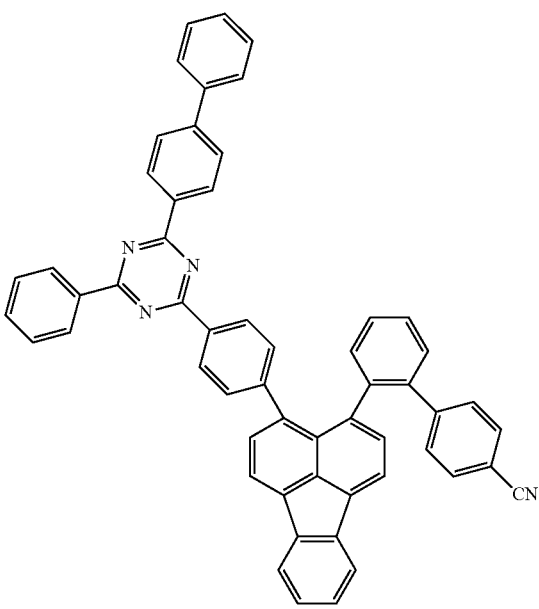
490
-continued
356
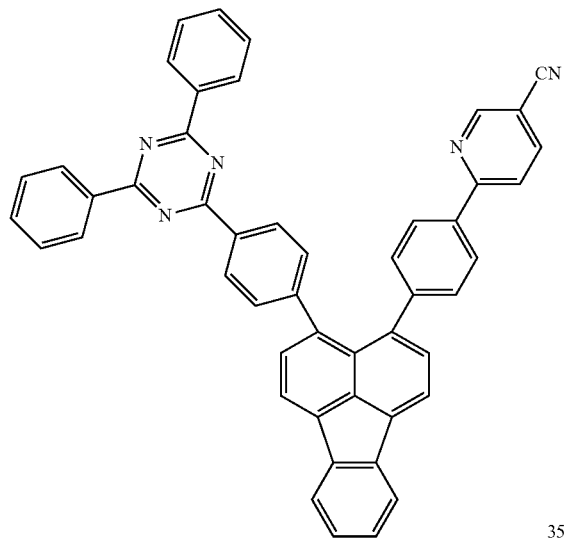
357
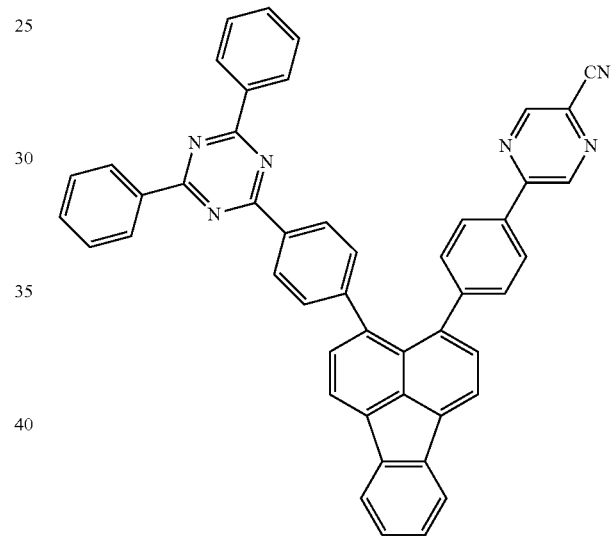
358
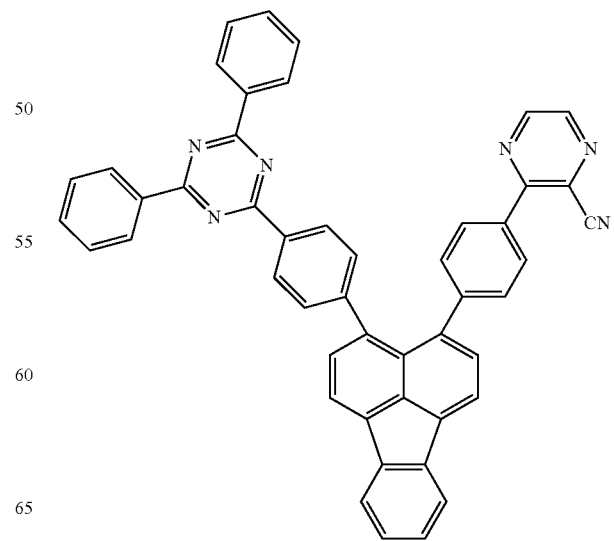

491
-continued
492
-continued
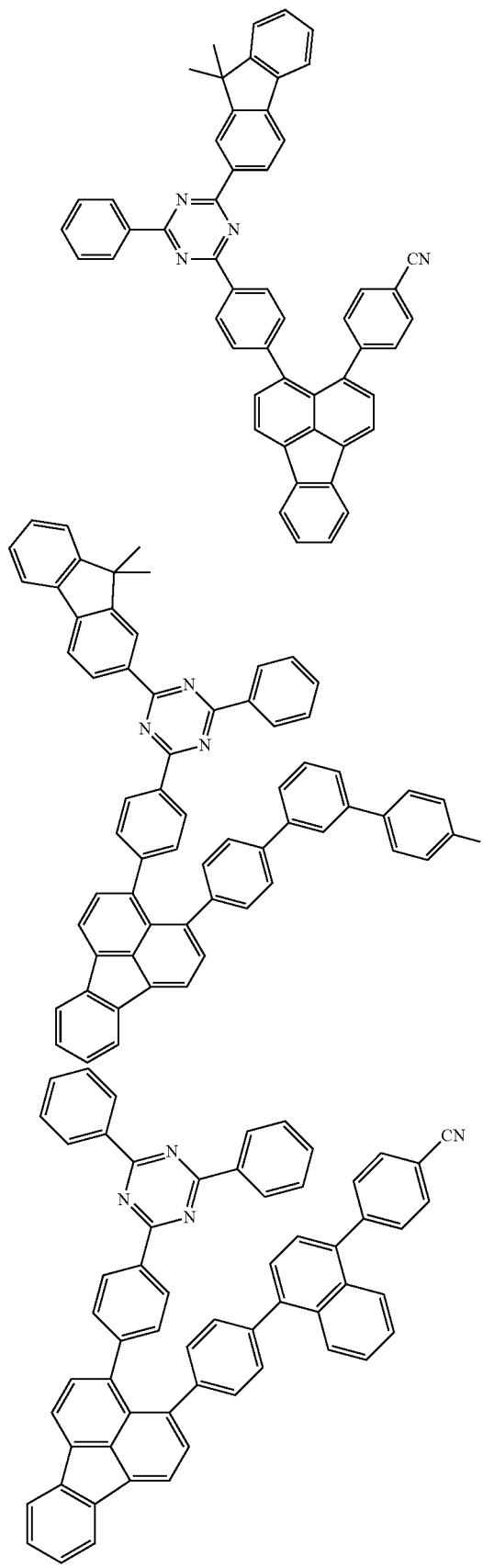
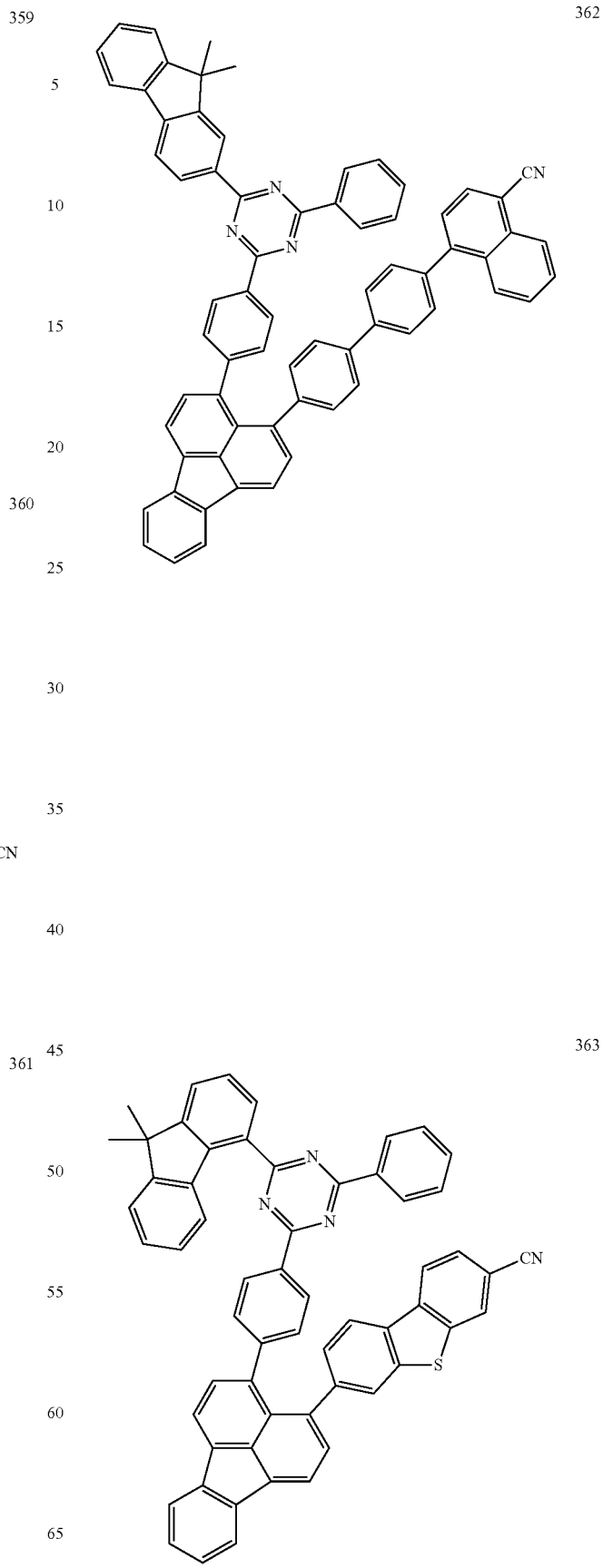

493
-continued
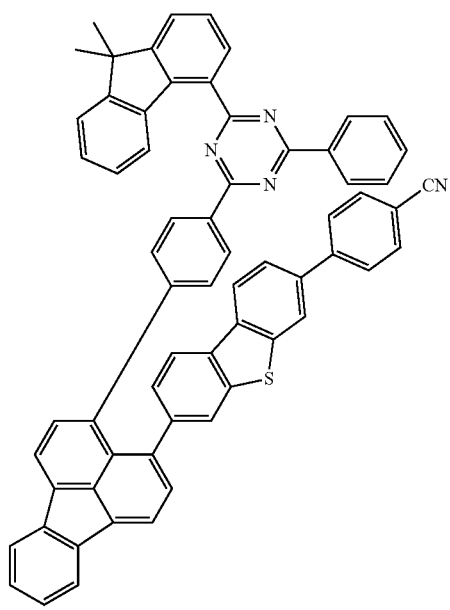
364
494
-continued
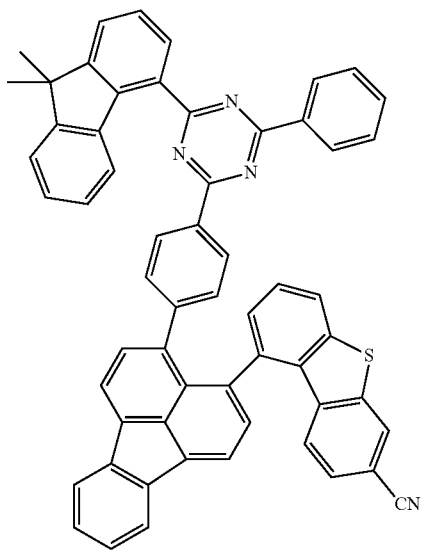
366
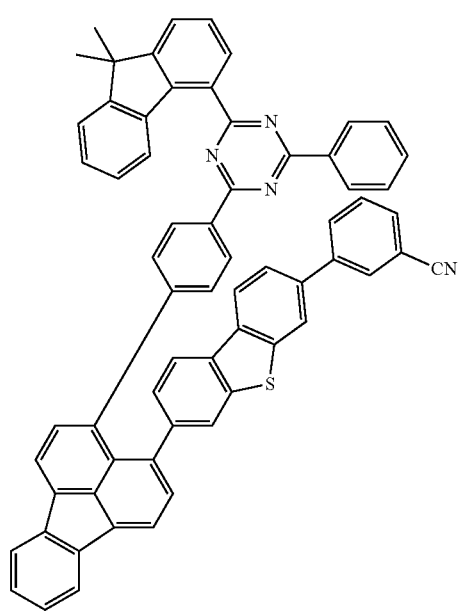
365
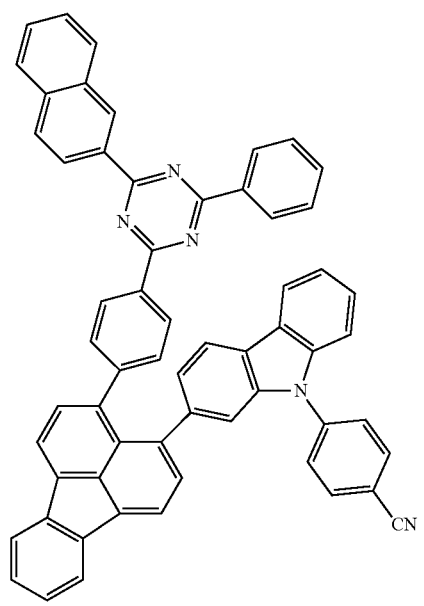
367

495
-continued
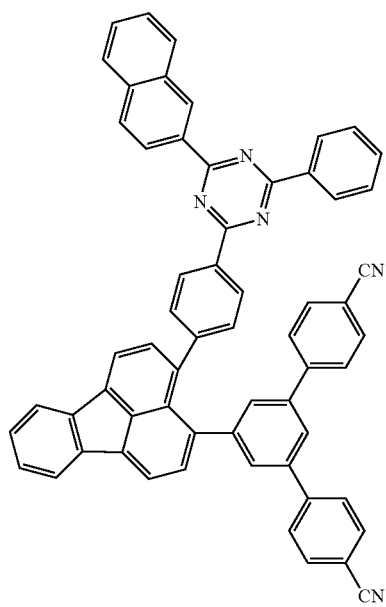
496
-continued
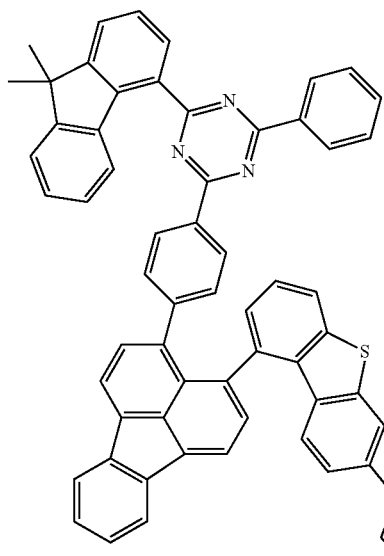
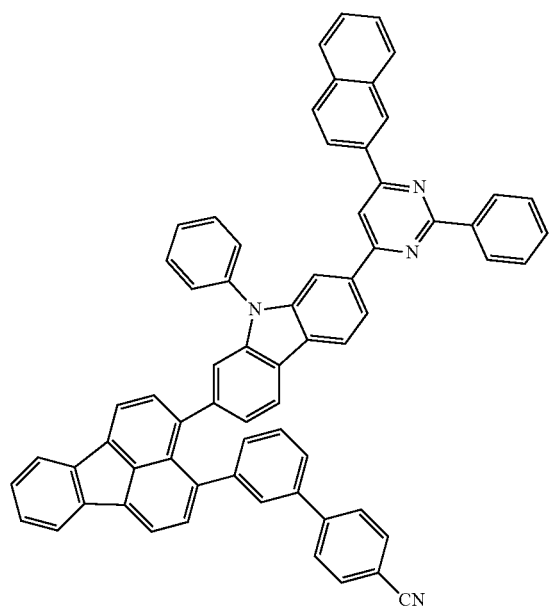
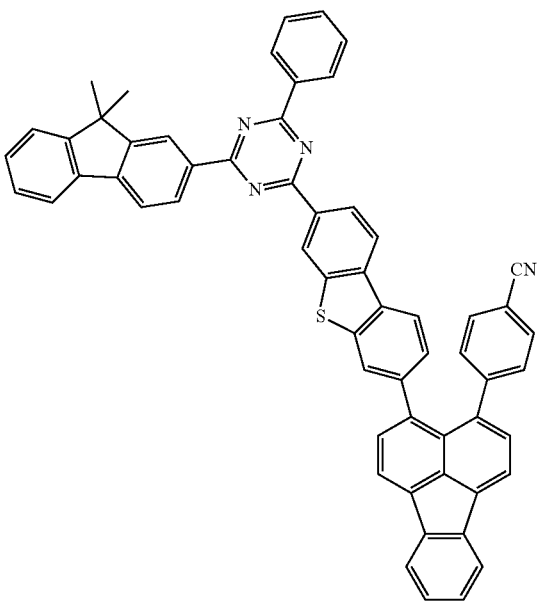

497
-continued
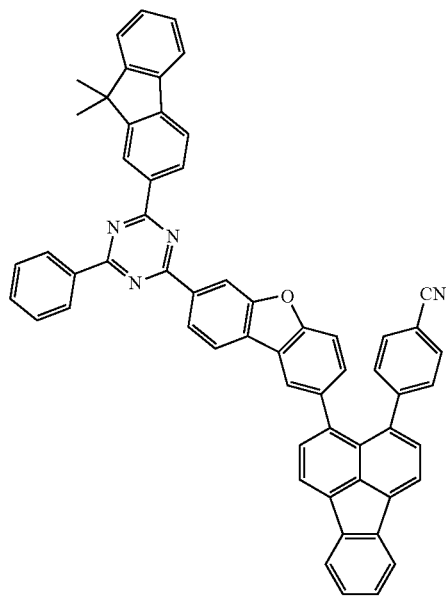
372
498
-continued
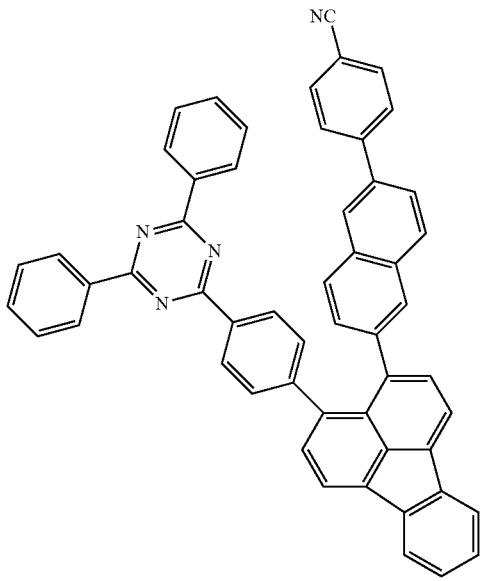
374
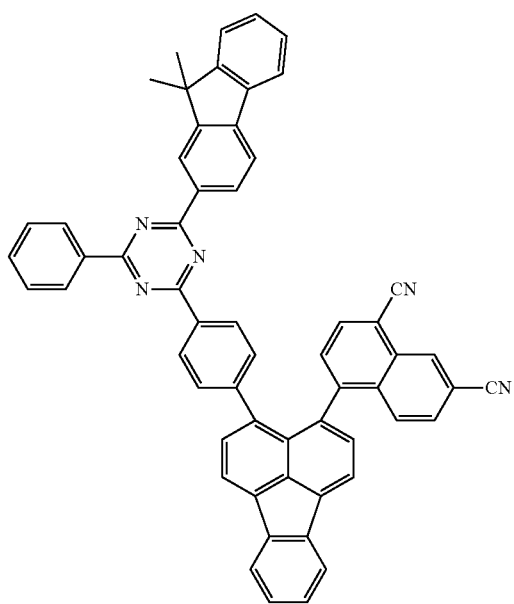
373
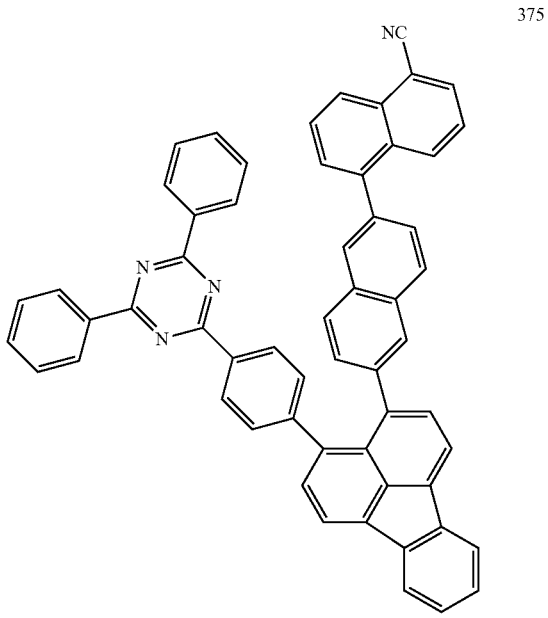
375

499
-continued
376
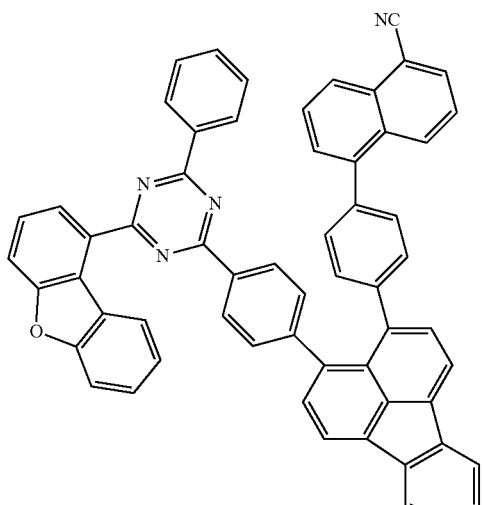
377
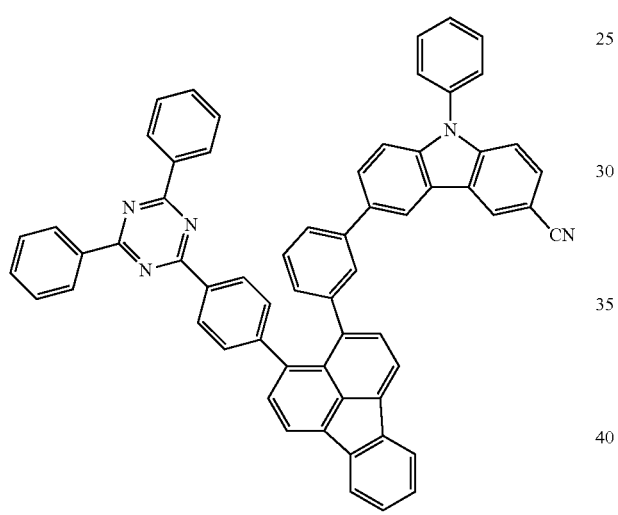
378
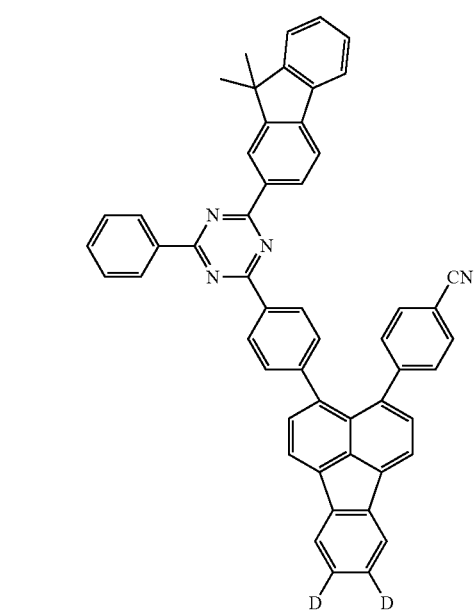
500
-continued
379
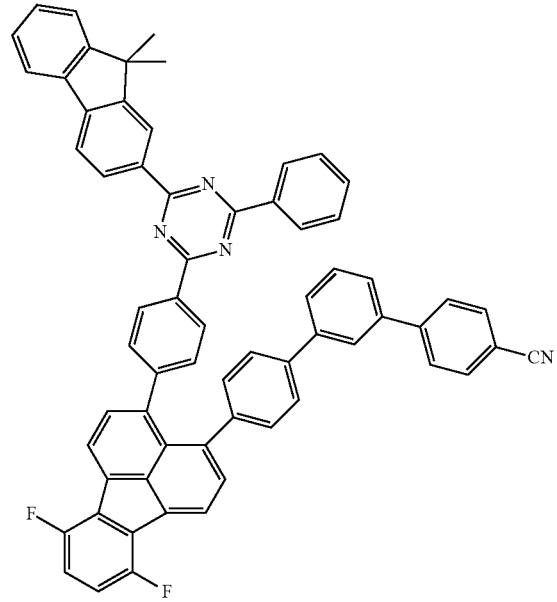
380
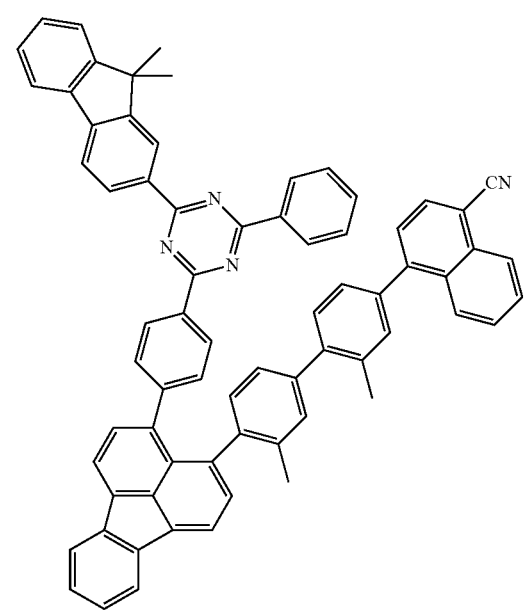

501
-continued
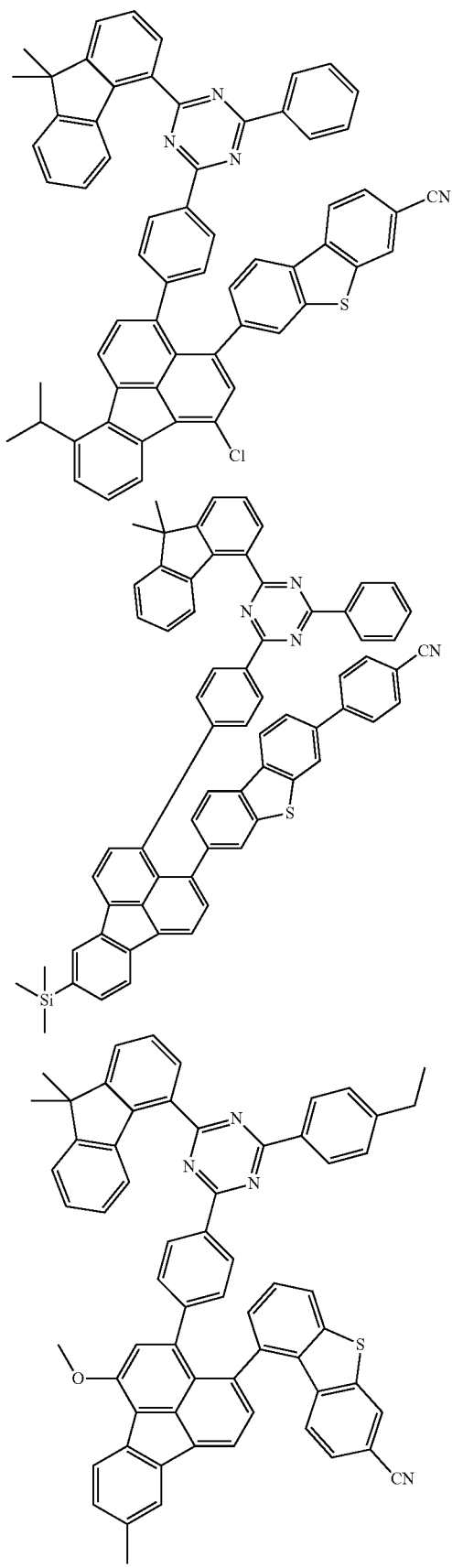
502
-continued

503
-continued
388
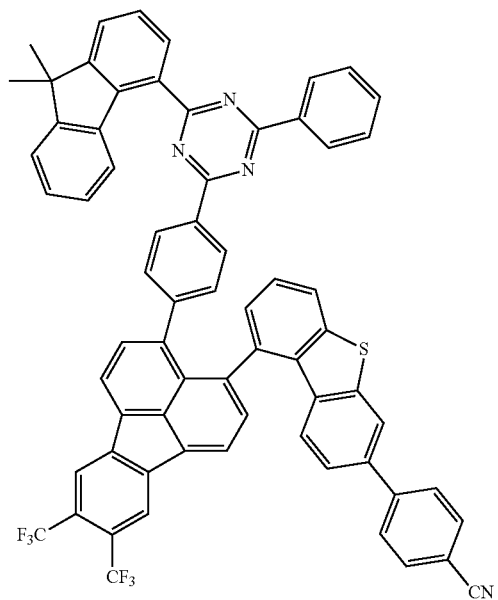
504
-continued
386
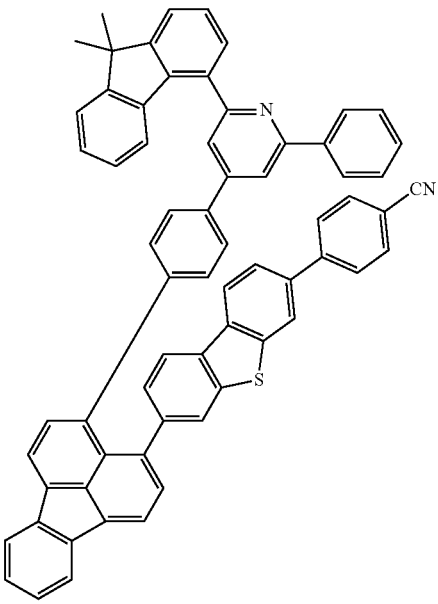
387
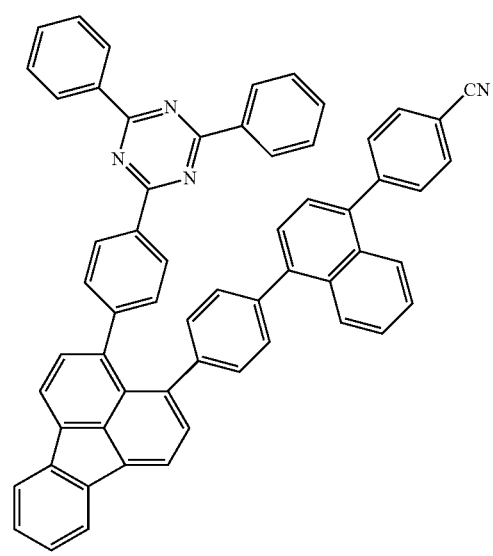
389
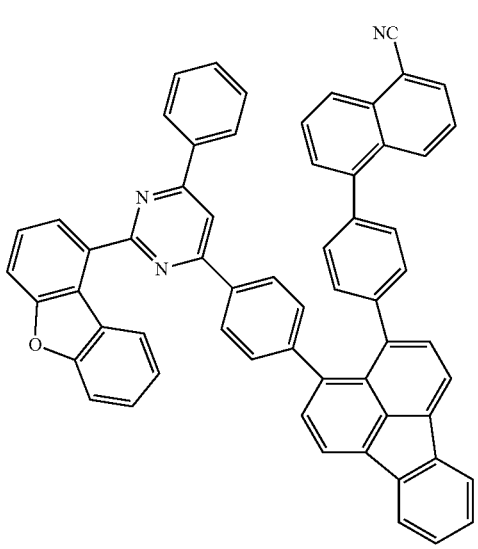

505
-continued

390

506
-continued

392

391

393

394
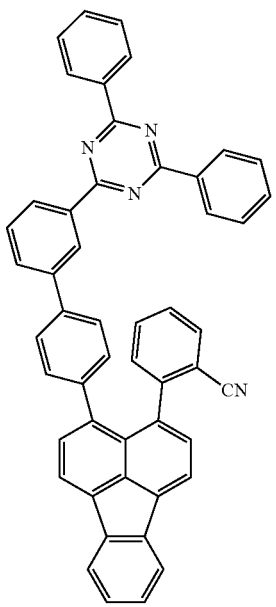
396
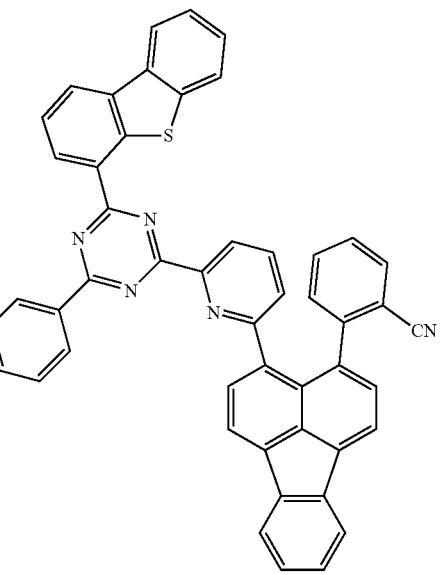
395
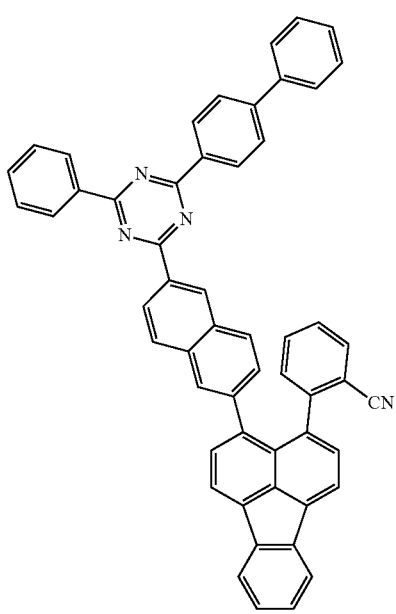
397
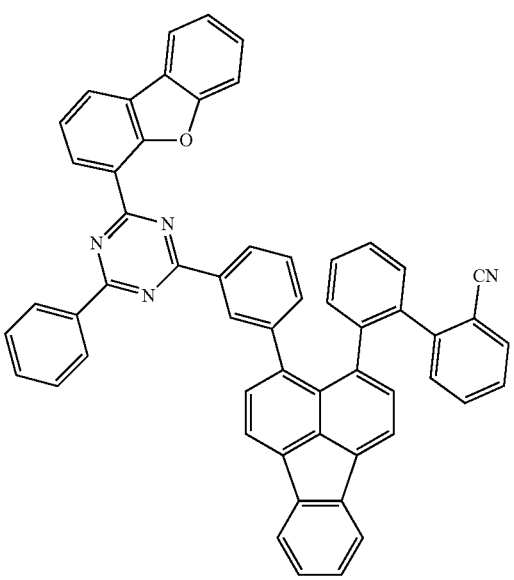

509
-continued

398

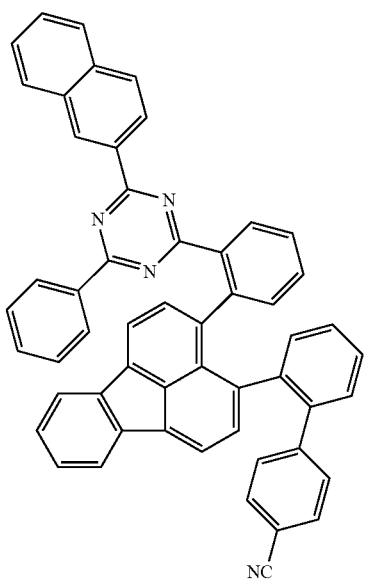

399

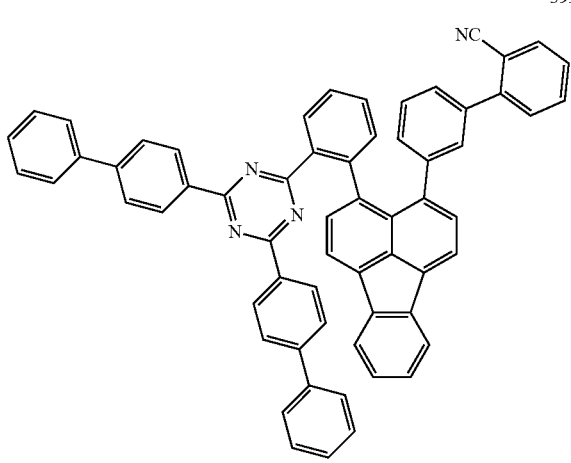

510
-continued

400

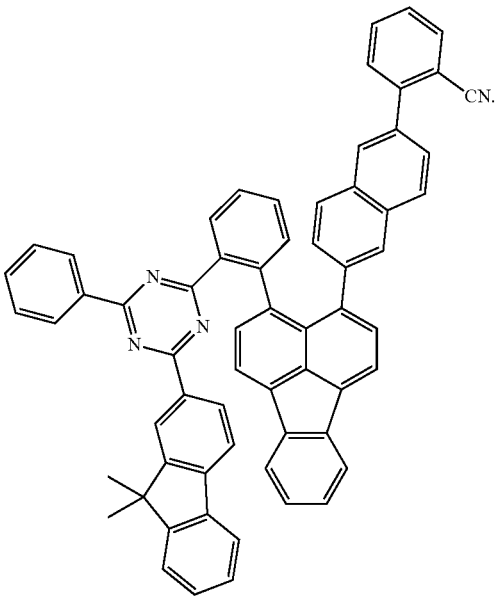

16. An electronic device, comprising an anode and a cathode disposed oppositely, and a functional layer disposed between the anode and the cathode; wherein the functional layer comprises an electron transport layer, and the electron transport layer comprises the organic compound according to claim 1.

17. The electronic device according to claim 16, wherein the electronic device is an organic electroluminescent device or a photoelectric conversion device.

18. An electronic apparatus, comprising the electronic device of claim 16.

* * * * *